(12) United States Patent
Park et al.

(10) Patent No.: US 10,991,885 B2
(45) Date of Patent: *Apr. 27, 2021

(54) COMPOUND FOR ORGANIC ELECTRONIC ELEMENT, ORGANIC ELECTRONIC ELEMENT USING THE SAME AND ELECTRONIC DEVICE THEREOF

(71) Applicant: DUK SAN NEOLUX CO., LTD., Cheonan-si (KR)

(72) Inventors: Junghwan Park, Seoul (KR); Sunhee Lee, Cheonan-si (KR); Soungyun Mun, Yongin-si (KR); Daesung Kim, Yongin-si (KR); Hwasoon Jung, Anseong-si (KR); Wonsam Kim, Cheonan-si (KR); Jihun Byun, Cheonan-si (KR); Bumsung Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 18 days.

This patent is subject to a terminal disclaimer.

(21) Appl. No.: 15/867,334

(22) Filed: Jan. 10, 2018

(65) Prior Publication Data

US 2019/0013477 A1 Jan. 10, 2019

Related U.S. Application Data

(63) Continuation of application No. 14/361,268, filed as application No. PCT/KR2012/009531 on Nov. 13, 2012, now Pat. No. 9,905,773.

(30) Foreign Application Priority Data

Nov. 28, 2011 (KR) .................. 10-2011-0125342
Sep. 21, 2012 (KR) .................. 10-2012-0105232

(51) Int. Cl.
| | | |
|---|---|---|
| *H01L 51/54* | (2006.01) | |
| *H01L 51/00* | (2006.01) | |
| *C07D 491/048* | (2006.01) | |
| *C07D 495/04* | (2006.01) | |
| *C07D 519/00* | (2006.01) | |
| *H01L 51/50* | (2006.01) | |

(52) U.S. Cl.
CPC ...... *H01L 51/0058* (2013.01); *C07D 491/048* (2013.01); *C07D 495/04* (2013.01); *C07D 519/00* (2013.01); *H01L 51/006* (2013.01); *H01L 51/0052* (2013.01); *H01L 51/0061* (2013.01); *H01L 51/0067* (2013.01); *H01L 51/0071* (2013.01); *H01L 51/0072* (2013.01); *H01L 51/5016* (2013.01); *H01L 51/0081* (2013.01); *H01L 51/0085* (2013.01); *Y02E 10/549* (2013.01)

(58) Field of Classification Search
CPC ............... H01L 51/0032; H01L 51/005; H01L 51/0051; H01L 51/0052; H01L 51/006; H01L 51/0061; H01L 51/0067; H01L 51/0017; H01L 51/0072; H01L 51/0073; H01L 51/0074; H01L 51/0081; H01L 51/0085; H01L 51/50; H01L 51/5012; H01L 51/5016; H01L 51/5048; H01L 51/5056; H01L 51/5072; C07D 19/00; C07D 495/00; C07D 495/02; C07D 495/04; C07D 491/00; C07D 491/01; C07D 491/04; C07D 491/044; C07D 491/048; Y02E 10/549
USPC ....... 428/690, 691, 917, 411.4, 336; 427/58, 427/66; 313/500–512; 257/40, 80–104, 257/E51.001–E51.052; 252/301.16–301.35; 548/417, 407, 305.1; 544/294, 215, 212, 230, 284, 279; 546/256, 121, 276.7

See application file for complete search history.

(56) References Cited

U.S. PATENT DOCUMENTS

| | | | | |
|---|---|---|---|---|
| 9,290,513 B2* | 3/2016 | Park | ..................... | C07D 495/14 |
| 9,570,689 B2* | 2/2017 | Park | ..................... | C07D 491/04 |
| 9,799,835 B2* | 10/2017 | Kim | ..................... | C07D 487/04 |
| 9,905,773 B2* | 2/2018 | Park | ..................... | H01L 51/0071 |
| 2009/0309488 A1* | 12/2009 | Kato | ..................... | C07D 307/91 |
| | | | | 313/504 |
| 2010/0012931 A1* | 1/2010 | Kato | ..................... | C07D 209/86 |
| | | | | 257/40 |
| 2011/0279020 A1* | 11/2011 | Inoue | ..................... | C07D 209/82 |
| | | | | 313/504 |
| 2011/0315975 A1* | 12/2011 | Kai | ..................... | C07D 487/04 |
| | | | | 257/40 |
| 2012/0168734 A1* | 7/2012 | Park | ..................... | C07D 491/147 |
| | | | | 257/40 |

FOREIGN PATENT DOCUMENTS

| | | | | |
|---|---|---|---|---|
| KR | 20110066766 A | * | 6/2011 | |
| WO | WO-2010113726 A1 | * | 10/2010 | ............ C07D 487/04 |
| WO | WO-2011019173 A2 | * | 2/2011 | ......... C07D 491/147 |

OTHER PUBLICATIONS

Machine translation of KR2011-0066766. (Year: 2011).*

* cited by examiner

*Primary Examiner* — Andrew K Bohaty
(74) *Attorney, Agent, or Firm* — Vorys, Sater, Seymour & Pease LLP; Mih Suhn Koh

(57) ABSTRACT

A compound represented by Formula 1. An organic electric element includes a first electrode, a second electrode, and an organic material layer between the first electrode and the second electrode. The organic material layer includes the compound represented by Formula 1. When the organic electric element includes the compound in the organic material layer, luminous efficiency, stability, and life span can be improved.

17 Claims, 1 Drawing Sheet

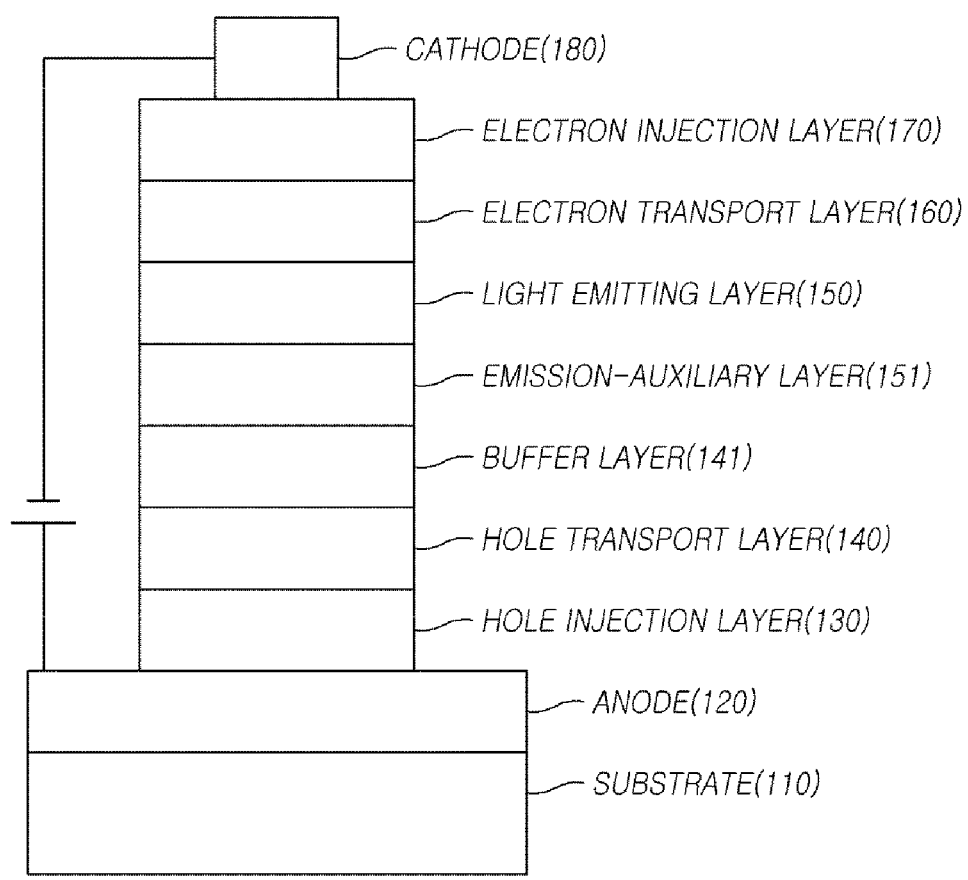

COMPOUND FOR ORGANIC ELECTRONIC ELEMENT, ORGANIC ELECTRONIC ELEMENT USING THE SAME AND ELECTRONIC DEVICE THEREOF

CROSS-REFERENCE TO RELATED APPLICATION

This patent application claims benefit under 35 U.S.C. 119(e), 120, 121, or 365(c), and is a National Stage entry from International Application No. PCT/KR2012/009531, filed Nov. 13, 2012, which claims priority to Korean Patent Application No. 10-2011-01256342, filed on Nov. 18, 2011, and Korean Patent Application No. 10-2012-0105232, filed on Sep. 21, 2012, the contents of which are hereby incorporated by reference for all purposes as if fully set forth herein.

BACKGROUND

Technical Field

The present invention relates to a compound including a five-membered hetero ring, an organic electronic element using the same, and an electronic device including the organic electronic element.

Background Art

In general, an organic light emitting phenomenon refers to a phenomenon in which electric energy is converted into light energy by an organic material. An organic electronic element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electronic element, and for example, may include a hole injection layer, a hole transport layer, a light emitting layer, an electron transport layer, an electron injection layer, and the like.

A material used as an organic material layer in an organic electronic element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Especially, much research has been conducted on an organic material to be inserted into a hole transport layer or a buffer layer for the excellent life span characteristic of an organic electronic element. To this end, a hole injection layer material is required, which provides holes with high mobility from an anode to an organic layer while forming a thin film with high uniformity and low crystallinity after its deposition.

Further, it is required to develop a hole injection layer material that retards penetration/diffusion of metal oxides from an anode electrode (ITO) into an organic layer, which is one cause for the shortened life span of an organic electronic element, and has stability against Joule heat generated during the operation of an organic electronic element, that is, a high glass transition temperature. Also, it has been reported that a low glass transition temperature of a hole transport layer material has a great effect on the life span of an organic electronic element because the uniformity of a thin film surface collapses during the operation of the element. In general, deposition is a main method of forming an OLED, and thus there is an actual need to develop a material that is durable to such a deposition method, that is, a highly heat-resistant material.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

In order to allow an organic electronic element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electronic element has not yet been fully developed. Accordingly, there is a continuous need to develop new materials for an organic material layer.

SUMMARY

In order to solve one or more of the above-mentioned problems occurring in the prior art, an aspect of the present invention is to provide a compound including a five-membered hetero ring, which allows an organic electronic element to have high luminous efficiency and low driving voltage and to be improved in color purity and life span, an organic electronic element using the same, and an electronic device including the organic electronic element.

In accordance with an aspect of the present invention, there is provided a compound represented by Formula below.

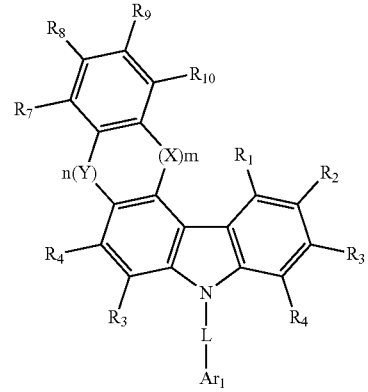

In another aspect of the present invention, there are provided an organic electronic 10 element using the compound represented by Formula above and an electronic device including the organic electronic element.

By using a new compound essentially including a compound including a five-membered hetero ring according to embodiments of the present invention, an organic electronic element according to one or more embodiments of the present invention not only has high luminous efficiency and low driving voltage, but can also be improved in color purity and life span.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings. In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

Unless otherwise stated, the term "halo" or "halogen" as used herein includes fluorine, chlorine, bromine, and iodine.

Unless otherwise stated, the term "alkyl" or "alkyl group" as used herein has, but not limited to, 1 to 60 carbon atoms.

Unless otherwise stated, the term "alkenyl" or "alkynyl" as used herein has, but not limited to, double or triple bonds of 2 to 60 carbon atoms.

Unless otherwise stated, the term "cycloalkyl" as used herein means, but not limited to, alkyl forming a ring having 3 to 60 carbon atoms.

Unless otherwise stated, the term "alkoxy" as used herein has, but not limited to, 1 to 60 carbon atoms.

Unless otherwise stated, the term "aryl group" or "arylene group" as used herein has, but not limited to, 6 to 60 carbon atoms.

Herein, the aryl group or arylene group means a monocyclic or polycyclic aromatic group, and examples of the aryl group may include a phenyl group, a biphenyl group, a fluorine group, and a spirofluorene group.

Unless otherwise stated, the term "heteroalkyl" as used herein means alkyl containing one or more heteroatoms.

Unless otherwise stated, the term "heteroaryl group" or "heteroarylene group" as used herein means, but not limited to, a $C_3$ to $C_{60}$ aryl or arylene group containing one or more heteroatoms, includes both monocyclic and polycyclic rings, and may also be formed in conjunction with an adjacent group.

Unless otherwise stated, the term "heterocyclic alkyl" or "heterocyclic group" as used herein contains one or more heteroatoms, has 2 to 60 carbon atoms, includes both monocyclic and polycyclic rings, and may also be formed in conjunction with an adjacent group. Also, the heterocyclic group may mean an alicyclic and/or aromatic group containing heteroatoms.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "saturated or unsaturated ring" means a saturated or unsaturated aliphatic ring, an aromatic ring having 6 to 60 carbon atoms, or a hetero ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_6$ to $C_{20}$ arylthio group, a $C_2$ to $C_{20}$ alkenyl group, a $C_2$ to $C_{20}$ alkynyl group, a $C_3$ to $C_{20}$ cycloalkyl group, a $C_6$ to $C_{60}$ aryl group, a $C_6$ to $C_{20}$ aryl group substituted by deuterium, a $C_8$ to $C_{20}$ arylalkenyl group, a silane group, a boron group, a germanium group, and a $C_5$ to $C_{20}$ heterocyclic group.

The FIGURE illustrates an organic electronic element according to an embodiment of the present invention.

Referring to the FIGURE, an organic electronic element 100 according to an embodiment of the present invention includes a first electrode 120, a second electrode 180, and an organic material layer between the first electrode 120 and the second electrode 180, which are formed on a substrate 110, and the organic material layer contains the compound represented by Formula 1. Here, the first electrode 120 may be an anode (positive electrode), and the second electrode 180 may be a cathode (negative electrode). In the case of an inverted organic electronic element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electronic element according to an embodiment of the present invention may further include protective layer formed on at least one side of the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For example, the inventive compound may be used as the light emitting layer 150, the hole transport layer 140, and/or the emission-auxiliary layer 151. Since depending on the type and position of a substituent to be attached, a band gap, electrical properties, interfacial properties, and the like may vary even in the same core, long life span and high efficiency can be simultaneously achieved when an optimal combination of energy levels and T1 values, inherent material properties (mobility, interfacial properties, etc.), and the like among the respective layers included in the organic material layer is given.

Accordingly, in the present invention, a combination of energy levels and T1 values, inherent material properties (mobility, interfacial properties, etc.), and the like among the respective layers included in the organic material layer is optimized by forming the light emitting layer by using the compound represented by Formula 1, and thus the life span and efficiency of the organic electronic element can be improved at the same time.

The organic electronic element according to an embodiment of the present invention may be manufactured using a PVD (physical vapor deposition) method. For example, the organic electronic element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by means of a soluble process or solvent process, for example, spin coating, dip coating, doctor blading, screen printing, inkjet printing, or thermal transfer, instead of deposition.

According to used materials, the organic electronic element according to an embodiment of the present invention may be of a top emission type, a bottom emission type, or a dual emission type.

Further, the organic electronic element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electronic element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

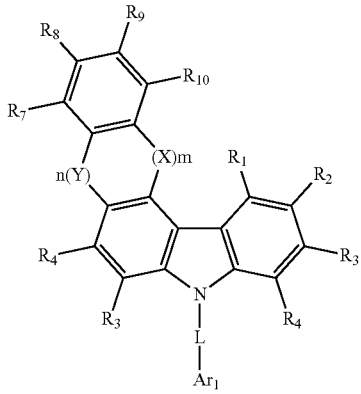

[Formula 1]

In Formula 1 above, i) $R_1$ to $R_{10}$ are independently selected from the group consisting of hydrogen, deuterium, halogen, a $C_6$ to $C_{60}$ aryl group, a fluorenyl group, a fused ring group of a $C_3$ to $C_{60}$ aliphatic ring and a $C_6$ to $C_{60}$ aromatic ring, a $C_2$ to $C_{60}$ heterocyclic group containing at least one heteroatom selected from O, N, S, Si, and P, -L-N(R')(R''), a $C_1$ to $C_{50}$ alkyl group, a $C_2$ to $C_{20}$ alkenyl group, a $C_1$ to $C_{30}$ alkoxy group, and a $C_6$ to $C_{30}$ aryloxy group, or ii) any two adjacent groups of $R_1$ to $R_{10}$ are linked together to form a fused ring (wherein, remaining groups not forming a ring are as defined above in i)).

Only when $R_5$ and $R_6$ are linked to each other to form a ring, $R_1$ to $R_4$ and $R_7$ to $R_{10}$ all may be hydrogen at the same time. When $R_5$ and $R_6$ are not linked to each other and thus do not form a ring, at least one of $R_1$ to $R_4$ and at least one of $R_7$ to $R_{10}$ must not be hydrogen.

That is, $R_1$ to $R_4$ and $R_7$ to $R_{10}$ each may be hydrogen, but all may be hydrogen at the same time only when $R_5$ and $R_6$ are linked to each other to form a ring. When $R_5$ and $R_6$ are linked to each other to form a ring, at least one of $R_1$ to $R_4$ and $R_7$ to $R_{10}$ may be any substituent other than hydrogen as defined above. When $R_5$ and $R_6$ are not linked to each other to form a ring, at least one of $R_1$ to $R_4$ must be a substituent other than hydrogen, and at the same time, at least one (one or more) of $R_7$ to $R_{10}$ must be a substituent other than hydrogen. Thus, when $R_5$ and $R_6$ does not form a ring, there is excluded the case where all of $R_1$ to $R_4$ are hydrogen and/or all of $R_7$ to $R_{10}$ are hydrogen.

Also, when any two adjacent groups of $R_1$ to $R_{10}$ are linked together to form a fused ring, the fact that any two adjacent groups of $R_1$ to $R_{10}$ are linked together to form a fused ring means that $R_1$ and $R_2$, $R_2$ and $R_3$, $R_3$ and $R_4$, $R_5$ and $R_6$, $R_7$ and $R_8$, and/or $R_8$ and $R_9$ are each linked to each other to form a ring.

A ring formed by any two adjacent groups of $R_1$ to $R_{10}$ not only may be a monocyclic or polycyclic aromatic ring or a hetero ring containing at least one heteroatom, but may also take a form in which an aromatic ring and an aliphatic ring are fused. By way of example, any two adjacent groups of $R_1$ to $R_{10}$ are linked together to form an aromatic ring such as benzene, naphthalene, or phenanthrene, wherein the formed aromatic ring may have 6 to 60 nuclear carbon atoms. For example, when $R_7$ and $R_8$ are linked together to form a benzene ring and $R_9$ and $R_{10}$ are linked together to form a benzene ring, and $R_9$ and $R_{10}$ are linked together to form a benzene ring, phenanthrene may be formed together with a benzene ring moiety in which the benzene rings are linked.

Also, $R_1$ and $R_{10}$ may be linked together to form a hetero ring such as thiophene, furan, pyridine, indole, or quinoline, wherein the formed hetero ring may have 2 to 60 nuclear carbon atoms. Further, in the case of a polycyclic ring, it may be a fused polycyclic ring, a non-fused polycyclic ring in which a plurality of cycles are not fused, or a mixed ring in which a fused polycyclic ring and a non-fused polycyclic ring are mixed.

In Formula 1 above, X and Y are independently S, O, or $SiR_{31}R_{32}$. Here, $R_{31}$ and $R_{32}$ may be independently hydrogen, a $C_6$ to $C_{60}$ aryl group, a $C_2$ to $C_{60}$ heterocyclic group containing at least one heteroatom selected from O, N, S, Si, and P, or a $C_1$ to $C_{50}$ alkyl group. In Formula 1 above, m and n each may be 0 or 1, with the proviso that the case where both m and n are 0 is excluded. Since m+n must assume an integer equal to or greater than 1, at least one of X and Y has to exist.

L is selected from the group consisting of a single bond; a $C_6$ to $C_{60}$ arylene group; a fluorenyl group; a $C_2$ to $C_{60}$ heterocyclic group containing at least one heteroatom selected from O, N, S, Si, and P; and a bivalent aliphatic hydrocarbon group. Here, the arylene group, the fluorenyl group, the heterocyclic group, and the aliphatic hydrocarbon group may be substituted by one or more substituents selected from the group consisting of a nitro group, a cyano group, a halogen group, a $C_1$ to $C_{20}$ alkyl group, a $C_6$ to $C_{20}$ aryl group, a $C_2$ to $C_{20}$ heterocyclic group, a $C_1$ to $C_{20}$ alkoxy group, and an amino group.

Further, $Ar_1$ may be a $C_2$ to $C_{60}$ heterocyclic group containing at least one heteroatom selected from O, N, S, Si, and P, a $C_6$ to $C_{60}$ aryl group, a fluorenyl group, or —N(R')(R").

R' and R" may be independently a $C_2$ to $C_{60}$ heterocyclic group containing at least one heteroatom selected from O, N, S, Si, and P, a $C_6$ to $C_{60}$ aryl group, or a fluorenyl group.

When $R_1$ to $R_{12}$, $Ar_1$, R', and R" are an aryl group, $R_1$ to $R_{12}$, $Ar_1$, R', and R" may be substituted by one or more substituents selected from the group consisting of deuterium, halogen, a silane group, a boron group, a germanium group, a cyano group, a nitro group, a $C_1$ to $C_{20}$ alkylthio group, a $C_1$ to $C_{20}$ alkoxy group, a $C_1$ to $C_{20}$ alkyl group, a $C_2$ to $C_{20}$ alkenyl group, a $C_2$ to $C_{20}$ alkynyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group.

When $R_1$ to $R_{12}$, $Ar_1$, R', and R" are an heterocyclic group, $R_1$ to $R_{12}$, $Ar_1$, R', and R" may be substituted by one or more substituents selected from the group consisting of deuterium, halogen, a silane group, a cyano group, a nitro group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group.

When $R_1$ to $R_{10}$, $Ar_1$, R', and R" are a fluorenyl group, $R_1$ to $R_{10}$, $Ar_1$, R', and R" may be substituted by one or more substituents selected from the group consisting of deuterium, halogen, a silane group, a cyano group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group.

When $R_1$ to $R_{10}$ are a fused ring group, $R_1$ to $R_{10}$ may be substituted by one or more substituents selected from the group consisting of deuterium, halogen, a silane group, a boron group, a germanium group, a cyano group, a nitro group, a $C_1$ to $C_{20}$ alkylthio group, a $C_1$ to $C_{20}$ alkoxy group, a $C_1$ to $C_{20}$ alkyl group, a $C_2$ to $C_{20}$ alkenyl group, a $C_2$ to $C_{20}$ alkynyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group.

When $R_1$ to $R_{12}$ are an alkyl group, $R_1$ to $R_{12}$ may be substituted by one or more substituents selected from the group consisting of halogen, a silane group, a boron group, a cyano group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_7$ to $C_{20}$ arylalkyl group, and a $C_8$ to $C_{20}$ arylalkenyl group.

When $R_1$ to $R_{10}$ are an alkenyl group, $R_1$ to $R_{10}$ may be substituted by one or more substituents selected from the group consisting of deuterium, halogen, a silane group, a cyano group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group.

When $R_1$ to $R_{10}$ are an alkoxy group, $R_1$ to $R_{10}$ may be substituted by one or more substituents selected from the group consisting of deuterium, halogen, a silane group, a $C_1$ to $C_{20}$ alkyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group.

When $R_1$ to $R_{10}$ are an aryloxy group, $R_1$ to $R_{10}$ may be substituted by one or more substituents selected from the group consisting of deuterium, a silane group, a cyano group, a $C_1$ to $C_{20}$ alkyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group.

The compound represented by Formula 1 above may be represented by one of Formulas below.

[Formula 2]

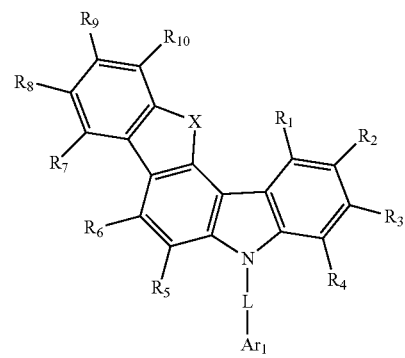

[Formula 3]

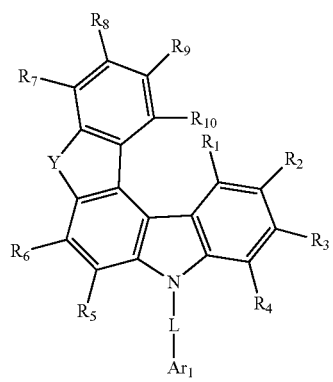

[Formula 4]
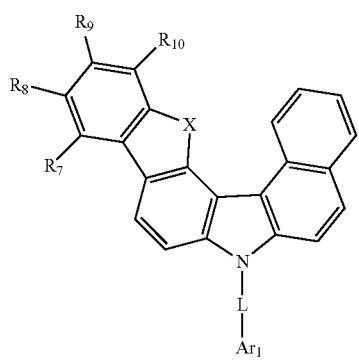
[Formula 5]
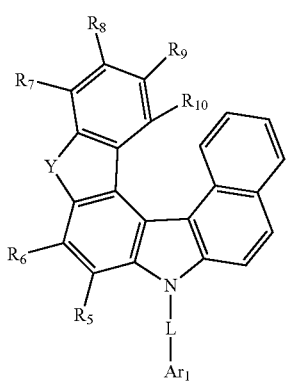
[Formula 6]
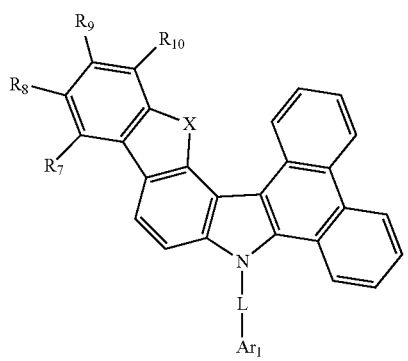
[Formula 7]
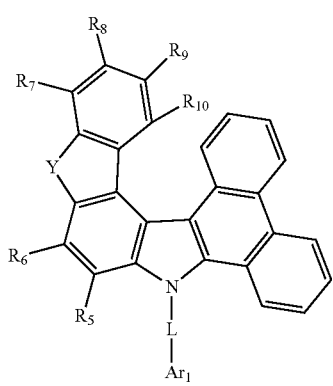
[Formula 8]
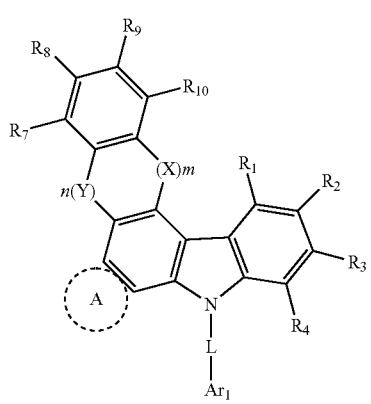
[Formula 9]
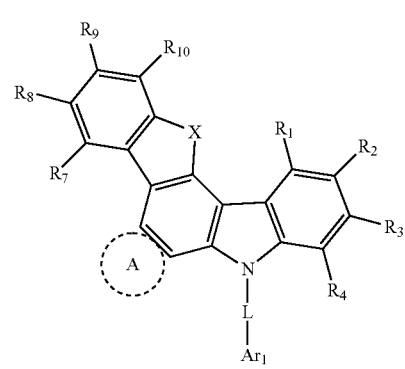
[Formula 10]
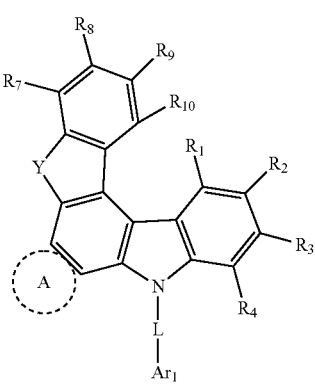
[Formula 11]
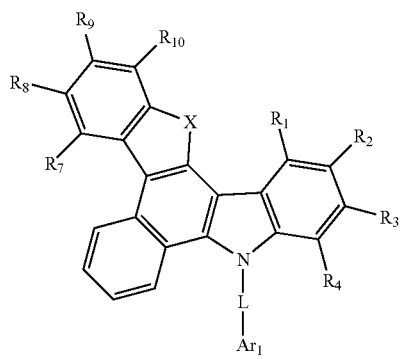

[Formula 12]
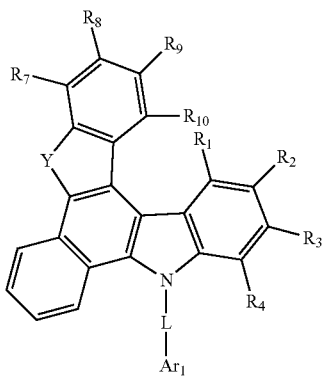
[Formula 13]
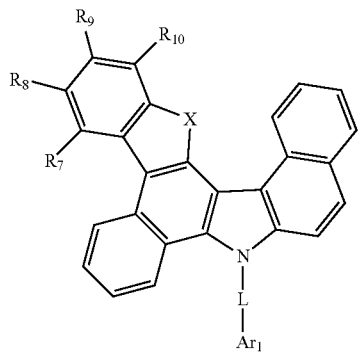
[Formula 14]
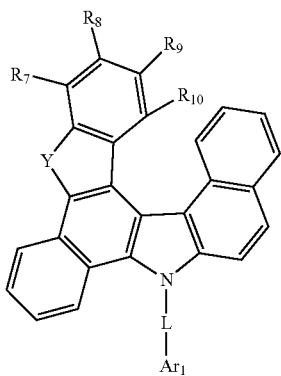
[Formula 15]
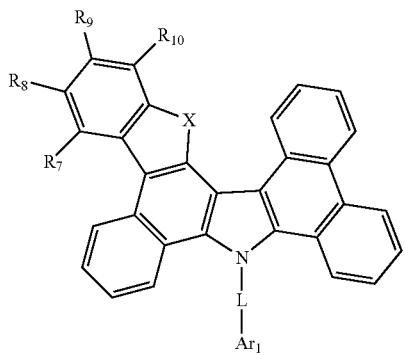
[Formula 16]
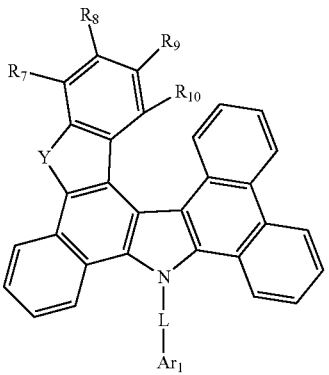
[Formula 17]
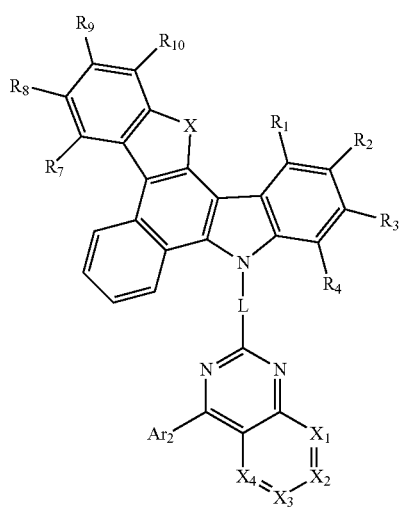
[Formula 18]
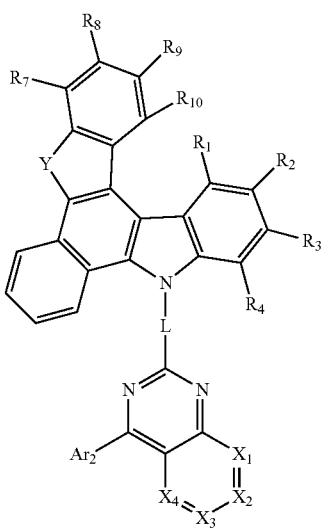
More specially, the compound represented by Formula 1 above may be one of compounds below.

1-1
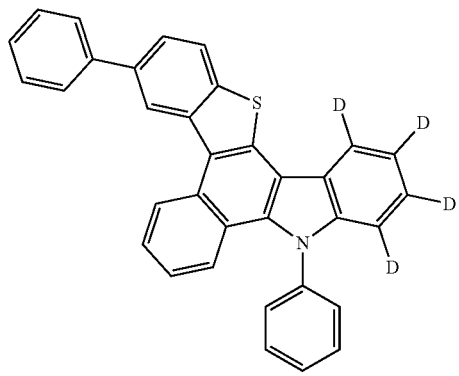
1-2
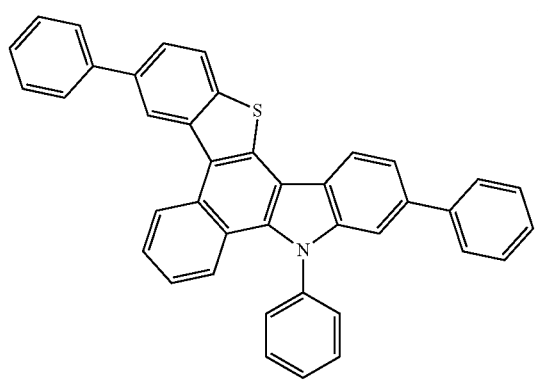
1-3
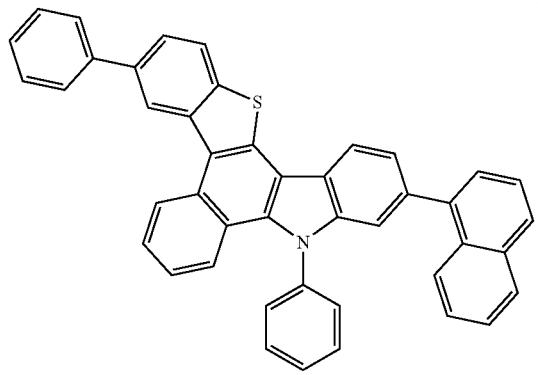
1-4
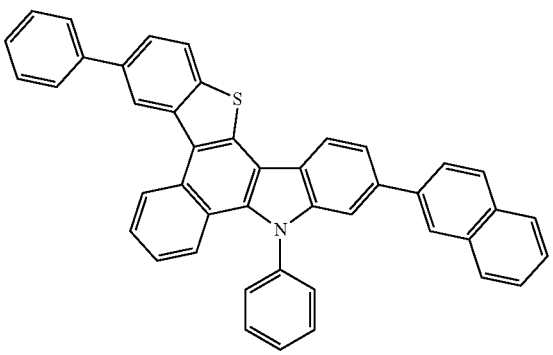
1-5
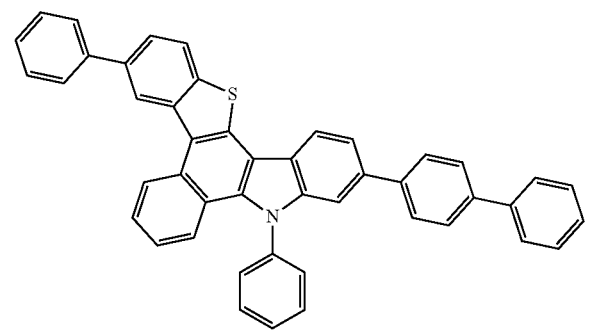
1-6
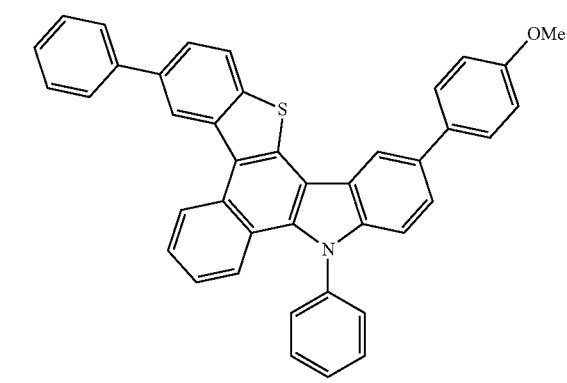
1-7
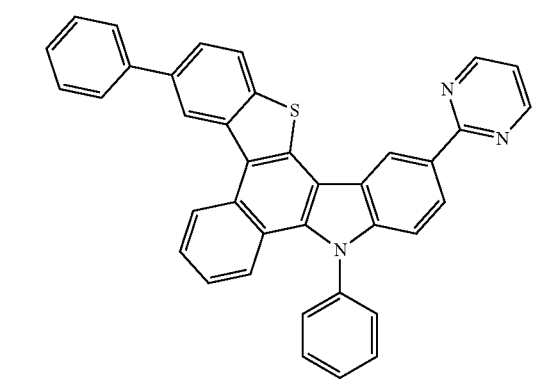
1-8
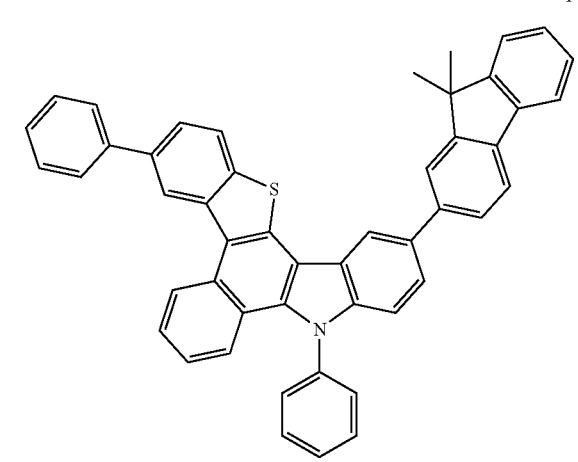

-continued
1-9
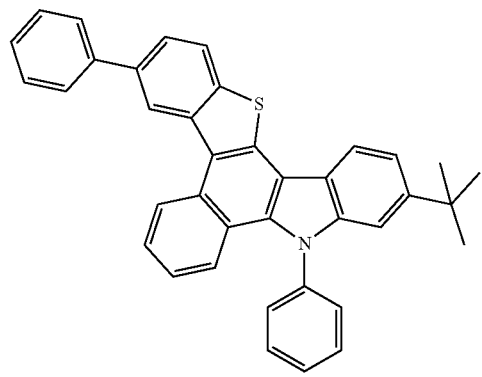
1-10
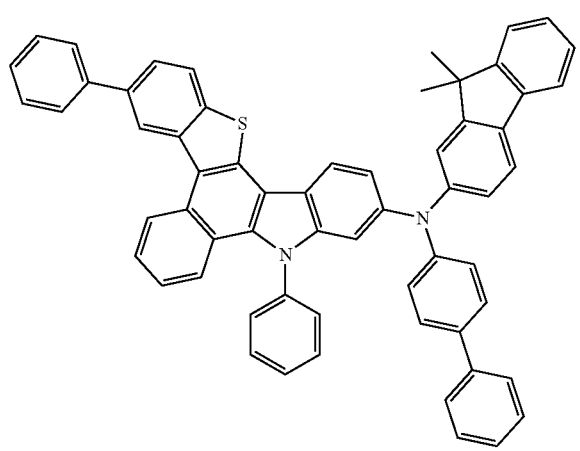
1-11
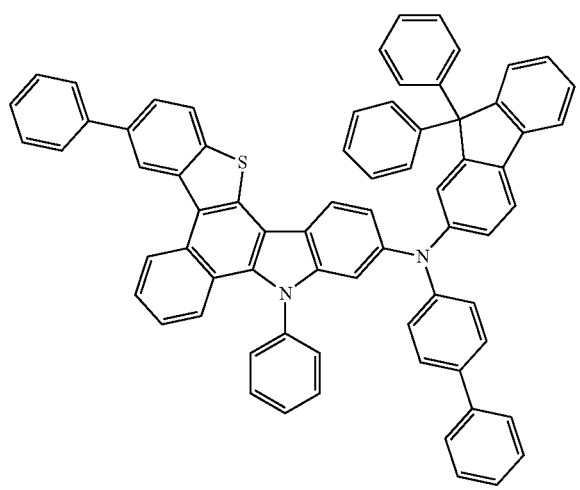
-continued
1-12
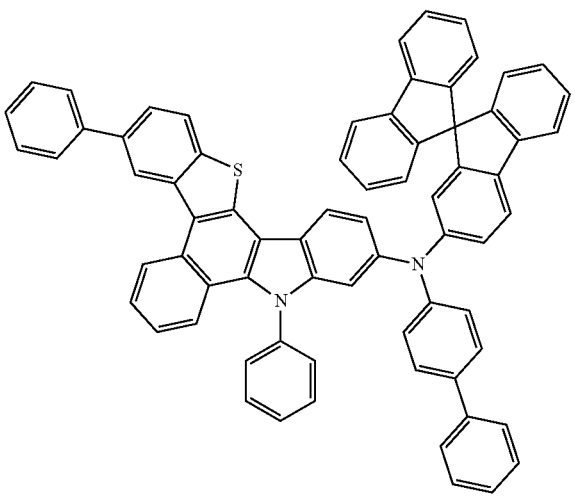
1-13
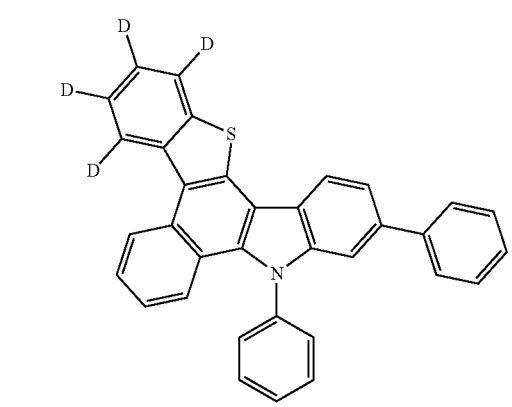
1-14
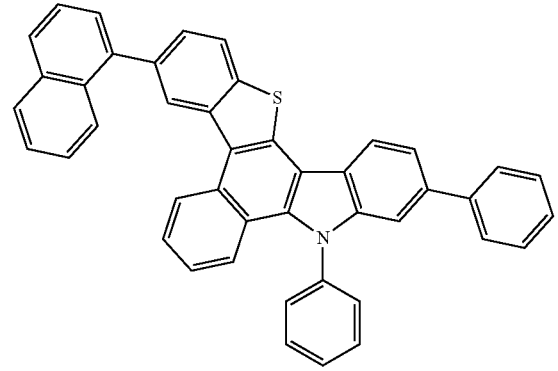

1-15
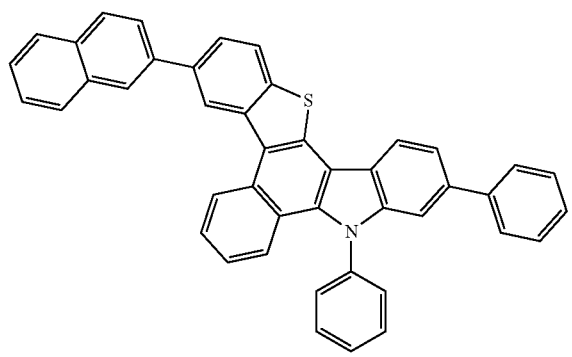
1-16
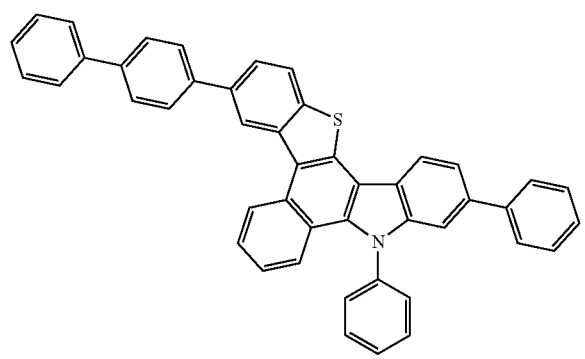
1-17
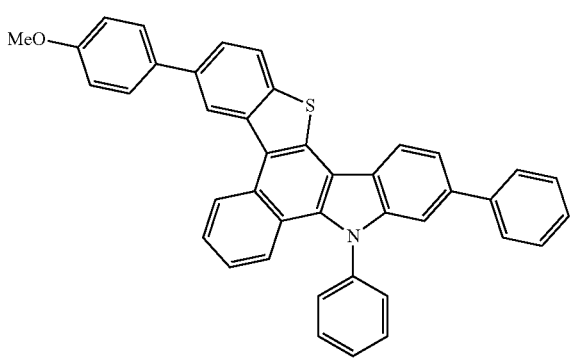
1-18
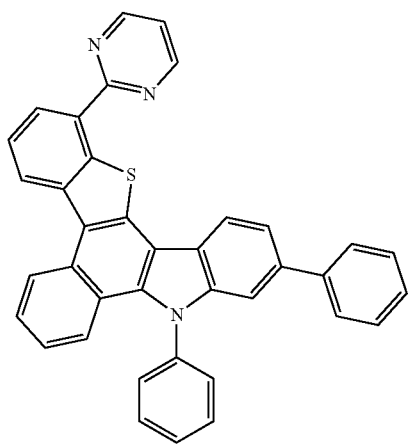
1-19
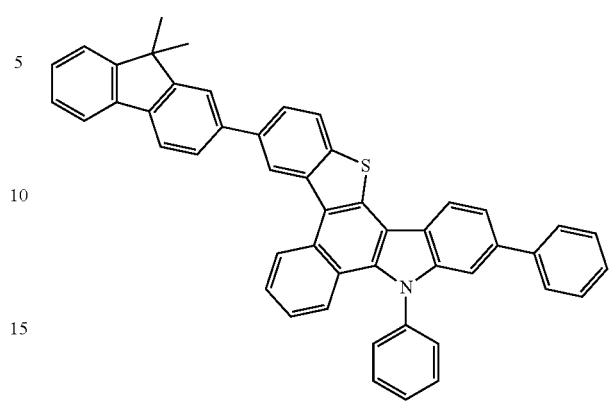
1-20
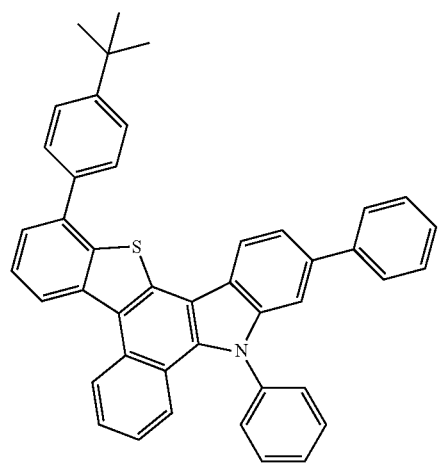
1-21
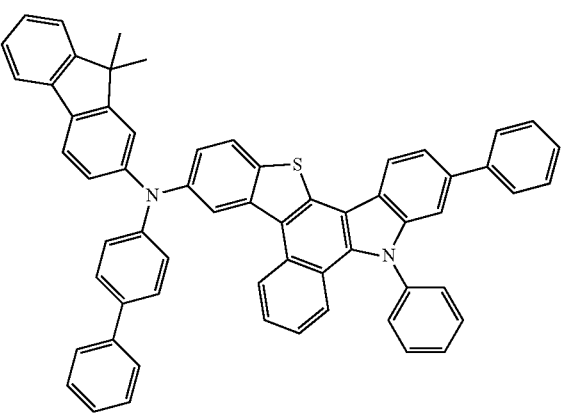

-continued
1-22
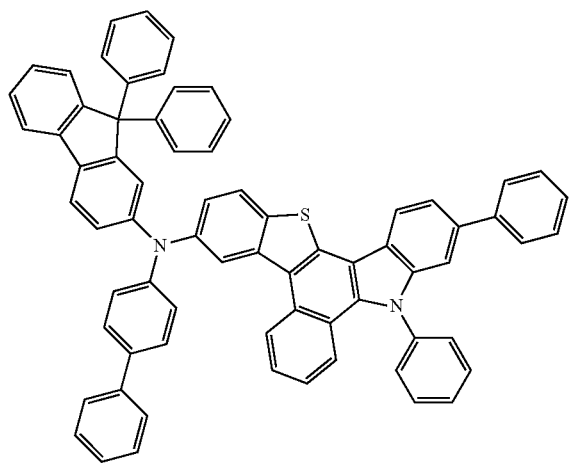
1-23
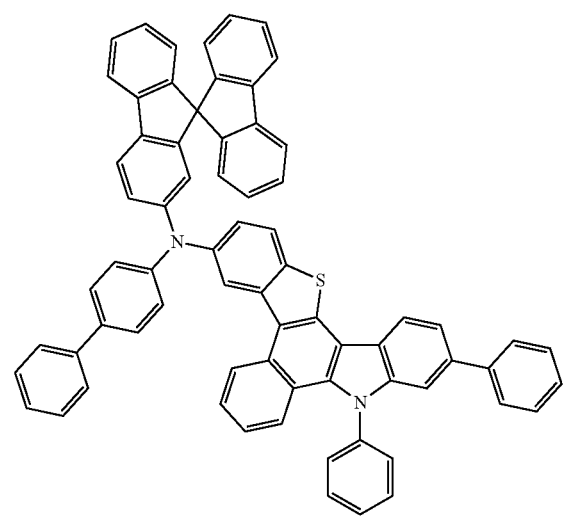
1-24
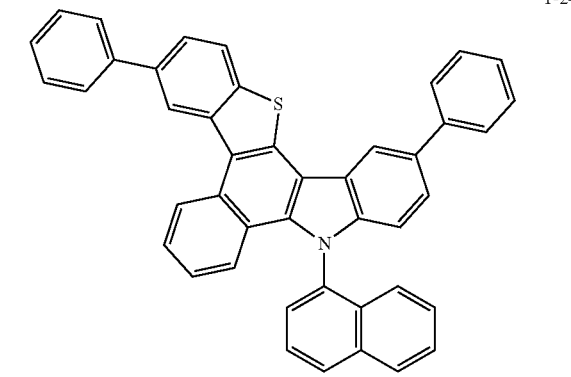
-continued
1-25
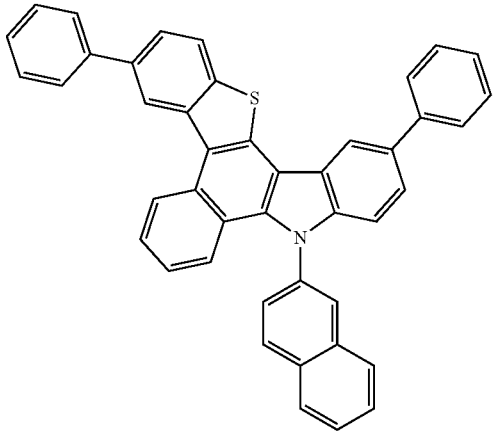
1-26
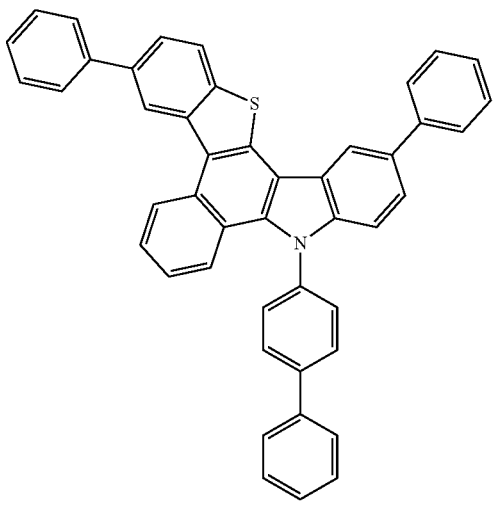
1-27
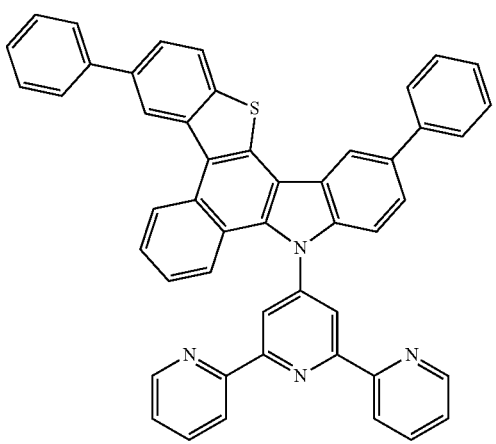

1-28
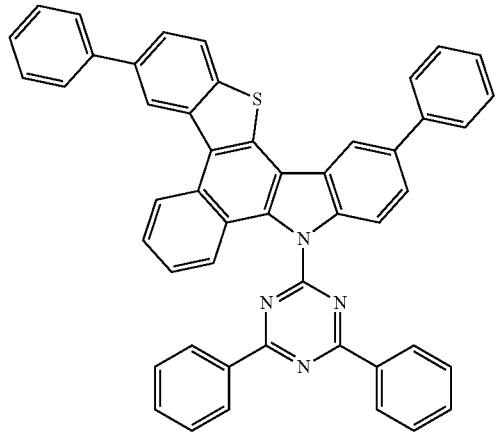
1-29
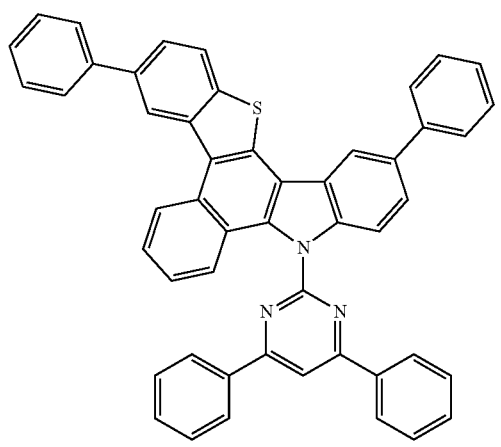
1-30
1-31
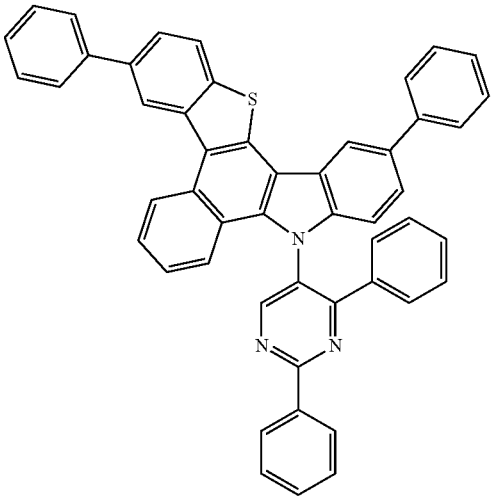
1-32
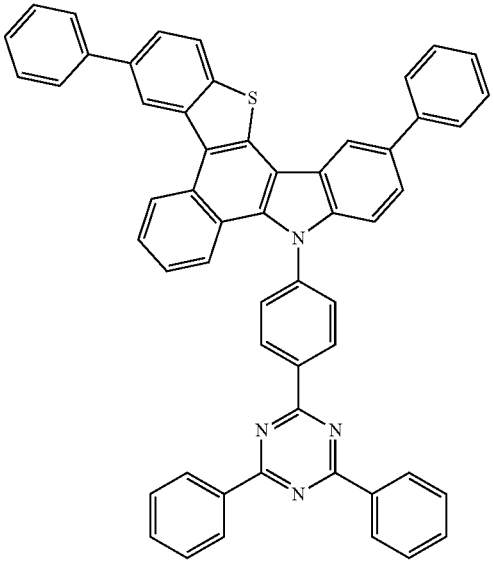
1-33
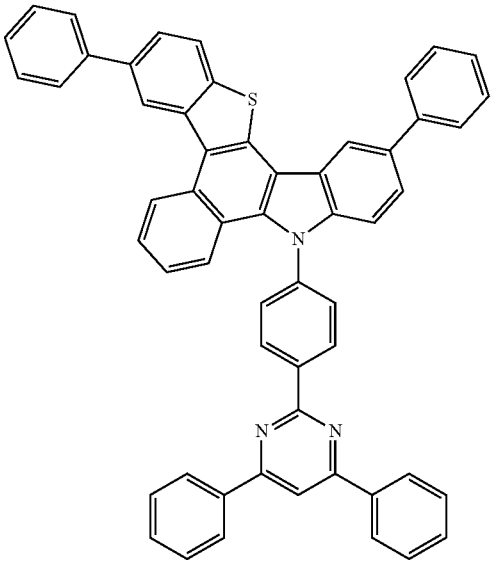

1-34
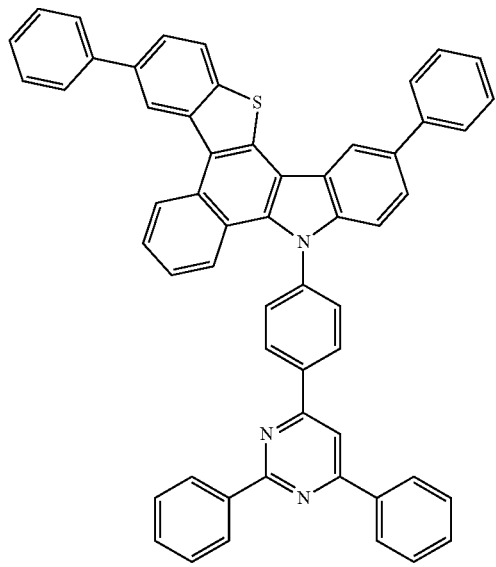
1-35
1-36
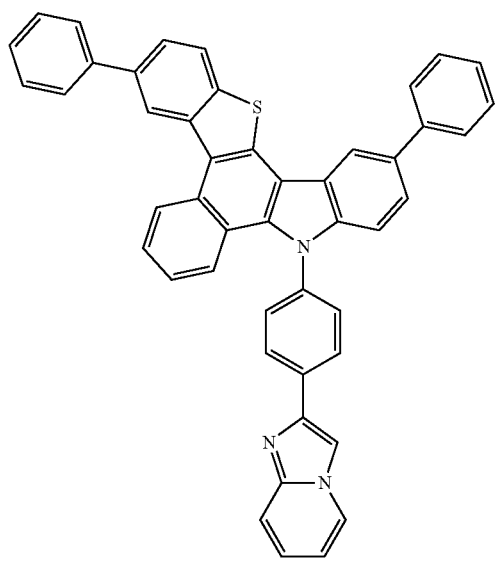
1-37
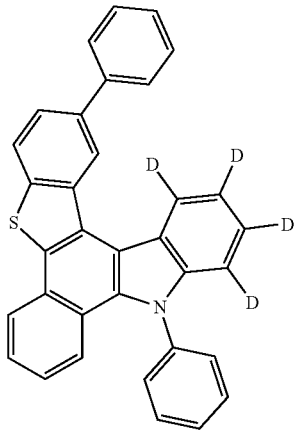
1-38
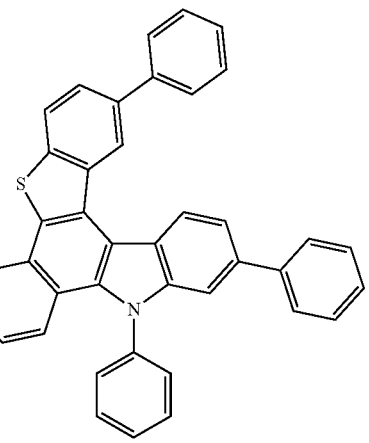
1-39
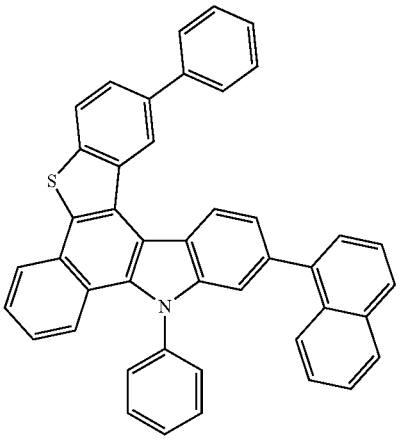

25
-continued
1-40
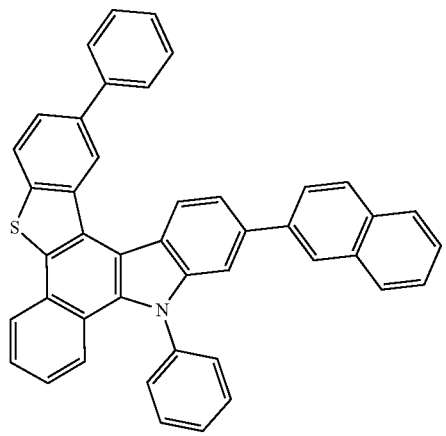
1-41
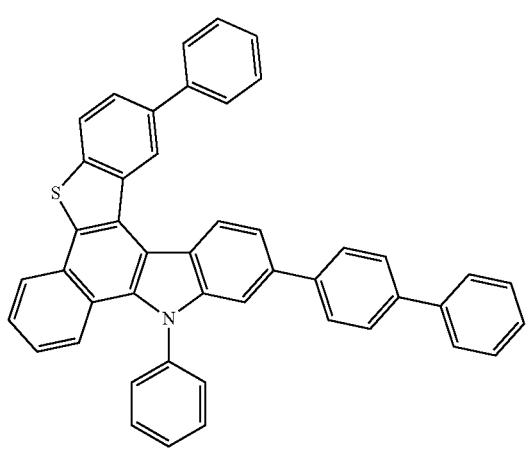
1-42
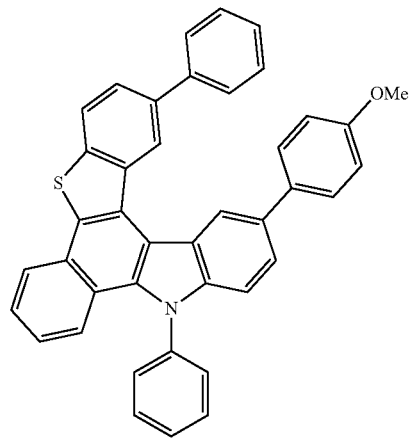
26
-continued
1-43
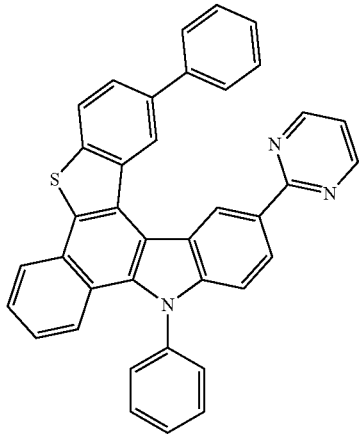
1-44
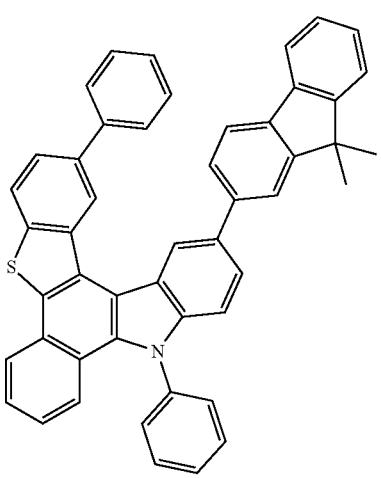
1-45
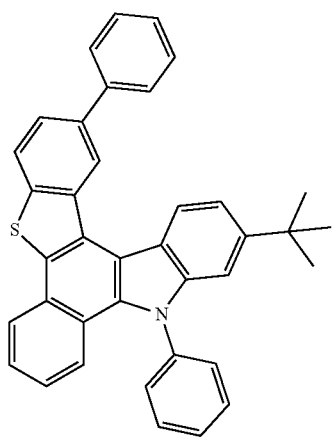

-continued
1-46
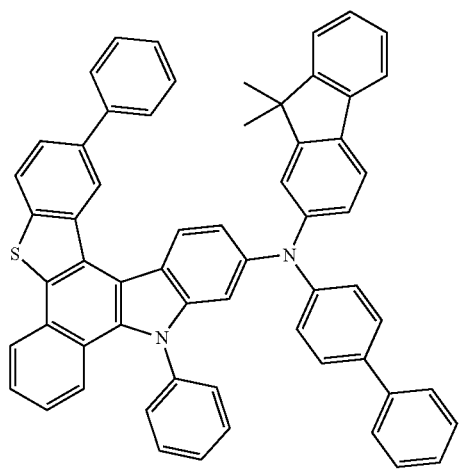
1-47
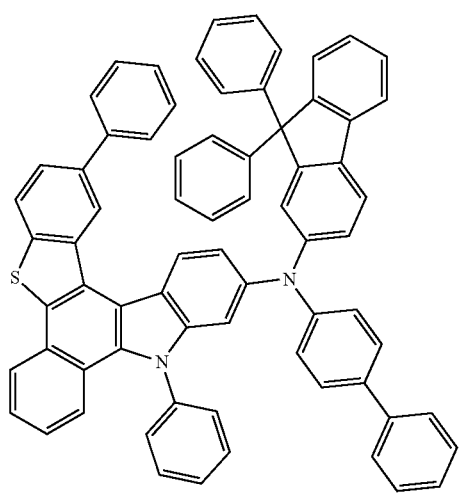
1-48
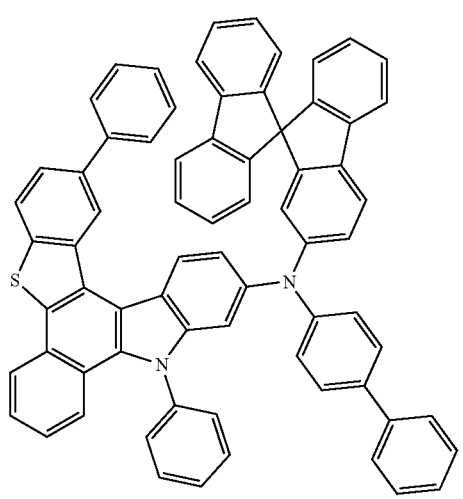
-continued
1-49
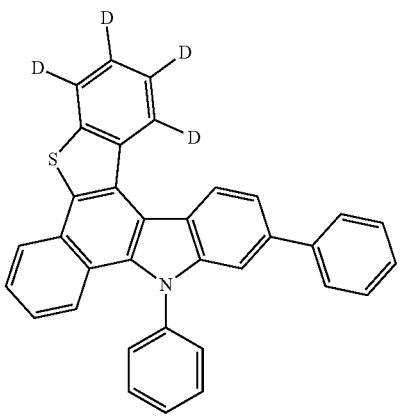
1-50
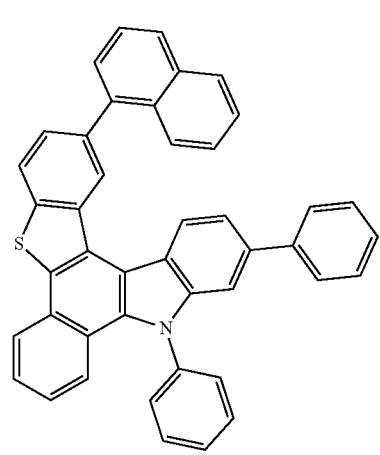
1-51
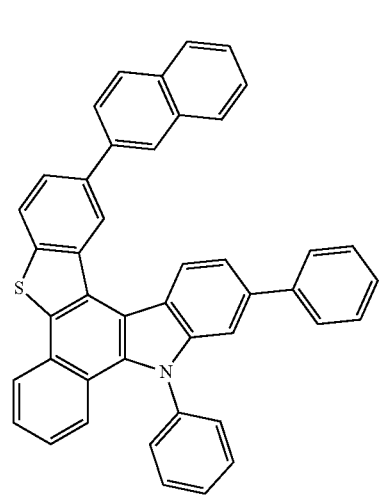

1-52
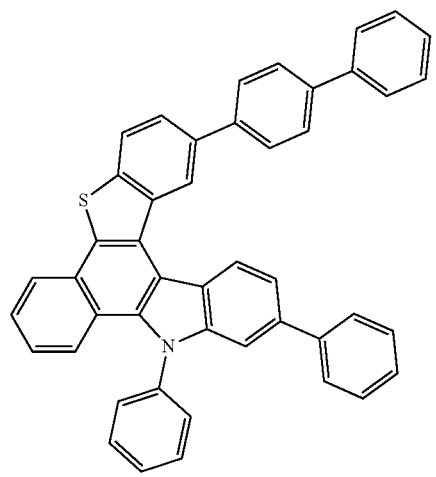
1-53
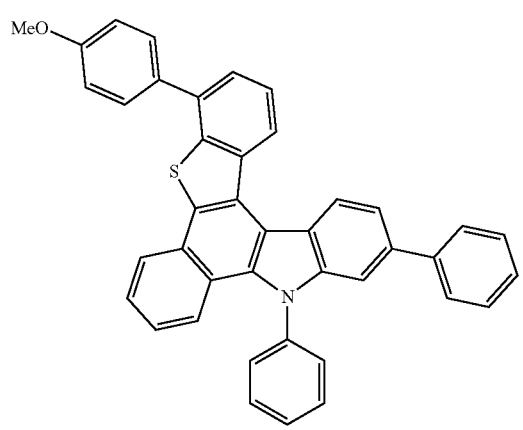
1-54
1-55
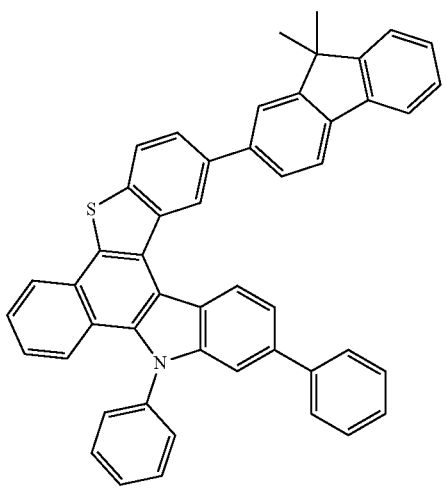
1-56
1-57

-continued
1-58
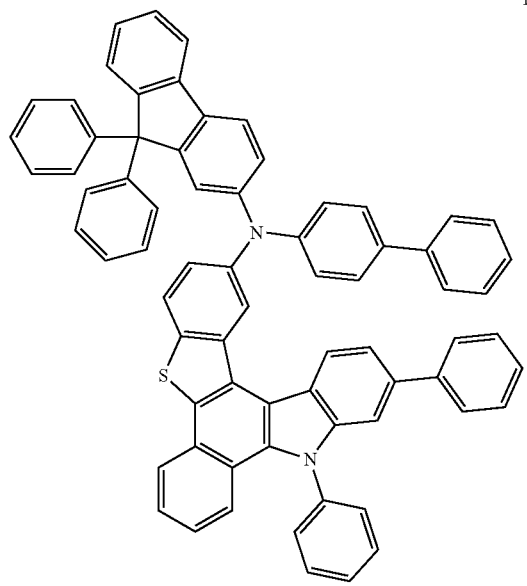
1-59
1-60
-continued
1-61
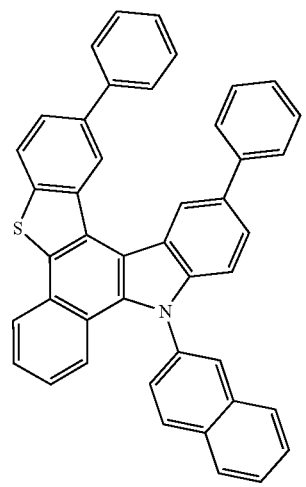
1-62
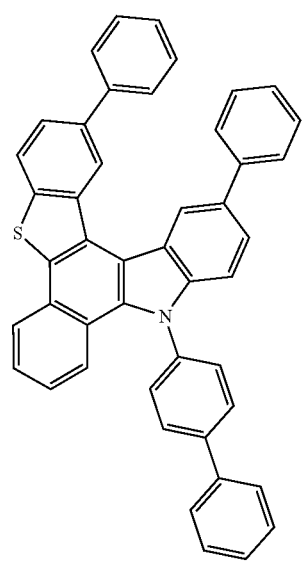
1-63
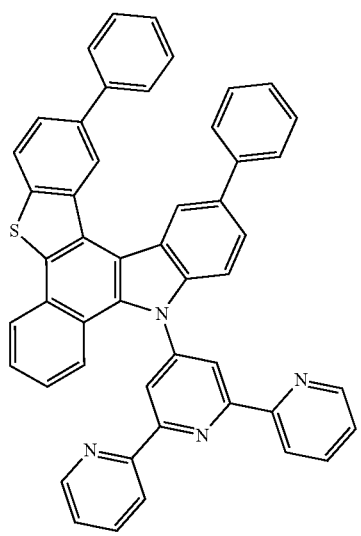

1-64
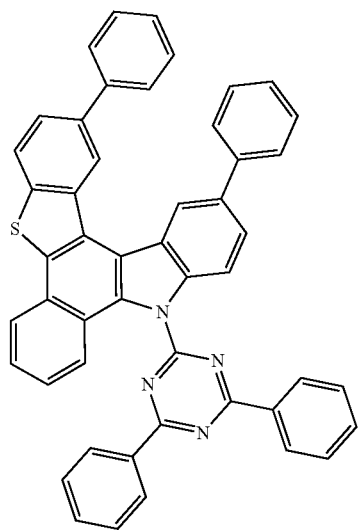
1-65
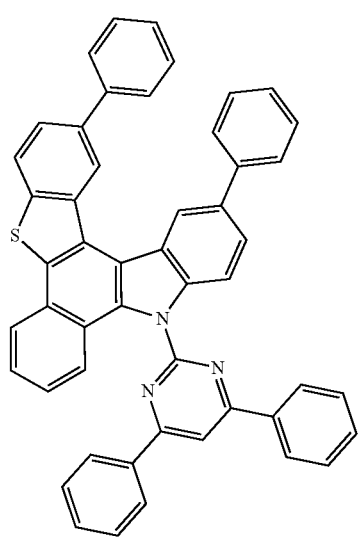
1-66
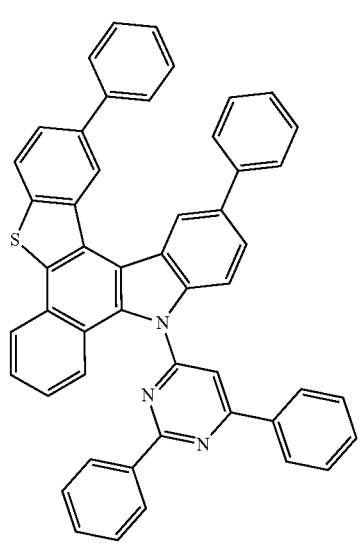
1-67
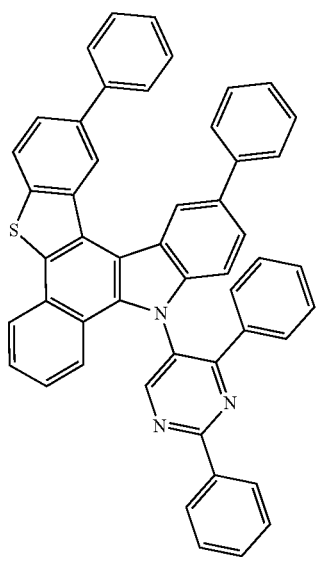
1-68
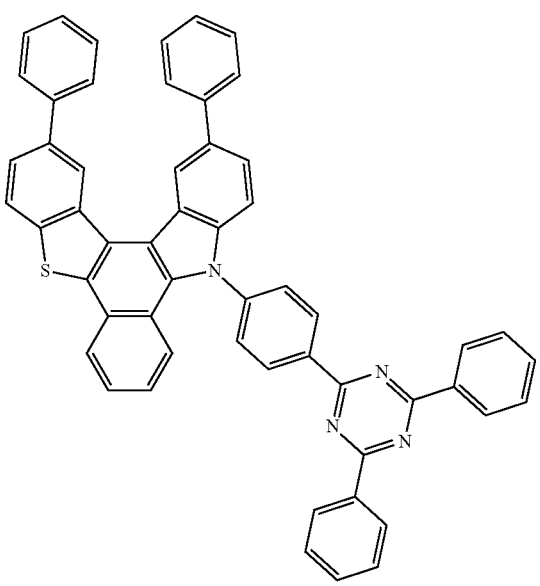

1-69
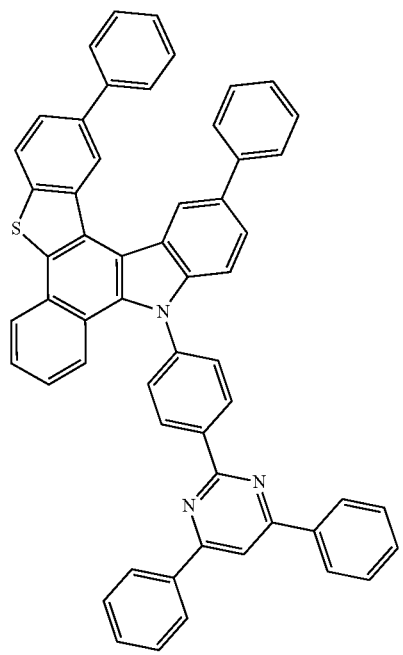
1-70
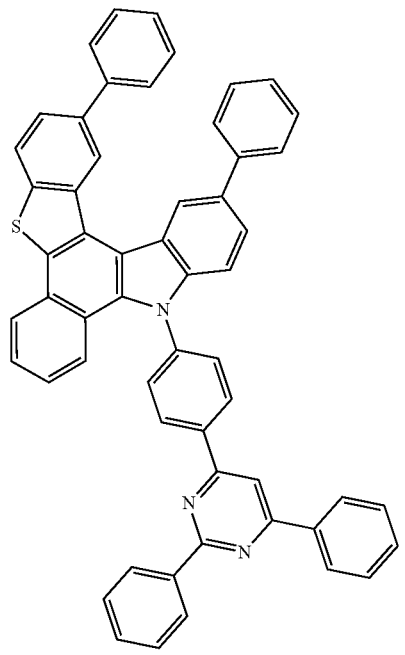
1-71
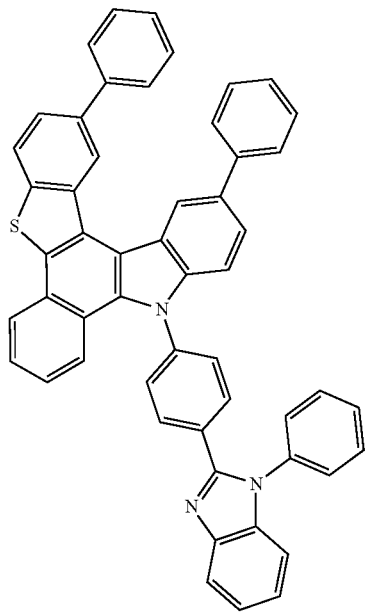
1-72
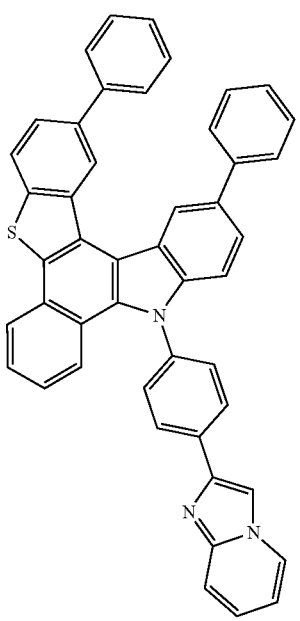

1-73
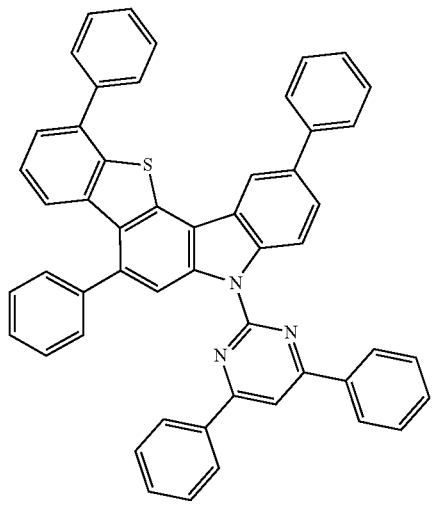
1-74
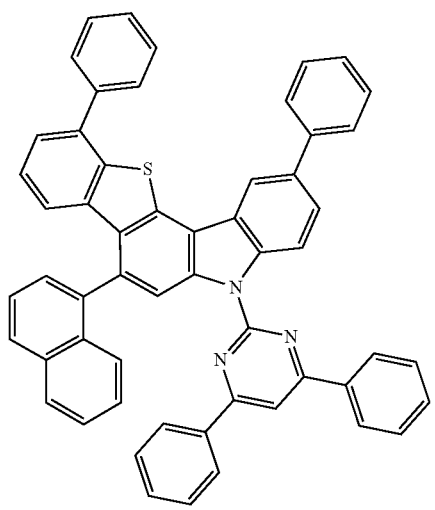
1-75
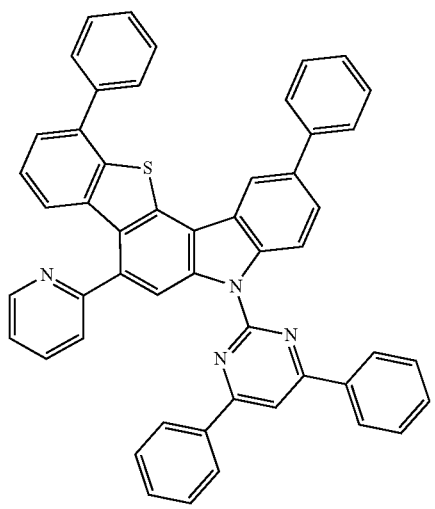
1-76
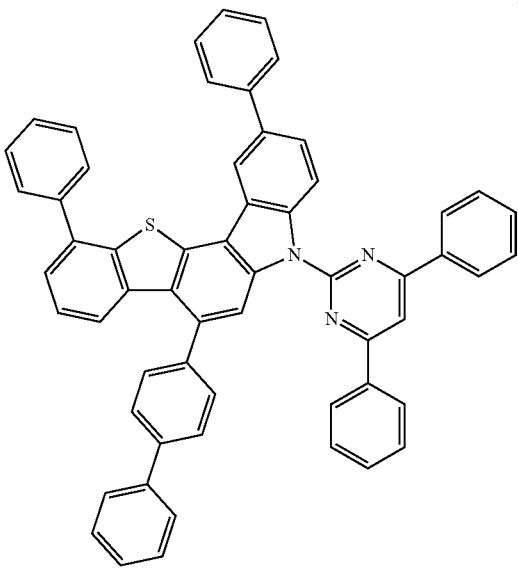
1-77
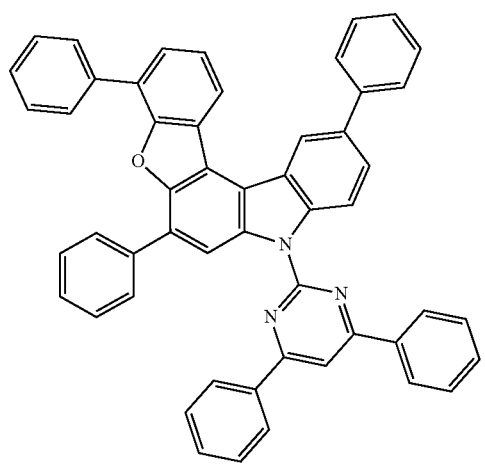
1-78
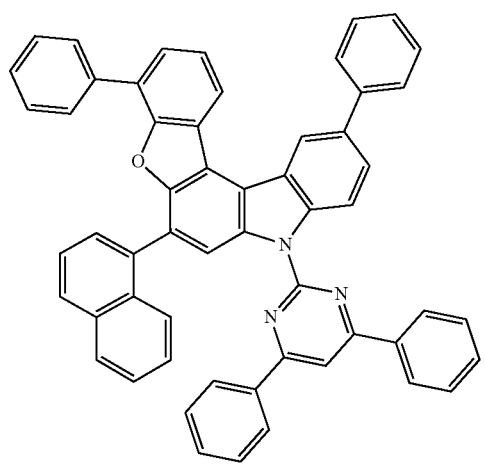

-continued
1-79
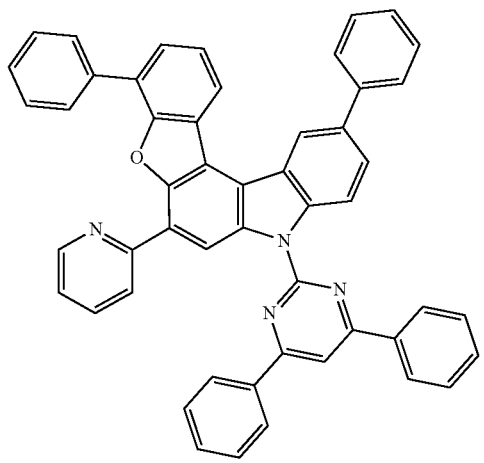
1-80
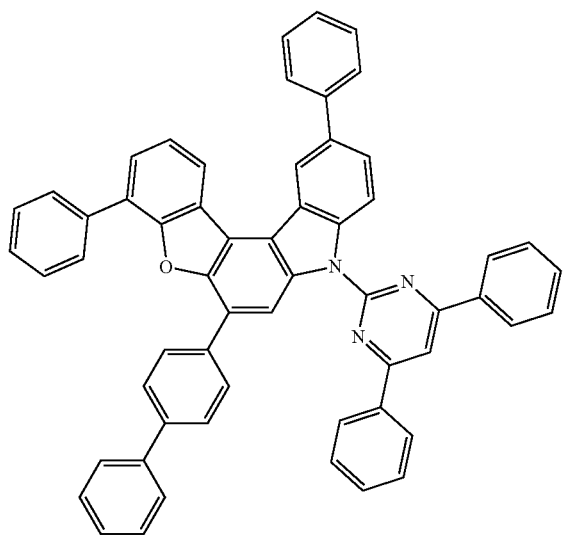
1-81
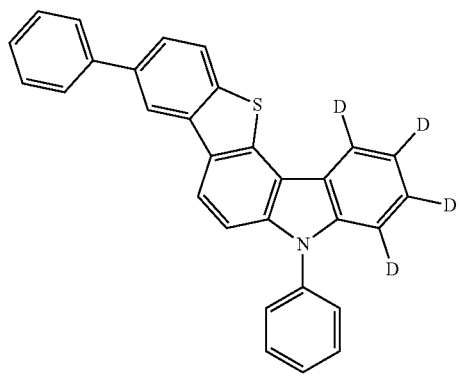
-continued
1-82
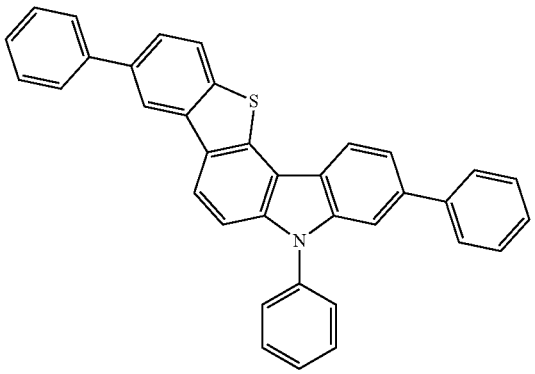
1-83
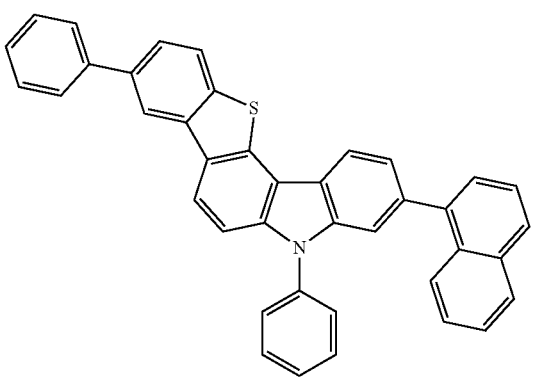
1-84
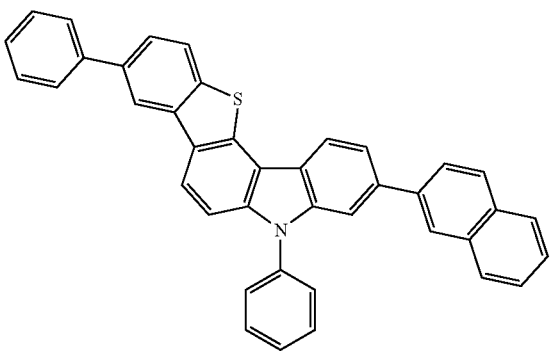
1-85
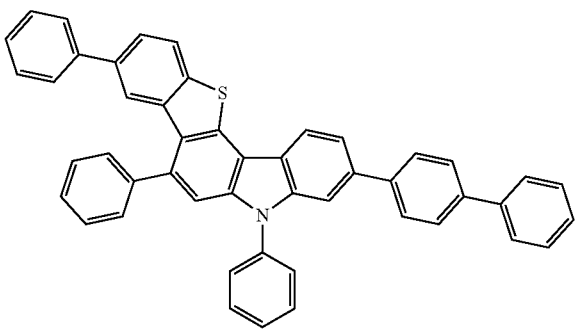

-continued
1-86
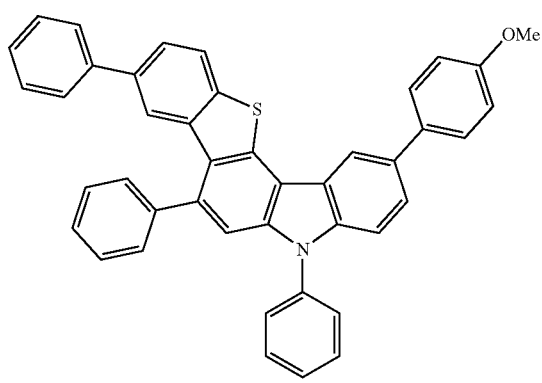
1-87
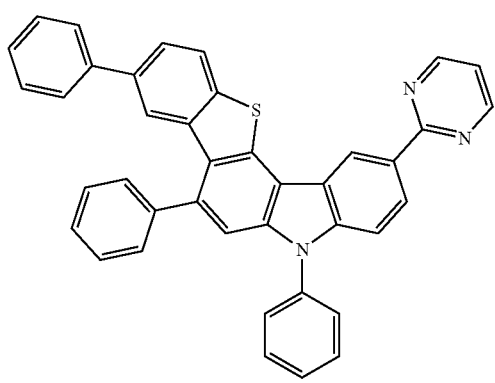
1-88
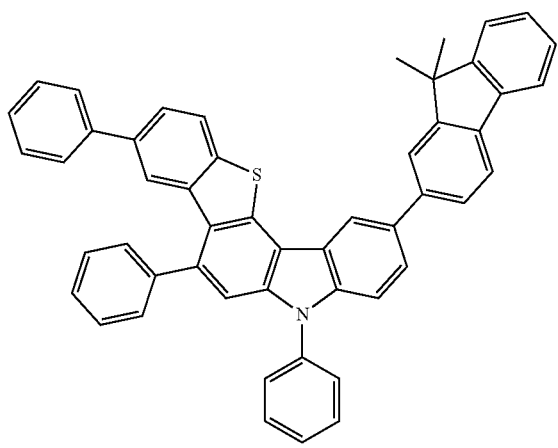
1-89
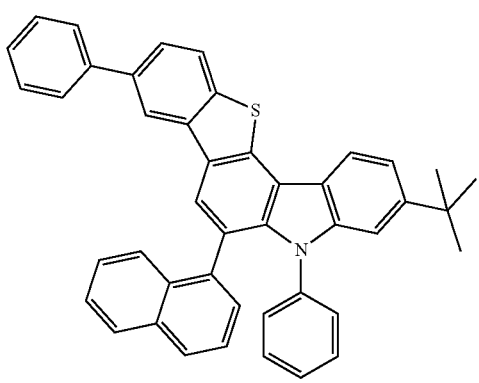
-continued
1-90
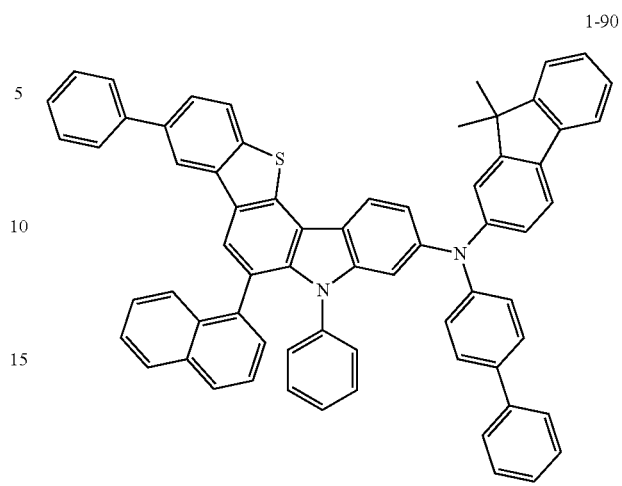
1-91
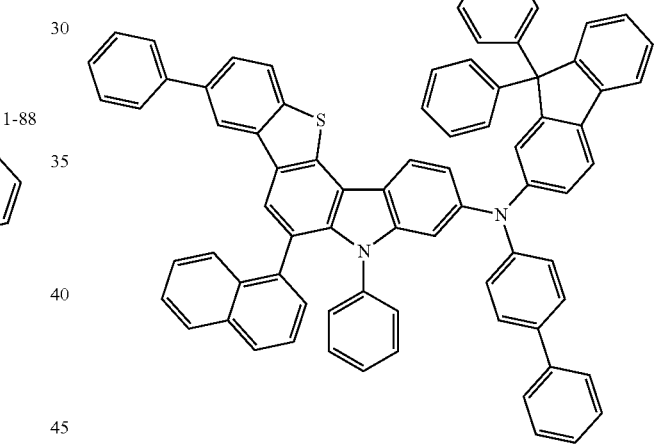
1-92
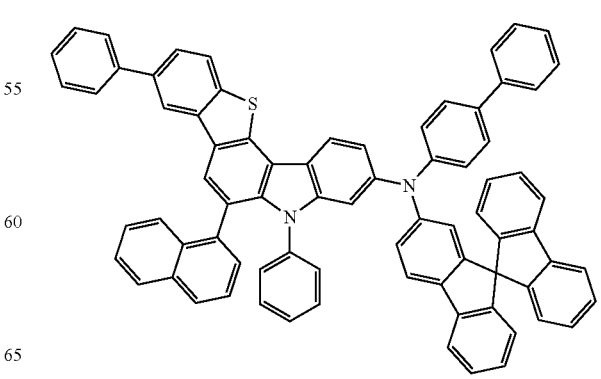

1-93
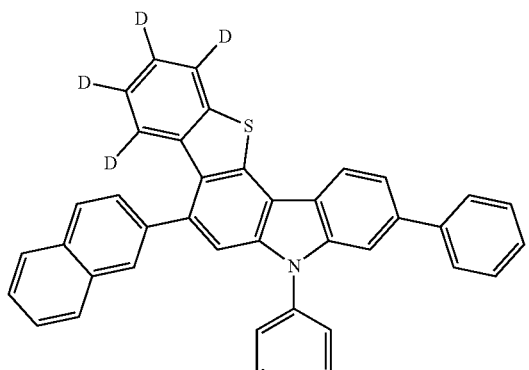
1-94
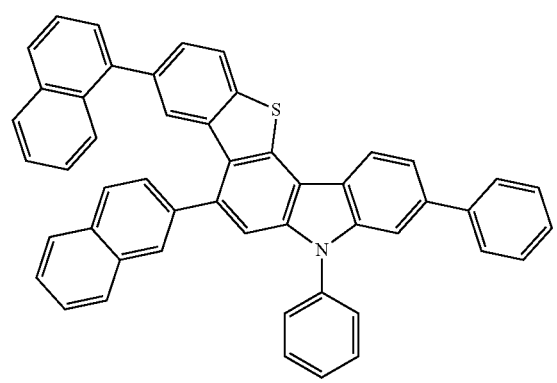
1-95
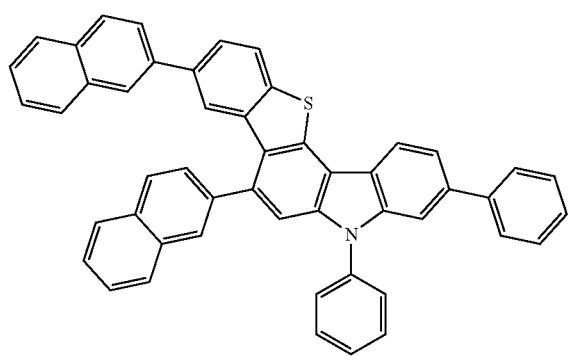
1-96
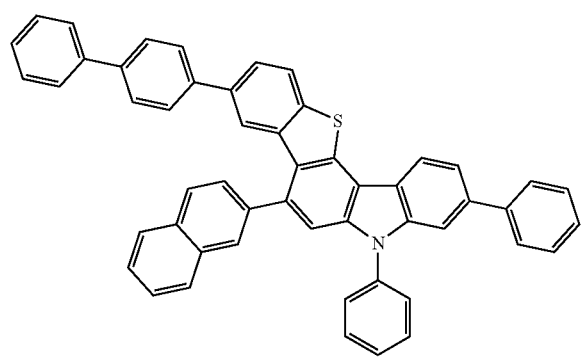
1-97
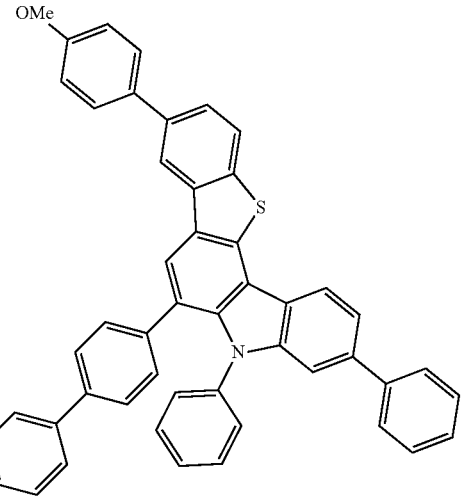
1-98
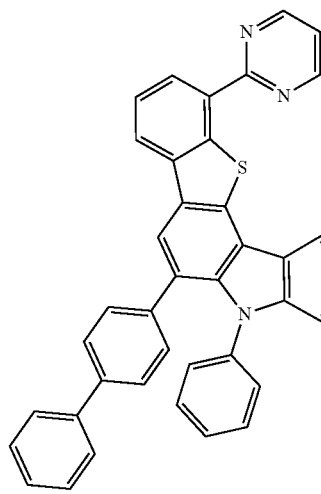
1-99
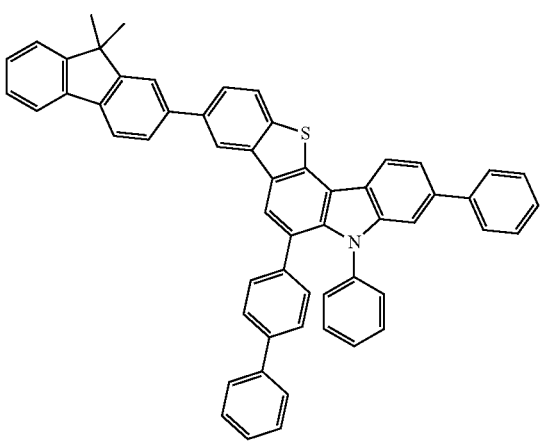

1-100
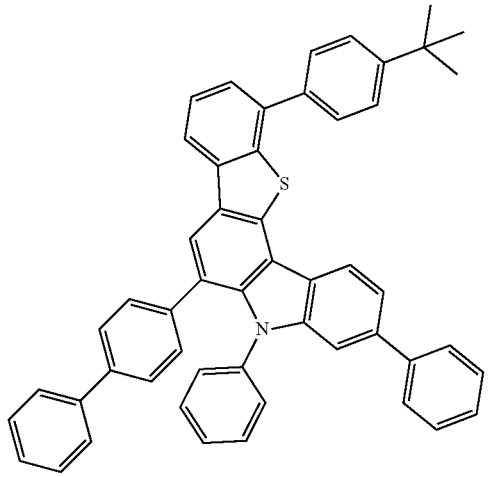
1-101
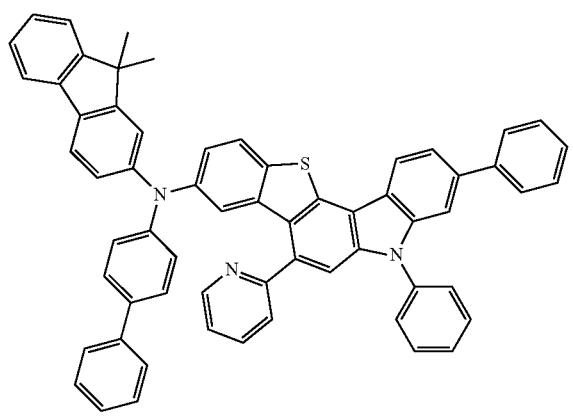
1-102
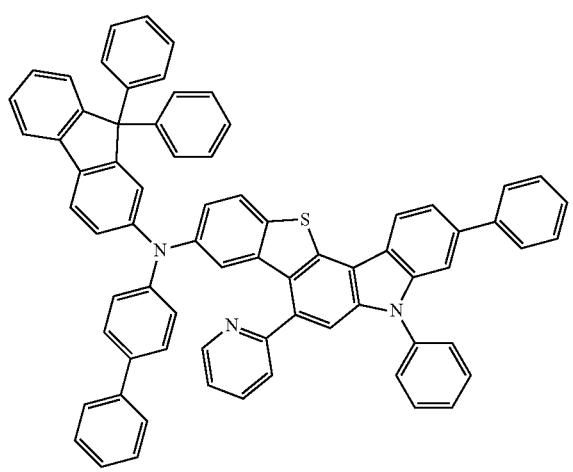
1-103
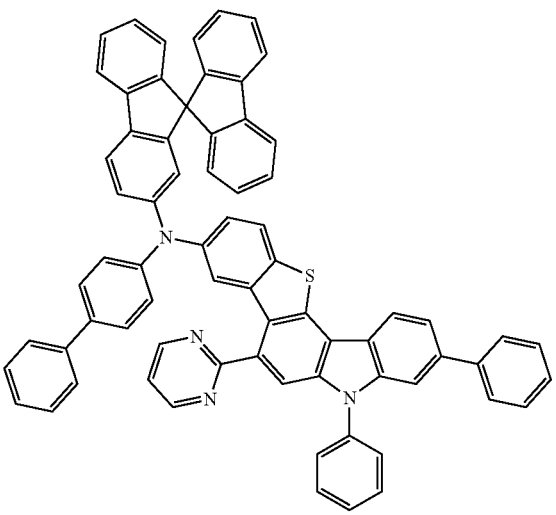
1-104
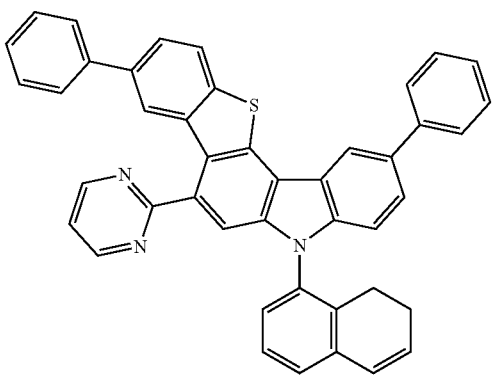
1-105
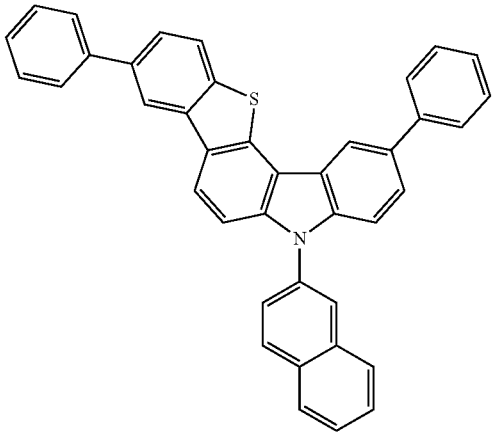

1-106
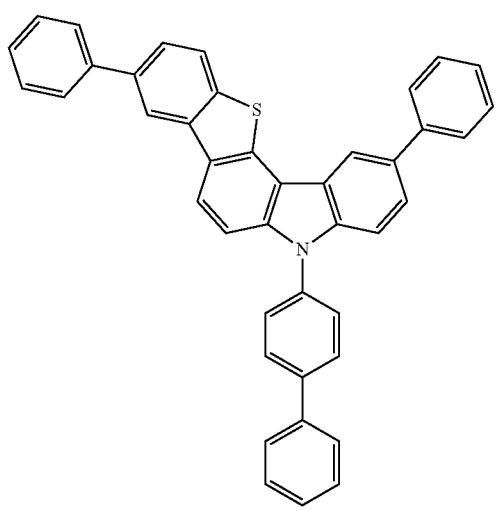
1-107
1-108
1-109
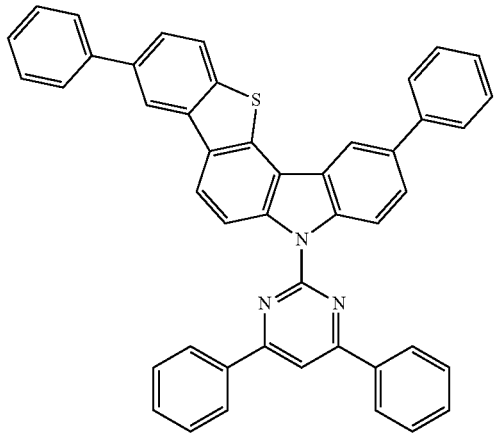
1-110
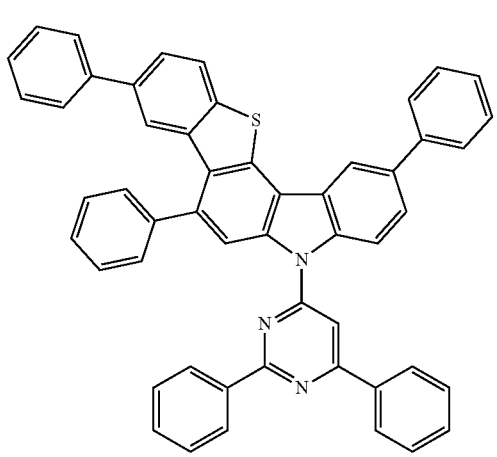
1-111
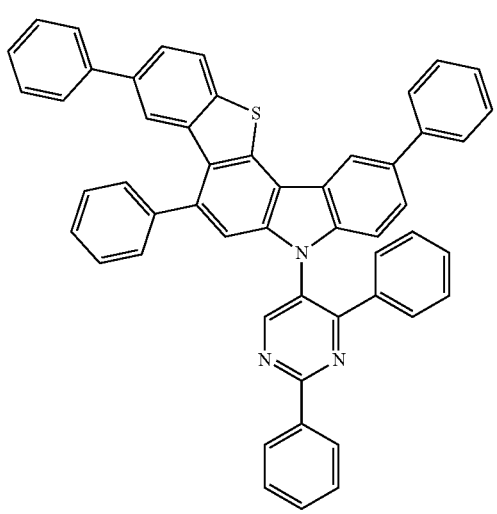

49
-continued
1-112
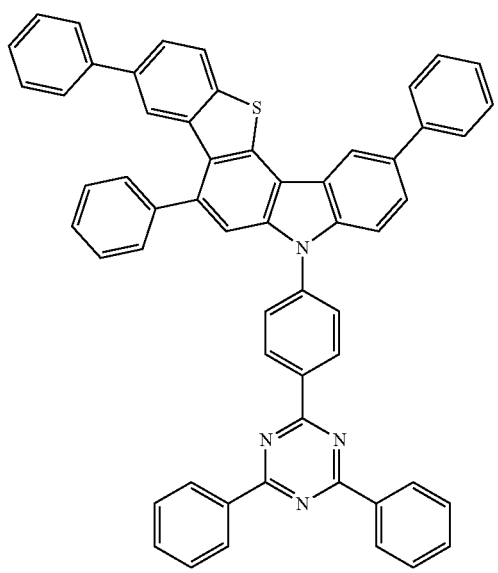
1-113
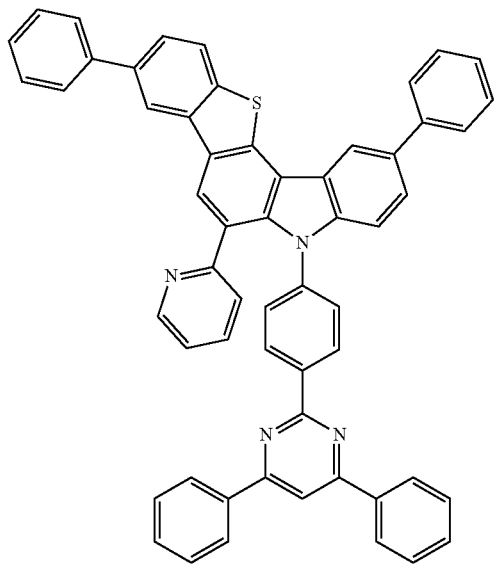
50
-continued
1-114
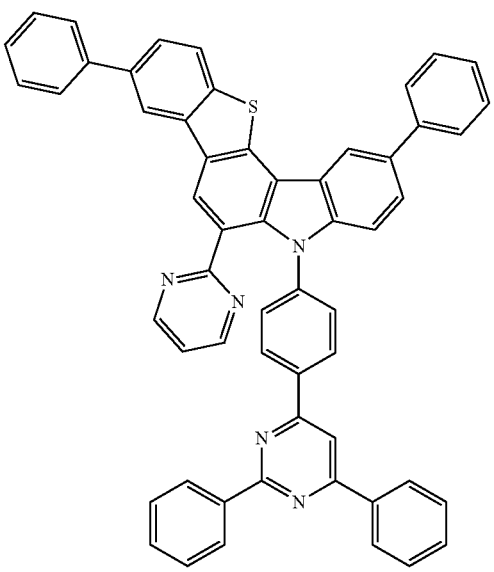
1-115

-continued
1-116
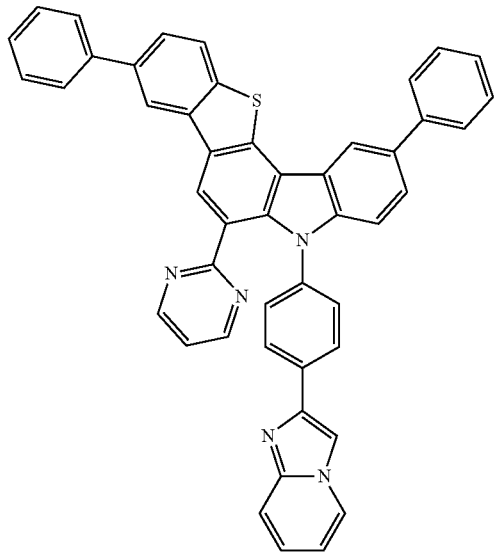
1-117
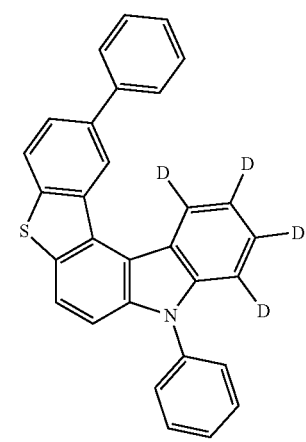
1-118
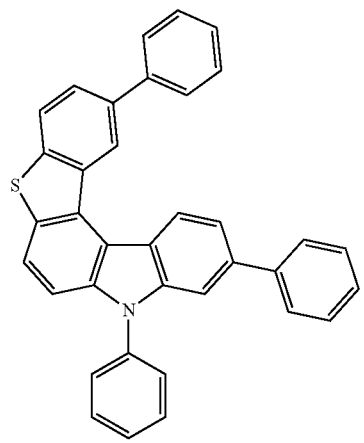
-continued
1-119
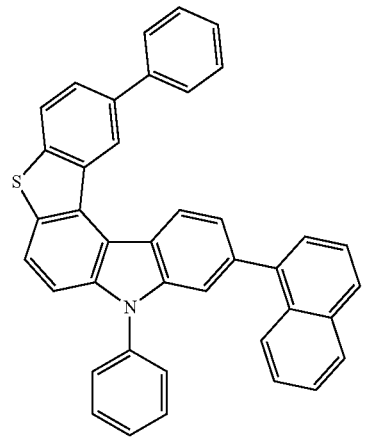
1-120
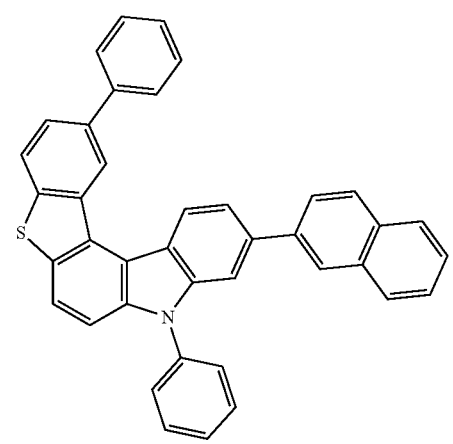
1-121
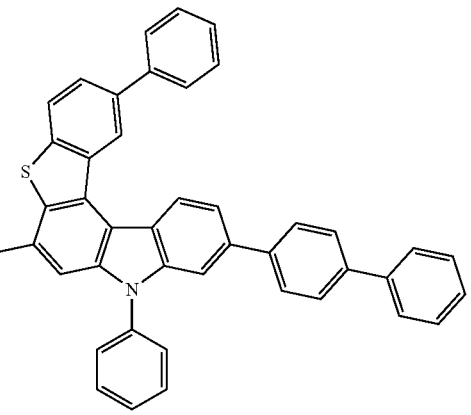

1-122
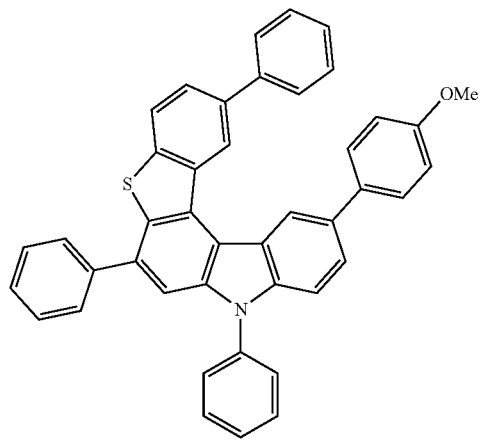
1-123
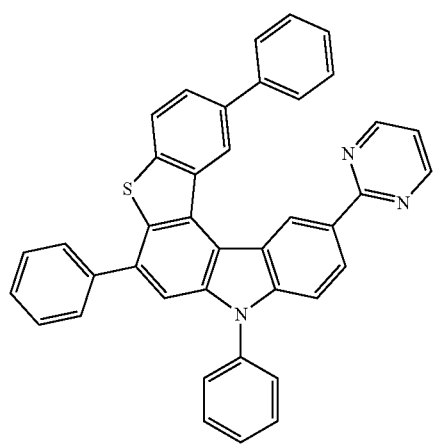
1-124
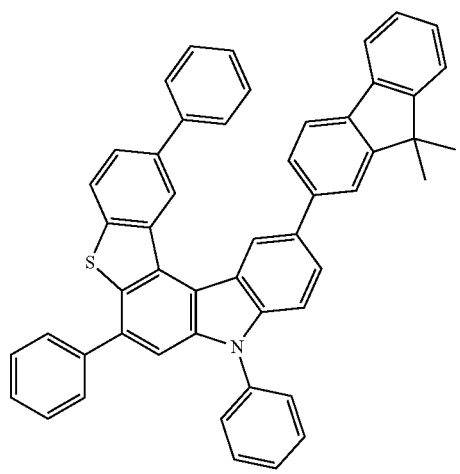
1-125
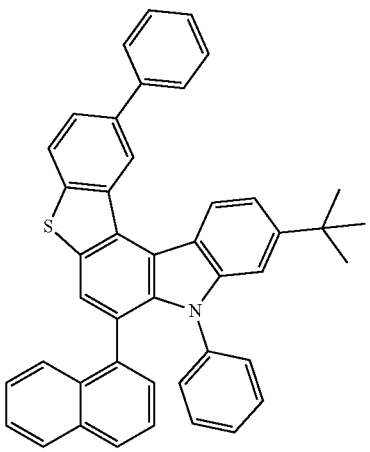
1-126
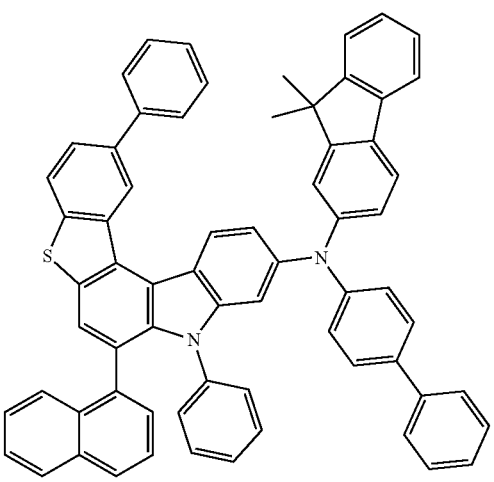
1-127
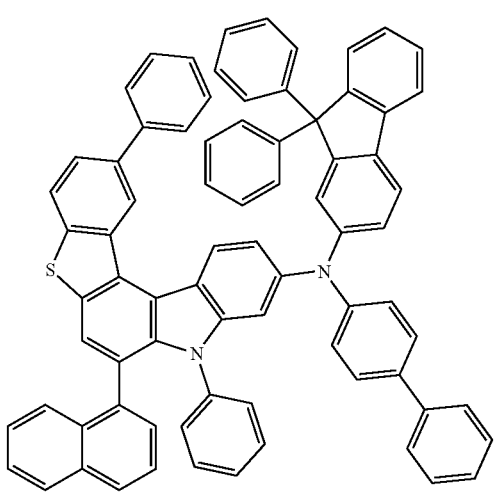

1-128
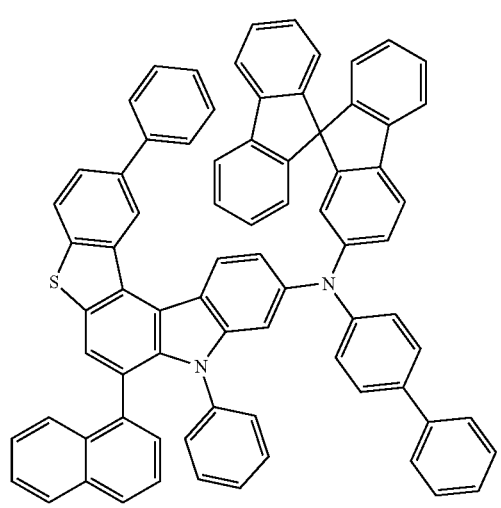
1-129
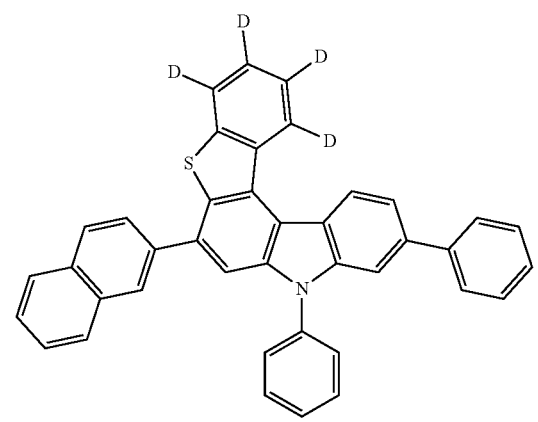
1-130
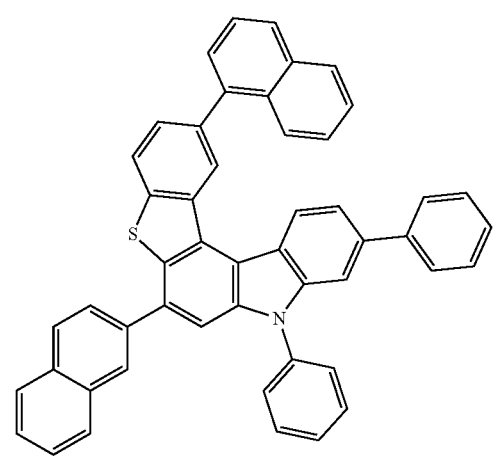
1-131
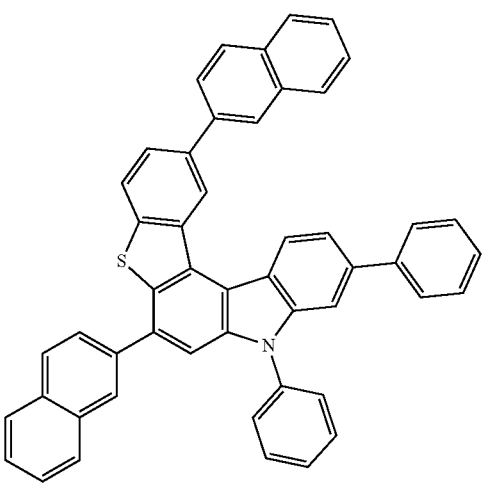
1-132
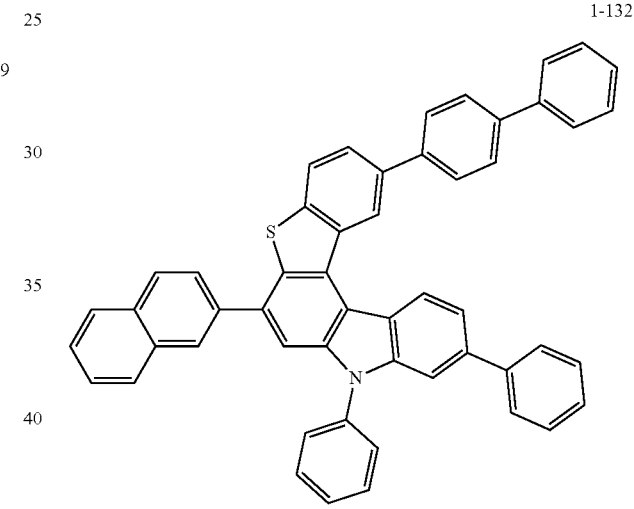
1-133
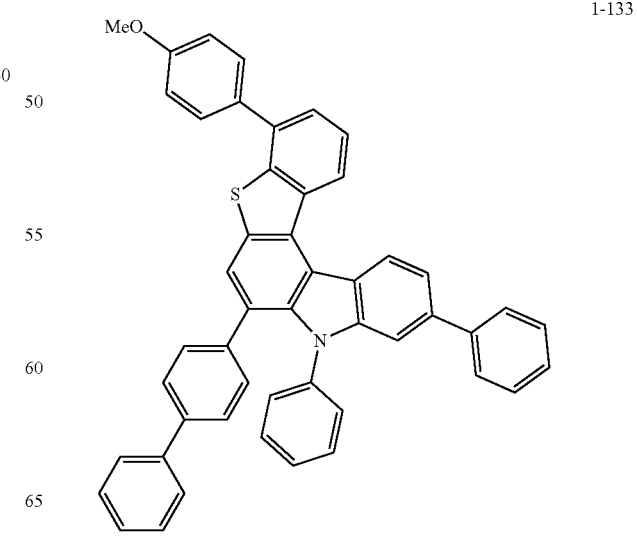

1-134
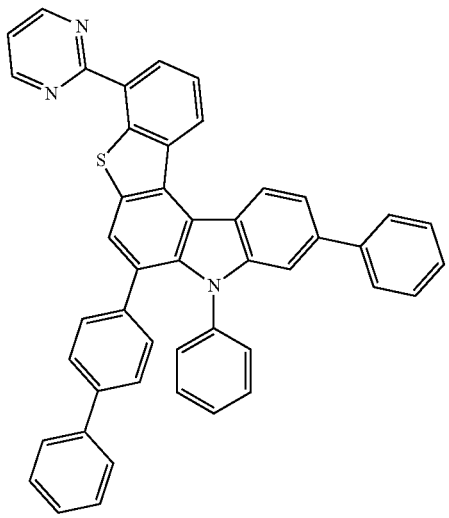
1-135
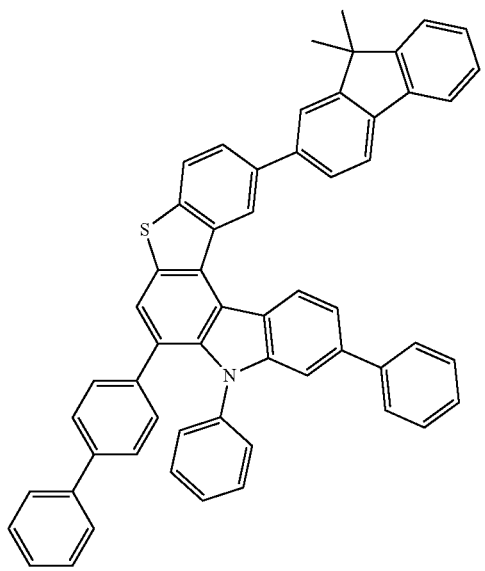
1-136
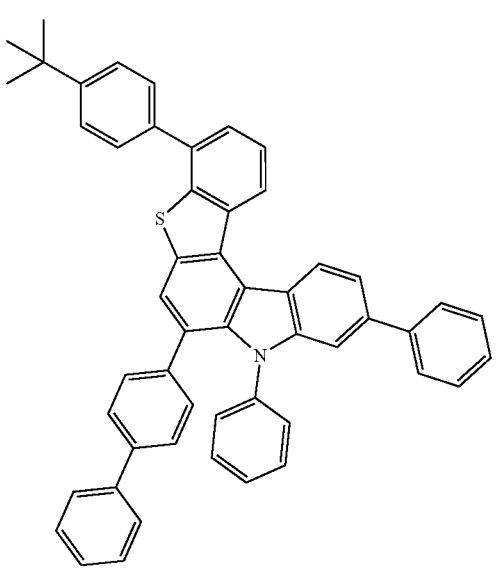
1-137
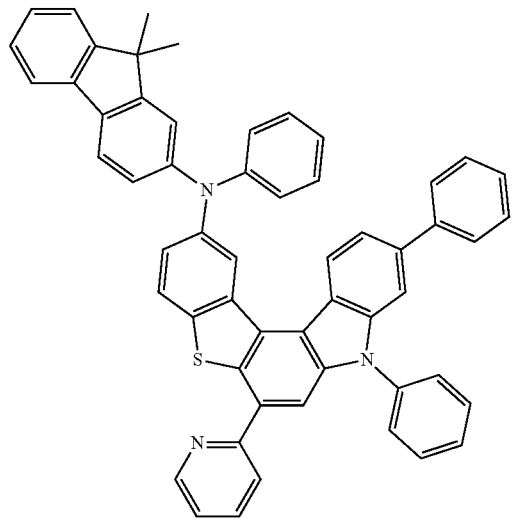
1-138
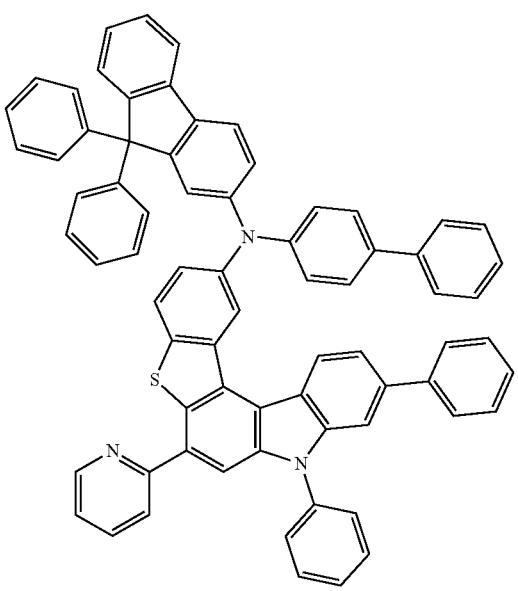

1-139
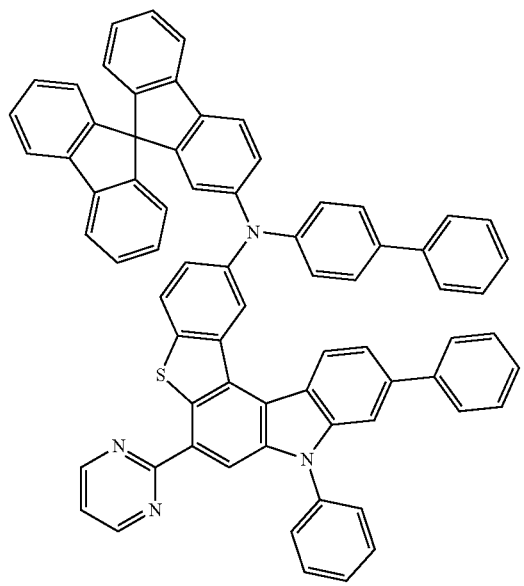
1-140
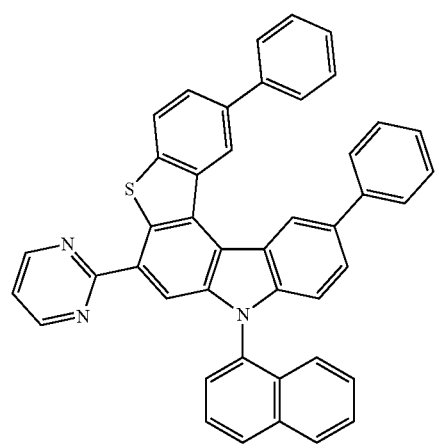
1-141
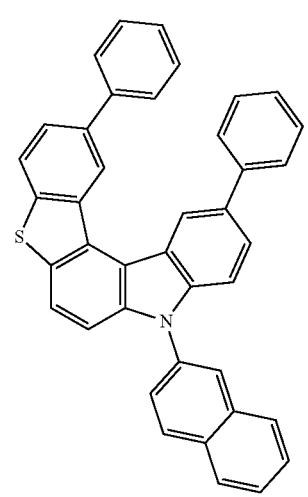
1-142
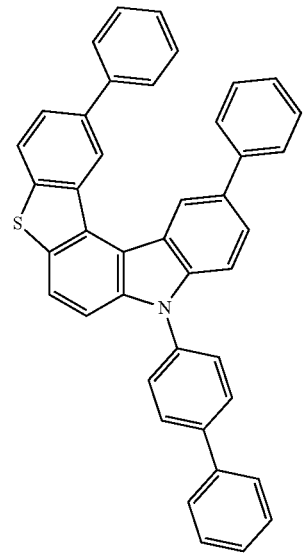
1-143
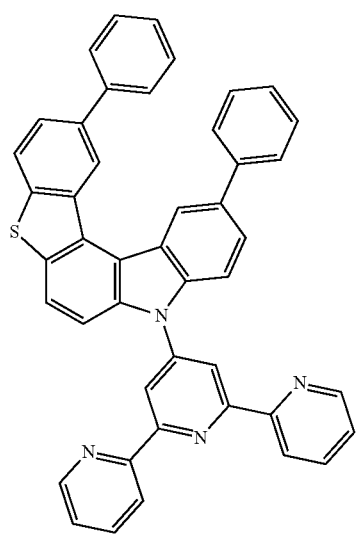
1-144
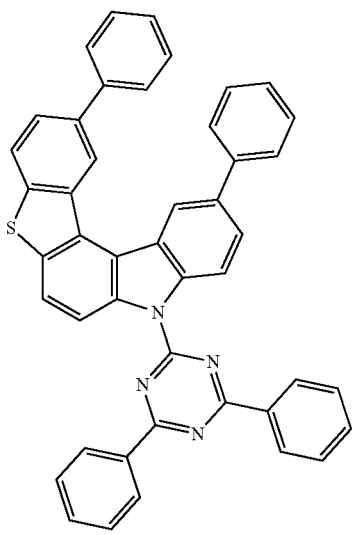

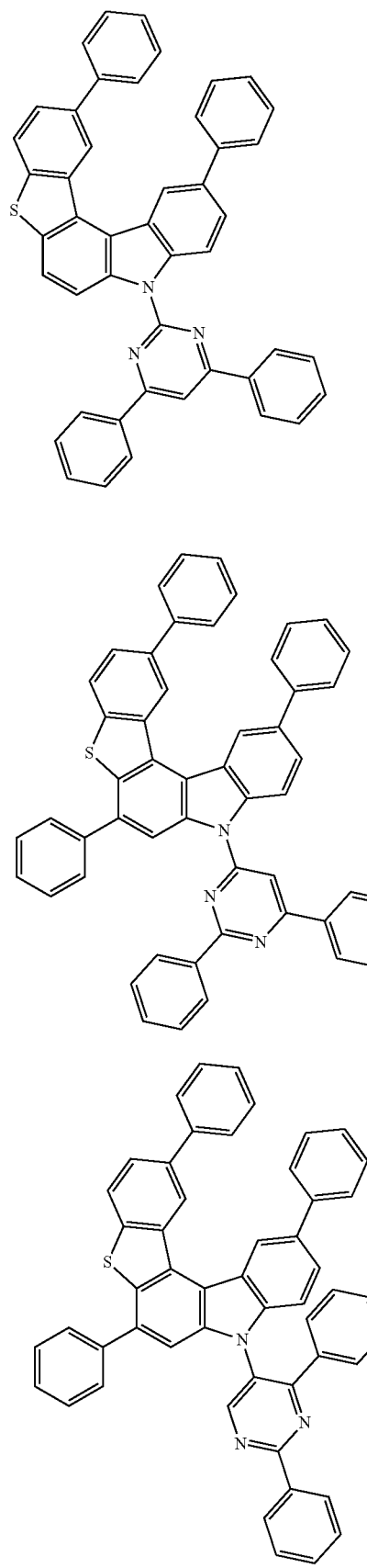
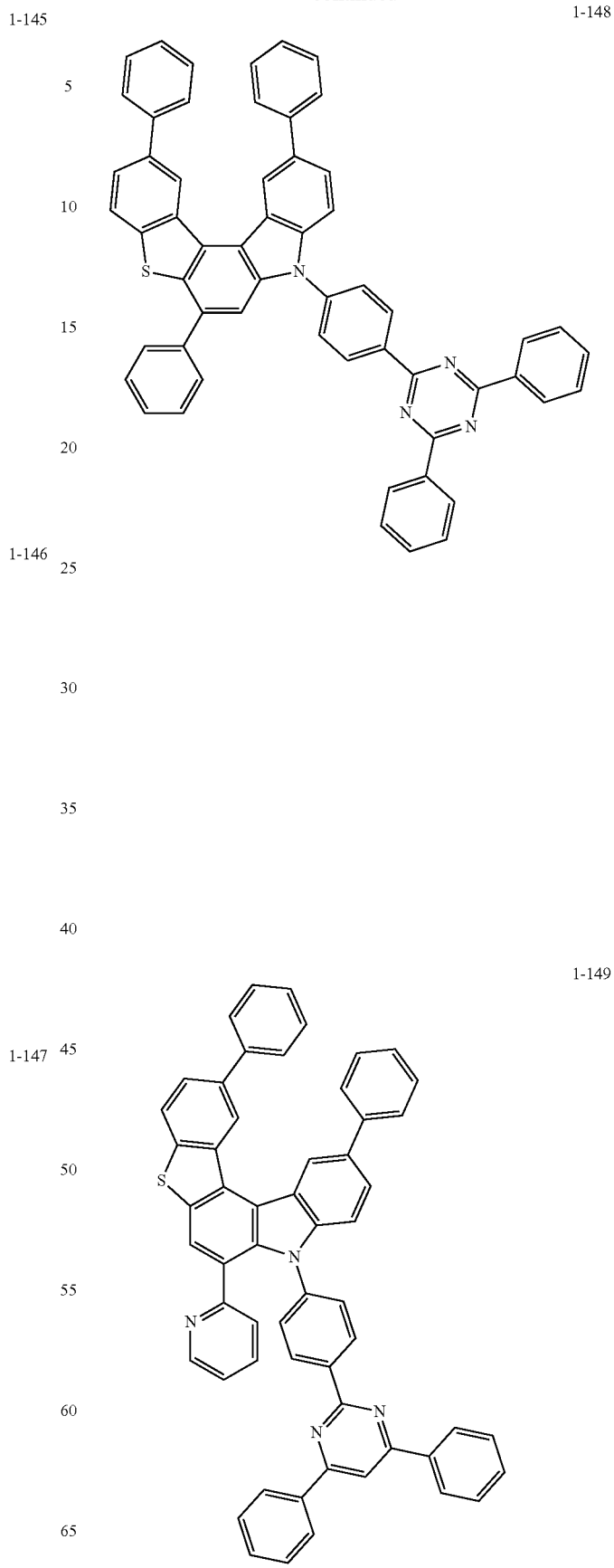

1-150
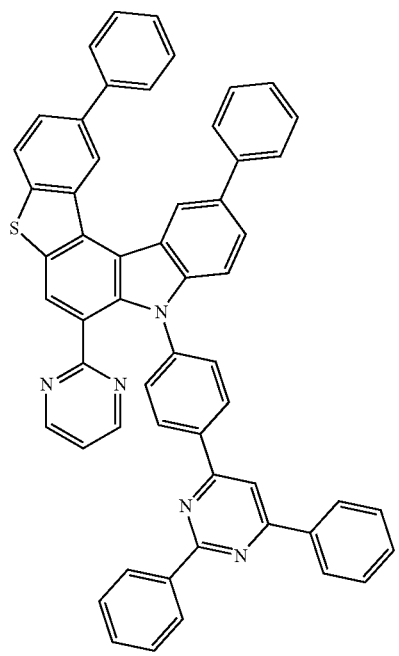
1-151
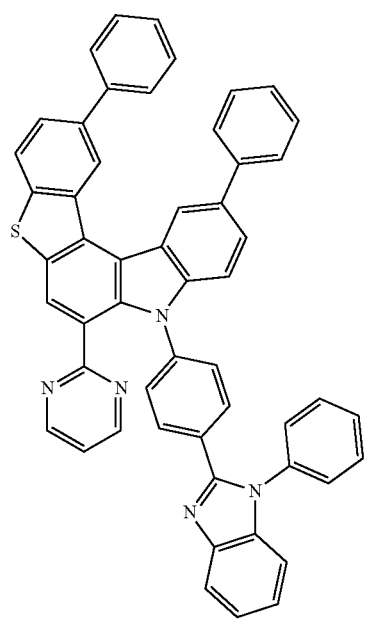
1-152
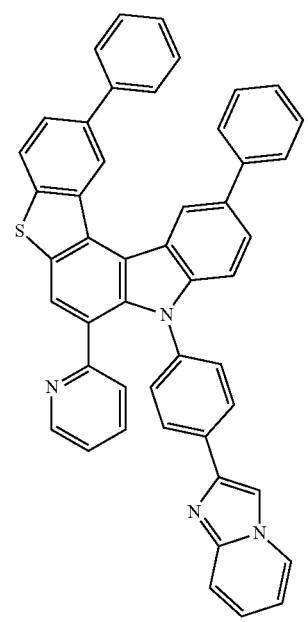
1-153
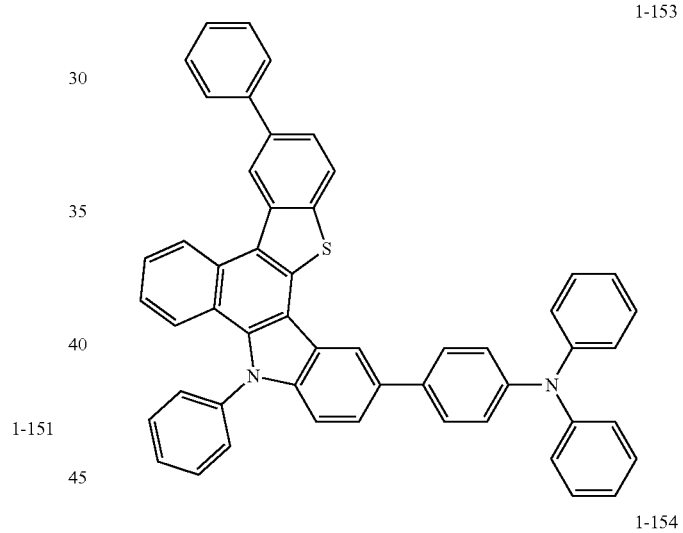
1-154
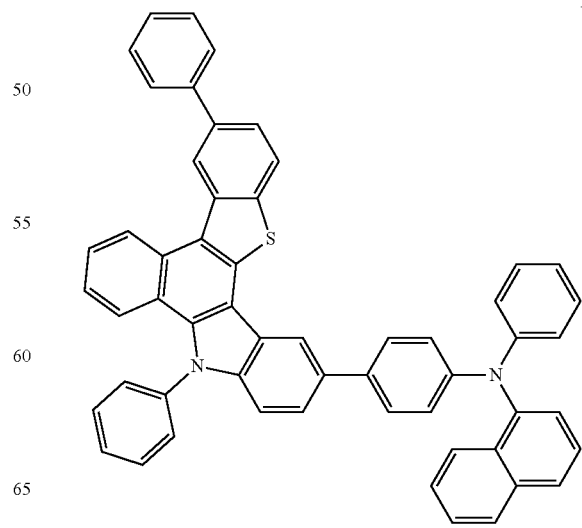

1-155
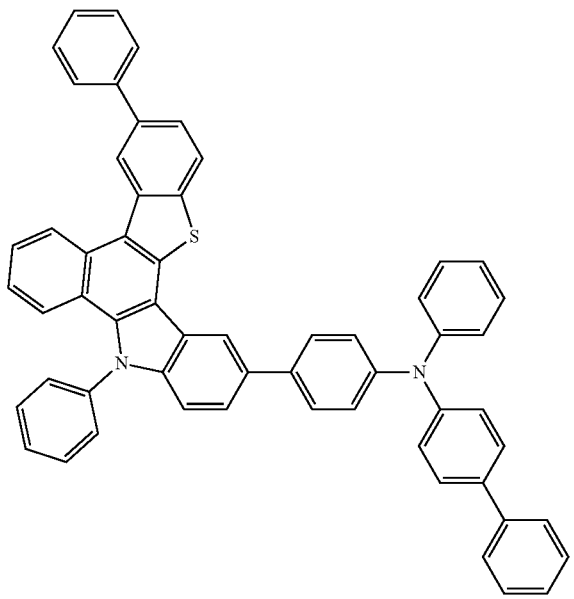
1-156
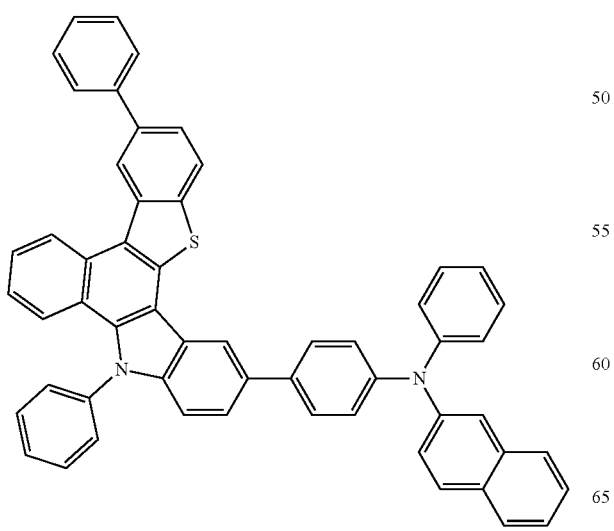
1-157
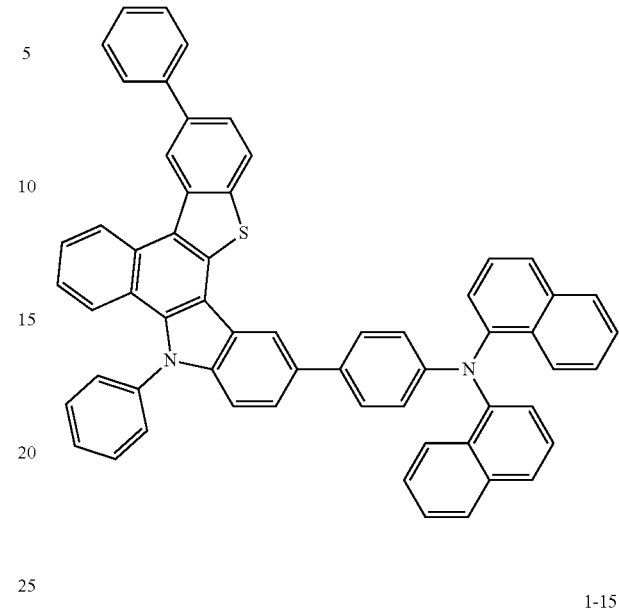
1-158
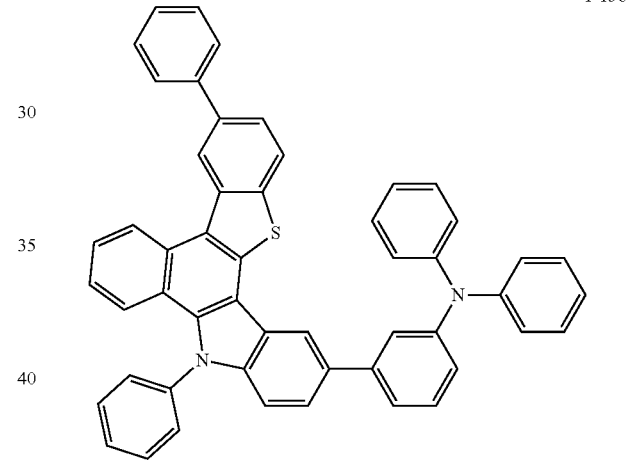
1-159
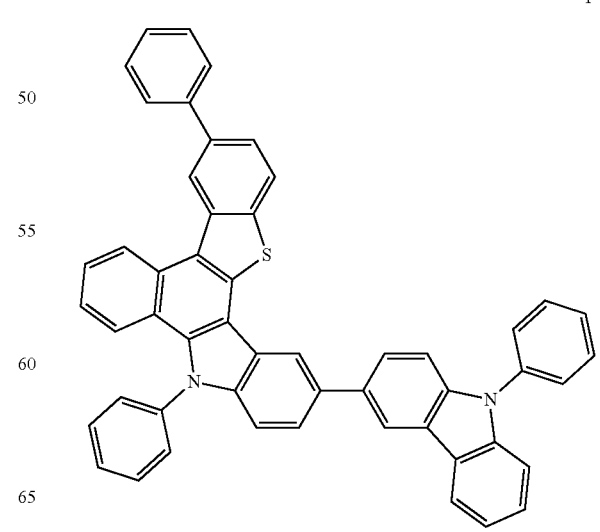

US 10,991,885 B2
-continued
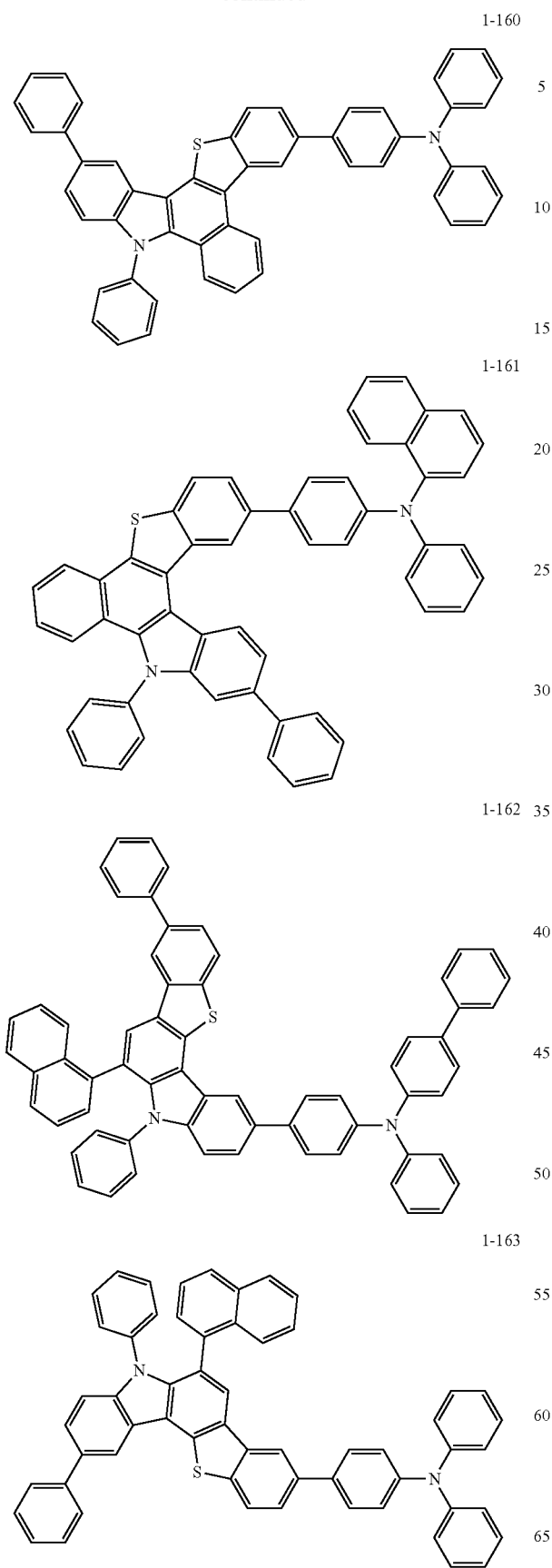
1-160
1-161
1-162
1-163
-continued
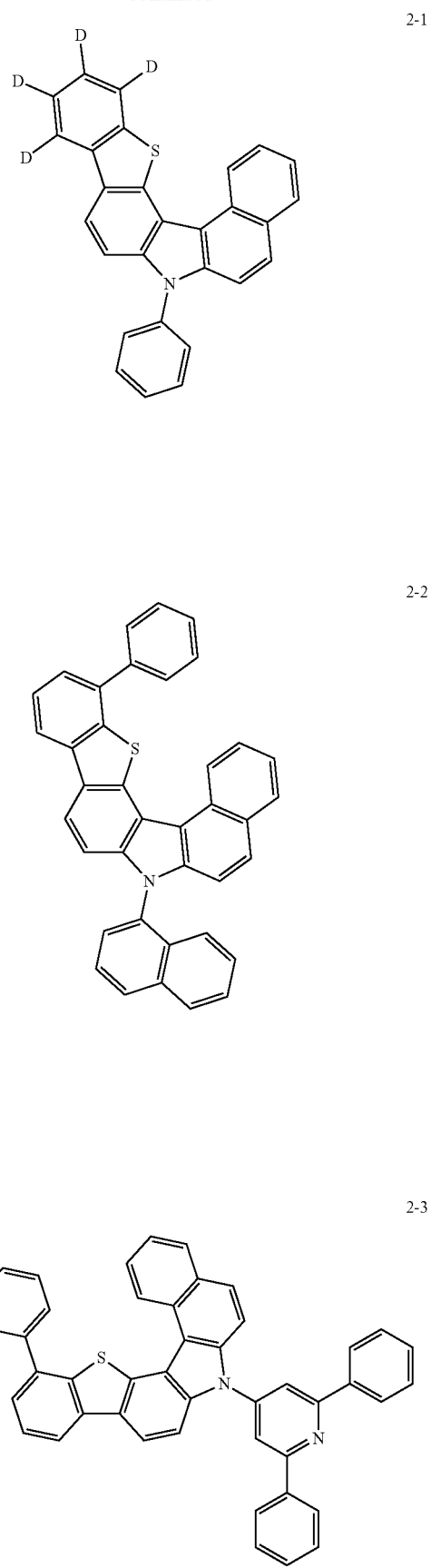
2-1
2-2
2-3

-continued
2-4
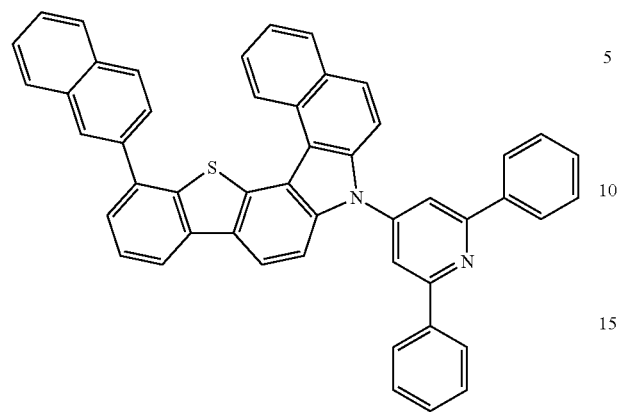
2-5
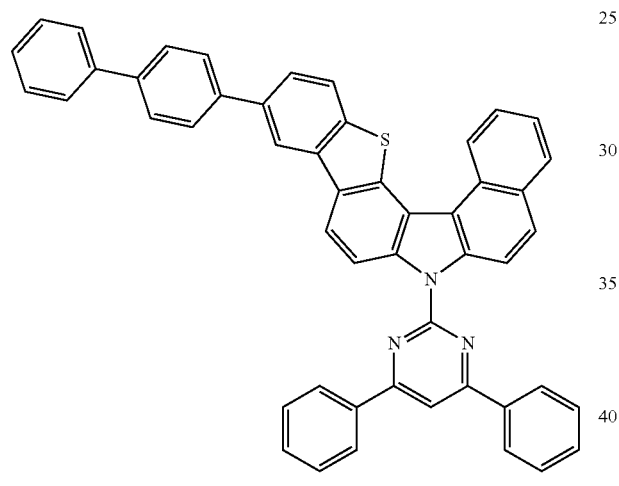
2-6
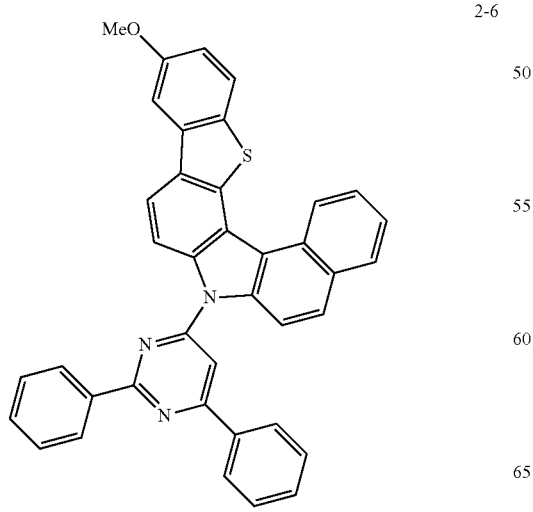
-continued
2-7
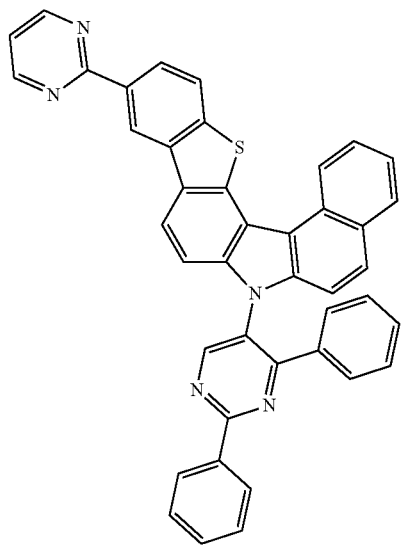
2-8
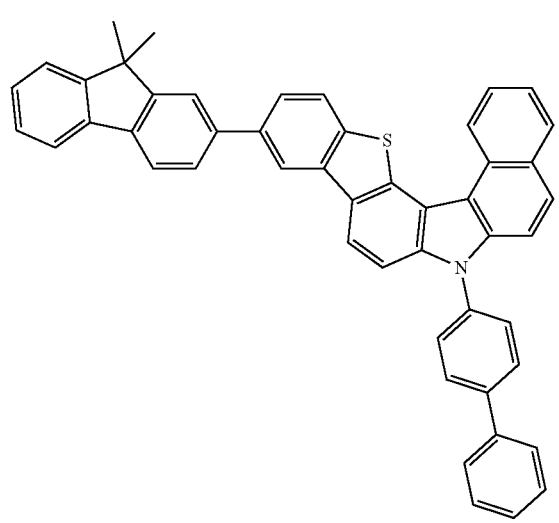
2-9
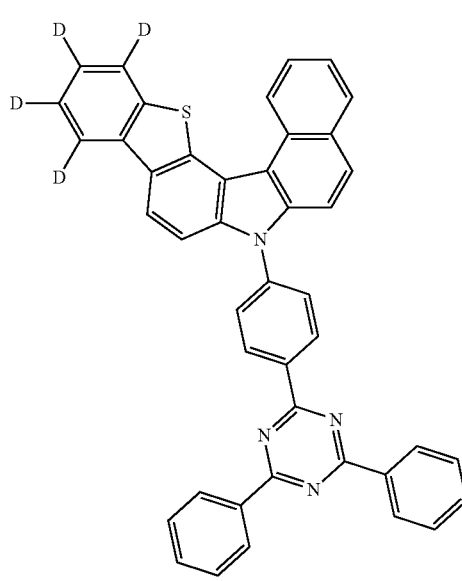

-continued
2-10
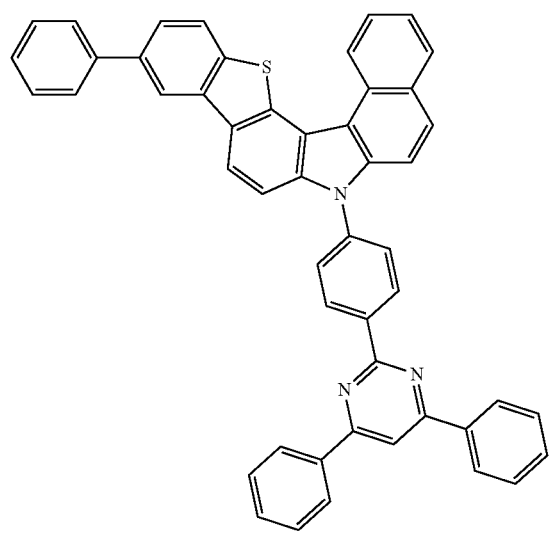
2-11
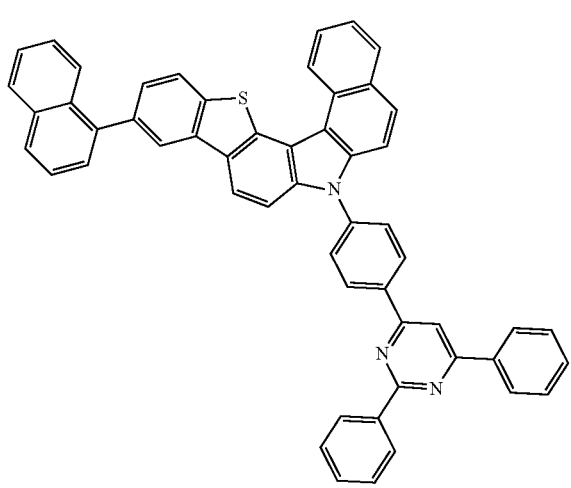
2-12
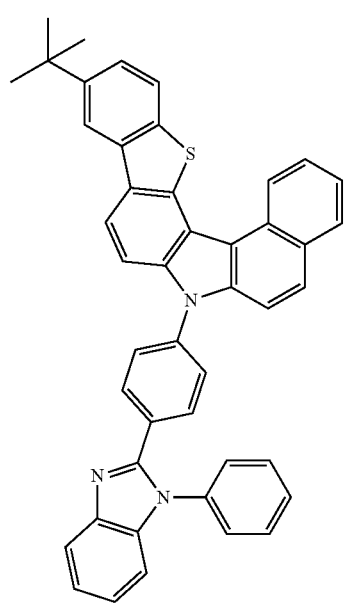
-continued
2-13
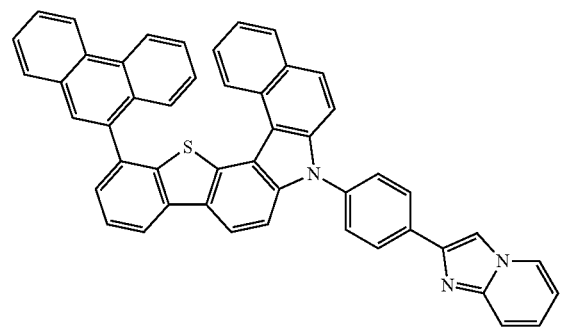
2-14
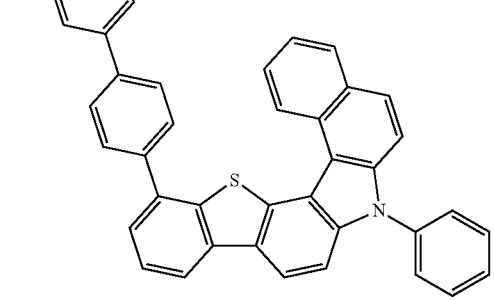
2-15
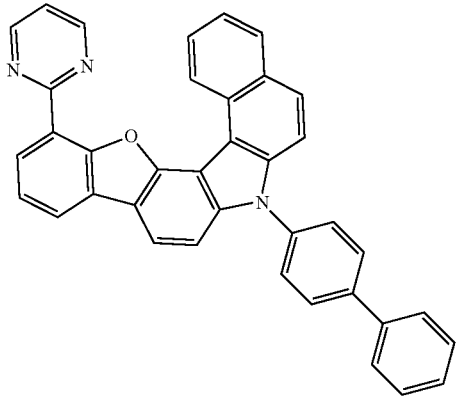
2-16
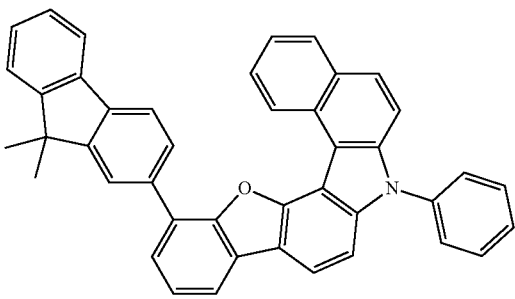

2-17
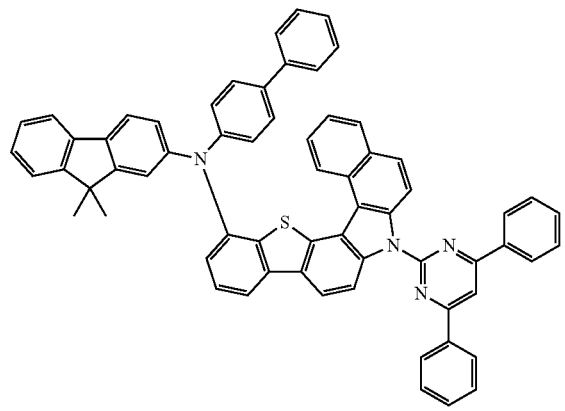
2-19
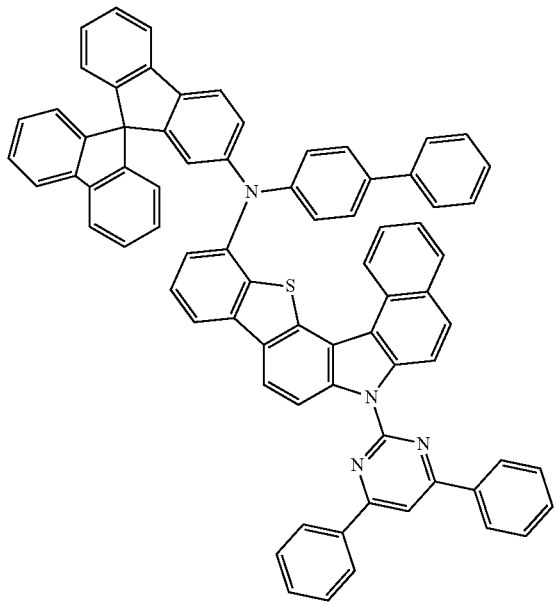
2-18
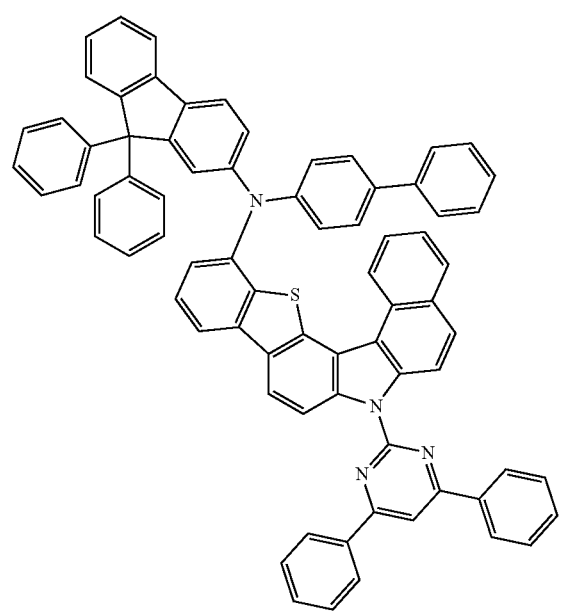
2-20
2-21
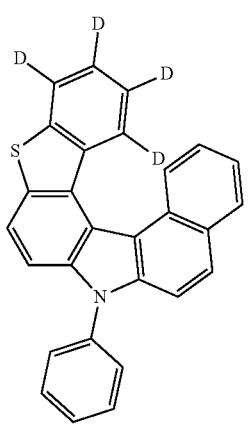

2-22
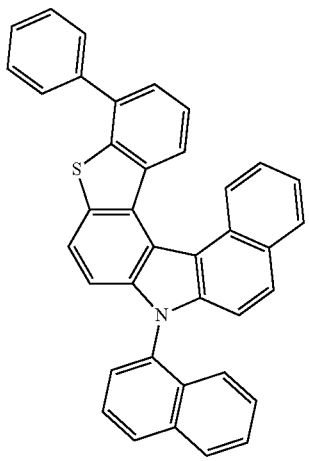
2-25
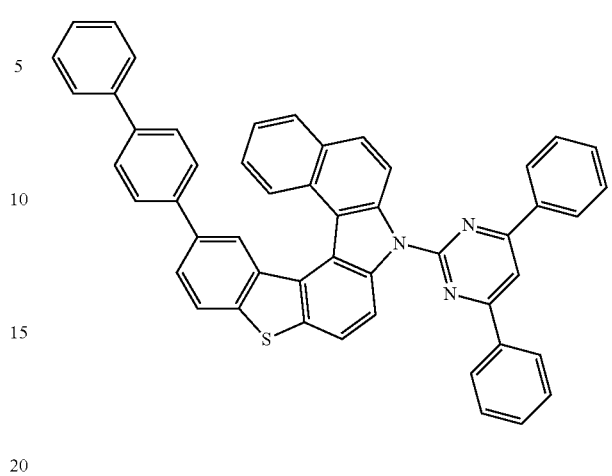
2-23
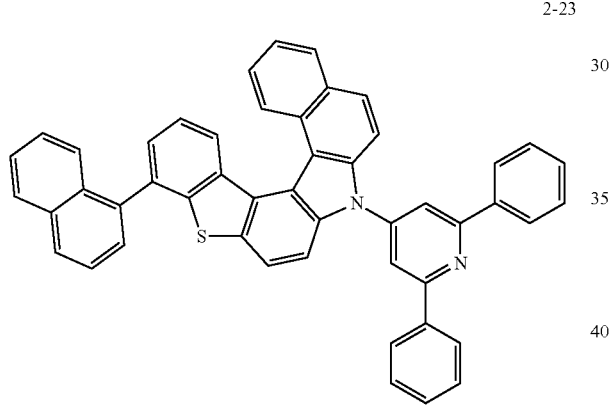
2-26
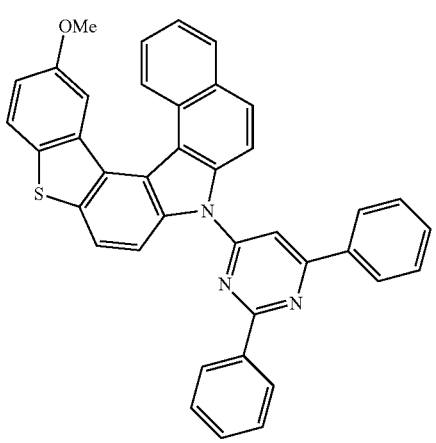
2-24
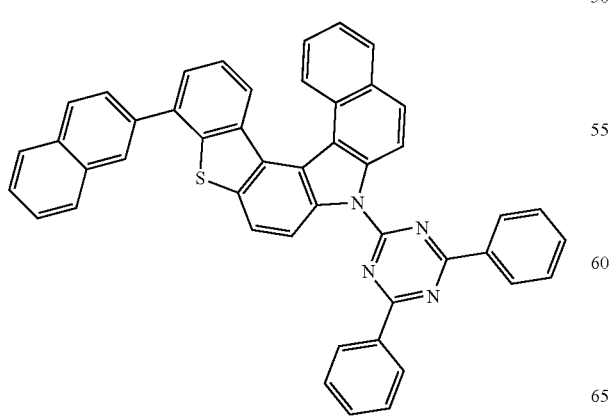
2-27
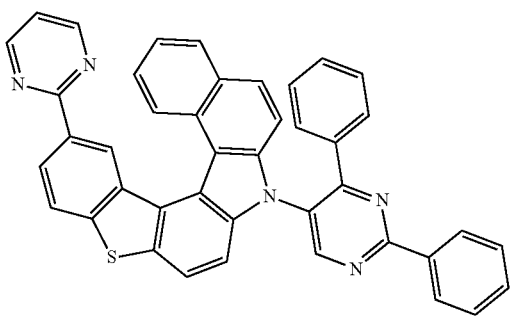

2-28
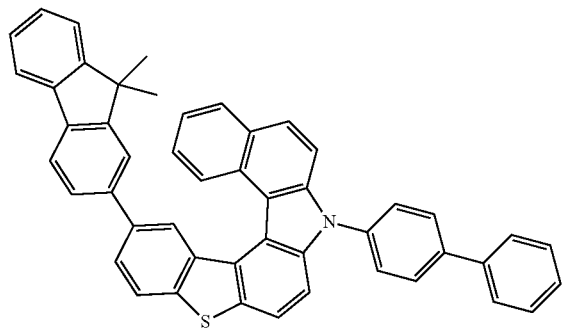
2-29
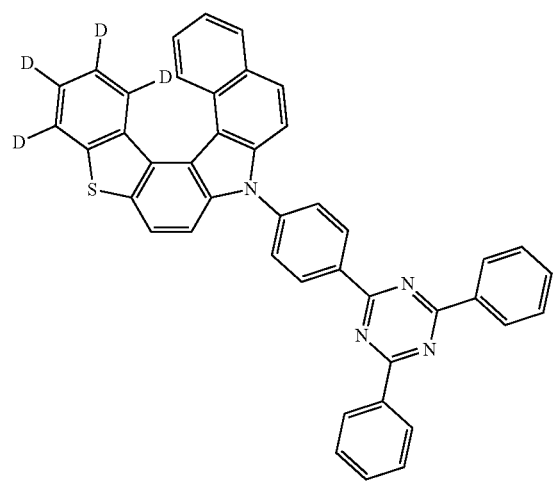
2-30
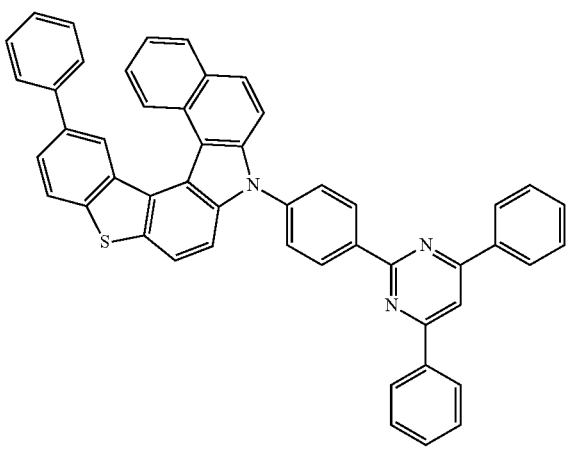
2-31
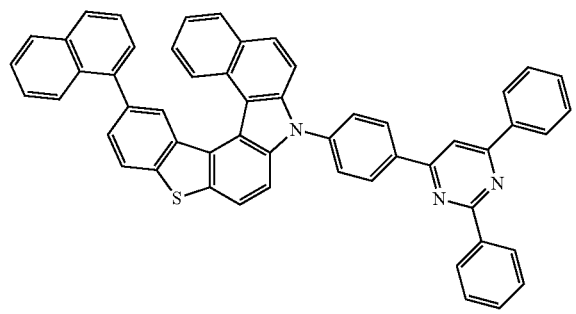
2-32
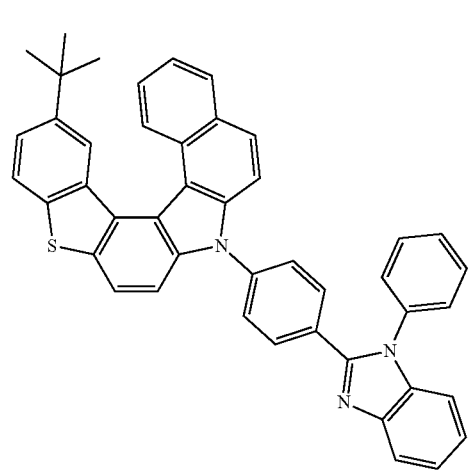
2-33
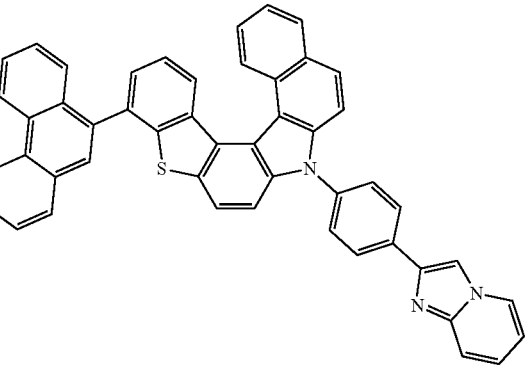

2-34
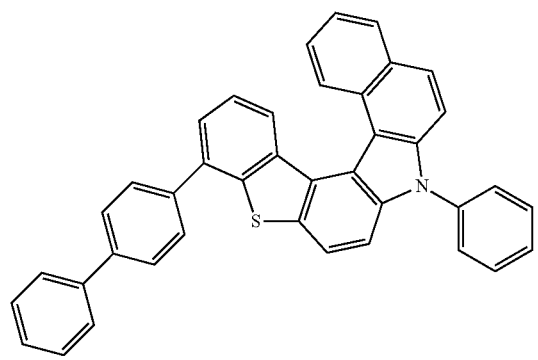
2-35
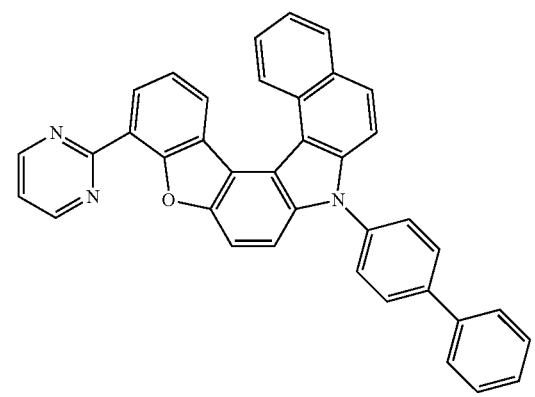
2-36
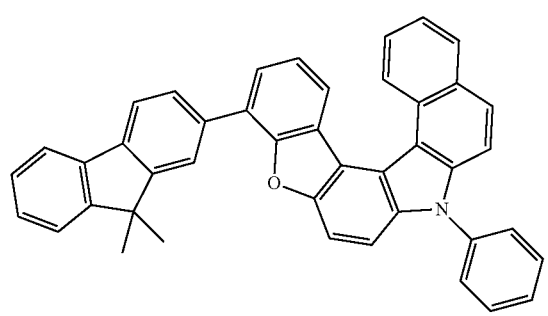
2-37
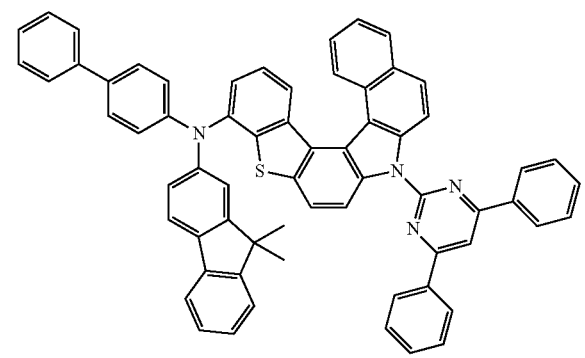
2-38
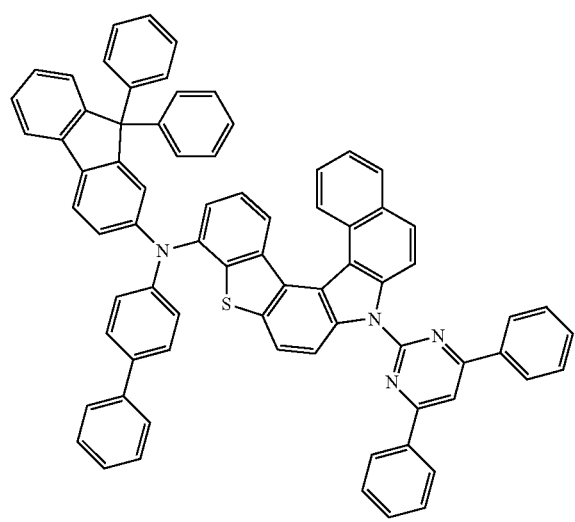
2-39
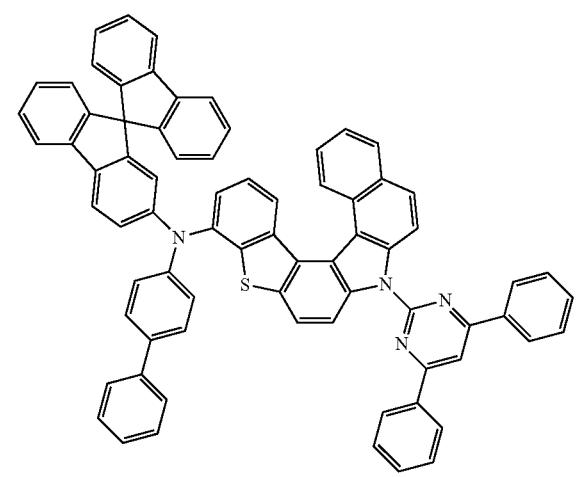

-continued
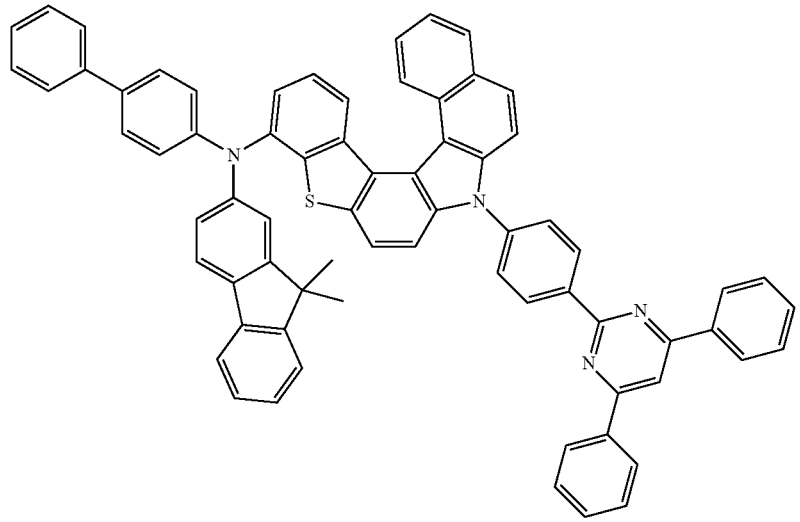
2-40
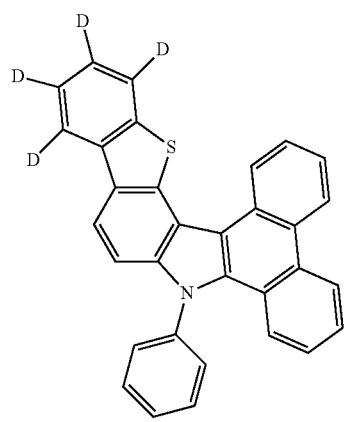
2-41
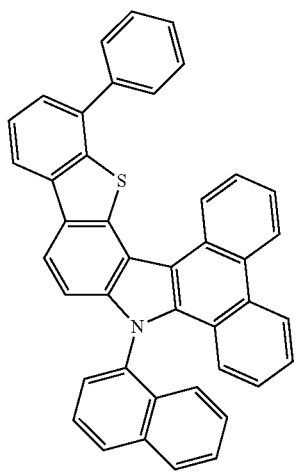
2-42
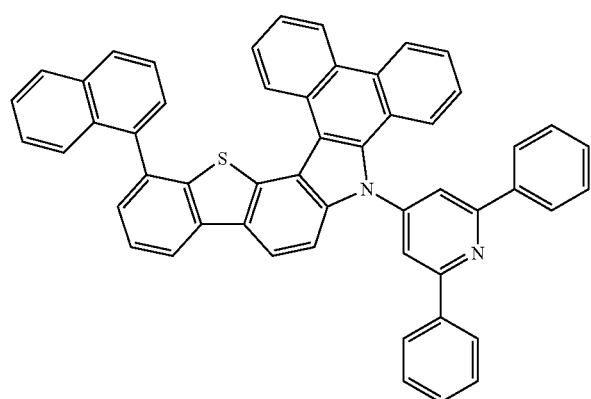
2-43
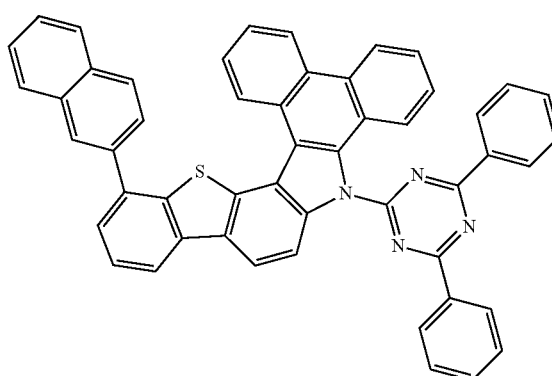
2-44

-continued
2-45
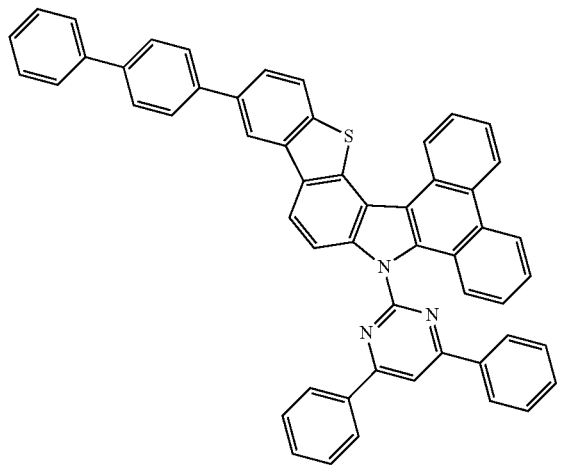
2-46
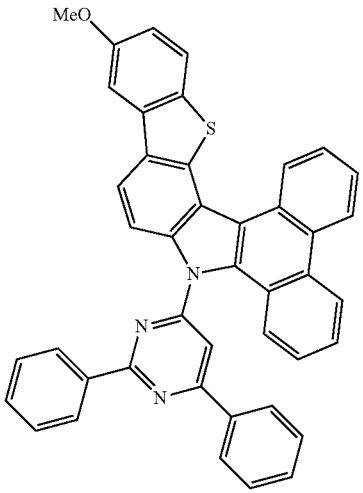
2-47
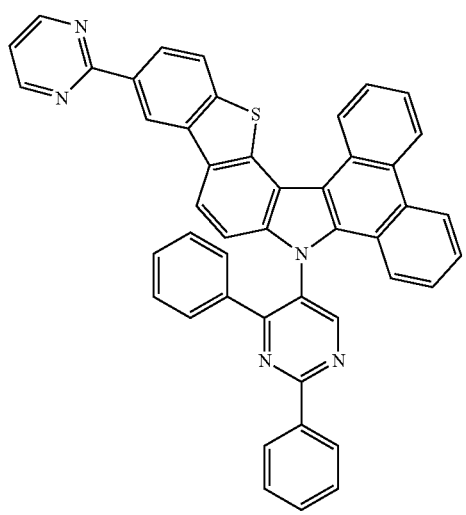
2-48
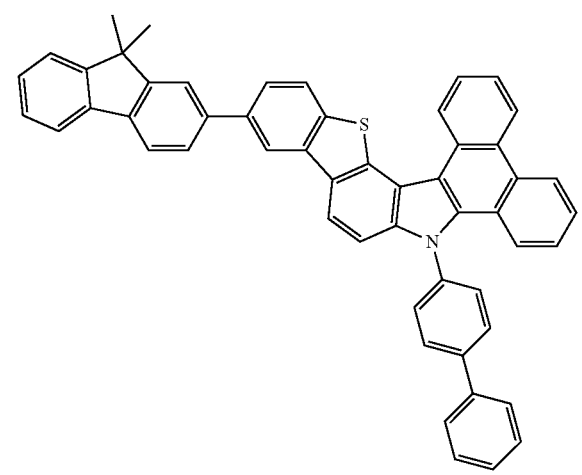
2-49
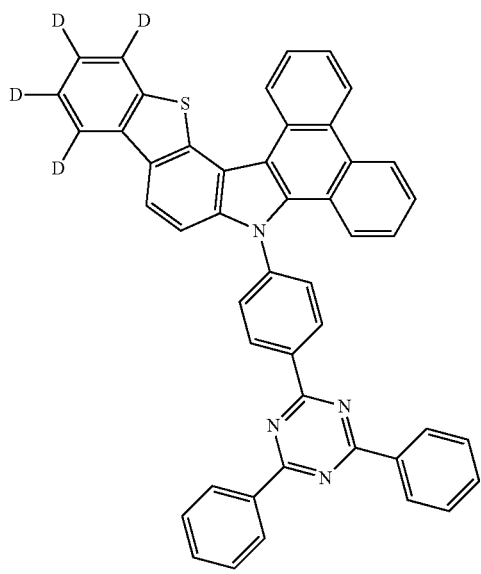
2-50
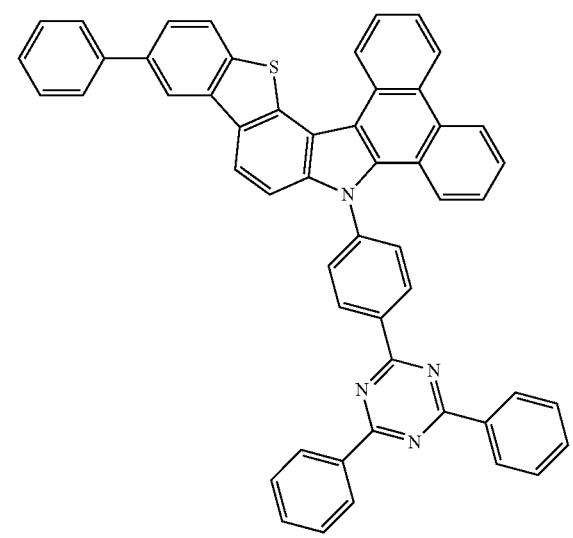

-continued
2-51
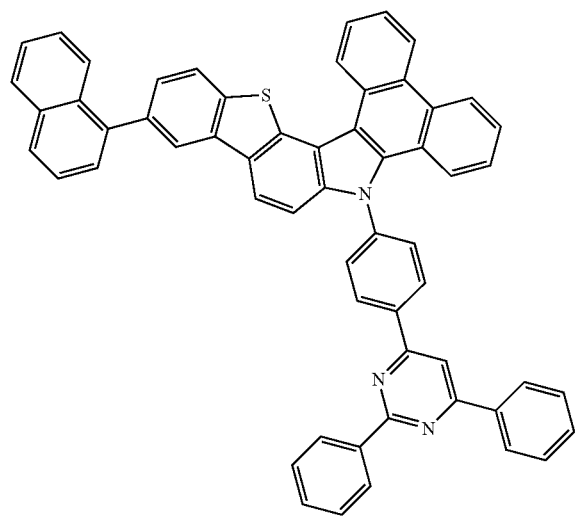
2-52
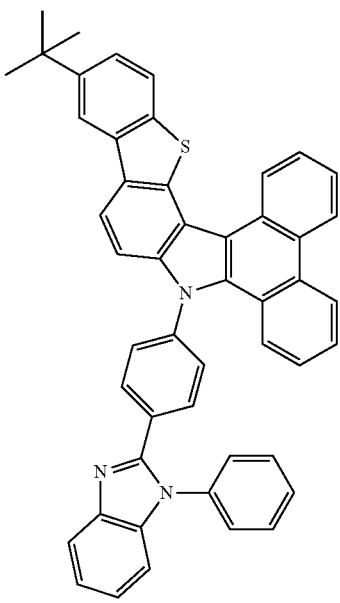
2-53
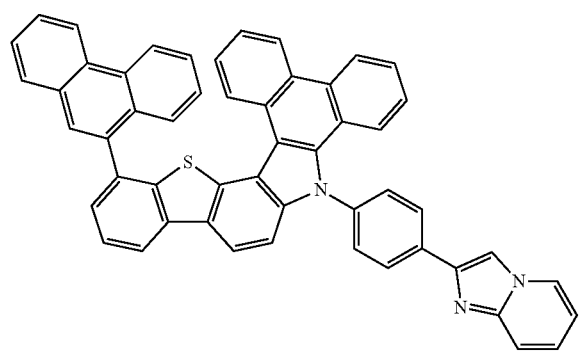
2-54
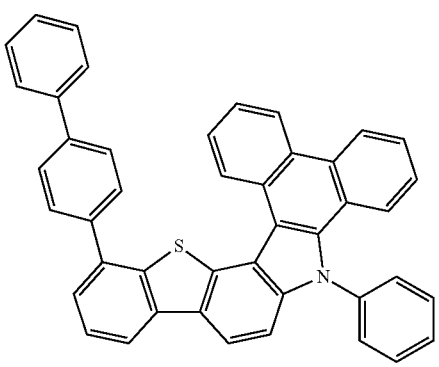
2-55
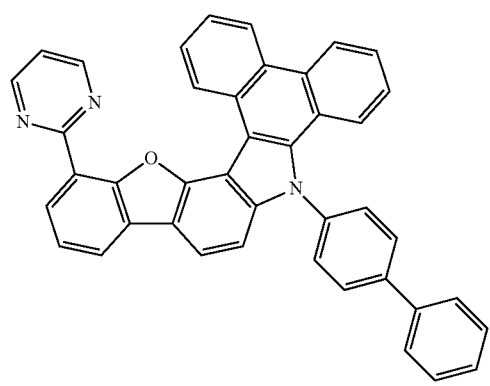
2-56
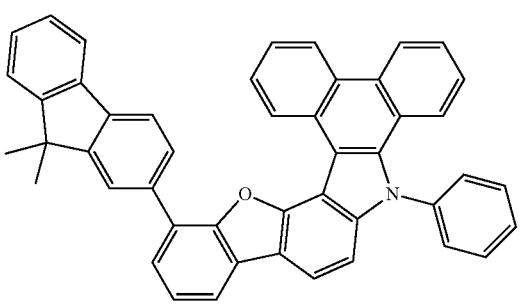

-continued
2-57
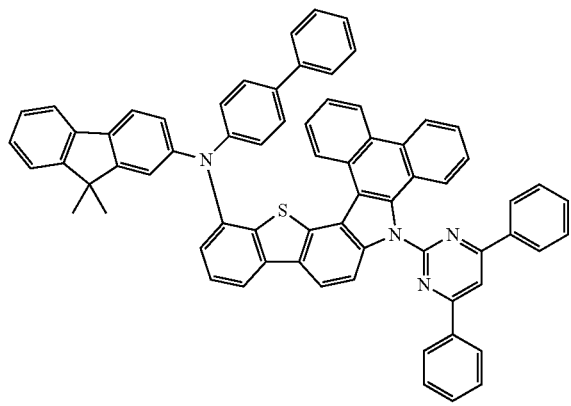
2-58
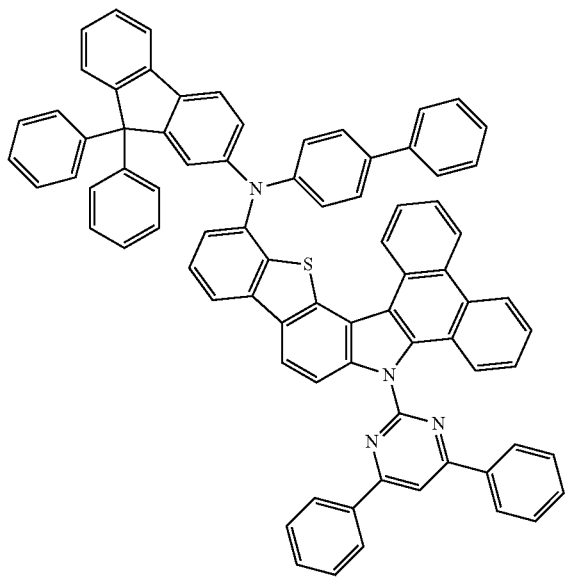
2-59
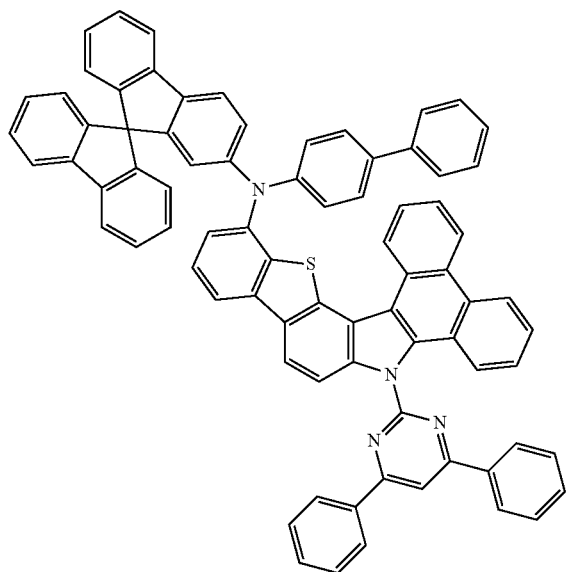

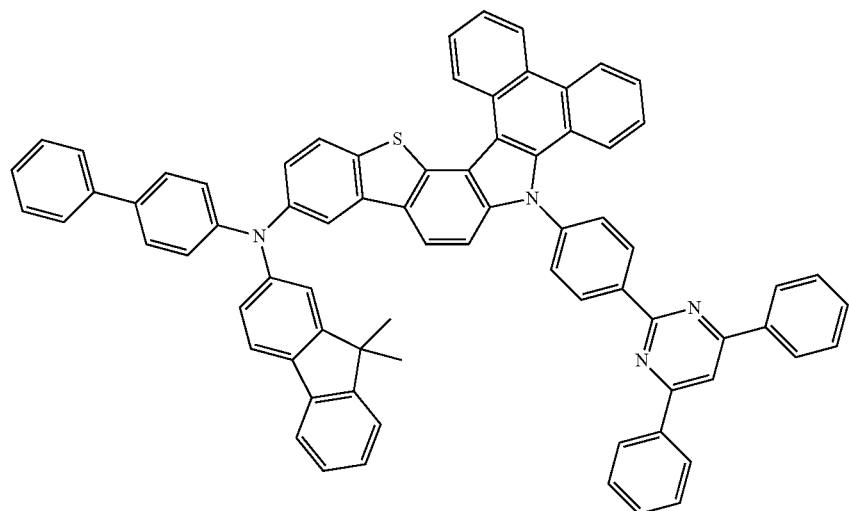
2-60
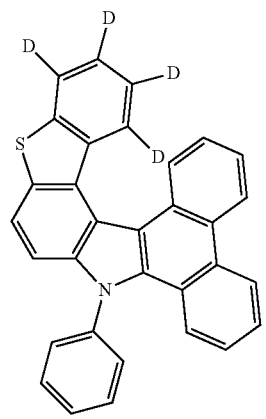
2-61
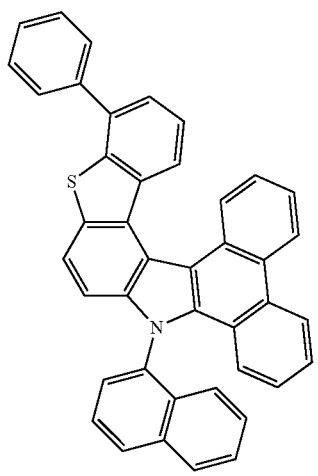
2-62
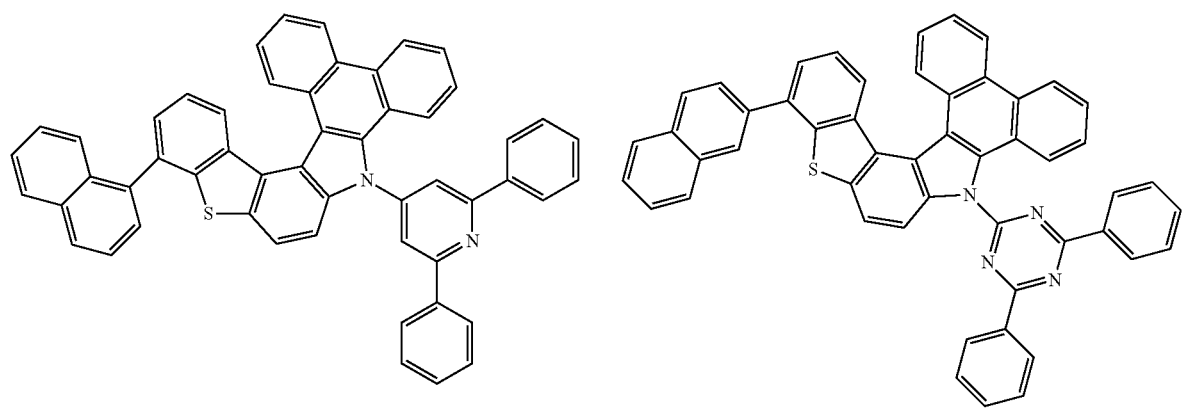
2-63 2-64

-continued
2-65
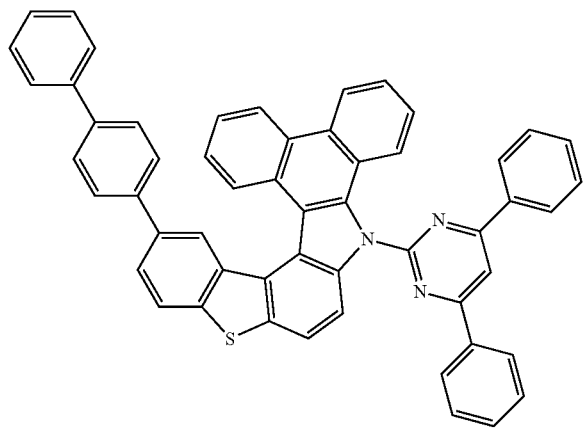
2-66
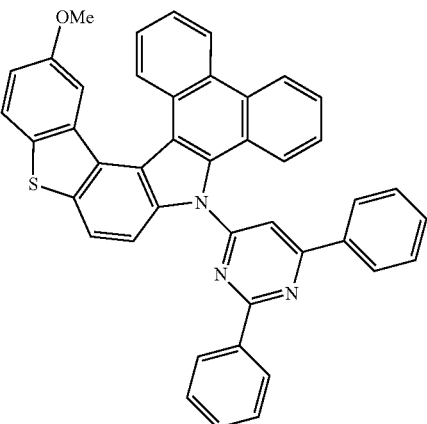
2-67
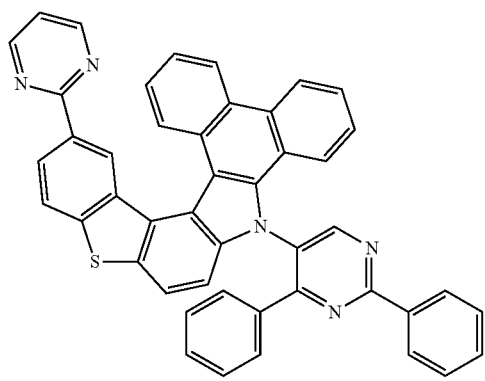
2-68
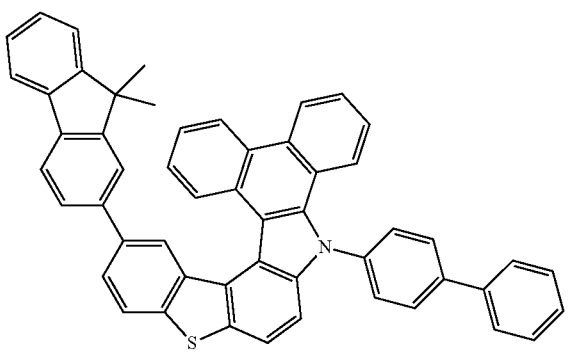
2-69
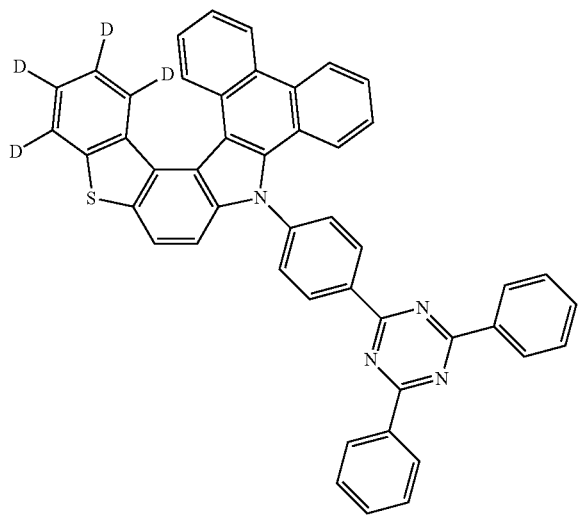
2-70
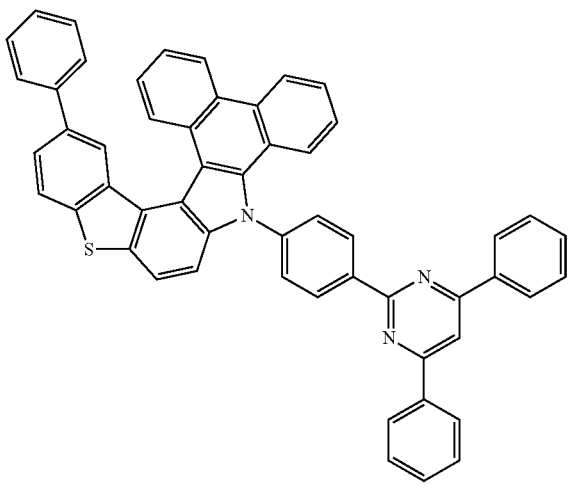

-continued
2-71
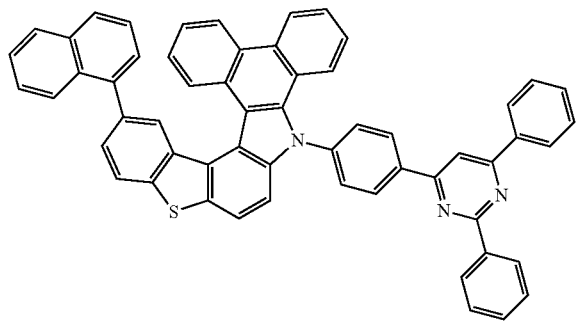
2-72
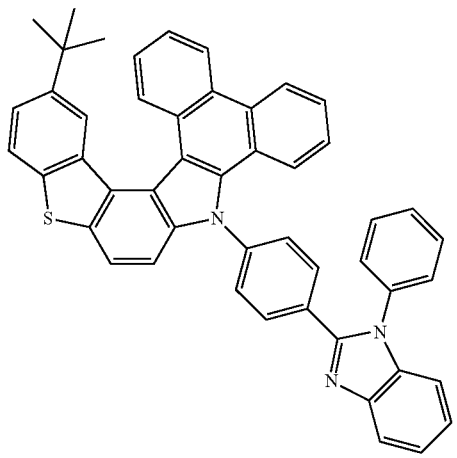
2-73
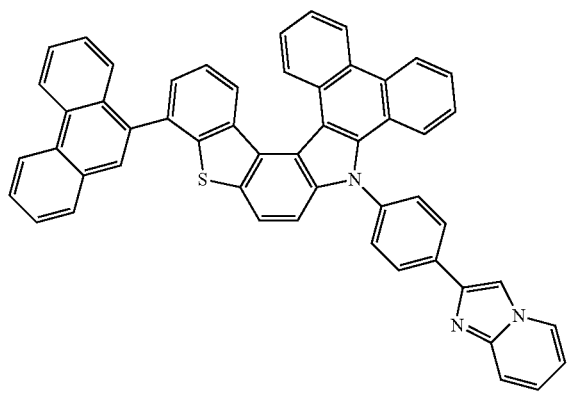
2-74
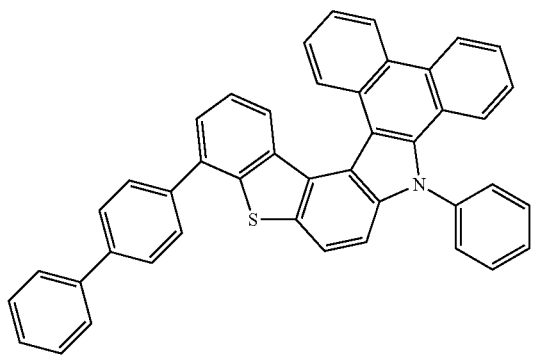
2-75
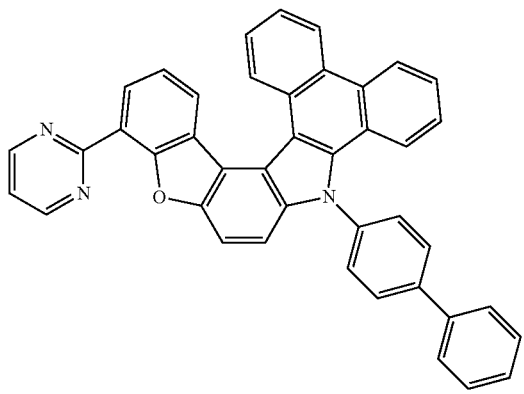
2-76
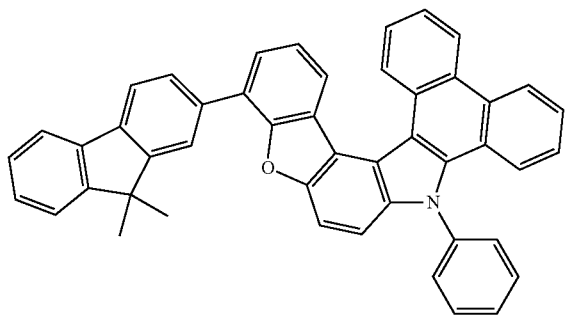

-continued
2-77
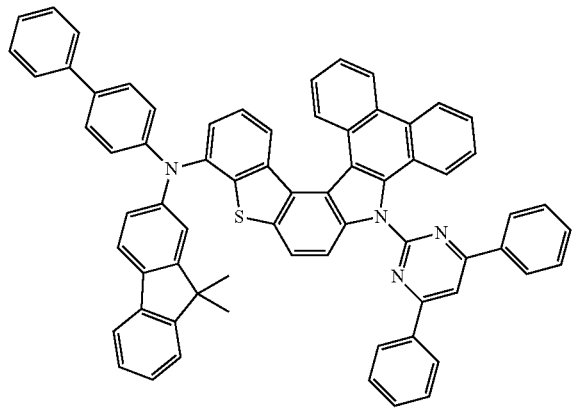
2-78
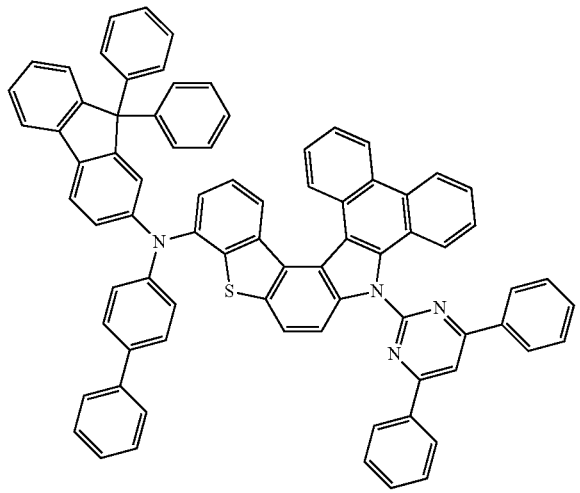
2-79
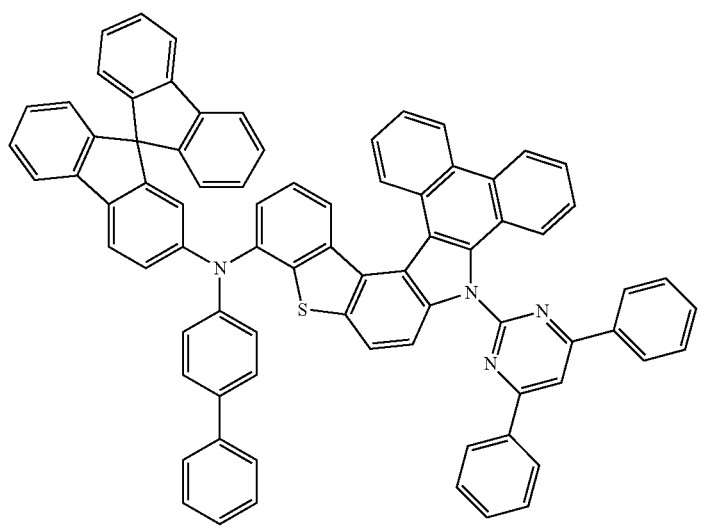
2-80
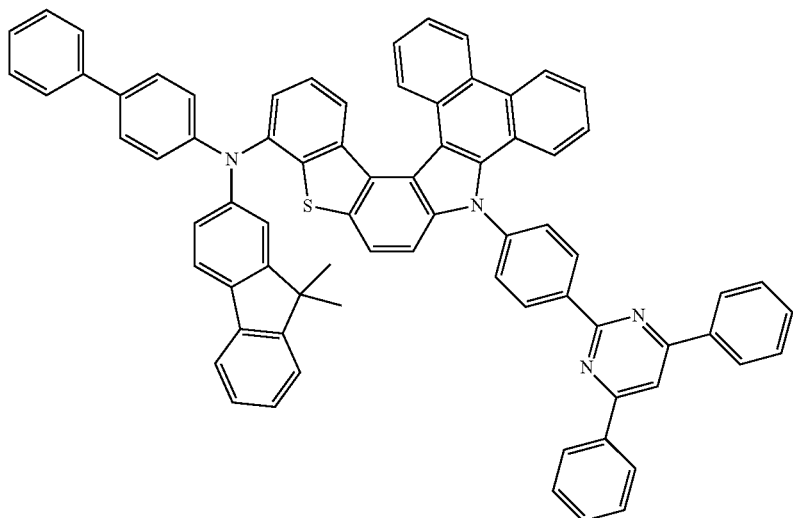

-continued
3-1
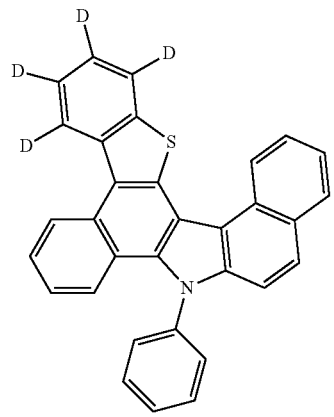
3-2
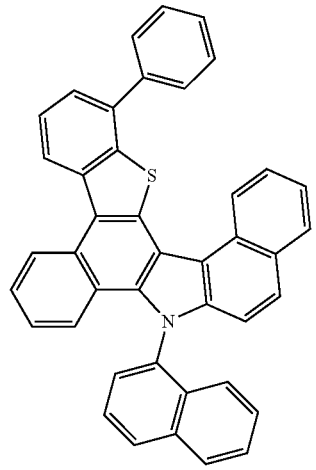
3-3
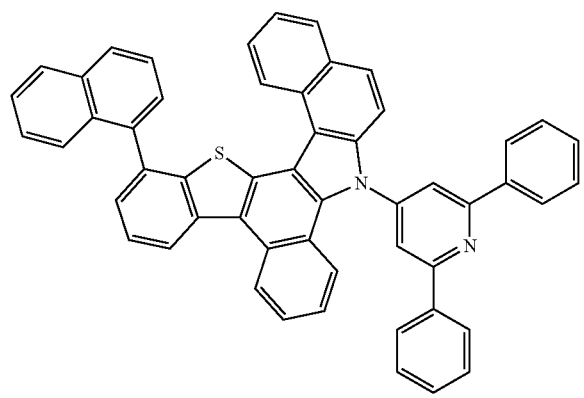
3-4
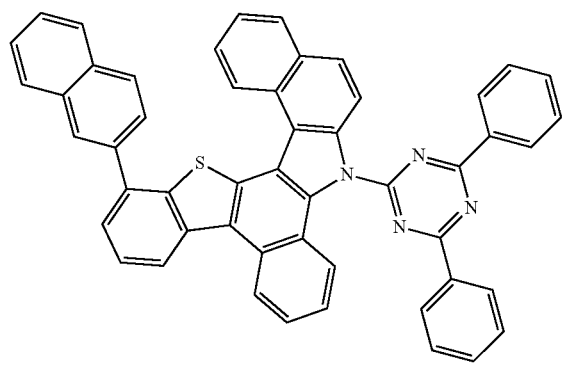
3-5
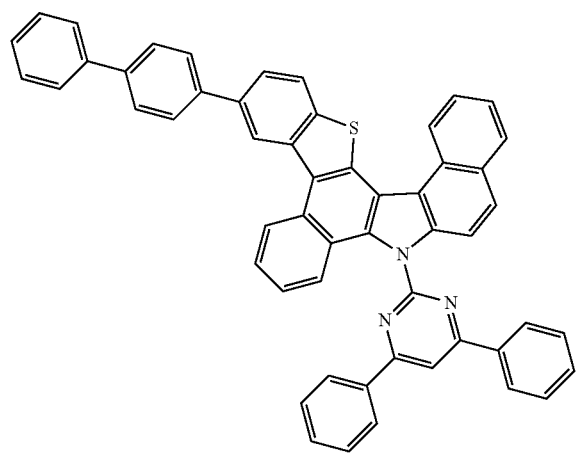
3-6
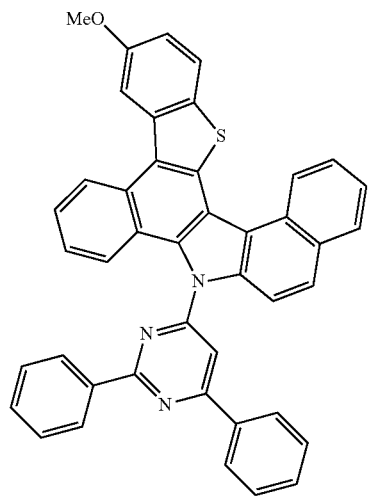

3-7
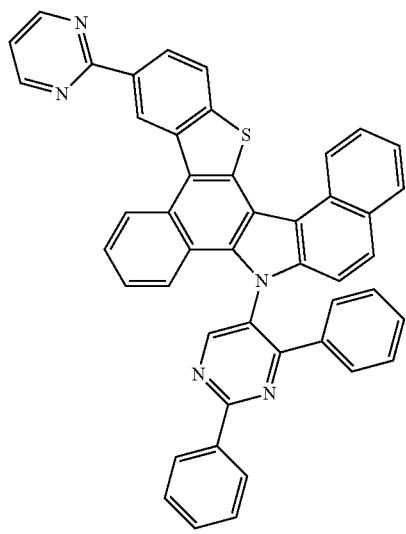
3-8
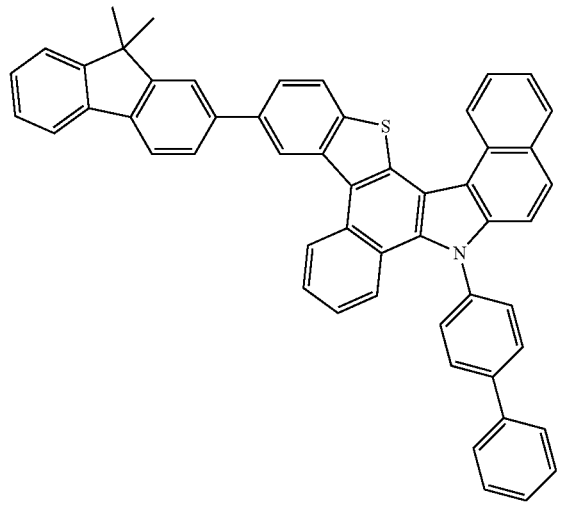
3-9
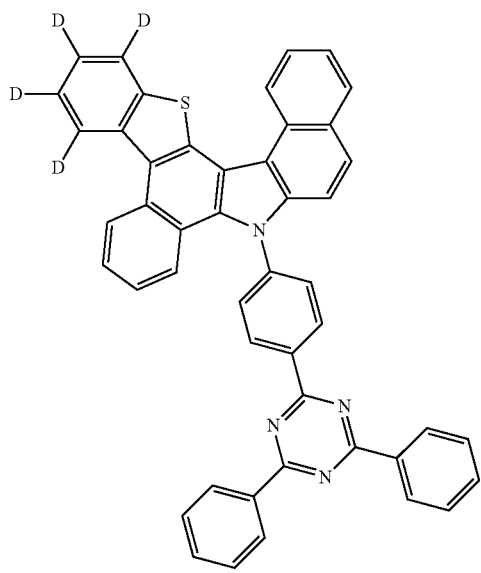
3-10
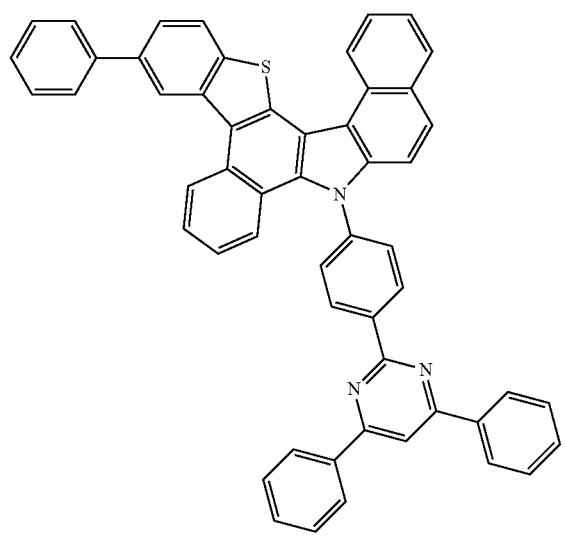

-continued
3-11
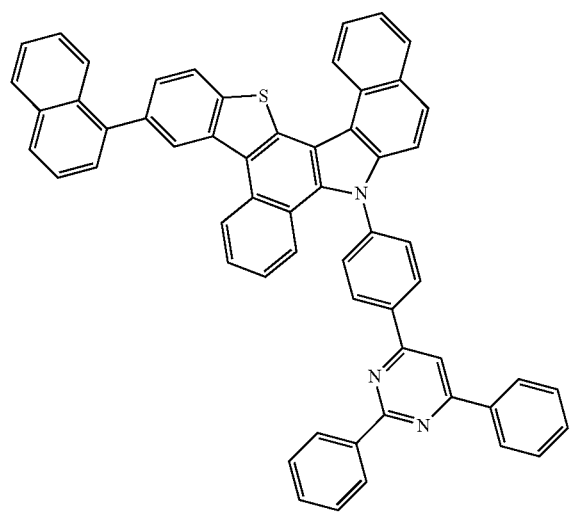
3-12
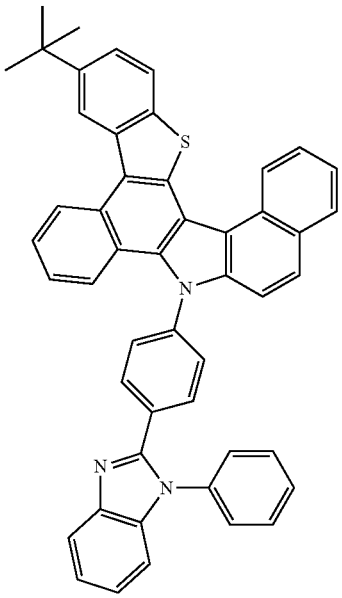
3-13
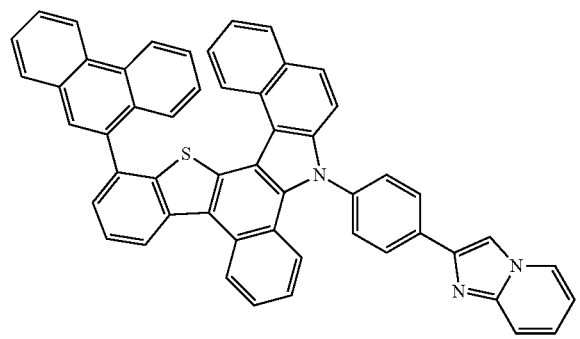
3-14
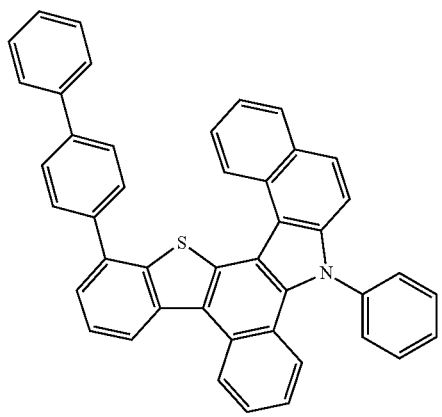
3-15
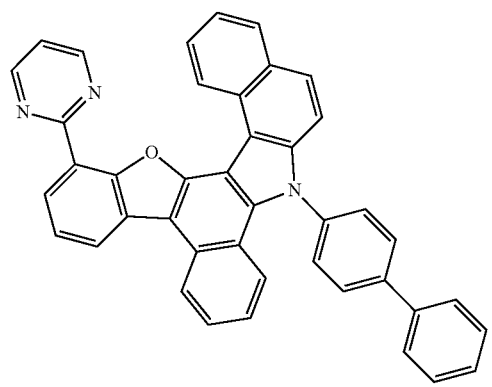
3-16
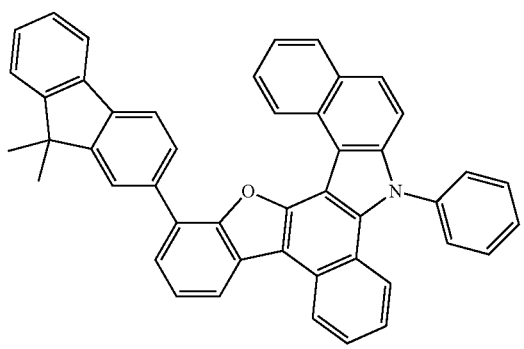

3-17
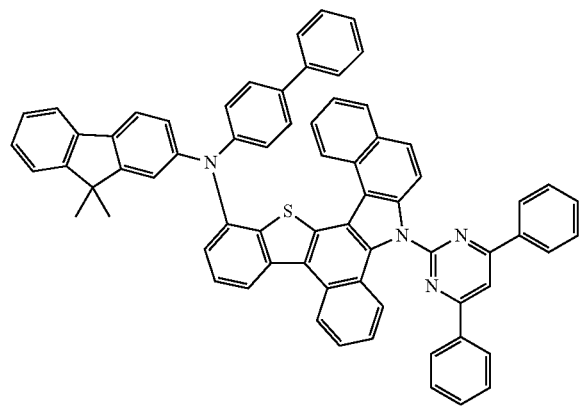
3-18
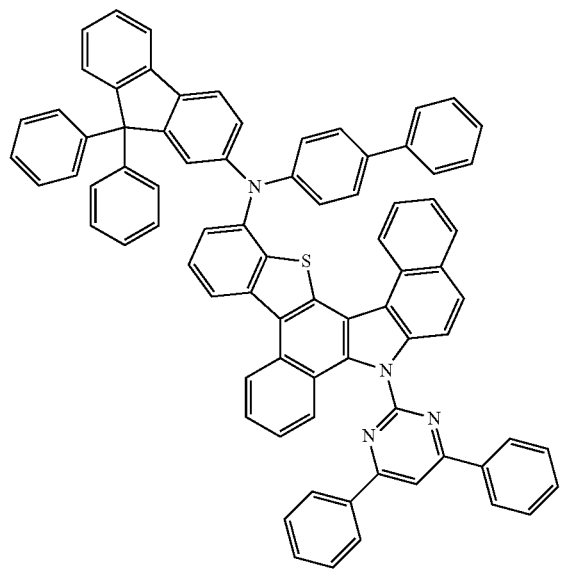
3-19
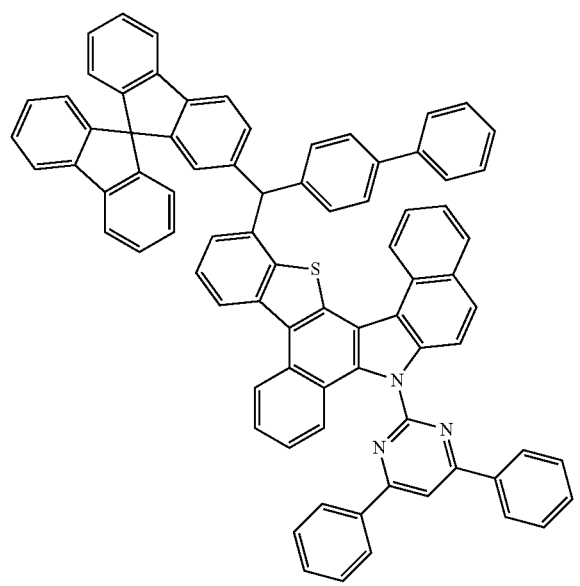

3-20
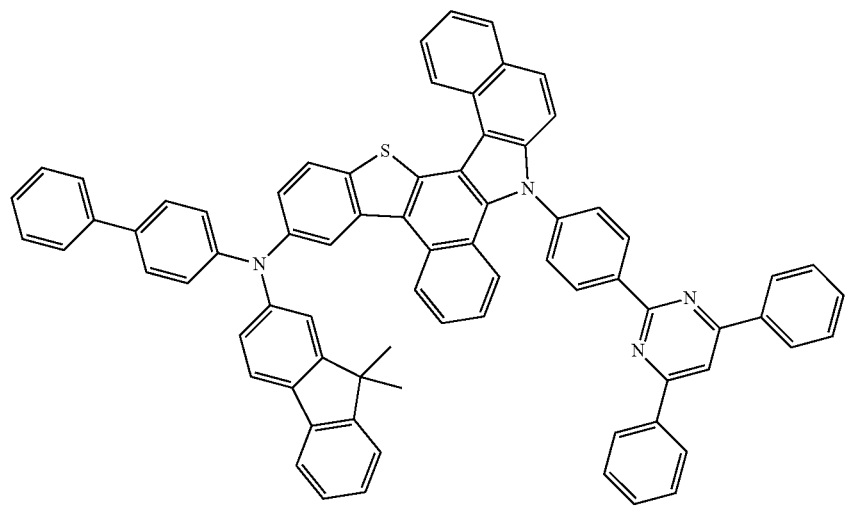
3-21
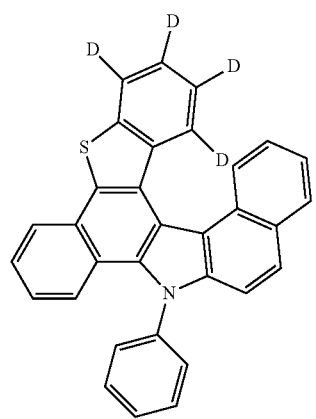
3-22
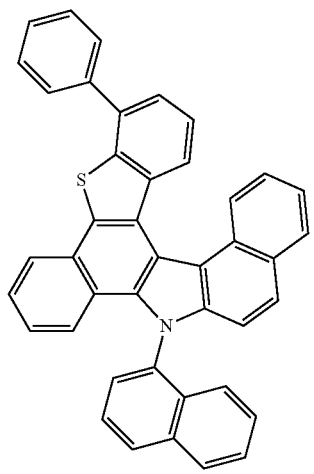
3-23
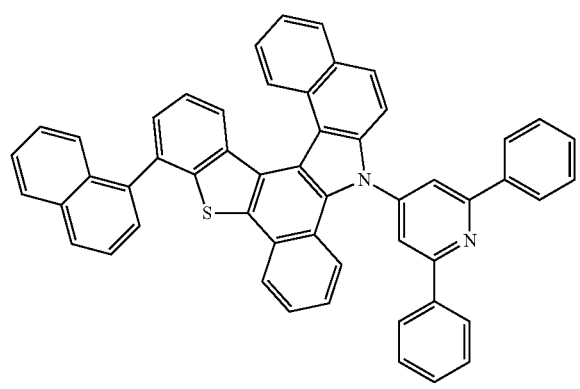
3-24
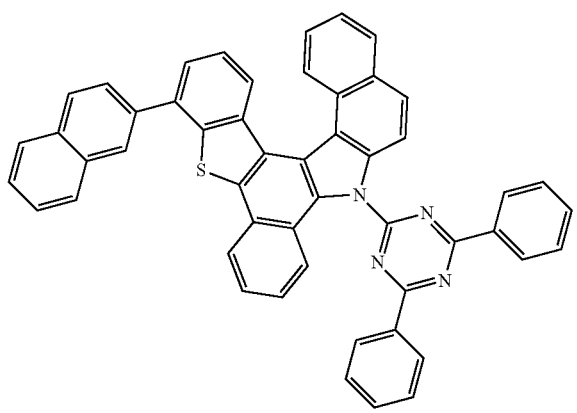

-continued
3-25
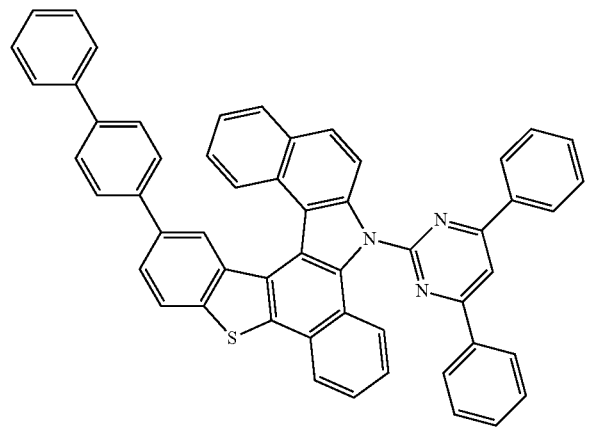
3-26
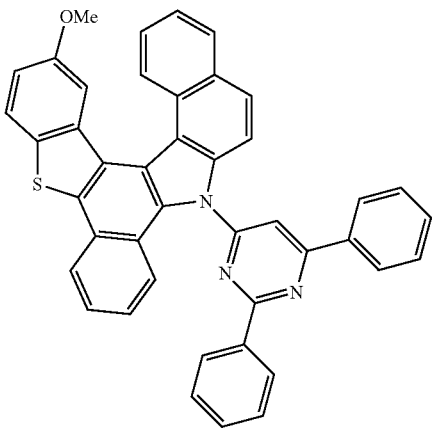
3-27
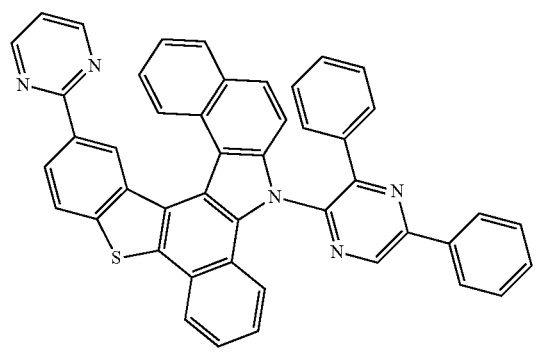
3-28
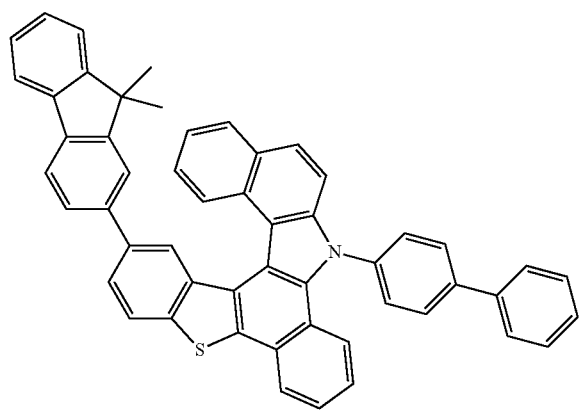
3-29
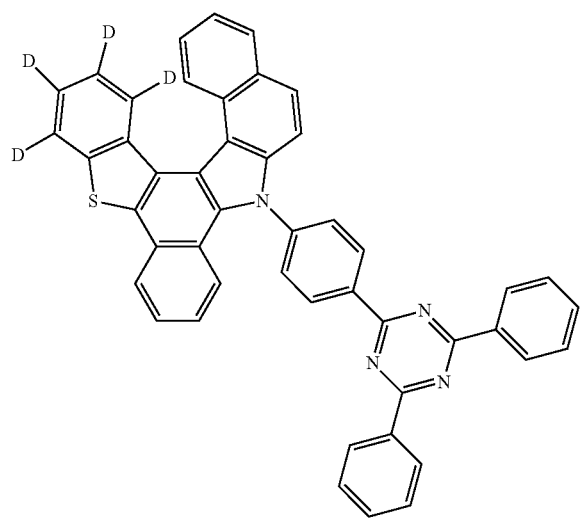
3-30
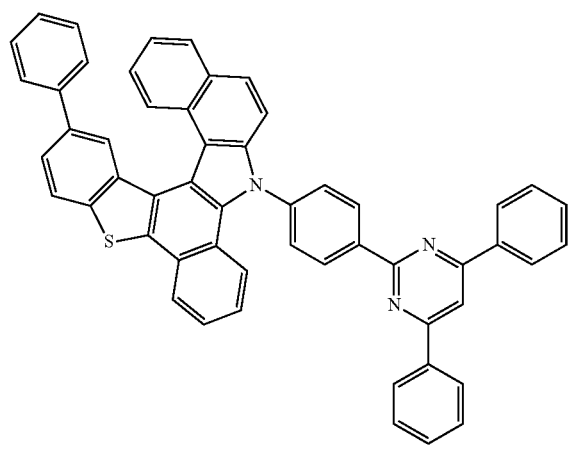

-continued
3-31
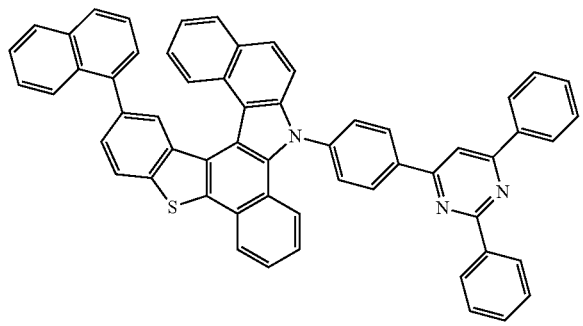
3-32
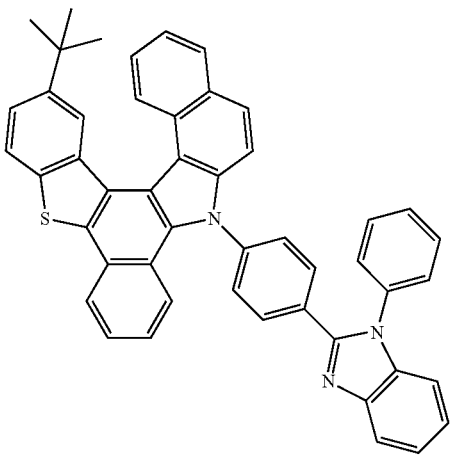
3-33
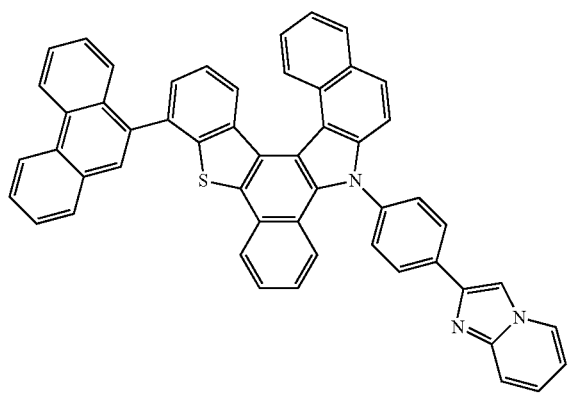
3-34
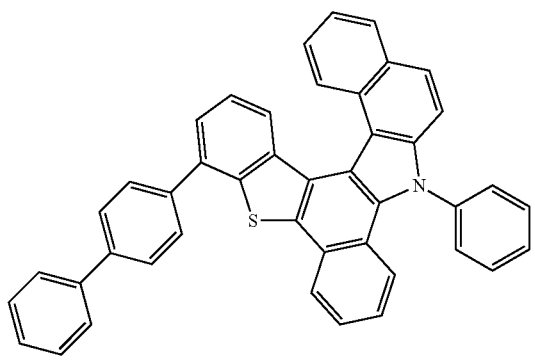
3-35
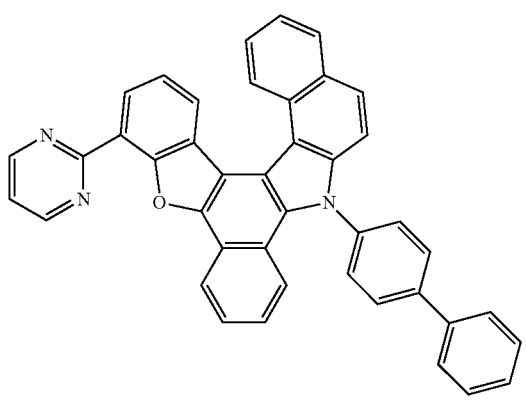
3-36
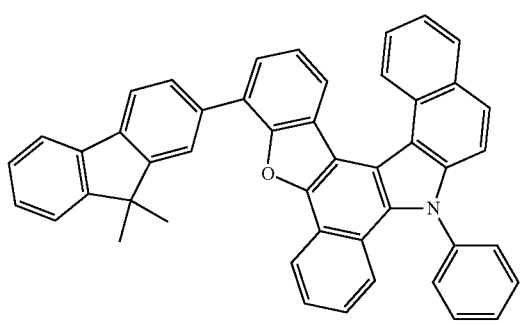

-continued
3-37
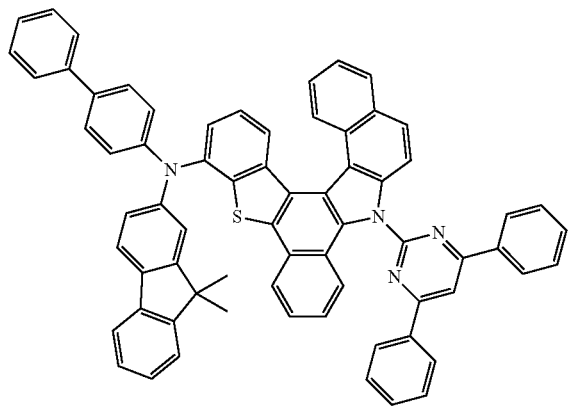
3-38
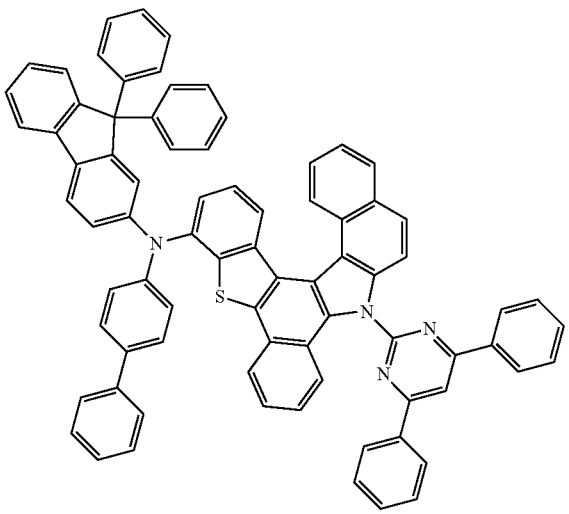
3-39
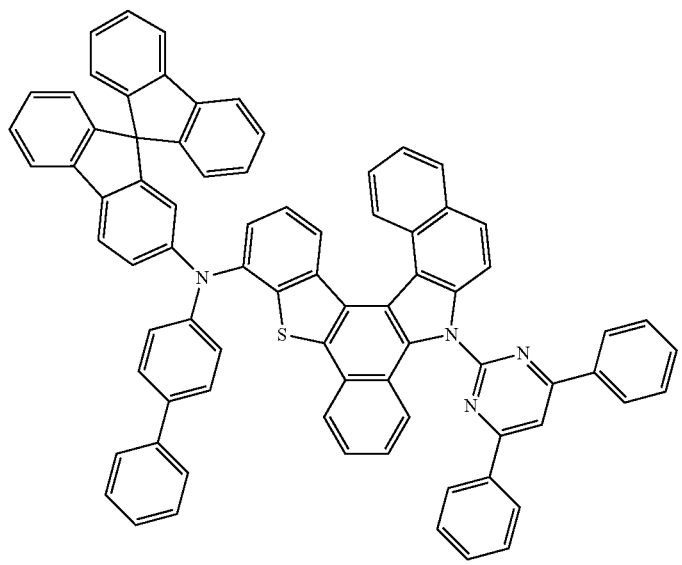
3-40
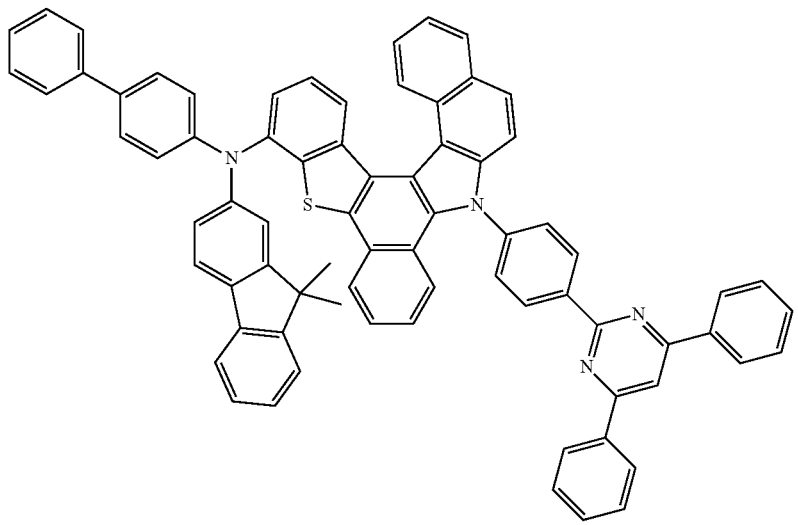

3-41
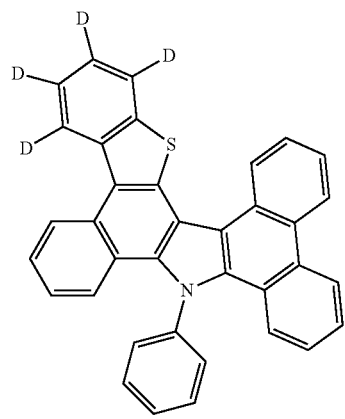
3-42
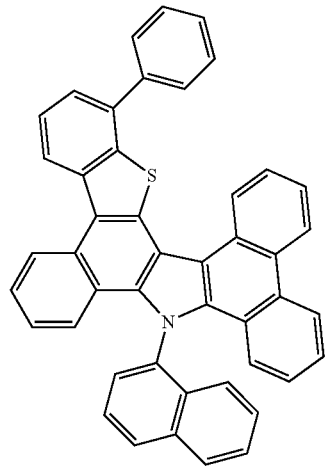
3-43
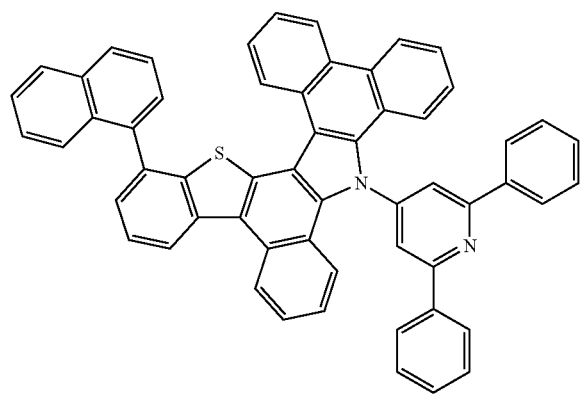
3-44
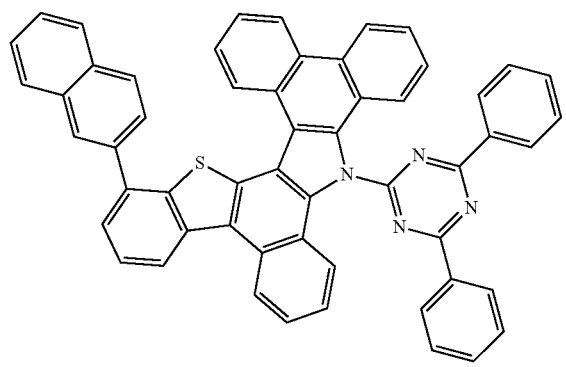
3-45
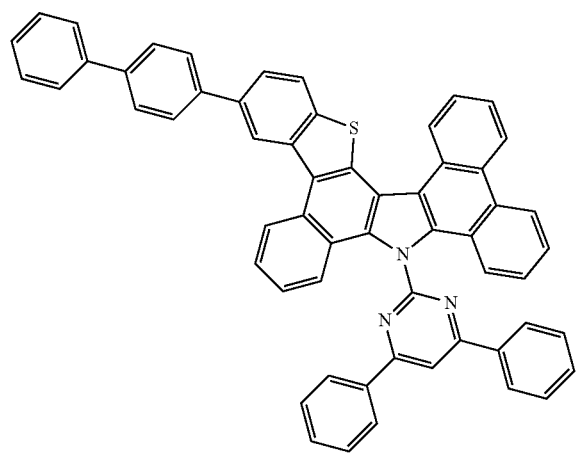
3-46
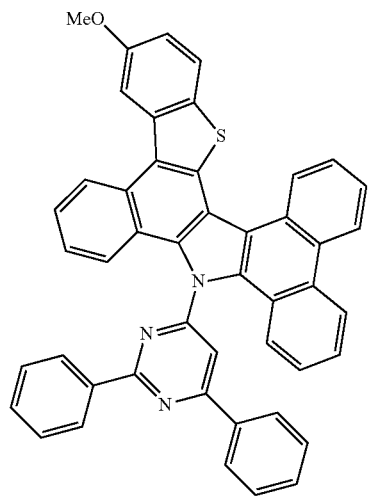

3-47
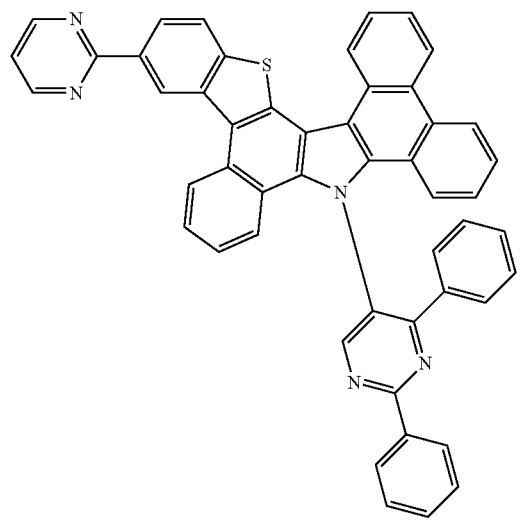
3-48
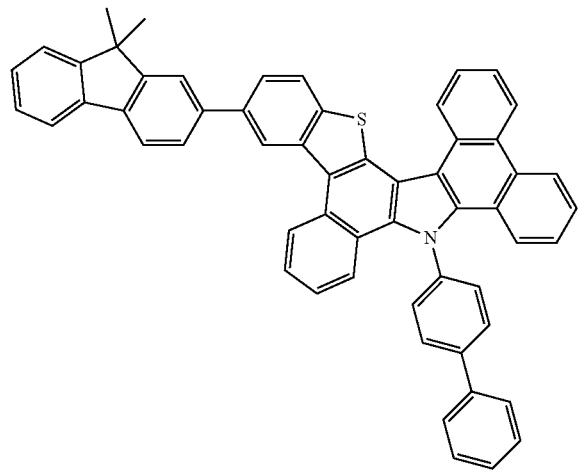
3-49
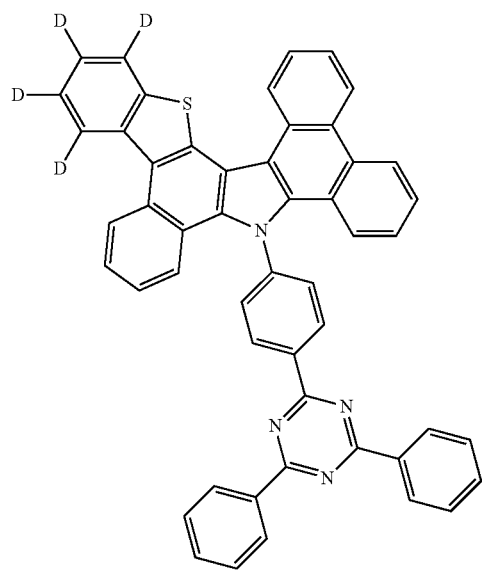
3-50
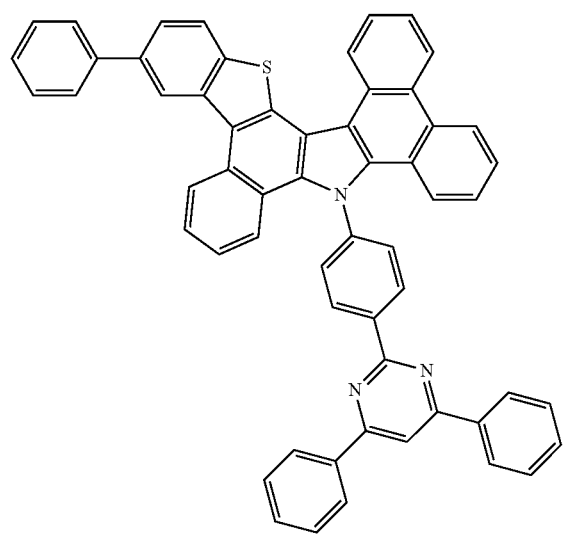

-continued
3-51
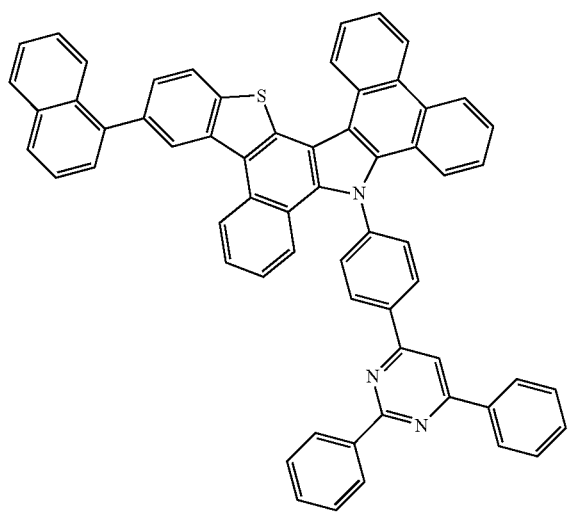
3-52
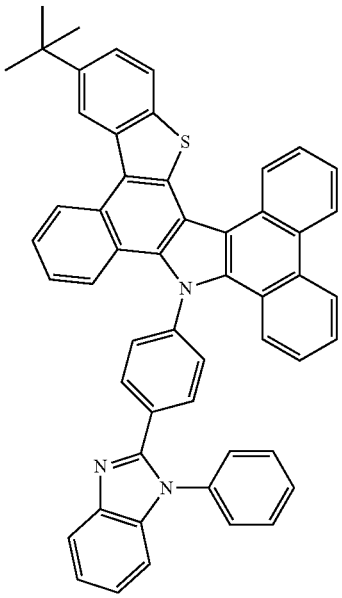
3-53
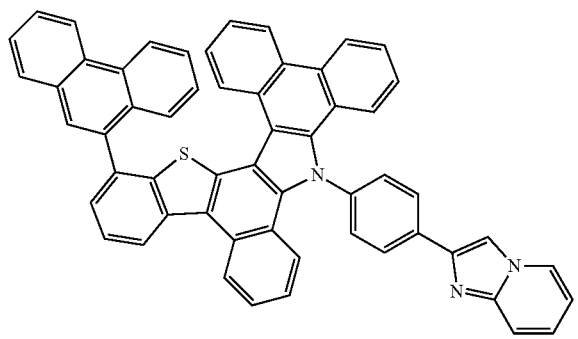
3-54
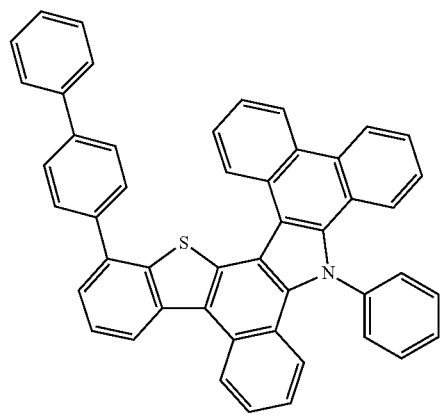
3-55
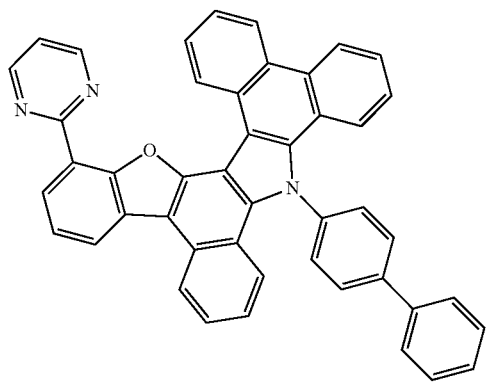
3-56
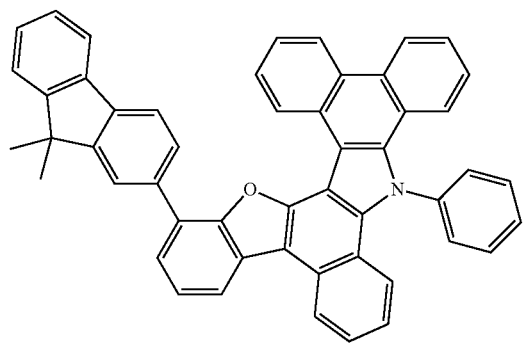

-continued
3-57
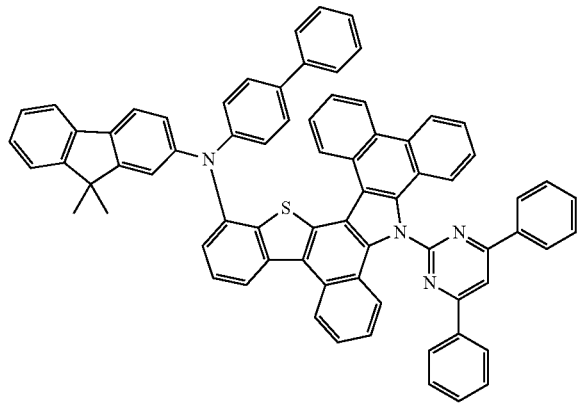
3-58
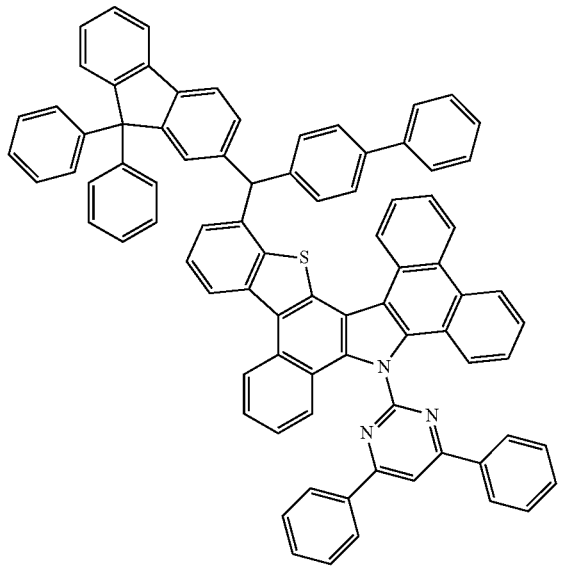
3-59
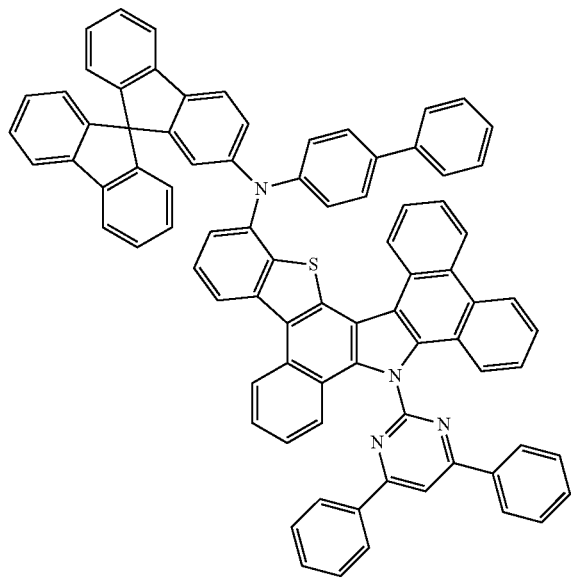
3-60
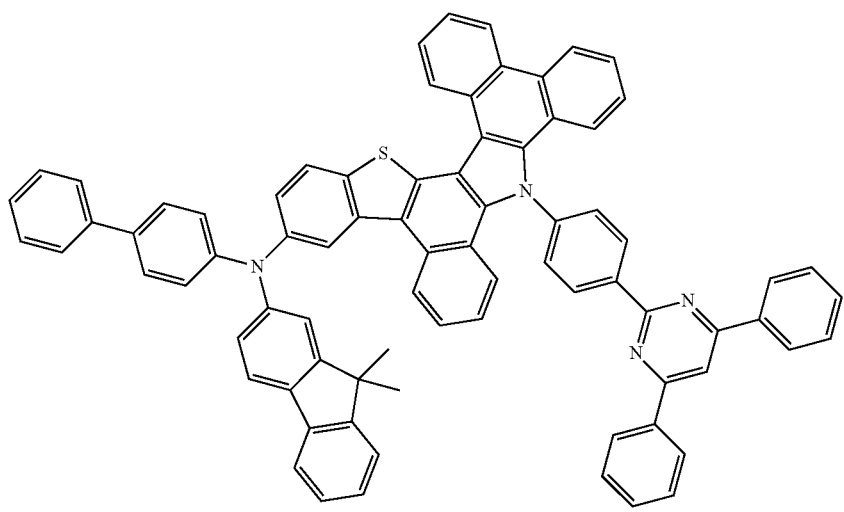

-continued
3-61
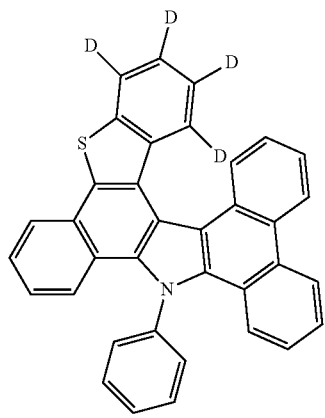
3-62
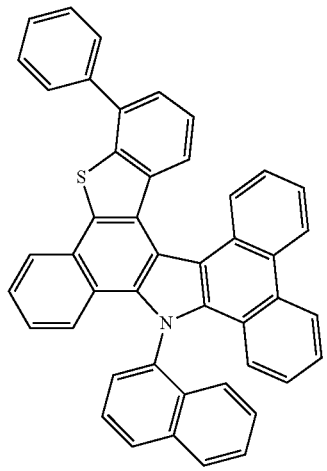
3-63
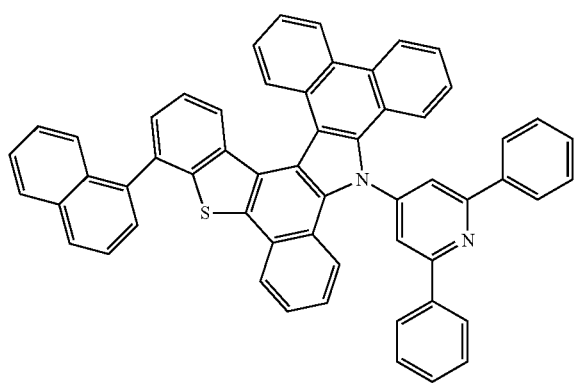
3-64
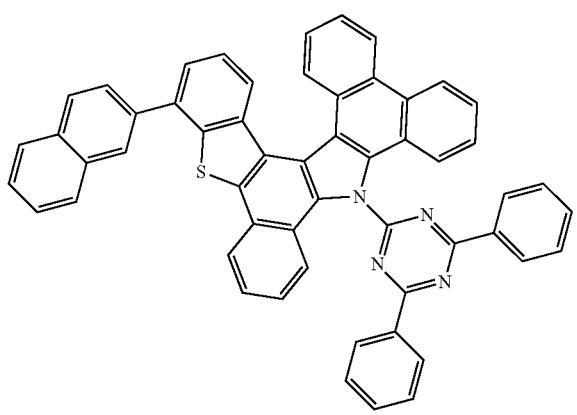
3-65
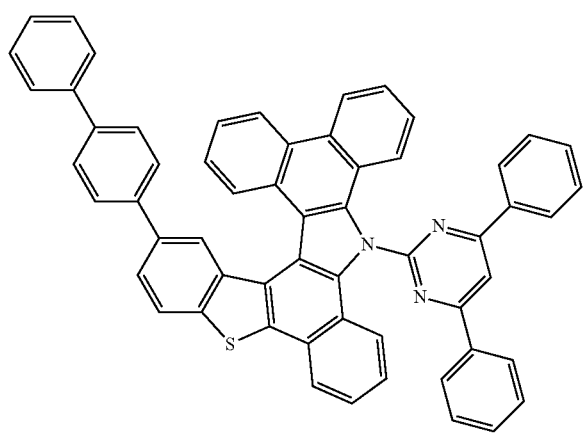
3-66
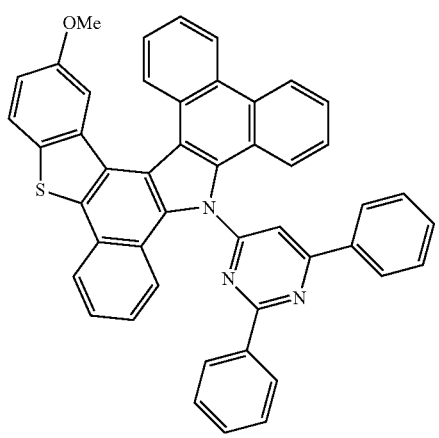

-continued
3-67
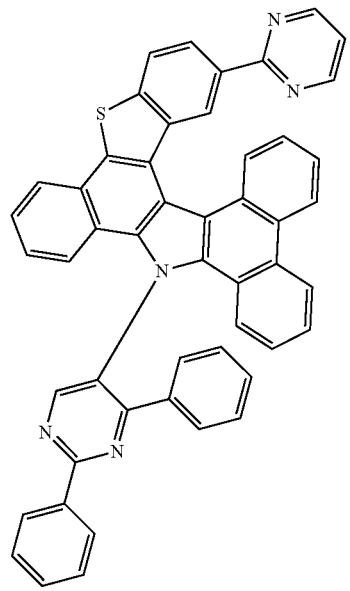
3-68
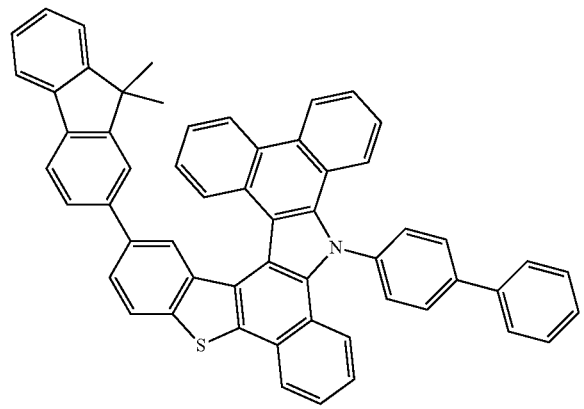
3-69
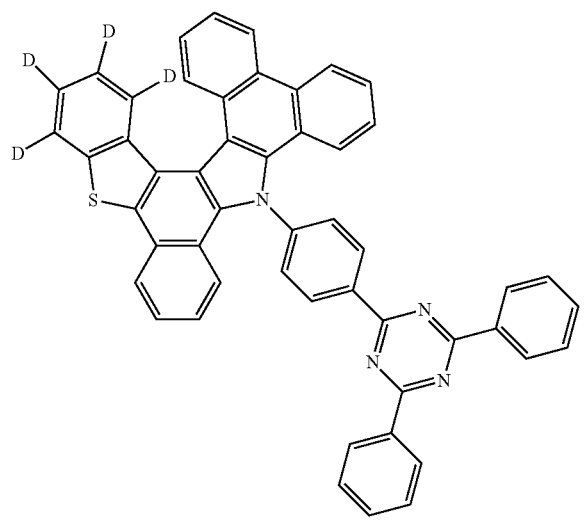
3-70
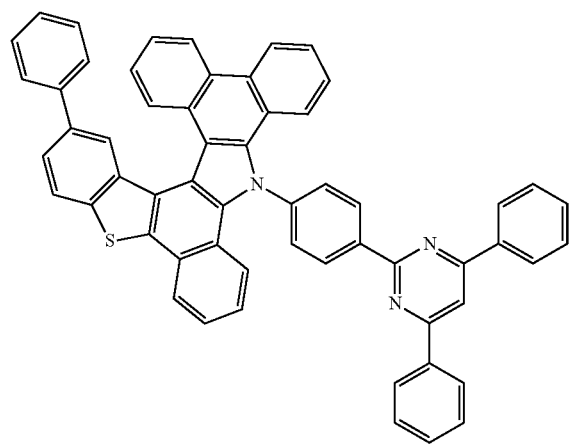
3-71
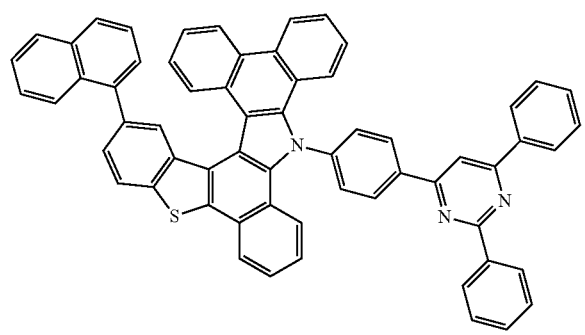
3-72
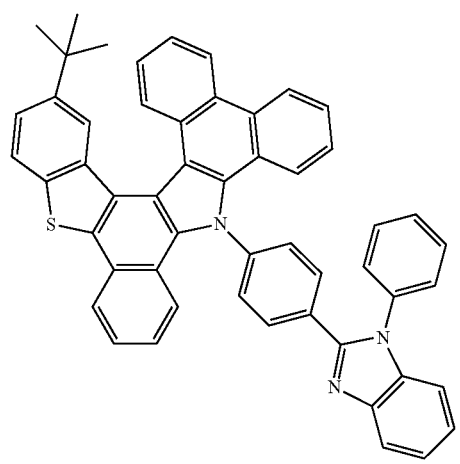

-continued
3-73
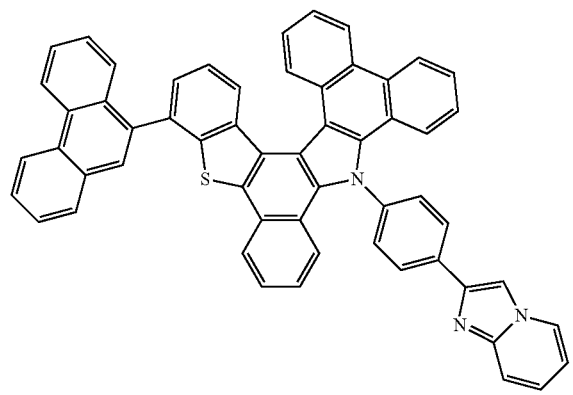
3-74
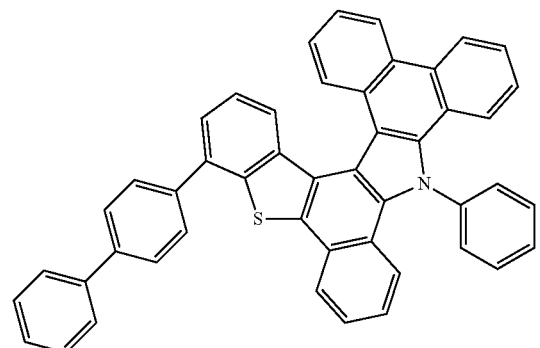
3-75
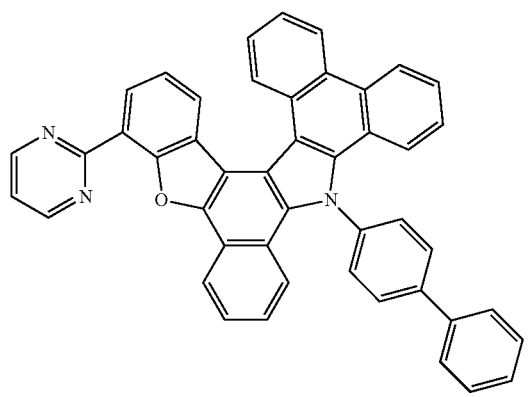
3-76
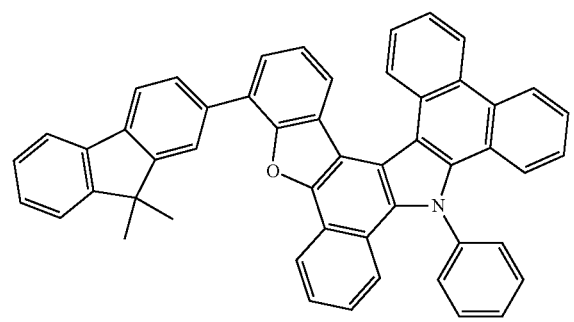
3-77
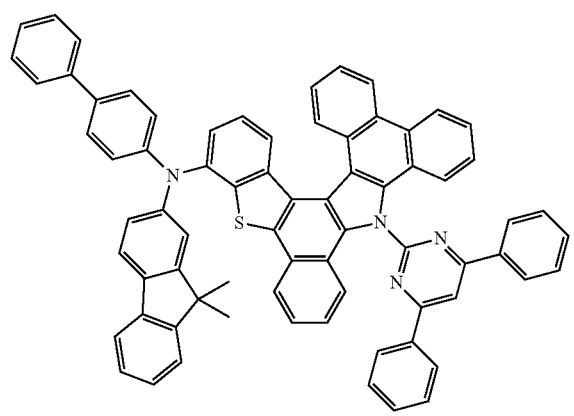
3-78
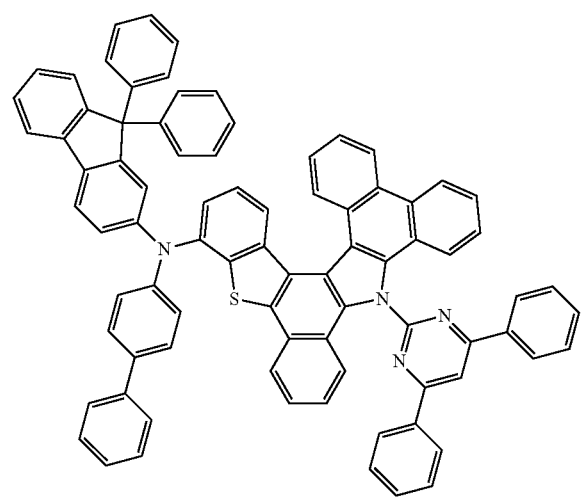

-continued
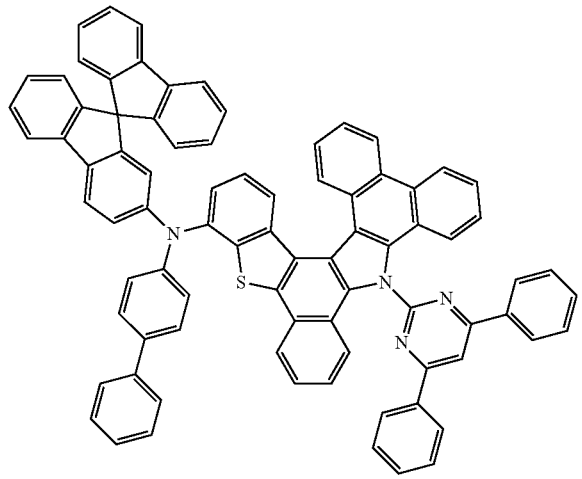
3-79
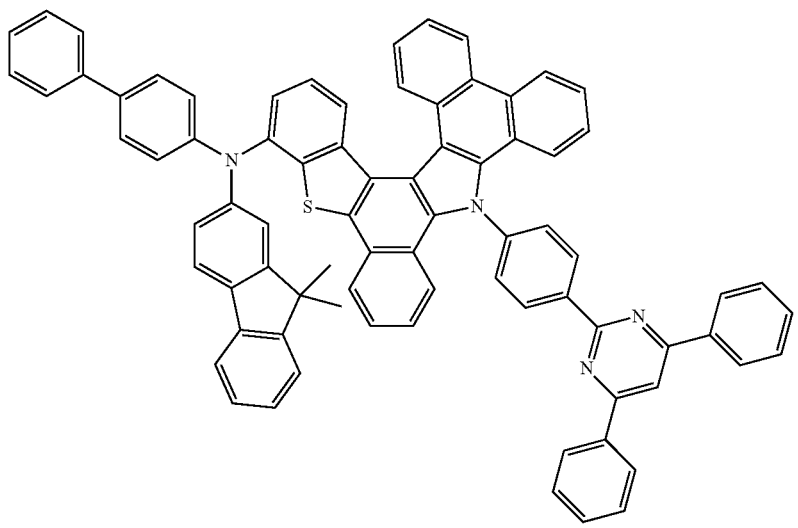
3-80
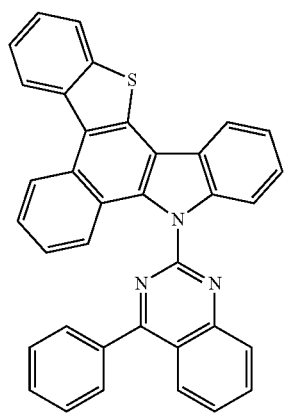
4-1
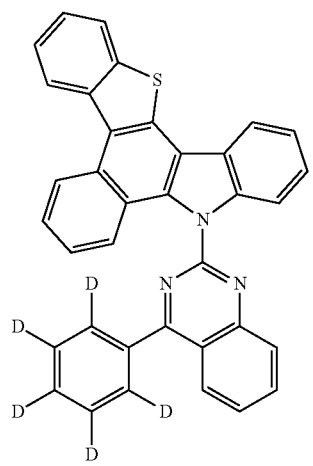
4-2

-continued
4-3
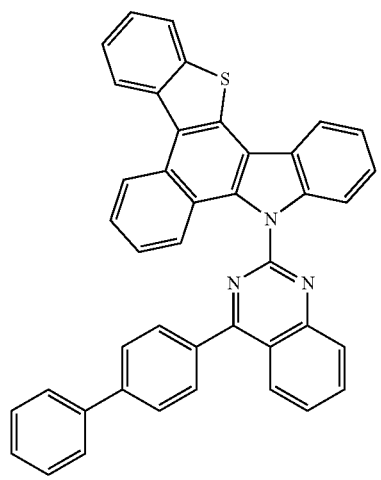
4-4
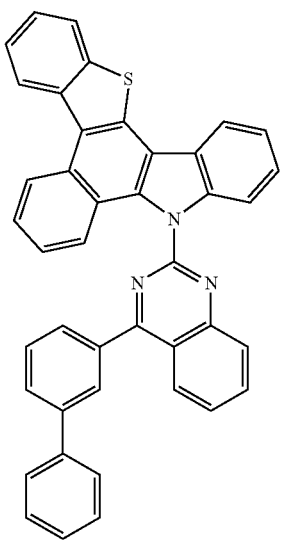
4-5
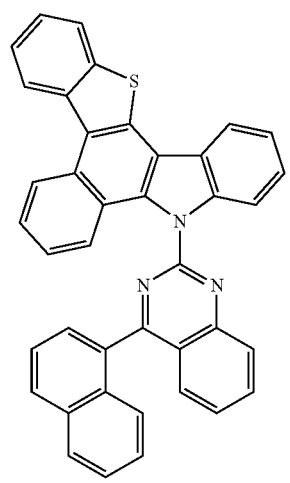
4-6
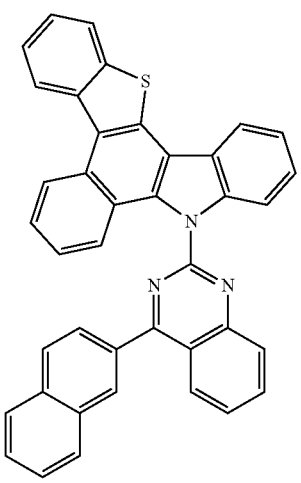
4-7
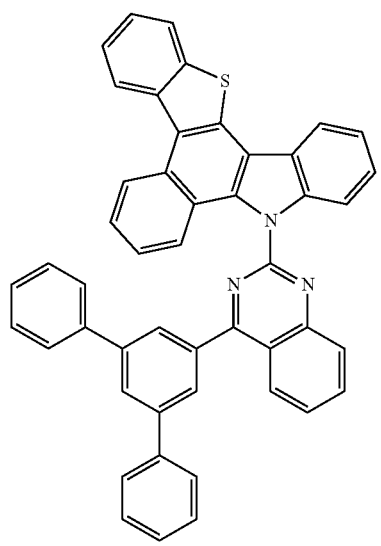
4-8
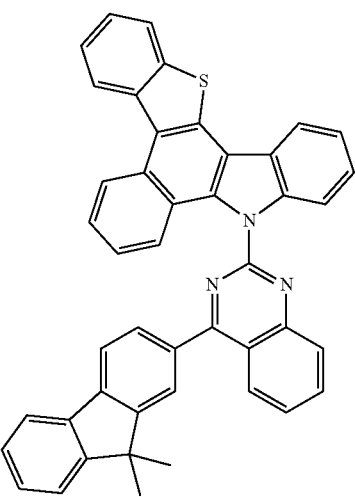

-continued
4-9
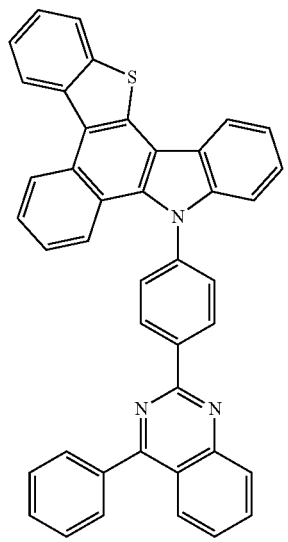
4-10
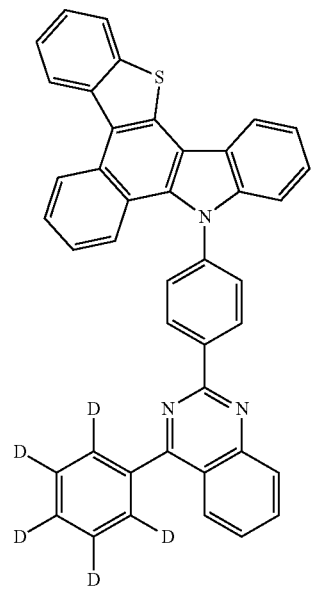
4-11
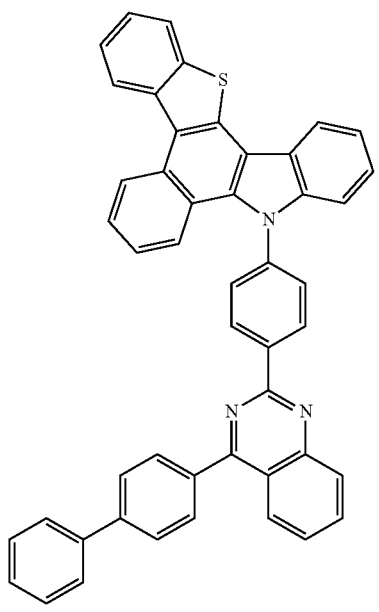
4-12
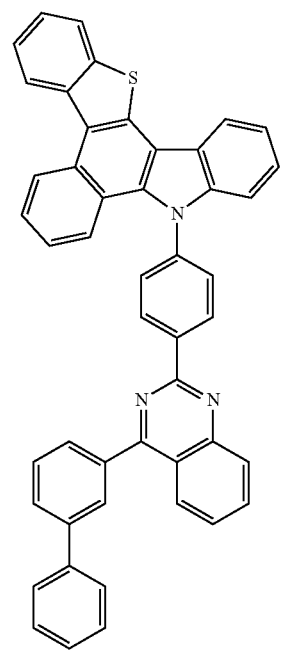

4-13
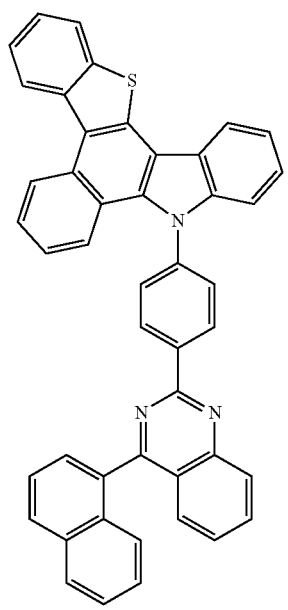
4-14
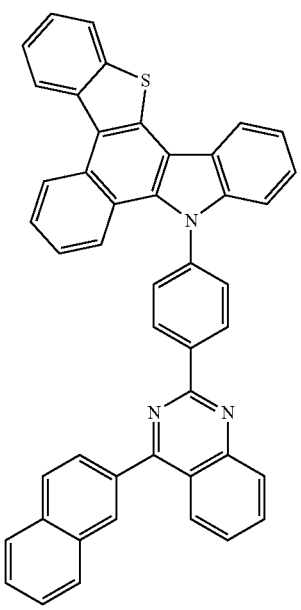
4-15
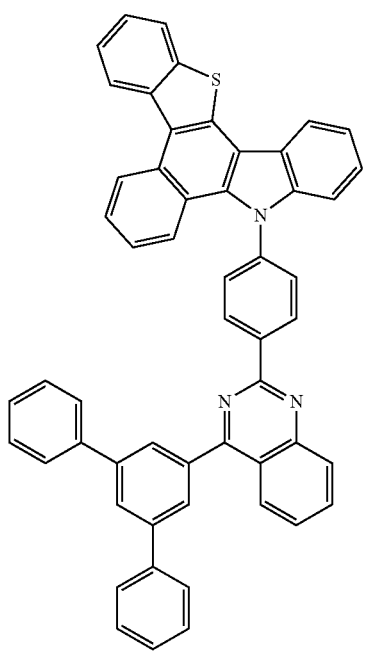
4-16
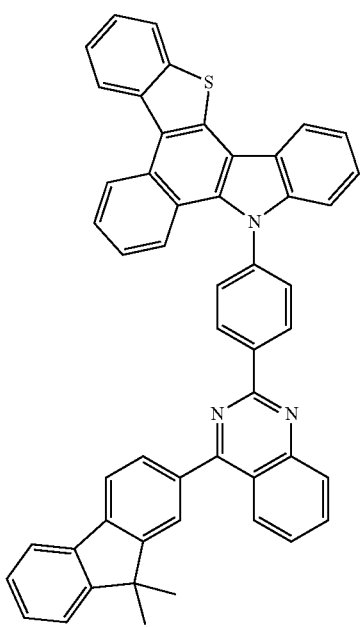

-continued
4-17
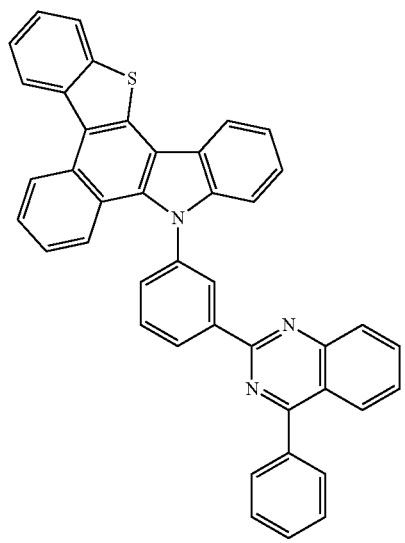
4-18
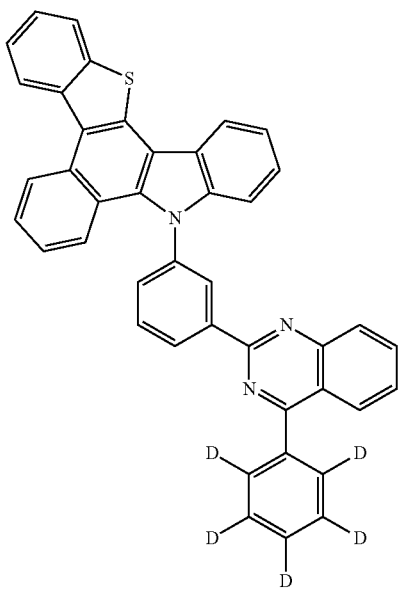
4-19
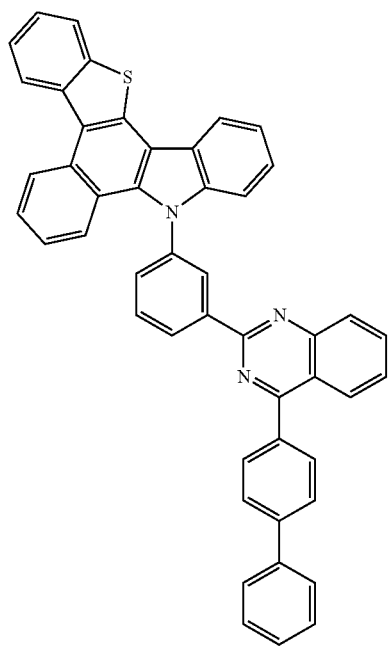
4-20
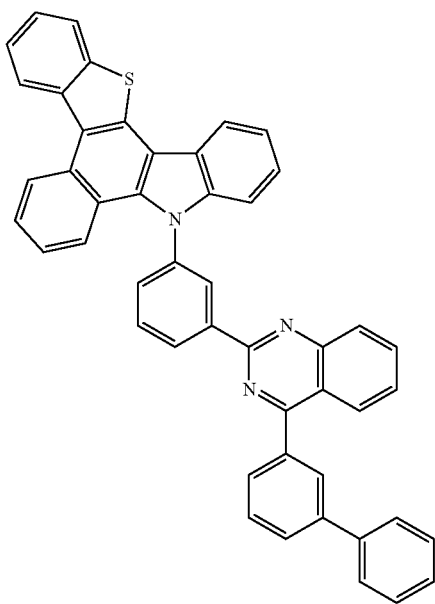

-continued
4-21
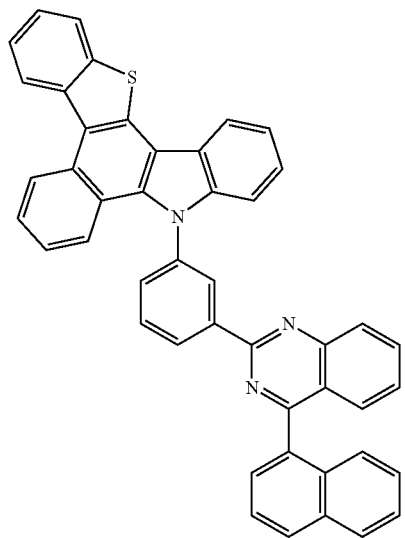
4-22
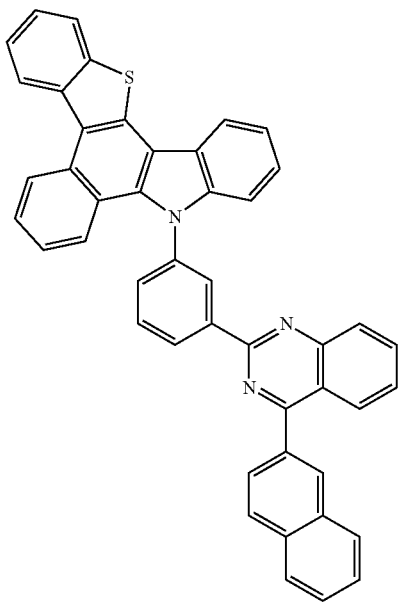
4-23
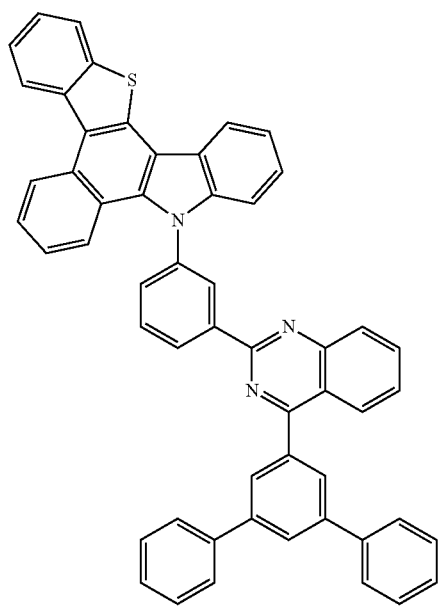
4-24
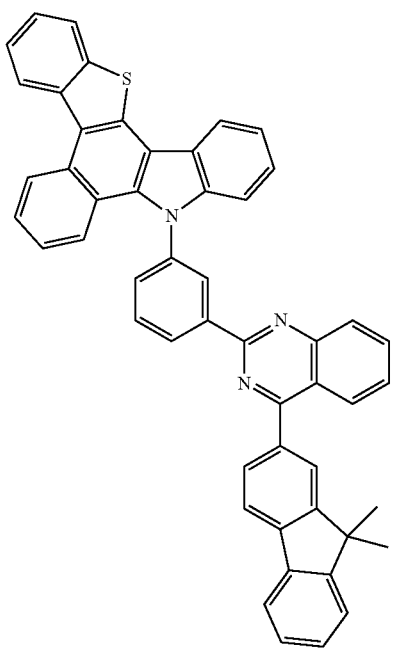

-continued
4-25
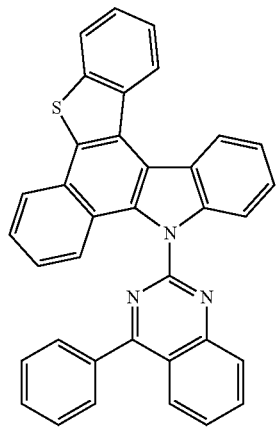
4-26
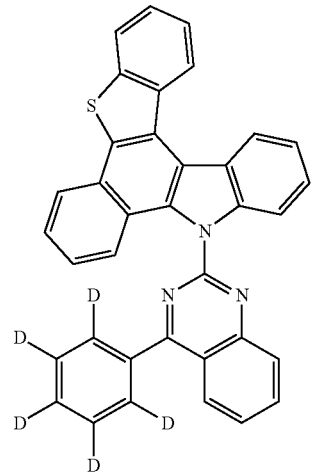
4-27
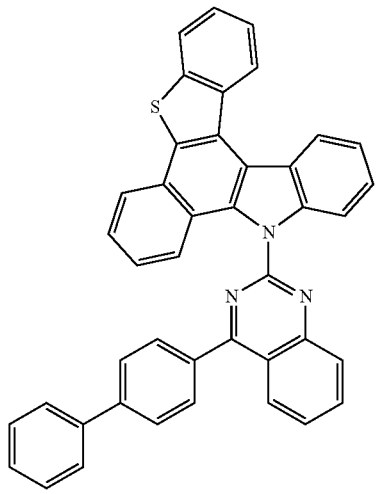
4-28
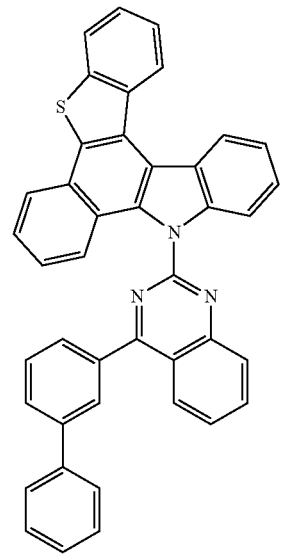
4-29
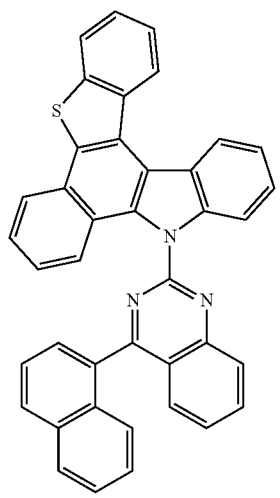
4-30
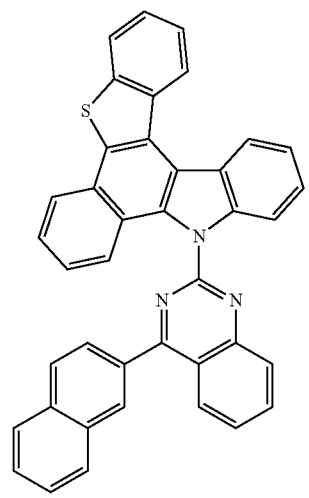

-continued
4-31
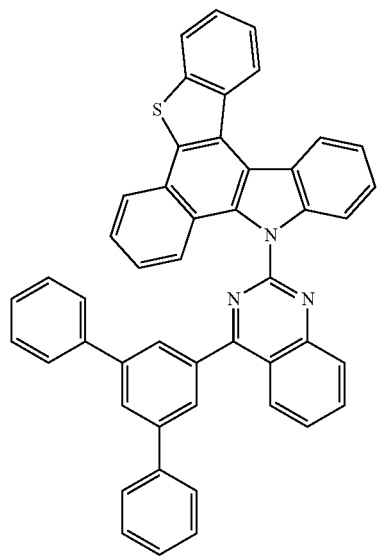
4-32
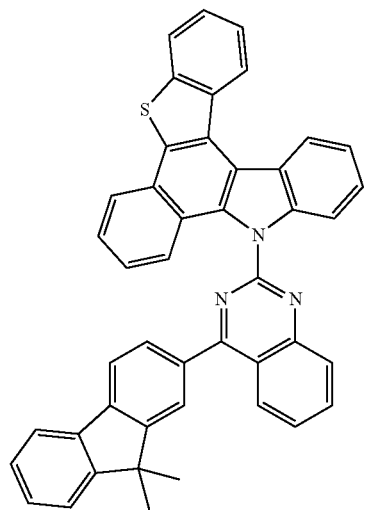
4-33
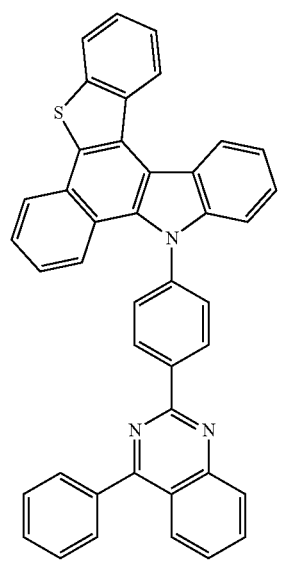
4-34
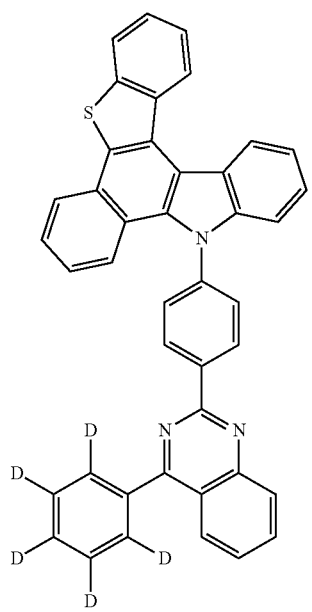

-continued
4-35
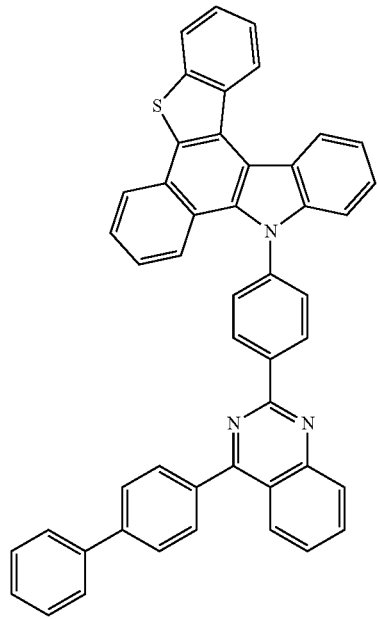
4-36
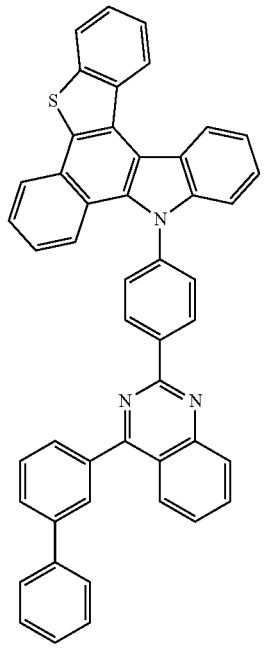
4-37
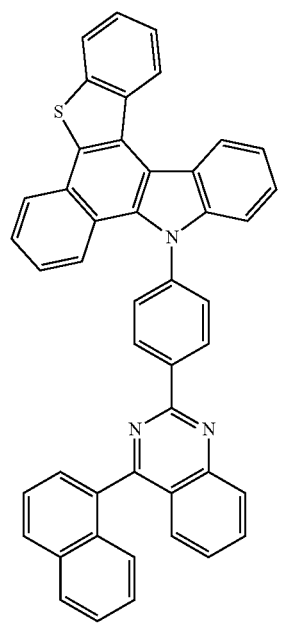
4-38
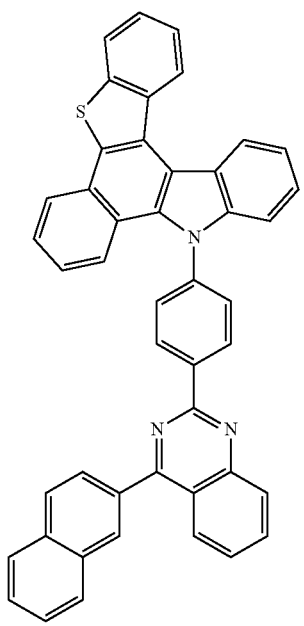

-continued
4-39
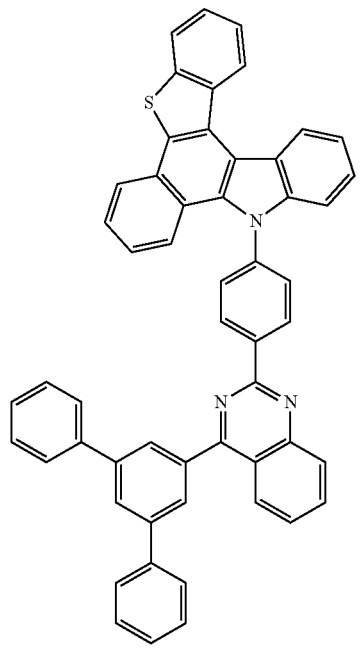
4-40
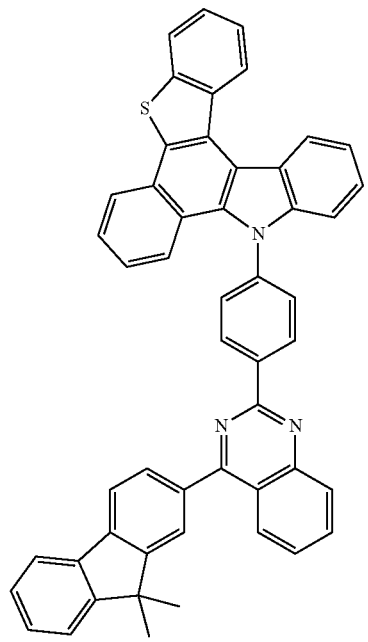
4-41
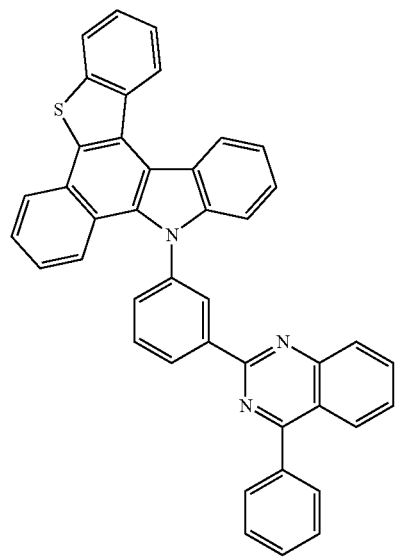
4-42
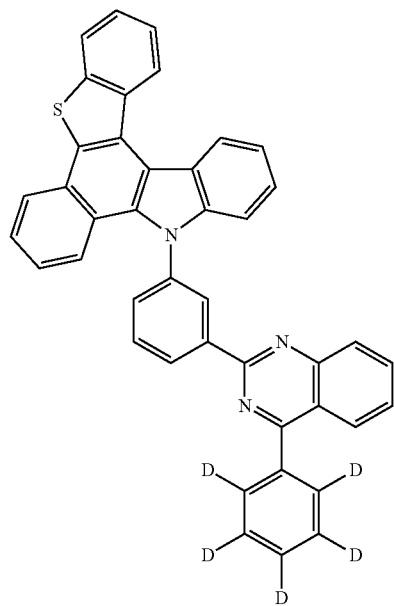

-continued
4-43
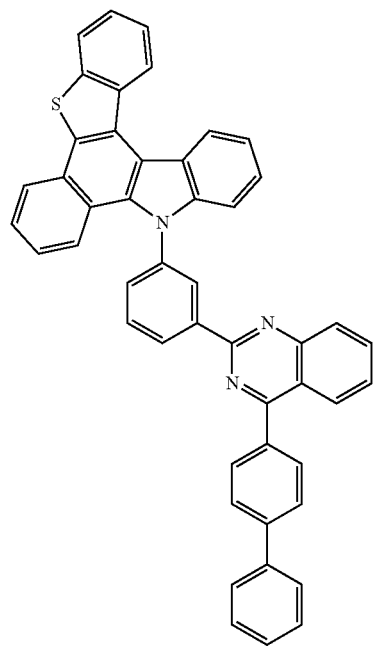
4-44
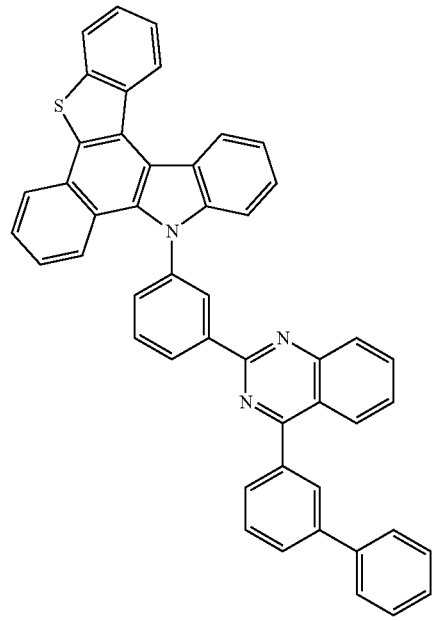
4-45
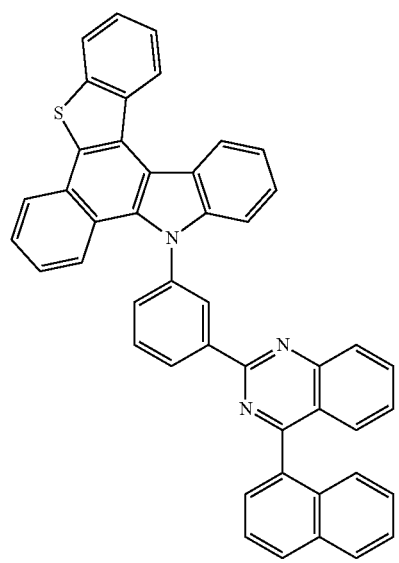
4-46
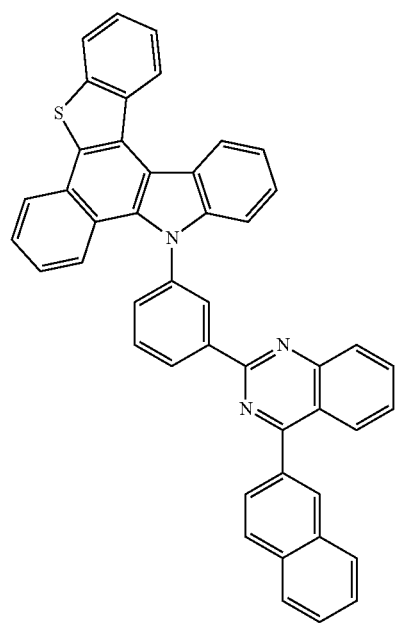

-continued
4-47
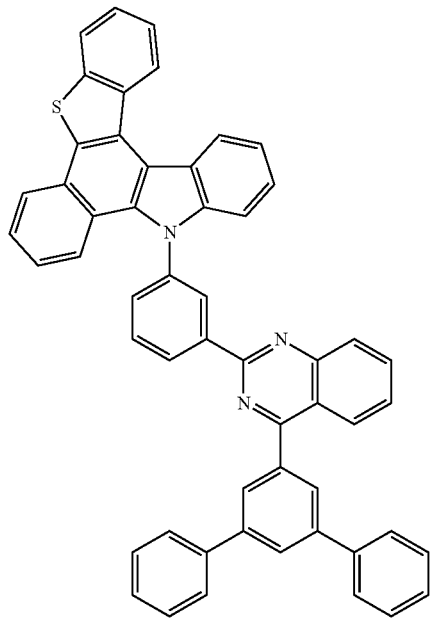
4-48
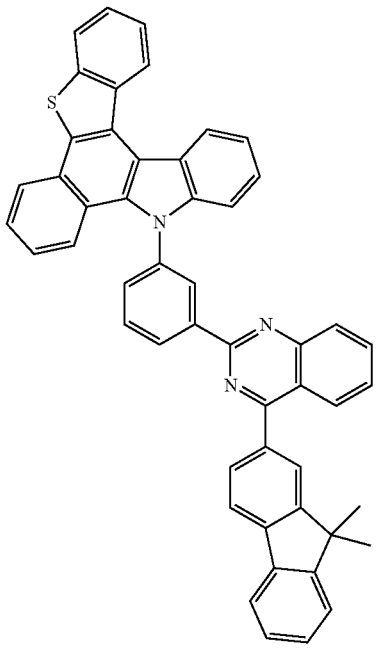
5-1
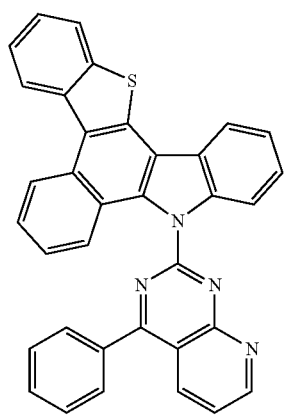
5-2
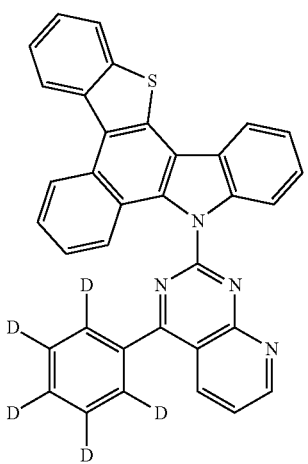
5-3
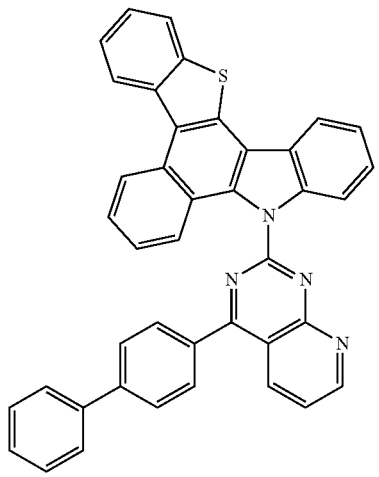
5-4
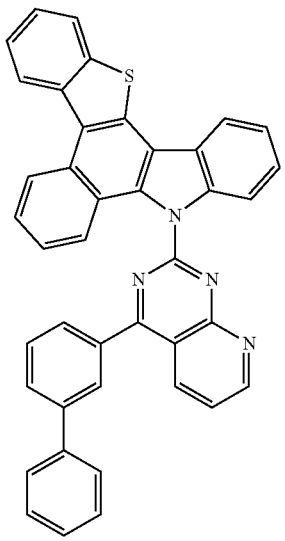

-continued
5-5
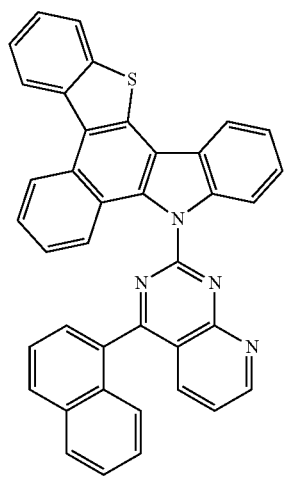
5-6
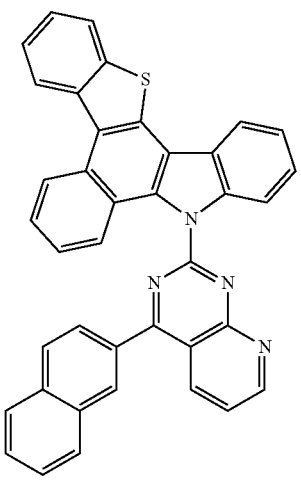
5-7
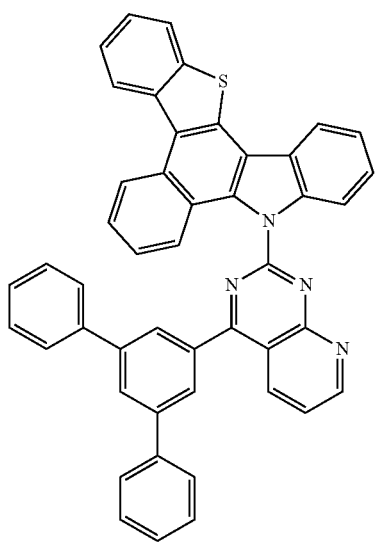
5-8
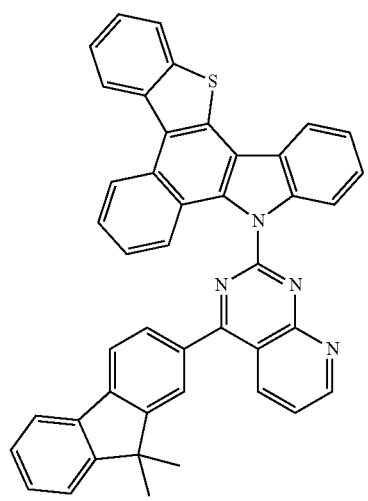
5-9
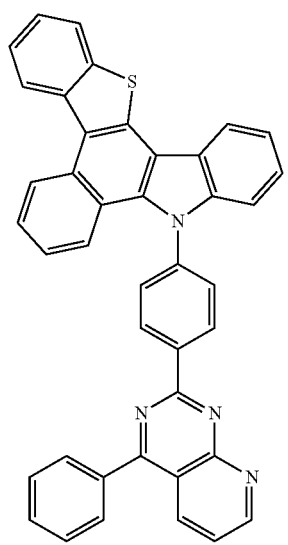
5-10
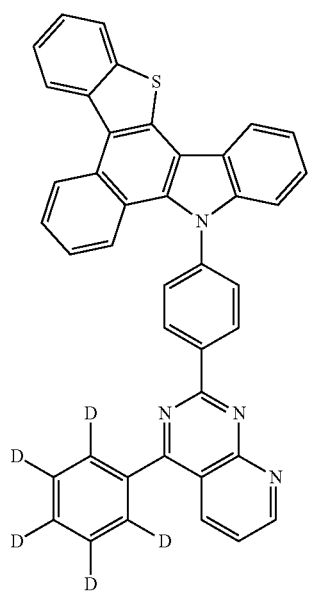

-continued
5-11
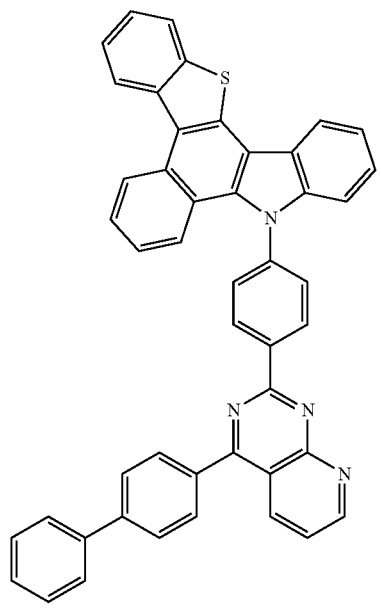
5-12
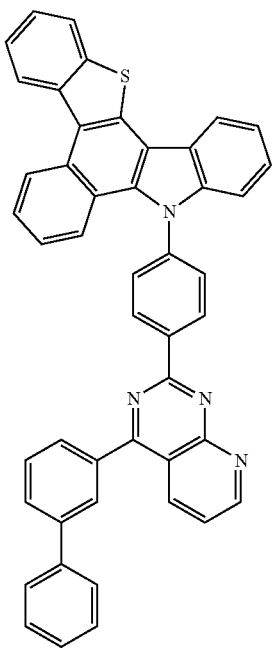
5-13
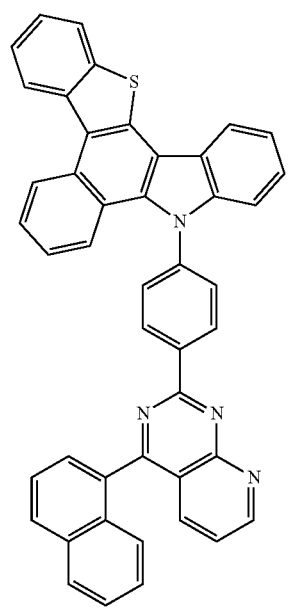
5-14
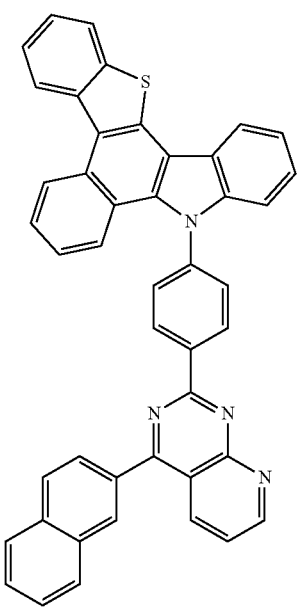

5-15
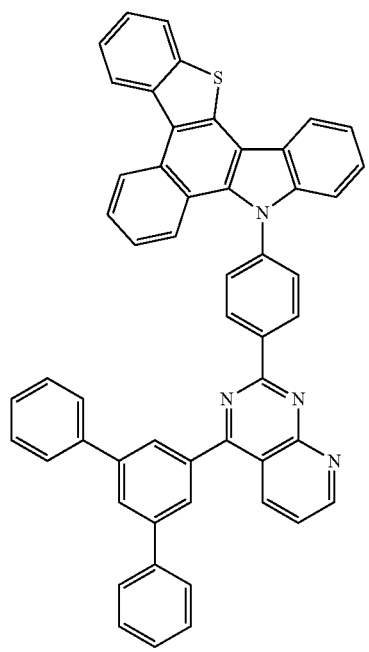
5-16
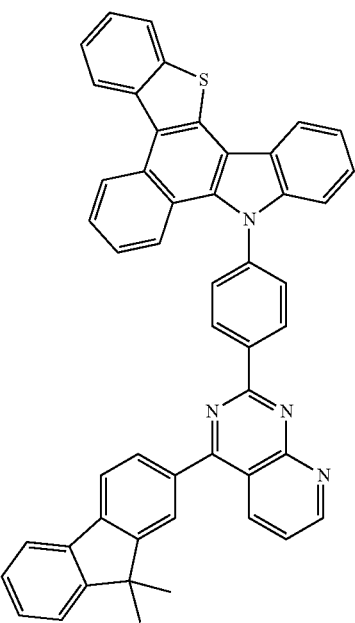
5-17
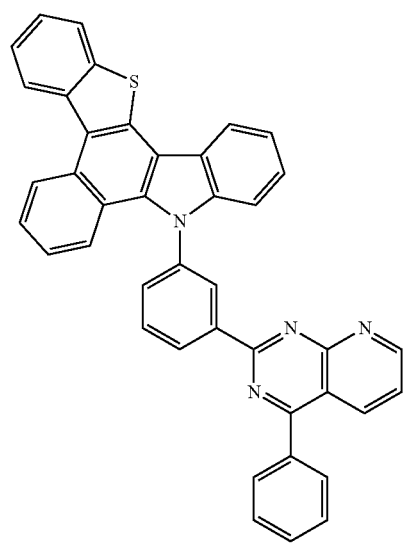
5-18
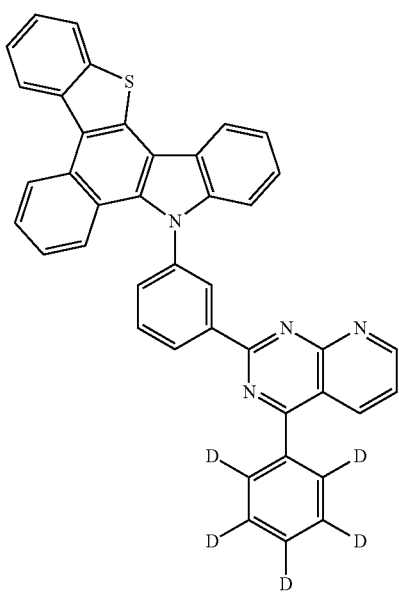

-continued
5-19
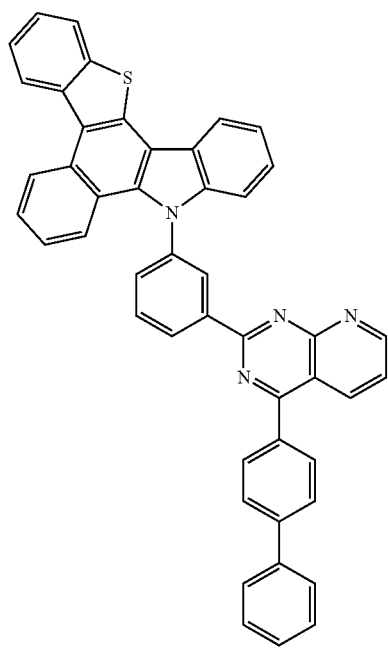
5-20
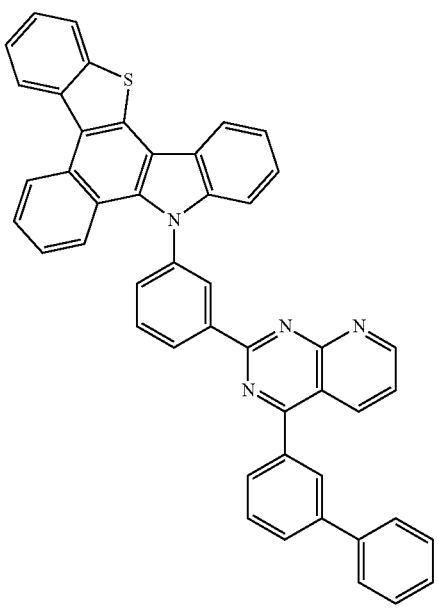
5-21
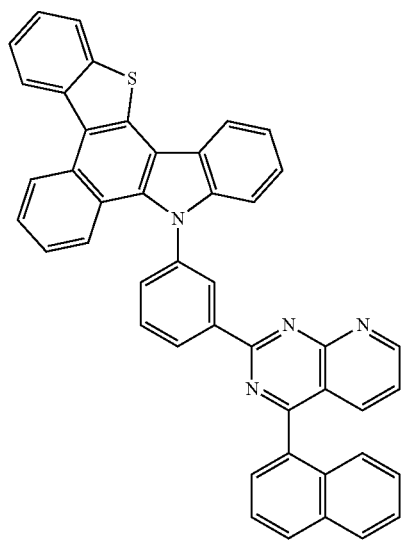
5-22
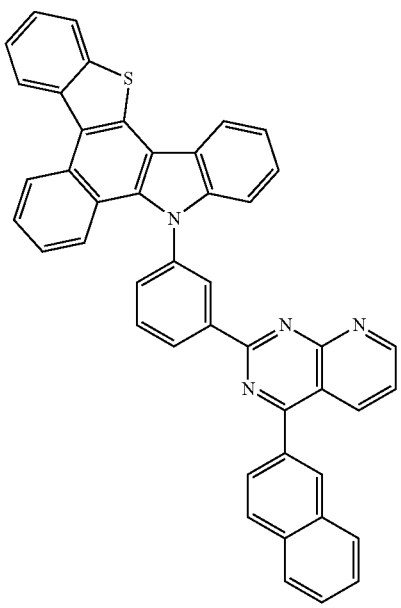

5-23
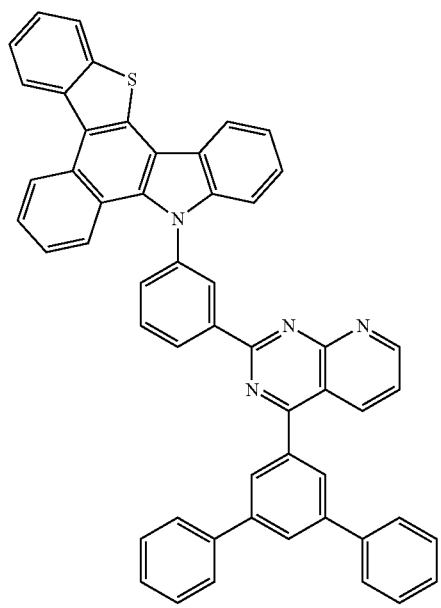
5-24
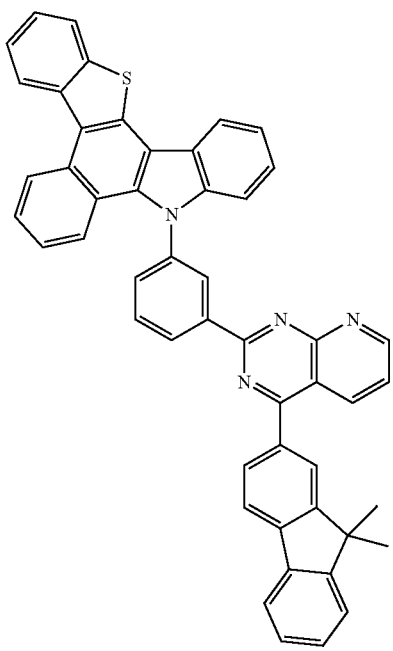
5-25
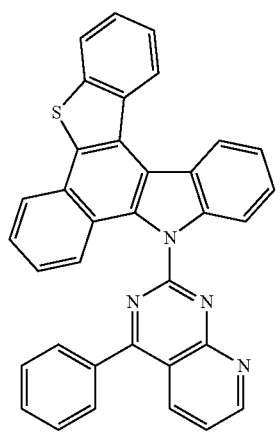
5-26
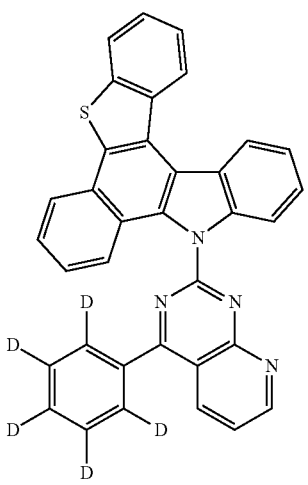

-continued
5-27
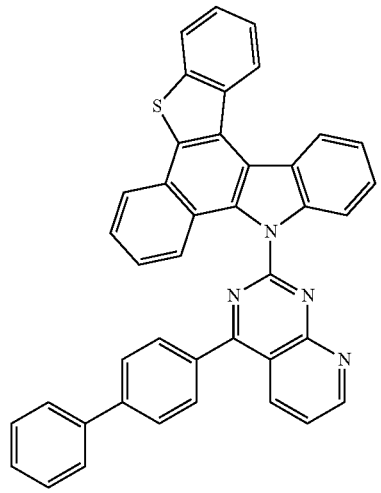
5-28
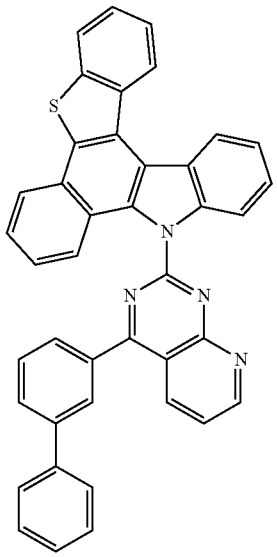
5-29
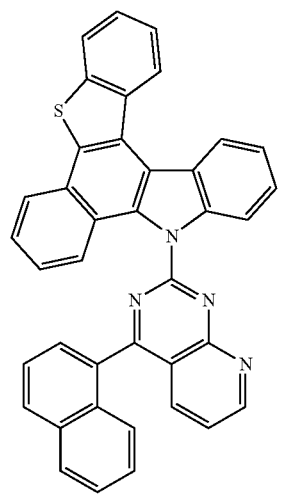
5-30
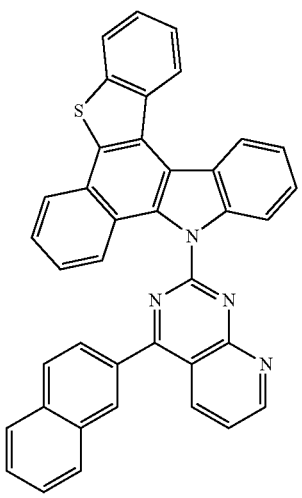
5-31
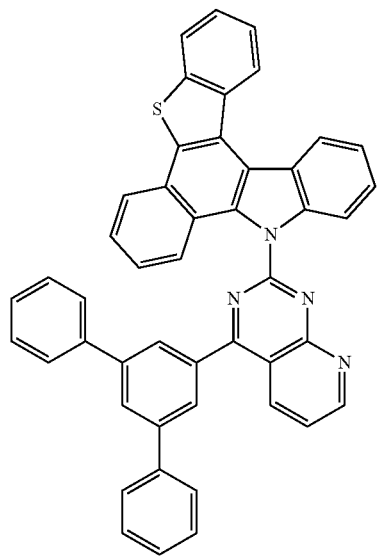
5-32
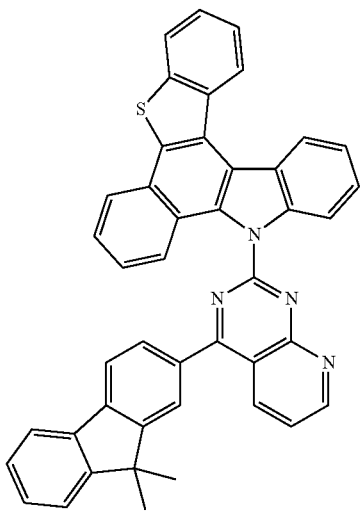

-continued
5-33
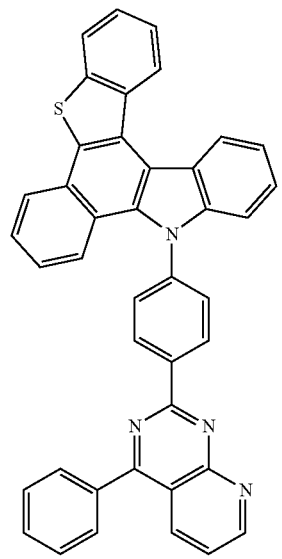
5-34
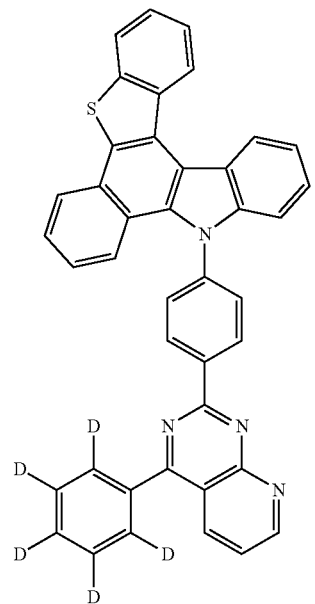
5-35
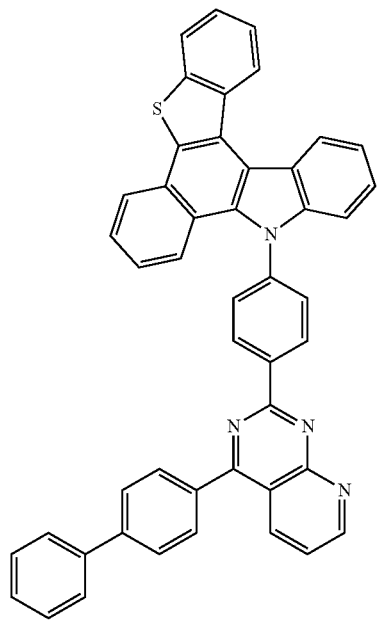
5-36
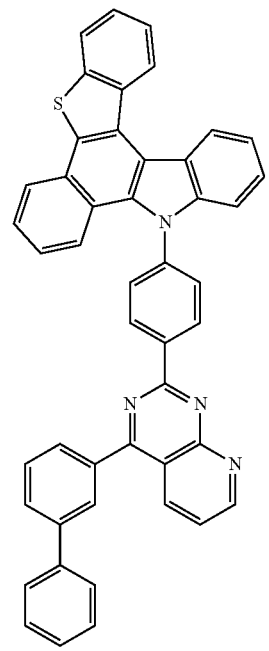

-continued
5-37
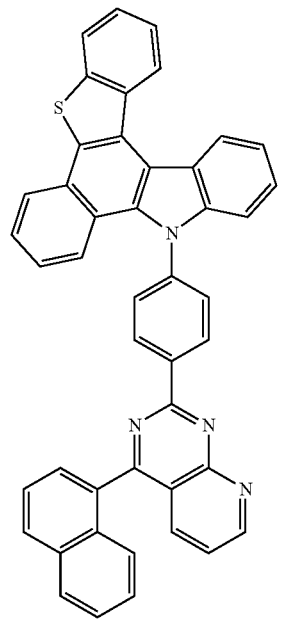
5-38
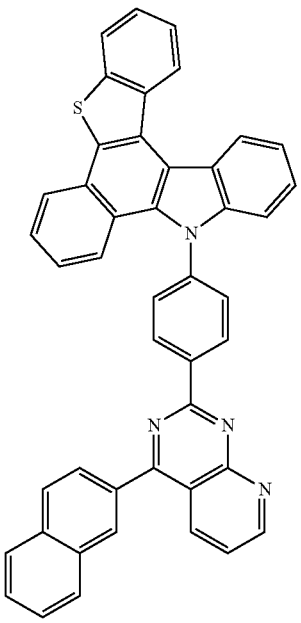
5-39
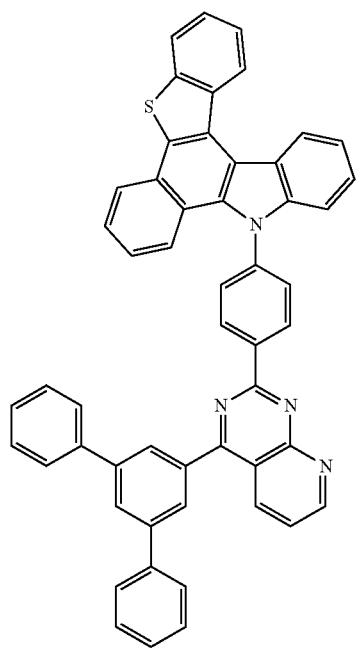
5-40
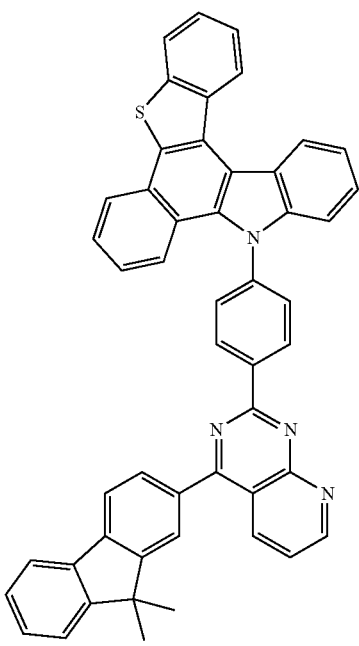

-continued
5-41
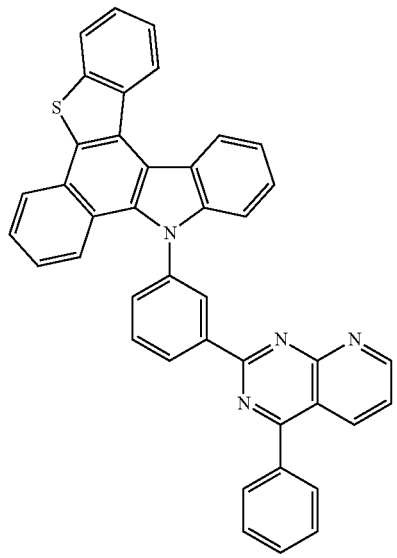
5-42
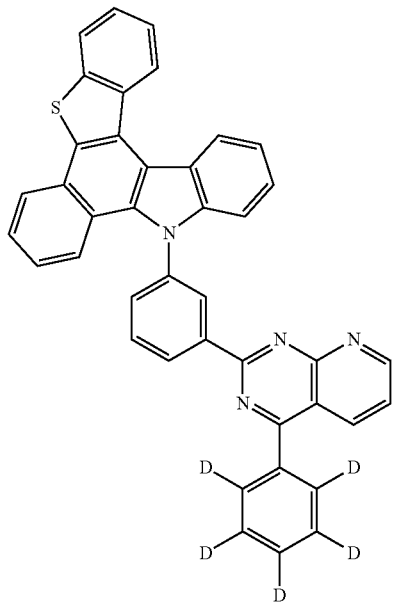
5-43
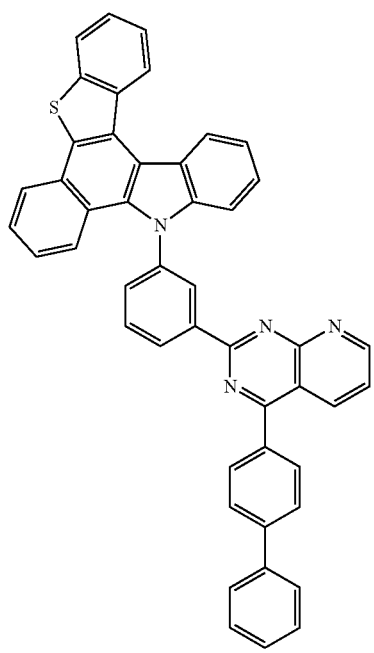
5-44
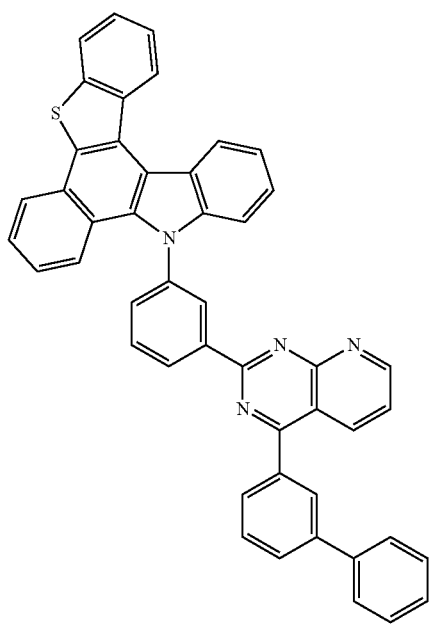

-continued
5-45
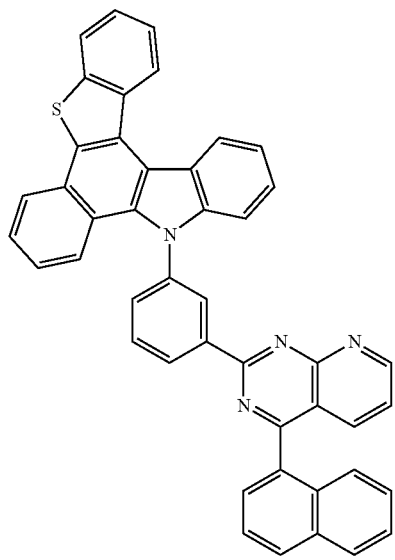
5-46
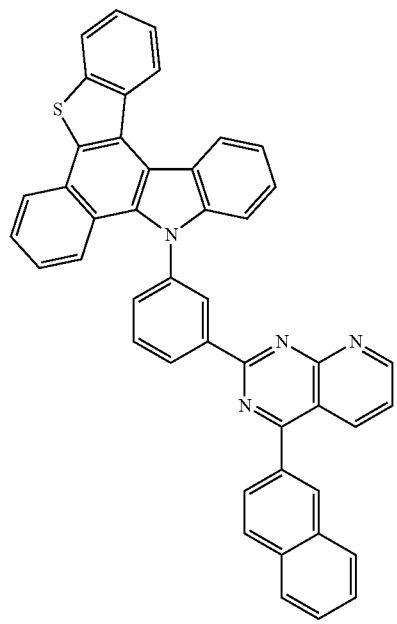
5-47
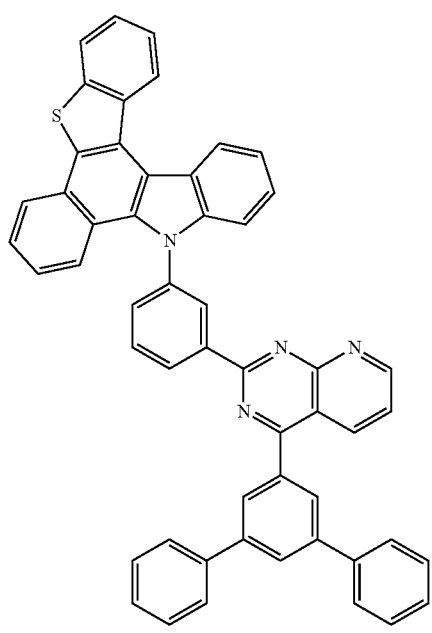
5-48
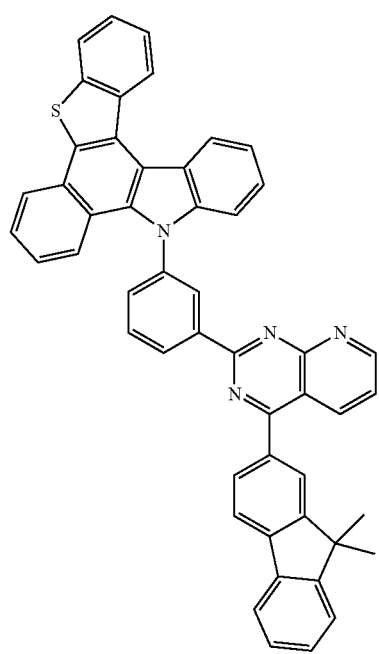

-continued
6-1
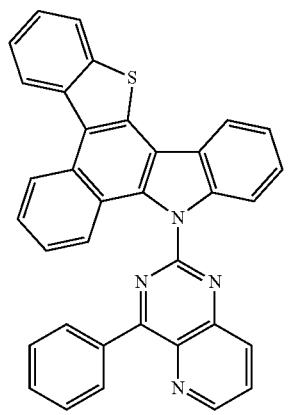
6-2
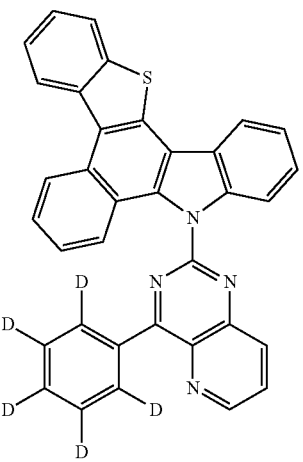
6-3
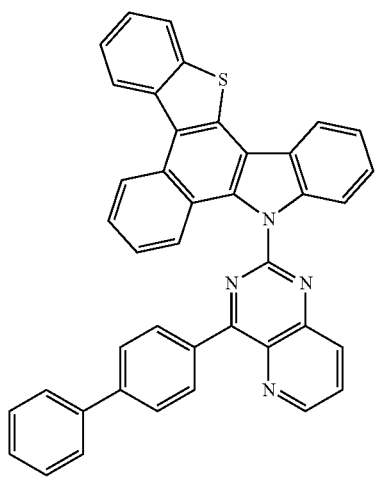
6-4
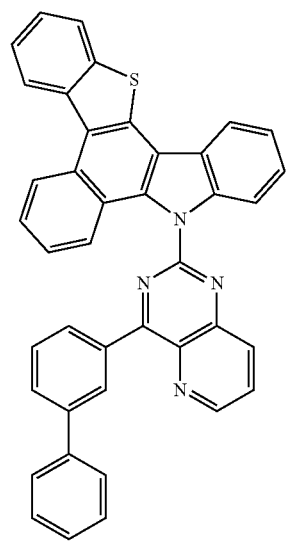
6-5
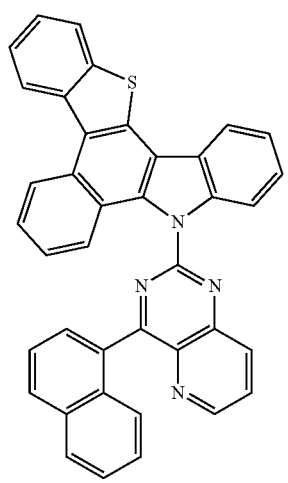
6-6
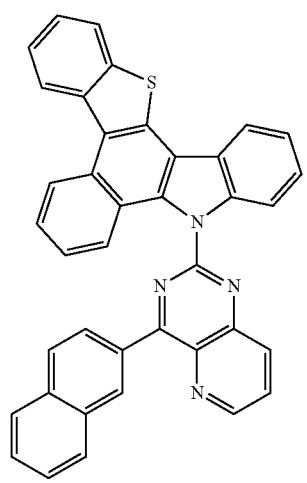

6-7
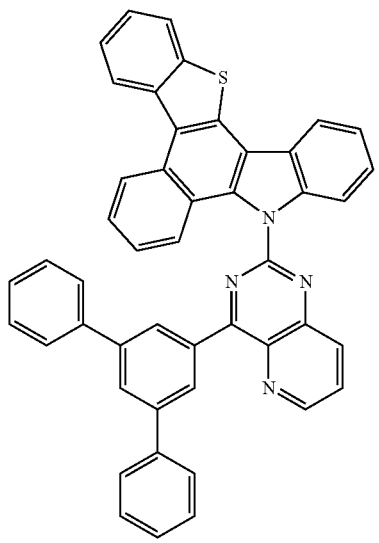
6-8
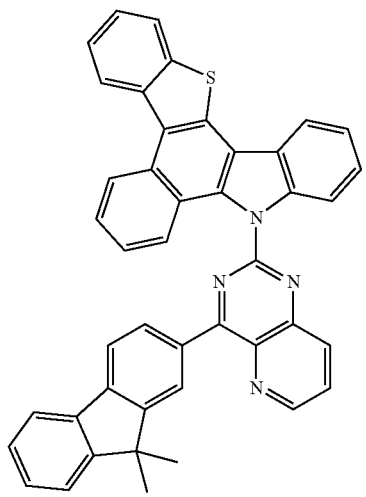
6-9
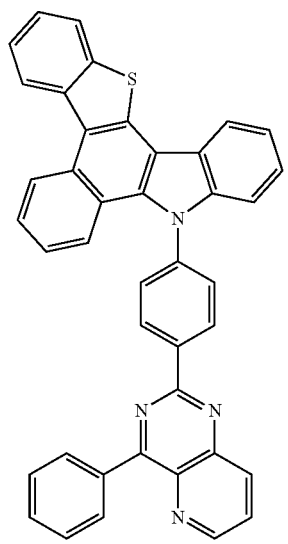
6-10
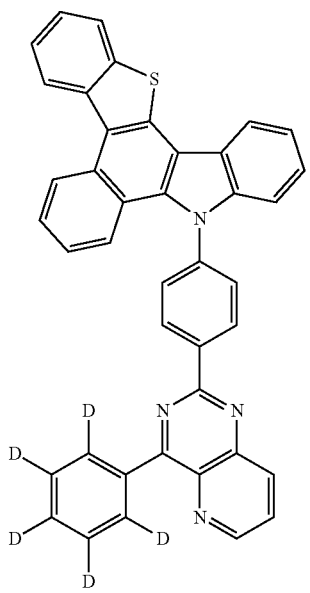

-continued
6-11
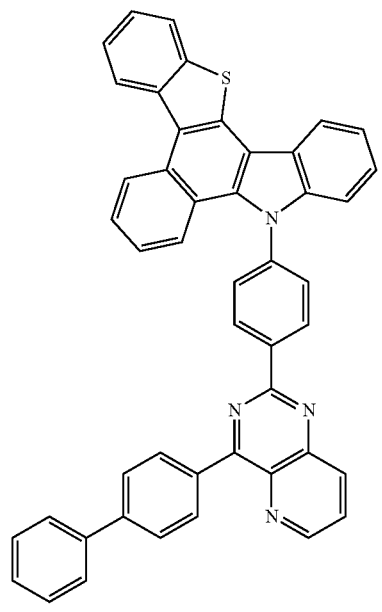
6-12
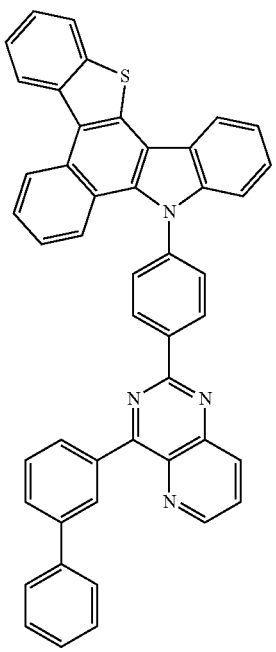
6-13
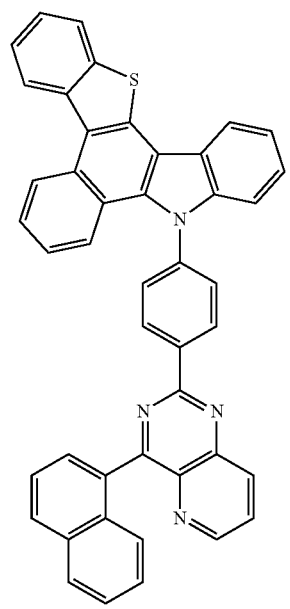
6-14
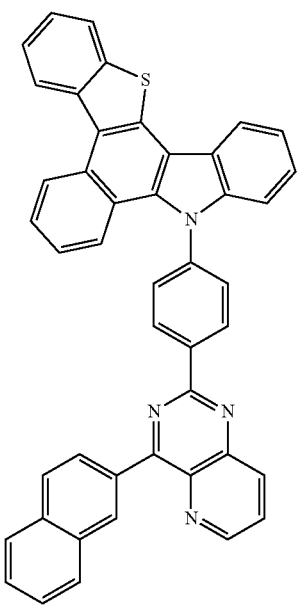

-continued
6-15
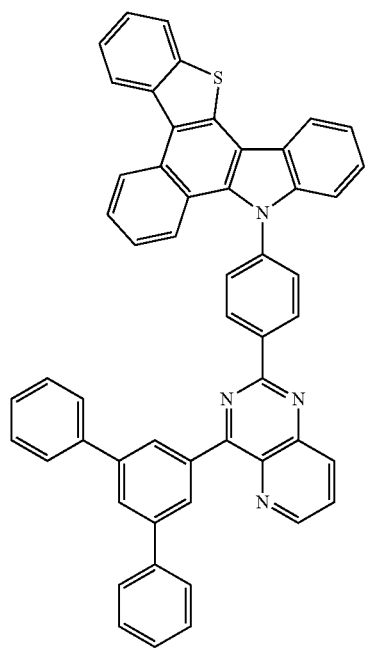
6-16
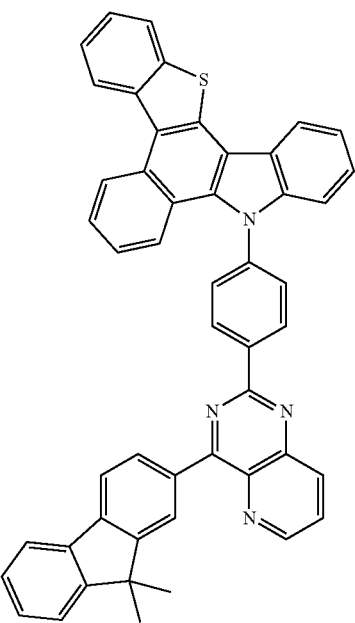
6-17
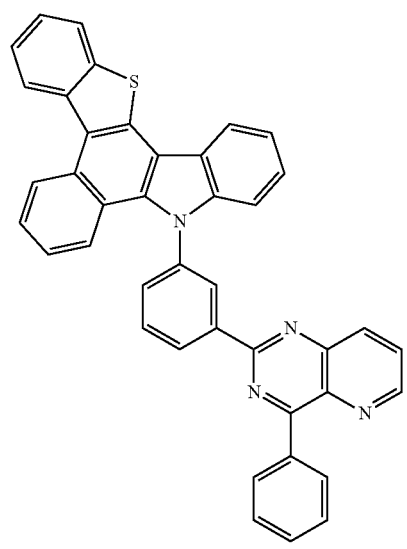
6-18
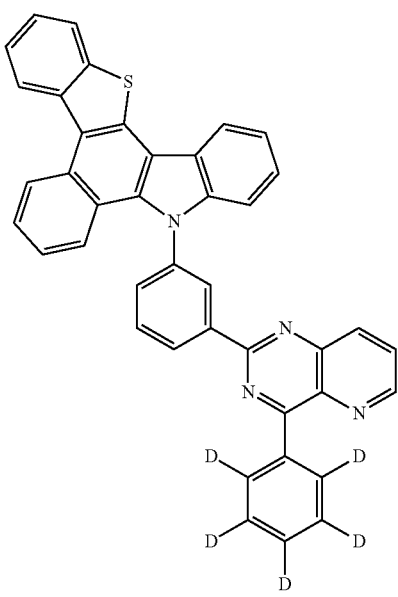

-continued
6-19
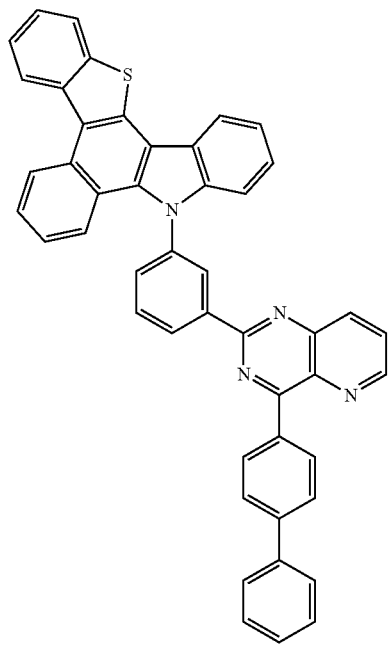
6-20
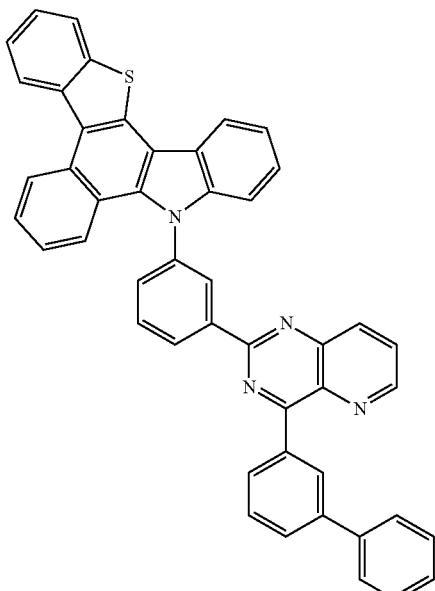
6-21
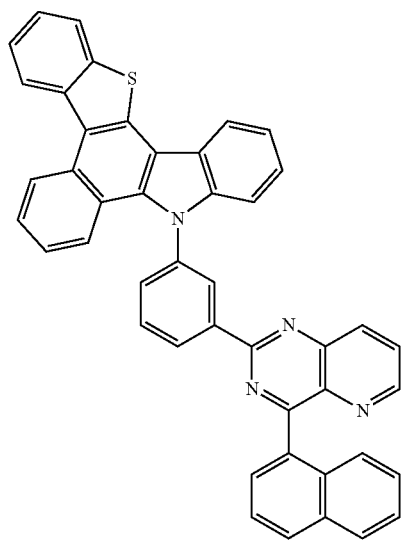
6-22
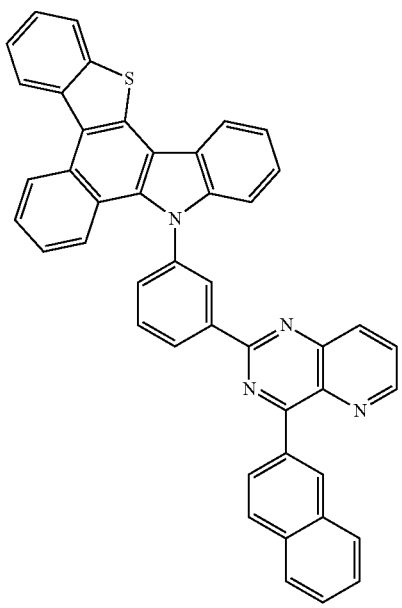

6-23
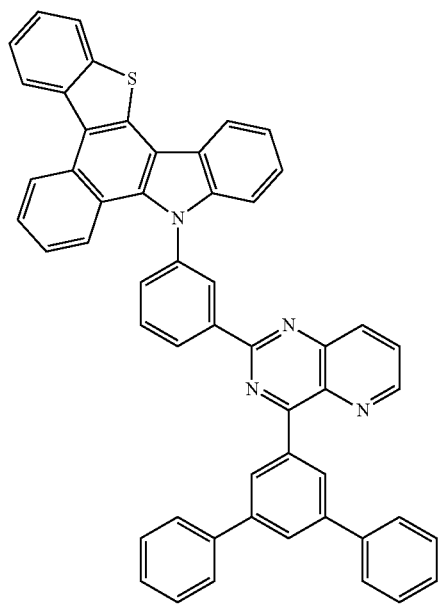
6-24
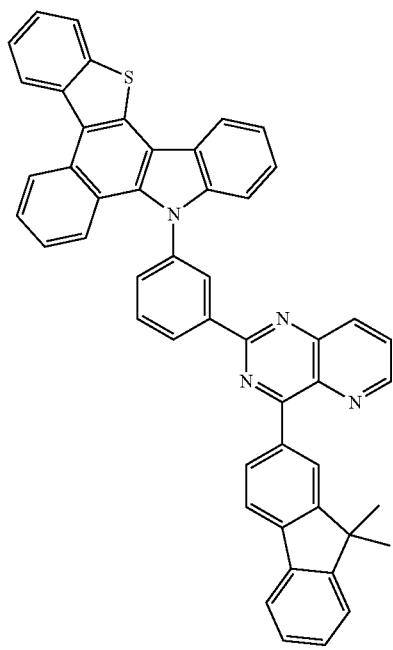
6-25
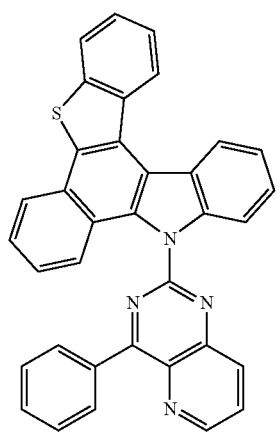
6-26
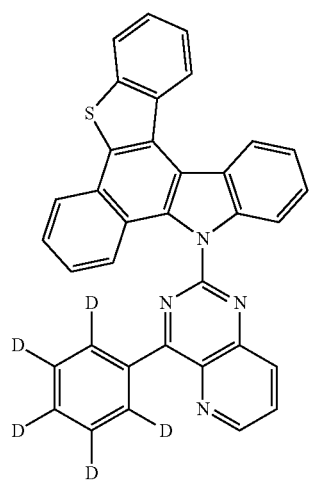

-continued
6-27
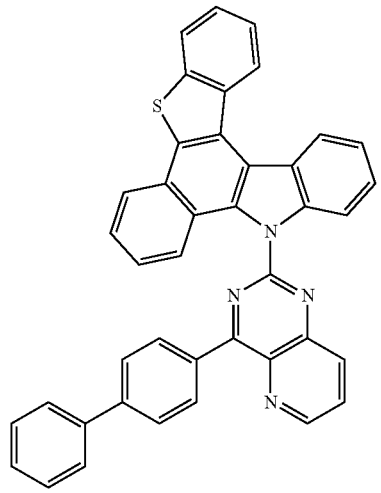
6-28
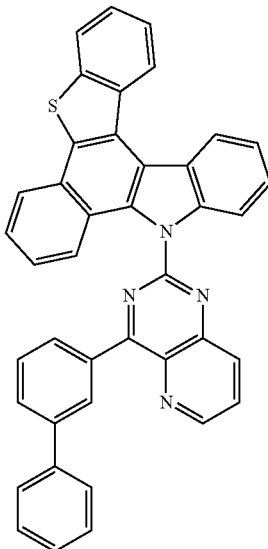
6-29
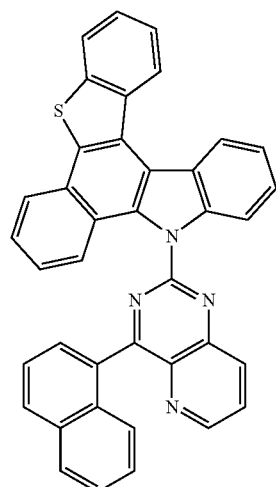
6-30
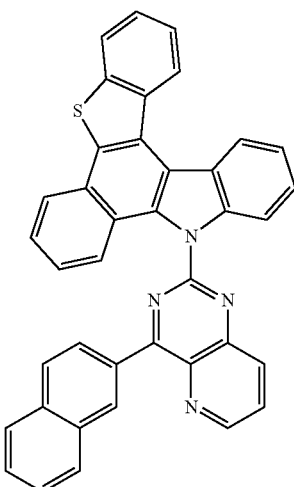
6-31
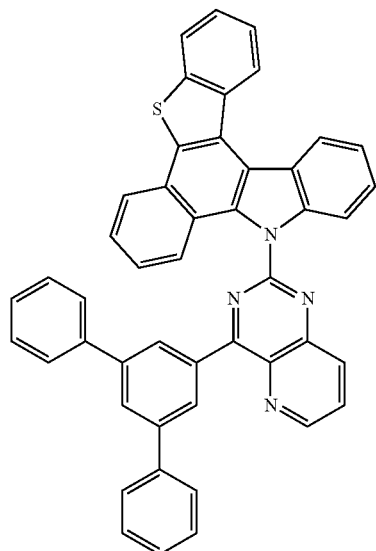
6-32
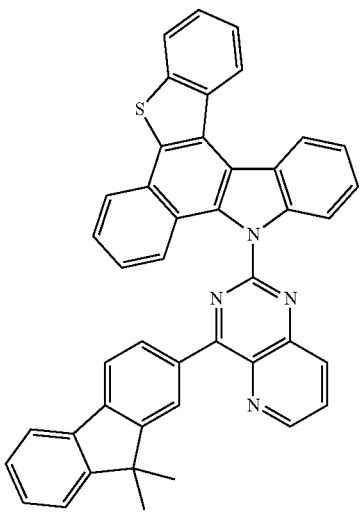

-continued
6-33
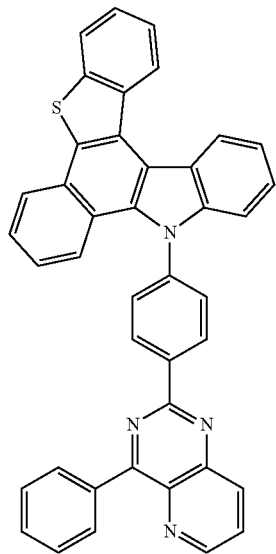
6-34
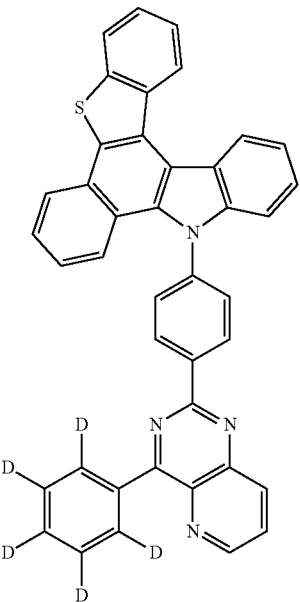
6-35
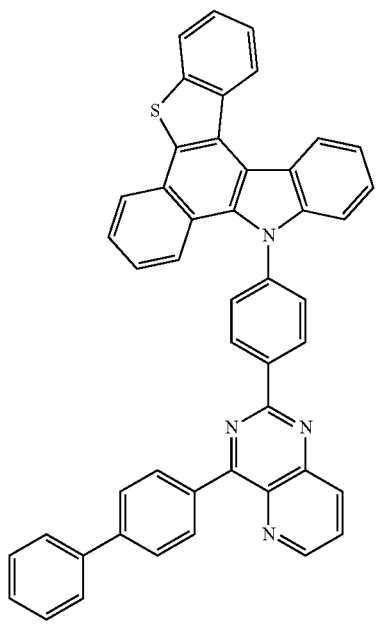
6-36
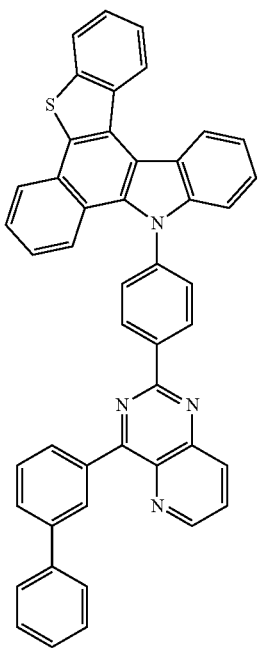

6-37
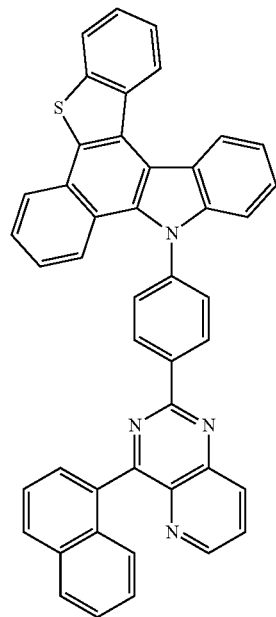
6-38
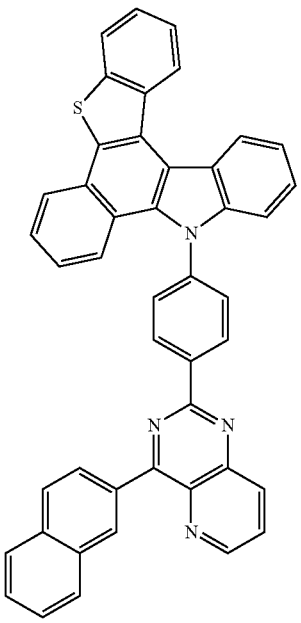
6-39
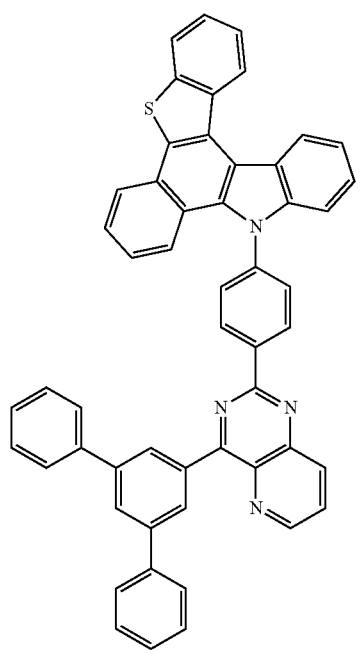
6-40
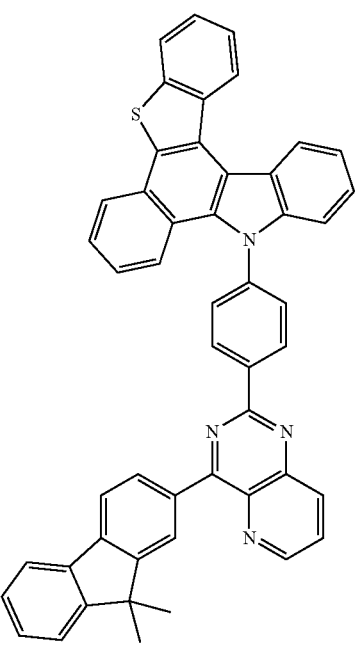

6-41
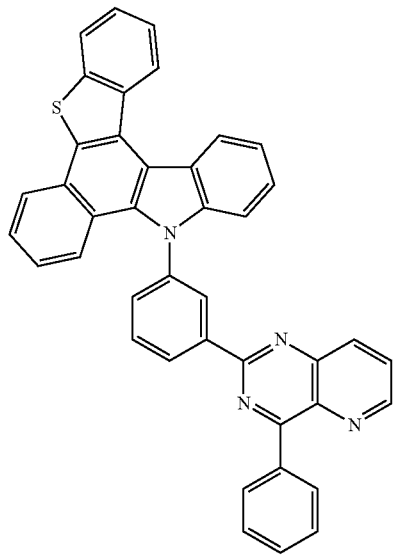
6-42
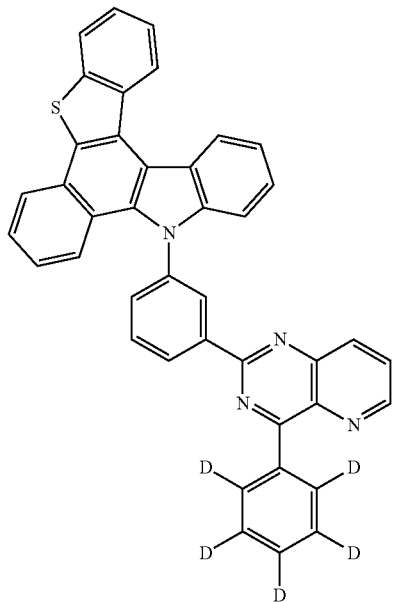
6-43
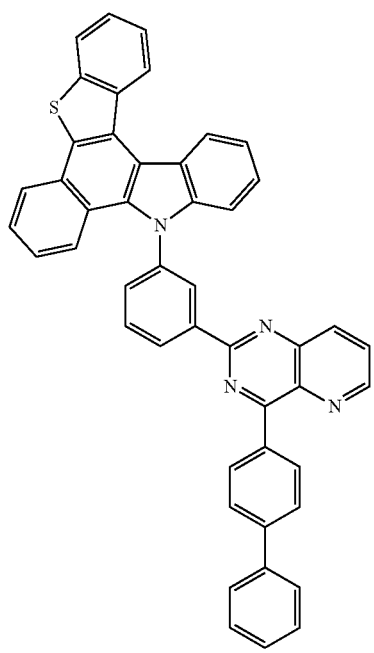
6-44
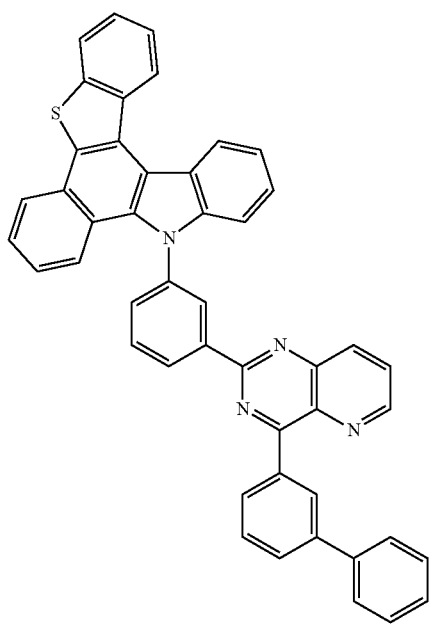

6-45

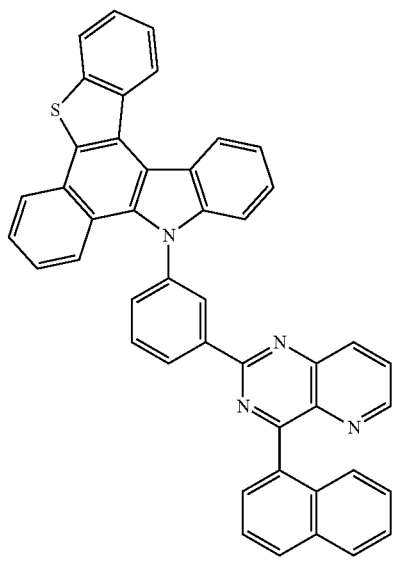

6-46

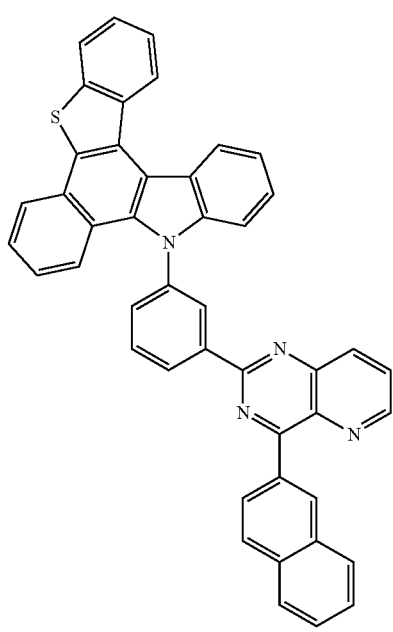

6-47

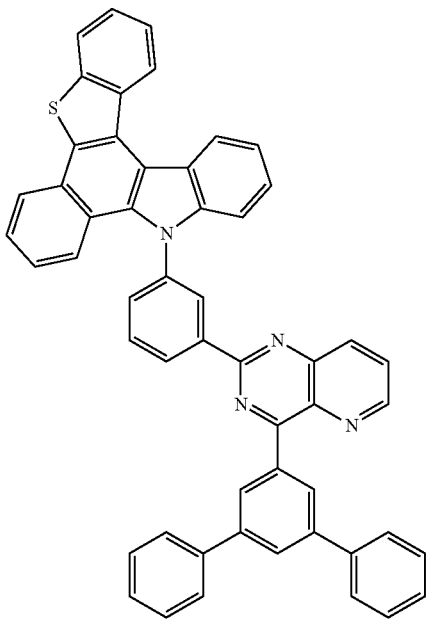

6-48

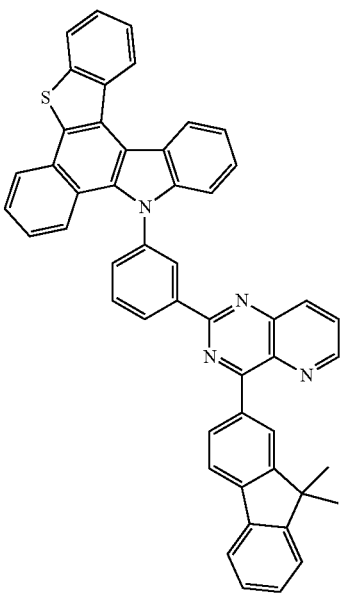

Hereinafter, the present invention will be described in more detail through Synthesis Examples of the inventive compound represented by Formula 1 above and Preparation Examples of an organic electronic element. However, the following examples are only for illustrative purposes and are not intended to limit the scope of the invention.

Synthesis Example

By way of example, the inventive compound is prepared by reacting one of Sub 1 to Sub 12 and Sub 13, as represented in Reaction Scheme 1 below. Although the following synthesis methods will be described by exemplifying the case where X is S, synthesis is carried out in the same manner as in the following synthesis method even when X is O or Si, so a separate description thereof will be omitted. In the following Synthesis Example, $R_1$ corresponds to $R_1$ to $R_4$ of Formula 1, $R_2$ corresponds to $R_7$ to $R_{10}$ of Formula 1, and $R_3$ corresponds to $R_5$ and $R_6$ of Formula 1.
<Reaction Scheme 1>
[Method 1]
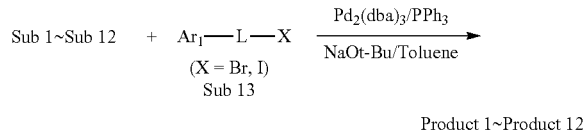
[Method 2]
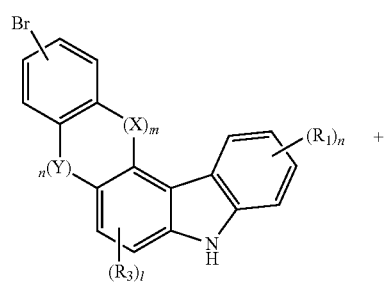
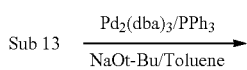
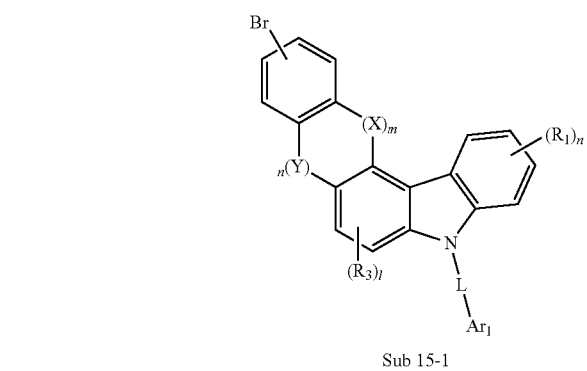
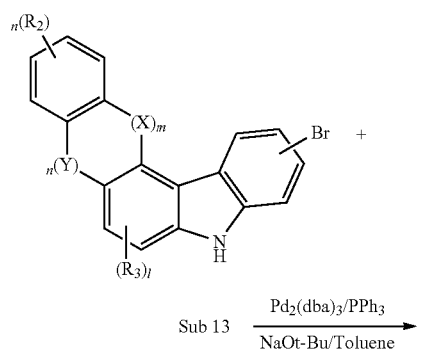
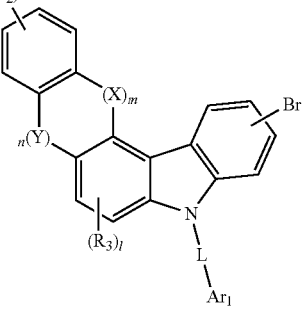
Sub 15-2
[Method 2-1]
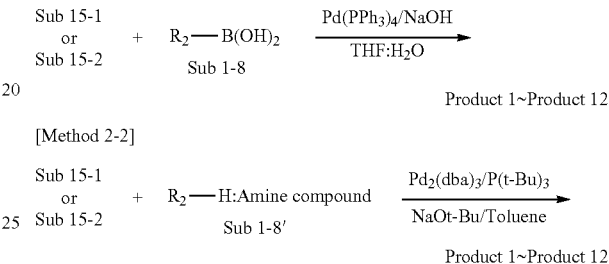
[Method 2-2]
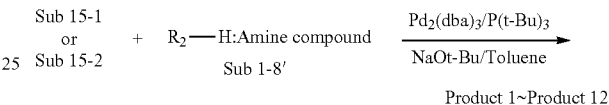
Sub 1 to Sub 12 of Reaction Scheme 1 may be synthesized by synthesis methods below.
Example 1
Synthesis Example of Sub 1
<Reaction Scheme 2>
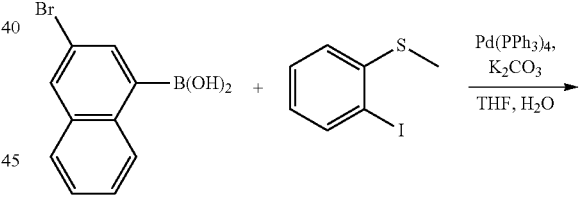
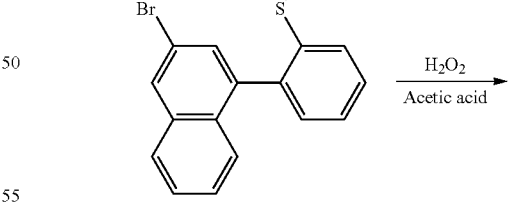
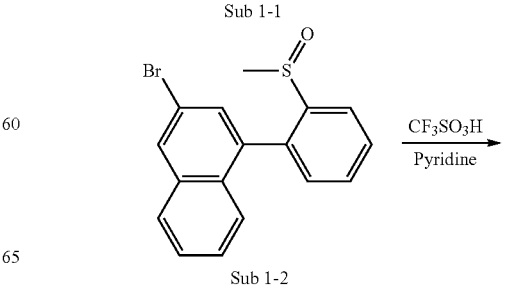

-continued

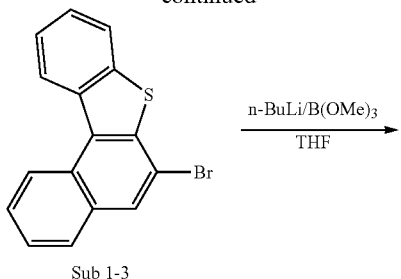

Sub 1-3

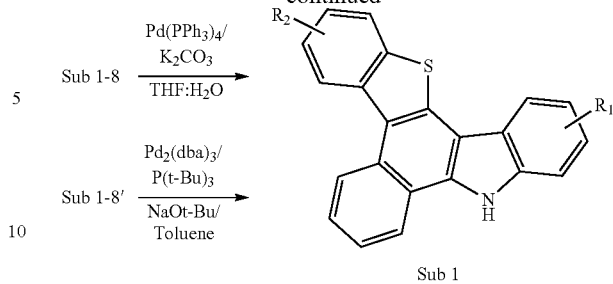

Sub 1

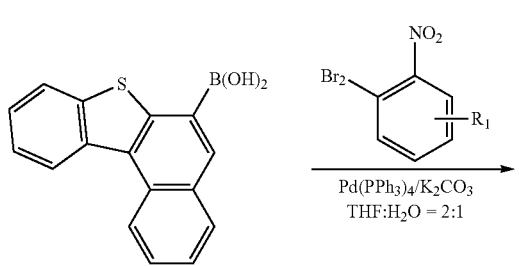

Sub 1-4

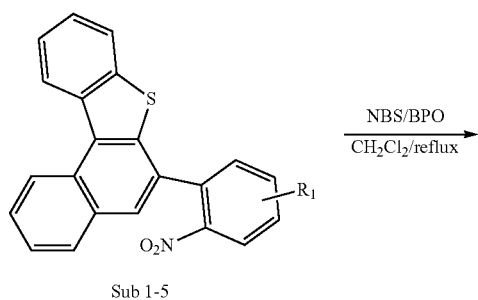

Sub 1-5

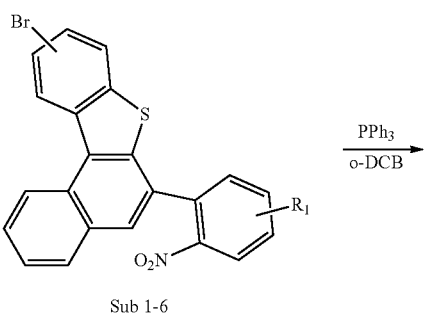

Sub 1-6

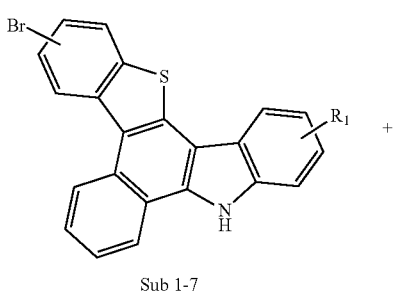

Sub 1-7

(1) Synthesis Method of Sub 1-1

3-iodonaphthalene-1-boronic acid, (2-bromophenyl)(methyl)sulfane, Pd(PPh$_3$)$_4$, and K$_2$CO$_3$ were put into a round bottom flask, THF and water (2:1) as a reaction solvent were poured into the round bottom flask, and then the reactants were refluxed under stirring at 70° C. Upon completion of the reaction, the reaction product was extracted with CH$_2$Cl$_2$ and water, and then the extracted organic layer was dried with MgSO$_4$ and concentrated. Subsequently, the produced organic material was separated by a silica gel column and recrystallized to obtain product Sub 1-1 (yield: 68%).

(2) Synthesis Method of Sub 1-2

After Sub 1-1 and acetic acid were put into a round bottom flask, Sub 1-1 was dissolved in acetic acid, and a mixed solution of hydrogen peroxide and acetic acid was added dropwise to the reactants, followed by stirring at room temperature for 6 hours. Upon completion of the reaction, acetic acid was removed using a vacuum apparatus, and the product Sub 1-2 was obtained using a silica gel column (yield: 69%).

(3) Synthesis Method of Sub 1-3

Sub 1-2 and trifluoromethanesulfonic acid were put into a round bottom flask, the reactants were stirred at room temperature for 24 hours, water and pyridine (8:1) were added dropwise to the reactants, and then the reactants were refluxed for 30 minutes. The temperature of the reaction product was lowered, the reaction product was extracted with CH$_2$Cl$_2$ and water, and then the extracted organic layer was dried with MgSO$_4$ and concentrated. Subsequently, the produced organic material was separated by a silica gel column to obtain product Sub 1-3 (yield: 67%).

(4) Synthesis Method of Sub 1-4

After Sub 1-3 and anhydrous THF were put into a round bottom flask, Sub 103 was dissolved in anhydrous THF, the temperature of the reaction flask was lowered to −78° C., and then n-BuLi (2.5M in hexane) was added dropwise to the reactants. The reaction flask was stirred at 0° C. for 1 hour, the temperature of the reaction flask was lowered to −78° C., and trimethyl borate was added dropwise to the reactants, followed by stirring at room temperature for 12 hours. Upon completion of the reaction, the reaction product was added with 2N—HCl, was stirred for 30 minutes, and then was extracted with ether and water. The extracted organic layer was dried with MgSO$_4$ and concentrated, and then the produced organic material was separated by a silica gel column to obtain product Sub 1-4 (yield: 65%).

(5) Synthesis Method of Sub 1-5

Sub 1-4 and 1-bromo-2-nitrobenzene substituted by R$_1$, Pd(PPh$_3$)$_4$, and K$_2$CO$_3$ were put into a round bottom flask, THF and water (2:1) as a reaction solvent were poured into the round bottom flask, and then the reactants were refluxed under stirring for 24 hours. Upon completion of the reaction, the temperature of the reaction product was lowered to room temperature, the reaction product was extracted with CH$_2$Cl$_2$ and water, and then the extracted organic layer was dried with MgSO$_4$ and concentrated. Subsequently, the produced organic material was separated by a silica gel column to obtain product Sub 1-5 (yield: 63%).

(6) Synthesis Method of Sub 1-6

Sub 1-5 and NBS (N-bromosuccinimide) were put into a round bottom flask, and were dissolved in CH$_2$Cl$_2$, followed by reflux under stirring for 7 hours. Upon completion of the reaction, the temperature of the reaction product was lowered to room temperature, an aqueous NaHCO$_3$ solution was added to the reaction product, followed by stirring for 30 minutes. Subsequently, the reaction product was extracted with CH$_2$Cl$_2$ and water, the extracted organic layer was dried with MgSO$_4$ and concentrated, and then the produced organic material was separated by a silica gel column to obtain product Sub 1-6 (yield: 65%).

(7) Synthesis Method of Sub 1-7

Sub 1-6, PPh$_3$, and o-dichlorobenzene were put into a round bottom flask, and Sub 1-6 and PPh$_3$ were dissolved in o-dichlorobenzene, followed by reflux under stirring for 24 hours. Upon completion of the reaction, the solvent was removed using vacuum distillation, and then the concentrated product was separated by a silica gel column and recrystallized to obtain product Sub 1-7 (yield: 61%).

(8) Example of Sub 1-8

Examples of Sub 1-8 include, but not limited to, the following compounds.

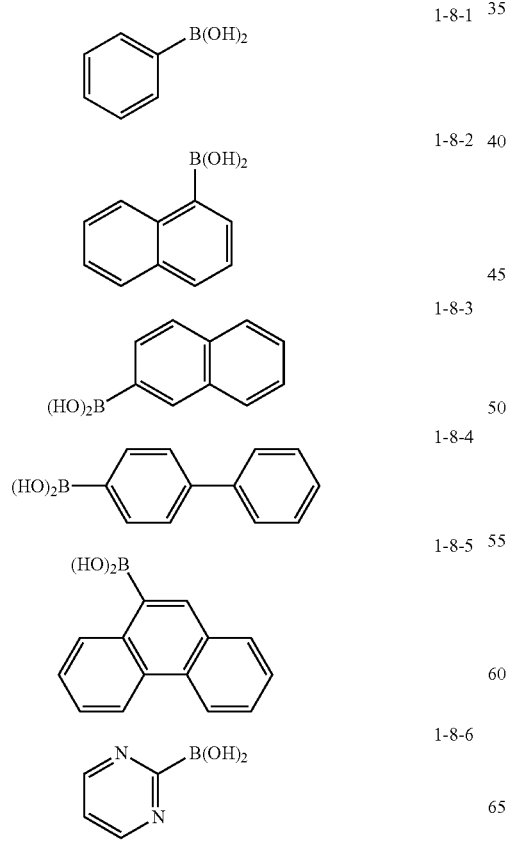

1-8-1

1-8-2

1-8-3

1-8-4

1-8-5

1-8-6

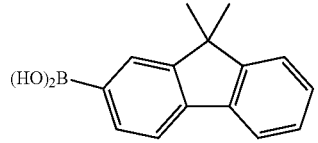

1-8-7

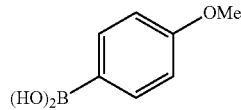

1-8-8

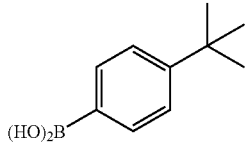

1-8-9

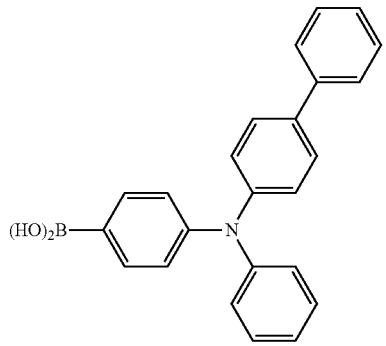

1-8-10

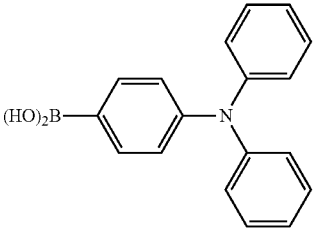

1-8-11

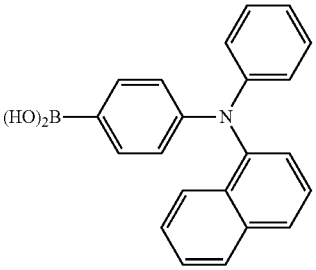

1-8-12

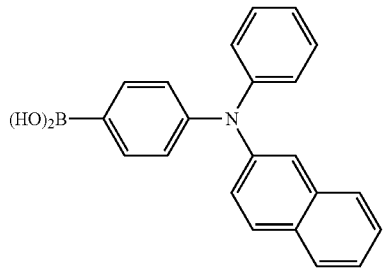

1-8-13

-continued 1-8-14

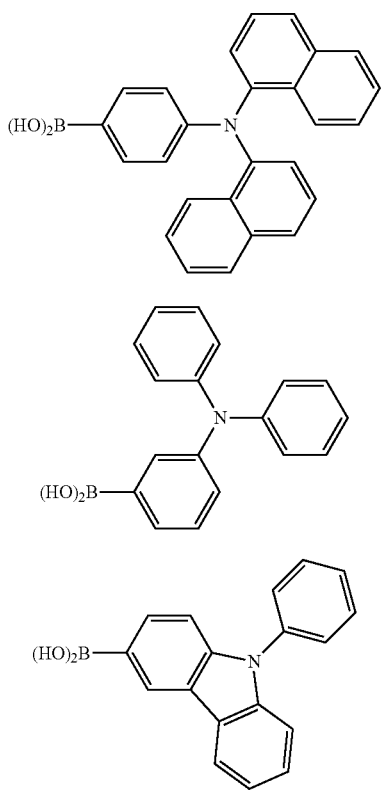

1-8-15

1-8-16

-continued 1-8'-1

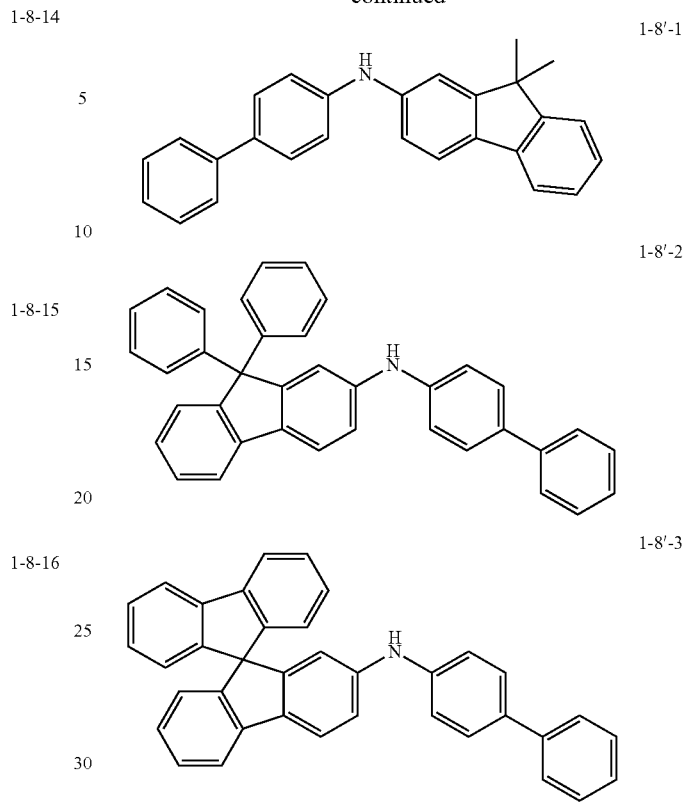

1-8'-2

1-8'-3

TABLE 1

| Compound | FD-MS | Compound | FD-MS |
| --- | --- | --- | --- |
| Sub 1-8-1 | m/z = 122.05($C_6H_7BO_2$ = 121.93) | Sub 1-8-2 | m/z = 172.07($C_{10}H_9BO_2$ = 171.99) |
| Sub 1-8-3 | m/z = 172.07($C_{10}H_9BO_2$ = 171.99) | Sub 1-8-4 | m/z = 198.09($C_{12}H_{11}BO_2$ = 198.0 3) |
| Sub 1-8-5 | m/z = 222.09($C_{14}H_{11}BO_2$ = 222.05) | Sub 1-8-6 | m/z = 124.04($C_4H_5BN_2O_2$ = 123.91) |
| Sub 1-8-7 | m/z = 238.12($C_{15}H_{15}BO_2$ = 238.09) | Sub 1-8-8 | m/z = 152.06($C_7H_9BO_3$ = 151.96) |
| Sub 1-8-9 | m/z = 178.12($C_{10}H_{15}BO_2$ = 178.04) | Sub 1-8-10 | m/z = 365.16($C_{24}H_{20}BNO_2$ = 365.23) |
| Sub 1-8-11 | m/z = 289.13($C_{18}H_{16}BNO_2$ = 289.14) | Sub 1-8-12 | m/z = 339.14($C_{22}H_{18}BNO_2$ = 339.19) |
| Sub 1-8-13 | m/z = 339.14($C_{22}H_{18}BNO_2$ = 339.19) | Sub 1-8-14 | m/z = 389.16($C_{25}H_{20}BNO_2$ = 389.25) |
| Sub 1-8-15 | m/z = 289.13($C_{18}H_{16}BNO_2$ = 289.14) | Sub 1-8-16 | m/z = 287.11($C_{18}H_{14}BNO_2$ = 287.12) |
| Sub 1-8'-1 | m/z = 361.18($C_{27}H_{23}N$ = 361.48) | Sub 1-8'-2 | m/z = 485.21 ($C_{37}H_{27}N$ = 485.62) |
| Sub 1-8'-3 | m/z = 483.20($C_{37}H_{25}N$ = 483.60) | | |

(9) Synthesis Method of Sub 1 (Using Sub 1-8)

Compound Sub 1-7 (1 equivalent weight), compound Sub 1-8 (1.1 equivalent weight), Pd(PPh$_3$)$_4$ (0.03 equivalent weight), NaOH (3 equivalent weight), and water were put into a round bottom flask, and then the reactants were refluxed under stirring. Upon completion of the reaction, the reaction product was extracted with ether and water, the extracted organic layer was dried with MgSO$_4$ and concentrated, and then the produced organic material was separated by a silica gel column and recrystallized to obtain product Sub 1.

(10) Synthesis Method of Sub 1 (Using Sub 1-8')

Compound Sub 1-7 (1.1 equivalent weight), compound Sub 1-8' (1 equivalent weight), Pd$_2$(dba)$_3$ (0.04 equivalent weight), P(t-Bu)$_3$ (0.1 equivalent weight), NaOt-Bu (3 equivalent weight), and toluene (10.5 mL/1 mmol) were put into a round bottom flask, and then the reactants were subjected to the reaction at 100° C. Upon completion of the reaction, the reaction product was extracted with ether and water, the extracted organic layer was dried with MgSO$_4$ and concentrated, and then the produced organic material was separated by a silica gel column and recrystallized to obtain product Sub 1.

Example 2

Synthesis Example of Sub 2

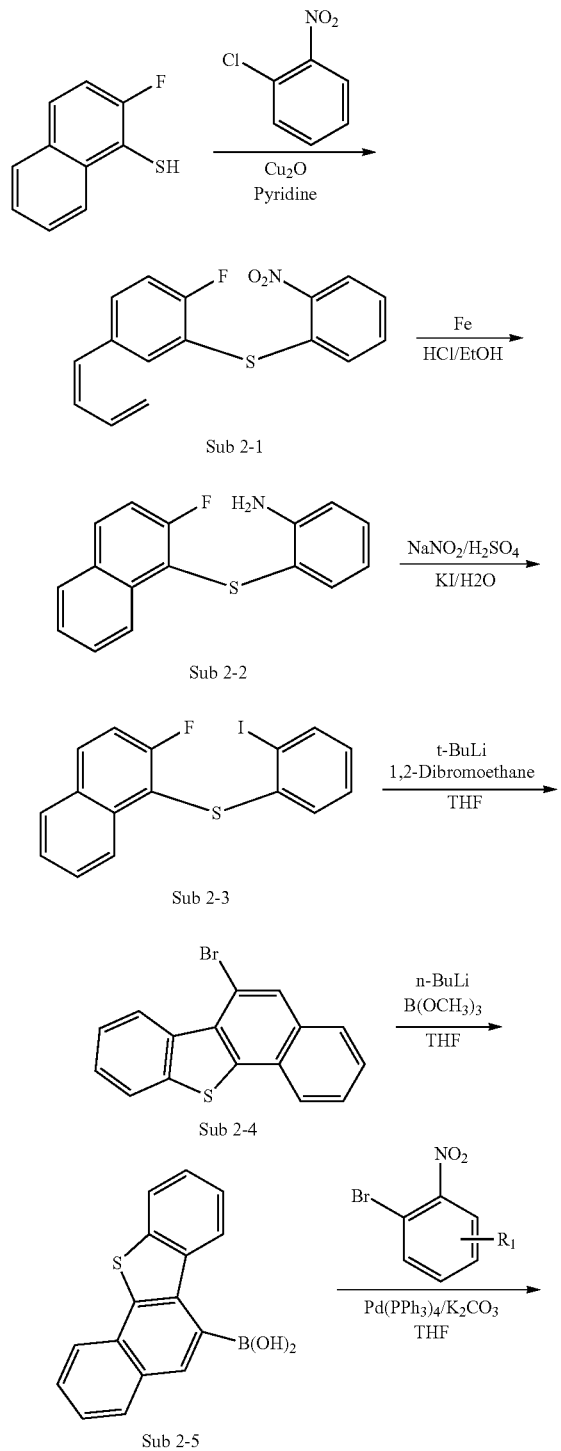

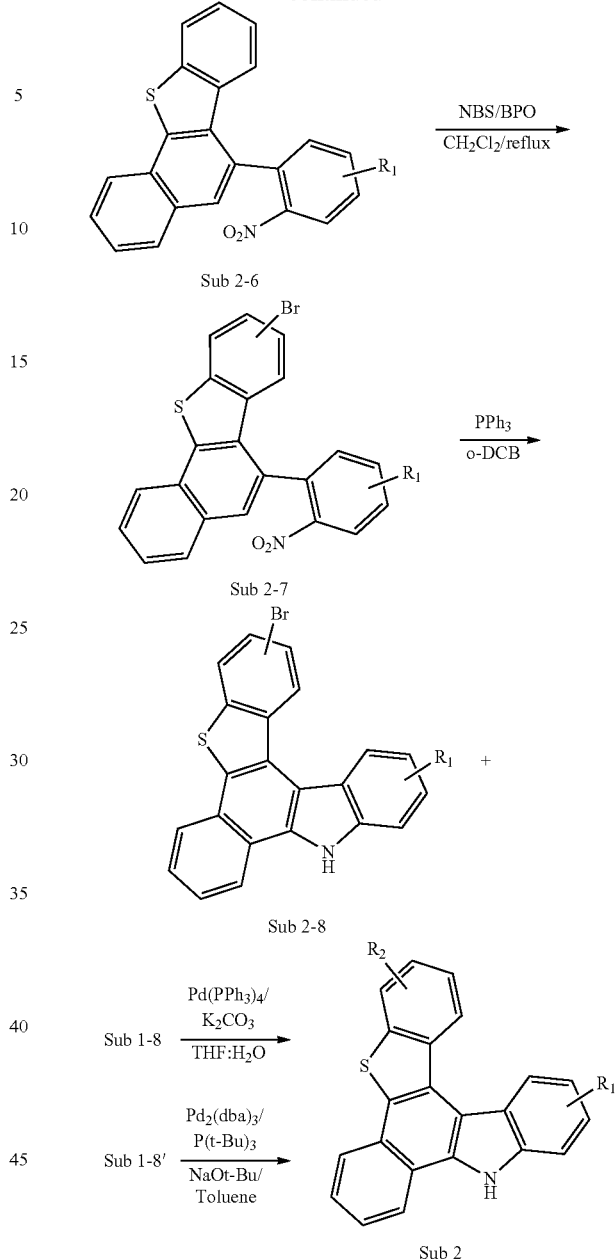

(1) Synthesis Method of Sub 2-1

Under nitrogen, 2-fluoronaphthalene-1-thiol, $Cu_2O$, and 1-chloro-2-nitrobenzene were dissolved in a pyridine solvent, and the reactants were refluxed for 12 hours. Upon completion of the reaction, the temperature of the reaction product was lowered to room temperature, 1M-HCl was added to the reaction product, and then the reaction product was extracted with ether and washed with water. The extracted organic layer was dried with $MgSO_4$ and vacuum-concentrated, and then the resultant product was separated by a silica gel column to obtain desired Sub 2-1 (yield 68%).

(2) Synthesis Method of Sub 2-2

The synthesized Sub 2-1 and iron powder were dissolved in a mixed solution of ethanol and HCl, and the reactants were refluxed for 6 hours. Subsequently, the reaction product was filtrated using Celite, extracted with ethyl acetate, and then washed with water. A small amount of water was removed from the extract by anhydrous $MgSO_4$, the extract was subjected to vacuum-filtration, and then the filtrated organic solvent was concentrated. The resultant product was separated by a silica gel column to obtain desired Sub 2-2 (yield: 65%).

(3) Synthesis Method of Sub 2-3

The obtained Sub 2-2 was dissolved in a mixed solution of $H_2O$ and $H_2SO_4$, and $NaNO_2$ and KI dissolved in $H_2O$ were slowly added dropwise to the reactants. After the adding, the reactants were stirred at room temperature for 30 minutes, and copper powder was added to the reactants, followed by reflux for 30 minutes. Upon completion of the reaction, the temperature of reaction product was lowered to room temperature, and then the reaction product was extracted with $CH_2Cl_2$ and washed with $Na_2S_2O_3$. A small amount of water was removed from the extract by anhydrous $MgSO_4$, the extract was subjected to vacuum-filtration, and then the filtrated organic solvent was concentrated. The resultant product was separated by a silica gel column to obtain desired Sub 2-3 (yield: 63%).

(4) Synthesis Method of Sub 2-4

The obtained Sub 2-3 was dissolved in anhydrous THF (tetrahydrofuran), and the temperature of reactants was lowered to −78° C. t-BuLi (1.5M in pentane) was slowly added dropwise to the reactants, the reactants were stirred for 1 hour at −78° C., the temperature of the reactants was raised to 0° C., and then the reactant were stirred again for 30 minutes. Subsequently, the temperature of the reactants was lowered to −78° C. again, and 1,2-dibromoethane was added dropwise to the reactants, followed by stirring for 1 hour at room temperature. Upon completion of the reaction, the reaction product was extracted with ethyl acetate and washed with water. A small amount of water was removed from the extract by anhydrous $MgSO_4$, the extract was subjected to vacuum-filtration, and then the filtrated organic solvent was concentrated. The resultant product was separated by a silica gel column to obtain desired Sub 2-4 (yield: 65%).

(5) Synthesis Method of Sub 2-5

The obtained Sub 2-4 was dissolved in anhydrous THF, the temperature of reactants was lowered to −78° C., n-BuLi (2.5M in hexane) was slowly added dropwise to the reactants, and then the reactants were stirred for 1 hour at 0° C. Subsequently, the temperature of the reactants was lowered to −78° C., and trimethyl borate was added dropwise to the reactants, followed by stirring for 12 hours at room temperature. Upon completion of the reaction, the reaction product was added with 2N—HCl, stirred for 30 minutes, and then extracted with ether. Water within the extract was removed by anhydrous $MgSO_4$, the extract was subjected to vacuum-filtration, and then the filtrated organic solvent was concentrated. The resultant product was separated by a silica gel column to obtain desired Sub 2-5 (yield: 63%).

(6) Synthesis Method of Sub 2-6

The obtained Sub 2-5, 1-bromo-2-nitrobenzene substituted by $R_1$, $Pd(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and washed with water. A small amount of water was removed from the extract by anhydrous $MgSO_4$, the extract was subjected to vacuum-filtration, and then the filtrated organic solvent was concentrated. The resultant product was separated by a silica gel column to obtain desired Sub 2-6.

(7) Synthesis Method of Sub 2-7

The obtained Sub 2-6 and NBS (N-bromosuccinimide) were dissolved in $CH_2Cl_2$, and then the reactants were refluxed for 7 hours. Upon completion of the reaction, the temperature of reaction product was lowered to room temperature, an aqueous sodium bicarbonate solution was added to the reaction product, and then the reaction product was extracted with $CH_2Cl_2$ and distilled water. Water within the extract was removed by anhydrous $MgSO_4$, the extract was subjected to vacuum-filtration, and then the filtrated organic solvent was concentrated. The resultant product was separated by a silica gel column and recrystallized to obtain desired Sub 2-7.

(8) Synthesis Method of Sub 2-8

The obtained 2-7 and triphenylphosphine were dissolved in o-dichlorobenzene, and then the reactants were refluxed for 24 hours. Upon completion of the reaction, the solvent was removed from the reaction product by using vacuum distillation, and then the concentrated product was separated by a silica gel column to obtain desired Sub 2-8.

(9) Synthesis Method of Sub 2 (Using Sub 1-8)

Compound Sub 1-7 (1 equivalent weight), compound Sub 1-8 (1.1 equivalent weight), $Pd(PPh_3)_4$ (0.03 equivalent weight), NaOH (3 equivalent weight), and water were put into a round bottom flask, and then the reactants were refluxed under stirring. Upon completion of the reaction, the reaction product was extracted with ether and water, the extracted organic layer was dried with $MgSO_4$ and concentrated, and then the produced organic material was separated by a silica gel column and recrystallized to obtain product Sub 2.

(10) Synthesis Method of Sub 2 (Using Sub 1-8')

Compound Sub 1-7 (1.1 equivalent weight), compound Sub 1-8' (1 equivalent weight), $Pd_2(dba)_3$ (0.04 equivalent weight), $P(t-Bu)_3$ (0.1 equivalent weight), NaOt-Bu (3 equivalent weight), and toluene (10.5 mL/1 mmol) were put into a round bottom flask, and then the reactants were subjected to the reaction at 100° C. Upon completion of the reaction, the reaction product was extracted with ether and water, the extracted organic layer was dried with $MgSO_4$ and concentrated, and then the produced organic material was separated by a silica gel column and recrystallized to obtain product Sub 2.

Example 3

Synthesis Example of Sub 3

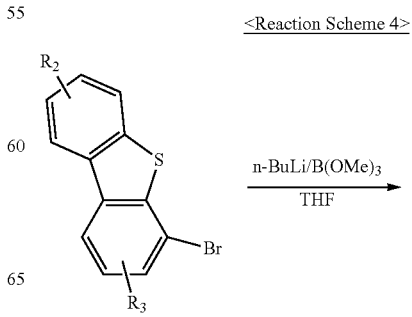

<Reaction Scheme 4>

-continued

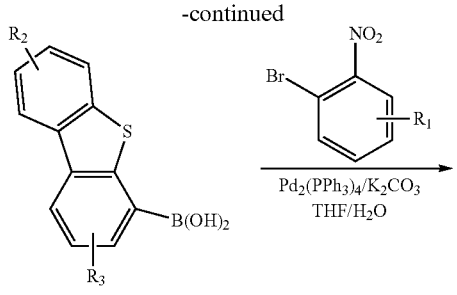

Sub 3-1

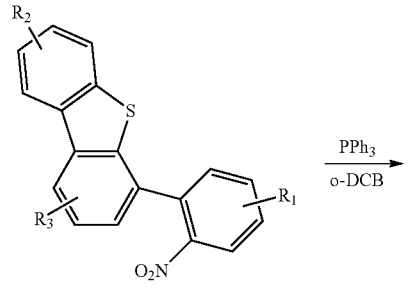

Sub 3-2

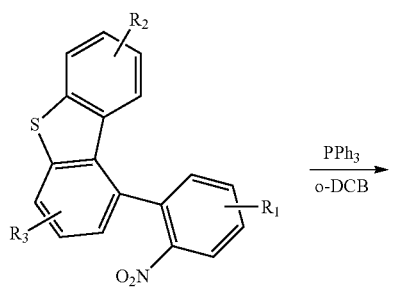

Sub 3

Example 4

Synthesis Example of Sub 4

<Reaction Scheme 5>

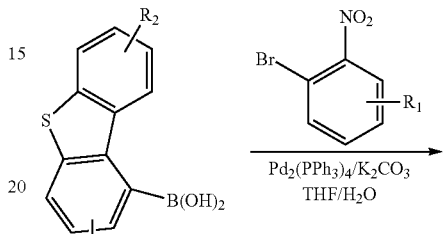

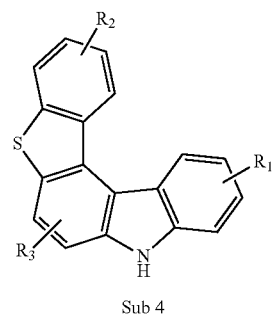

Sub 4-1

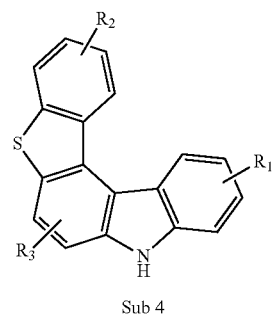

Sub 4

(1) Synthesis Method of Sub 3-1

4-bromodibenzothiophene substituted by $R_2$ and $R_3$ was dissolved in anhydrous THF, the temperature of reactants was lowered to −78° C., n-BuLi (2.5M in hexane) was slowly added dropwise to the reactants, and then the reactants were stirred for 1 hour at 0° C. Subsequently, the temperature of the reactants was lowered to −78° C., and trimethyl borate was added dropwise to the reactants, followed by stirring for 12 hours at room temperature. Upon completion of the reaction, the reaction product was added with 2N—HCl, stirred for 30 minutes, and then extracted with ether. Water within the extract was removed by anhydrous $MgSO_4$, the extract was subjected to vacuum-filtration, and then the filtrated organic solvent was concentrated. The resultant product was separated by a silica gel column and recrystallized to obtain product Sub 3-1.

(2) Synthesis Method of Sub 3-2

The obtained Sub 3-1, 1-bromo-2-nitrobenzene substituted by $R_1$, $Pd_2(PPh_3)_4$, and $K_2CO_3$ were dissolved in anhydrous THF and water, and then the reactants were refluxed for 24 hours. Upon completion of the reaction, the temperature of reaction product was lowered to room temperature, and then the reaction product was extracted with $CH_2Cl_2$ and washed with water. The extracted organic layer was dried with $MgSO_4$ and vacuum-concentrated, and then the resultant product was separated by a silica gel column to obtain product Sub 3-2.

(3) Synthesis Method of Sub 3

The obtained Sub 3-2 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column to obtain product Sub 3.

(1) Synthesis Method of Sub 4-1

Dibenzothiophene-1-yl-boronic acid substituted by $R_2$ and $R_3$, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 4-1.

(2) Synthesis Method of Sub 4

The obtained Sub 4-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 4.

Example 5

Synthesis Example of Sub 5

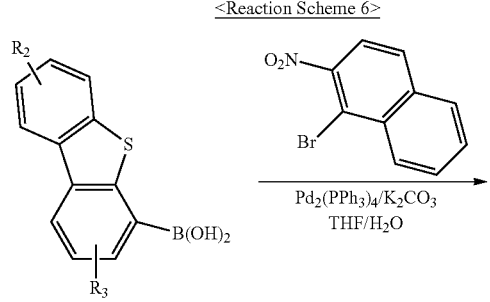

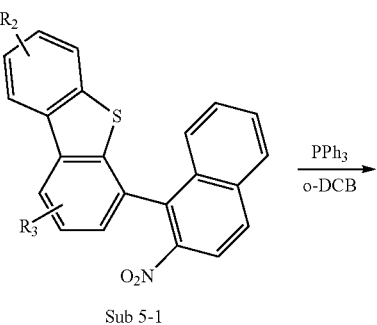

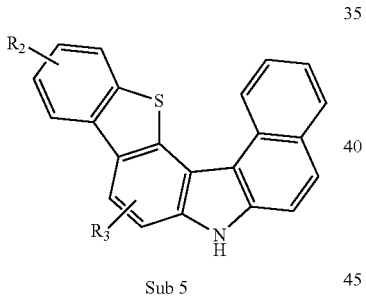

Sub 5

(1) Synthesis Method of Sub 5-1

Dibenzothiophene-4-yl-boronic acid substituted by $R_2$ and $R_3$, 1-bromo-2-nitronaphthalene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 5-1.

(2) Synthesis Method of Sub 5

The obtained Sub 5-1 and triphenylphosphine were dissolved in o-dichlorobenzene, and then the reactants were refluxed for 24 hours. Upon completion of the reaction, the solvent was removed using vacuum distillation, and then the concentrated product was separated by column chromatography to obtain product Sub 5.

Example 6

Synthesis Example of Sub 6

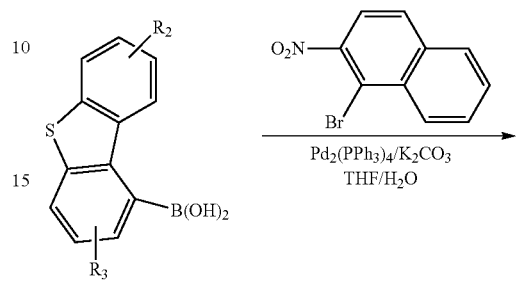

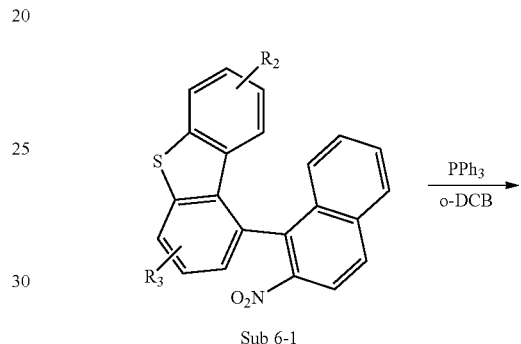

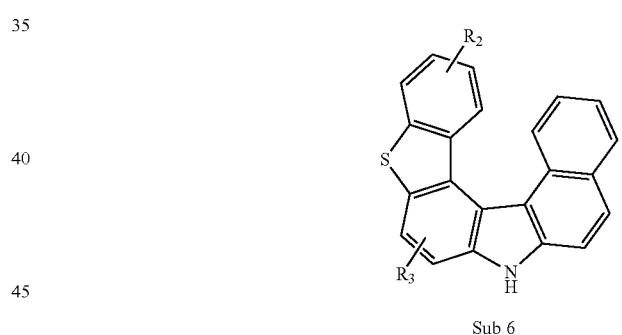

Sub 6

(1) Synthesis Method of Sub 6-1

Dibenzothiophene-1-yl-boronic acid substituted by $R_2$ and $R_3$, 1-bromo-2-nitronaphthalene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 6-1.

(2) Synthesis Method of Sub 6

The obtained Sub 6-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 6.

Example 7

Synthesis Example of Sub 7

<Reaction Scheme 8>

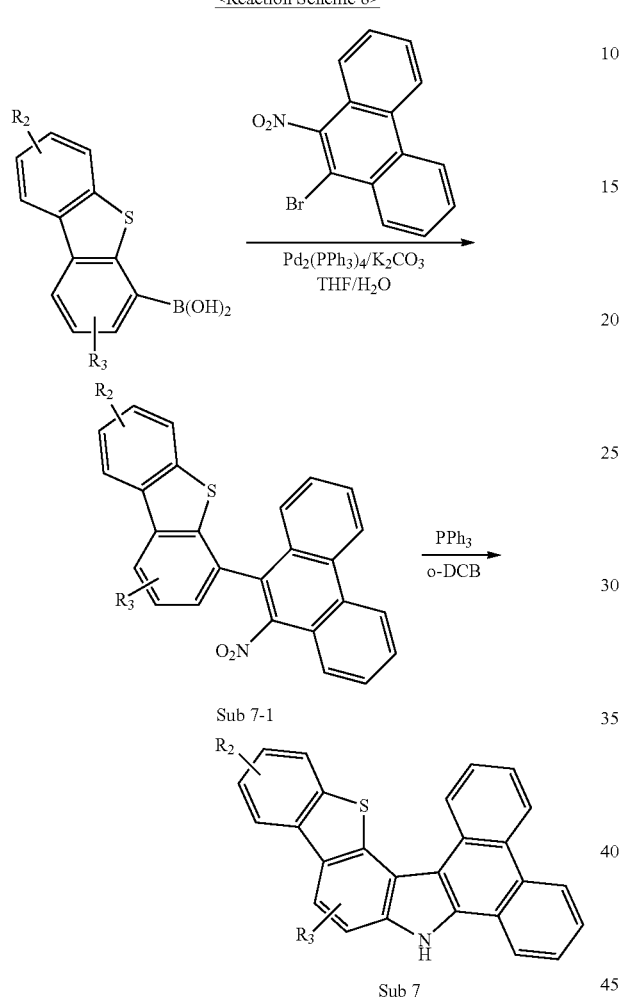

(1) Synthesis Method of Sub 7-1

Dibenzothiophene-4-yl-boronic acid substituted by $R_2$ and $R_3$, 9-bromo-10-nitrophenanthrene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 7-1.

(2) Synthesis Method of Sub 7

The obtained Sub 7-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 7.

Example 8

Synthesis Example of Sub 8

<Reaction Scheme 9>

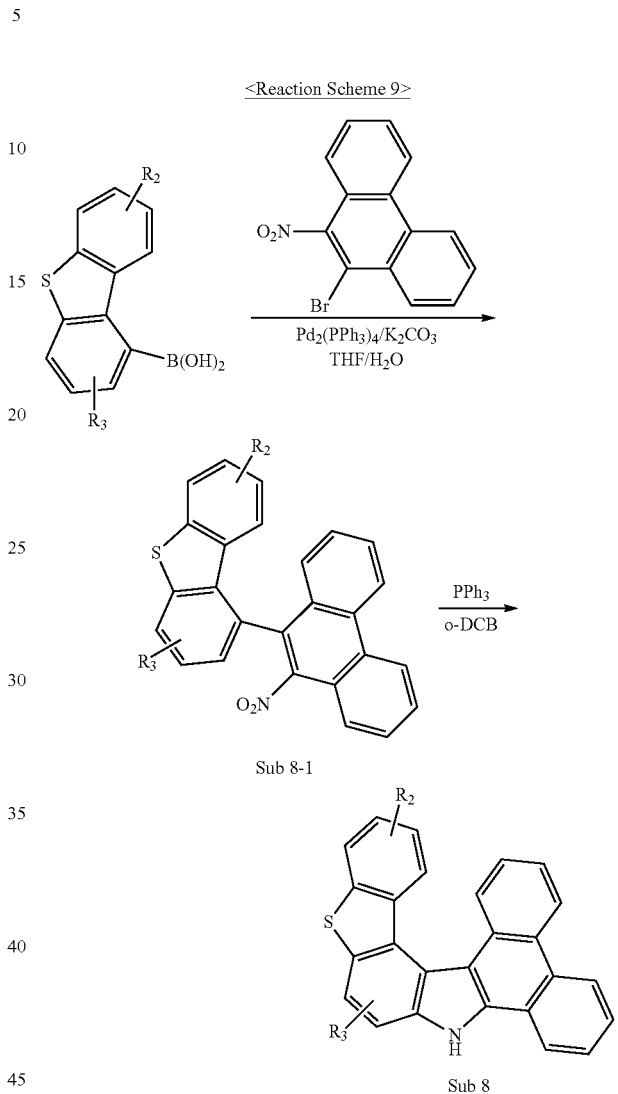

(1) Synthesis Method of Sub 8-1

Dibenzothiophene-1-yl-boronic acid substituted by $R_2$ and $R_3$, 9-bromo-10-nitrophenanthrene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 8-1.

(2) Synthesis Method of Sub 8

The obtained Sub 8-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 8.

Example 9

Synthesis Example of Sub 9

<Reaction Scheme 10>

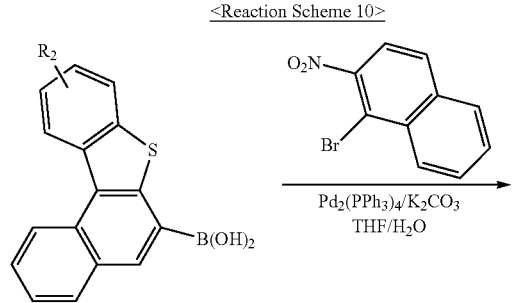

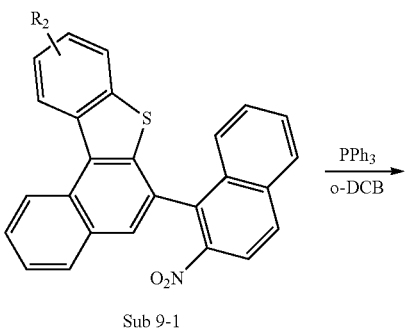

Sub 9-1

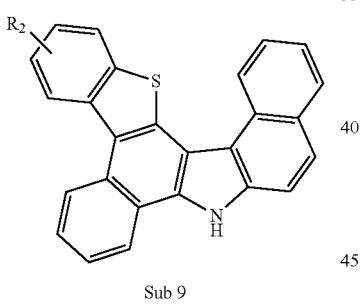

Sub 9

(1) Synthesis Method of Sub 9-1

Benzonaphthothiophene-6-yl-boronic acid substituted by $R_2$, 1-bromo-2-nitronaphthalene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 9-1.

(2) Synthesis Method of Sub 9

The obtained Sub 9-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 9.

Example 10

Synthesis Example of Sub 10

<Reaction Scheme 11>

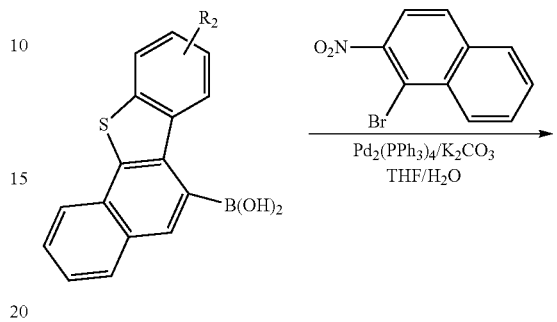

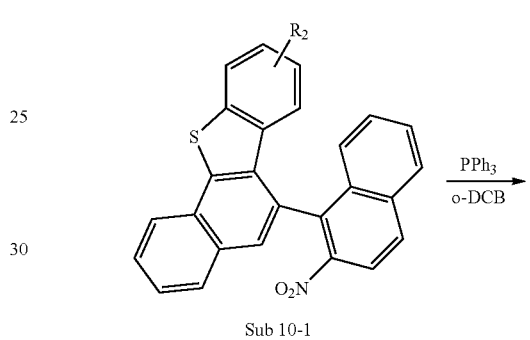

Sub 10-1

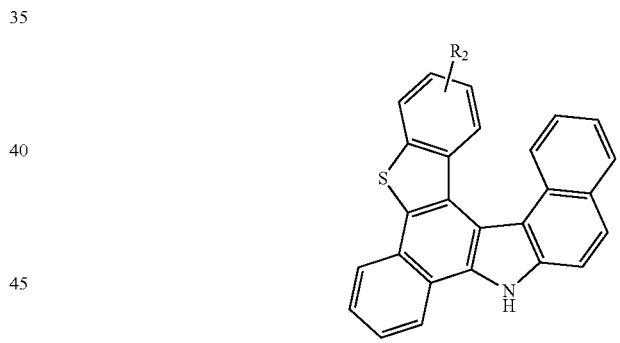

Sub 10

(1) Synthesis Method of Sub 10-1

Benzonaphthothiophene-6-yl-boronic acid substituted by $R_2$, 1-bromo-2-nitronaphthalene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 10-1.

(2) Synthesis Method of Sub 10

The obtained Sub 10-1 and triphenylphosphine were dissolved in o-dichlorobenzene, and then the reactants were refluxed for 24 hours. Upon completion of the reaction, the solvent was removed using vacuum distillation, and then the concentrated product was separated by a silica gel column and recrystallized to obtain product Sub 10.

Example 11

Synthesis Example of Sub 11

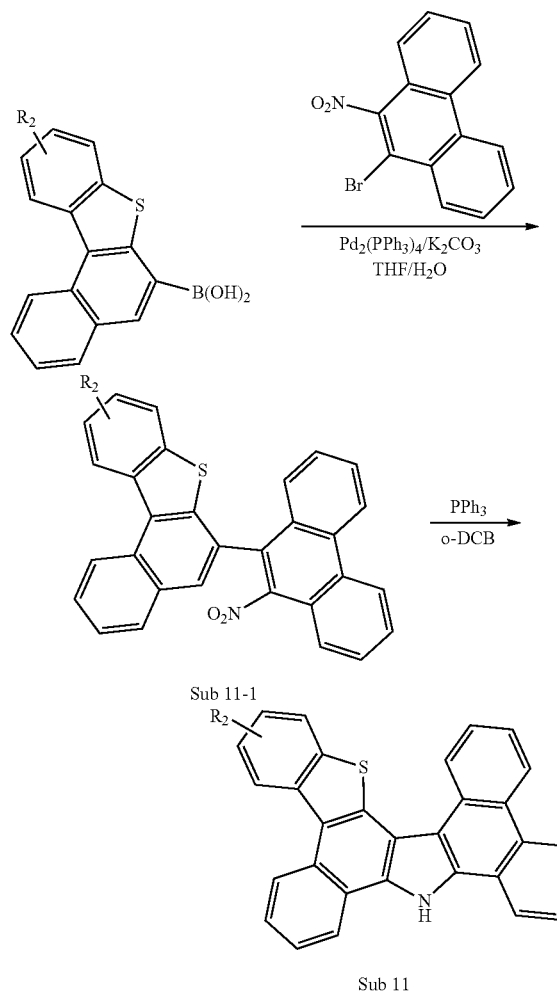

Sub 11

(1) Synthesis Method of Sub 11-1

Benzonaphthothiophene-6-yl-boronic acid substituted by $R_2$, 9-bromo-10-nitrophenanthrene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 11-1.

(2) Synthesis Method of Sub 11

The obtained Sub 11-1 and triphenylphosphine were dissolved in o-dichlorobenzene, and then the reactants were refluxed for 24 hours. Upon completion of the reaction, the solvent was removed using vacuum distillation, and then the concentrated product was separated by column chromatography to obtain product Sub 11.

Example 12

Synthesis Example of Sub 12

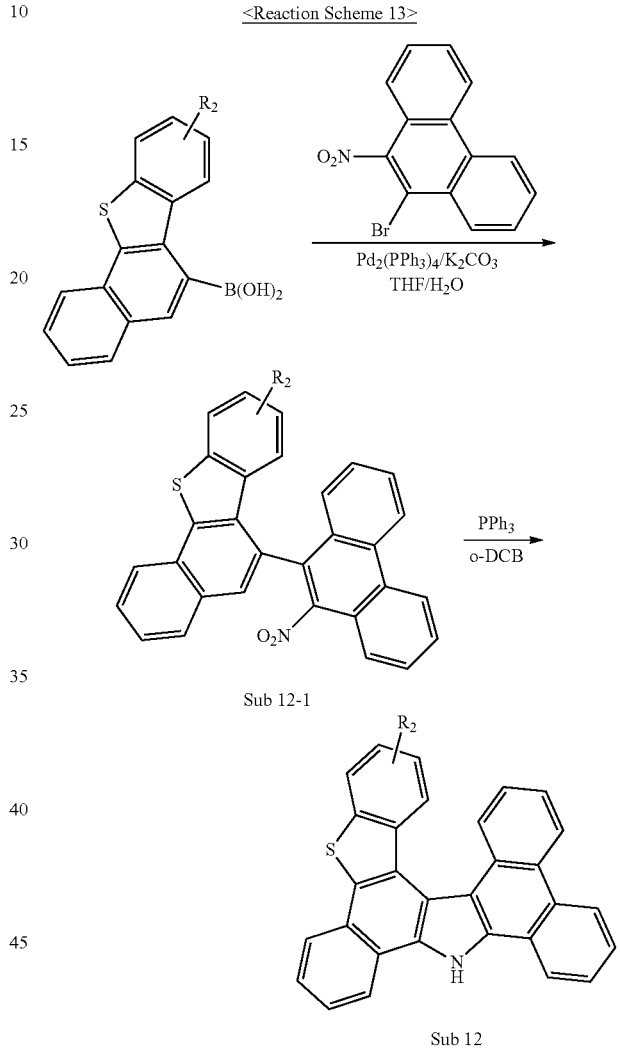

Sub 12

(1) Synthesis Method of Sub 12-1

Benzonaphthothiophene-6-yl-boronic acid substituted by $R_2$, 1-bromo-2-nitronaphthalene, $Pd_2(PPh_3)_4$, and $K_2CO_3$ were dissolved in anhydrous THF and a small amount of water, and then the reactants were refluxed for 24 hours. Upon completion of the reaction, the temperature of reaction product was lowered to room temperature, and then the reaction product was extracted with $CH_2Cl_2$ and water. The extracted organic layer was dried with $MgSO_4$ and vacuum-concentrated, and then the resultant product was separated by a silica gel column to obtain product Sub 12-1.

(2) Synthesis Method of Sub 12

The obtained Sub 12-1 and triphenylphosphine were dissolved in o-dichlorobenzene, and then the reactants were refluxed for 24 hours. Upon completion of the reaction, the solvent was removed using vacuum distillation, and then the concentrated product was separated by column chromatography to obtain product Sub 12.
Example 13
As described above, the final compound may be synthesized by Reaction Scheme 1 by way of example.
Synthesis Example of Product
[Method 1]
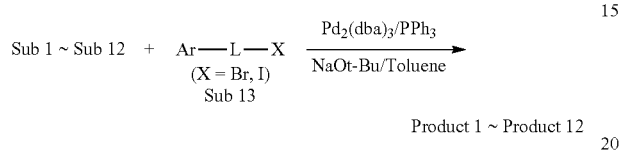
[Method 2]
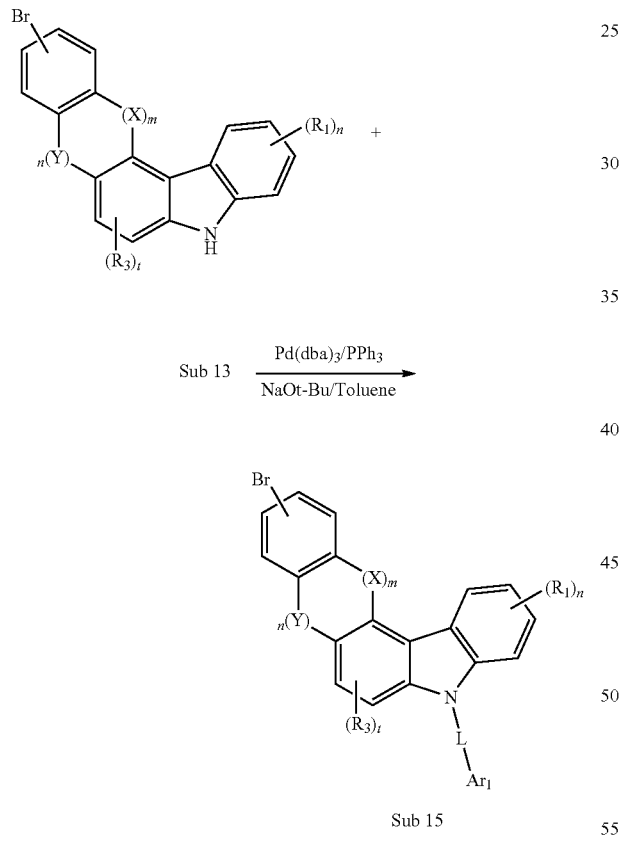
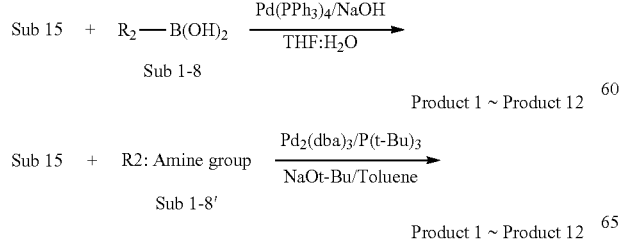
Example of Sub 13
Examples of Sub 13 include, but not limited to, the following compounds.
Sub 13-1
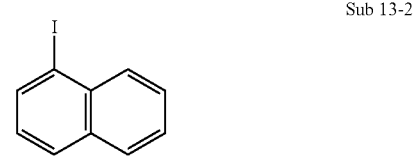
Sub 13-2
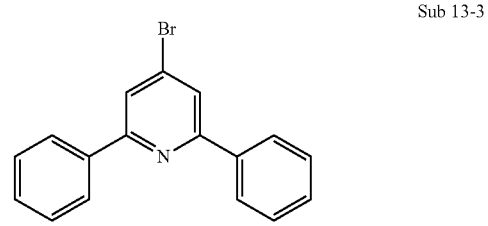
Sub 13-3
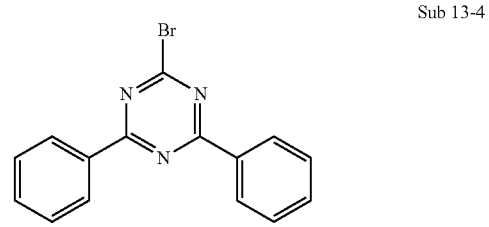
Sub 13-4
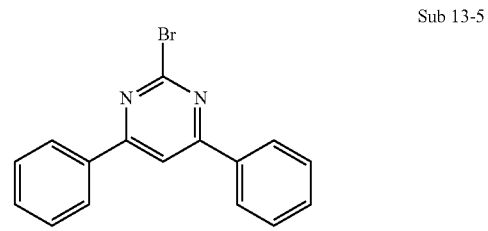
Sub 13-5
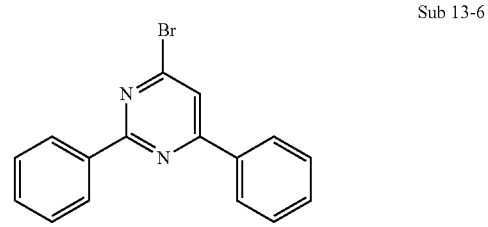
Sub 13-6
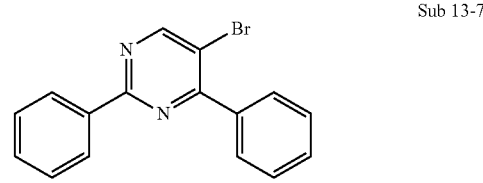
Sub 13-7

-continued
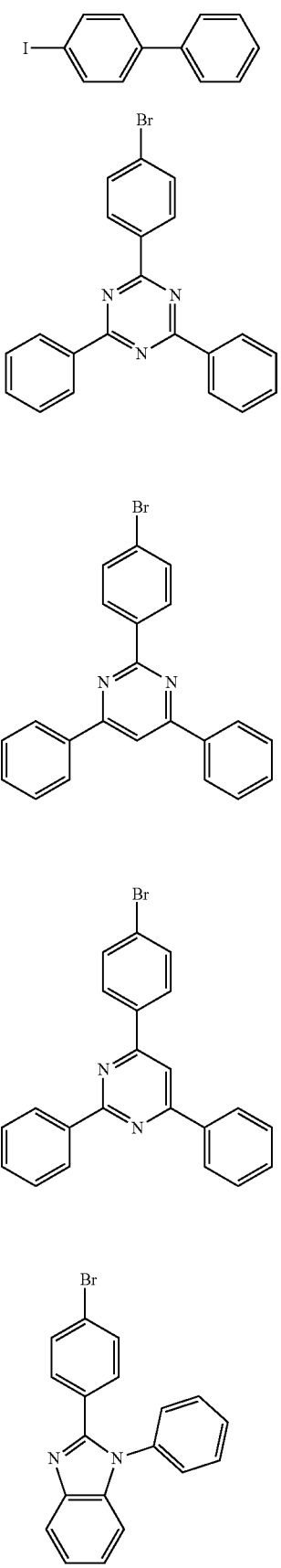
Sub 13-8
Sub 13-9
Sub 13-10
Sub 13-11
Sub 13-12
-continued
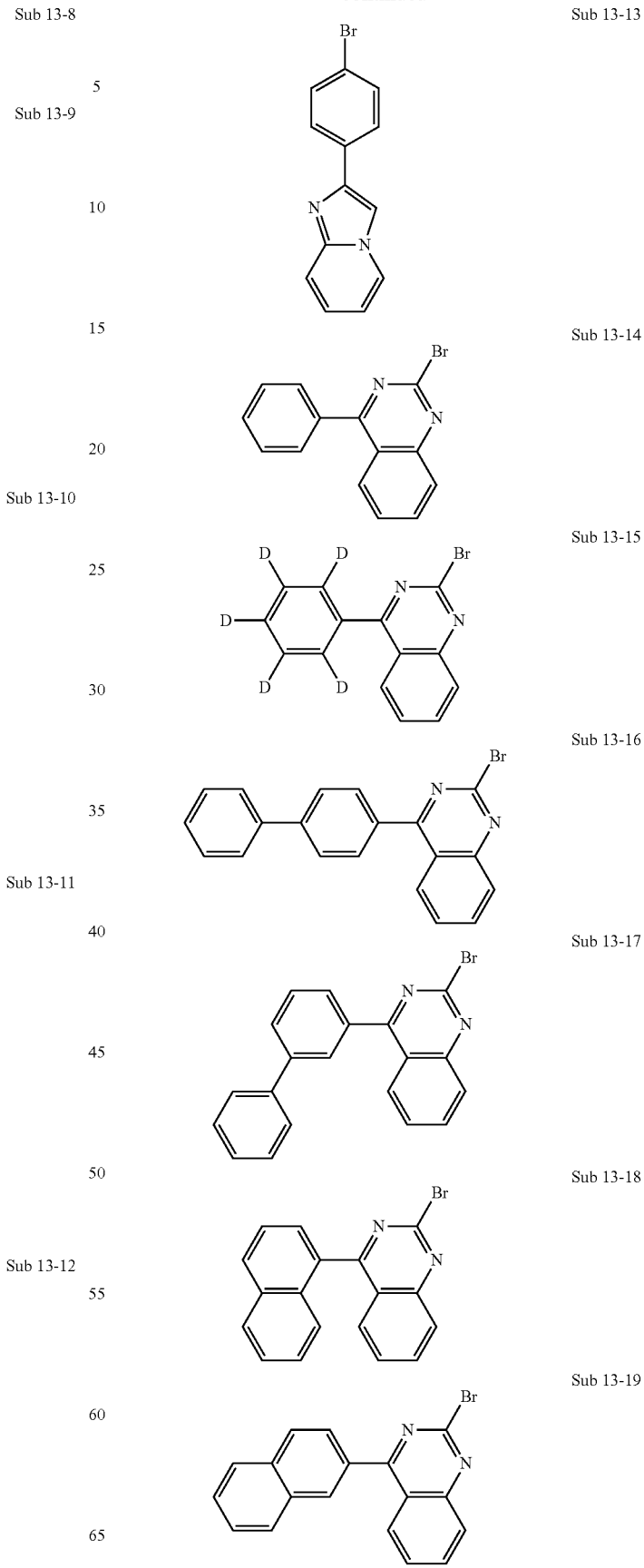
Sub 13-13
Sub 13-14
Sub 13-15
Sub 13-16
Sub 13-17
Sub 13-18
Sub 13-19

-continued
Sub 13-20
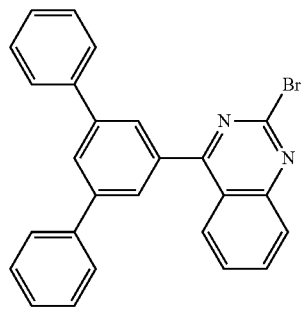
Sub 13-21
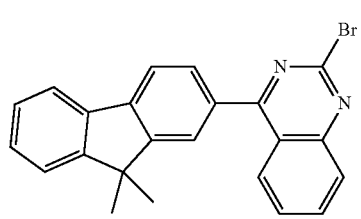
Sub 13-22
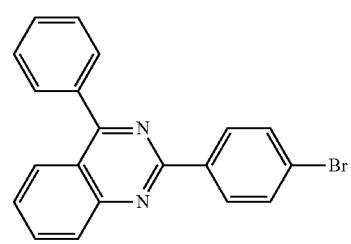
Sub 13-23
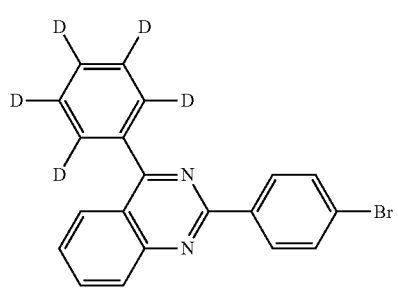
Sub 13-24
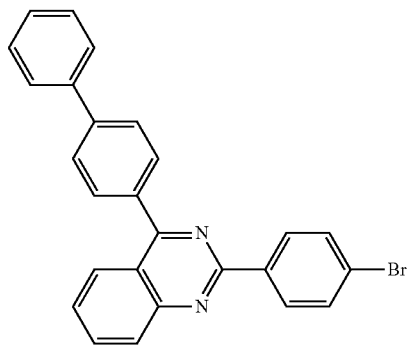
-continued
Sub 13-25
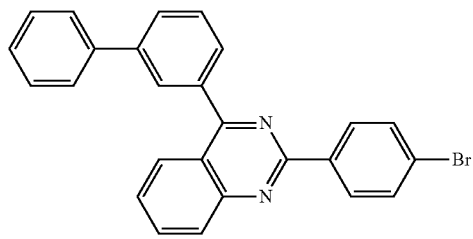
Sub 13-26
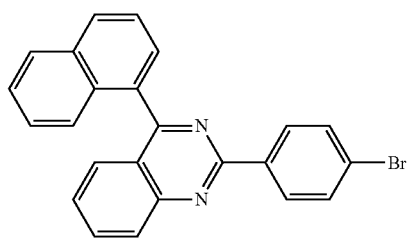
Sub 13-27
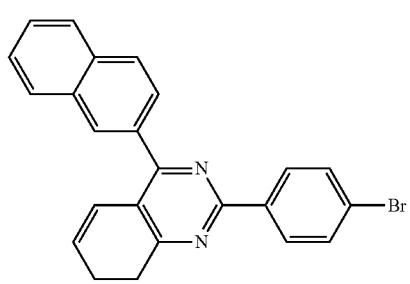
Sub 13-28
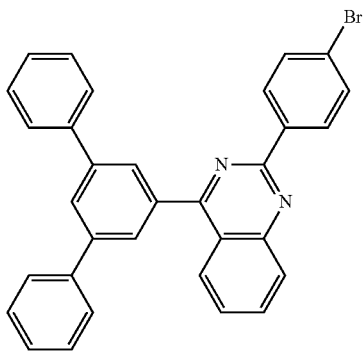
Sub 13-29
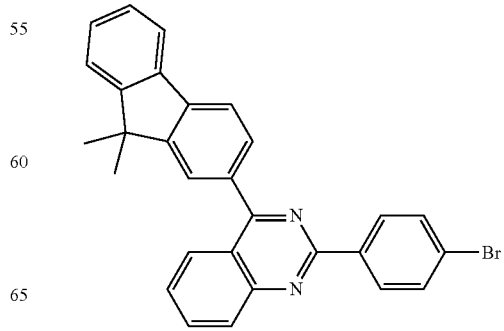

Sub 13-30
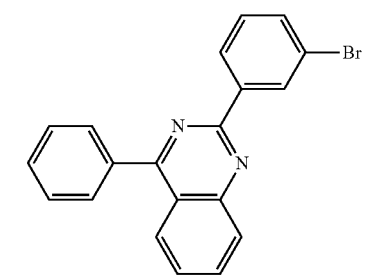
Sub 13-35
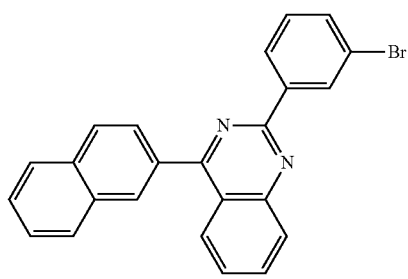
Sub 13-31
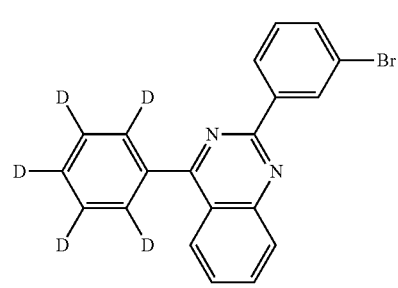
Sub 13-36
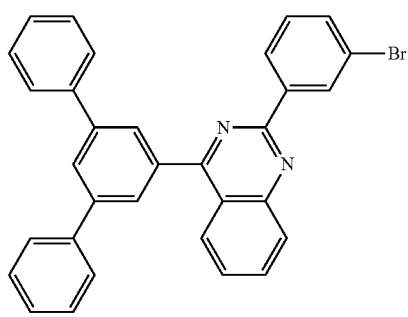
Sub 13-32
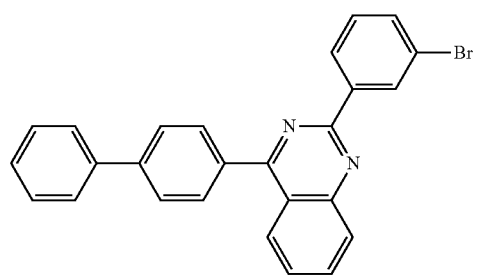
Sub 13-37
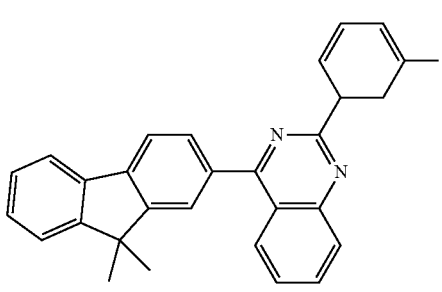
Sub 13-33
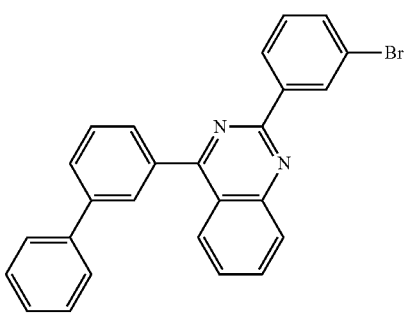
Sub 13-38
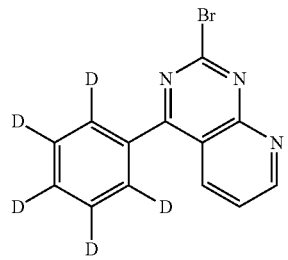
Sub 13-39
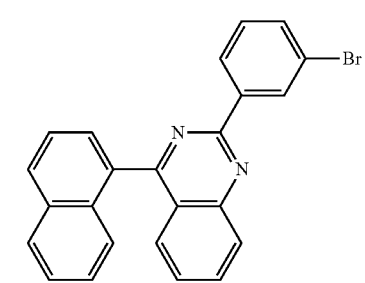
Sub 13-34
Sub 13-40
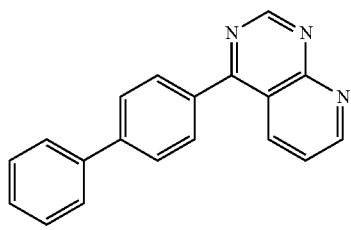

| | |
|---|---|
| Sub 13-41 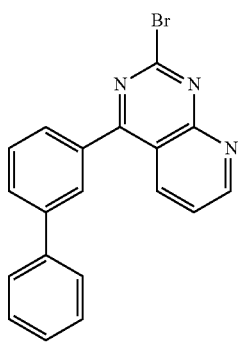 | Sub 13-46 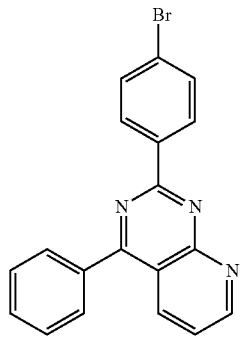 |
| Sub 13-42 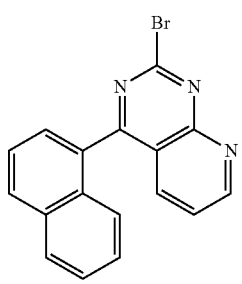 | Sub 13-47 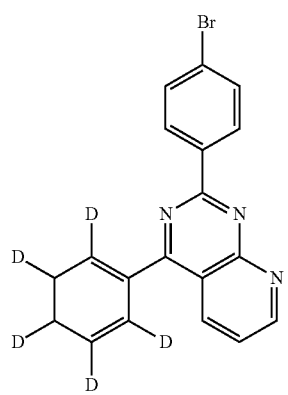 |
| Sub 13-43 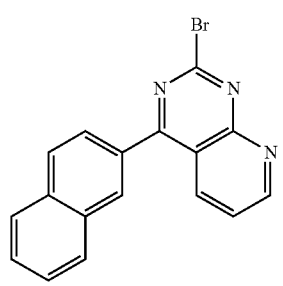 | Sub 13-48 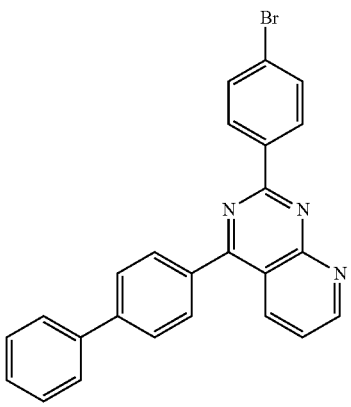 |
| Sub 13-44 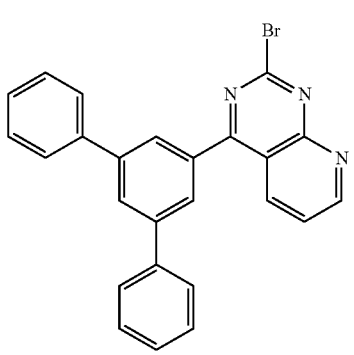 | Sub 13-49 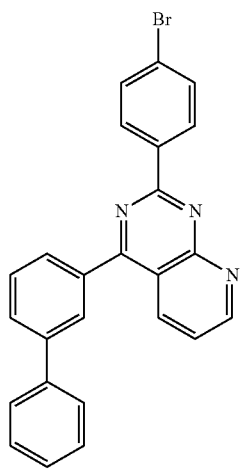 |
| Sub 13-45 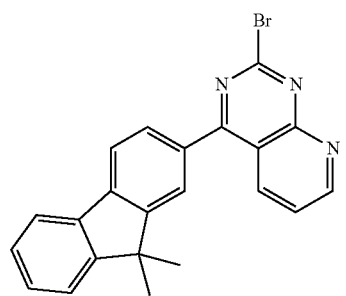 | |

Sub 13-50
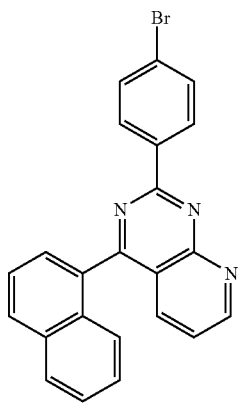
Sub 13-51
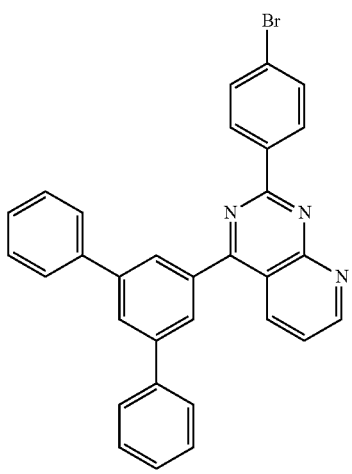
Sub 13-52
Sub 13-53
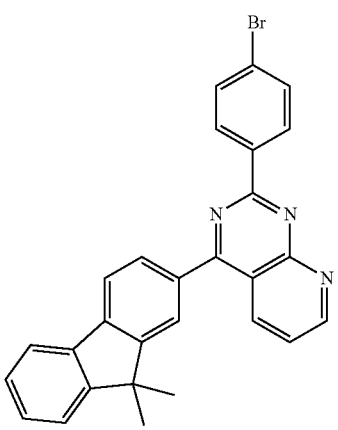
Sub 13-54
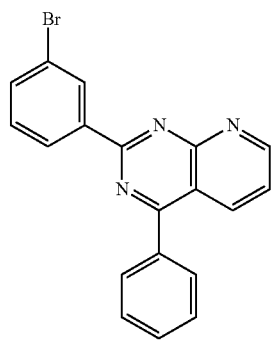
Sub 13-55
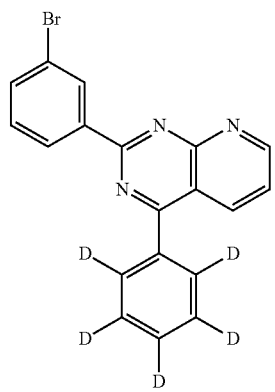
Sub 13-56
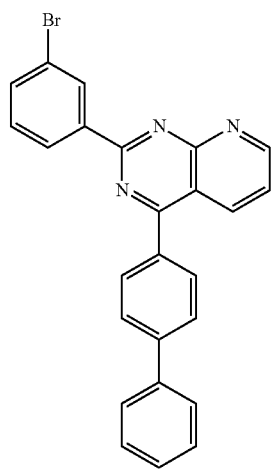

| 227 -continued | | 228 -continued | |
|---|---|---|---|
| 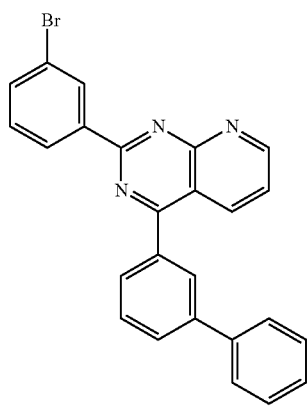 | Sub 13-57 | 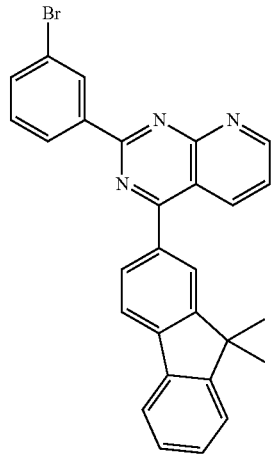 | Sub 13-61 |
| 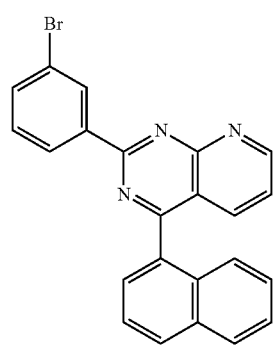 | Sub 13-58 | 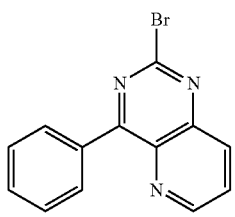 | Sub 13-62 |
| | | 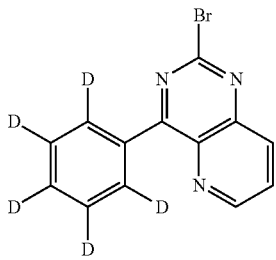 | Sub 13-63 |
| | Sub 13-59 | | |
| | | 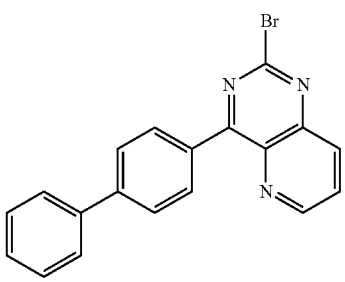 | Sub 13-64 |
| 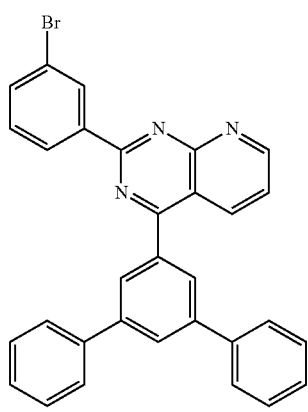 | Sub 13-60 | 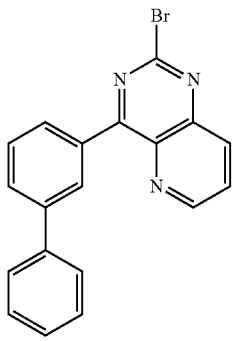 | Sub 13-65 |

Sub 13-66
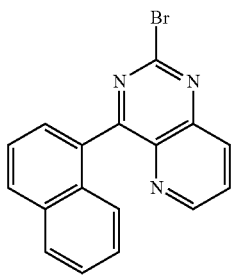
Sub 13-67
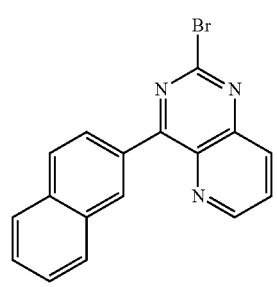
Sub 13-68
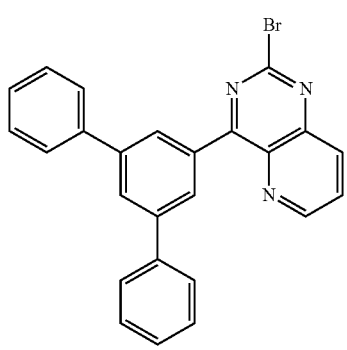
Sub 13-69
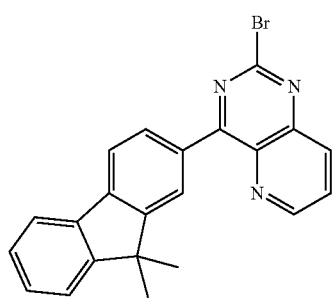
Sub 13-70
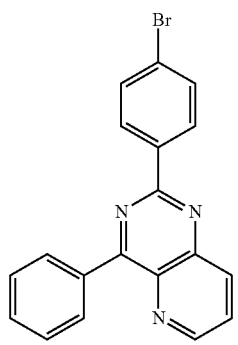
Sub 13-71
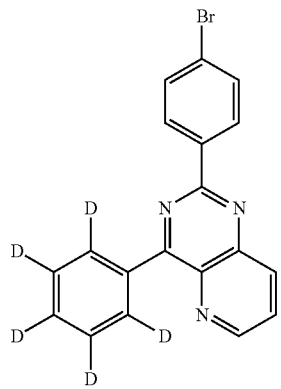
Sub 13-72
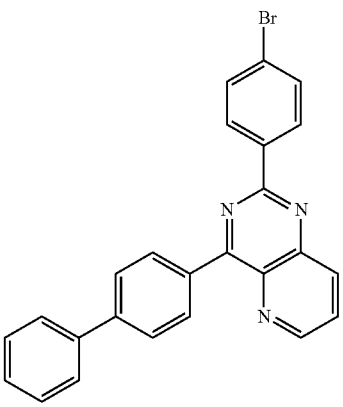
Sub 13-73
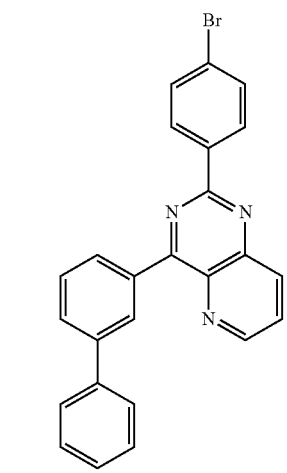

Sub 13-74
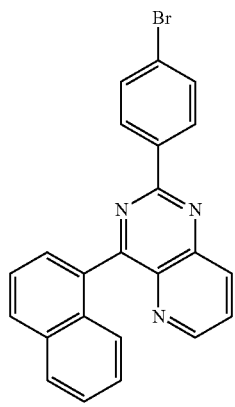
Sub 13-75
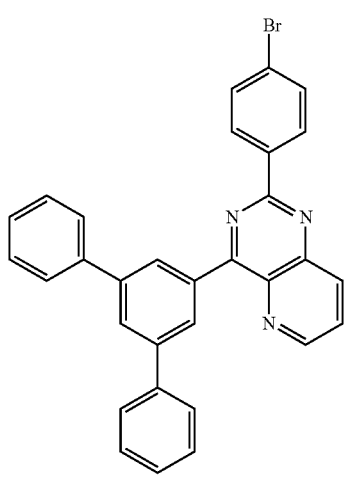
Sub 13-76
Sub 13-77
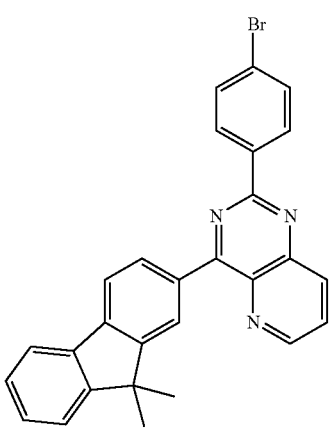
Sub 13-78
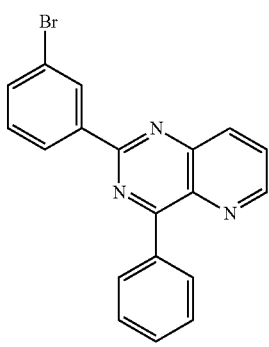
Sub 13-79
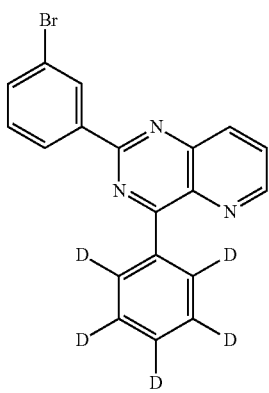
Sub 13-80
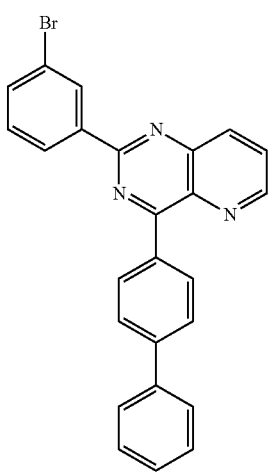

-continued

Sub 13-81
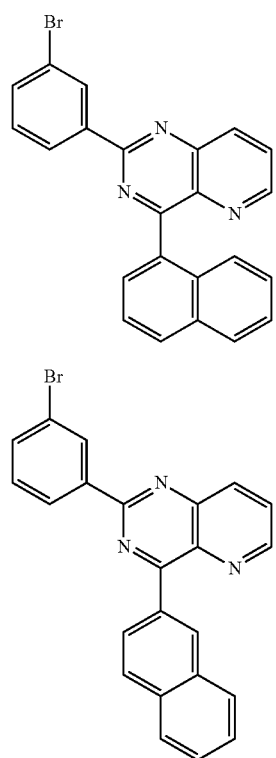

Sub 13-82
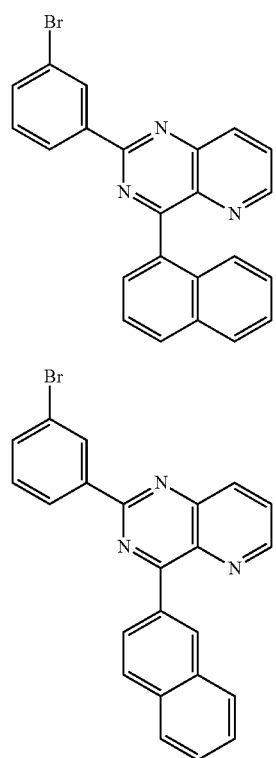

Sub 13-83
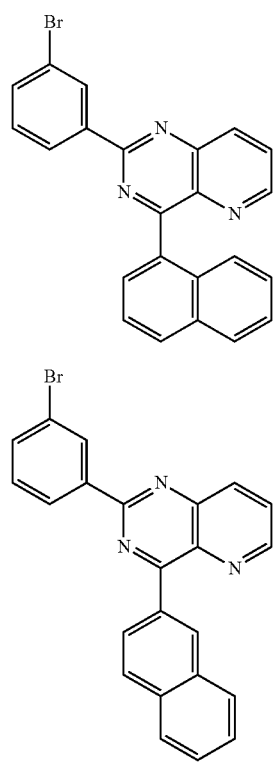

-continued

Sub 13-84
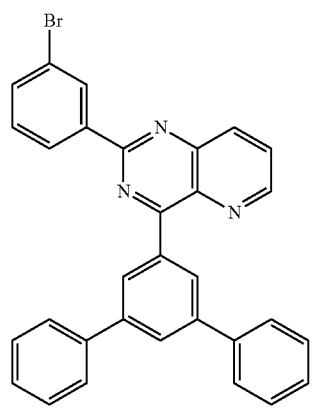

Sub 13-85
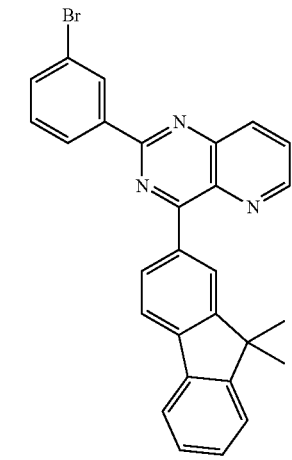

TABLE 2

| Compound | FD-MS | Compound | FD-MS |
|---|---|---|---|
| Sub 13-1 | m/z = 203.94($C_6H_5I$ = 204.01) | Sub 13-2 | m/z = 253.96($C_{10}H_7I$ = 254.07) |
| Sub 13-3 | m/z = 309.02($C_{17}H_{12}BrN$ = 310.19) | Sub 13-4 | m/z = 311.01($C_{15}H_{10}BrN_3$ = 312.16) |
| Sub 13-5 | m/z = 310.01($C_{16}H_{11}BrN_2$ = 311.18) | Sub 13-6 | m/z = 310.01($C_{16}H_{11}BrN_2$ = 311.18) |
| Sub 13-7 | m/z = 310.01($C_{16}H_{11}BrN_2$ = 311.18) | Sub 13-8 | m/z = 279.97($C_{12}H_9I$ = 280.10) |
| Sub 13-9 | m/z = 387.04($C_{21}H_{14}BrN_3$ = 388.26) | Sub 13-10 | m/z = 386.04($C_{22}H_{15}BrN_2$ = 387.27) |
| Sub 13-11 | m/z = 386.04($C_{22}H_{15}BrN_2$ = 387.27) | Sub 13-12 | m/z = 348.03($C_{19}H_{13}BrN_2$ = 349.22) |
| Sub 13-13 | m/z = 271.99($C_{13}H_9BrN_2$ = 273.13) | Sub 13-14 | m/z = 283.99($C_{14}H_9BrN_2$ = 285.14) |
| Sub 13-15 | m/z = 289.03($C_{14}H_4D_5BrN_2$ = 290.17) | Sub 13-16 | m/z = 360.03($C_{20}H_{13}BrN_2$ = 361.23) |
| Sub 13-17 | m/z = 360.03($C_{20}H_{13}BrN_2$ = 361.23) | Sub 13-18 | m/z = 334.01($C_{18}H_{11}BrN_2$ = 335.20) |
| Sub 13-19 | m/z = 334.01($C_{18}H_{11}BrN_2$ = 335.20) | Sub 13-20 | m/z = 436.06($C_{26}H_{17}BrN_2$ = 437.33) |
| Sub 13-21 | m/z = 400.06($C_{23}H_{17}BrN_2$ = 401.30) | Sub 13-22 | m/z = 360.03($C_{20}H_{13}BrN_2$ = 361.23) |
| Sub 13-23 | m/z = 365.06($C_{20}H_8D_5BrN_2$ = 366.27) | Sub 13-24 | m/z = 436.06($C_{26}H_{17}BrN_2$ = 437.33) |
| Sub 13-25 | m/z = 436.06($C_{26}H_{17}BrN_2$ = 437.33) | Sub 13-26 | m/z = 410.04($C_{24}H_{15}BrN_2$ = 411.29) |
| Sub 13-27 | m/z = 410.04($C_{24}H_{15}BrN_2$ = 411.29) | Sub 13-28 | m/z = 512.09($C_{32}H_{21}BrN_2$ = 513.43) |
| Sub 13-29 | m/z = 476.09($C_{29}H_{21}BrN_2$ = 477.39) | Sub 13-30 | m/z = 360.03($C_{20}H_{13}BrN_2$ = 361.23) |
| Sub 13-31 | m/z = 365.06($C_{20}H_8D_5BrN_2$ = 366.27) | Sub 13-32 | m/z = 436.06($C_{26}H_{17}BrN_2$ = 437.33) |
| Sub 13-33 | m/z = 436.06($C_{26}H_{17}BrN_2$ = 437.33) | Sub 13-34 | m/z = 410.04($C_{24}H_{15}BrN_2$ = 411.29) |
| Sub 13-35 | m/z = 410.04($C_{24}H_{15}BrN_2$ = 411.29) | Sub 13-36 | m/z = 512.09($C_{32}H_{21}BrN_2$ = 513.43) |

TABLE 2-continued

| Compound | FD-MS | Compound | FD-MS |
|---|---|---|---|
| Sub 13-37 | m/z = 476.09 ($C_{29}H_{21}BrN_2$ = 477.39) | Sub 13-38 | m/z = 284.99 ($C_{13}H_8BrN_3$ = 286.13) |
| Sub 13-39 | m/z = 290.02 ($C_{13}H_3D_5BrN_3$ = 291.16) | Sub 13-40 | m/z = 361.02 ($C_{19}H_{12}BrN_3$ = 362.22) |
| Sub 13-41 | m/z = 361.02 ($C_{19}H_{12}BrN_3$ = 362.22) | Sub 13-42 | m/z = 335.01 ($C_{17}H_{10}BrN_3$ = 336.19) |
| Sub 13-43 | m/z = 335.01 ($C_{17}H_{10}BrN_3$ = 336.19) | Sub 13-44 | m/z = 437.05 ($C_{25}H_{16}BrN_3$ = 438.32) |
| Sub 13-45 | m/z = 401.05 ($C_{22}H_{16}BrN_3$ = 402.29) | Sub 13-46 | m/z = 361.02 ($C_{19}H_{12}BrN_3$ = 362.22) |
| Sub 13-47 | m/z = 366.05 ($C_{19}H_7D_5BrN_3$ = 367.25) | Sub 13-48 | m/z = 437.05 ($C_{25}H_{16}BrN_3$ = 438.32) |
| Sub 13-49 | m/z = 437.05 ($C_{25}H_{16}BrN_3$ = 438.32) | Sub 13-50 | m/z = 411.04 ($C_{23}H_{14}BrN_3$ = 412.28) |
| Sub 13-51 | m/z = 411.04 ($C_{23}H_{14}BrN_3$ = 412.28) | Sub 13-52 | m/z = 513.08 ($C_{31}H_{20}BrN_3$ = 514.41) |
| Sub 13-53 | m/z = 477.08 ($C_{28}H_{20}BrN_3$ = 478.38) | Sub 13-54 | m/z = 361.02 ($C_{19}H_{12}BrN_3$ = 362.22) |
| Sub 13-55 | m/z = 366.05 ($C_{19}H_7D_5BrN_3$ = 367.25) | Sub 13-56 | m/z = 437.05 ($C_{25}H_{16}BrN_3$ = 438.32) |
| Sub 13-57 | m/z = 437.05 ($C_{25}H_{16}BrN_3$ = 438.32) | Sub 13-58 | m/z = 411.04 ($C_{23}H_{14}BrN_3$ = 412.28) |
| Sub 13-59 | m/z = 411.04 ($C_{23}H_{14}BrN_3$ = 412.28) | Sub 13-60 | m/z = 513.08 ($C_{31}H_{20}BrN_3$ = 514.41) |
| Sub 13-61 | m/z = 477.08 ($C_{28}H_{20}BrN_3$ = 478.38) | Sub 13-62 | m/z = 284.99 ($C_{13}H_8BrN_3$ = 286.13) |
| Sub 13-63 | m/z = 290.02 ($C_{13}H_3D_5BrN_3$ = 291.16) | Sub 13-64 | m/z = 361.02 ($C_{19}H_{12}BrN_3$ = 362.22) |
| Sub 13-65 | m/z = 361.02 ($C_{19}H_{12}BrN_3$ = 362.22) | Sub 13-66 | m/z = 335.01 ($C_{17}H_{10}BrN_3$ = 336.19) |
| Sub 13-67 | m/z = 335.01 ($C_{17}H_{10}BrN_3$ = 336.19) | Sub 13-68 | m/z = 437.05 ($C_{25}H_{16}BrN_3$ = 438.32) |
| Sub 13-69 | m/z = 401.05 ($C_{22}H_{16}BrN_3$ = 402.29) | Sub 13-70 | m/z = 361.02 ($C_{19}H_{12}BrN_3$ = 362.22) |
| Sub 13-71 | m/z = 366.05 ($C_{19}H_7D_5BrN_3$ = 367.25) | Sub 13-72 | m/z = 437.05 ($C_{25}H_{16}BrN_3$ = 438.32) |
| Sub 13-73 | m/z = 437.05 ($C_{25}H_{16}BrN_3$ = 438.32) | Sub 13-74 | m/z = 411.04 ($C_{23}H_{14}BrN_3$ = 412.28) |
| Sub 13-75 | m/z = 411.04 ($C_{23}H_{14}BrN_3$ = 412.28) | Sub 13-76 | m/z = 513.08 ($C_{31}H_{20}BrN_3$ = 514.41) |
| Sub 13-77 | m/z = 477.08 ($C_{28}H_{20}BrN_3$ = 478.38) | Sub 13-78 | m/z = 361.02 ($C_{19}H_{12}BrN_3$ = 362.22) |
| Sub 13-79 | m/z = 366.05 ($C_{19}H_7D_5BrN_3$ = 367.25) | Sub 13-80 | m/z = 437.05 ($C_{25}H_{16}BrN_3$ = 438.32) |
| Sub 13-81 | m/z = 437.05 ($C_{25}H_{16}BrN_3$ = 438.32) | Sub 13-82 | m/z = 411.04 ($C_{23}H_{14}BrN_3$ = 412.28) |
| Sub 13-83 | m/z = 411.04 ($C_{23}H_{14}BrN_3$ = 412.28) | Sub 13-84 | m/z = 513.08 ($C_{31}H_{20}BrN_3$ = 514.41) |
| Sub 13-85 | m/z = 477.08 ($C_{28}H_{20}BrN_3$ = 478.38) | | |

Using Sub 1 to Sub 12, Sub 1-8 or Sub 1-8', Sub 13, and Sub 15, products were obtained through Method 1 and Method 2.

[Method 1]

Compound Sub 1 to Sub 12 (1 equivalent weight), compound Sub 13 (1.2 equivalent weight), Pd$_2$(dba)$_3$ (0.05 equivalent weight), P(t-Bu)$_3$ (0.1 equivalent weight), NaOt-Bu (3 equivalent weight), and toluene (10.5 mL/1 mmol) were put into a round bottom flask, and then the reactants were subjected to the reaction at 100° C. Upon completion of the reaction, the reaction product was extracted with ether and water, the extracted organic layer was dried with MgSO$_4$ and concentrated, and then the produced organic material was separated by a silica gel column and recrystallized to obtain a desired product.

[Method 2-1]

Compound Sub 15 (1 equivalent weight) obtained in the above synthesis was dissolved in THF, compound Sub 1-8 (1.2 equivalent weight), Pd(PPh$_3$)$_4$ (0.03 equivalent weight), NaOH (3 equivalent weight), and water were added, and then the reactants were refluxed under stirring. Upon completion of the reaction, the reaction product was extracted with ether and water, the extracted organic layer was dried with MgSO$_4$ and concentrated, and then the produced organic material was separated by a silica gel column and recrystallized to obtain a desired product.

[Method 2-2]

Compound Sub 15 (1 equivalent weight), compound Sub 1-8' (1.2 equivalent weight), Pd$_2$(dba)$_3$ (0.05 equivalent weight), P(t-Bu)$_3$ (0.1 equivalent weight), NaOt-Bu (3 equivalent weight), and toluene (10.5 mL/1 mmol) were put into a round bottom flask, and then the reactants were subjected to the reaction at 100° C. Upon completion of the reaction, the reaction product was extracted with ether and water, the extracted organic layer was dried with MgSO$_4$ and concentrated, and then the produced organic material was separated by a silica gel column and recrystallized to obtain a desired product.

Example 14

Synthesis Example of Product 1-8 (Method 1)

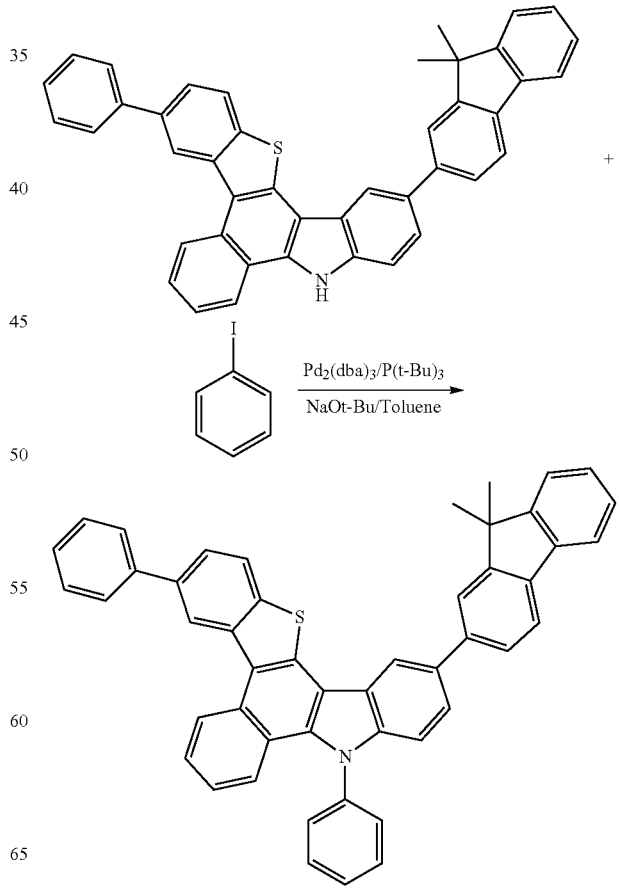

A five-membered heterocyclic compound (11.8 g, 20 mmol) and iodobenzene (4.9 g, 24 mmol) were mixed with toluene (210 mL), and Pd$_2$(dba)$_3$ (0.92 g, 1 mmol), P(t-Bu)$_3$ (0.4 g, 2 mmol), and NaOt-Bu (5.8 g, 60 mmol) were added respectively, followed by reflux under stirring at 100° C. for 24 hours. The reaction product was extracted with methylene chloride and water, the extracted organic layer was dried with MgSO$_4$ and concentrated, and then the produced organic material was separated by a silica gel column and recrystallized to obtain 8.7 g of product 1-8 (yield 65%).

Example 15

Synthesis Example of Product 1-29 (Method 1)

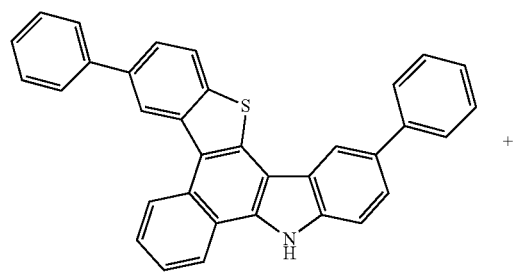

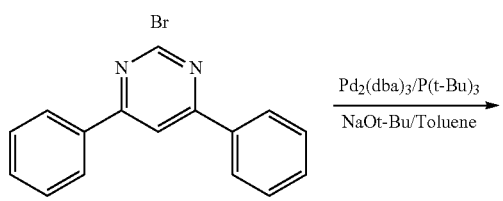

Using a five-membered heterocyclic compound (9.5 g, 20 mmol), 2-bromo-4,6-diphenylpyrimidine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 9.5 g of product 1-29 (yield 67%) was obtained in the same manner as described in the synthesis method of product 1-8.

Example 16

Synthesis Example of Product 1-56 (Method 1)

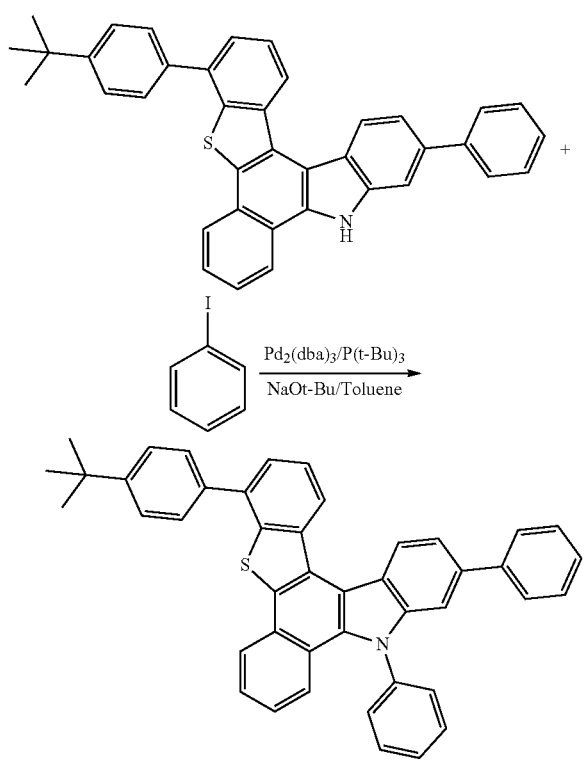

Using a five-membered heterocyclic compound (10.6 g, 20 mmol), iodobenzene (4.9 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 8.5 g of product 1-56 (yield 70%) was obtained in the same manner as described in the synthesis method of product 1-8.

Example 17

Synthesis Example of Product 1-69 (Method 1)

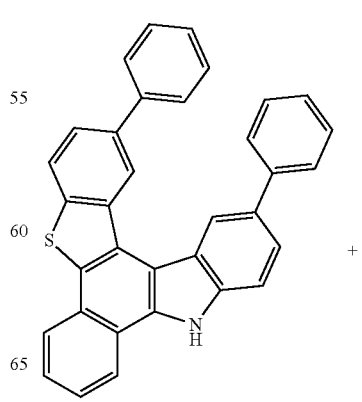

-continued

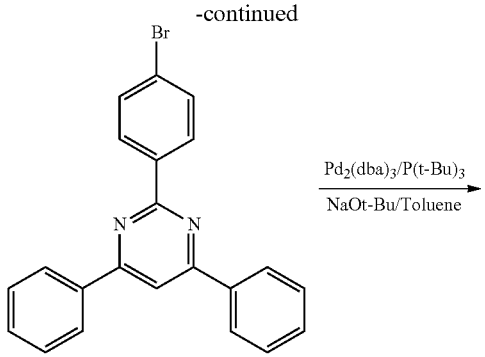

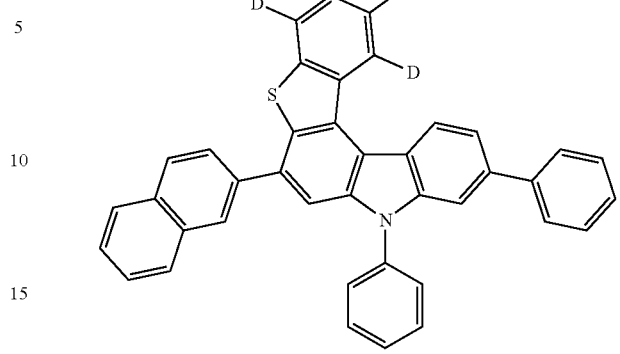

-continued

Using a five-membered heterocyclic compound (9.6 g, 20 mmol), iodobenzene (4.9 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 7.2 g of product 1-129 (yield 65%) was obtained in the same manner as described in the synthesis method of product 1-8.

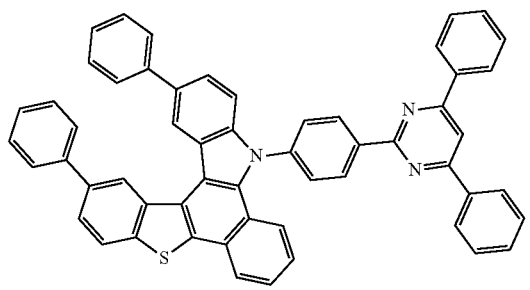

Using a five-membered heterocyclic compound (9.5 g, 20 mmol), 2-(4-bromophenyl)-4,6-diphenylpyrimidine (9.3 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 10.6 g of product 1-69 (yield 68%) was obtained in the same manner as described in the synthesis method of product 1-8.

Example 18

Synthesis Example of Product 1-129 (Method 1)

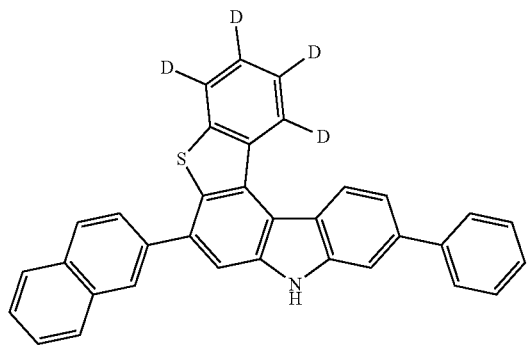

+

Example 19

Synthesis Example of Product 2-5 (Method 1)

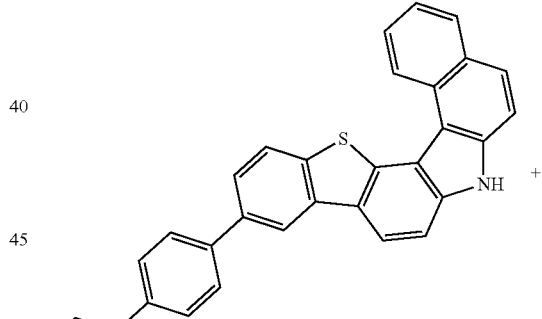

+

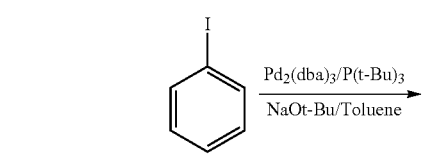

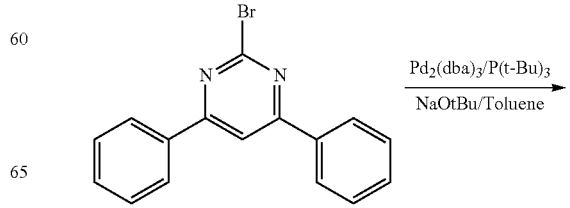

-continued

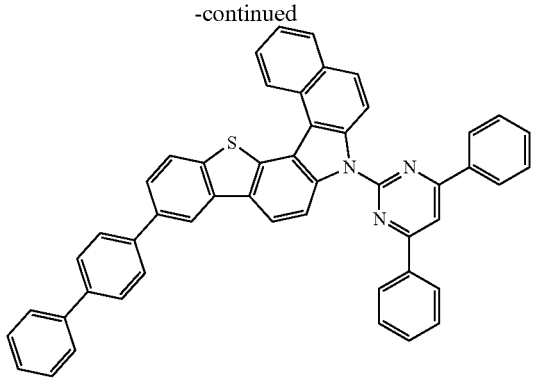

Using a five-membered heterocyclic compound (9.5 g, 20 mmol), 2-bromo-4,6-diphenylpyrimidine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 9.18 g of product 2-5 (yield 65%) was obtained in the same manner as described in the synthesis method of product 1-8.

Example 20

Synthesis Example of Product 2-25 (Method 1)

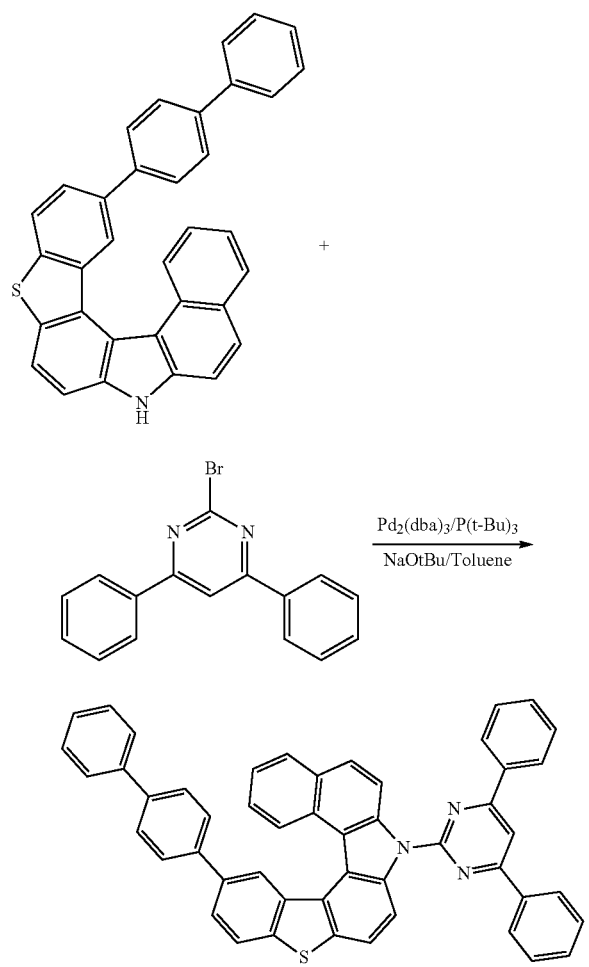

Using a five-membered heterocyclic compound (9.5 g, 20 mmol), 2-bromo-4,6-diphenylpyrimidine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 9.18 g of product 2-25 (yield 65%) was obtained in the same manner as described in the synthesis method of product 1-8.

Example 21

Synthesis Example of Product 3-5 (Method 1)

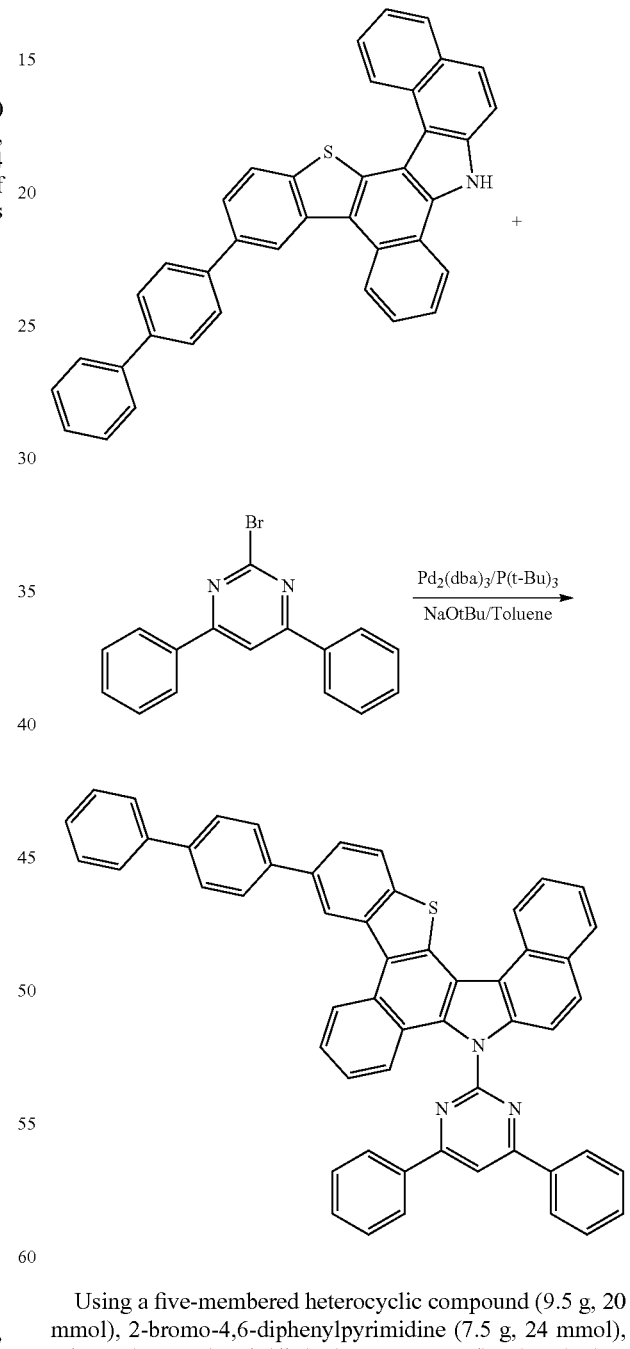

Using a five-membered heterocyclic compound (9.5 g, 20 mmol), 2-bromo-4,6-diphenylpyrimidine (7.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 8.47 g of product 3-5 (yield 60%) was obtained in the same manner as described in the synthesis method of product 1-8.

Synthesis Example of Product 3-30 (Method 1)

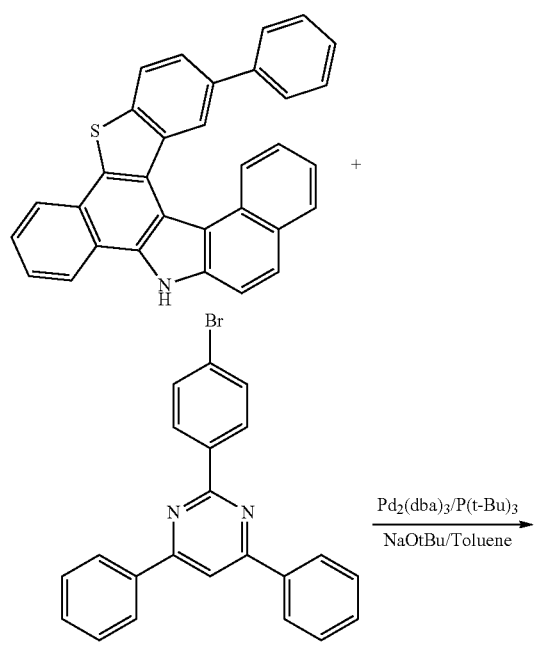

A five-membered heterocyclic compound (9.0 g, 20 mmol) and 2-(4-bromophenyl)-4,6-diphenylpyrimidine (9.3 g, 24 mmol) were mixed with toluene, and Pd$_2$(dba)$_3$, PPh$_3$, and NaOt-Bu were added respectively, followed by reflux under stirring for 24 hours. The reaction product was extracted with ether and water, the extracted organic layer was dried with MgSO$_4$ and concentrated, and then the produced organic material was separated by a silica gel column and recrystallized to obtain 9.37 g of product 3-30 (yield 62%).

Synthesis Example of Product 4-1 (Method 1)

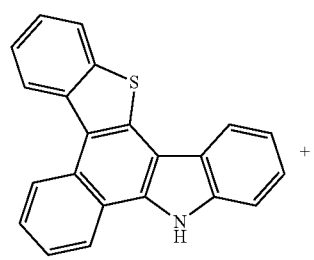

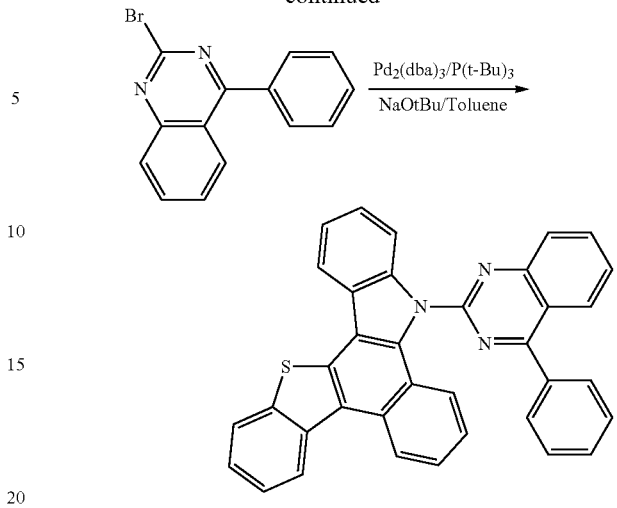

Using a five-membered heterocyclic compound (6.5 g, 20 mmol), 2-bromo-4-phenylquinazoline (6.8 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 7.2 g of product 4-1 (yield 68%) was obtained in the same manner as described in the synthesis method of product 1-8.

Synthesis Example of Product 4-11 (Method 1)

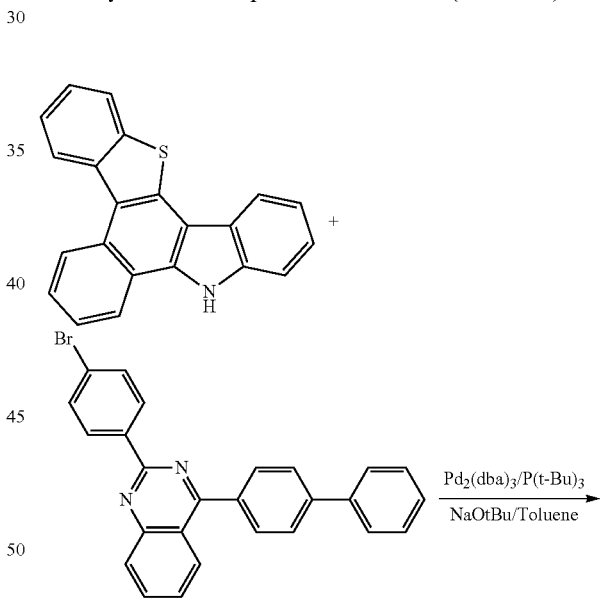

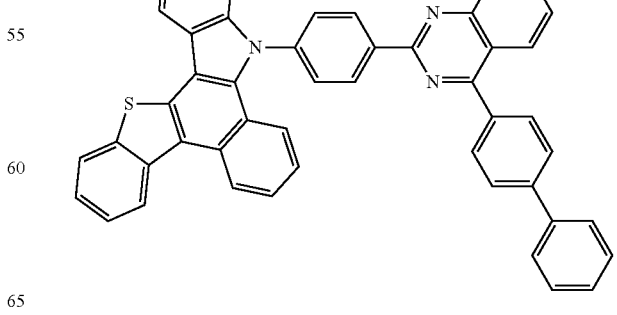

Using a five-membered heterocyclic compound (6.5 g, 20 mmol), 2-bromo-4-phenylquinazoline (10.5 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 8.7 g of product 4-11 (yield 64%) was obtained in the same manner as described in the synthesis method of product 1-8.

Synthesis Example of Product 4-17 (Method 1)

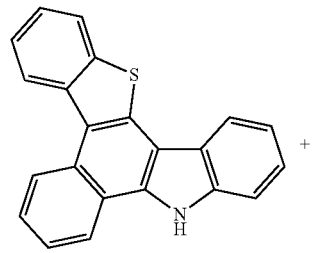

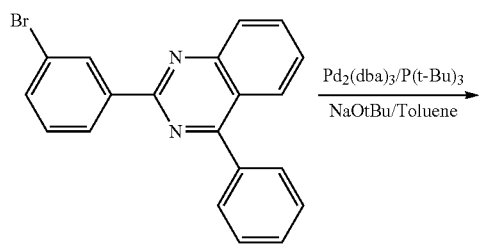

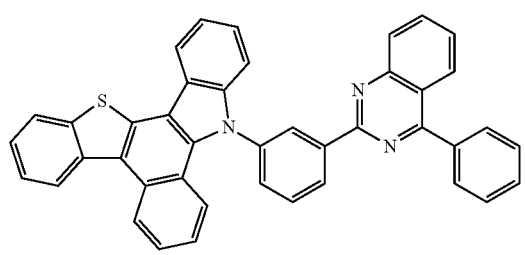

Using a five-membered heterocyclic compound (6.5 g, 20 mmol), 2-(3-bromophenyl)-4-phenylquinazoline (8.7 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 7.4 g of product 4-17 (yield 61%) was obtained in the same manner as described in the synthesis method of product 1-8.

Synthesis Example of Product 4-25 (Method 1)

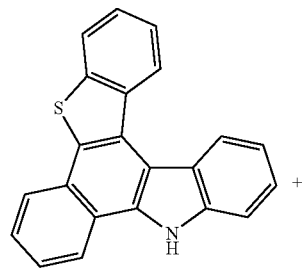

-continued

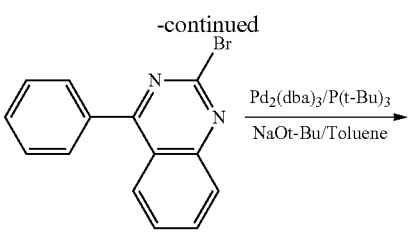

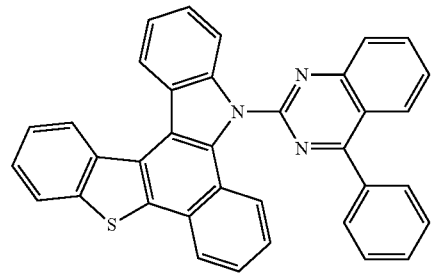

Using a five-membered heterocyclic compound (6.5 g, 20 mmol), 2-bromo-4-phenylquinazoline (6.8 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 7.1 g of product 4-25 (yield 67%) was obtained in the same manner as described in the synthesis method of product 1-8.

Synthesis Example of Product 5-1 (Method 1)

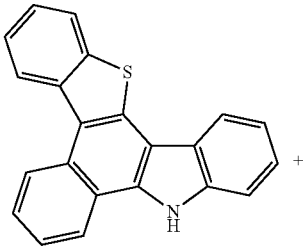

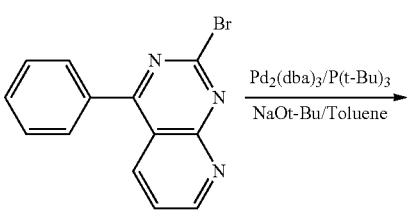

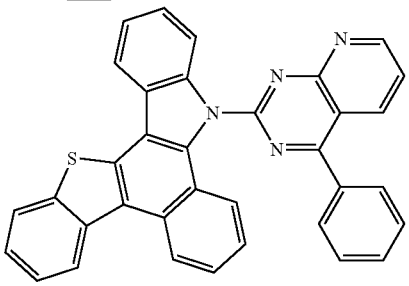

Using a five-membered heterocyclic compound (6.5 g, 20 mmol), 2-bromo-4-phenylpyrido[2,3-d]pyrimidine (6.9 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 6.7 g of product 5-1 (yield 63%) was obtained in the same manner as described in the synthesis method of product 1-8.

Synthesis Example of Product 6-4 (Method 1)

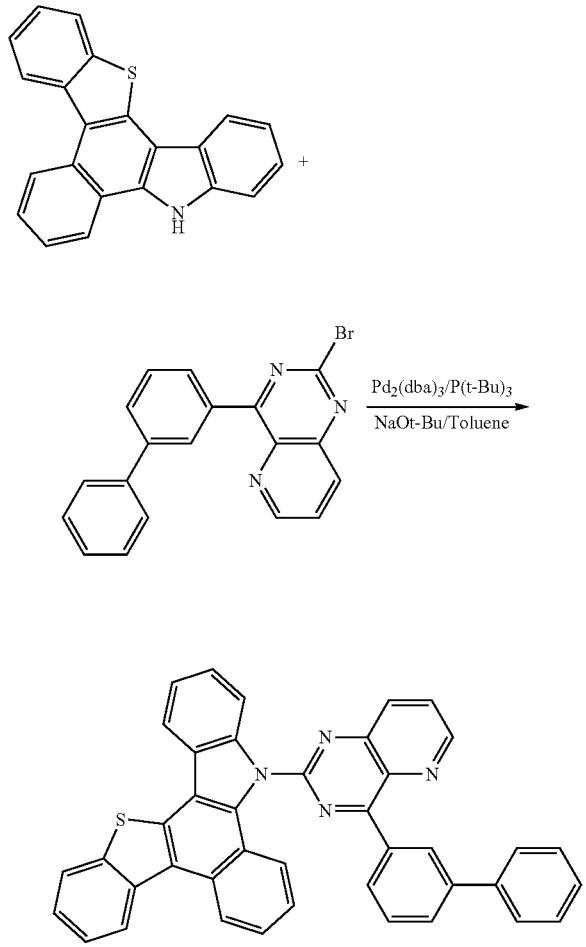

Using a five-membered heterocyclic compound (6.5 g, 20 mmol), 4-([1,1'-biphenyl]-3-yl)-2-bromopyrido[3,2-d]pyrimidine (8.7 g, 24 mmol), toluene (210 mL), Pd$_2$(dba)$_3$ (0.92 g, 1 mmol), P(t-Bu)$_3$ (0.4 g, 2 mmol), and NaOt-Bu (5.8 g, 60 mmol), 7.5 g of product 6-4 (yield 62%) was obtained in the same manner as described in the synthesis method of product 1-8.

Synthesis Example of Product 1-157 (Method 2-1)

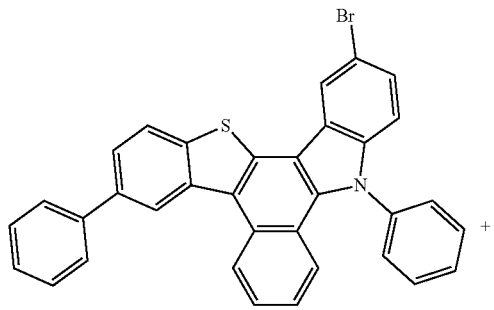

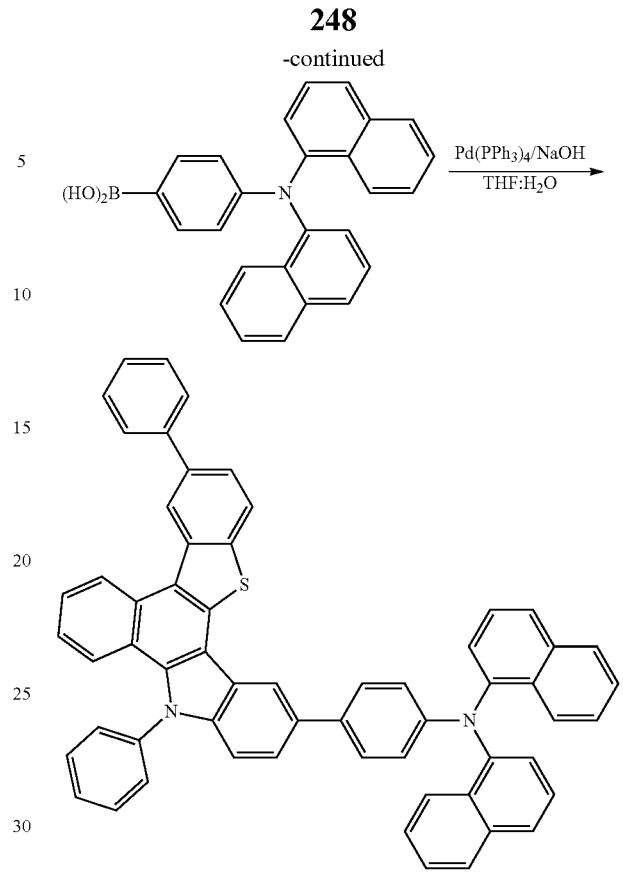

A five-membered heterocyclic compound (11.09 g, 20 mmol) and (4-(di(naphthalene-1-yl)amino)phenyl)boronic acid (9.3 g, 24 mmol) were dissolved in THF, and Pd(PPh$_3$)$_4$ (0.7 g, 0.6 mmol), NaOH (2.4 g, 60 mmol), and water were added respectively, followed by reflux under stirring. Upon completion of the reaction, the reaction product was extracted with ether and water, the extracted organic layer was dried with MgSO$_4$ and concentrated, and then the produced organic material was separated by a silica gel column and recrystallized to obtain 10.2 g of product 1-157 (yield 62%).

Synthesis Example of Product 1-10 (Method 2-2)

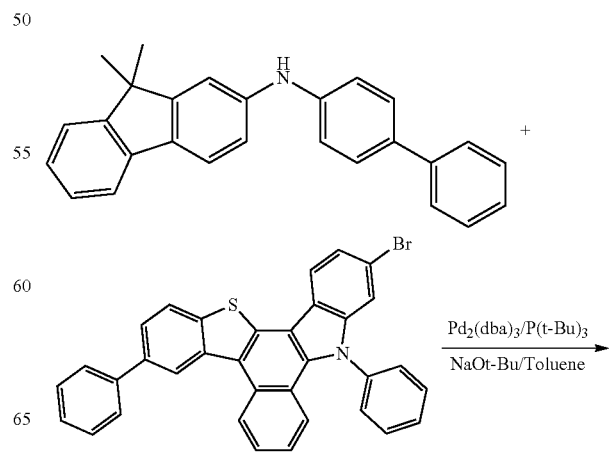

-continued

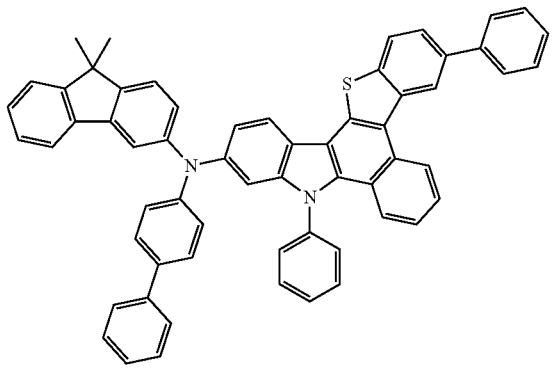

Using N-([1,1'-biphenyl]-4-yl)-9,9-dimethyl-9H-fluoren-2-amine (7.2 g, 20 mmol), a five-membered heterocyclic compound (13.3 g, 24 mmol), toluene (210 mL), $Pd_2(dba)_3$ (0.92 g, 1 mmol), $P(t-Bu)_3$ (0.4 g, 2 mmol), and NaOt-Bu (5.8 g, 60 mmol), 10.7 g of product 1-10 (yield 64%) was obtained in the same manner as described in the synthesis method of product 1-8.

Field desorption mass spectrometry (FD-MS) for compounds 1-1 to 6-48 are given in Table 3 below.

TABLE 3

| Compound | FD-MS | Compound | FD-MS |
|---|---|---|---|
| 1-1 | m/z = 479.16($C_{34}H_{17}D_4NS$ = 479.63) | 1-2 | m/z = 551.17($C_{40}H_{25}NS$ = 551.70) |
| 1-3 | m/z = 601.19($C_{44}H_{27}NS$ = 601.76) | 1-4 | m/z = 601.19($C_{44}H_{27}NS$ = 601.76) |
| 1-5 | m/z = 627.20($C_{46}H_{29}NS$ = 627.79) | 1-6 | m/z = 581.18($C_{41}H_{27}NOS$ = 581.72) |
| 1-7 | m/z = 553.16($C_{38}H_{23}N_3S$ = 553.67) | 1-8 | m/z = 667.23($C_{49}H_{33}NS$ = 667.86) |
| 1-9 | m/z = 531.20($C_{38}H_{29}NS$ = 531.71) | 1-10 | m/z = 834.31($C_{61}H_{42}N_2S$ = 835.06) |
| 1-11 | m/z = 958.34($C_{71}H_{46}N_2S$ = 959.20) | 1-12 | m/z = 956.32($C_{71}H_{44}N_2S$ = 957.19) |
| 1-13 | m/z = 479.16($C_{64}H_{17}D_4NS$ = 479.63) | 1-14 | m/z = 601.19($C_{44}H_{27}NS$ = 601.76) |
| 1-15 | m/z = 601.19($C_{44}H_{27}NS$ = 601.76) | 1-16 | m/z = 627.20($C_{46}H_{29}NS$ = 627.79) |
| 1-17 | m/z = 581.18($C_{41}H_{27}NOS$ = 581.72) | 1-18 | m/z = 553.16($C_{38}H_{23}N_3S$ = 553.67) |
| 1-19 | m/z = 667.23($C_{49}H_{33}NS$ = 667.86) | 1-20 | m/z = 607.23($C_{44}H_{33}NS$ = 607.80) |
| 1-21 | m/z = 834.31($C_{61}H_{42}N_2S$ = 835.06) | 1-22 | m/z = 958.34($C_{71}H_{46}N_2S$ = 959.20) |
| 1-23 | m/z = 956.32($C_{71}H_{44}N_2S$ = 957.19) | 1-24 | m/z = 601.19($C_{44}H_{27}NS$ = 601.76) |
| 1-25 | m/z = 601.19($C_{44}H_{27}NS$ = 601.76) | 1-26 | m/z = 627.20($C_{46}H_{29}NS$ = 627.79) |
| 1-27 | m/z = 706.22($C_{49}H_{30}N_4S$ = 706.85) | 1-28 | m/z = 706.22($C_{49}H_{30}N_4S$ = 706.85) |
| 1-29 | m/z = 705.22($C_{50}H_{31}N_3S$ = 705.87) | 1-30 | m/z = 705.22($C_{50}H_{31}N_3S$ = 705.87) |
| 1-31 | m/z = 705.22($C_{50}H_{31}N_3S$ = 705.87) | 1-32 | m/z = 782.25($C_{55}H_{34}N_4S$ = 782.95) |
| 1-33 | m/z = 781.26($C_{56}H_{35}M_3S$ = 78.1.96) | 1-34 | m/z = 781.26($C_{56}H_{35}N_3S$ = 781.96) |
| 1-35 | m/z = 743.24($C_{53}H_{33}N_3S$ = 743.91) | 1-36 | m/z = 667.21($C_{47}H_{29}N_3S$ = 667.82) |
| 1-37 | m/z = 479.16($C_{34}H_{17}D_4NS$ = 479.63) | 1-38 | m/z = 551.17($C_{40}H_{25}NS$ = 551.70) |
| 1-39 | m/z = 601.19($C_{44}H_{27}NS$ = 601.76) | 1-40 | m/z = 601.19($C_{44}H_{27}NS$ = 601.76) |
| 1-41 | m/z = 627.20($C_{46}H_{29}NS$ = 627.79) | 1-42 | m/z = 581.18($C_{41}H_{27}NOS$ = 581.72) |
| 1-43 | m/z = 553.16($C_{38}H_{23}N_3S$ = 553.67) | 1-44 | m/z = 667.23($C_{49}H_{33}NS$ = 667.86) |
| 1-45 | m/z = 531.20($C_{38}H_{29}NS$ = 531.71) | 1-46 | m/z = 834.31($C_{61}H_{42}N_2S$ = 835.06) |
| 1-47 | m/z = 958.34($C_{71}H_{46}N_2S$ = 959.20) | 1-48 | m/z = 956.32($C_{71}H_{44}N_2S$ = 957.19) |
| 1-49 | m/z = 479.16($C_{64}H_{17}D_4NS$ = 479.63) | 1-50 | m/z = 601.19($C_{44}H_{27}NS$ = 601.76) |
| 1-51 | m/z = 601.19($C_{44}H_{27}NS$ = 601.76) | 1-52 | m/z = 627.20($C_{46}H_{29}NS$ = 627.79) |
| 1-53 | m/z = 581.18($C_{41}H_{27}NOS$ = 581.72) | 1-54 | m/z = 553.16($C_{38}H_{23}N_3S$ = 553.67) |
| 1-55 | m/z = 667.23($C_{49}H_{33}NS$ = 667.86) | 1-56 | m/z = 607.23($C_{44}H_{33}NS$ = 607.80) |
| 1-57 | m/z = 834.31($C_{61}H_{42}N_2S$ = 835.06) | 1-58 | m/z = 958.34($C_{71}H_{46}N_2S$ = 959.20) |
| 1-59 | m/z = 956.32($C_{71}H_{44}N_2S$ = 957.19) | 1-60 | m/z = 601.19($C_{44}H_{27}NS$ = 601.76) |
| 1-61 | m/z = 601.19($C_{44}H_{27}NS$ = 601.76) | 1-62 | m/z = 627.20($C_{46}H_{29}NS$ = 627.79) |
| 1-63 | m/z = 706.22($C_{49}H_{30}N_4S$ = 706.85) | 1-64 | m/z = 706.22($C_{49}H_{30}N_4S$ = 706.85) |
| 1-65 | m/z = 705.22($C_{50}H_{31}N_3S$ = 705.87) | 1-66 | m/z = 705.22($C_{50}H_{31}N_3S$ = 705.87) |
| 1-67 | m/z = 705.22($C_{50}H_{31}N_3S$ = 705.87) | 1-68 | m/z = 782.25($C_{55}H_{34}N_4S$ = 782.95) |
| 1-69 | m/z = 781.26($C_{56}H_{35}N_3S$ = 781.96) | 1-70 | m/z = 781.26($C_{56}H_{35}N_3S$ = 781.96) |
| 1-71 | m/z = 743.24($C_{53}H_{33}N_3S$ = 743.91) | 1-72 | m/z = 667.21($C_{47}H_{29}N_3S$ = 667.82) |
| 1-73 | m/z = 731.24($C_{52}H_{33}N_3S$ = 731.90) | 1-74 | m/z = 781.26($C_{56}H_{35}N_3S$ = 78196) |
| 1-75 | m/z = 732.23($C_{51}H_{32}N_4S$ = 732.89) | 1-76 | m/z = 807.27($C_{58}H_{37}N_3S$ = 808.00) |
| 1-77 | m/z = 715.26($C_{52}H_{33}N_3O$ = 715.84) | 1-78 | m/z = 765.28($C_{56}H_{35}N_3O$ = 765.90) |
| 1-79 | m/z = 716.26($C_{51}H_{32}N_4O$ = 716.83) | 1-80 | m/z = 791.29($C_{58}H_{37}N_3O$ = 791.93) |
| 1-81 | m/z = 429.15($C_{30}H_{15}D_4NS$ = 429.57) | 1-82 | m/z = 501.16($C_{36}H_{23}NS$ = 501.64) |
| 1-83 | m/z = 551.17($C_{40}H_{25}NS$ = 551.70) | 1-84 | m/z = 551.17($C_{40}H_{25}NS$ = 551.70) |
| 1-85 | m/z = 627.20($C_{48}H_{31}NS$ = 653.83) | 1-86 | m/z = 607.20($C_{43}H_{29}NOS$ = 607.76) |
| 1-87 | m/z = 579.18($C_{40}H_{25}N_3S$ = 579.71) | 1-88 | m/z = 693.25($C_{51}H_{35}NS$ = 693.90) |
| 1-89 | m/z = 607.23($C_{44}H_{33}NS$ = 607.80) | 1-90 | m/z = 910.34($C_{67}H_{46}N_2S$ = 911.16) |
| 1-91 | m/z = 1034.37($C_{77}H_{50}N_2S$ = 1035.30) | 1-92 | m/z = 1032.35($C_{77}H_{48}N_2S$ = 1033.28) |
| 1-93 | m/z = 555.20($C_{40}H_{21}D_4NS$ = 555.72) | 1-94 | m/z = 677.22($C_{50}H_{31}NS$ = 677.85) |
| 1-95 | m/z = 677.22($C_{50}H_{31}NS$ = 677.85) | 1-96 | m/z = 703.23($C_{52}H_{33}NS$ = 703.89) |
| 1-97 | m/z = 652.21($C_{48}H_{30}NS$ = 652.82) | 1-98 | m/z = 655.21($C_{46}H_{29}N_3S$ = 655.81) |
| 1-99 | m/z = 769.28($C_{57}H_{39}NS$ = 769.99) | 1-100 | m/z = 709.28($C_{52}H_{39}NS$ = 709.94) |
| 1-101 | m/z = 861.32($C_{62}H_{43}N_3S$ = 862.09) | 1-102 | m/z = 985.35($C_{72}H_{47}N_3S$ = 986.23) |
| 1-103 | m/z = 984.33($C_{71}H_{44}N_4S$ = 985.20) | 1-104 | m/z = 629.19($C_{44}H_{27}N_3S$ = 629.77) |
| 1-105 | m/z = 551.17$C_{40}H_{25}NS$ = 551.70) | 1-106 | m/z = 577.19($C_{42}H_{27}NS$ = 577.74) |
| 1-107 | m/z = 656.20($C_{45}H_{28}N_4S$ = 656.80) | 1-108 | m/z = 656.20($C_{45}H_{28}N_4S$ = 656.80) |
| 1-109 | m/z = 655.21($C_{46}H_{29}N_3S$ = 655.81) | 1-110 | m/z = 731.24($C_{52}H_{33}N_3S$ = 731.90) |

TABLE 3-continued

| Compound | FD-MS | Compound | FD-MS |
|---|---|---|---|
| 1-111 | m/z = 731.24($C_{52}H_{33}N_3S$ = 731.90) | 1-112 | m/z = 808.27($C_{57}H_{36}N_4S$ = 808.99) |
| 1-113 | m/z = 808.27($C_{57}H_{36}N_4S$ = 808.99) | 1-114 | m/z = 809.26($C_{35}H_{35}N_5S$ = 809.98) |
| 1-115 | m/z = 771.25($C_{53}H_{33}N_5S$ = 771.93) | 1-116 | m/z = 694.22($C_{48}H_{20}N_4S$ = 694.84) |
| 1-117 | m/z = 429.15($C_{30}H_{15}D_4NS$ = 429.57) | 1-118 | m/z = 501.16($C_{36}H_{23}NS$ = 501.64) |
| 1-119 | m/z = 551.17($C_{40}H_{25}NS$ = 551.70) | 1-120 | m/z = 551.17($C_{40}H_{25}NS$ = 551.70) |
| 1-121 | m/z = 627.20($C_{48}H_{31}$ = 653.83) | 1-122 | m/z = 607.20($C_{43}H_{29}NOS$ = 607.76) |
| 1-123 | m/z = 579.18($C_{40}H_{25}N_3S$ = 579.71) | 1-124 | m/z = 693.25($C_{51}H_{35}NS$ = 693.90) |
| 1-125 | m/z = 607.23($C_{44}H_{33}NS$ = 607.80) | 1-126 | m/z = 910.34($C_{67}H_{46}N_2S$ = 911.16) |
| 1-127 | m/z = 1034.37($C_{77}H_{50}N_2S$ = 1035.30) | 1-128 | m/z = 1032.35($C_{77}H_{48}N_2S$ = 1033.28) |
| 1-129 | m/z = 555.20($C_{40}H_{21}D_4NS$ = 555.72) | 1-130 | m/z = 677.22($C_{50}H_{31}NS$ = 677.85) |
| 1-131 | m/z = 677.22($C_{50}H_{31}NS$ = 677.85) | 1-132 | m/z = 703.23($C_{52}H_{33}NS$ = 703.89) |
| 1-133 | m/z = 652.21($C_{48}H_{30}N_2S$ = 652.82) | 1-134 | m/z = 655.21($C_{46}H_{29}N_3S$ = 655.81) |
| 1-135 | m/z = 769.28($C_{57}H_{39}NS$ = 769.99) | 1-136 | m/z = 709.28($C_{52}H_{39}NS$ = 709.94) |
| 1-137 | m/z = 861.32($C_{62}H_{43}N_3S$ = 862.09) | 1-138 | m/z = 985.35($C_{72}H_{47}N_3S$ = 986.23) |
| 1-139 | m/z = 984.33($C_{71}H_{44}N_4S$ = 985.20) | 1-140 | m/z = 629.19($C_{44}H_{27}N_3S$ = 629.77) |
| 1-141 | m/z = 551.17$C_{40}H_{25}NS$ = 551.70) | 1-142 | m/z = 577.19($C_{42}H_{27}NS$ = 577.74) |
| 1-143 | m/z = 656.20($C_{45}H_{28}N_4S$ = 656.80) | 1-144 | m/z = 656.20($C_{45}H_{28}N_4S$ = 656.80) |
| 1-145 | m/z = 655.21($C_{46}H_{29}N_3S$ = 655 81) | 1-146 | m/z = 731.24($C_{52}H_{33}N_3S$ = 731.90) |
| 1-147 | m/z = 731.24($C_{52}H_{33}N_3S$ = 731.90) | 1-148 | m/z = 808.27($C_{57}H_{36}N_4S$ = 808.99) |
| 1-149 | m/z = 808.27($C_{57}H_{36}N_4S$ = 808.99) | 1-150 | m/z = 809.26($C_{56}H_{35}N_5S$ = 809.98) |
| 1-151 | m/z = 771.25($C_{53}H_{33}N_5S$ = 771.93) | 1-152 | m/z = 694.22($C_{48}H_{20}N_4S$ = 694.84) |
| 1-153 | m/z = 718.24 ($C_{52}H_{34}N_2S$ = 718.90) | 1-154 | m/z = 768.26 ($C_{56}H_{36}N_2S$ = 768.96) |
| 1-155 | m/z = 794.28 ($C_{58}H_{38}N_2S$ = 795.00) | 1-156 | m/z = 768.26 ($C_{56}H_{36}N_2S$ = 768.96) |
| 1-157 | m/z = 818.28 ($C_{60}H_{38}N_2S$ = 819.02) | 1-158 | m/z = 718.24 ($C_{52}H_{34}N_2S$ = 718.90) |
| 1-159 | m/z = 716.23 ($C_{52}H_{32}N_2S$ = 716.89) | 1-160 | m/z = 718.24 ($C_{52}H_{34}N_2S$ = 718.90) |
| 1-161 | m/z = 768.26 ($C_{56}H_{36}N_2S$ = 768.96) | 1-162 | m/z = 870.31 ($C_{64}H_{42}N_2S$ = 871.10) |
| 1-163 | m/z = 794.28 ($C_{58}H_{38}N_2S$ = 795.00) | | |
| 2-1 | m/z = 403.13($C_{28}H_{13}D_4NS$ = 403.53) | 2-2 | m/z = 525.16($C_{38}H_{23}NS$ = 525.66) |
| 2-3 | m/z = 678.21($C_{49}H_{30}N_2S$ = 678.84) | 2-4 | m/z = 680.20($C_{47}H_{28}N_4S$ = 680.82) |
| 2-5 | m/z = 705.22($C_{50}H_{31}N_3S$ = 705.87) | 2-6 | m/z = 583.17($C_{39}H_{25}N_3OS$ = 583.70) |
| 2-7 | m/z = 631.18($C_{42}H_{25}N_5S$ = 631.75) | 2-8 | m/z = 667.23($C_{49}H_{33}NS$ = 667.86) |
| 2-9 | m/z = 634.21($C_{43}H_{22}N_4S$ = 634.78) | 2-10 | m/z = 705.22($C_{50}H_{31}N_3S$ = 705.87) |
| 2-11 | m/z = 755.24($C_{54}H_{33}N_3S$ = 755.92) | 2-12 | m/z = 647.24($C_{45}H_{33}N_3S$ = 647.83) |
| 2-13 | m/z = 691.21($C_{49}H_{29}N_3S$ = 691.84) | 2-14 | m/z = 551.17($C_{40}H_{25}NS$ = 551.70) |
| 2-15 | m/z = 537.18($C_{38}H_{23}N_3O$ = 537.61) | 2-16 | m/z = 575.22($C_{49}H_{29}NO$ = 575.70) |
| 2-17 | m/z = 912.33($C_{65}H_{44}N_4S$ = 913.14) | 2-18 | m/z = 1036.36($C_{75}H_{48}N_4S$ = 1037.28) |
| 2-19 | m/z = 1034.34($C_{75}H_{46}N_4S$ = 1035.26) | 2-20 | m/z = 988.36($C_{71}H_{48}N_4S$ = 989.23) |
| 2-21 | m/z = 403.13($C_{28}H_{13}D_4NS$ = 403.53) | 2-22 | m/z = 525.16($C_{38}H_{23}NS$ = 525.66) |
| 2-23 | m/z = 678.21($C_{49}H_{30}N_2S$ = 678.84) | 2-24 | m/z = 680.20($C_{47}H_{28}N_4S$ = 680.82) |
| 2-25 | m/z = 705.22($C_{50}H_{31}N_3S$ = 705.87) | 2-26 | m/z = 583.17($C_{39}H_{25}N_3OS$ = 583.70) |
| 2-27 | m/z = 631.18($C_{42}H_{25}N_5S$ = 631.75) | 2-28 | m/z = 667.23($C_{49}H_{33}NS$ = 667.86) |
| 2-29 | m/z = 634.21($C_{43}H_{22}N_4S$ = 634.78) | 2-30 | m/z = 705.22($C_{50}H_{31}N_3S$ = 705.87) |
| 2-31 | m/z = 755.24($C_{54}H_{33}N_3S$ = 755.92) | 2-32 | m/z = 647.24($C_{45}H_{33}N_3S$ = 647.83) |
| 2-33 | m/z = 691.21($C_{49}H_{29}N_3S$ = 691.84) | 2-34 | m/z = 551.17($C_{40}H_{25}NS$ = 551.70) |
| 2-35 | m/z = 537.18($C_{38}H_{23}N_3O$ = 537.61) | 2-36 | m/z = 575.22($C_{49}H_{29}NO$ = 575.70) |
| 2-37 | m/z = 912.33($C_{65}H_{44}N_4S$ = 913.14) | 2-38 | m/z = 1036.36($C_{75}H_{48}N_4S$ = 1037.28) |
| 2-39 | m/z = 1034.34($C_{75}H_{46}N_4S$ = 1035.26) | 2-40 | m/z = 988.36($C_{71}H_{48}N_4S$ = 989.23) |
| 2-41 | m/z = 453.15($C_{32}H_{15}D_4NS$ = 453.59) | 2-42 | m/z = 575.17($C_{42}H_{25}NS$ = 575.72) |
| 2-43 | m/z = 728.23($C_{53}H_{32}N_2S$ = 728.90 | 2-44 | m/z = 730.22($C_{51}H_{30}N_4S$ = 730.88) |
| 2-45 | m/z = 755.24($C_{54}H_{33}N_3S$ = 755.92) | 2-46 | m/z = 633.19($C_{43}H_{27}N_3OS$ = 633.76) |
| 2-47 | m/z = 681.20($C_{46}H_{27}N_5S$ = 681.81) | 2-48 | m/z = 717.25($C_{53}H_{35}NS$ = 717.92) |
| 2-49 | m/z = 684.23($C_{47}H_{24}D_4N_4S$ = 684.84) | 2-50 | m/z = 755.24($C_{54}H_{33}N_3S$ = 755.92) |
| 2-51 | m/z = 805.26($C_{56}H_{35}N_3S$ = 805.98) | 2-52 | m/z = 697.26($C_{49}H_{35}N_3S$ = 697.89) |
| 2-53 | m/z = 741.22($C_{53}H_{31}N_3S$ = 741.90) | 2-54 | m/z = 601.19($C_{44}H_{27}NS$ = 601.76) |
| 2-55 | m/z = 587.20($C_{42}H_{25}N_3O$ = 587.67) | 2-56 | m/z = 625.24($C_{47}H_{31}NO$ = 625.76) |
| 2-57 | m/z = 962.34($C_{69}H_{46}N_4S$ = 963.20) | 2-58 | m/z = 1086.38($C_{79}H_{50}N_4S$ = 1087.38) |
| 2-59 | m/z = 1084.36($C_{79}H_{48}N_4S$ = 1085.32) | 2-60 | m/z = 1038.38($C_{75}H_{50}N_4S$ = 1039.29) |
| 2-61 | m/z = 453.15($C_{32}H_{15}D_4NS$ = 453.59) | 2-62 | m/z = 575.17($C_{42}H_{25}NS$ = 575.72) |
| 2-63 | m/z = 728.23($C_{53}H_{32}N_2S$ = 728.90 | 2-64 | m/z = 730.22($C_{51}H_{30}N_4S$ = 730.88) |
| 2-65 | m/z = 755.24($C_{54}H_{33}N_3S$ = 755.92) | 2-66 | m/z = 633.19($C_{43}H_{27}N_3OS$ = 633.76) |
| 2-67 | m/z = 681.20($C_{46}H_{27}N_5S$ = 681.81) | 2-68 | m/z = 717.25($C_{53}H_{35}NS$ = 717.92) |
| 2-69 | m/z = 684.23($C_{47}H_{24}D_4N_4S$ = 684.84) | 2-70 | m/z = 755.24($C_{54}H_{33}N_3S$ = 755.92) |
| 2-71 | m/z = 805.26($C_{56}H_{35}N_3S$ = 805.98) | 2-72 | m/z = 697.26($C_{49}H_{35}M_3S$ = 697.89) |
| 2-73 | m/z = 741.22($C_{53}H_{31}N_3S$ = 741.90) | 2-74 | m/z = 601.19($C_{44}H_{27}NS$ = 601.76) |
| 2-75 | m/z = 587.20($C_{42}H_{25}N_3O$ = 587.67) | 2-76 | m/z = 625.24($C_{47}H_{31}NO$ = 625.76) |
| 2-77 | m/z = 962.34($C_{69}H_{46}N_4S$ = 963.20) | 2-78 | m/z = 1086.38($C_{79}H_{50}N_4S$ = 1087.38) |
| 2-79 | m/z = 1084.36($C_{79}H_{48}N_4S$ = 1085.32) | 2-80 | m/z = 1038.38($C_{75}H_{50}N_4S$ = 1039.29) |
| 3-1 | m/z = 453.15($C_{32}H_{15}D_4NS$ = 453.59) | 3-2 | m/z = 575.17($C_{42}H_{25}NS$ = 575.72) |
| 3-3 | m/z = 728.23($C_{53}H_{32}N_2S$ = 728.90 | 3-4 | m/z = 730.22($C_{51}H_{30}N_4S$ = 730.88) |
| 3-5 | m/z = 755.24($C_{54}H_{33}N_3S$ = 755.92) | 3-6 | m/z = 633.19($C_{43}H_{27}N_3OS$ = 633.76) |
| 3-7 | m/z = 681.20($C_{46}H_{27}N_5S$ = 681.81) | 3-8 | m/z = 717.25($C_{53}H_{35}NS$ = 717.92) |
| 3-9 | m/z = 684.23($C_{47}H_{24}D_4N_4S$ = 684.84) | 3-10 | m/z = 755.24($C_{54}H_{33}N_3S$ = 755.92) |

TABLE 3-continued

| Compound | FD-MS | Compound | FD-MS |
| --- | --- | --- | --- |
| 3-11 | m/z = 805.26($C_{56}H_{35}N_3S$ = 805.98) | 3-12 | m/z = 697.26($C_{49}H_{35}N_3S$ = 697.89) |
| 3-13 | m/z = 741.22($C_{53}H_{31}N_3S$ = 741.90) | 3-14 | m/z = 601.19($C_{44}H_{27}NS$ = 601.76) |
| 3-15 | m/z = 587.20($C_{42}H_{25}N_3O$ = 587.67) | 3-16 | m/z = 625.24($C_{47}H_{31}NO$ = 625.76) |
| 3-17 | m/z = 962.34($C_{69}H_{46}N_4S$ = 963.20) | 3-18 | m/z = 1086.38($C_{79}H_{50}N_4S$ = 1087.38) |
| 3-19 | m/z = 1084.36($C_{79}H_{48}N_4S$ = 1085.32) | 3-20 | m/z = 1038.38($C_{75}H_{50}N_4S$ = 1039.29) |
| 3-21 | m/z = 453.15($C_{32}H_{15}D_4NS$ = 453.59) | 3-22 | m/z = 575.17($C_{42}H_{25}NS$ = 575.72) |
| 3-23 | m/z = 728.23($C_{53}H_{32}N_2S$ = 728.90) | 3-24 | m/z = 730.22($C_{51}H_{30}N_4S$ = 730.88) |
| 3-25 | m/z = 755.24($C_{54}H_{33}N_3S$ = 755.92) | 3-26 | m/z = 633.19($C_{43}H_{27}N_3OS$ = 633.76) |
| 3-27 | m/z = 681.20($C_{46}H_{27}N_5S$ = 681.81) | 3-28 | m/z = 717.25($C_{53}H_{35}NS$ = 717.92) |
| 3-29 | m/z = 684.23($C_{47}H_{24}D_4N_4S$ = 684.84) | 3-30 | m/z = 755.24($C_{54}H_{33}N_3S$ = 755.92) |
| 3-31 | m/z = 805.26($C_{55}H_{35}N_3S$ = 805.98) | 3-32 | m/z = 697.26($C_{49}H_{35}N_3S$ = 697.89) |
| 3-33 | m/z = 741.22($C_{53}H_{31}N_3S$ = 741.90) | 3-34 | m/z = 601.19($C_{44}H_{27}NS$ = 601.76) |
| 3-35 | m/z = 587.20($C_{42}H_{25}N_3O$ = 587.67) | 3-36 | m/z = 625.24($C_{47}H_{31}NO$ = 625.76) |
| 3-37 | m/z = 962.34($C_{69}H_{46}N_4S$ = 963.20) | 3-38 | m/z = 1086.38($C_{79}H_{50}N_4S$ = 1087.38) |
| 3-39 | m/z = 1084.36($C_{79}H_{48}N_4S$ = 1085.32) | 3-40 | m/z = 1038.38($C_{75}H_{50}N_4S$ = 1039.29) |
| 3-41 | m/z = 503.16($C_{38}H_{17}D_4NS$ = 503.65) | 3-42 | m/z = 658.19($C_{46}H_{27}NS$ = 625.78) |
| 3-43 | m/z = 778.24($C_{57}H_{34}N_2S$ = 778.96) | 3-44 | m/z = 780.23($C_{55}H_{32}N_4S$ = 780.93) |
| 3-45 | m/z = 805.26($C_{53}H_{35}N_3S$ = 805.98) | 3-46 | m/z = 683.20($C_{47}H_{29}N_3OS$ = 683.82) |
| 3-47 | m/z = 731.21($C_{50}H_{29}N_5S$ = 731.86) | 3-48 | m/z = 767.26($C_{57}H_{37}NS$ = 767.98) |
| 3-49 | m/z = 734.24($C_{51}H_{26}D_4N_4S$ = 734.90) | 3-50 | m/z = 805.26($C_{58}H_{35}N_3S$ = 805.98) |
| 3-51 | m/z = 855.27($C_{62}H_{37}N_3S$ = 856.04) | 3-52 | m/z = 747.27($C_{53}H_{37}N_3S$ = 747.95) |
| 3-53 | m/z = 791.24($C_{57}H_{33}N_3S$ = 791.96) | 3-54 | m/z = 651.20($C_{48}H_{29}NS$ = 651.82) |
| 3-55 | m/z = 637.22($C_{46}H_{27}N_3O$ = 637.73) | 3-56 | m/z = 675.26($C_{51}H_{33}NO$ = 675.81) |
| 3-57 | m/z = 1012.36($C_{73}H_{48}N_4S$ = 1013.25) | 3-58 | m/z = 1136.39($C_{83}H_{52}N_4S$ = 1137.39) |
| 3-59 | m/z = 1134.38($C_{83}H_{50}N_4S$ = 1135.38) | 3-60 | m/z = 1088.39($C_{79}H_{52}N_4S$ = 1089.35) |
| 3-61 | m/z = 503.16($C_{38}H_{17}D_4NS$ = 503.65) | 3-62 | m/z = 658.19($C_{46}H_{27}NS$ = 625.78) |
| 3-63 | m/z = 778.24($C_{57}H_{34}N_2S$ = 778.96) | 3-64 | m/z = 780.23($C_{55}H_{32}N_4S$ = 780.93) |
| 3-65 | m/z = 805.26($C_{53}H_{35}N_3S$ = 805.98) | 3-66 | m/z = 683.20($C_{47}H_{29}N_3OS$ = 683.82) |
| 3-67 | m/z = 731.21($C_{50}H_{29}N_5S$ = 731.86) | 3-68 | m/z = 767.26($C_{57}H_{37}NS$ = 767.98) |
| 3-69 | m/z = 734.24($C_{51}H_{26}D_4N_4S$ = 734.90) | 3-70 | m/z = 805.26($C_{58}H_{35}N_3S$ = 805.98) |
| 3-71 | m/z = 855.27($C_{62}H_{37}N_3S$ = 856.04) | 3-72 | m/z = 747.27($C_{53}H_{37}N_3S$ = 747.95) |
| 3-73 | m/z = 791.24($C_{57}H_{33}N_3S$ = 791.96) | 3-74 | m/z = 651.20($C_{48}H_{29}NS$ = 651.82) |
| 3-75 | m/z = 637.22($C_{46}H_{27}N_3O$ = 637.73) | 3-76 | m/z = 675.26($C_{51}H_{33}NO$ = 675.81) |
| 3-77 | m/z = 1012.36($C_{73}H_{48}N_4S$ = 1013.25) | 3-78 | m/z = 1136.39($C_{83}H_{52}N_4S$ = 1137.39) |
| 3-79 | m/z = 1134.38($C_{83}H_{50}N_4S$ = 1135.38) | 3-80 | m/z = 1088.39($C_{79}H_{52}N_4S$ = 1089.35) |
| 4-1 | m/z = 527.15 ($C_{36}H_{21}N_3S$ = 527.64) | 4-2 | m/z = 532.18 ($C_{36}H_{16}D_5N_3S$ = 532.67) |
| 4-3 | m/z = 603.18 ($C_{42}H_{25}N_3S$ = 603.73) | 4-4 | m/z = 603.18 ($C_{42}H_{25}N_3S$ = 603.73) |
| 4-5 | m/z = 577.16 ($C_{40}H_{23}N_3S$ = 577.70) | 4-6 | m/z = 577.16 ($C_{40}H_{23}N_3S$ = 577.70) |
| 4-7 | m/z = 679.21 ($C_{48}H_{29}N_3S$ = 679.83) | 4-8 | m/z = 643.21 ($C_{45}H_{29}N_3S$ = 643.80) |
| 4-9 | m/z = 603.18 ($C_{42}H_{25}N_3S$ = 603.73) | 4-10 | m/z = 608.21 ($C_{42}H_{20}D_5N_3S$ = 608.76) |
| 4-11 | m/z = 679.21 ($C_{48}H_{29}N_3S$ = 679.83) | 4-12 | m/z = 679.21 ($C_{48}H_{29}N_3S$ = 679.83) |
| 4-13 | m/z = 653.19 ($C_{46}H_{27}N_3S$ = 653.79) | 4-14 | m/z = 653.19 ($C_{46}H_{27}N_3S$ = 653.79) |
| 4-15 | m/z = 755.24 ($C_{54}H_{33}N_3S$ = 755.92) | 4-16 | m/z = 719.24 ($C_{51}H_{33}N_3S$ = 719.89) |
| 4-17 | m/z = 603.18 ($C_{42}H_{25}N_3S$ = 603.73) | 4-18 | m/z = 608.21 ($C_{42}H_{20}D_5N_3S$ = 608.76) |
| 4-19 | m/z = 679.21 ($C_{48}H_{29}N_3S$ = 679.83) | 4-20 | m/z = 679.21 ($C_{48}H_{29}N_3S$ = 679.83) |
| 4-21 | m/z = 653.19 ($C_{46}H_{27}N_3S$ = 653.79) | 4-22 | m/z = 653.19 ($C_{46}H_{27}N_3S$ = 653.79) |
| 4-23 | m/z = 755.24 ($C_{54}H_{33}N_3S$ = 755.92) | 4-24 | m/z = 719.24 ($C_{51}H_{33}N_3S$ = 719.89) |
| 4-25 | m/z = 527.15 ($C_{36}H_{21}N_3S$ = 527.64) | 4-26 | m/z = 532.18 ($C_{36}H_{16}D_5N_3S$ = 532.67) |
| 4-27 | m/z = 603.18 ($C_{42}H_{25}N_3S$ = 603.73) | 4-28 | m/z = 603.18 ($C_{42}H_{25}N_3S$ = 603.73) |
| 4-29 | m/z = 577.16 ($C_{40}H_{23}N_3S$ = 577.70) | 4-30 | m/z = 577.16 ($C_{40}H_{23}N_3S$ = 577.70) |
| 4-31 | m/z = 679.21 ($C_{48}H_{29}N_3S$ = 679.83) | 4-32 | m/z = 643.21 ($C_{45}H_{29}N_3S$ = 643.80) |
| 4-33 | m/z = 603.18 ($C_{42}H_{25}N_3S$ = 603.73) | 4-34 | m/z = 608.21 ($C_{42}H_{20}D_5N_3S$ = 608.76) |
| 4-35 | m/z = 679.21 ($C_{48}H_{29}N_3S$ = 679.83) | 4-36 | m/z = 679.21 ($C_{48}H_{29}N_3S$ = 679.83) |
| 4-37 | m/z = 653.19 ($C_{46}H_{27}N_3S$ = 653.79) | 4-38 | m/z = 653.19 ($C_{46}H_{27}N_3S$ = 653.79) |
| 4-39 | m/z = 755.24 ($C_{54}H_{33}N_3S$ = 755.92) | 4-40 | m/z = 719.24 ($C_{51}H_{33}N_3S$ = 719.89) |
| 4-41 | m/z = 603.18 ($C_{42}H_{25}N_3S$ = 603.73) | 4-42 | m/z = 608.21 ($C_{42}H_{20}D_5N_3S$ = 608.76) |
| 4-43 | m/z = 679.21 ($C_{48}H_{29}N_3S$ = 679.83) | 4-44 | m/z = 679.21 ($C_{48}H_{29}N_3S$ = 679.83) |
| 4-45 | m/z = 653.19 ($C_{46}H_{27}N_3S$ = 653.79) | 4-46 | m/z = 653.19 ($C_{46}H_{27}N_3S$ = 653.79) |
| 4-47 | m/z = 755.24 ($C_{54}H_{33}N_3S$ = 755.92) | 4-48 | m/z = 719.24 ($C_{51}H_{33}N_3S$ = 719.89) |
| 5-1 | m/z = 528.14 ($C_{35}H_{20}N_4S$ = 528.63) | 5-2 | m/z = 533.17 ($C_{35}H_{15}D_5N_4S$ = 533.66) |
| 5-3 | m/z = 604.17 ($C_{41}H_{24}N_4S$ = 604.72) | 5-4 | m/z = 604.17 ($C_{41}H_{24}N_4S$ = 604.72) |
| 5-5 | m/z = 578.16 ($C_{39}H_{22}N_4S$ = 578.68) | 5-6 | m/z = 578.16 ($C_{39}H_{22}N_4S$ = 578.68) |
| 5-7 | m/z = 680.20 ($C_{47}H_{28}N_4S$ = 680.82) | 5-8 | m/z = 644.20 ($C_{44}H_{28}N_4S$ = 644.78) |
| 5-9 | m/z = 604.17 ($C_{41}H_{24}N_4S$ = 604.72) | 5-10 | m/z = 609.20 ($C_{41}H_{19}D_5N_4S$ = 609.75) |
| 5-11 | m/z = 680.20 ($C_{47}H_{28}N_4S$ = 680.82) | 5-12 | m/z = 680.20 ($C_{47}H_{28}N_4S$ = 680.82) |
| 5-13 | m/z = 654.19 ($C_{45}H_{26}N_4S$ = 654.78) | 5-14 | m/z = 654.19 ($C_{45}H_{26}N_4S$ = 654.78) |
| 5-15 | m/z = 756.23 ($C_{53}H_{32}N_4S$ = 756.91) | 5-16 | m/z = 720.23 ($C_{50}H_{32}N_4S$ = 720.88) |
| 5-17 | m/z = 604.17 ($C_{41}H_{24}N_4S$ = 604.72) | 5-18 | m/z = 609.20 ($C_{41}H_{19}D_5N_4S$ = 609.75) |
| 5-19 | m/z = 680.20 ($C_{47}H_{28}N_4S$ = 680.82) | 5-20 | m/z = 680.20 ($C_{47}H_{28}N_4S$ = 680.82) |
| 5-21 | m/z = 654.19 ($C_{45}H_{26}N_4S$ = 654.78) | 5-22 | m/z = 654.19 ($C_{45}H_{26}N_4S$ = 654.78) |
| 5-23 | m/z = 756.23 ($C_{53}H_{32}N_4S$ = 756.91) | 5-24 | m/z = 720.23 ($C_{50}H_{32}N_4S$ = 720.88) |
| 5-25 | m/z = 528.14 ($C_{35}H_{20}N_4S$ = 528.63) | 5-26 | m/z = 533.17 ($C_{35}H_{15}D_5N_4S$ = 533.66) |
| 5-27 | m/z = 604.17 ($C_{41}H_{24}N_4S$ = 604.72) | 5-28 | m/z = 604.17 ($C_{41}H_{24}N_4S$ = 604.72) |
| 5-29 | m/z = 578.16 ($C_{39}H_{22}N_4S$ = 578.68) | 5-30 | m/z = 578.16 ($C_{39}H_{22}N_4S$ = 578.68) |

TABLE 3-continued

| Compound | FD-MS | Compound | FD-MS |
|---|---|---|---|
| 5-31 | m/z = 680.20 ($C_{47}H_{28}N_4S$ = 680.82) | 5-32 | m/z = 644.20 ($C_{44}H_{28}N_4S$ = 644.78) |
| 5-33 | m/z = 604.17 ($C_{41}H_{24}N_4S$ = 604.72) | 5-34 | m/z = 609.20 ($C_{41}H_{19}D_5N_4S$ = 609.75) |
| 5-35 | m/z = 680.20 ($C_{47}H_{28}N_4S$ = 680.82) | 5-36 | m/z = 680.20 ($C_{47}H_{28}N_4S$ = 680.82) |
| 5-37 | m/z = 654.19 ($C_{45}H_{26}N_4S$ = 654.78) | 5-38 | m/z = 654.19 ($C_{45}H_{26}N_4S$ = 654.78) |
| 5-39 | m/z = 756.23 ($C_{53}H_{32}N_4S$ = 756.91) | 5-40 | m/z = 720.23 ($C_{50}H_{32}N_4S$ = 720.88) |
| 5-41 | m/z = 604.17 ($C_{41}H_{24}N_4S$ = 604.72) | 5-42 | m/z = 609.20 ($C_{41}H_{19}D_5N_4S$ = 609.75) |
| 5-43 | m/z = 680.20 ($C_{47}H_{28}N_4S$ = 680.82) | 5-44 | m/z = 680.20 ($C_{47}H_{28}N_4S$ = 680.82) |
| 5-45 | m/z = 654.19 ($C_{45}H_{26}N_4S$ = 654.78) | 5-46 | m/z = 654.19 ($C_{45}H_{26}N_4S$ = 654.78) |
| 5-47 | m/z = 756.23 ($C_{53}H_{32}N_4S$ = 756.91) | 5-48 | m/z = 720.23 ($C_{50}H_{32}N_4S$ = 720.88) |
| 6-1 | m/z = 528.14 ($C_{35}H_{20}N_4S$ = 528.63) | 6-2 | m/z = 533.17 ($C_{35}H_{15}D_5N_4S$ = 533.66) |
| 6-3 | m/z = 604.17 ($C_{41}H_{24}N_4S$ = 604.72) | 6-4 | m/z = 604.17 ($C_{41}H_{24}N_4S$ = 604.72) |
| 6-5 | m/z = 578.16 ($C_{39}H_{22}N_4S$ = 578.68) | 6-6 | m/z = 578.16 ($C_{39}H_{22}N_4S$ = 578.68) |
| 6-7 | m/z = 680.20 ($C_{47}H_{28}N_4S$ = 680.82) | 6-8 | m/z = 644.20 ($C_{44}H_{28}N_4S$ = 644.78) |
| 6-9 | m/z = 604.17 ($C_{41}H_{24}N_4S$ = 604.72) | 6-10 | m/z = 609.20 ($C_{41}H_{19}D_5N_4S$ = 609.75) |
| 6-11 | m/z = 680.20 ($C_{47}H_{28}N_4S$ = 680.82) | 6-12 | m/z = 680.20 ($C_{47}H_{28}N_4S$ = 680.82) |
| 6-13 | m/z = 654.19 ($C_{45}H_{26}N_4S$ = 654.78) | 6-14 | m/z = 654.19 ($C_{45}H_{26}N_4S$ = 654.78) |
| 6-15 | m/z = 756.23 ($C_{53}H_{32}N_4S$ = 756.91) | 6-16 | m/z = 720.23 ($C_{50}H_{32}N_4S$ = 720.88) |
| 6-17 | m/z = 604.17 ($C_{41}H_{24}N_4S$ = 604.72) | 6-18 | m/z = 609.20 ($C_{41}H_{19}D_5N_4S$ = 609.75) |
| 6-19 | m/z = 680.20 ($C_{47}H_{28}N_4S$ = 680.82) | 6-20 | m/z = 680.20 ($C_{47}H_{28}N_4S$ = 680.82) |
| 6-21 | m/z = 654.19 ($C_{45}H_{26}N_4S$ = 654.78) | 6-22 | m/z = 654.19 ($C_{45}H_{26}N_4S$ = 654.78) |
| 6-23 | m/z = 756.23 ($C_{53}H_{32}N_4S$ = 756.91) | 6-24 | m/z = 720.23 ($C_{50}H_{32}N_4S$ = 720.88) |
| 6-25 | m/z = 528.14 ($C_{35}H_{20}N_4S$ = 528.63) | 6-26 | m/z = 533.17 ($C_{35}H_{15}D_5N_4S$ = 533.66) |
| 6-27 | m/z = 604.17 ($C_{41}H_{24}N_4S$ = 604.72) | 6-28 | m/z = 604.17 ($C_{41}H_{24}N_4S$ = 604.72) |
| 6-29 | m/z = 578.16 ($C_{39}H_{22}N_4S$ = 578.68) | 6-30 | m/z = 578.16 ($C_{39}H_{22}N_4S$ = 578.68) |
| 6-31 | m/z = 680.20 ($C_{47}H_{28}N_4S$ = 680.82) | 6-32 | m/z = 644.20 ($C_{44}H_{28}N_4S$ = 644.78) |
| 6-33 | m/z = 604.17 ($C_{41}H_{24}N_4S$ = 604.72) | 6-34 | m/z = 609.20 ($C_{41}H_{19}D_5N_4S$ = 609.75) |
| 6-35 | m/z = 680.20 ($C_{47}H_{28}N_4S$ = 680.82) | 6-36 | m/z = 680.20 ($C_{47}H_{28}N_4S$ = 680.82) |
| 6-37 | m/z = 654.19 ($C_{45}H_{26}N_4S$ = 654.78) | 6-38 | m/z = 654.19 ($C_{45}H_{26}N_4S$ = 654.78) |
| 6-39 | m/z = 756.23 ($C_{53}H_{32}N_4S$ = 756.91) | 6-40 | m/z = 720.23 ($C_{50}H_{32}N_4S$ = 720.88) |
| 6-41 | m/z = 604.17 ($C_{41}H_{24}N_4S$ = 604.72) | 6-42 | m/z = 609.20 ($C_{41}H_{19}D_5N_4S$ = 609.75) |
| 6-43 | m/z = 680.20 ($C_{47}H_{28}N_4S$ = 680.82) | 6-44 | m/z = 680.20 ($C_{47}H_{28}N_4S$ = 680.82) |
| 6-45 | m/z = 654.19 ($C_{45}H_{26}N_4S$ = 654.78) | 6-46 | m/z = 654.19 ($C_{45}H_{26}N_4S$ = 654.78) |
| 6-47 | m/z = 756.23 ($C_{53}H_{32}N_4S$ = 756.91) | 6-48 | m/z = 720.23 ($C_{50}H_{32}N_4S$ = 720.88) |

Fabrication and Evaluation of Organic Electronic Element

Test Example 1

Organic light emitting diodes (OLEDs) were fabricated according to a conventional method by using the synthesized inventive compounds as a light emitting host material of a light emitting layer. Each OLED was fabricated as follows. First, an ITO layer (anode) was formed on a glass substrate, and a film of $N^1$-(naphthalene-2-yl)-$N^4$,$N^4$-bis(4-(naphthalene-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Subsequently, a film of 4,4-bis[N-(1-naphthyl)-N-phenylamino]biphenyl (hereinafter abbreviated as "NPD") was vacuum-deposited with a thickness of 20 nm on the hole injection layer to form a hole transport layer. Also, a light emitting layer with a thickness of 30 nm was deposited on the hole transport layer by doping the hole transport layer with the inventive compound (1-1 to 3-80) as a host material and Ir(ppy)$_3$[tris(2-phenylpyridine)-iridium] as a dopant material in a weight ratio of 95:5. Next, a film of (1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Comparative Example 1

An OLED was manufactured in the same manner as described in Test Example 1, except that Comparative Compound 1 represented below was used as the host material of the light emitting layer, instead of the inventive compound.

<Comparative Compound 1> CBP

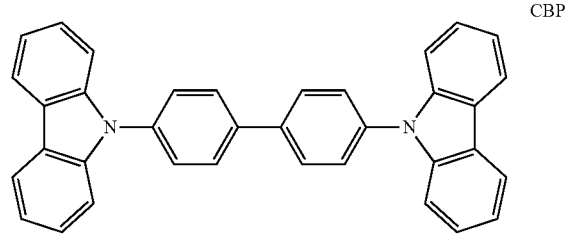 [SMILES: c1ccc2c(c1)c1ccccc1n2-c1ccc(-c2ccc(-n3c4ccccc4c4ccccc43)cc2)cc1]

Comparative Example 2

An OLED was manufactured in the same manner as described in Test Example 1, except that Comparative Compound 2 represented below was used as the host material of the light emitting layer, instead of the inventive compound.

Comparative Compound 2

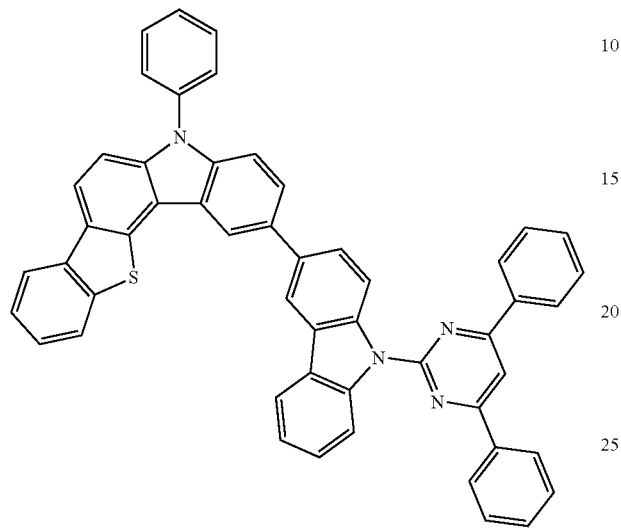

Comparative Example 3

An OLED was manufactured in the same manner as described in Test Example 1, except that Comparative Compound 3 represented below was used as the host material of the light emitting layer, instead of the inventive compound.

Comparative Compound 3

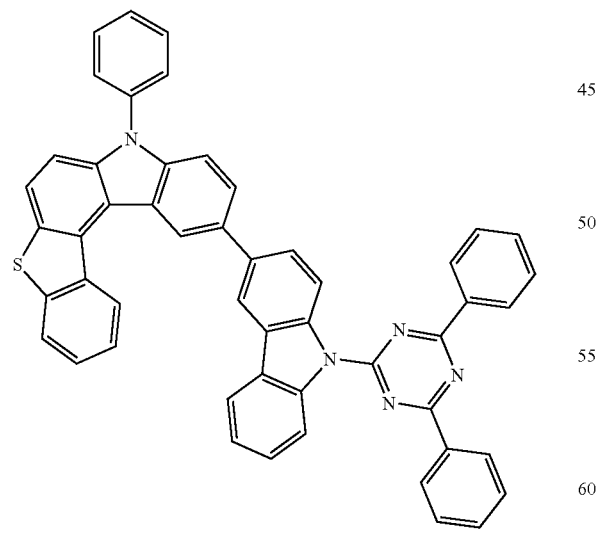

Comparative Example 4

An OLED was manufactured in the same manner as described in Test Example 1, except that Comparative Compound 4 represented below was used as the host material of the light emitting layer, instead of the inventive compound.

Comparative Compound 4

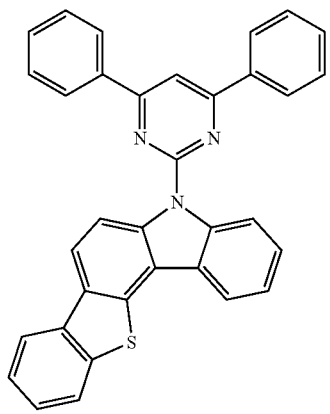 [SMILES: c1ccc(-c2cc(-c3ccccc3)nc(-n3c4ccccc4c4c5sc6ccccc6c5ccc43)n2)cc1]

Comparative Example 5

An OLED was manufactured in the same manner as described in Test Example 1, except that Comparative Compound 5 represented below was used as the host material of the light emitting layer, instead of the inventive compound.

Comparative Compound 5

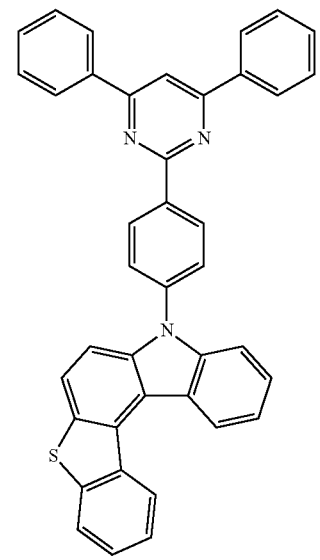 [SMILES: c1ccc(-c2cc(-c3ccccc3)nc(-c3ccc(-n4c5ccccc5c5c6c(ccc54)sc4ccccc46)cc3)n2)cc1]

A forward bias DC voltage was applied to each of the OLEDs manufactured through Test Example 1 and Comparative Examples, and electro-luminescence (EL) characteristics of the OLED were measured by PR-650 (Photoresearch). Also, T95 life span was measured by life span measuring equipment (Mcscience) at a reference brightness of 300 cd/m². Table 4 below shows evaluation results according to the manufactured OLEDs.

In Table 4, Example 1 to Example 312 represent the inventive OLEDs manufactured according to Test Example 1.

Also, in Tables below, "Comp. Ex." indicates "Comparative Example", "Ex." indicates "Example", "Comp. Mat." indicates "Comparative Material", and "Comp." indicates "Compound".

TABLE 4

|  | Compound | Voltage | Current Density (mA/cm$^2$) | Brightness (cd/m$^2$) | Efficiency | Lifetime T(95) | CIE (x, y) |
|---|---|---|---|---|---|---|---|
| Comp. Ex. (1) | Comp. Mat. 1 | 6.2 | 6.3 | 300 | 4.8 | 60.8 | (0.33, 0.61) |
| Comp. Ex. (2) | Comp. Mat. 2 | 5.8 | 5.9 | 300 | 5.1 | 70.6 | (0.33, 0.61) |
| Comp. Ex. (3) | Comp. Mat. 3 | 5.7 | 6.0 | 300 | 5.0 | 65.6 | (0.33, 0.61) |
| Comp. Ex. (4) | Comp. Mat. 4 | 5.6 | 5.8 | 300 | 5.2 | 82.5 | (0.33, 0.61) |
| Comp. Ex. (5) | Comp. Mat. 5 | 5.6 | 5.9 | 300 | 5.1 | 86.7 | (0.33, 0.61) |
| Ex. (1) | Comp. (1-1) | 5.3 | 4.6 | 300 | 6.5 | 96.0 | (0.32, 0.61) |
| Ex. (2) | Comp. (1-2) | 5.2 | 5.1 | 300 | 5.8 | 152.3 | (0.33, 0.60) |
| Ex. (3) | Comp. (1-3) | 5.4 | 5.4 | 300 | 5.6 | 122.8 | (0.30, 0.61) |
| Ex. (4) | Comp. (1-4) | 5.5 | 5.1 | 300 | 5.9 | 124.5 | (0.33, 0.61) |
| Ex. (5) | Comp. (1-5) | 5.4 | 5.2 | 300 | 5.8 | 150.7 | (0.31, 0.60) |
| Ex. (6) | Comp. (1-6) | 5.2 | 4.6 | 300 | 6.5 | 104.6 | (0.33, 0.61) |
| Ex. (7) | Comp. (1-7) | 5.5 | 4.9 | 300 | 6.1 | 135.1 | (0.32, 0.60) |
| Ex. (8) | Comp. (1-8) | 5.0 | 4.7 | 300 | 6.3 | 152.5 | (0.32, 0.61) |
| Ex. (9) | Comp. (1-9) | 5.5 | 4.8 | 300 | 6.3 | 107.7 | (0.33, 0.60) |
| Ex. (10) | Comp. (1-10) | 5.3 | 4.5 | 300 | 6.6 | 128.0 | (0.30, 0.60) |
| Ex. (11) | Comp. (1-11) | 5.5 | 4.5 | 300 | 6.7 | 101.0 | (0.30, 0.61) |
| Ex. (12) | Comp. (1-12) | 5.4 | 4.7 | 300 | 6.4 | 96.7 | (0.31, 0.61) |
| Ex. (13) | Comp. (1-13) | 5.0 | 4.8 | 300 | 6.2 | 131.0 | (0.31, 0.61) |
| Ex. (14) | Comp. (1-14) | 5.6 | 5.3 | 300 | 5.6 | 144.6 | (0.31, 0.60) |
| Ex. (15) | Comp. (1-15) | 5.2 | 4.5 | 300 | 6.7 | 115.2 | (0.31, 0.60) |
| Ex. (16) | Comp. (1-16) | 5.3 | 5.5 | 300 | 5.5 | 137.2 | (0.32, 0.61) |
| Ex. (17) | Comp. (1-17) | 5.1 | 5.5 | 300 | 5.4 | 120.8 | (0.31, 0.61) |
| Ex. (18) | Comp. (1-18) | 5.9 | 5.8 | 300 | 5.1 | 66.2 | (0.33, 0.60) |
| Ex. (19) | Comp. (1-19) | 5.0 | 4.9 | 300 | 6.1 | 122.2 | (0.31, 0.60) |
| Ex. (20) | Comp. (1-20) | 5.2 | 5.0 | 300 | 6.0 | 126.9 | (0.32, 0.61) |
| Ex. (21) | Comp. (1-21) | 5.1 | 4.8 | 300 | 6.2 | 109.7 | (0.32, 0.61) |
| Ex. (22) | Comp. (1-22) | 5.1 | 5.1 | 300 | 5.9 | 97.5 | (0.33, 0.60) |
| Ex. (23) | Comp. (1-23) | 5.0 | 5.3 | 300 | 5.7 | 105.9 | (0.30, 0.61) |
| Ex. (24) | Comp. (1-24) | 5.0 | 5.2 | 300 | 5.8 | 138.6 | (0.31, 0.61) |
| Ex. (25) | Comp. (1-25) | 5.1 | 5.0 | 300 | 6.0 | 101.2 | (0.30, 0.60) |
| Ex. (26) | Comp. (1-26) | 5.6 | 5.0 | 300 | 6.0 | 137.0 | (0.33, 0.61) |
| Ex. (27) | Comp. (1-27) | 5.2 | 4.6 | 300 | 6.5 | 154.3 | (0.32, 0.61) |
| Ex. (28) | Comp. (1-28) | 5.3 | 4.9 | 300 | 6.2 | 143.3 | (0.33, 0.60) |
| Ex. (29) | Comp. (1-29) | 5.1 | 5.0 | 300 | 6.0 | 119.3 | (0.30, 0.61) |
| Ex. (30) | Comp. (1-30) | 5.0 | 5.5 | 300 | 5.5 | 153.5 | (0.31, 0.61) |
| Ex. (31) | Comp. (1-31) | 5.4 | 4.4 | 300 | 6.8 | 107.8 | (0.31, 0.60) |
| Ex. (32) | Comp. (1-32) | 5.4 | 4.5 | 300 | 6.6 | 103.4 | (0.33, 0.61) |
| Ex. (33) | Comp. (1-33) | 5.2 | 4.4 | 300 | 6.8 | 97.7 | (0.32, 0.60) |
| Ex. (34) | Comp. (1-34) | 5.1 | 5.2 | 300 | 5.8 | 114.8 | (0.32, 0.61) |
| Ex. (35) | Comp. (1-35) | 5.5 | 4.6 | 300 | 6.5 | 143.5 | (0.33, 0.60) |
| Ex. (36) | Comp. (1-36) | 5.2 | 5.3 | 300 | 5.7 | 93.8 | (0.30, 0.60) |
| Ex. (37) | Comp. (1-37) | 5.3 | 4.7 | 300 | 6.4 | 123.3 | (0.30, 0.60) |
| Ex. (38) | Comp. (1-38) | 5.0 | 5.2 | 300 | 5.8 | 109.7 | (0.32, 0.61) |
| Ex. (39) | Comp. (1-39) | 5.1 | 4.7 | 300 | 6.3 | 131.2 | (0.30, 0.61) |
| Ex. (40) | Comp. (1-40) | 5.2 | 4.5 | 300 | 6.7 | 115.5 | (0.31, 0.60) |
| Ex. (41) | Comp. (1-41) | 5.1 | 4.5 | 300 | 6.7 | 134.6 | (0.31, 0.60) |
| Ex. (42) | Comp. (1-42) | 5.2 | 5.4 | 300 | 5.5 | 133.3 | (0.32, 0.61) |
| Ex. (43) | Comp. (1-43) | 5.8 | 5.8 | 300 | 5.1 | 74.8 | (0.31, 0.61) |
| Ex. (44) | Comp. (1-44) | 5.3 | 5.3 | 300 | 5.6 | 107.0 | (0.33, 0.60) |
| Ex. (45) | Comp. (1-45) | 5.1 | 4.7 | 300 | 6.4 | 95.6 | (0.31, 0.60) |
| Ex. (46) | Comp. (1-46) | 5.4 | 4.8 | 300 | 6.2 | 144.5 | (0.32, 0.60) |
| Ex. (47) | Comp. (1-47) | 5.3 | 4.9 | 300 | 6.1 | 103.0 | (0.32, 0.61) |
| Ex. (48) | Comp. (1-48) | 5.5 | 4.9 | 300 | 6.1 | 144.6 | (0.33, 0.60) |
| Ex. (49) | Comp. (1-49) | 5.5 | 4.6 | 300 | 6.5 | 120.7 | (0.30, 0.61) |
| Ex. (50) | Comp. (1-50) | 5.4 | 4.6 | 300 | 6.5 | 99.7 | (0.31, 0.61) |
| Ex. (51) | Comp. (1-51) | 5.4 | 4.4 | 300 | 6.7 | 149.1 | (0.31, 0.60) |
| Ex. (52) | Comp. (1-52) | 5.4 | 4.4 | 300 | 6.8 | 147.5 | (0.33, 0.61) |
| Ex. (53) | Comp. (1-53) | 5.5 | 4.8 | 300 | 6.2 | 120.9 | (0.32, 0.61) |
| Ex. (54) | Comp. (1-54) | 5.8 | 6.0 | 300 | 5.0 | 69.3 | (0.33, 0.60) |
| Ex. (55) | Comp. (1-55) | 5.4 | 5.3 | 300 | 5.7 | 122.7 | (0.30, 0.61) |
| Ex. (56) | Comp. (1-56) | 5.5 | 5.0 | 300 | 6.0 | 149.3 | (0.31, 0.60) |
| Ex. (57) | Comp. (1-57) | 5.6 | 4.6 | 300 | 6.5 | 131.6 | (0.31, 0.60) |
| Ex. (58) | Comp. (1-58) | 5.3 | 4.7 | 300 | 6.4 | 137.6 | (0.33, 0.61) |
| Ex. (59) | Comp. (1-59) | 5.3 | 5.2 | 300 | 5.7 | 143.1 | (0.32, 0.60) |
| Ex. (60) | Comp. (1-60) | 5.1 | 5.3 | 300 | 5.7 | 153.7 | (0.32, 0.61) |
| Ex. (61) | Comp. (1-61) | 5.4 | 5.5 | 300 | 5.4 | 136.5 | (0.33, 0.60) |
| Ex. (62) | Comp. (1-62) | 5.3 | 4.5 | 300 | 6.7 | 109.8 | (0.30, 0.60) |
| Ex. (63) | Comp. (1-63) | 5.2 | 5.1 | 300 | 5.9 | 99.5 | (0.30, 0.61) |
| Ex. (64) | Comp. (1-64) | 5.1 | 4.8 | 300 | 6.3 | 123.9 | (0.32, 0.60) |
| Ex. (65) | Comp. (1-65) | 5.3 | 4.5 | 300 | 6.7 | 123.0 | (0.31, 0.61) |

TABLE 4-continued

| | Compound | Voltage | Current Density (mA/cm$^2$) | Brightness (cd/m$^2$) | Efficiency | Lifetime T(95) | CIE (x, y) |
|---|---|---|---|---|---|---|---|
| Ex. (66) | Comp. (1-66) | 5.2 | 5.0 | 300 | 6.0 | 101.2 | (0.31, 0.60) |
| Ex. (67) | Comp. (1-67) | 5.1 | 4.8 | 300 | 6.3 | 111.2 | (0.31, 0.60) |
| Ex. (68) | Comp. (1-68) | 5.5 | 4.9 | 300 | 6.1 | 137.0 | (0.32, 0.61) |
| Ex. (69) | Comp. (1-69) | 5.1 | 4.7 | 300 | 6.4 | 137.6 | (0.31, 0.61) |
| Ex. (70) | Comp. (1-70) | 5.6 | 5.5 | 300 | 5.4 | 99.6 | (0.33, 0.60) |
| Ex. (71) | Comp. (1-71) | 5.5 | 4.7 | 300 | 6.3 | 96.8 | (0.31, 0.60) |
| Ex. (72) | Comp. (1-72) | 5.3 | 4.7 | 300 | 6.4 | 148.9 | (0.32, 0.61) |
| Ex. (73) | Comp. (1-73) | 5.1 | 5.4 | 300 | 5.5 | 154.5 | (0.32, 0.61) |
| Ex. (74) | Comp. (1-74) | 5.5 | 5.0 | 300 | 6.0 | 129.6 | (0.33, 0.60) |
| Ex. (75) | Comp. (1-75) | 5.3 | 4.4 | 300 | 6.8 | 130.1 | (0.30, 0.61) |
| Ex. (76) | Comp. (1-76) | 5.4 | 5.2 | 300 | 5.8 | 120.1 | (0.31, 0.61) |
| Ex. (77) | Comp. (1-77) | 5.4 | 5.4 | 300 | 5.6 | 127.2 | (0.31, 0.60) |
| Ex. (78) | Comp. (1-78) | 5.4 | 4.5 | 300 | 6.6 | 101.6 | (0.33, 0.61) |
| Ex. (79) | Comp. (1-79) | 5.5 | 5.2 | 300 | 5.8 | 139.0 | (0.32, 0.61) |
| Ex. (80) | Comp. (1-80) | 5.1 | 5.1 | 300 | 5.9 | 130.6 | (0.33, 0.60) |
| Ex. (81) | Comp. (1-81) | 5.4 | 5.2 | 300 | 5.8 | 110.4 | (0.32, 0.61) |
| Ex. (82) | Comp. (1-82) | 5.3 | 4.5 | 300 | 6.7 | 153.1 | (0.33, 0.60) |
| Ex. (83) | Comp. (1-83) | 5.5 | 5.0 | 300 | 6.0 | 101.8 | (0.30, 0.61) |
| Ex. (84) | Comp. (1-84) | 5.5 | 4.8 | 300 | 6.3 | 138.3 | (0.30, 0.61) |
| Ex. (85) | Comp. (1-85) | 5.4 | 5.0 | 300 | 6.0 | 123.3 | (0.31, 0.60) |
| Ex. (86) | Comp. (1-86) | 5.4 | 5.1 | 300 | 5.9 | 117.5 | (0.33, 0.61) |
| Ex. (87) | Comp. (1-87) | 5.1 | 4.5 | 300 | 6.7 | 142.0 | (0.32, 0.60) |
| Ex. (88) | Comp. (1-88) | 5.2 | 4.9 | 300 | 6.1 | 105.8 | (0.32, 0.61) |
| Ex. (89) | Comp. (1-89) | 5.3 | 4.9 | 300 | 6.2 | 128.2 | (0.33, 0.60) |
| Ex. (90) | Comp. (1-90) | 5.5 | 4.6 | 300 | 6.5 | 146.9 | (0.30, 0.60) |
| Ex. (91) | Comp. (1-91) | 5.4 | 4.6 | 300 | 6.6 | 132.3 | (0.30, 0.61) |
| Ex. (92) | Comp. (1-92) | 5.5 | 4.5 | 300 | 6.6 | 137.6 | (0.31, 0.61) |
| Ex. (93) | Comp. (1-93) | 5.6 | 5.0 | 300 | 6.0 | 124.3 | (0.31, 0.61) |
| Ex. (94) | Comp. (1-94) | 5.5 | 5.4 | 300 | 5.6 | 142.9 | (0.31, 0.60) |
| Ex. (95) | Comp. (1-95) | 5.0 | 4.5 | 300 | 6.7 | 113.2 | (0.31, 0.60) |
| Ex. (96) | Comp. (1-96) | 5.2 | 4.5 | 300 | 6.7 | 114.8 | (0.32, 0.61) |
| Ex. (97) | Comp. (1-97) | 5.2 | 5.2 | 300 | 5.8 | 137.8 | (0.31, 0.61) |
| Ex. (98) | Comp. (1-98) | 5.7 | 5.9 | 300 | 5.1 | 69.6 | (0.33, 0.60) |
| Ex. (99) | Comp. (1-99) | 5.4 | 5.4 | 300 | 5.6 | 143.6 | (0.31, 0.60) |
| Ex. (100) | Comp. (1-100) | 5.0 | 5.4 | 300 | 5.6 | 137.7 | (0.32, 0.61) |
| Ex. (101) | Comp. (1-101) | 5.5 | 5.0 | 300 | 6.0 | 131.6 | (0.32, 0.61) |
| Ex. (102) | Comp. (1-102) | 5.3 | 4.8 | 300 | 6.2 | 151.6 | (0.33, 0.60) |
| Ex. (103) | Comp. (1-103) | 5.1 | 4.4 | 300 | 6.7 | 133.9 | (0.30, 0.61) |
| Ex. (104) | Comp. (1-104) | 5.4 | 4.9 | 300 | 6.2 | 98.1 | (0.31, 0.61) |
| Ex. (105) | Comp. (1-105) | 5.6 | 4.7 | 300 | 6.3 | 137.3 | (0.30, 0.60) |
| Ex. (106) | Comp. (1-106) | 5.4 | 5.2 | 300 | 5.7 | 148.7 | (0.33, 0.61) |
| Ex. (107) | Comp. (1-107) | 5.4 | 5.2 | 300 | 5.7 | 129.4 | (0.32, 0.61) |
| Ex. (108) | Comp. (1-108) | 5.3 | 4.8 | 300 | 6.3 | 152.8 | (0.33, 0.60) |
| Ex. (109) | Comp. (1-109) | 5.5 | 4.5 | 300 | 6.6 | 136.2 | (0.30, 0.61) |
| Ex. (110) | Comp. (1-110) | 5.6 | 5.0 | 300 | 6.0 | 108.8 | (0.31, 0.61) |
| Ex. (111) | Comp. (1-111) | 5.1 | 5.0 | 300 | 6.0 | 125.3 | (0.31, 0.60) |
| Ex. (112) | Comp. (1-112) | 5.4 | 4.7 | 300 | 6.3 | 151.4 | (0.33, 0.61) |
| Ex. (113) | Comp. (1-113) | 5.3 | 5.1 | 300 | 5.9 | 107.2 | (0.32, 0.60) |
| Ex. (114) | Comp. (1-114) | 5.5 | 4.7 | 300 | 6.4 | 151.1 | (0.32, 0.61) |
| Ex. (115) | Comp. (1-115) | 5.2 | 4.9 | 300 | 6.1 | 94.4 | (0.33, 0.61) |
| Ex. (116) | Comp. (1-116) | 5.5 | 5.0 | 300 | 6.0 | 106.1 | (0.30, 0.60) |
| Ex. (117) | Comp. (1-117) | 5.1 | 4.5 | 300 | 6.7 | 123.1 | (0.30, 0.61) |
| Ex. (118) | Comp. (1-118) | 5.5 | 5.3 | 300 | 5.7 | 138.0 | (0.32, 0.61) |
| Ex. (119) | Comp. (1-119) | 5.4 | 5.3 | 300 | 5.7 | 104.1 | (0.30, 0.61) |
| Ex. (120) | Comp. (1-120) | 5.0 | 5.1 | 300 | 5.9 | 120.4 | (0.31, 0.60) |
| Ex. (121) | Comp. (1-121) | 5.1 | 4.8 | 300 | 6.3 | 113.5 | (0.31, 0.61) |
| Ex. (122) | Comp. (1-122) | 5.5 | 5.0 | 300 | 5.9 | 141.4 | (0.32, 0.61) |
| Ex. (123) | Comp. (1-123) | 5.8 | 5.9 | 300 | 5.1 | 66.6 | (0.31, 0.61) |
| Ex. (124) | Comp. (1-124) | 5.2 | 4.7 | 300 | 6.4 | 99.5 | (0.33, 0.60) |
| Ex. (125) | Comp. (1-125) | 5.2 | 5.4 | 300 | 5.6 | 116.9 | (0.31, 0.60) |
| Ex. (126) | Comp. (1-126) | 5.4 | 5.4 | 300 | 5.5 | 130.0 | (0.32, 0.60) |
| Ex. (127) | Comp. (1-127) | 5.3 | 5.2 | 300 | 5.7 | 144.6 | (0.32, 0.61) |
| Ex. (128) | Comp. (1-128) | 5.2 | 4.9 | 300 | 6.2 | 119.8 | (0.33, 0.60) |
| Ex. (129) | Comp. (1-129) | 5.4 | 4.8 | 300 | 6.3 | 144.0 | (0.30, 0.61) |
| Ex. (130) | Comp. (1-130) | 5.2 | 4.9 | 300 | 6.2 | 118.5 | (0.31, 0.61) |
| Ex. (131) | Comp. (1-131) | 5.4 | 5.4 | 300 | 5.6 | 95.2 | (0.31, 0.60) |
| Ex. (132) | Comp. (1-132) | 5.3 | 5.5 | 300 | 5.5 | 126.8 | (0.33, 0.60) |
| Ex. (133) | Comp. (1-133) | 5.3 | 4.5 | 300 | 6.6 | 97.2 | (0.32, 0.61) |
| Ex. (134) | Comp. (1-134) | 5.7 | 5.8 | 300 | 5.1 | 76.9 | (0.33, 0.60) |
| Ex. (135) | Comp. (1-135) | 5.6 | 5.0 | 300 | 6.0 | 143.9 | (0.30, 0.61) |
| Ex. (136) | Comp. (1-136) | 5.1 | 4.7 | 300 | 6.4 | 107.4 | (0.31, 0.61) |
| Ex. (137) | Comp. (1-137) | 5.2 | 4.7 | 300 | 6.4 | 125.5 | (0.31, 0.60) |
| Ex. (138) | Comp. (1-138) | 5.4 | 4.9 | 300 | 6.1 | 96.3 | (0.33, 0.61) |
| Ex. (139) | Comp. (1-139) | 5.2 | 5.1 | 300 | 5.9 | 126.4 | (0.32, 0.60) |
| Ex. (140) | Comp. (1-140) | 5.4 | 4.9 | 300 | 6.1 | 144.8 | (0.32, 0.60) |
| Ex. (141) | Comp. (1-141) | 5.6 | 4.9 | 300 | 6.2 | 152.7 | (0.33, 0.60) |

TABLE 4-continued

|  | Compound | Voltage | Current Density (mA/cm$^2$) | Brightness (cd/m$^2$) | Efficiency | Lifetime T(95) | CIE (x, y) |
| --- | --- | --- | --- | --- | --- | --- | --- |
| Ex. (142) | Comp. (1-142) | 5.2 | 4.4 | 300 | 6.8 | 98.5 | (0.30, 0.60) |
| Ex. (143) | Comp. (1-143) | 5.4 | 5.4 | 300 | 5.6 | 143.6 | (0.30, 0.61) |
| Ex. (144) | Comp. (1-144) | 5.1 | 5.0 | 300 | 6.0 | 142.0 | (0.32, 0.60) |
| Ex. (145) | Comp. (1-145) | 5.4 | 5.3 | 300 | 5.7 | 97.6 | (0.31, 0.61) |
| Ex. (146) | Comp. (1-146) | 5.1 | 4.4 | 300 | 6.8 | 141.5 | (0.31, 0.60) |
| Ex. (147) | Comp. (1-147) | 5.5 | 5.1 | 300 | 5.8 | 102.9 | (0.31, 0.60) |
| Ex. (148) | Comp. (1-148) | 5.3 | 4.5 | 300 | 6.7 | 151.2 | (0.32, 0.61) |
| Ex. (149) | Comp. (1-149) | 5.4 | 4.6 | 300 | 6.5 | 154.8 | (0.31, 0.61) |
| Ex. (150) | Comp. (1-150) | 5.2 | 4.8 | 300 | 6.2 | 105.8 | (0.33, 0.60) |
| Ex. (151) | Comp. (1-151) | 5.1 | 4.7 | 300 | 6.4 | 113.0 | (0.31, 0.60) |
| Ex. (152) | Comp. (1-152) | 5.5 | 5.3 | 300 | 5.6 | 111.4 | (0.32, 0.61) |
| Ex. (153) | Comp. (2-1) | 5.3 | 5.0 | 300 | 6.0 | 116.6 | (0.31, 0.60) |
| Ex. (154) | Comp. (2-2) | 5.4 | 4.6 | 300 | 6.5 | 122.1 | (0.32, 0.61) |
| Ex. (155) | Comp. (2-3) | 5.4 | 5.3 | 300 | 5.6 | 115.0 | (0.31, 0.61) |
| Ex. (156) | Comp. (2-4) | 5.4 | 5.5 | 300 | 5.4 | 126.9 | (0.33, 0.60) |
| Ex. (157) | Comp. (2-5) | 5.2 | 4.6 | 300 | 6.5 | 124.0 | (0.31, 0.60) |
| Ex. (158) | Comp. (2-6) | 5.3 | 4.5 | 300 | 6.6 | 94.3 | (0.32, 0.60) |
| Ex. (159) | Comp. (2-7) | 5.5 | 4.6 | 300 | 6.5 | 108.0 | (0.32, 0.61) |
| Ex. (160) | Comp. (2-8) | 5.3 | 4.5 | 300 | 6.7 | 126.7 | (0.33, 0.60) |
| Ex. (161) | Comp. (2-9) | 5.4 | 5.4 | 300 | 5.5 | 108.5 | (0.30, 0.61) |
| Ex. (162) | Comp. (2-10) | 5.0 | 4.7 | 300 | 6.4 | 103.9 | (0.31, 0.61) |
| Ex. (163) | Comp. (2-11) | 5.5 | 4.7 | 300 | 6.3 | 103.0 | (0.31, 0.60) |
| Ex. (164) | Comp. (2-12) | 5.1 | 5.0 | 300 | 6.0 | 137.1 | (0.33, 0.61) |
| Ex. (165) | Comp. (2-13) | 5.1 | 5.2 | 300 | 5.8 | 137.2 | (0.32, 0.61) |
| Ex. (166) | Comp. (2-14) | 5.4 | 5.4 | 300 | 5.6 | 150.5 | (0.33, 0.60) |
| Ex. (167) | Comp. (2-15) | 5.8 | 5.8 | 300 | 5.2 | 74.4 | (0.30, 0.61) |
| Ex. (168) | Comp. (2-16) | 5.2 | 5.1 | 300 | 5.9 | 111.5 | (0.31, 0.61) |
| Ex. (169) | Comp. (2-17) | 5.1 | 5.5 | 300 | 5.4 | 122.0 | (0.31, 0.60) |
| Ex. (170) | Comp. (2-18) | 5.4 | 4.7 | 300 | 6.3 | 126.2 | (0.33, 0.61) |
| Ex. (171) | Comp. (2-19) | 5.4 | 4.9 | 300 | 6.1 | 105.7 | (0.32, 0.60) |
| Ex. (172) | Comp. (2-20) | 5.5 | 4.5 | 300 | 6.6 | 116.0 | (0.32, 0.60) |
| Ex. (173) | Comp. (2-21) | 5.6 | 4.4 | 300 | 6.7 | 106.8 | (0.33, 0.60) |
| Ex. (174) | Comp. (2-22) | 5.1 | 4.9 | 300 | 6.1 | 138.3 | (0.30, 0.60) |
| Ex. (175) | Comp. (2-23) | 5.3 | 4.9 | 300 | 6.1 | 147.3 | (0.30, 0.61) |
| Ex. (176) | Comp. (2-24) | 5.5 | 5.3 | 300 | 5.7 | 145.5 | (0.32, 0.60) |
| Ex. (177) | Comp. (2-25) | 5.3 | 5.1 | 300 | 5.9 | 145.3 | (0.31, 0.60) |
| Ex. (178) | Comp. (2-26) | 5.1 | 4.5 | 300 | 6.6 | 140.8 | (0.31, 0.60) |
| Ex. (179) | Comp. (2-27) | 5.9 | 5.8 | 300 | 5.2 | 74.1 | (0.31, 0.60) |
| Ex. (180) | Comp. (2-28) | 5.3 | 5.3 | 300 | 5.7 | 150.3 | (0.32, 0.61) |
| Ex. (181) | Comp. (2-29) | 5.3 | 4.6 | 300 | 6.5 | 100.0 | (0.31, 0.61) |
| Ex. (182) | Comp. (2-30) | 5.5 | 4.7 | 300 | 6.3 | 95.0 | (0.33, 0.60) |
| Ex. (183) | Comp. (2-31) | 5.4 | 4.6 | 300 | 6.5 | 109.2 | (0.32, 0.61) |
| Ex. (184) | Comp. (2-32) | 5.6 | 5.3 | 300 | 5.6 | 122.8 | (0.32, 0.60) |
| Ex. (185) | Comp. (2-33) | 5.3 | 4.7 | 300 | 6.4 | 120.9 | (0.32, 0.61) |
| Ex. (186) | Comp. (2-34) | 5.4 | 4.7 | 300 | 6.4 | 114.0 | (0.33, 0.60) |
| Ex. (187) | Comp. (2-35) | 5.8 | 6.1 | 300 | 5.0 | 71.6 | (0.30, 0.61) |
| Ex. (188) | Comp. (2-36) | 5.1 | 4.7 | 300 | 6.4 | 147.6 | (0.31, 0.61) |
| Ex. (189) | Comp. (2-37) | 5.1 | 5.5 | 300 | 5.4 | 98.3 | (0.31, 0.60) |
| Ex. (190) | Comp. (2-38) | 5.5 | 5.2 | 300 | 5.8 | 143.6 | (0.33, 0.61) |
| Ex. (191) | Comp. (2-39) | 5.4 | 4.6 | 300 | 6.5 | 111.6 | (0.32, 0.61) |
| Ex. (192) | Comp. (2-40) | 5.5 | 5.4 | 300 | 5.5 | 118.1 | (0.33, 0.60) |
| Ex. (193) | Comp. (2-41) | 5.3 | 4.5 | 300 | 6.7 | 126.8 | (0.30, 0.61) |
| Ex. (194) | Comp. (2-42) | 5.1 | 5.4 | 300 | 5.5 | 140.6 | (0.31, 0.61) |
| Ex. (195) | Comp. (2-43) | 5.5 | 5.5 | 300 | 5.4 | 119.5 | (0.31, 0.60) |
| Ex. (196) | Comp. (2-44) | 5.1 | 4.7 | 300 | 6.4 | 147.4 | (0.33, 0.60) |
| Ex. (197) | Comp. (2-45) | 5.4 | 4.5 | 300 | 6.6 | 128.6 | (0.32, 0.60) |
| Ex. (198) | Comp. (2-46) | 5.3 | 4.5 | 300 | 6.7 | 105.9 | (0.32, 0.61) |
| Ex. (199) | Comp. (2-47) | 5.9 | 6.1 | 300 | 4.9 | 70.2 | (0.33, 0.60) |
| Ex. (200) | Comp. (2-48) | 5.1 | 4.4 | 300 | 6.8 | 145.4 | (0.30, 0.60) |
| Ex. (201) | Comp. (2-49) | 5.3 | 5.1 | 300 | 5.9 | 140.0 | (0.30, 0.61) |
| Ex. (202) | Comp. (2-50) | 5.6 | 4.6 | 300 | 6.5 | 106.3 | (0.32, 0.61) |
| Ex. (203) | Comp. (2-51) | 5.5 | 4.9 | 300 | 6.2 | 145.0 | (0.31, 0.61) |
| Ex. (204) | Comp. (2-52) | 5.0 | 5.3 | 300 | 5.6 | 110.7 | (0.31, 0.60) |
| Ex. (205) | Comp. (2-53) | 5.2 | 4.6 | 300 | 6.6 | 103.1 | (0.31, 0.60) |
| Ex. (206) | Comp. (2-54) | 5.1 | 4.7 | 300 | 6.4 | 141.5 | (0.32, 0.60) |
| Ex. (207) | Comp. (2-55) | 5.7 | 5.9 | 300 | 5.1 | 67.9 | (0.31, 0.61) |
| Ex. (208) | Comp. (2-56) | 5.5 | 4.8 | 300 | 6.3 | 97.3 | (0.33, 0.60) |
| Ex. (209) | Comp. (2-57) | 5.5 | 5.4 | 300 | 5.6 | 101.7 | (0.31, 0.60) |
| Ex. (210) | Comp. (2-58) | 5.2 | 5.3 | 300 | 5.6 | 133.0 | (0.32, 0.61) |
| Ex. (211) | Comp. (2-59) | 5.6 | 5.1 | 300 | 5.9 | 138.2 | (0.32, 0.61) |
| Ex. (212) | Comp. (2-60) | 5.0 | 5.0 | 300 | 6.0 | 104.2 | (0.33, 0.60) |
| Ex. (213) | Comp. (2-61) | 5.5 | 4.9 | 300 | 6.1 | 139.1 | (0.33, 0.60) |
| Ex. (214) | Comp. (2-62) | 5.4 | 4.7 | 300 | 6.3 | 140.0 | (0.30, 0.61) |
| Ex. (215) | Comp. (2-63) | 5.1 | 5.4 | 300 | 5.5 | 110.6 | (0.31, 0.61) |
| Ex. (216) | Comp. (2-64) | 5.3 | 4.8 | 300 | 6.2 | 115.1 | (0.31, 0.60) |
| Ex. (217) | Comp. (2-65) | 5.1 | 5.0 | 300 | 6.1 | 133.8 | (0.33, 0.61) |

TABLE 4-continued

|  | Compound | Voltage | Current Density (mA/cm$^2$) | Brightness (cd/m$^2$) | Efficiency | Lifetime T(95) | CIE (x, y) |
|---|---|---|---|---|---|---|---|
| Ex. (218) | Comp. (2-66) | 5.5 | 4.7 | 300 | 6.4 | 139.9 | (0.32, 0.61) |
| Ex. (219) | Comp. (2-67) | 5.8 | 6.0 | 300 | 5.0 | 72.9 | (0.33, 0.60) |
| Ex. (220) | Comp. (2-68) | 5.1 | 4.7 | 300 | 6.3 | 139.3 | (0.30, 0.61) |
| Ex. (221) | Comp. (2-69) | 5.4 | 4.9 | 300 | 6.2 | 130.1 | (0.31, 0.61) |
| Ex. (222) | Comp. (2-70) | 5.4 | 4.7 | 300 | 6.4 | 137.3 | (0.31, 0.61) |
| Ex. (223) | Comp. (2-71) | 5.3 | 4.6 | 300 | 6.5 | 134.3 | (0.33, 0.61) |
| Ex. (224) | Comp. (2-72) | 5.4 | 4.4 | 300 | 6.8 | 135.6 | (0.32, 0.60) |
| Ex. (225) | Comp. (2-73) | 5.2 | 5.3 | 300 | 5.6 | 128.3 | (0.32, 0.60) |
| Ex. (226) | Comp. (2-74) | 5.0 | 5.5 | 300 | 5.4 | 109.4 | (0.33, 0.60) |
| Ex. (227) | Comp. (2-75) | 5.9 | 5.9 | 300 | 5.1 | 73.5 | (0.30, 0.60) |
| Ex. (228) | Comp. (2-76) | 5.2 | 4.9 | 300 | 6.1 | 154.0 | (0.30, 0.61) |
| Ex. (229) | Comp. (2-77) | 5.3 | 5.5 | 300 | 5.5 | 141.4 | (0.32, 0.60) |
| Ex. (230) | Comp. (2-78) | 5.4 | 5.1 | 300 | 5.9 | 109.7 | (0.31, 0.61) |
| Ex. (231) | Comp. (2-79) | 5.2 | 5.0 | 300 | 6.1 | 152.5 | (0.31, 0.60) |
| Ex. (232) | Comp. (2-80) | 5.4 | 4.5 | 300 | 6.6 | 128.6 | (0.31, 0.60) |
| Ex. (233) | Comp. (3-1) | 5.0 | 4.9 | 300 | 6.2 | 117.0 | (0.30, 0.61) |
| Ex. (234) | Comp. (3-2) | 5.4 | 5.2 | 300 | 5.7 | 132.8 | (0.31, 0.61) |
| Ex. (235) | Comp. (3-3) | 5.5 | 5.2 | 300 | 5.8 | 105.4 | (0.31, 0.60) |
| Ex. (236) | Comp. (3-4) | 5.1 | 4.7 | 300 | 6.4 | 145.9 | (0.33, 0.61) |
| Ex. (237) | Comp. (3-5) | 5.0 | 4.8 | 300 | 6.2 | 150.1 | (0.32, 0.61) |
| Ex. (238) | Comp. (3-6) | 5.3 | 5.5 | 300 | 5.5 | 105.4 | (0.31, 0.60) |
| Ex. (239) | Comp. (3-7) | 5.8 | 6.0 | 300 | 5.0 | 69.1 | (0.30, 0.61) |
| Ex. (240) | Comp. (3-8) | 5.1 | 4.9 | 300 | 6.2 | 125.5 | (0.31, 0.61) |
| Ex. (241) | Comp. (3-9) | 5.1 | 4.7 | 300 | 6.4 | 125.0 | (0.31, 0.60) |
| Ex. (242) | Comp. (3-10) | 5.0 | 5.0 | 300 | 5.9 | 99.4 | (0.33, 0.61) |
| Ex. (243) | Comp. (3-11) | 5.5 | 4.4 | 300 | 6.8 | 145.1 | (0.32, 0.60) |
| Ex. (244) | Comp. (3-12) | 5.1 | 4.6 | 300 | 6.5 | 109.4 | (0.32, 0.60) |
| Ex. (245) | Comp. (3-13) | 5.3 | 5.1 | 300 | 5.8 | 140.3 | (0.33, 0.60) |
| Ex. (246) | Comp. (3-14) | 5.0 | 4.5 | 300 | 6.7 | 140.2 | (0.30, 0.60) |
| Ex. (247) | Comp. (3-15) | 5.8 | 5.8 | 300 | 5.2 | 71.7 | (0.30, 0.61) |
| Ex. (248) | Comp. (3-16) | 5.0 | 5.2 | 300 | 5.8 | 147.4 | (0.32, 0.61) |
| Ex. (249) | Comp. (3-17) | 5.2 | 5.5 | 300 | 5.5 | 107.1 | (0.31, 0.61) |
| Ex. (250) | Comp. (3-18) | 5.3 | 5.5 | 300 | 5.5 | 123.2 | (0.31, 0.60) |
| Ex. (251) | Comp. (3-19) | 5.3 | 4.6 | 300 | 6.6 | 140.3 | (0.31, 0.60) |
| Ex. (252) | Comp. (3-20) | 5.3 | 4.8 | 300 | 6.3 | 125.1 | (0.32, 0.61) |
| Ex. (253) | Comp. (3-21) | 5.0 | 4.6 | 300 | 6.5 | 154.8 | (0.31, 0.61) |
| Ex. (254) | Comp. (3-22) | 5.5 | 5.0 | 300 | 6.0 | 113.5 | (0.33, 0.60) |
| Ex. (255) | Comp. (3-23) | 5.4 | 4.6 | 300 | 6.5 | 153.0 | (0.31, 0.60) |
| Ex. (256) | Comp. (3-24) | 5.1 | 5.2 | 300 | 5.7 | 139.8 | (0.32, 0.61) |
| Ex. (257) | Comp. (3-25) | 5.3 | 4.8 | 300 | 6.2 | 97.3 | (0.32, 0.61) |
| Ex. (258) | Comp. (3-26) | 5.1 | 5.5 | 300 | 5.5 | 136.2 | (0.33, 0.60) |
| Ex. (259) | Comp. (3-27) | 5.7 | 6.1 | 300 | 4.9 | 73.1 | (0.30, 0.60) |
| Ex. (260) | Comp. (3-28) | 5.4 | 5.0 | 300 | 6.0 | 110.7 | (0.31, 0.61) |
| Ex. (261) | Comp. (3-29) | 5.3 | 4.6 | 300 | 6.6 | 143.2 | (0.31, 0.60) |
| Ex. (262) | Comp. (3-30) | 5.1 | 4.6 | 300 | 6.5 | 142.9 | (0.33, 0.61) |
| Ex. (263) | Comp. (3-31) | 5.1 | 5.3 | 300 | 5.7 | 98.4 | (0.32, 0.61) |
| Ex. (264) | Comp. (3-32) | 5.6 | 4.8 | 300 | 6.3 | 96.6 | (0.33, 0.60) |
| Ex. (265) | Comp. (3-33) | 5.5 | 5.2 | 300 | 5.8 | 116.4 | (0.30, 0.61) |
| Ex. (266) | Comp. (3-34) | 5.1 | 5.4 | 300 | 5.6 | 133.4 | (0.31, 0.61) |
| Ex. (267) | Comp. (3-35) | 5.7 | 5.8 | 300 | 5.2 | 77.3 | (0.31, 0.61) |
| Ex. (268) | Comp. (3-36) | 5.2 | 5.1 | 300 | 5.9 | 149.4 | (0.33, 0.61) |
| Ex. (269) | Comp. (3-37) | 5.5 | 4.5 | 300 | 6.6 | 130.0 | (0.32, 0.60) |
| Ex. (270) | Comp. (3-38) | 5.0 | 4.5 | 300 | 6.7 | 154.3 | (0.32, 0.61) |
| Ex. (271) | Comp. (3-39) | 5.5 | 5.0 | 300 | 6.0 | 97.8 | (0.33, 0.60) |
| Ex. (272) | Comp. (3-40) | 5.2 | 4.5 | 300 | 6.7 | 152.7 | (0.30, 0.60) |
| Ex. (273) | Comp. (3-41) | 5.5 | 5.4 | 300 | 5.6 | 129.2 | (0.30, 0.60) |
| Ex. (274) | Comp. (3-42) | 5.2 | 5.2 | 300 | 5.8 | 145.3 | (0.32, 0.61) |
| Ex. (275) | Comp. (3-43) | 5.0 | 4.9 | 300 | 6.2 | 112.5 | (0.31, 0.61) |
| Ex. (276) | Comp. (3-44) | 5.5 | 4.9 | 300 | 6.1 | 147.0 | (0.31, 0.61) |
| Ex. (277) | Comp. (3-45) | 5.1 | 5.5 | 300 | 5.5 | 106.9 | (0.31, 0.60) |
| Ex. (278) | Comp. (3-46) | 5.4 | 5.1 | 300 | 5.9 | 137.5 | (0.32, 0.61) |
| Ex. (279) | Comp. (3-47) | 5.7 | 5.8 | 300 | 5.2 | 74.5 | (0.33, 0.60) |
| Ex. (280) | Comp. (3-48) | 5.3 | 4.4 | 300 | 6.8 | 115.3 | (0.30, 0.60) |
| Ex. (281) | Comp. (3-49) | 5.3 | 4.5 | 300 | 6.7 | 117.7 | (0.31, 0.61) |
| Ex. (282) | Comp. (3-50) | 5.3 | 5.5 | 300 | 5.5 | 125.3 | (0.31, 0.60) |
| Ex. (283) | Comp. (3-51) | 5.2 | 4.5 | 300 | 6.6 | 108.6 | (0.33, 0.61) |
| Ex. (284) | Comp. (3-52) | 5.4 | 5.0 | 300 | 6.0 | 147.0 | (0.32, 0.60) |
| Ex. (285) | Comp. (3-53) | 5.3 | 4.6 | 300 | 6.5 | 122.4 | (0.32, 0.61) |
| Ex. (286) | Comp. (3-54) | 5.5 | 5.2 | 300 | 5.8 | 129.6 | (0.33, 0.60) |
| Ex. (287) | Comp. (3-55) | 5.8 | 5.9 | 300 | 5.1 | 70.1 | (0.30, 0.60) |
| Ex. (288) | Comp. (3-56) | 5.0 | 5.5 | 300 | 5.4 | 113.7 | (0.30, 0.61) |
| Ex. (289) | Comp. (3-57) | 5.0 | 5.0 | 300 | 6.0 | 135.9 | (0.32, 0.61) |
| Ex. (290) | Comp. (3-58) | 5.1 | 5.2 | 300 | 5.7 | 136.3 | (0.31, 0.61) |
| Ex. (291) | Comp. (3-59) | 5.5 | 5.0 | 300 | 6.1 | 105.0 | (0.31, 0.60) |
| Ex. (292) | Comp. (3-60) | 5.6 | 5.1 | 300 | 5.8 | 129.1 | (0.31, 0.60) |
| Ex. (293) | Comp. (3-61) | 5.4 | 4.5 | 300 | 6.7 | 144.2 | (0.32, 0.61) |

TABLE 4-continued

|  | Compound | Voltage | Current Density (mA/cm²) | Brightness (cd/m²) | Efficiency | Lifetime T(95) | CIE (x, y) |
|---|---|---|---|---|---|---|---|
| Ex. (294) | Comp. (3-62) | 5.3 | 5.0 | 300 | 6.0 | 132.7 | (0.33, 0.60) |
| Ex. (295) | Comp. (3-63) | 5.6 | 4.4 | 300 | 6.8 | 124.5 | (0.30, 0.60) |
| Ex. (296) | Comp. (3-64) | 5.3 | 4.5 | 300 | 6.6 | 94.9 | (0.30, 0.61) |
| Ex. (297) | Comp. (3-65) | 5.1 | 4.8 | 300 | 6.2 | 99.6 | (0.32, 0.61) |
| Ex. (298) | Comp. (3-66) | 5.0 | 4.9 | 300 | 6.1 | 132.0 | (0.31, 0.61) |
| Ex. (299) | Comp. (3-67) | 5.8 | 6.0 | 300 | 5.0 | 70.2 | (0.31, 0.60) |
| Ex. (300) | Comp. (3-68) | 5.4 | 5.4 | 300 | 5.6 | 117.5 | (0.31, 0.60) |
| Ex. (301) | Comp. (3-69) | 5.1 | 4.9 | 300 | 6.1 | 103.5 | (0.32, 0.61) |
| Ex. (302) | Comp. (3-70) | 5.1 | 4.6 | 300 | 6.6 | 110.1 | (0.31, 0.61) |
| Ex. (303) | Comp. (3-71) | 5.2 | 5.2 | 300 | 5.7 | 111.5 | (0.33, 0.60) |
| Ex. (304) | Comp. (3-72) | 5.5 | 4.6 | 300 | 6.5 | 153.2 | (0.31, 0.60) |
| Ex. (305) | Comp. (3-73) | 5.2 | 4.5 | 300 | 6.6 | 100.0 | (0.32, 0.61) |
| Ex. (306) | Comp. (3-74) | 5.5 | 5.2 | 300 | 5.8 | 107.9 | (0.32, 0.61) |
| Ex. (307) | Comp. (3-75) | 5.8 | 6.1 | 300 | 5.0 | 75.3 | (0.33, 0.60) |
| Ex. (308) | Comp. (3-76) | 5.0 | 4.9 | 300 | 6.1 | 114.3 | (0.30, 0.61) |
| Ex. (309) | Comp. (3-77) | 5.2 | 5.1 | 300 | 5.9 | 130.4 | (0.31, 0.61) |
| Ex. (310) | Comp. (3-78) | 5.2 | 5.3 | 300 | 5.7 | 117.2 | (0.31, 0.60) |
| Ex. (311) | Comp. (3-79) | 5.5 | 5.1 | 300 | 5.9 | 113.1 | (0.33, 0.61) |
| Ex. (312) | Comp. (3-80) | 5.0 | 4.8 | 300 | 6.2 | 150.8 | (0.32, 0.61) |

It can be seen from the results noted in Table 4 that the OLEDs manufactured using the inventive compounds showed low driving voltage, high efficiency, and/or long life span, as compared to Comparative Examples 1 to 5.

Also, in the case of the inventive compounds in which, similar to Comparative Examples 2 and 3, substituents bonded to positions $R_1$ to $R_4$ and $R_7$ to $R_{10}$ contain heterocyclic groups, they showed relatively high driving voltage, low efficiency, and short life span as in the case of Comparative Examples 2 and 3. This is believed because when heterocyclic groups are linked to $R_1$ and $R_2$, the band gap is relatively low, HOMO is increased, hole mobility is reduced, driving voltage is increased, resulting in low efficiency and short lifespan.

It can also be noted that Comparative Examples 4 and 5 in which $R_1$ to $R_4$ and $R_7$ to $R_{10}$ are hydrogen showed shorter life span than the inventive compounds.

Test Example 2

OLEDs were fabricated according to a conventional method by using the synthesized inventive compounds as a light emitting host material of a light emitting layer. Each OLED was fabricated as follows. First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Next, a light emitting layer with a thickness of 30 nm was deposited on the hole transport layer by doping the hole transport layer with the inventive compound (4-1 to 4-48) as a host material and (piq)2Ir(acac)[bis-(1-phenylisoquinolyl)iridium(III)acetylacetonate] as a dopant material in a weight ratio of 95:5. Also, BAlq was vacuum-deposited with a thickness of 10 nm on the light emitting layer to form a hole blocking layer, and a film of $Alq_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Comparative Example 6

An OLED was manufactured in the same manner as described in Test Example 2, except that Comparative Compound 1 was used as the host material of the light emitting layer, instead of the inventive compound.

Comparative Example 7

An OLED was manufactured in the same manner as described in Test Example 2, except that Comparative Compound 2 was used as the host material of the light emitting layer, instead of the inventive compound.

Comparative Example 8

An OLED was manufactured in the same manner as described in Test Example 2, except that Comparative Compound 3 was used as the host material of the light emitting layer, instead of the inventive compound.

Comparative Example 9

An OLED was manufactured in the same manner as described in Test Example 2, except that Comparative Compound 4 was used as the host material of the light emitting layer, instead of the inventive compound.

Comparative Example 10

An OLED was manufactured in the same manner as described in Test Example 2, except that Comparative Compound 5 was used as the host material of the light emitting layer, instead of the inventive compound.

A forward bias DC voltage was applied to each of the OLEDs manufactured through Test Example 2 and Comparative Examples, and EL characteristics of the OLED were measured by PR-650 (Photoresearch). Also, T95 life span was measured by life span measuring equipment (Mc-science) at a reference brightness of 300 cd/m². Table 5 below shows evaluation results according to the manufactured OLEDs.

In Table 5, Example 313 to Example 456 represent the inventive OLEDs manufactured according to Test Example 2.

TABLE 5

| | Compound | Driving Voltage | Current (mA/cm$^2$) | Brightness (cd/m$^2$) | Efficiency (cd/A) | T(95) | CIE x | CIE y |
|---|---|---|---|---|---|---|---|---|
| Comp. Ex. 6 | Comp. Mat. 1 | 6 | 7.3 | 300 | 4.1 | 56.3 | 0.62 | 0.37 |
| Comp. Ex. 7 | Comp. Mat. 2 | 5.8 | 5.5 | 300 | 5.5 | 92.3 | 0.62 | 0.37 |
| Comp. Ex. 8 | Comp. Mat. 3 | 5.8 | 5.6 | 300 | 5.4 | 93.8 | 0.62 | 0.37 |
| Comp. Ex. 9 | Comp. Mat. 4 | 5.5 | 6.0 | 300 | 5.0 | 68.8 | 0.62 | 0.37 |
| Comp. Ex. 10 | Comp. Mat. 5 | 5.5 | 5.9 | 300 | 5.1 | 71.8 | 0.62 | 0.37 |
| Ex. (313) | Comp. (4-1) | 5.3 | 5.2 | 300 | 5.8 | 94.8 | 0.66 | 0.32 |
| Ex. (314) | Comp. (4-2) | 5.4 | 4.4 | 300 | 6.8 | 135.6 | 0.67 | 0.33 |
| Ex. (315) | Comp. (4-3) | 5.1 | 4.5 | 300 | 6.6 | 115.3 | 0.67 | 0.33 |
| Ex. (316) | Comp. (4-4) | 5.2 | 3.9 | 300 | 7.7 | 137.9 | 0.65 | 0.33 |
| Ex. (317) | Comp. (4-5) | 5.3 | 5.4 | 300 | 5.6 | 86.6 | 0.67 | 0.32 |
| Ex. (318) | Comp. (4-6) | 5.0 | 3.7 | 300 | 8.2 | 96.9 | 0.66 | 0.32 |
| Ex. (319) | Comp. (4-7) | 5.3 | 4.6 | 300 | 6.5 | 106.9 | 0.66 | 0.33 |
| Ex. (320) | Comp. (4-8) | 5.1 | 3.6 | 300 | 8.4 | 117.6 | 0.66 | 0.33 |
| Ex. (321) | Comp. (4-9) | 5.2 | 4.1 | 300 | 7.4 | 109.9 | 0.66 | 0.32 |
| Ex. (322) | Comp. (4-10) | 5.3 | 5.1 | 300 | 5.9 | 142.7 | 0.66 | 0.32 |
| Ex. (323) | Comp. (4-11) | 5.1 | 4.0 | 300 | 7.5 | 142.1 | 0.66 | 0.32 |
| Ex. (324) | Comp. (4-12) | 5.3 | 5.5 | 300 | 5.5 | 85.9 | 0.66 | 0.33 |
| Ex. (325) | Comp. (4-13) | 5.3 | 4.5 | 300 | 6.6 | 111.1 | 0.67 | 0.32 |
| Ex. (326) | Comp. (4-14) | 5.5 | 4.3 | 300 | 7 | 110.9 | 0.66 | 0.33 |
| Ex. (327) | Comp. (4-15) | 5.0 | 4.8 | 300 | 6.2 | 136.3 | 0.65 | 0.32 |
| Ex. (328) | Comp. (4-16) | 5.1 | 6.1 | 300 | 4.9 | 144.7 | 0.66 | 0.32 |
| Ex. (329) | Comp. (4-17) | 5.2 | 5.1 | 300 | 5.9 | 120.5 | 0.66 | 0.32 |
| Ex. (330) | Comp. (4-18) | 5.3 | 4.3 | 300 | 6.9 | 96.4 | 0.66 | 0.32 |
| Ex. (331) | Comp. (4-19) | 5.3 | 3.8 | 300 | 7.8 | 147.5 | 0.65 | 0.33 |
| Ex. (332) | Comp. (4-20) | 5.1 | 6.3 | 300 | 4.8 | 135 | 0.65 | 0.32 |
| Ex. (333) | Comp. (4-21) | 5.4 | 3.8 | 300 | 8 | 118 | 0.67 | 0.33 |
| Ex. (334) | Comp. (4-22) | 4.9 | 5.8 | 300 | 5.2 | 113.2 | 0.66 | 0.32 |
| Ex. (335) | Comp. (4-23) | 4.9 | 6.4 | 300 | 4.7 | 130 | 0.67 | 0.33 |
| Ex. (336) | Comp. (4-24) | 5.2 | 5.4 | 300 | 5.6 | 95.3 | 0.66 | 0.33 |
| Ex. (337) | Comp. (4-25) | 5.4 | 3.6 | 300 | 8.3 | 106.4 | 0.65 | 0.32 |
| Ex. (338) | Comp. (4-26) | 5.2 | 4.6 | 300 | 6.5 | 133.6 | 0.66 | 0.32 |
| Ex. (339) | Comp. (4-27) | 5.1 | 3.8 | 300 | 7.8 | 98.4 | 0.67 | 0.32 |
| Ex. (340) | Comp. (4-28) | 5.4 | 4.5 | 300 | 6.7 | 101.8 | 0.65 | 0.33 |
| Ex. (341) | Comp. (4-29) | 5.7 | 3.9 | 300 | 7.6 | 132.2 | 0.65 | 0.33 |
| Ex. (342) | Comp. (4-30) | 5.2 | 4.1 | 300 | 7.3 | 130.7 | 0.66 | 0.32 |
| Ex. (343) | Comp. (4-31) | 5.3 | 5.1 | 300 | 5.9 | 107.4 | 0.67 | 0.33 |
| Ex. (344) | Comp. (4-32) | 5.5 | 3.5 | 300 | 8.5 | 109.4 | 0.66 | 0.33 |
| Ex. (345) | Comp. (4-33) | 4.9 | 3.8 | 300 | 7.9 | 125.4 | 0.66 | 0.32 |
| Ex. (346) | Comp. (4-34) | 4.7 | 4.5 | 300 | 6.6 | 134.6 | 0.66 | 0.33 |
| Ex. (347) | Comp. (4-35) | 4.5 | 4.7 | 300 | 6.3 | 114.2 | 0.66 | 0.32 |
| Ex. (348) | Comp. (4-36) | 5.2 | 3.7 | 300 | 8.0 | 107.2 | 0.65 | 0.32 |
| Ex. (349) | Comp. (4-37) | 5.3 | 3.8 | 300 | 7.8 | 124.7 | 0.65 | 0.33 |
| Ex. (350) | Comp. (4-38) | 4.7 | 3.9 | 300 | 7.6 | 140.7 | 0.66 | 0.33 |
| Ex. (351) | Comp. (4-39) | 5.1 | 4.3 | 300 | 7.0 | 138.3 | 0.66 | 0.33 |
| Ex. (352) | Comp. (4-40) | 5.0 | 4.8 | 300 | 6.3 | 111.1 | 0.65 | 0.32 |
| Ex. (353) | Comp. (4-41) | 4.6 | 3.6 | 300 | 8.4 | 138.5 | 0.66 | 0.32 |
| Ex. (354) | Comp. (4-42) | 4.6 | 4.6 | 300 | 6.5 | 123.8 | 0.66 | 0.32 |
| Ex. (355) | Comp. (4-43) | 5.4 | 3.5 | 300 | 8.5 | 135.8 | 0.67 | 0.32 |
| Ex. (356) | Comp. (4-44) | 5.3 | 4.0 | 300 | 7.5 | 116.6 | 0.67 | 0.33 |
| Ex. (357) | Comp. (4-45) | 5.1 | 4.0 | 300 | 7.5 | 147.8 | 0.66 | 0.32 |
| Ex. (358) | Comp. (4-46) | 4.6 | 3.7 | 300 | 8.2 | 117.5 | 0.65 | 0.33 |
| Ex. (359) | Comp. (4-47) | 5.3 | 4.6 | 300 | 6.5 | 136.2 | 0.67 | 0.32 |
| Ex. (360) | Comp. (4-48) | 5.1 | 4.3 | 300 | 7.0 | 99.5 | 0.66 | 0.33 |
| Ex. (361) | Comp. (5-1) | 5.3 | 4.2 | 300 | 7.1 | 136.3 | 0.66 | 0.33 |
| Ex. (362) | Comp. (5-2) | 4.6 | 4.2 | 300 | 7.2 | 114.3 | 0.66 | 0.32 |
| Ex. (363) | Comp. (5-3) | 4.7 | 3.6 | 300 | 8.4 | 128.6 | 0.67 | 0.33 |
| Ex. (364) | Comp. (5-4) | 4.8 | 4.4 | 300 | 6.8 | 111.8 | 0.67 | 0.32 |
| Ex. (365) | Comp. (5-5) | 5.2 | 4.1 | 300 | 7.4 | 140.8 | 0.65 | 0.32 |
| Ex. (366) | Comp. (5-6) | 5.1 | 3.7 | 300 | 8.1 | 142.4 | 0.66 | 0.32 |
| Ex. (367) | Comp. (5-7) | 5.3 | 4.2 | 300 | 7.2 | 120.8 | 0.66 | 0.33 |
| Ex. (368) | Comp. (5-8) | 5.2 | 4.9 | 300 | 6.1 | 147.3 | 0.66 | 0.32 |
| Ex. (369) | Comp. (5-9) | 5.2 | 3.7 | 300 | 8.1 | 111.0 | 0.66 | 0.33 |
| Ex. (370) | Comp. (5-10) | 5.4 | 4.2 | 300 | 7.1 | 120.2 | 0.65 | 0.33 |
| Ex. (371) | Comp. (5-11) | 4.6 | 4.7 | 300 | 6.4 | 102.1 | 0.66 | 0.33 |
| Ex. (372) | Comp. (5-12) | 5.3 | 4.1 | 300 | 7.3 | 138.0 | 0.67 | 0.33 |
| Ex. (373) | Comp. (5-13) | 4.8 | 4.9 | 300 | 6.1 | 120.0 | 0.66 | 0.32 |
| Ex. (374) | Comp. (5-14) | 4.5 | 4.7 | 300 | 6.4 | 116.3 | 0.65 | 0.32 |
| Ex. (375) | Comp. (5-15) | 4.9 | 3.7 | 300 | 8.2 | 105.7 | 0.66 | 0.32 |
| Ex. (376) | Comp. (5-16) | 4.9 | 4.3 | 300 | 6.9 | 117.7 | 0.66 | 0.32 |
| Ex. (377) | Comp. (5-17) | 4.6 | 3.9 | 300 | 7.6 | 137.8 | 0.66 | 0.33 |
| Ex. (378) | Comp. (5-18) | 5.2 | 3.9 | 300 | 7.8 | 132.4 | 0.65 | 0.32 |
| Ex. (379) | Comp. (5-19) | 4.7 | 3.8 | 300 | 7.9 | 130.3 | 0.67 | 0.32 |
| Ex. (380) | Comp. (5-20) | 5.2 | 4.1 | 300 | 7.3 | 132.6 | 0.67 | 0.32 |
| Ex. (381) | Comp. (5-21) | 5.2 | 4.2 | 300 | 7.2 | 102.5 | 0.66 | 0.32 |
| Ex. (382) | Comp. (5-22) | 5.0 | 4.7 | 300 | 6.3 | 139.5 | 0.66 | 0.32 |
| Ex. (383) | Comp. (5-23) | 4.9 | 4.9 | 300 | 6.2 | 108.4 | 0.66 | 0.32 |

TABLE 5-continued

|  | Compound | Driving Voltage | Current (mA/cm²) | Brightness (cd/m²) | Efficiency (cd/A) | T(95) | CIE x | CIE y |
|---|---|---|---|---|---|---|---|---|
| Ex. (384) | Comp. (5-24) | 5.3 | 4.0 | 300 | 7.5 | 135.9 | 0.65 | 0.33 |
| Ex. (385) | Comp. (5-25) | 5.0 | 3.7 | 300 | 8.1 | 135.1 | 0.65 | 0.32 |
| Ex. (386) | Comp. (5-26) | 5.4 | 3.7 | 300 | 8.0 | 118.1 | 0.65 | 0.32 |
| Ex. (387) | Comp. (5-27) | 5.4 | 4.4 | 300 | 6.8 | 128.6 | 0.67 | 0.33 |
| Ex. (388) | Comp. (5-28) | 4.8 | 4.5 | 300 | 6.6 | 138.4 | 0.67 | 0.32 |
| Ex. (389) | Comp. (5-29) | 4.7 | 4.9 | 300 | 6.1 | 134.4 | 0.65 | 0.33 |
| Ex. (390) | Comp. (5-30) | 5.2 | 3.8 | 300 | 7.8 | 100.9 | 0.65 | 0.32 |
| Ex. (391) | Comp. (5-31) | 4.9 | 4.9 | 300 | 6.1 | 126.6 | 0.66 | 0.32 |
| Ex. (392) | Comp. (5-32) | 5.5 | 4.5 | 300 | 6.6 | 103.8 | 0.65 | 0.32 |
| Ex. (393) | Comp. (5-33) | 4.6 | 3.7 | 300 | 8.1 | 106.3 | 0.67 | 0.33 |
| Ex. (394) | Comp. (5-34) | 5.3 | 4.2 | 300 | 7.2 | 135.6 | 0.65 | 0.32 |
| Ex. (395) | Comp. (5-35) | 4.7 | 3.9 | 300 | 7.6 | 146.7 | 0.67 | 0.33 |
| Ex. (396) | Comp. (5-36) | 5.3 | 4.6 | 300 | 6.6 | 104.6 | 0.65 | 0.33 |
| Ex. (397) | Comp. (5-37) | 4.8 | 4.0 | 300 | 7.4 | 130.2 | 0.66 | 0.33 |
| Ex. (398) | Comp. (5-38) | 4.6 | 4.5 | 300 | 6.7 | 114.7 | 0.66 | 0.32 |
| Ex. (399) | Comp. (5-39) | 5.5 | 3.9 | 300 | 7.8 | 116.6 | 0.65 | 0.33 |
| Ex. (400) | Comp. (5-40) | 5.4 | 3.8 | 300 | 8.0 | 140.2 | 0.66 | 0.33 |
| Ex. (401) | Comp. (5-41) | 5.0 | 4.1 | 300 | 7.3 | 122.7 | 0.66 | 0.33 |
| Ex. (402) | Comp. (5-42) | 4.6 | 4.1 | 300 | 7.3 | 105.8 | 0.66 | 0.33 |
| Ex. (403) | Comp. (5-43) | 4.9 | 4.5 | 300 | 6.6 | 113.8 | 0.67 | 0.33 |
| Ex. (404) | Comp. (5-44) | 4.8 | 3.6 | 300 | 8.4 | 140.2 | 0.67 | 0.32 |
| Ex. (405) | Comp. (5-45) | 5.0 | 4.3 | 300 | 7.0 | 135.2 | 0.66 | 0.33 |
| Ex. (406) | Comp. (5-46) | 4.6 | 3.7 | 300 | 8.1 | 108.2 | 0.66 | 0.33 |
| Ex. (407) | Comp. (5-47) | 4.6 | 5.0 | 300 | 6.0 | 123.2 | 0.65 | 0.33 |
| Ex. (408) | Comp. (5-48) | 5.1 | 3.6 | 300 | 8.4 | 104.6 | 0.66 | 0.32 |
| Ex. (409) | Comp. (6-1) | 4.9 | 4.6 | 300 | 6.5 | 126.5 | 0.66 | 0.33 |
| Ex. (410) | Comp. (6-2) | 5.4 | 3.9 | 300 | 7.8 | 104.8 | 0.67 | 0.33 |
| Ex. (411) | Comp. (6-3) | 4.6 | 4.6 | 300 | 6.6 | 127.3 | 0.66 | 0.32 |
| Ex. (412) | Comp. (6-4) | 5.1 | 4.5 | 300 | 6.7 | 117.6 | 0.67 | 0.32 |
| Ex. (413) | Comp. (6-5) | 4.8 | 4.0 | 300 | 7.4 | 112.3 | 0.65 | 0.32 |
| Ex. (414) | Comp. (6-6) | 5.1 | 4.5 | 300 | 6.6 | 129.9 | 0.66 | 0.33 |
| Ex. (415) | Comp. (6-7) | 5.0 | 4.5 | 300 | 6.7 | 119.6 | 0.67 | 0.33 |
| Ex. (416) | Comp. (6-8) | 5.3 | 4.0 | 300 | 7.4 | 113.1 | 0.66 | 0.32 |
| Ex. (417) | Comp. (6-9) | 4.7 | 3.8 | 300 | 7.9 | 127.6 | 0.65 | 0.32 |
| Ex. (418) | Comp. (6-10) | 4.6 | 4.2 | 300 | 7.2 | 137.4 | 0.65 | 0.32 |
| Ex. (419) | Comp. (6-11) | 5.0 | 4.2 | 300 | 7.1 | 140.8 | 0.67 | 0.32 |
| Ex. (420) | Comp. (6-12) | 5.1 | 4.6 | 300 | 6.5 | 111.4 | 0.66 | 0.33 |
| Ex. (421) | Comp. (6-13) | 5.4 | 4.7 | 300 | 6.4 | 114.7 | 0.66 | 0.33 |
| Ex. (422) | Comp. (6-14) | 4.7 | 5.0 | 300 | 6.0 | 144.9 | 0.67 | 0.33 |
| Ex. (423) | Comp. (6-15) | 5.5 | 4.0 | 300 | 7.4 | 149.3 | 0.65 | 0.32 |
| Ex. (424) | Comp. (6-16) | 5.3 | 3.9 | 300 | 7.6 | 112.9 | 0.67 | 0.32 |
| Ex. (425) | Comp. (6-17) | 4.8 | 4.3 | 300 | 7.0 | 122.6 | 0.66 | 0.32 |
| Ex. (426) | Comp. (6-18) | 5.1 | 4.8 | 300 | 6.2 | 107.5 | 0.67 | 0.33 |
| Ex. (427) | Comp. (6-19) | 5.3 | 4.2 | 300 | 7.1 | 124.4 | 0.66 | 0.33 |
| Ex. (428) | Comp. (6-20) | 4.9 | 5.1 | 300 | 5.9 | 109.5 | 0.66 | 0.32 |
| Ex. (429) | Comp. (6-21) | 5.1 | 4.6 | 300 | 6.5 | 128.1 | 0.66 | 0.32 |
| Ex. (430) | Comp. (6-22) | 4.6 | 4.8 | 300 | 6.3 | 132.7 | 0.67 | 0.33 |
| Ex. (431) | Comp. (6-23) | 4.7 | 4.4 | 300 | 6.8 | 128.1 | 0.66 | 0.32 |
| Ex. (432) | Comp. (6-24) | 5.2 | 3.6 | 300 | 8.4 | 143.4 | 0.66 | 0.32 |
| Ex. (433) | Comp. (6-25) | 5.5 | 4.0 | 300 | 7.5 | 127.8 | 0.66 | 0.32 |
| Ex. (434) | Comp. (6-26) | 5.5 | 3.9 | 300 | 7.6 | 140.2 | 0.66 | 0.33 |
| Ex. (435) | Comp. (6-27) | 4.7 | 4.3 | 300 | 7.0 | 141.6 | 0.66 | 0.33 |
| Ex. (436) | Comp. (6-28) | 4.9 | 4.6 | 300 | 6.6 | 112.1 | 0.65 | 0.33 |
| Ex. (437) | Comp. (6-29) | 4.5 | 4.1 | 300 | 7.3 | 127.0 | 0.67 | 0.33 |
| Ex. (438) | Comp. (6-30) | 4.7 | 4.4 | 300 | 6.7 | 106.7 | 0.67 | 0.33 |
| Ex. (439) | Comp. (6-31) | 4.7 | 3.6 | 300 | 8.4 | 128.4 | 0.65 | 0.33 |
| Ex. (440) | Comp. (6-32) | 5.0 | 4.9 | 300 | 6.2 | 106.2 | 0.66 | 0.32 |
| Ex. (441) | Comp. (6-33) | 4.5 | 3.9 | 300 | 7.7 | 112.0 | 0.66 | 0.32 |
| Ex. (442) | Comp. (6-34) | 4.7 | 3.6 | 300 | 8.4 | 117.0 | 0.66 | 0.33 |
| Ex. (443) | Comp. (6-35) | 4.7 | 5.0 | 300 | 6.0 | 132.7 | 0.66 | 0.33 |
| Ex. (444) | Comp. (6-36) | 5.4 | 3.8 | 300 | 7.9 | 98.6 | 0.67 | 0.32 |
| Ex. (445) | Comp. (6-37) | 5.0 | 4.6 | 300 | 6.5 | 116.6 | 0.65 | 0.33 |
| Ex. (446) | Comp. (6-38) | 5.2 | 5.1 | 300 | 5.9 | 108.9 | 0.65 | 0.32 |
| Ex. (447) | Comp. (6-39) | 4.6 | 4.6 | 300 | 6.6 | 118.9 | 0.66 | 0.32 |
| Ex. (448) | Comp. (6-40) | 5.4 | 3.8 | 300 | 7.9 | 106.4 | 0.65 | 0.33 |
| Ex. (449) | Comp. (6-41) | 4.6 | 3.7 | 300 | 8.2 | 129.9 | 0.67 | 0.33 |
| Ex. (450) | Comp. (6-42) | 4.7 | 3.8 | 300 | 7.9 | 133.3 | 0.67 | 0.33 |
| Ex. (451) | Comp. (6-43) | 4.7 | 4.2 | 300 | 7.2 | 108.7 | 0.67 | 0.32 |
| Ex. (452) | Comp. (6-44) | 5.3 | 3.6 | 300 | 8.4 | 134.2 | 0.66 | 0.32 |
| Ex. (453) | Comp. (6-45) | 4.6 | 4.2 | 300 | 7.2 | 139.6 | 0.66 | 0.32 |
| Ex. (454) | Comp. (6-46) | 5.5 | 4.2 | 300 | 7.2 | 100.7 | 0.66 | 0.32 |
| Ex. (455) | Comp. (6-47) | 4.8 | 5.0 | 300 | 6.0 | 116.0 | 0.66 | 0.32 |
| Ex. (456) | Comp. (6-48) | 4.7 | 4.7 | 300 | 6.4 | 112.8 | 0.67 | 0.33 |

It can be seen from the results noted in Table 5 that Examples using the inventive compounds, in which $R_5$ and $R_6$ are linked together to form a ring, as a phosphorescent red host showed higher efficiency and longer life span than Comparative Examples 6 to 10. Especially, in comparison between the inventive compounds and Comparative Examples 9 and 10 in which $R_1$ to $R_4$ and $R_7$ to $R_{10}$ are substituted by hydrogen, it can be noted that the inventive compounds showed higher efficiency and longer life span.

As can be seen from the results noted in Tables above, when the inventive OLED material is used as a light emitting host material of an OLED, color purity is enhanced, luminous efficiency is increased, and life span is significantly improved.

Test Example 3: Emission-Auxiliary Layer (Red)

Each OLED was fabricated as follows. First, an ITO layer (anode) was formed on a glass substrate, and 2-TNATA was vacuum-deposited on the ITO layer to form a hole injection layer with a thickness of 60 nm. Subsequently, NPD was vacuum-deposited with a thickness of 20 nm on the hole injection layer to form a hole transport layer. Next, the inventive compound (1-153 to 1-163) was vacuum-deposited with a thickness of 20 nm on the hole transport layer to form an emission-auxiliary layer. Thereafter, a light emitting layer with a thickness of 30 nm was deposited on the hole transport layer by doping the hole transport layer with CBP[4,4'-N,N'-dicarbazole-bisphenyl] as a host material and (piq)2Ir(acac)[bis-(1-phenylisoquinolyl)iridium(III) acetylacetonate] as a dopant material in a weight ratio of 95:5. Also, BAlq was vacuum-deposited with a thickness of 10 nm on the light emitting layer to form a hole blocking layer, and a film of $Alq_3$ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

Comparative Example 11

An OLED was manufactured in the same manner as described in Test Example 3, except that Comparative Compound 1 was used as the emission-auxiliary layer material, instead of the inventive compound.

Comparative Example 12

An OLED was manufactured in the same manner as described in Test Example 3, except that Comparative Compound 2 was used as the emission-auxiliary layer material, instead of the inventive compound.

Comparative Example 13

An OLED was manufactured in the same manner as described in Test Example 3, except that Comparative Compound 3 was used as the emission-auxiliary layer material, instead of the inventive compound.

Comparative Example 14

An OLED was manufactured in the same manner as described in Test Example 3, except that Comparative Compound 4 was used as the emission-auxiliary layer material, instead of the inventive compound.

Comparative Example 15

An OLED was manufactured in the same manner as described in Test Example 3, except that Comparative Compound 5 was used as the emission-auxiliary layer material, instead of the inventive compound.

Comparative Example 16

An OLED was manufactured in the same manner as described in Test Example 3, except that the emission-auxiliary layer was not formed.

A forward bias DC voltage was applied to each of the OLEDs manufactured through Test Example 3 and Comparative Examples, and EL characteristics of the OLED were measured by PR-650 (Photoresearch). Also, T95 life span was measured by life span measuring equipment (Mc-science) at a reference brightness of 300 $cd/m^2$. Table 6 below shows evaluation results according to the manufactured OLEDs.

In Table 6, Example 457 to Example 467 represent the inventive OLEDs manufactured according to Test Example 3.

TABLE 6

|  | Compound | Voltage | Current Density | Brightness (cd/m2) | Efficiency | Lifetime T(95) | CIE (x, y) |
|---|---|---|---|---|---|---|---|
| Comp. Ex. (11) | Comp. Mat. (1) | 5.8 | 6.3 | 300.0 | 4.8 | 82.0 | (0.62, 0.37) |
| Comp. Ex. (12) | Comp. Mat. (2) | 5.5 | 5.7 | 300.0 | 5.3 | 97.7 | (0.62, 0.37) |
| Comp. Ex. (13) | Comp. Mat. (3) | 5.5 | 5.8 | 300.0 | 5.1 | 96.5 | (0.62, 0.37) |
| Comp. Ex. (14) | Comp. Mat. (4) | 5.4 | 5.7 | 300.0 | 5.2 | 96.9 | (0.62, 0.37) |
| Comp. Ex. (15) | Comp. Mat. (5) | 5.5 | 5.5 | 300.0 | 5.4 | 92.7 | (0.62, 0.37) |
| Comp. Ex. (16) | 사용하지 않음 | 6 | 7.3 | 300.0 | 4.1 | 56.3 | (0.62, 0.37) |
| Ex. (457) | Comp. (1-153) | 4.6 | 4.8 | 300.0 | 6.3 | 140.1 | (0.66, 0.32) |
| Ex. (458) | Comp. (1-154) | 4.3 | 4.1 | 300.0 | 7.3 | 138.9 | (0.67, 0.32) |
| Ex. (459) | Comp. (1-155) | 4.4 | 4.1 | 300.0 | 7.3 | 135.5 | (0.66, 0.32) |
| Ex. (460) | Comp. (1-156) | 4.8 | 4.6 | 300.0 | 6.6 | 121.0 | (0.66, 0.33) |
| Ex. (461) | Comp. (1-157) | 4.9 | 4.3 | 300.0 | 7.0 | 140.0 | (0.66, 0.32) |
| Ex. (462) | Comp. (1-158) | 4.4 | 4.3 | 300.0 | 6.9 | 133.5 | (0.65, 0.32) |
| Ex. (463) | Comp. (1-159) | 4.6 | 4.2 | 300.0 | 7.2 | 118.4 | (0.66, 0.32) |
| Ex. (464) | Comp. (1-160) | 4.6 | 4.8 | 300.0 | 6.3 | 147.7 | (0.66, 0.33) |
| Ex. (465) | Comp. (1-161) | 4.6 | 4.5 | 300.0 | 6.7 | 147.8 | (0.66, 0.32) |
| Ex. (466) | Comp. (1-162) | 4.9 | 4.8 | 300.0 | 6.2 | 146.0 | (0.65, 0.32) |
| Ex. (467) | Comp. (1-163) | 4.4 | 4.0 | 300.0 | 7.5 | 132.8 | (0.66, 0.32) |

It can be seen from the results noted in Table 6 that luminous efficiency and life span are improved and driving voltage is reduced even when the inventive compound is used as an emission-auxiliary layer material.

It is obvious that even when the inventive compounds are used in other organic material layers of an OLED, for example, an electron injection layer, an electron transport layer, and a hole injection layer, the same effects can be obtained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula (1):

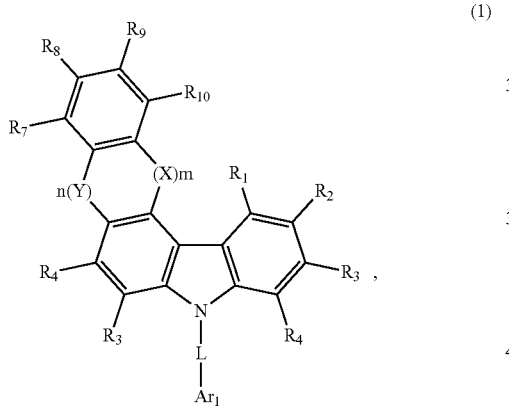

(1)

wherein $R_1$ to $R_{10}$ are independently selected from the group consisting of hydrogen, deuterium, halogen, a $C_6$ to $C_{60}$ aryl group, a fluorenyl group, a fused ring group of a $C_3$ to $C_{60}$ aliphatic ring and a $C_6$ to $C_{60}$ aromatic ring, a $C_2$ to $C_{60}$ heterocyclic group containing at least one heteroatom selected from the group consisting of O, N, S, Si, and P, -L-N(R')(R"), a $C_1$ to $C_{50}$ alkyl group, a $C_2$ to $C_{20}$ alkenyl group, a $C_1$ to $C_{30}$ alkoxy group, and a $C_6$ to $C_{30}$ aryloxy group; and any two adjacent groups of $R_1$ to $R_{10}$ are optionally linked together to form a fused ring, with the proviso that: (a) where $R_5$ and $R_6$ do not form a ring with each other, at least one of $R_1$ to $R_4$ is not hydrogen and at least one of $R_7$ to $R_{10}$ is not hydrogen; (b) where $R_5$ and $R_6$ form a ring with each other, either i) at least one of $R_1$ to $R_4$ is not hydrogen and at least one of $R_7$ to $R_{10}$ is not hydrogen, or ii) L-Ar$_1$ is a $C_7$-$C_{60}$ heterocyclic group containing pyridopyrimidine moiety in the compound; and (c) none of $R_2$, $R_8$ and $R_9$ is a polyheterocyclic group containing N or O, X and Y are independently S, O, or $SiR_{31}R_{32}$, wherein $R_{31}$ and $R_{32}$ are independently hydrogen, a $C_6$ to $C_{60}$ aryl group, a $C_2$ to $C_{60}$ heterocyclic group containing at least one heteroatom selected from the group consisting of O, N, S, Si, and P, or a $C_1$ to $C_{50}$ alkyl group, and m and n are each 0 or 1 with the proviso that m+n is an integer equal to or greater than 1;

L is selected from the group consisting of a single bond; a $C_6$ to $C_{60}$ arylene group; a fluorenyl group; a $C_2$ to $C_{60}$ heterocyclic group containing at least one heteroatom selected from the group consisting of O, N, S, Si, and P; and a bivalent aliphatic hydrocarbon group, wherein, the arylene group, the fluorenyl group, the heterocyclic group, and the aliphatic hydrocarbon group are optionally substituted by one or more substituents selected from the group consisting of a nitro group, a cyano group, a halogen group, a $C_1$ to $C_{20}$ alkyl group, a $C_6$ to $C_{20}$ aryl group, a $C_2$ to $C_{20}$ heterocyclic group, a $C_1$ to $C_{20}$ alkoxy group, and an amino group;

Ar$_1$ is a $C_2$ to $C_{60}$ heterocyclic group containing at least one heteroatom selected from the group consisting of O, N, S, Si, and P, a $C_6$ to $C_{60}$ aryl group, a fluorenyl group, or —N(R')(R"); and R' and R" are independently a $C_2$ to $C_{60}$ heterocyclic group containing at least one heteroatom selected from the group consisting of O, N, S, Si, and P, a $C_6$ to $C_{60}$ aryl group, or a fluorenyl group, wherein R' and R" do not form a fused ring with each other or with any adjacent group or ring;

where $R_1$ to $R_{10}$, Ar$_1$, R', and R" are an aryl group, $R_1$ to $R_{10}$, Ar$_1$, R', and R" are optionally substituted by one or more substituents selected from the group consisting of deuterium, halogen, a silane group, a boron group, a germanium group, a cyano group, a nitro group, a $C_1$ to $C_{20}$ alkylthio group, a $C_1$ to $C_{20}$ alkoxy group, a $C_1$ to $C_{20}$ alkyl group, a $C_2$ to $C_{20}$ alkenyl group, a $C_2$ to $C_{20}$ alkynyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group;

where $R_1$ to $R_4$ and $R_7$ to $R_{10}$ are heterocyclic group, $R_1$ to $R_4$ and $R_7$ to $R_{10}$ are optionally substituted by one or more substituents selected from the group consisting of deuterium, halogen, a silane group, a cyano group, a nitro group, a $C_1$ to $C_{20}$ alkoxy group, a $C_1$ to $C_{20}$ alkyl group, a $C_2$ to $C_{20}$ alkenyl group, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group;

where $R_5$, $R_6$, Ar$_1$, R', and R" are an heterocyclic group, $R_5$, $R_6$, Ar$_1$, R', and R" are optionally substituted by one or more substituents selected from the group consisting of deuterium, halogen, a silane group, a cyano group, a nitro group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group;

where $R_1$ to $R_{10}$, Ar$_1$, R', and R" are a fluorenyl group, $R_1$ to $R_{10}$, Ar$_1$, R', and R" are optionally substituted by one or more substituents selected from the group consisting of deuterium, halogen, a silane group, a cyano group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group;

where $R_1$ to $R_{10}$ are a fused ring group, $R_1$ to $R_{10}$ are optionally substituted by one or more substituents selected from the group consisting of deuterium, halogen, a silane group, a boron group, a germanium group, a cyano group, a nitro group, a $C_1$ to $C_{20}$ alkylthio group, a $C_1$ to $C_{20}$ alkoxy group, a $C_1$ to $C_{20}$ alkyl group, a $C_2$ to $C_{20}$ alkenyl group, a $C_2$ to $C_{20}$ alkynyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group;

where $R_1$ to $R_{10}$ are an alkyl group, $R_1$ to $R_{10}$ are optionally substituted by one or more substituents selected from the group consisting of halogen, a silane group, a boron group, a cyano group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_7$ to $C_{20}$ arylalkyl group, and a $C_8$ to $C_{20}$ arylalkenyl group;

where $R_1$ to $R_{10}$ are an alkenyl group, $R_1$ to $R_{10}$ are optionally substituted by one or more substituents selected from the group consisting of deuterium, halogen, a silane group, a cyano group, a $C_1$ to $C_{20}$ alkoxy group, a $C_1$ to $C_{20}$ alkyl group, a $C_2$ to $C_{20}$ alkenyl group, a $C_6$ to $C_{20}$ aryl group, a $C_6$ to $C_{20}$ aryl group substituted by deuterium, a $C_2$ to $C_{20}$ heterocyclic group, a $C_3$ to $C_{20}$ cycloalkyl group, a $C_7$ to $C_{20}$ arylalkyl group, and a $C_8$ to $C_{20}$ arylalkenyl group;

where $R_1$ to $R_{10}$ are an alkoxy group, $R_1$ to $R_{10}$ are optionally substituted by one or more substituents selected from the group consisting of deuterium, halogen, a silane group, a $C_1$ to $C_{20}$ alkyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group; and where $R_1$ to $R_{10}$ are an aryloxy group, $R_1$ to $R_{10}$ are optionally substituted by one or more substituents selected from the group consisting of deuterium, a silane group, a cyano group, a $C_1$ to $C_{20}$ alkyl group, a $C_6$ to $C_{20}$ aryl group, a $C_6$ to $C_{20}$ aryl group substituted by deuterium, a $C_2$ to $C_{20}$ heterocyclic group, and a $C_3$ to $C_{20}$ cycloalkyl group.

2. The compound of claim 1, wherein the compound of Formula (1) is represented by one of the following formulas:

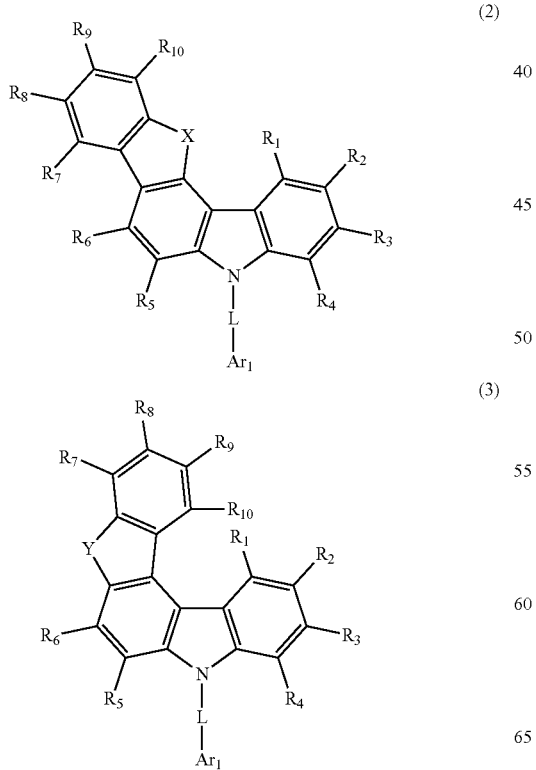

(2)

(3)

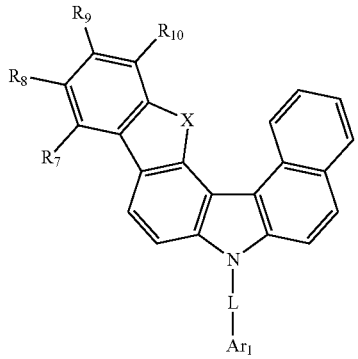

(4)

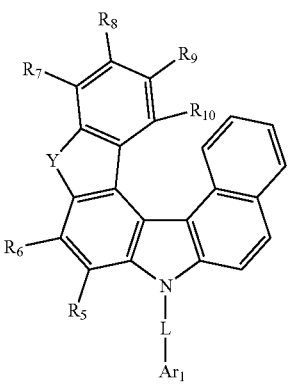

(5)

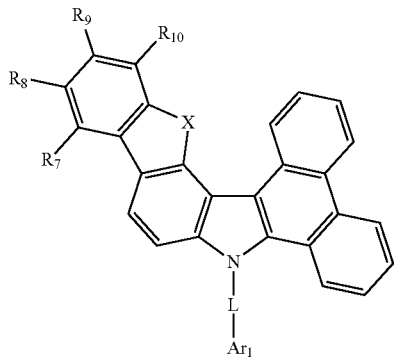

(6)

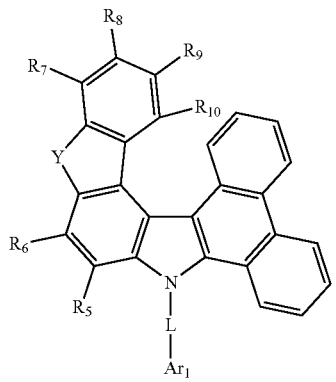

(7)

wherein $R_1$ to $R_{10}$, X, Y, L, and $Ar_1$ are the same as defined in claim 1.

3. The compound of claim 1, wherein the compound of Formula (1) is represented by the following formula:
(8)
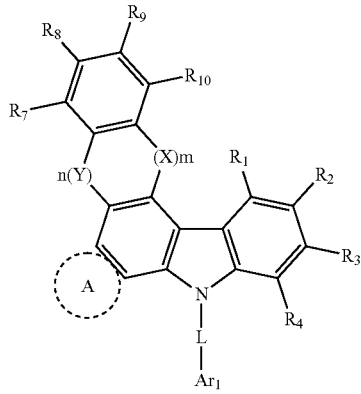
wherein $R_1$ to $R_{10}$, X, Y, m, n, L, and $Ar_1$ are the same as defined in claim 1, and the ring A is an aromatic ring or a hetero aromatic ring.
4. The compound of claim 3, wherein the compound is represented by one of the following formulas:
(9)
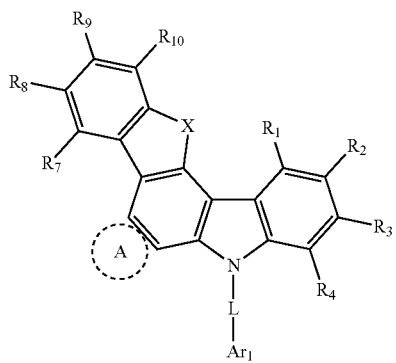
(10)
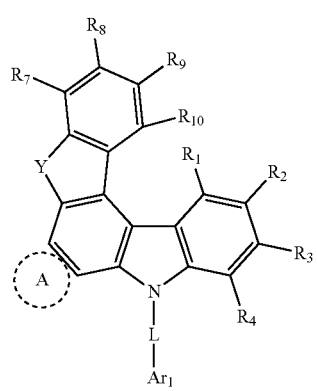
-continued
(11)
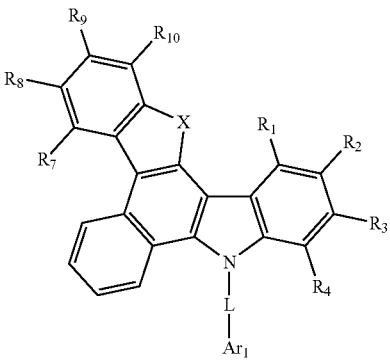
(12)
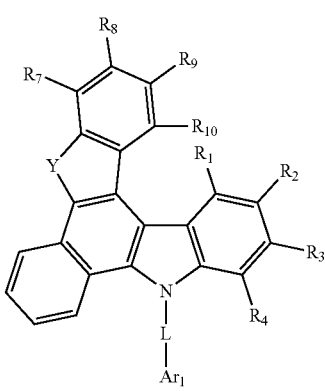
(13)
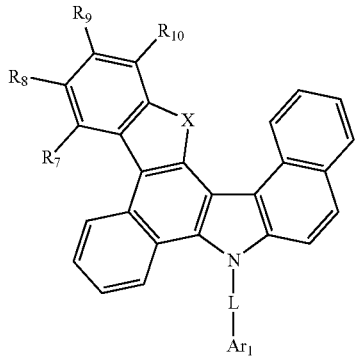

(14)
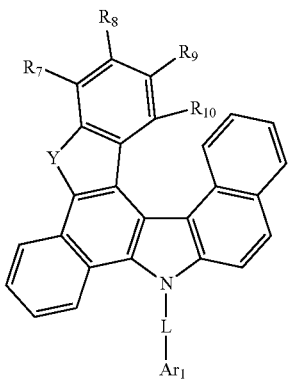

(15)
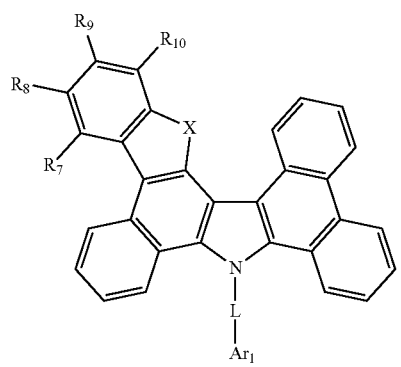

(16)
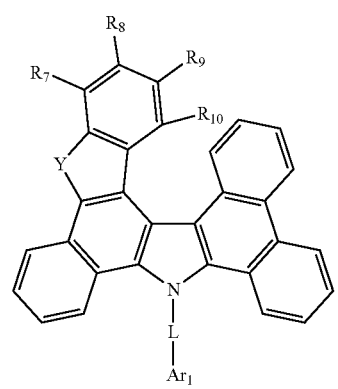

(17)
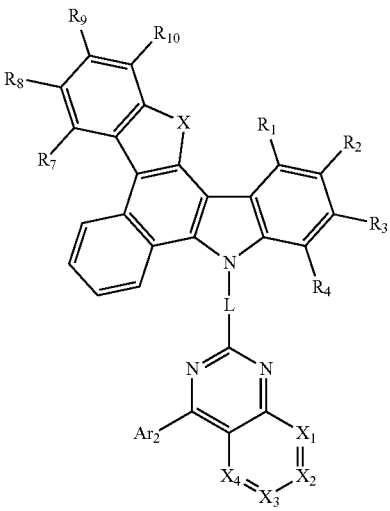

(18)
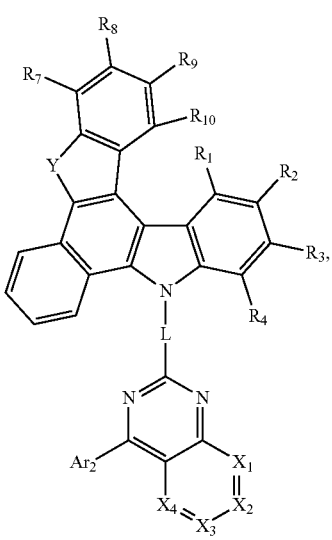

wherein $R_1$ to $R_4$, $R_7$ to $R_{10}$, X, Y, L, and $Ar_1$ are the same as defined in claim 1, the ring A is an aromatic ring or a hetero ring, $Ar_2$ is selected from the group consisting of hydrogen, deuterium, a halogen group, a $C_1$ to $C_{20}$ alkyl group, a $C_2$ to $C_{20}$ alkenyl group, a $C_1$ to $C_{20}$ alkoxy group, -L-N(R')(R''), a $C_6$ to $C_{20}$ aryl group, a $C_6$ to $C_{20}$ aryl group substituted by deuterium, a $C_7$ to $C_{20}$ arylalkyl group, a $C_8$ to $C_{20}$ arylalkenyl group, a $C_2$ to $C_{20}$ heterocyclic group, a nitrile group, and an acetylene group, and $X_1$ to $X_4$ are $CR_{21}$ or N wherein, $R_{21}$ is hydrogen, deuterium, a $C_6$ to $C_{20}$ aryl group, or a $C_2$ to $C_{20}$ heterocyclic group.

5. A compound selected from the following compounds:
1-1
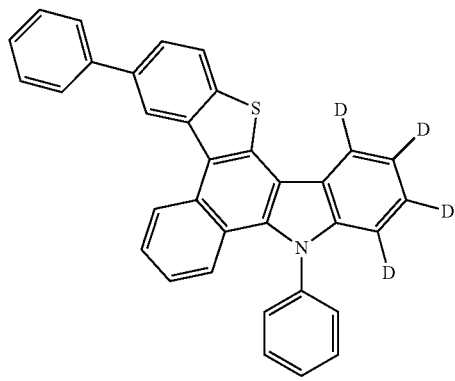
1-2
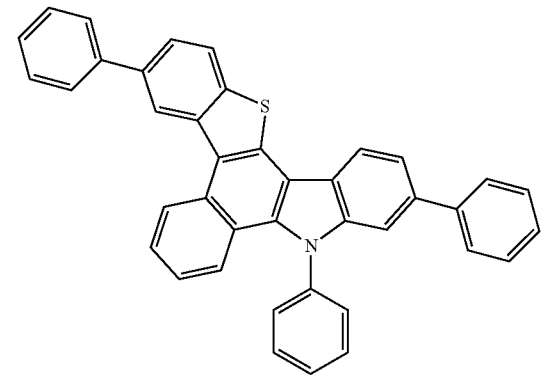
1-3
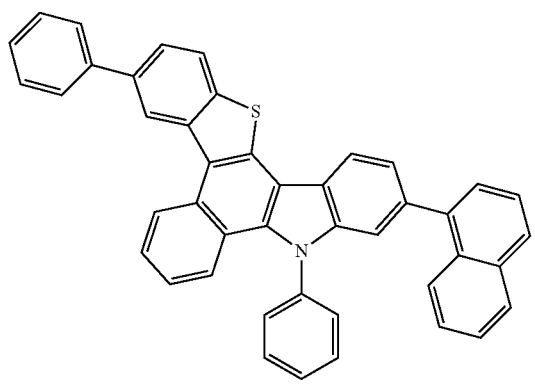
1-4
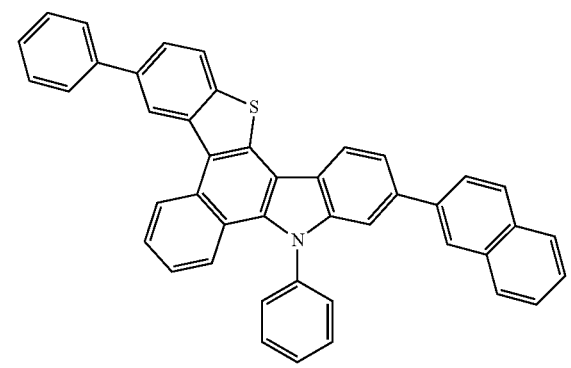
1-5
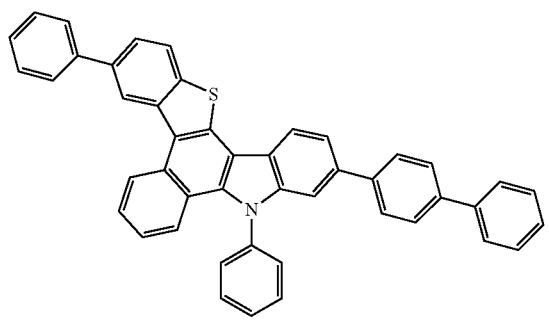
1-6
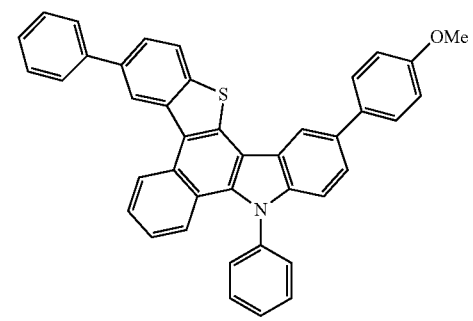
1-7
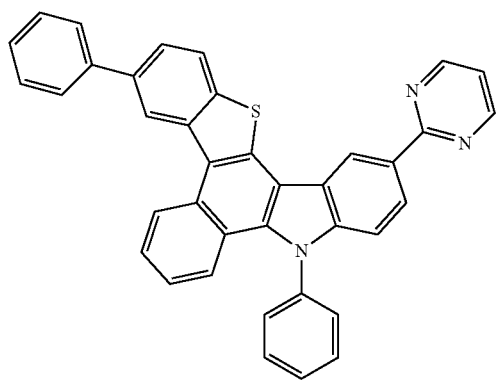
1-8
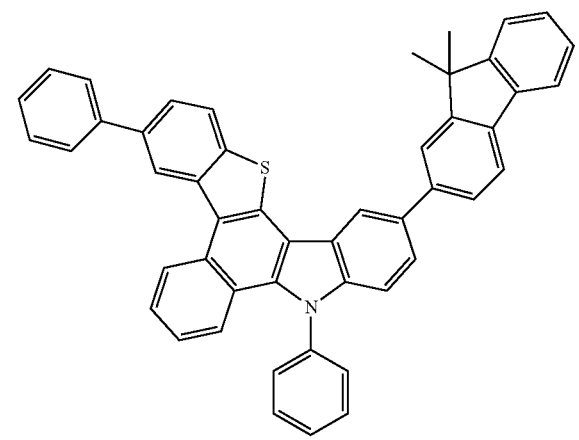

-continued
| 1-9 | 1-10 |
|---|---|
| 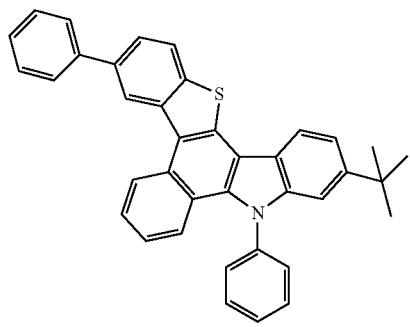 | 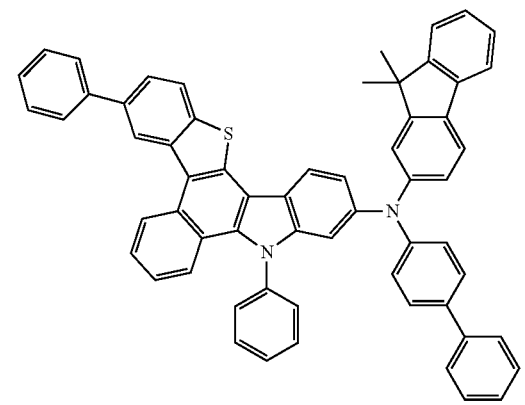 |
| 1-11 | 1-12 |
|---|---|
| 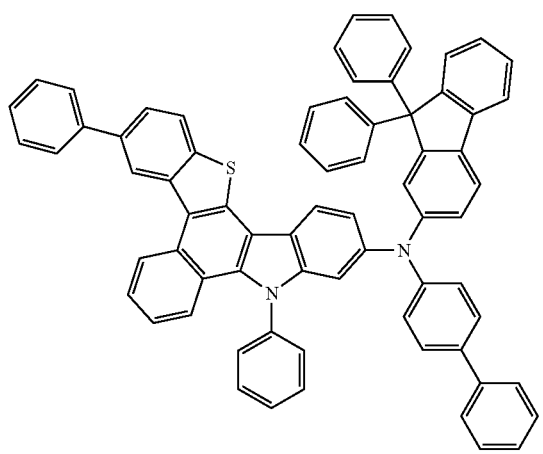 | |
| 1-13 | 1-14 |
|---|---|
| 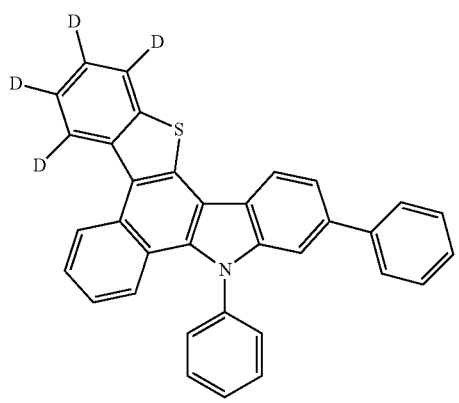 | 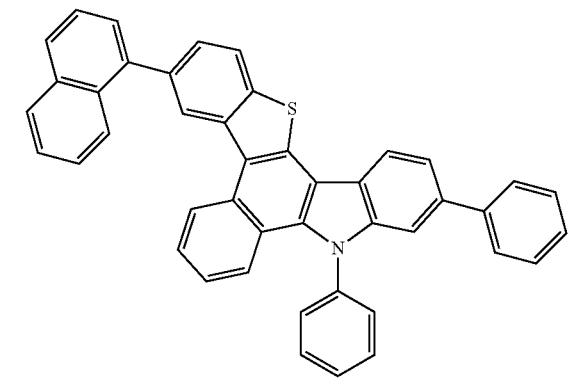 |
| 1-15 | 1-16 |
|---|---|
| 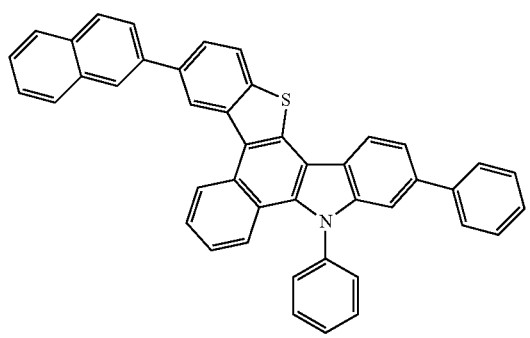 | 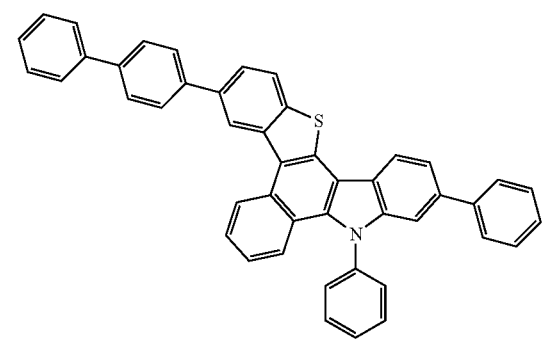 |

-continued
1-17
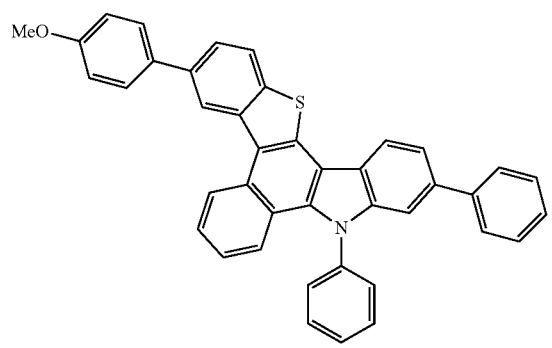
1-18
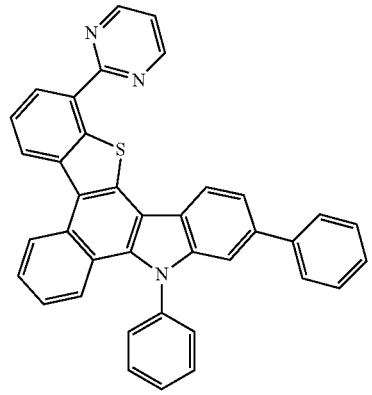
1-19
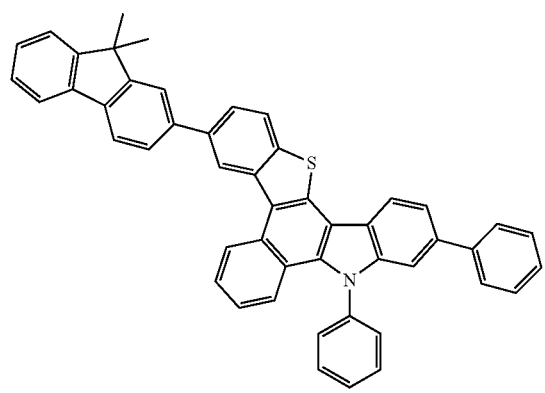
1-20
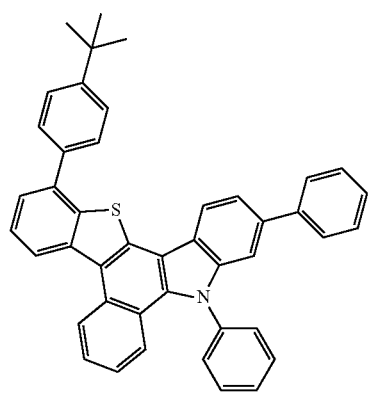
1-21
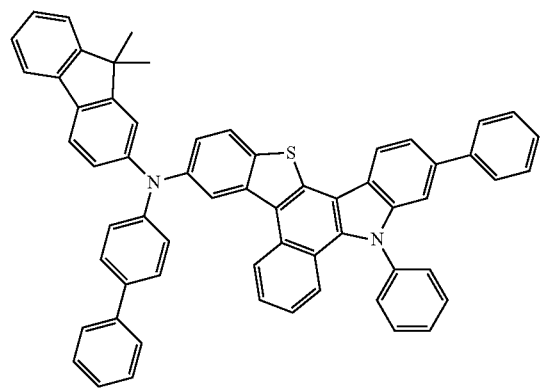
1-22
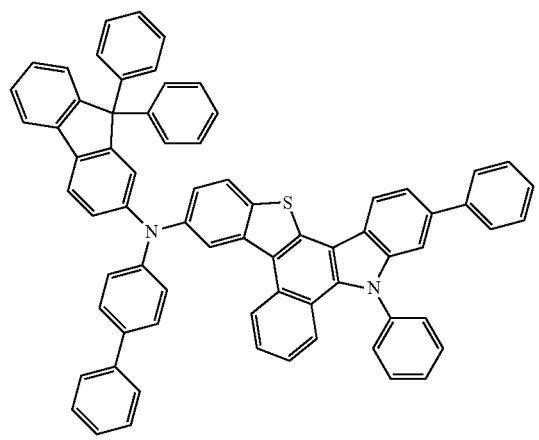

-continued
1-23
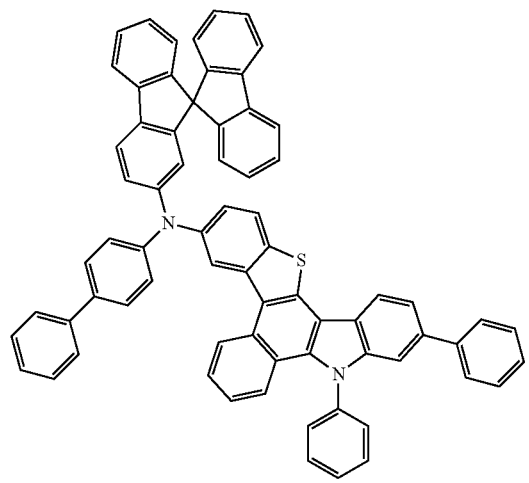
1-24
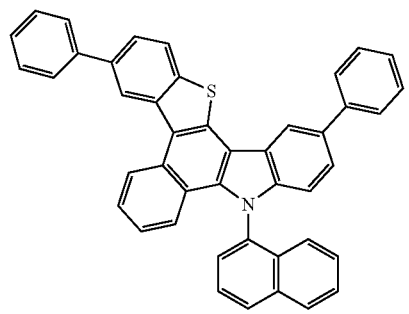
1-25
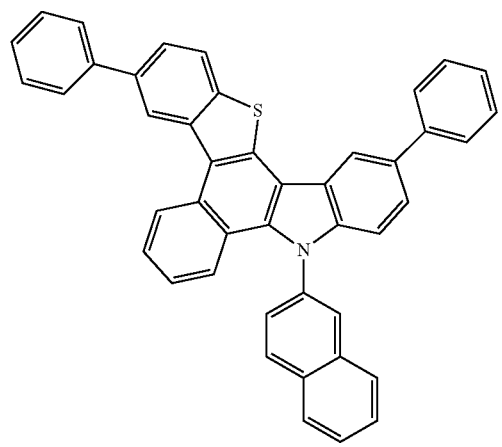
1-26
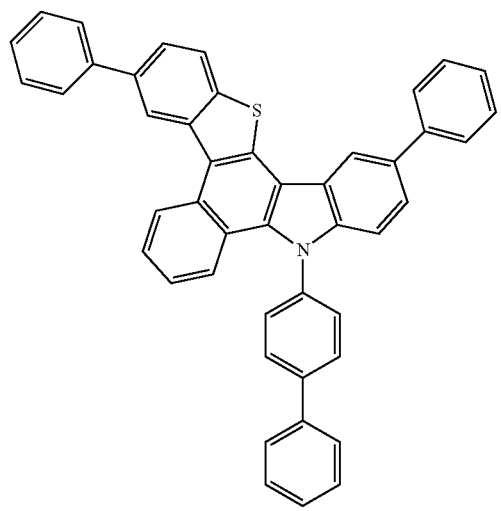
1-27
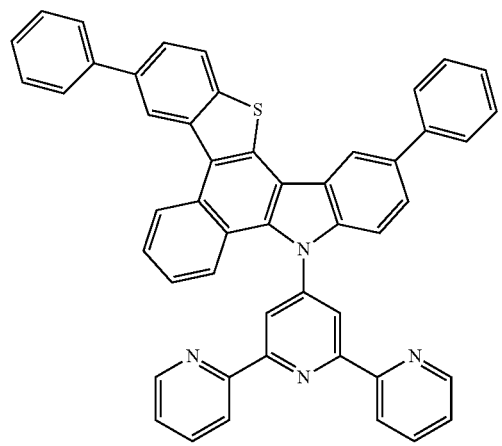
1-28
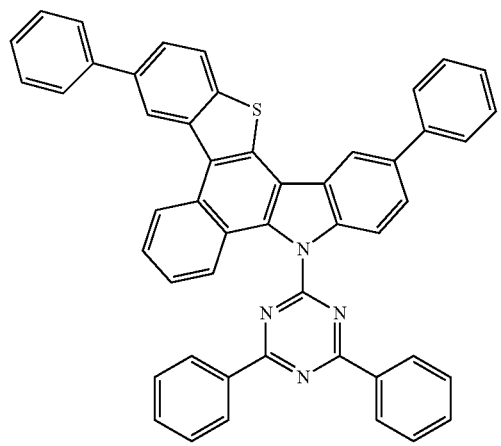

-continued
1-29
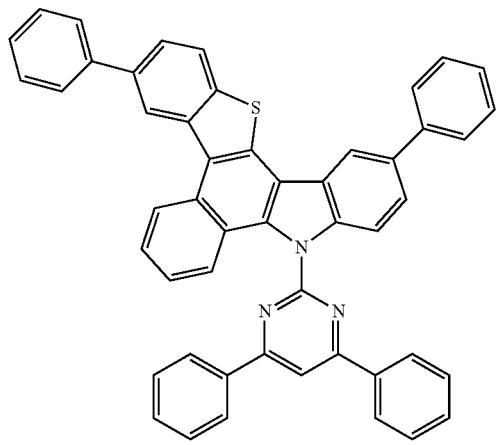
1-30
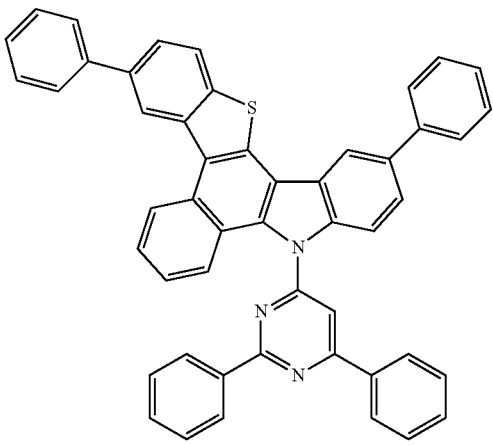
1-31
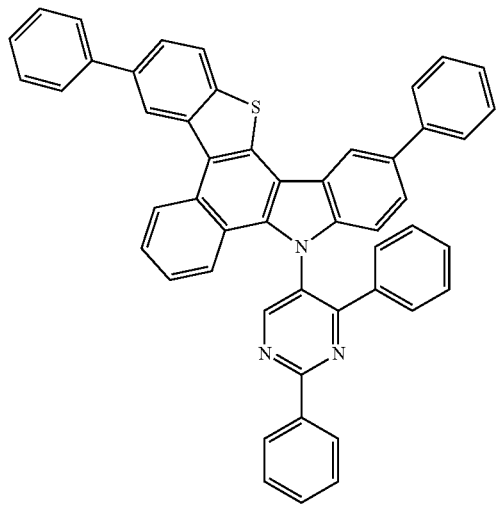
1-32
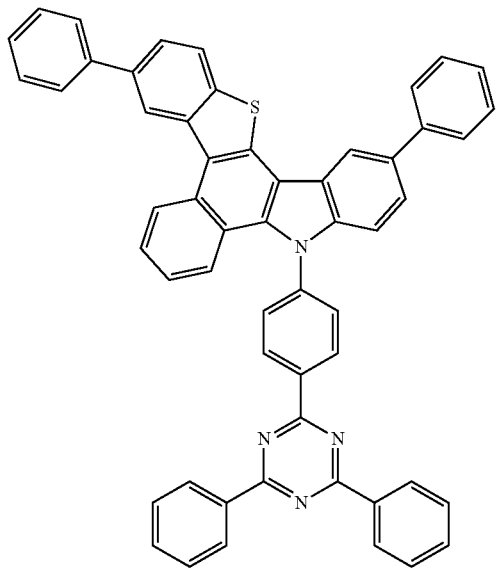
1-33
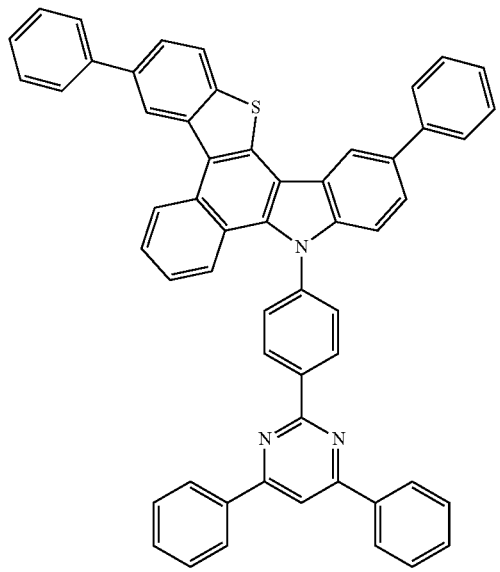
1-34
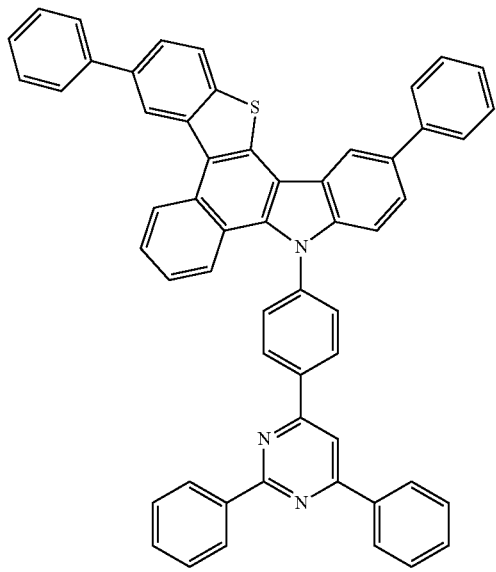

1-35
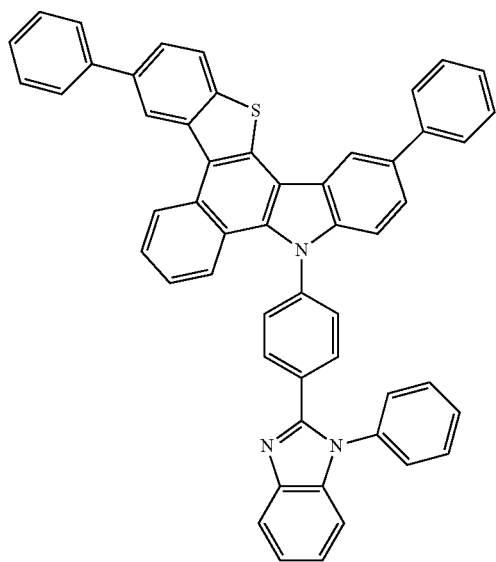
1-36
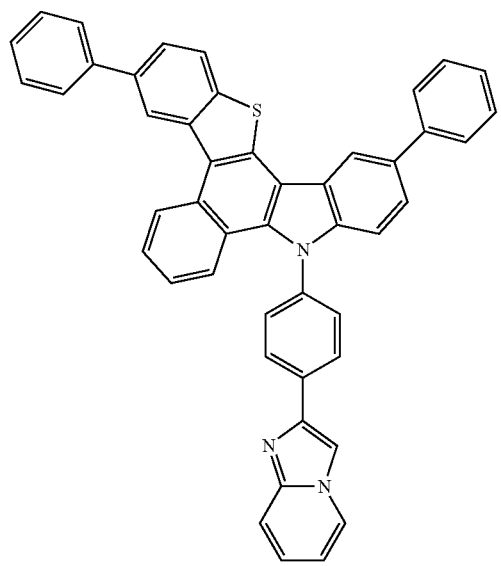
1-37
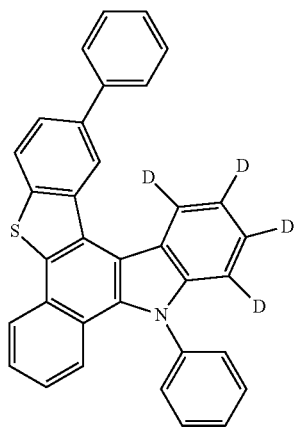
1-38
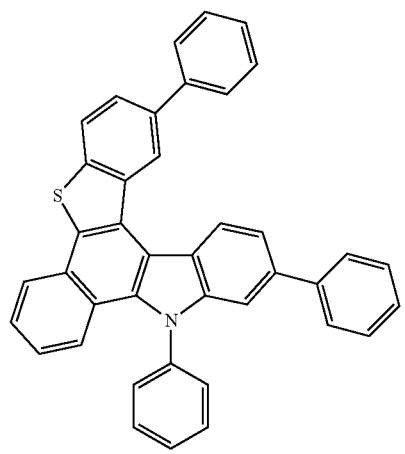
1-39
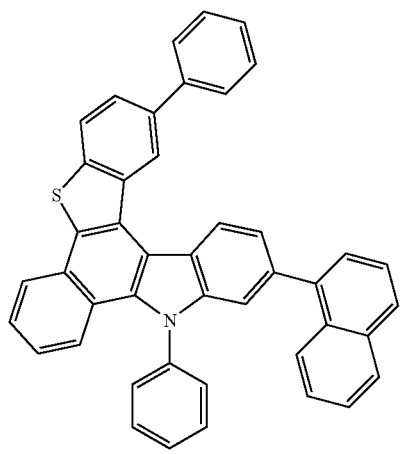
1-40
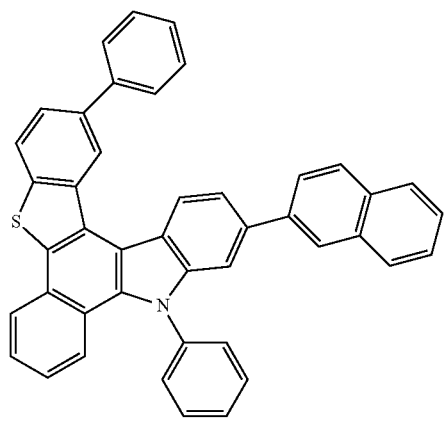

-continued
1-41
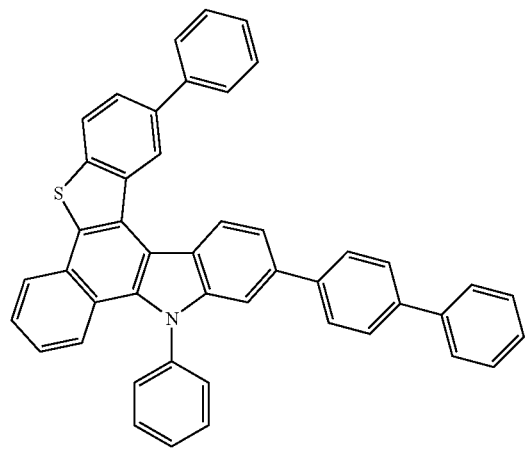
1-42
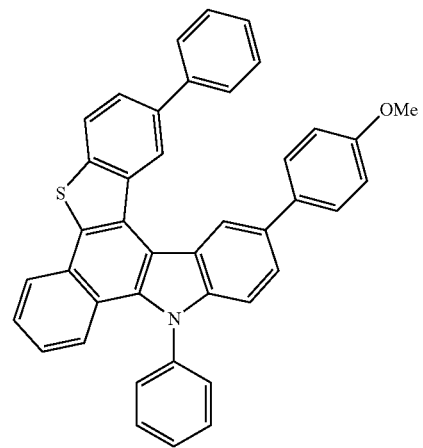
1-43
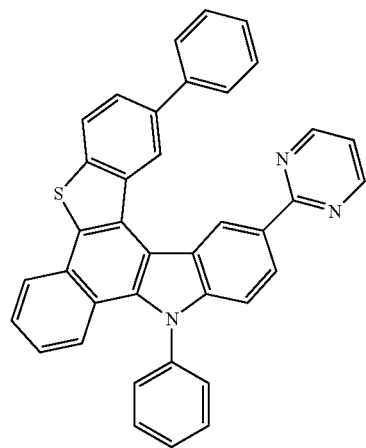
1-44
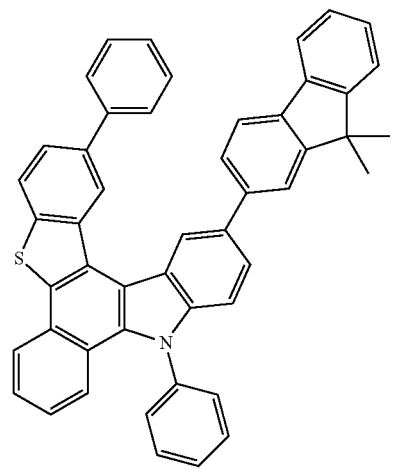
1-45
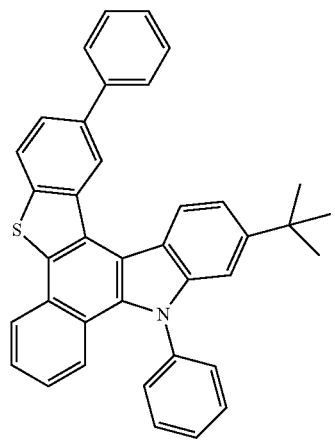
1-46
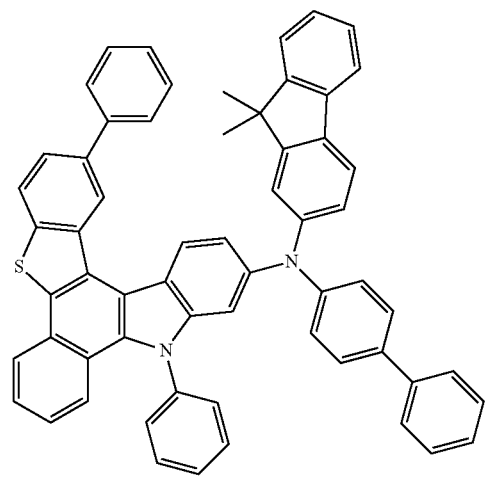

-continued
1-47
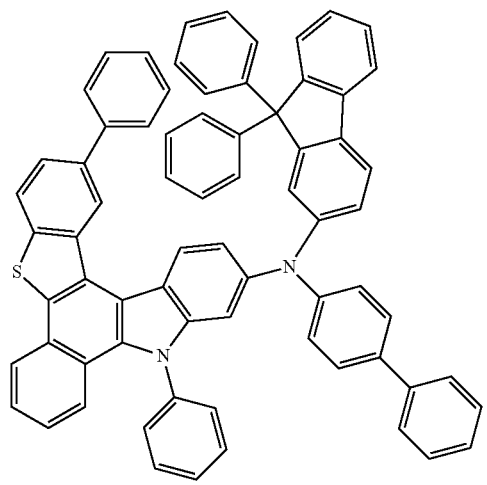
1-48
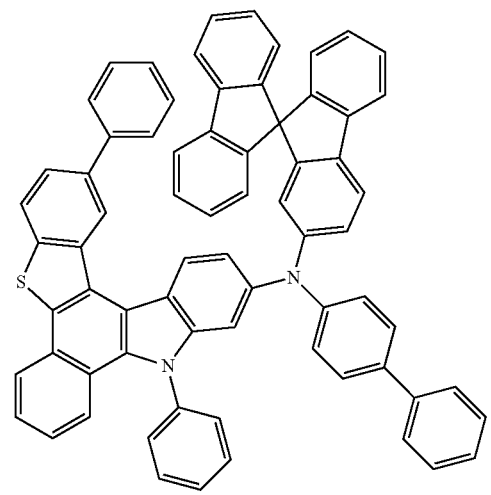
1-49
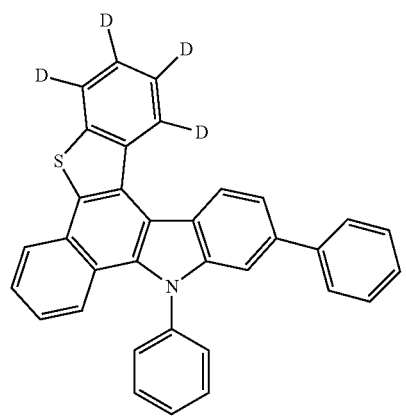
1-50
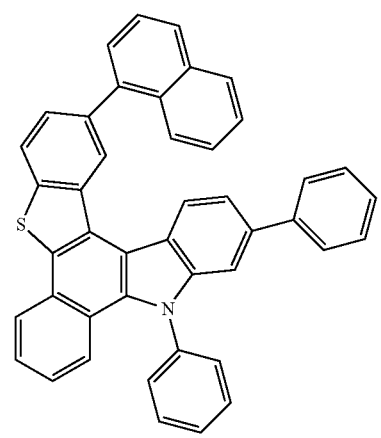
1-51
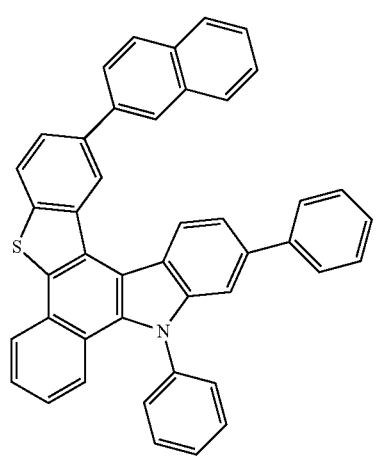
1-52
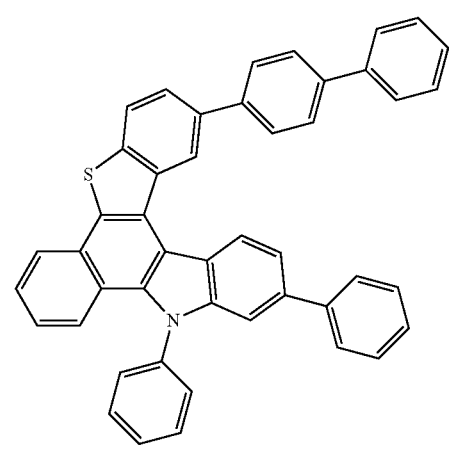

-continued
1-53
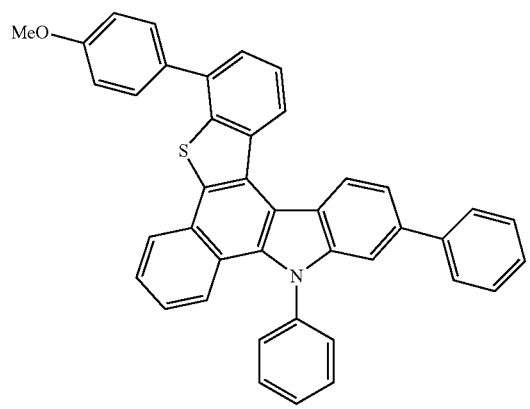
1-54
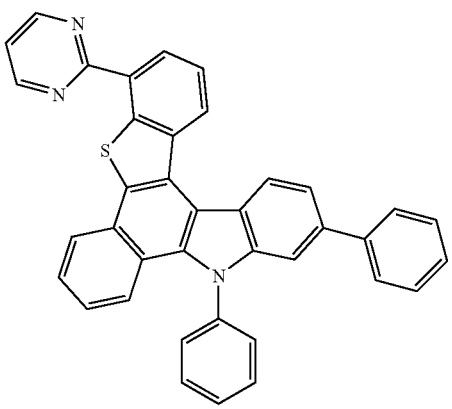
1-55
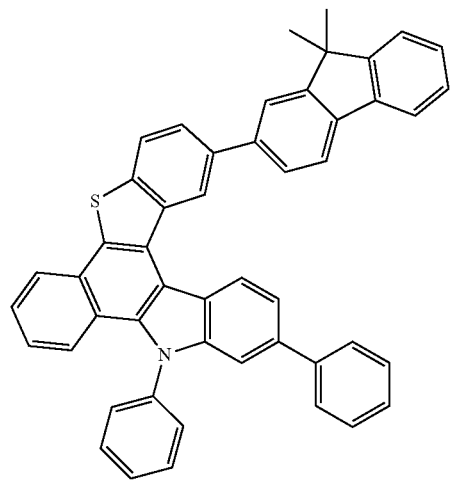
1-56
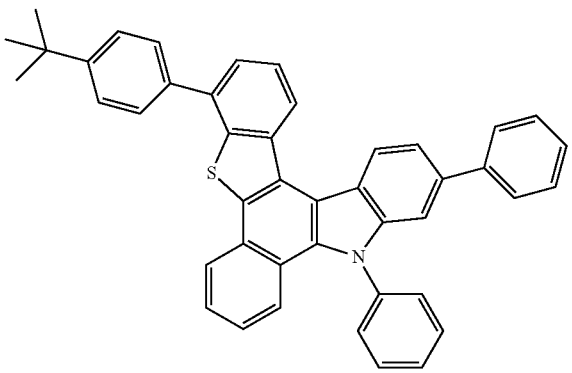
1-57
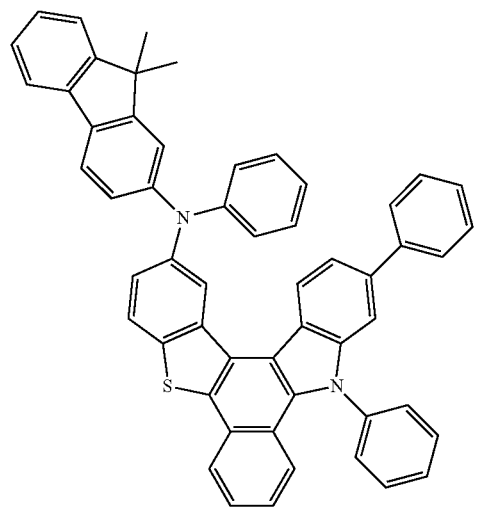
1-58
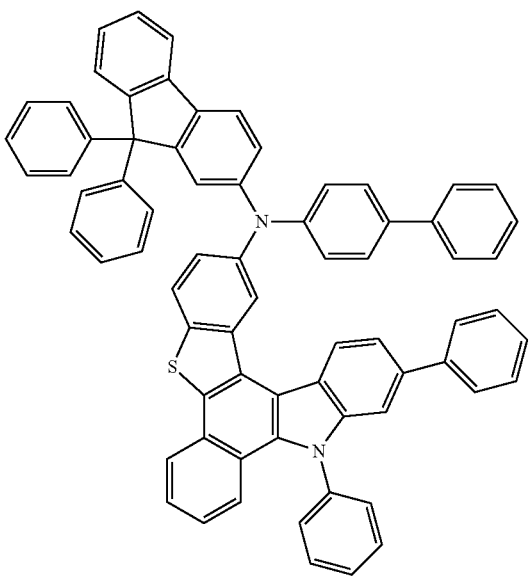

-continued
1-59
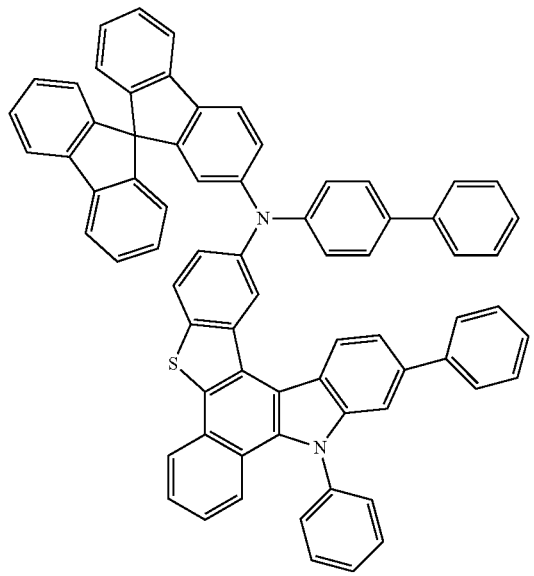
1-60
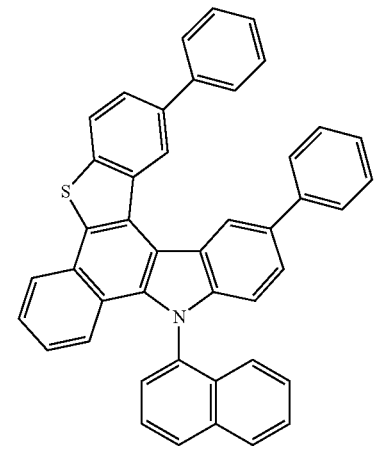
1-61
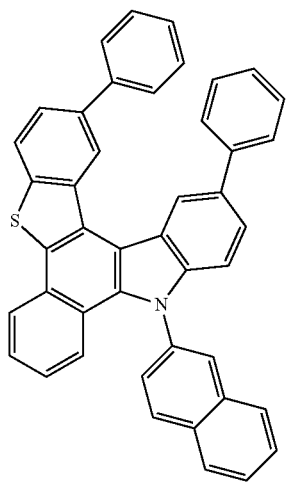
1-62
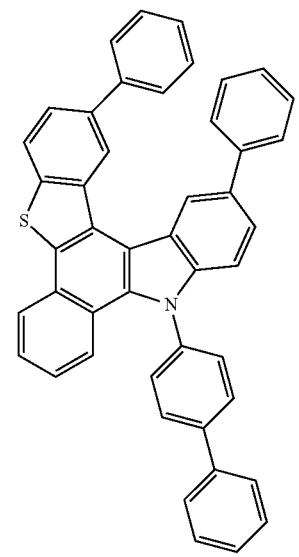
1-63
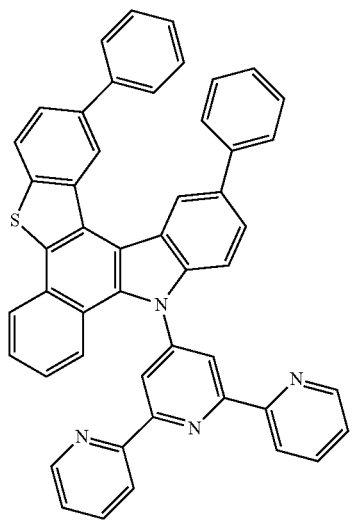
1-64
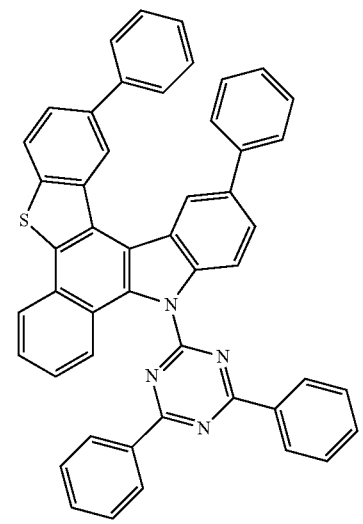

1-65
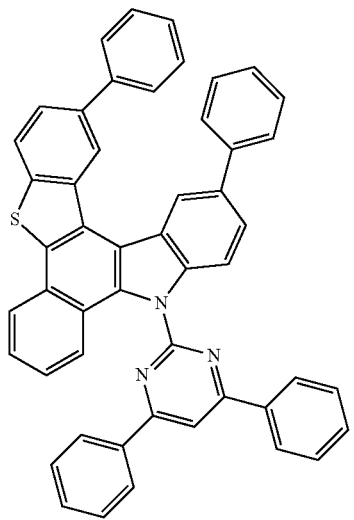
1-66
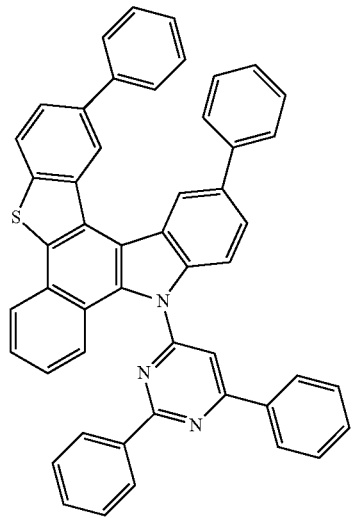
1-67
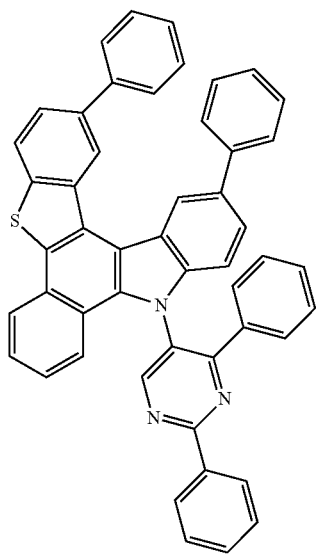
1-68
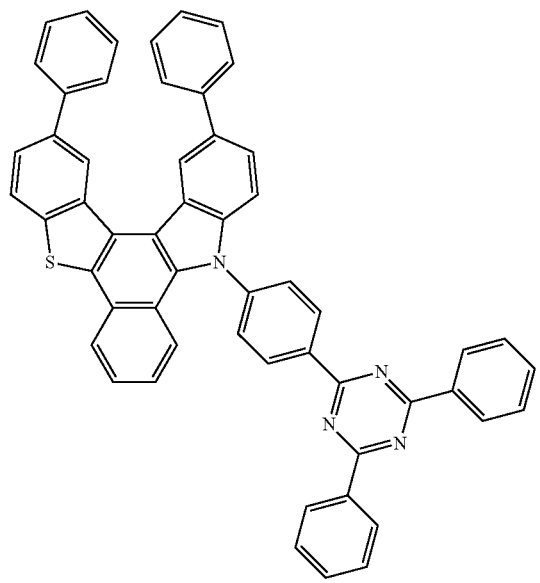

-continued
1-69
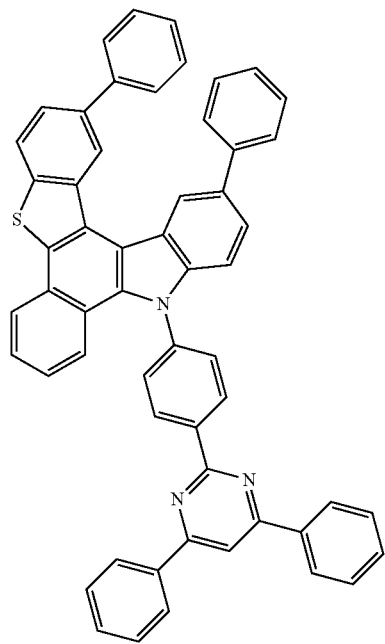
1-70
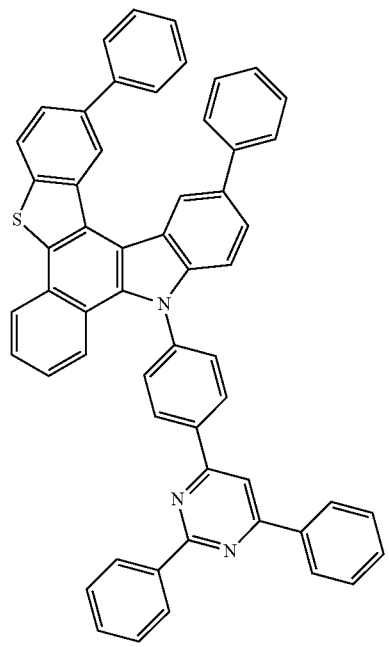
1-71
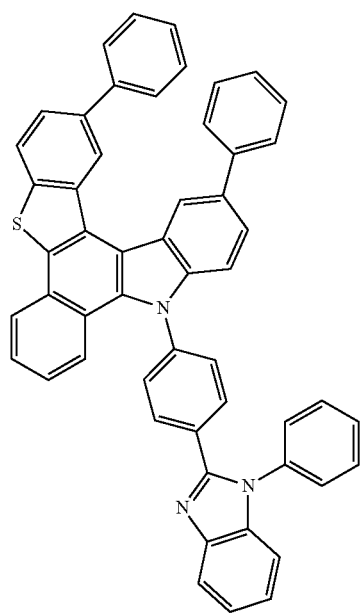
1-72
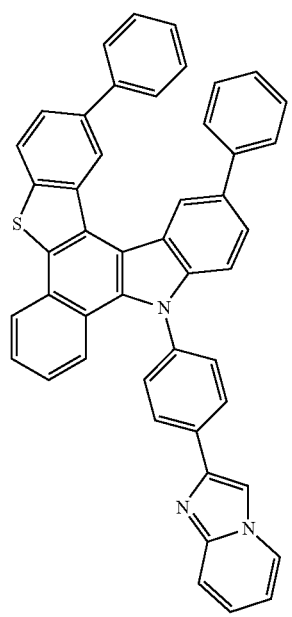

-continued
1-73
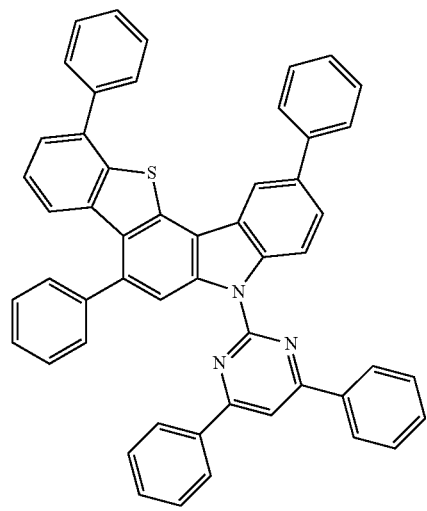
1-74
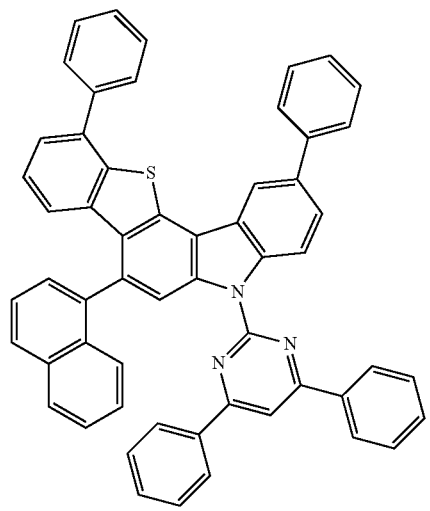
1-75
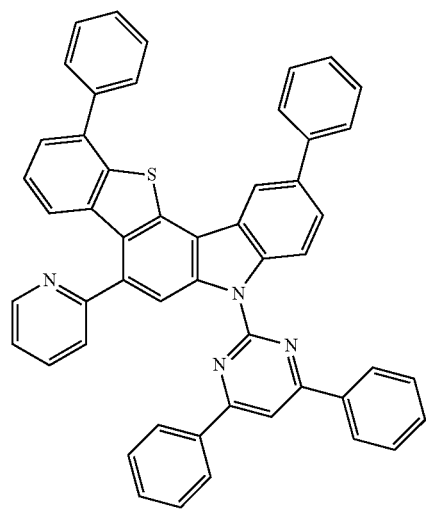
1-76
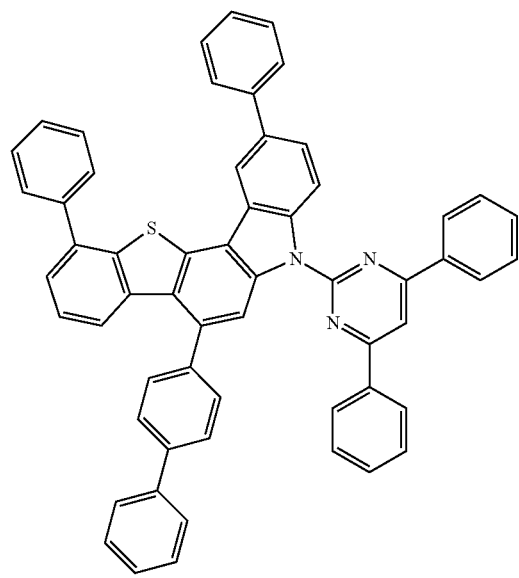
1-77
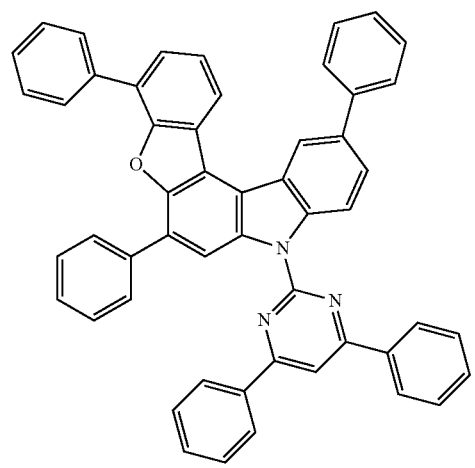
1-78
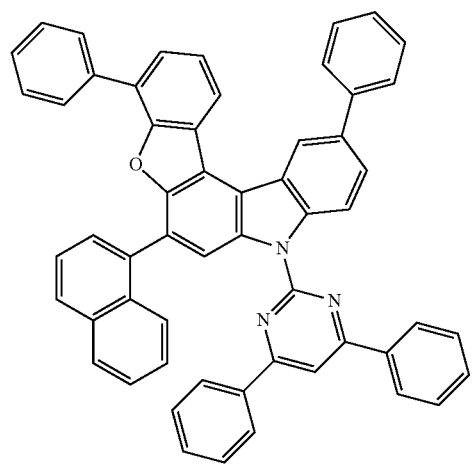

1-79
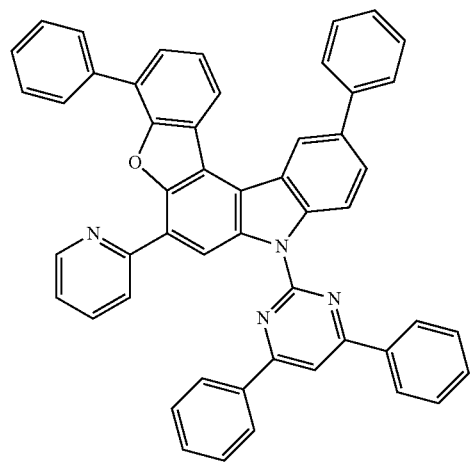
1-80
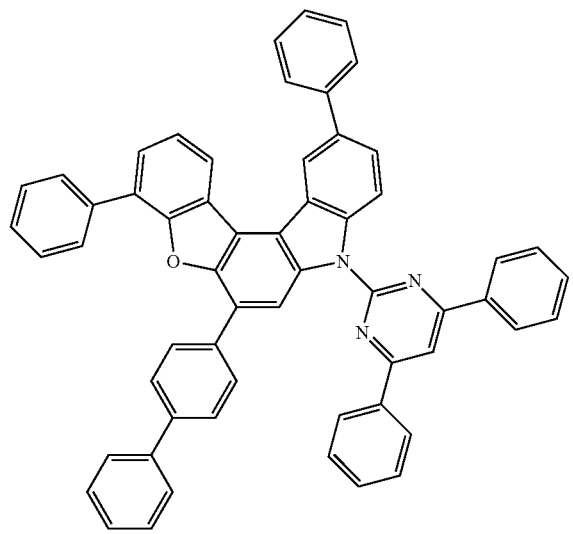
1-81
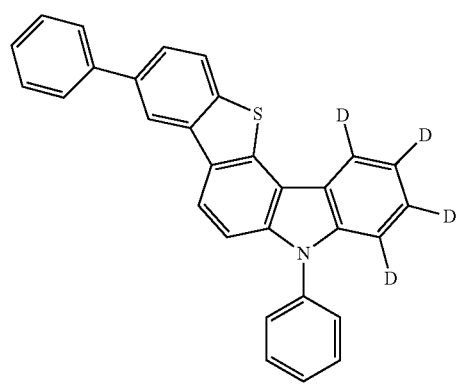
1-82
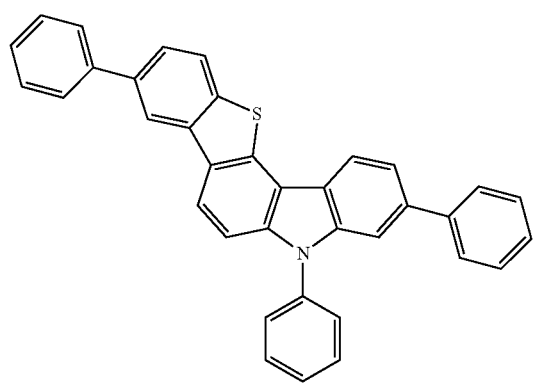
1-83
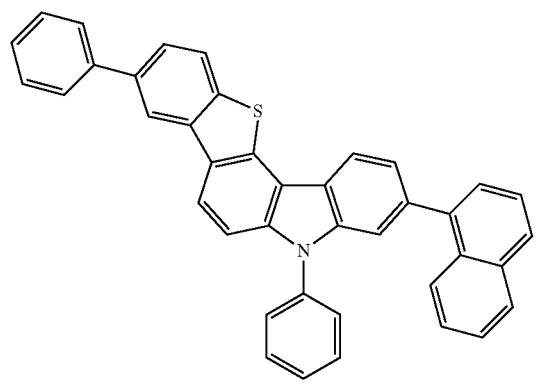
1-84
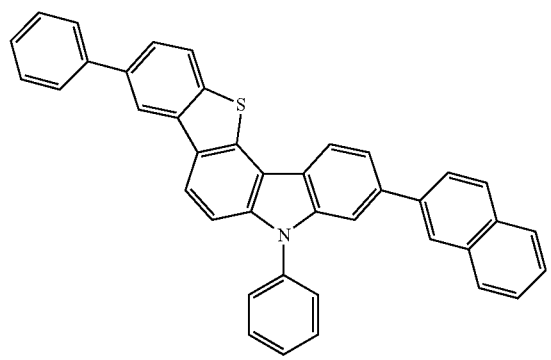
1-85
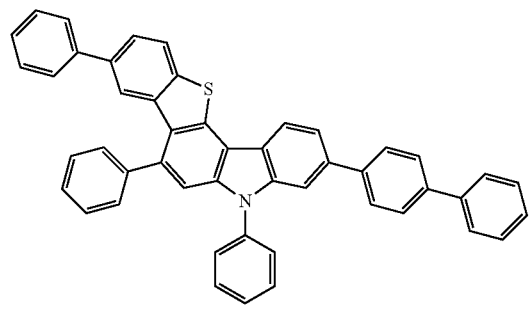
1-86
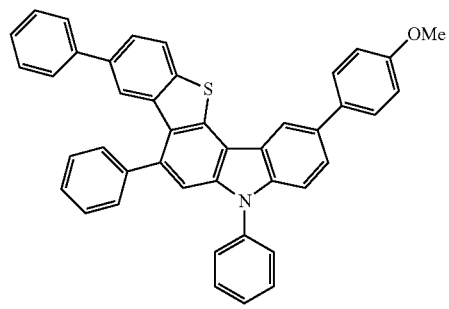

-continued
1-87
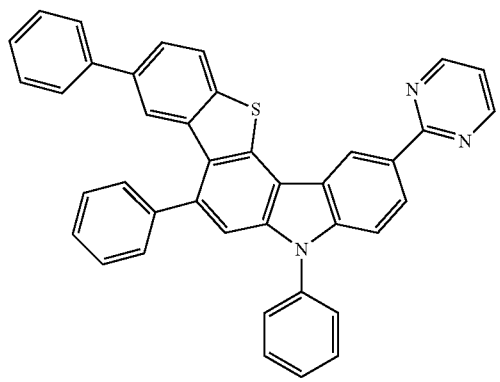
1-88
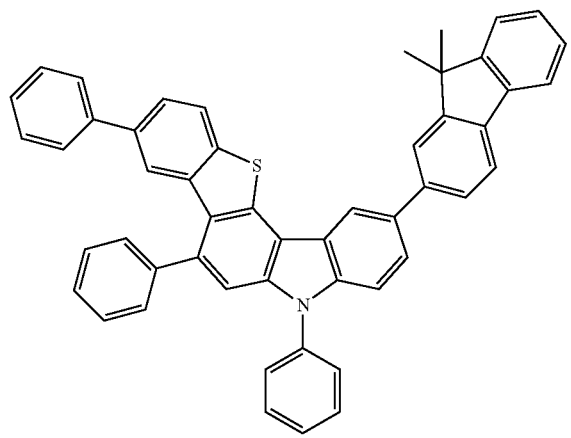
1-89
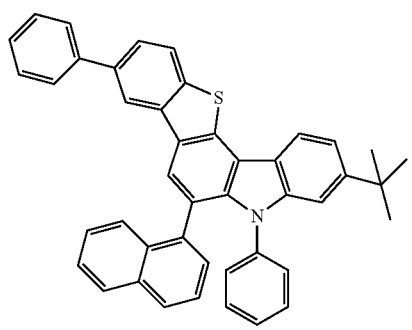
1-90
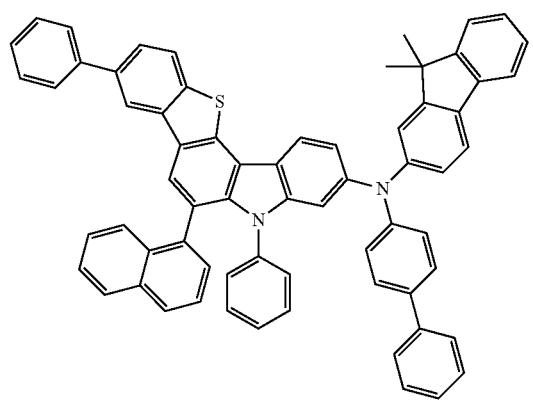
1-91
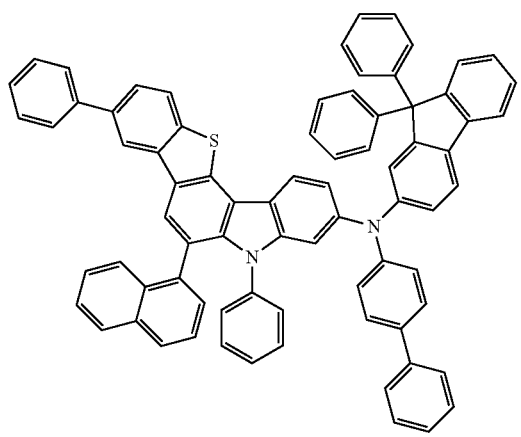
1-92
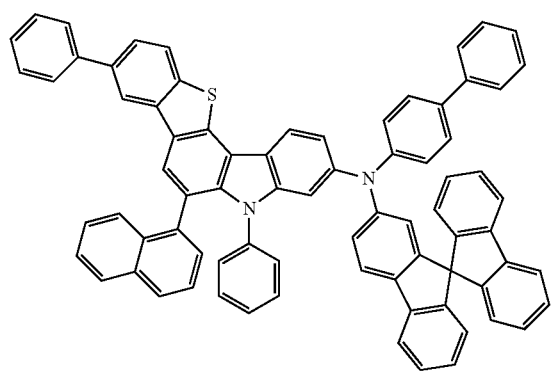

-continued
1-93
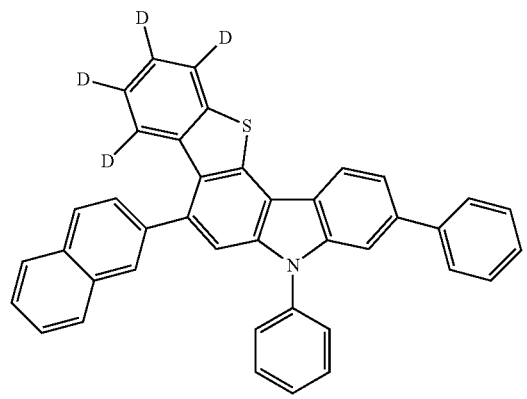
1-94
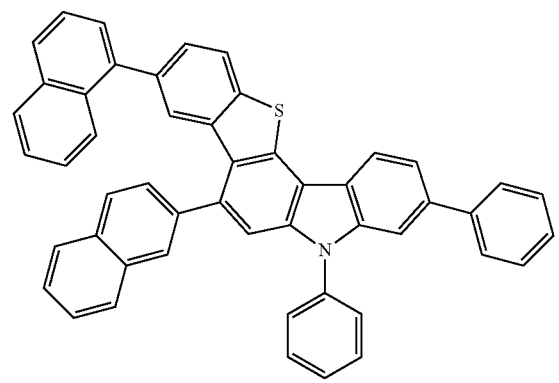
1-95
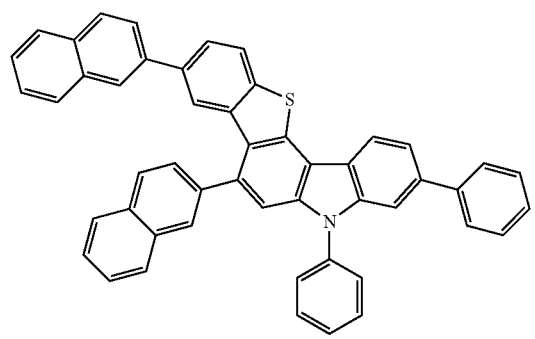
1-96
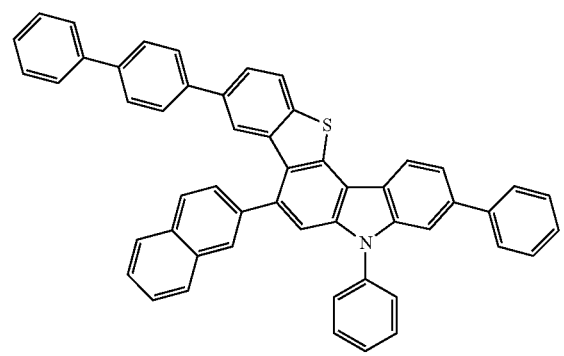
1-97
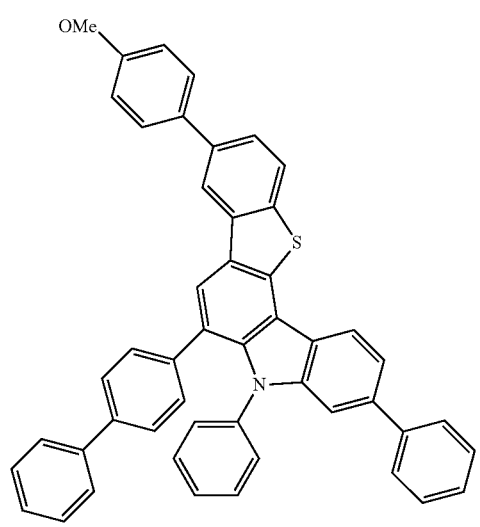
1-98
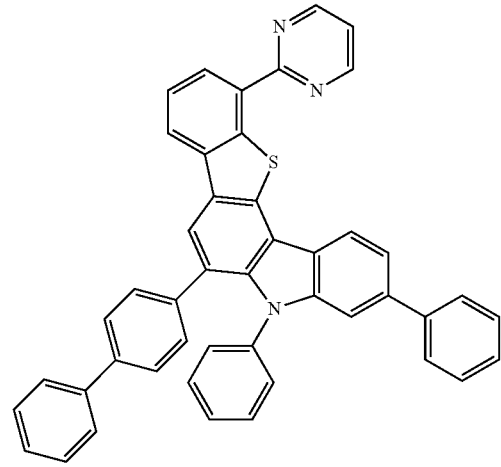

-continued
1-99
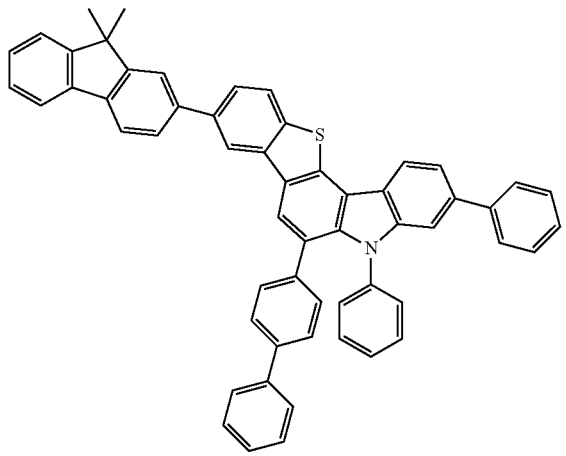
1-100
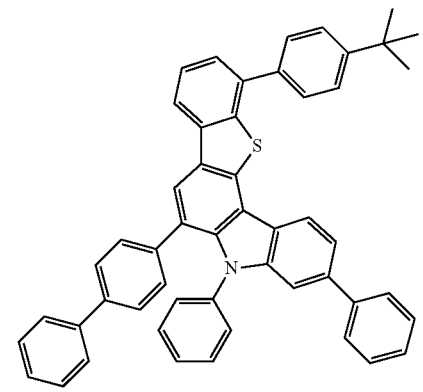
1-101
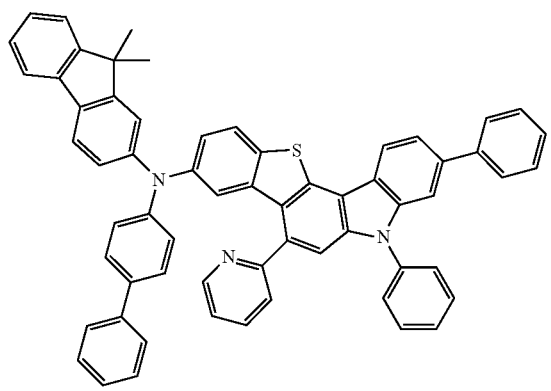
1-102
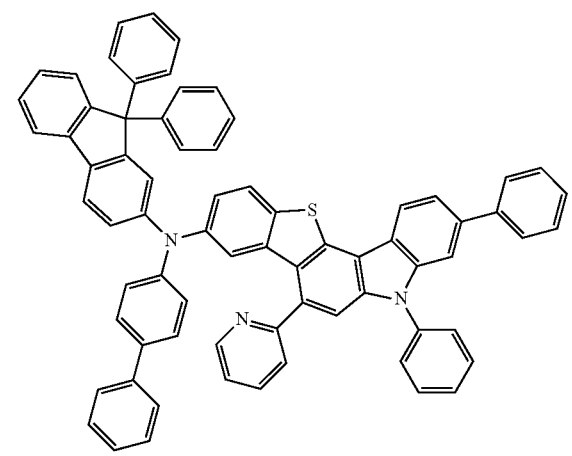
1-103
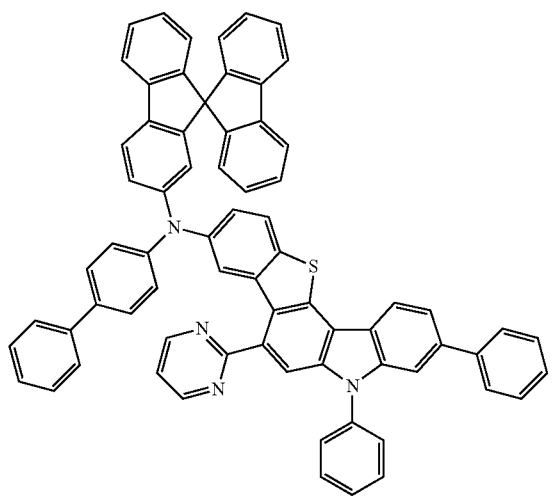
1-104
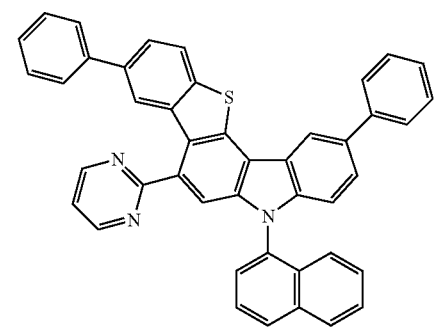

-continued
1-105
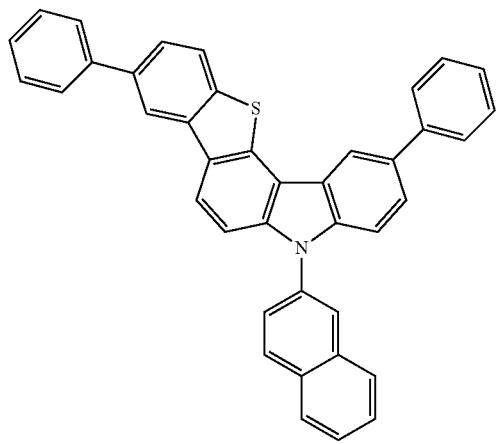
1-106
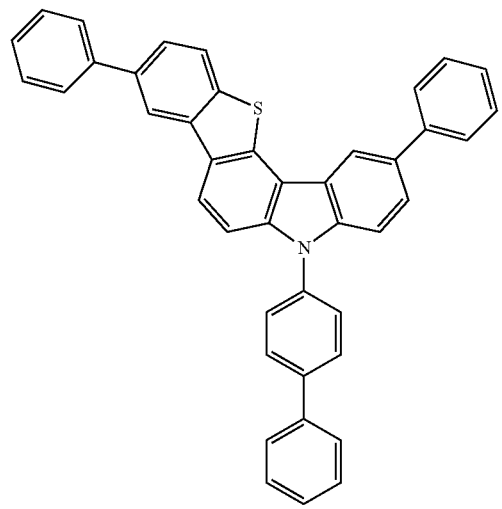
1-107
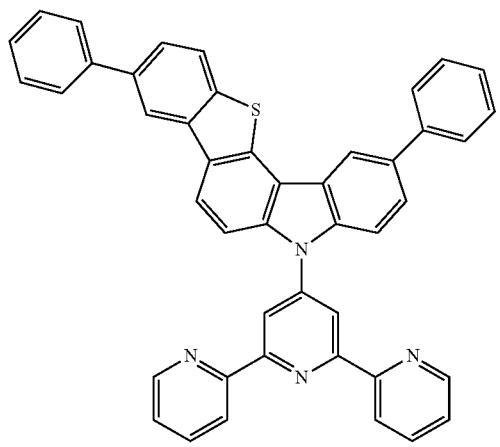
1-108
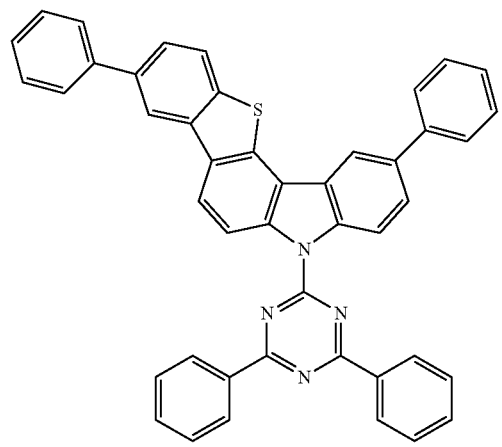
1-109
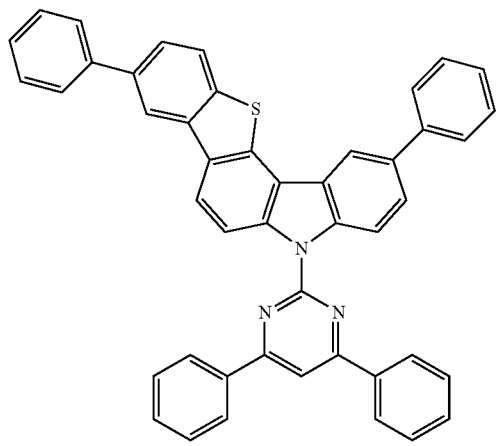
1-110
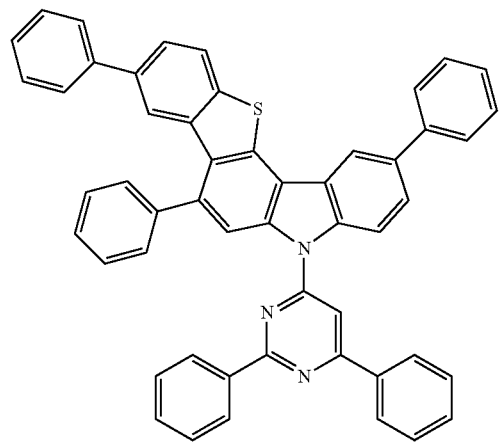

-continued
1-111
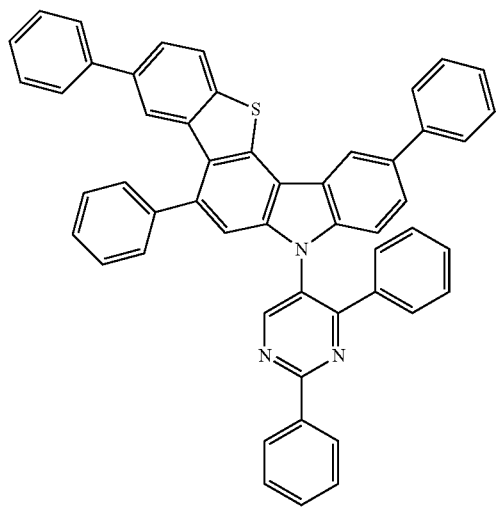
1-112
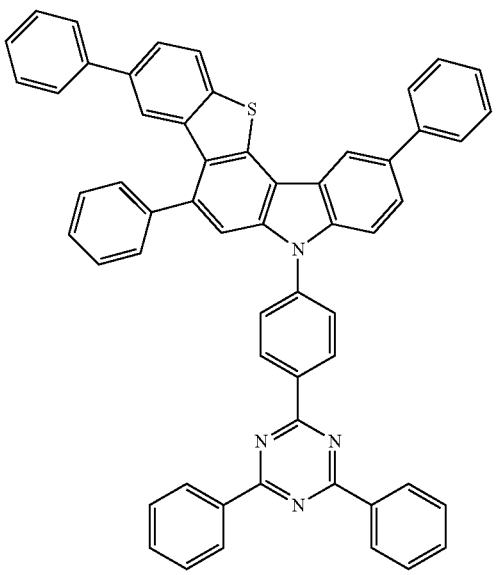
1-113
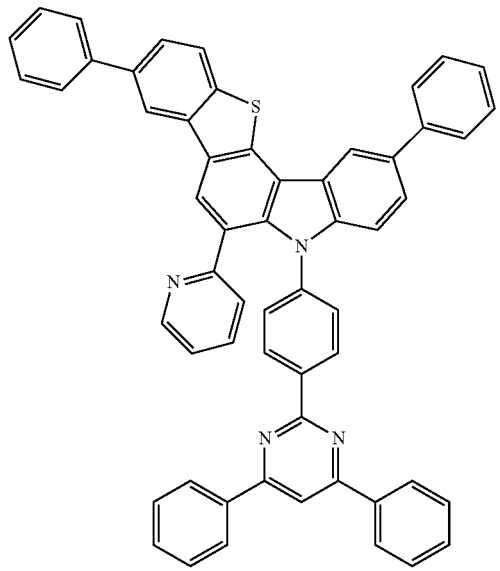
1-114
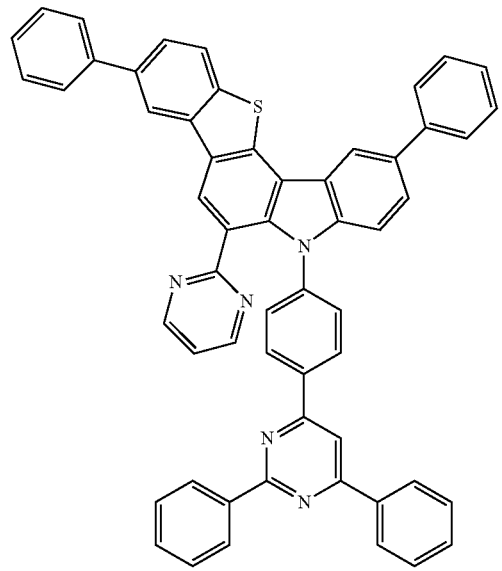

-continued
1-115
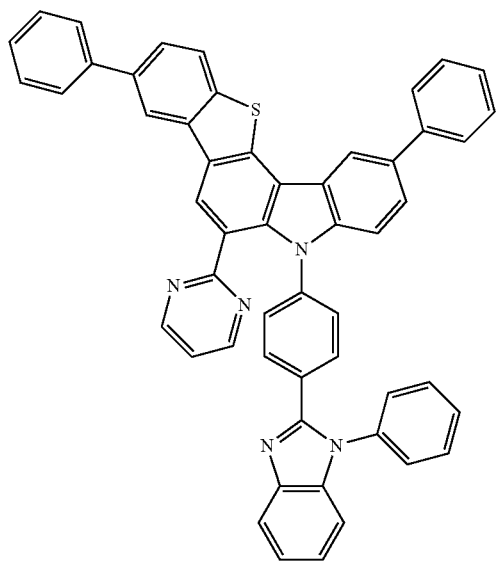
1-116
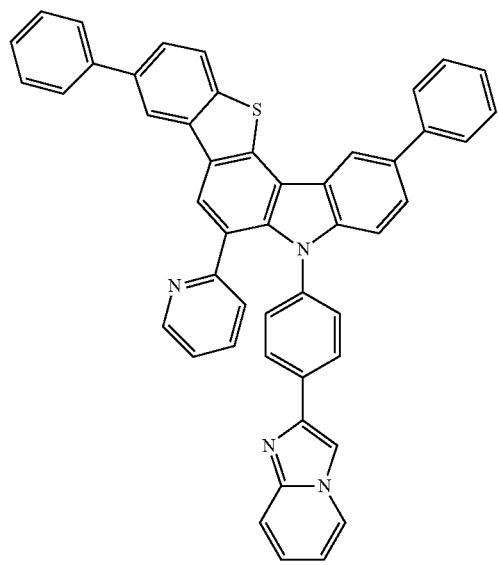
1-117
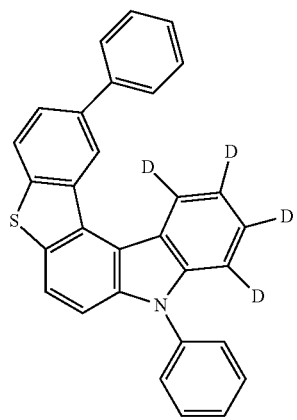
1-118
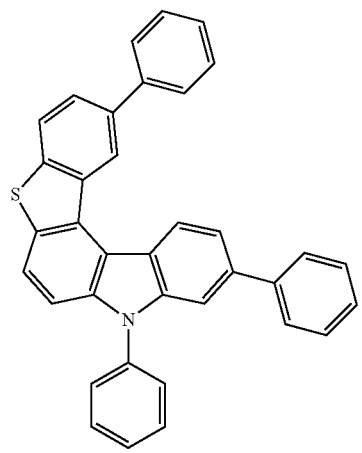
1-119
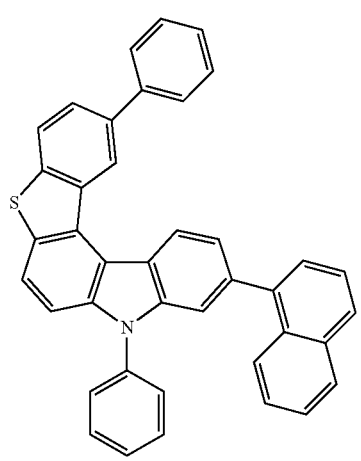
1-120
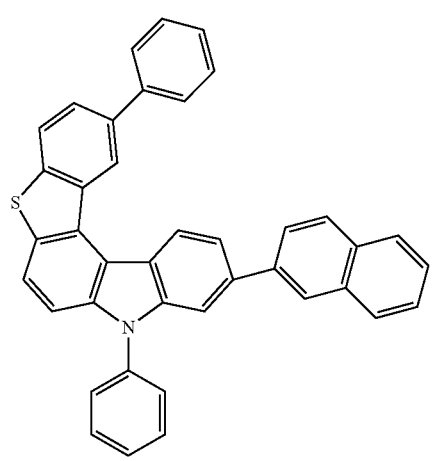

-continued
1-121
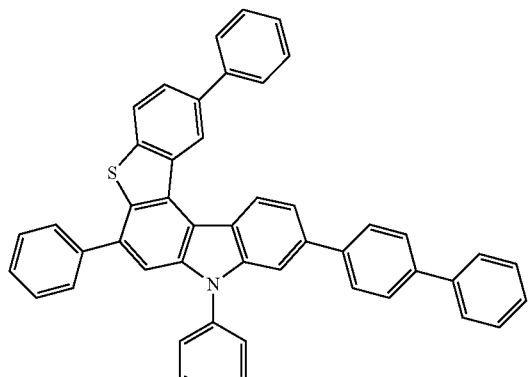
1-122
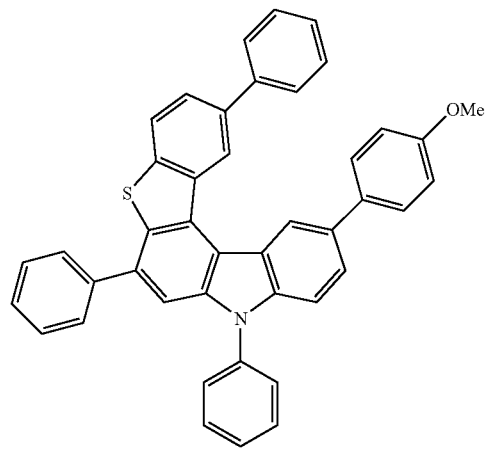
1-123
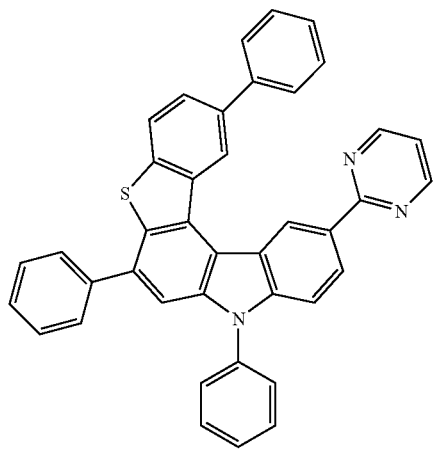
1-124
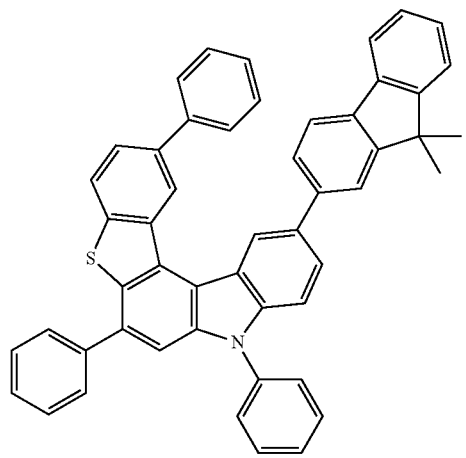
1-125
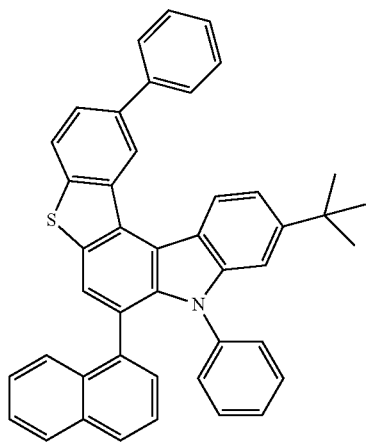
1-126
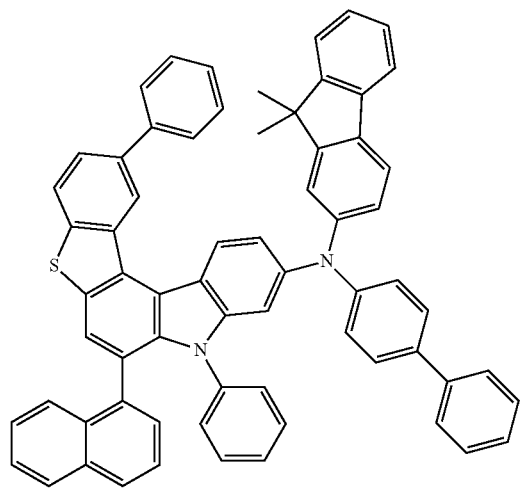

-continued
1-127
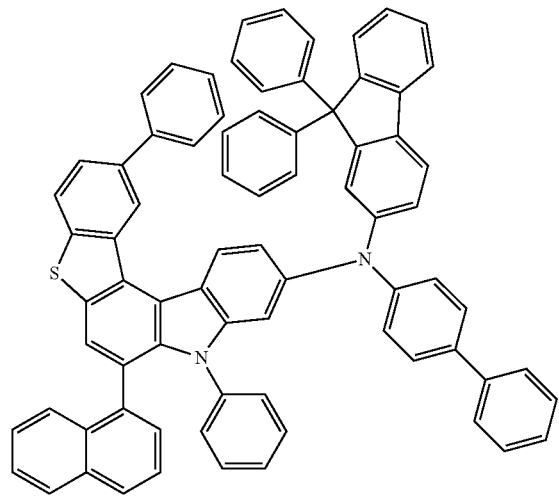
1-128
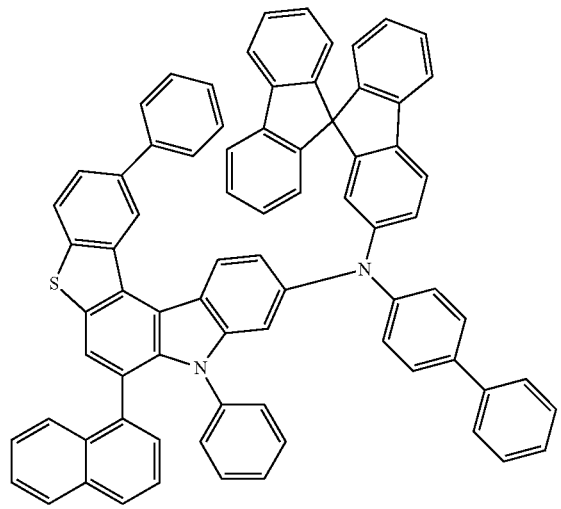
1-129
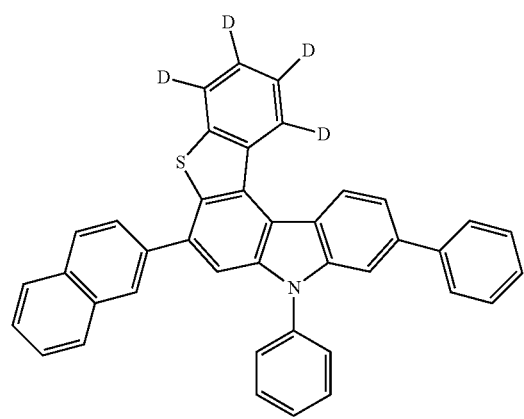
1-130
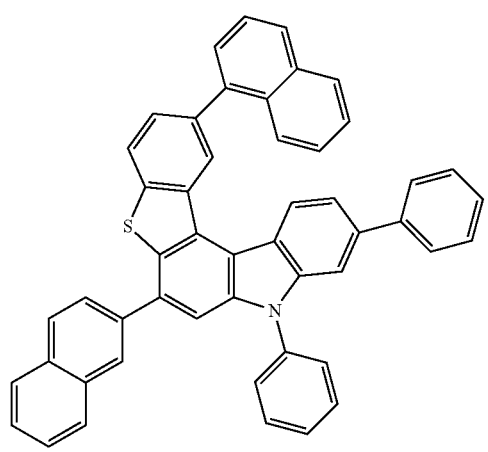
1-131
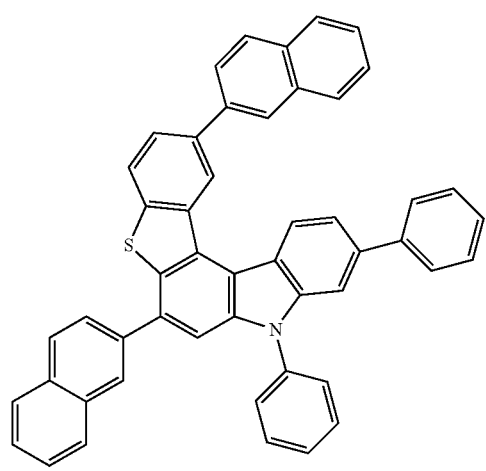
1-132
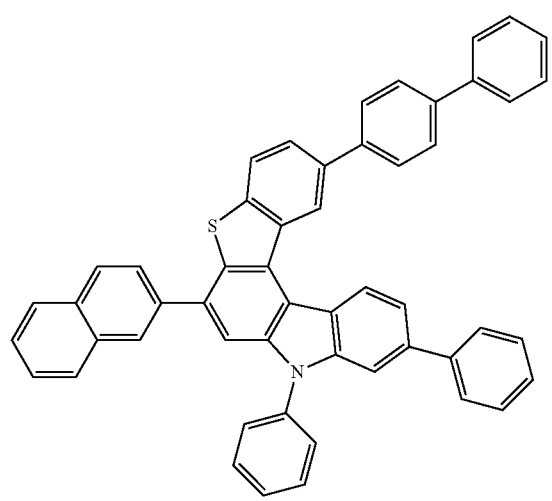

-continued
1-133
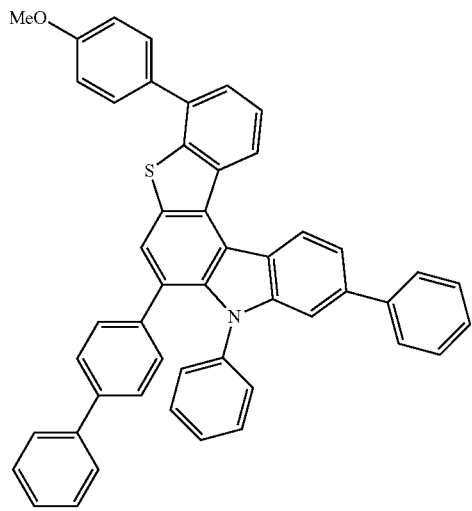
1-134
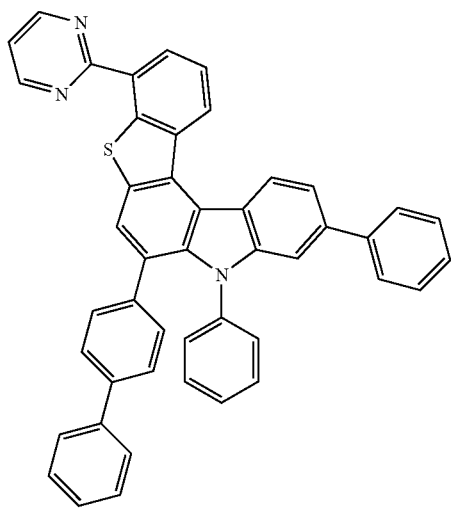
1-135
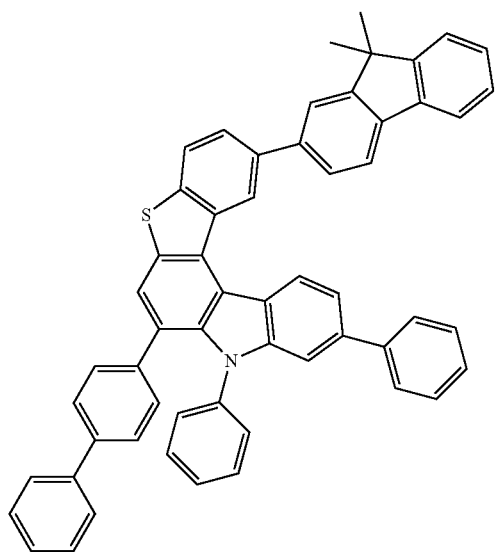
1-136
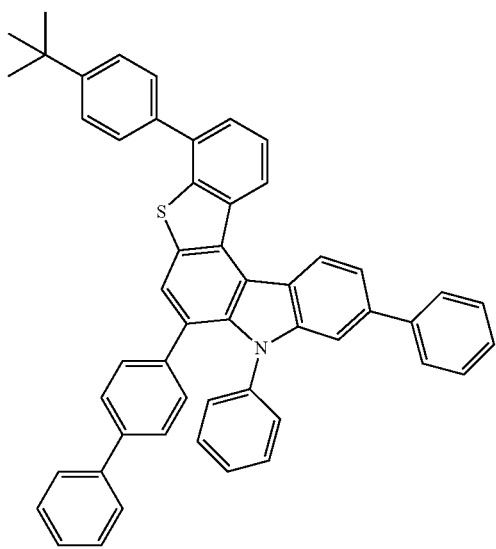
1-137
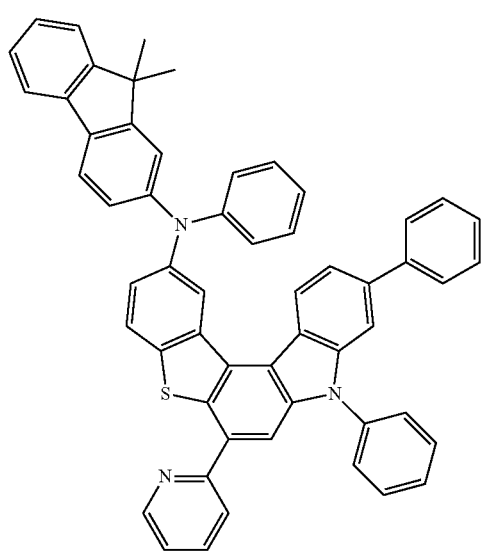
1-138
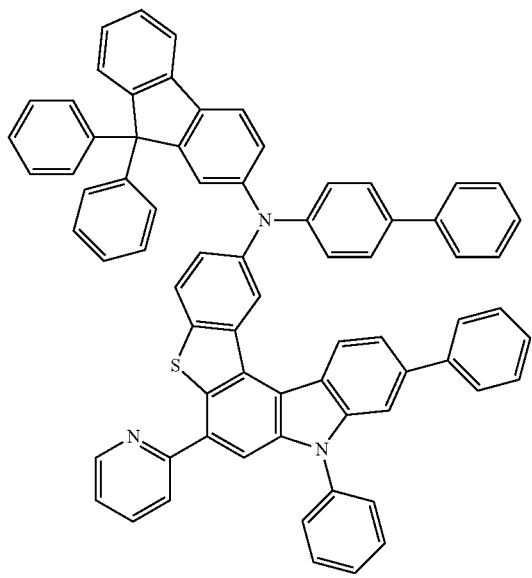

1-139
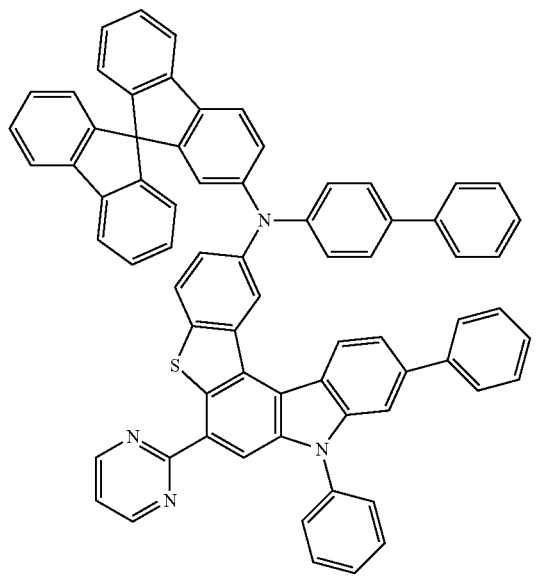
1-140
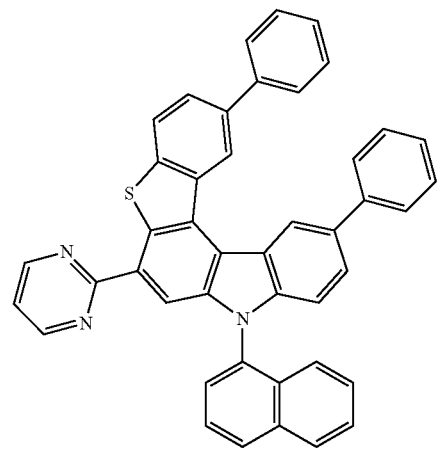
1-141
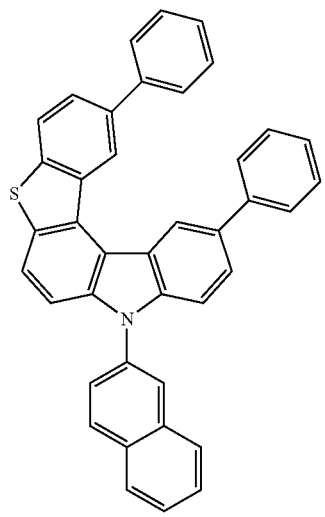
1-142
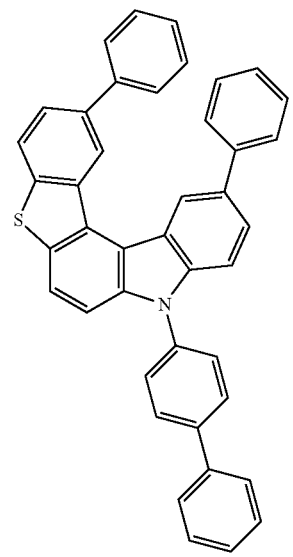
1-143
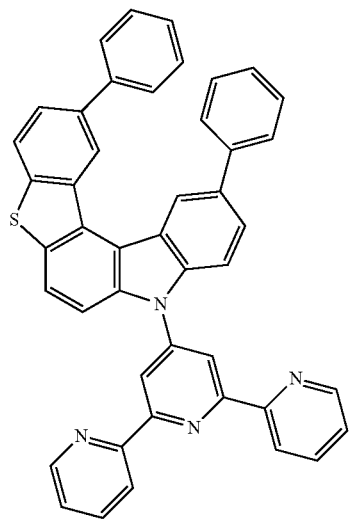
1-144
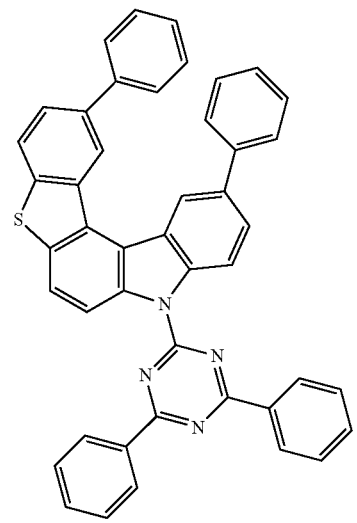

-continued
1-145
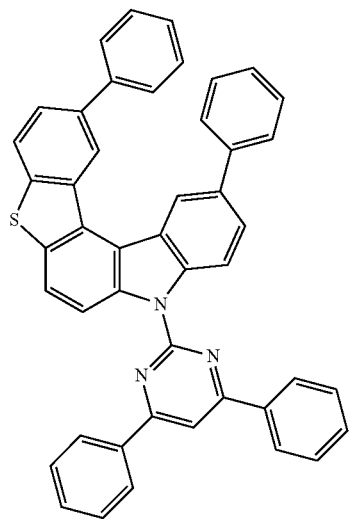
1-146
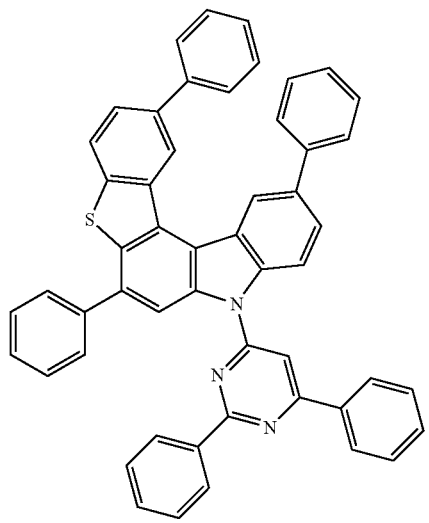
1-147
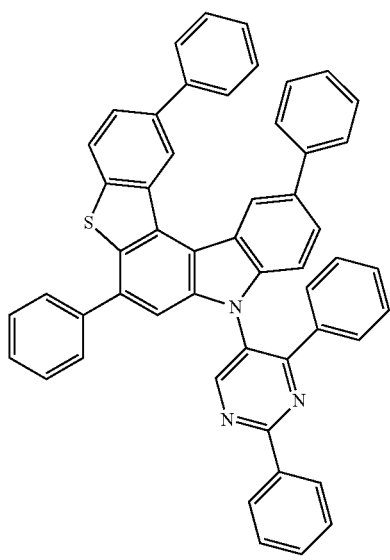
1-148
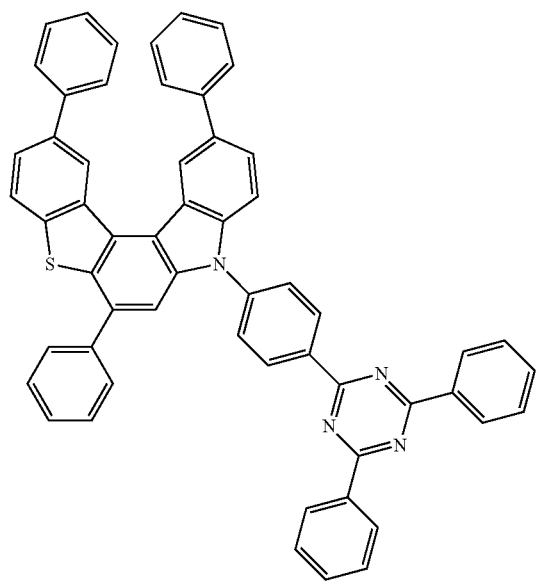

1-149
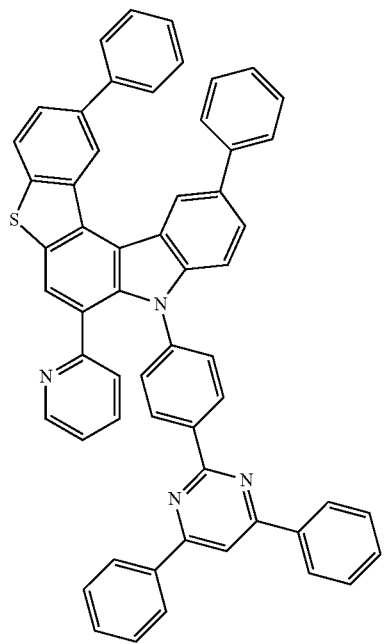
1-150
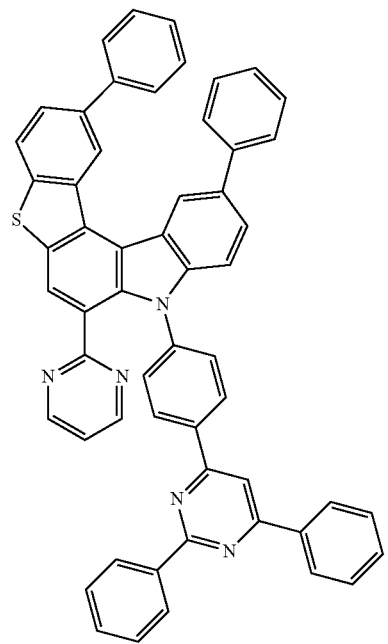
1-151
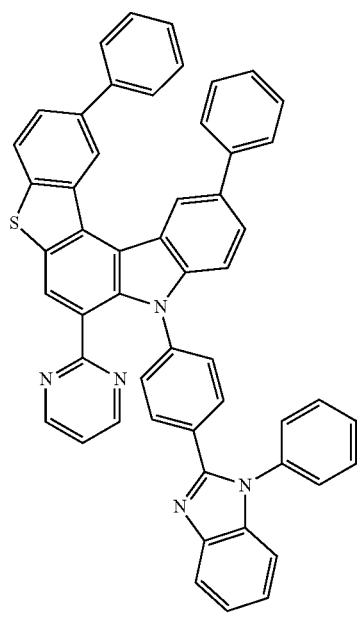
1-152
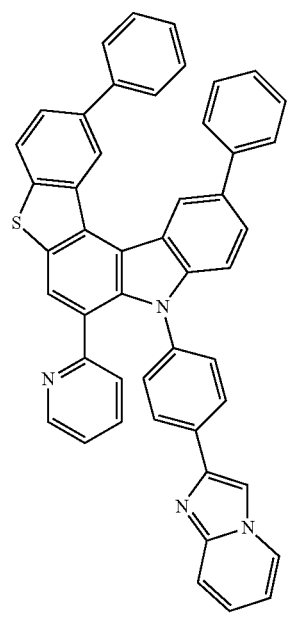

-continued
1-153
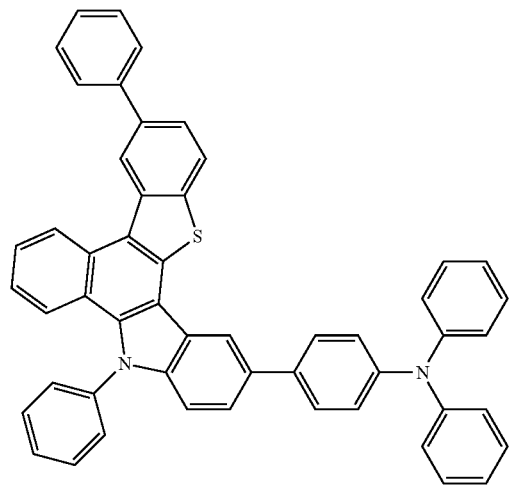
1-154
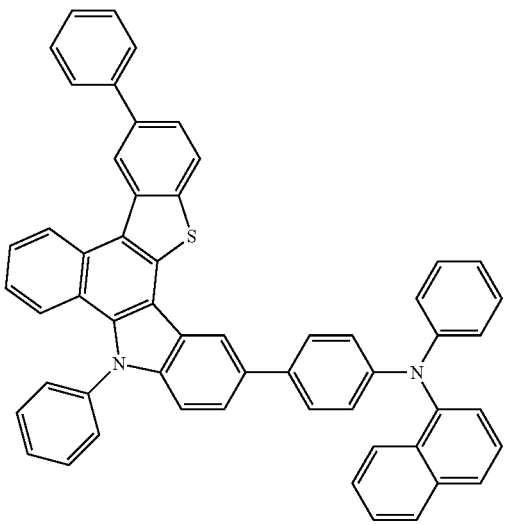
1-155
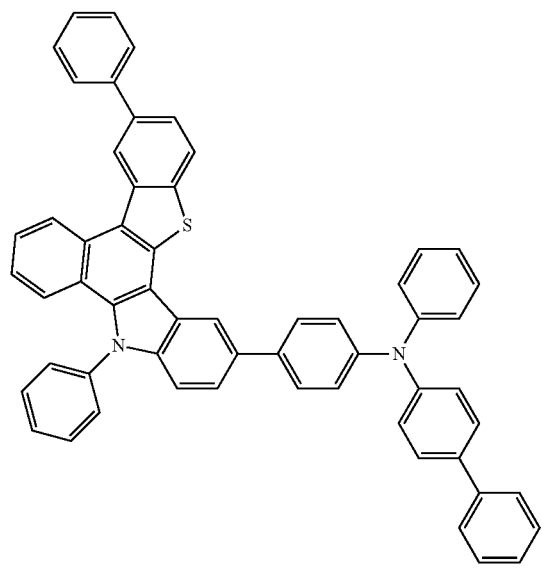
1-156
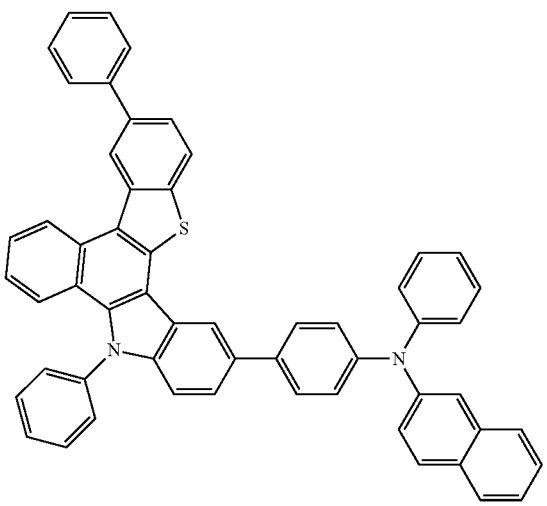
1-157
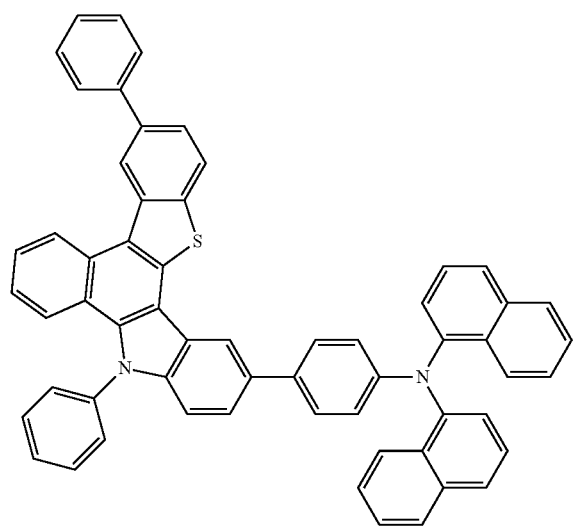
1-158
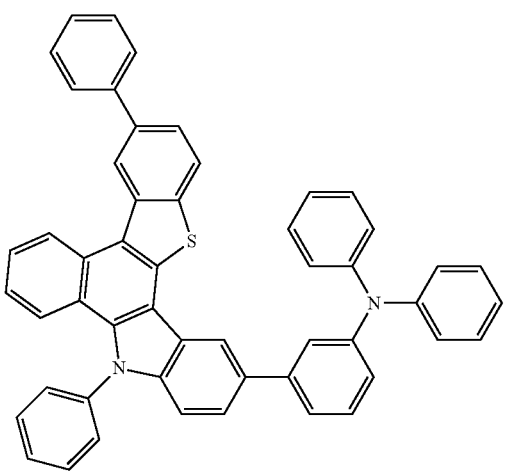

-continued
1-159
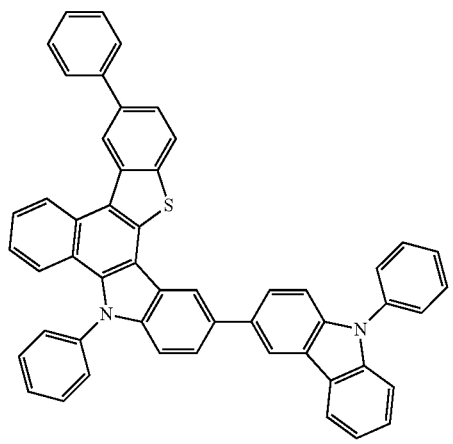
1-160
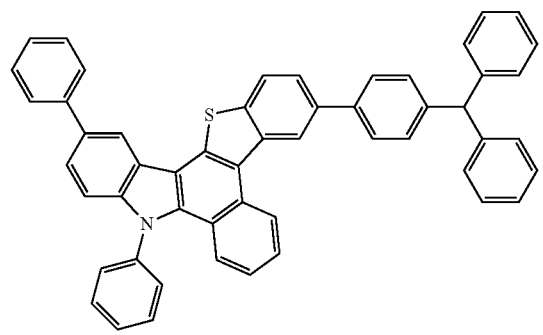
1-161
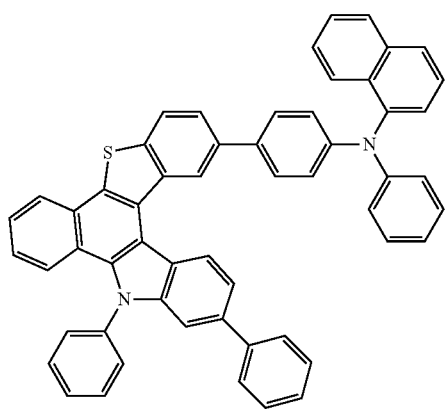
1-162
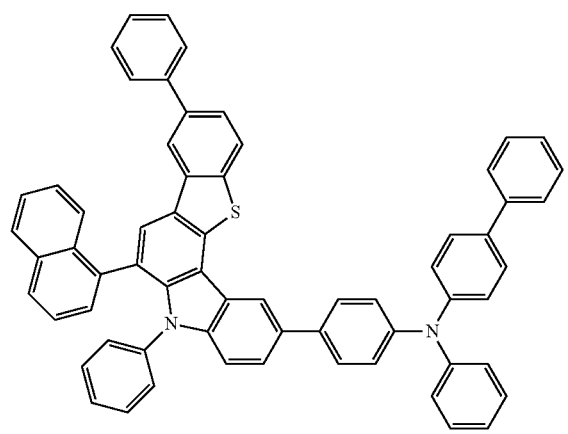
1-163
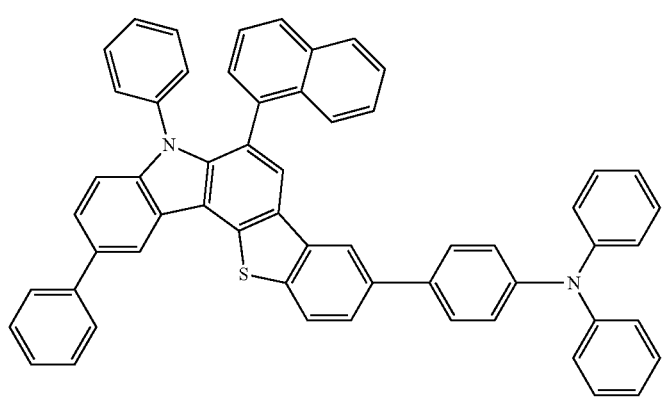

-continued
2-1
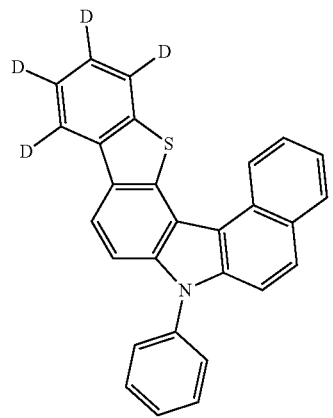
2-2
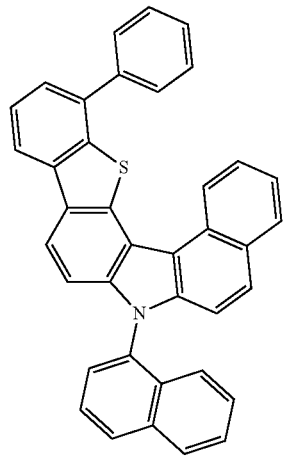
2-3
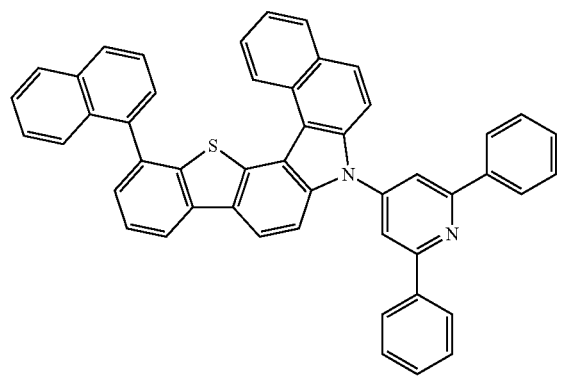
2-4
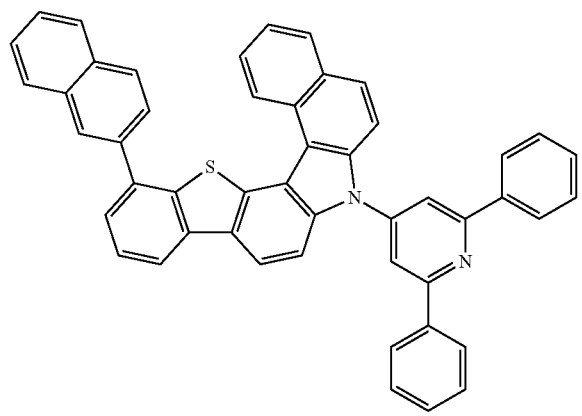
2-5
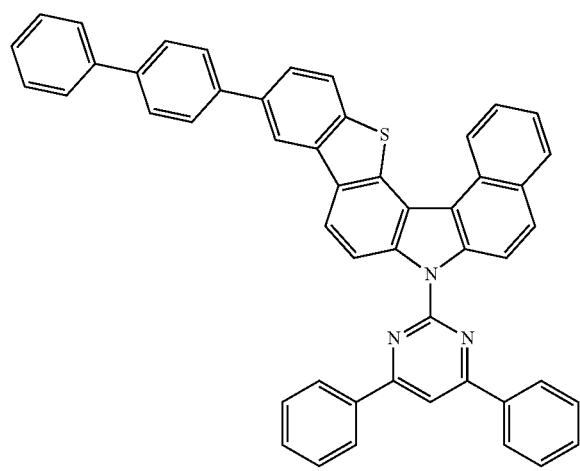
2-6
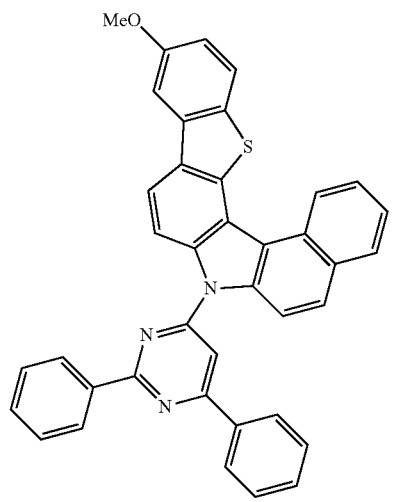

-continued
2-7
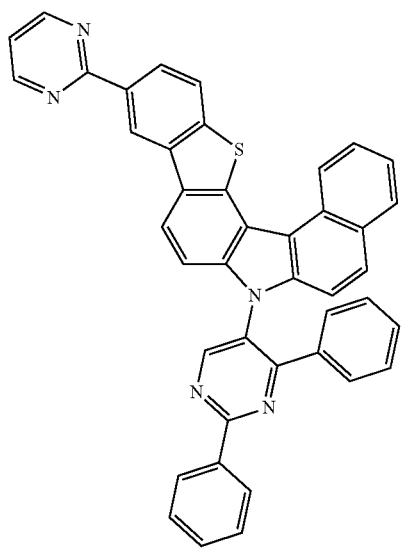
2-8
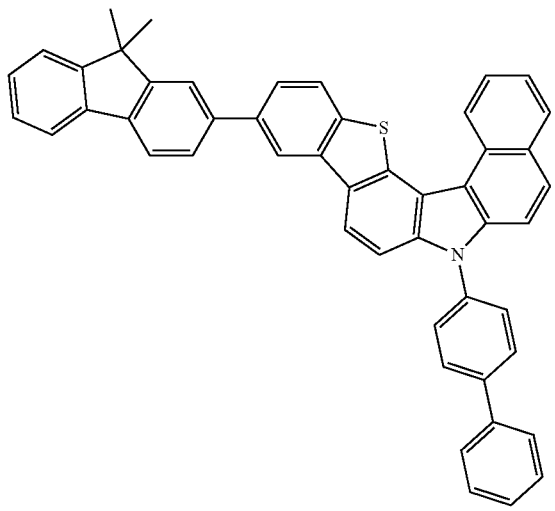
2-9
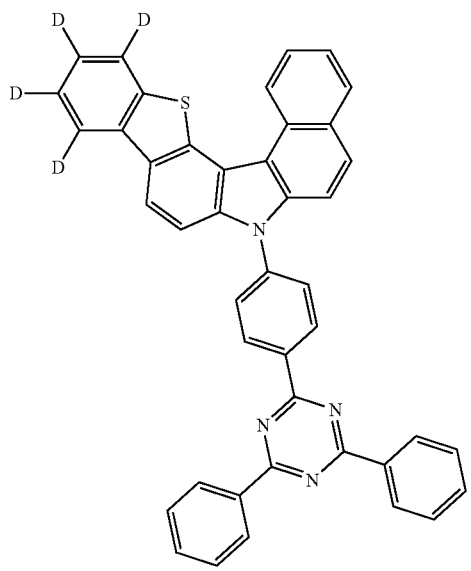
2-10
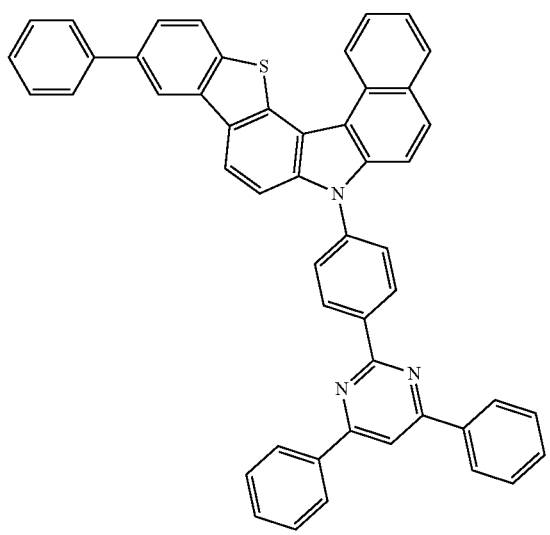
2-11
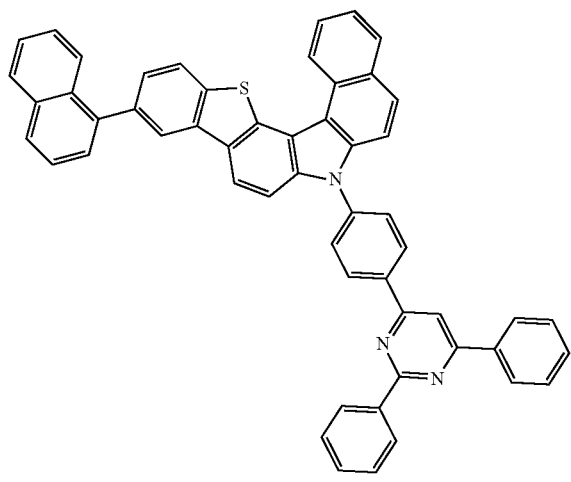
2-12
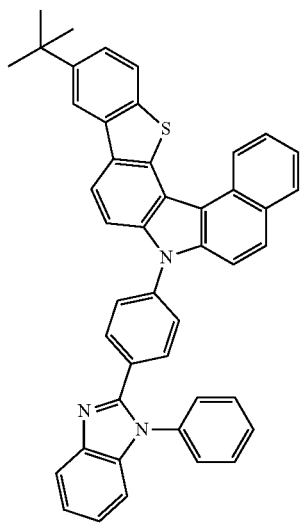

-continued
2-13
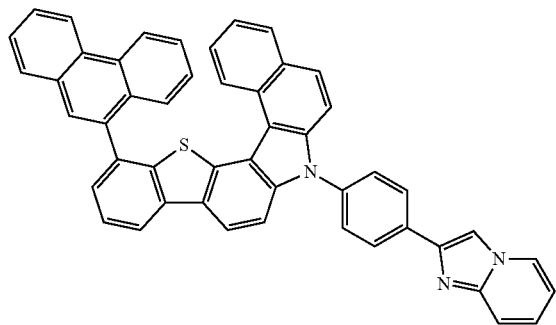
2-14
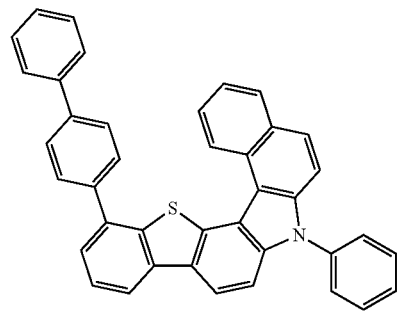
2-15
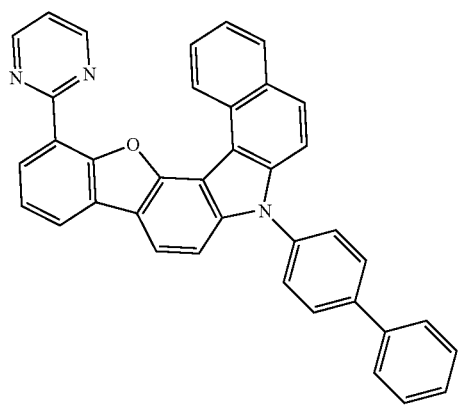
2-16
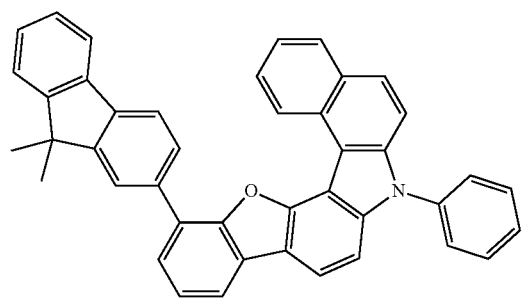
2-17
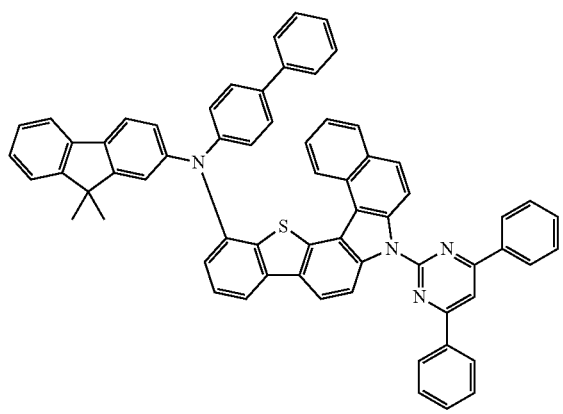
2-18
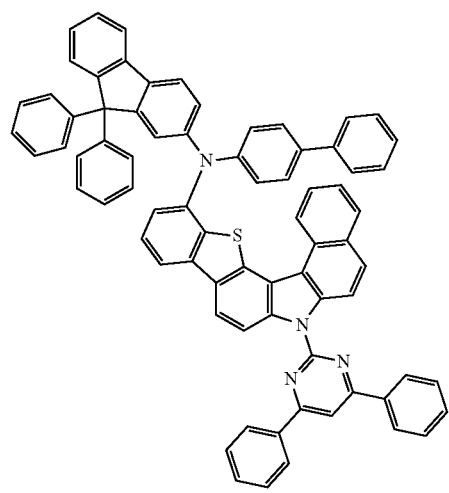

-continued
2-19
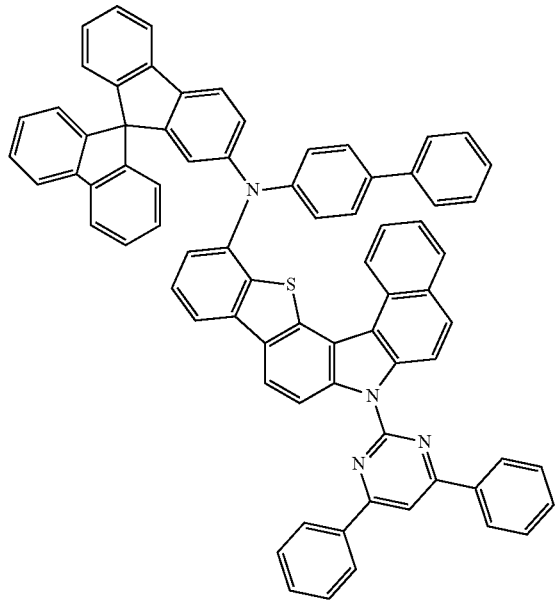
2-20
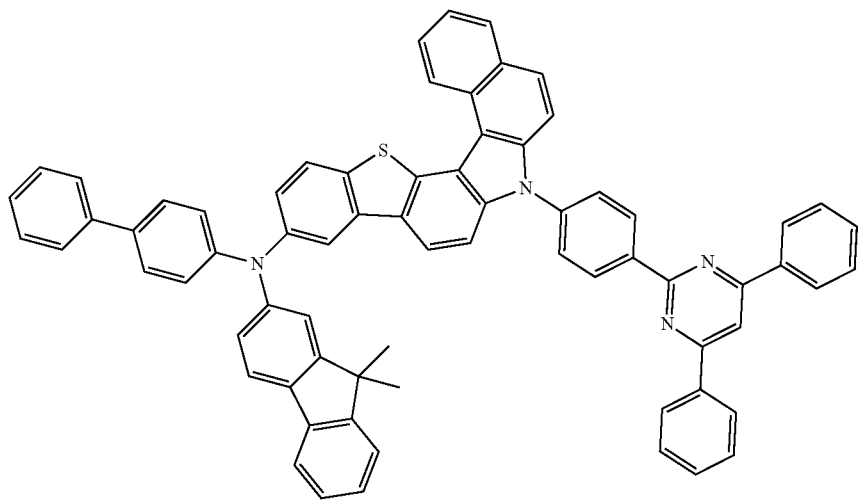
2-21
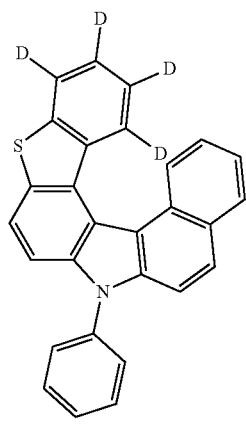
2-22
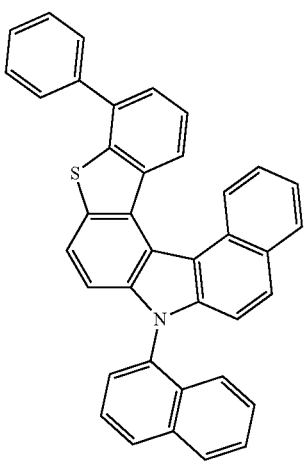

-continued
2-23
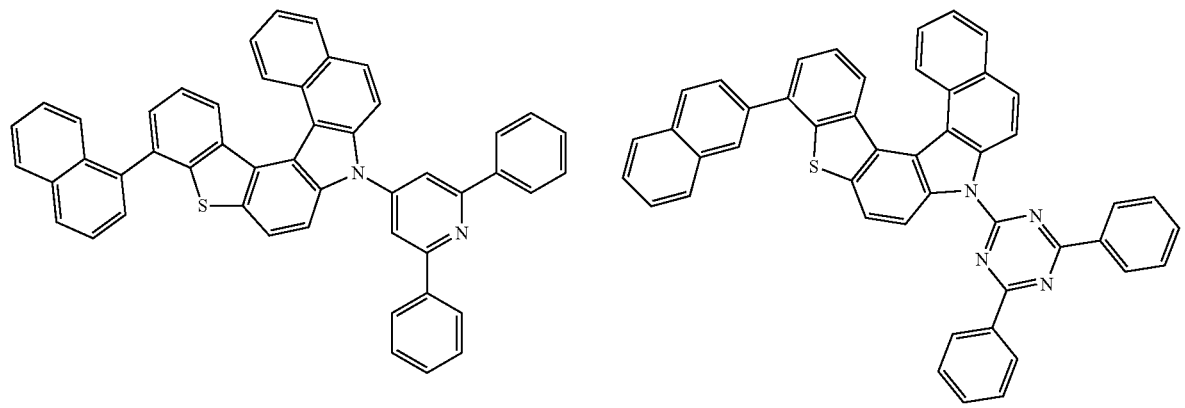
2-24
2-25
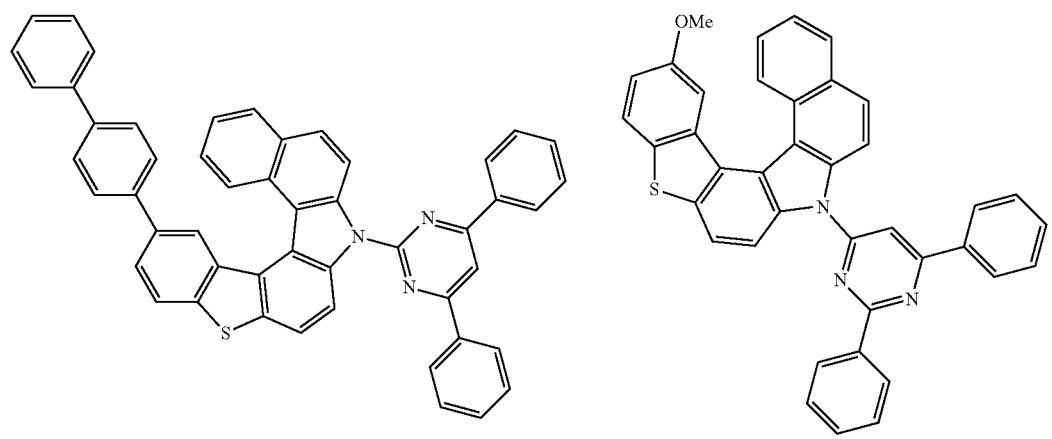
2-26
2-27
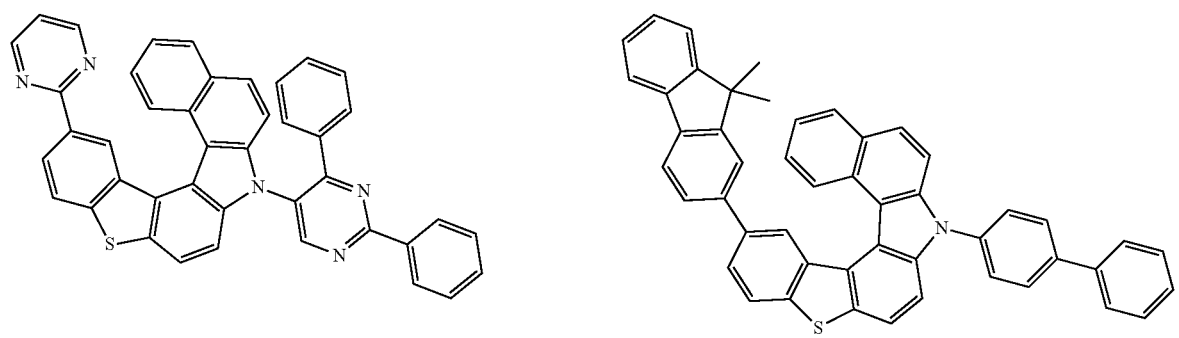
2-28

-continued
2-29
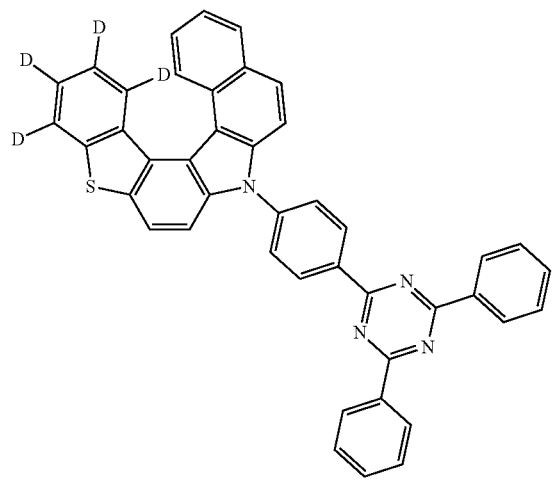
2-30
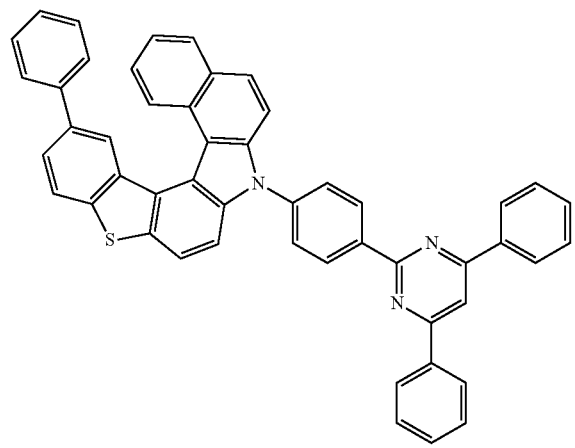
2-31
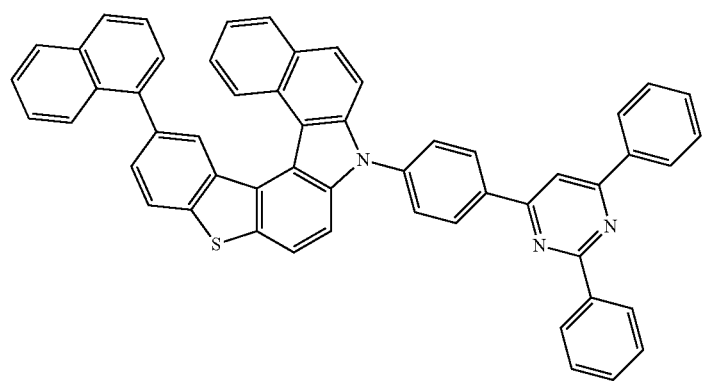
2-32
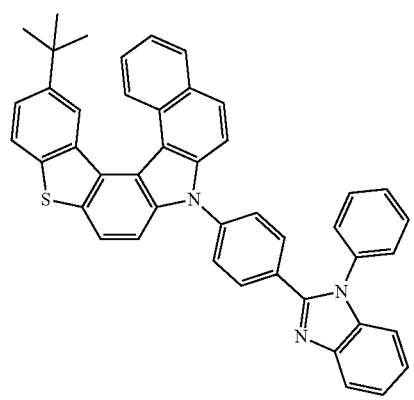
2-33
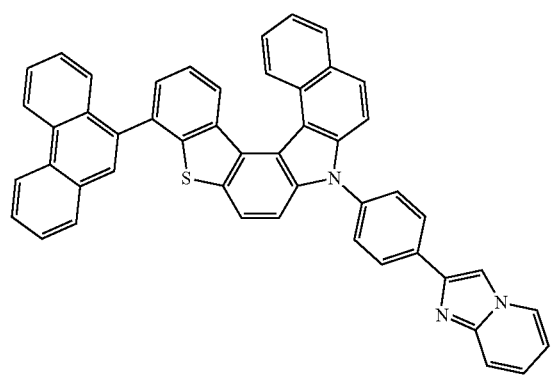

2-34
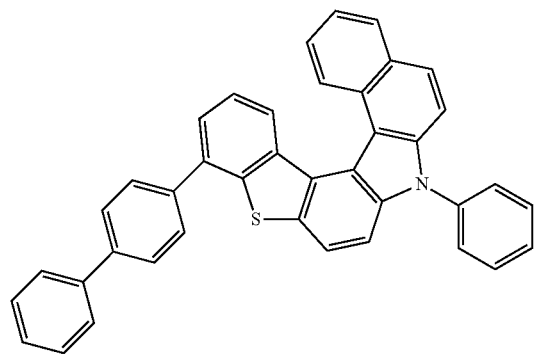
2-35
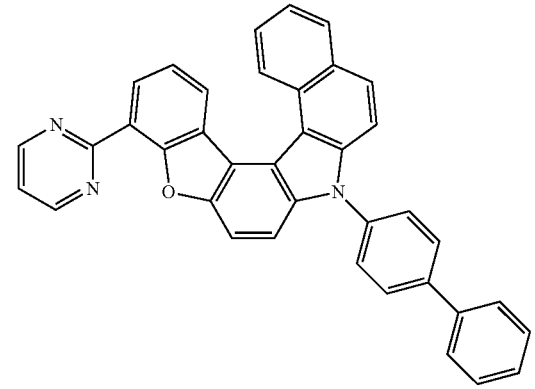
2-36
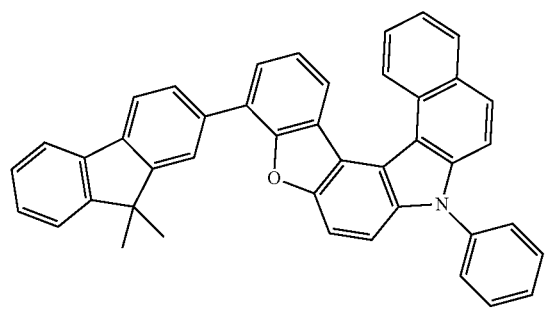
2-37
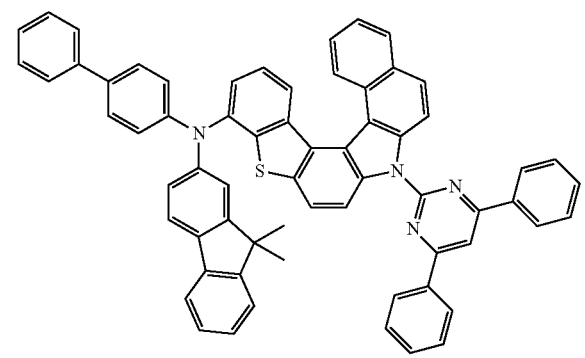
2-38
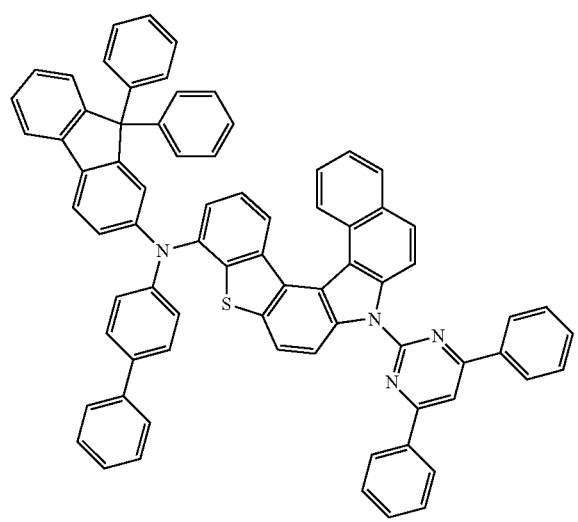
2-39
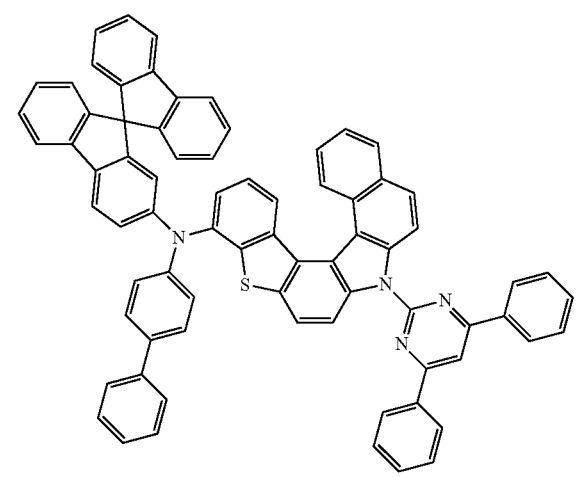

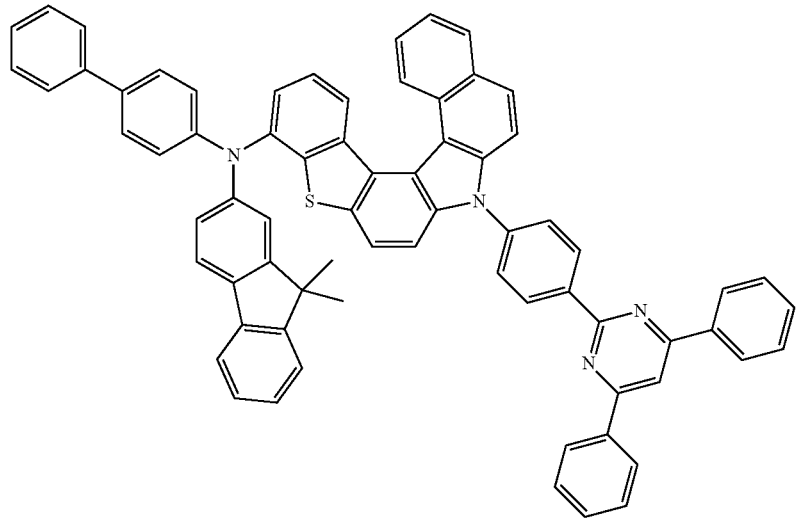
2-40
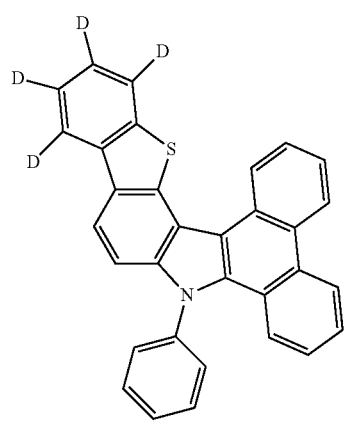
2-41
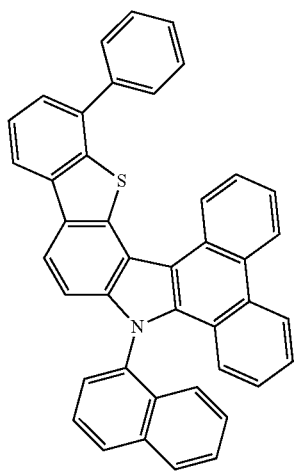
2-42
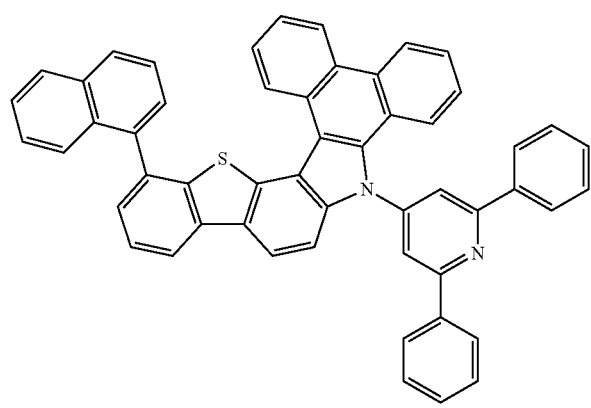
2-43
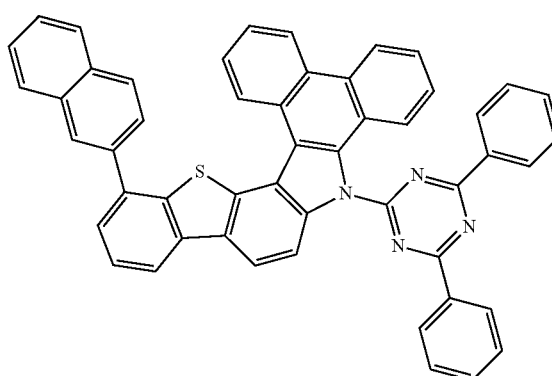
2-44

-continued
2-45
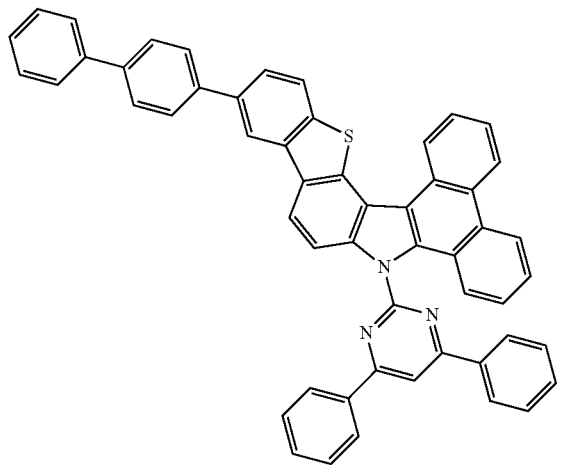
2-46
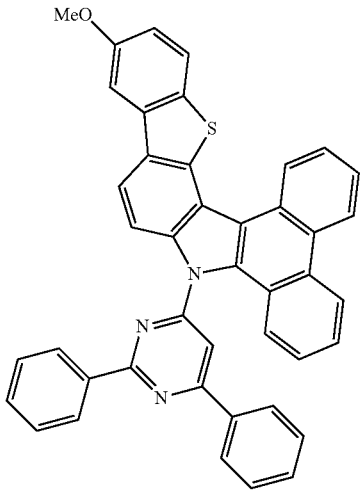
2-47
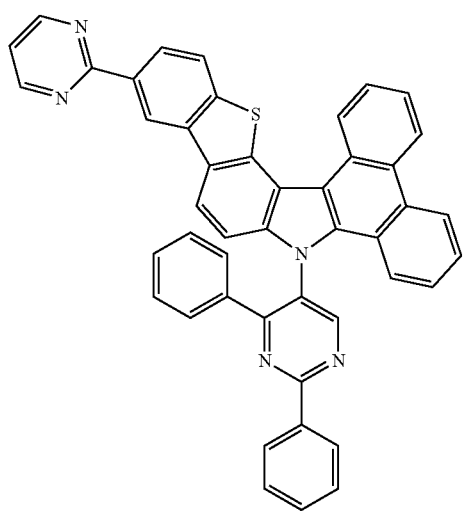
2-48
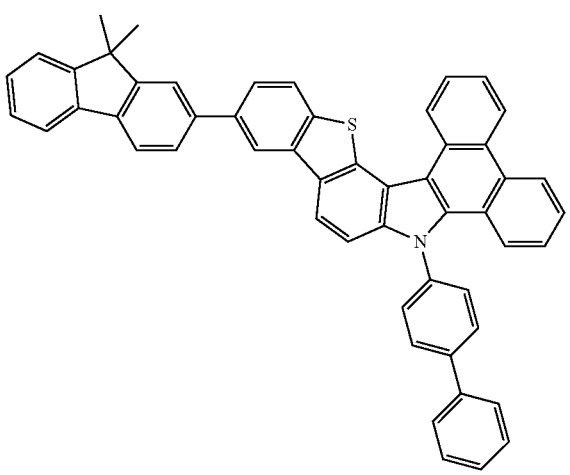
2-49
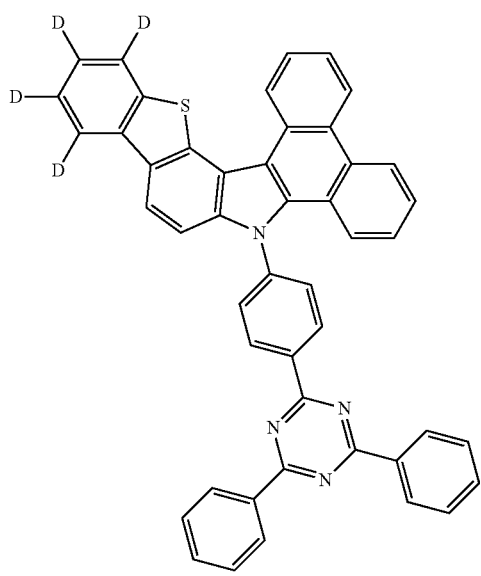
2-50
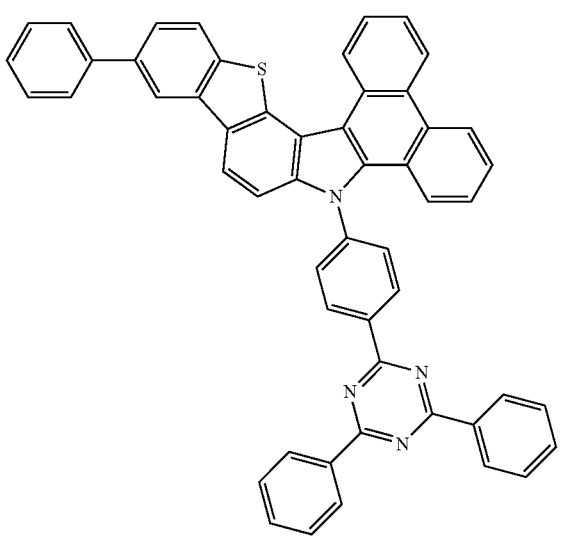

-continued
2-51
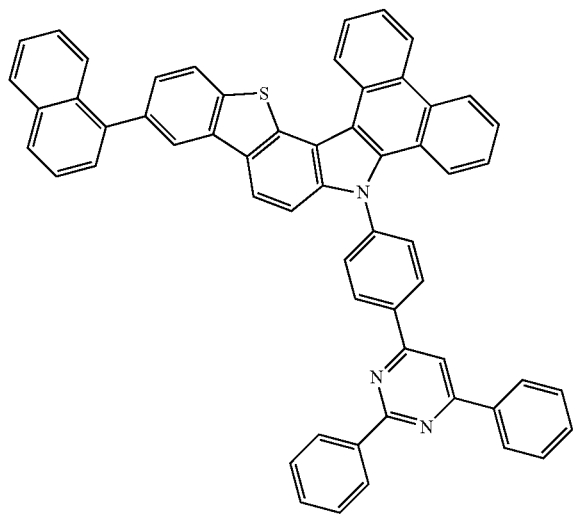
2-52
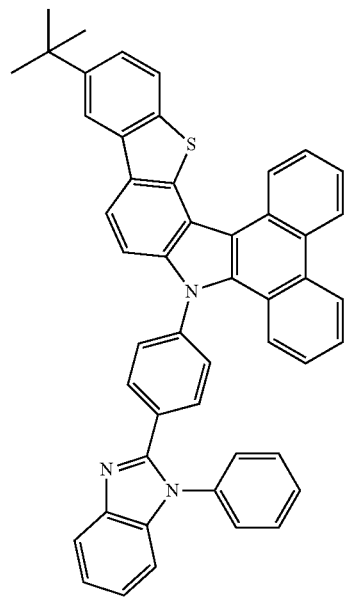
2-53
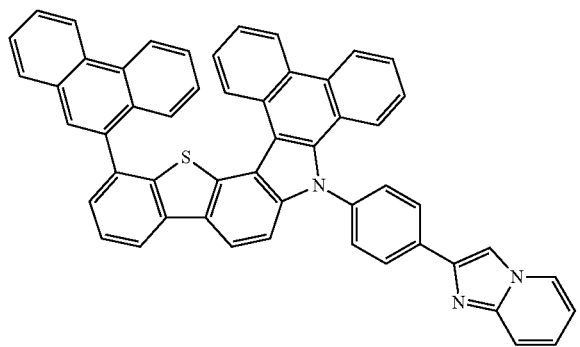
2-54
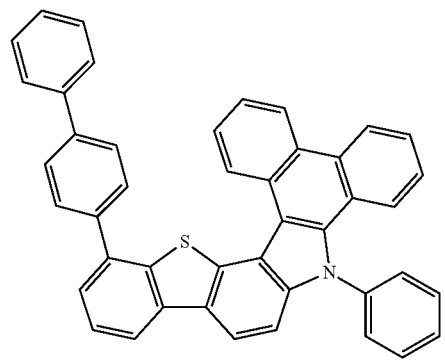
2-55
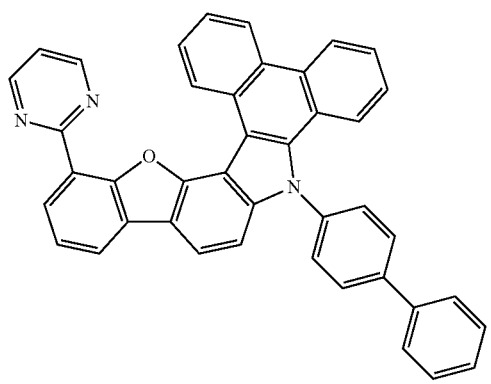
2-56
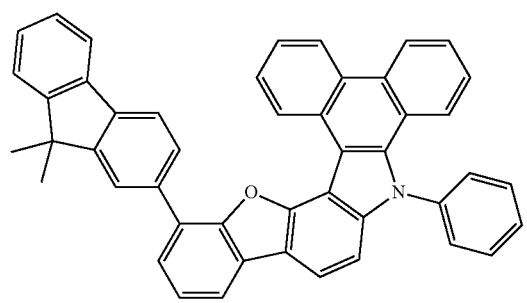

2-57
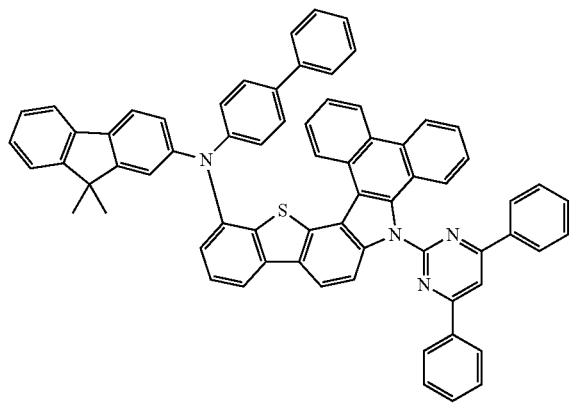
2-58
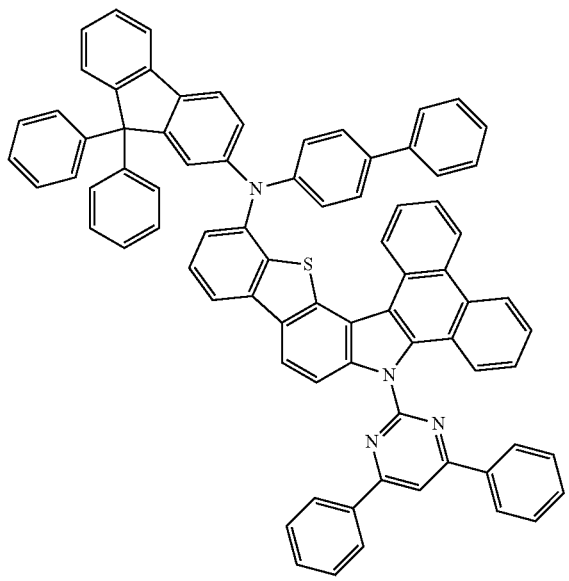
2-59
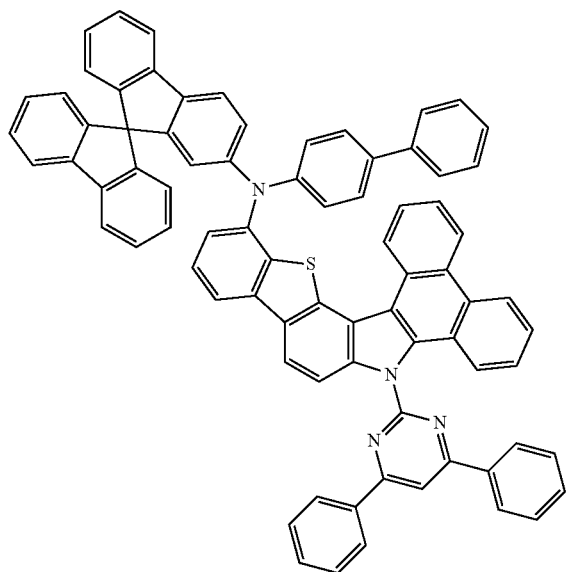

-continued
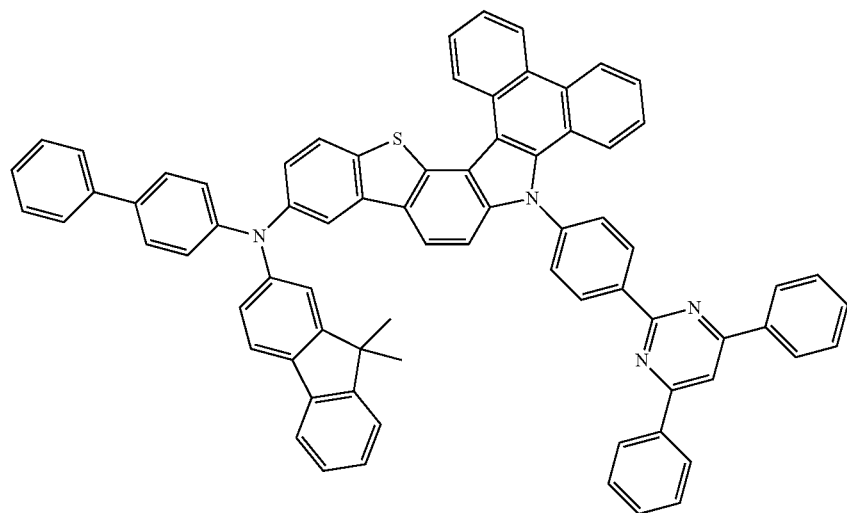
2-60
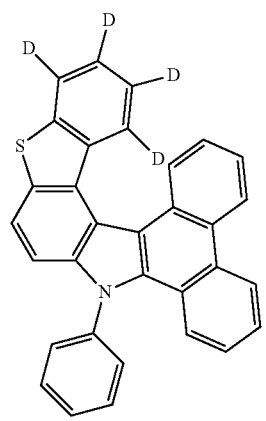
2-61
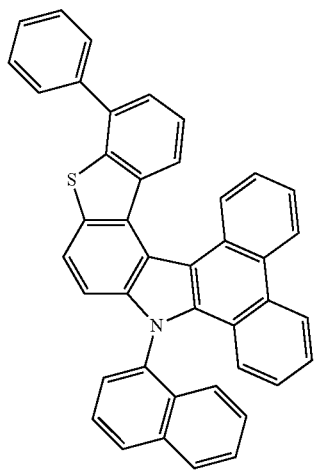
2-62
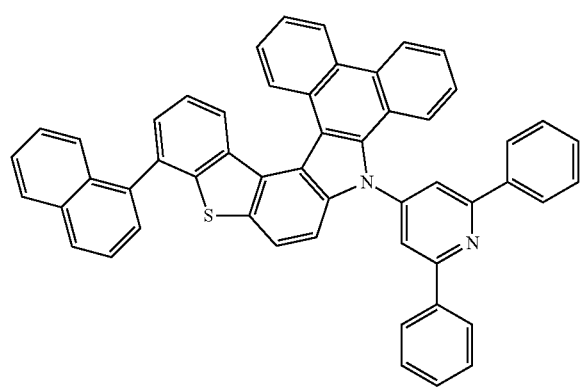
2-63
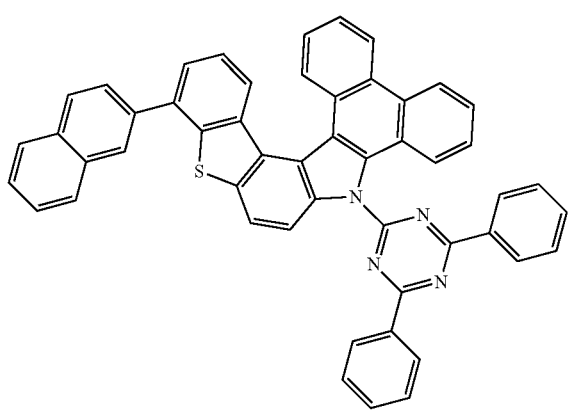
2-64

-continued
2-65
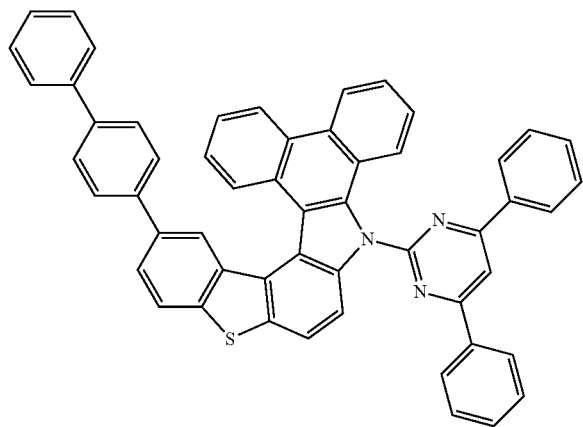
2-66
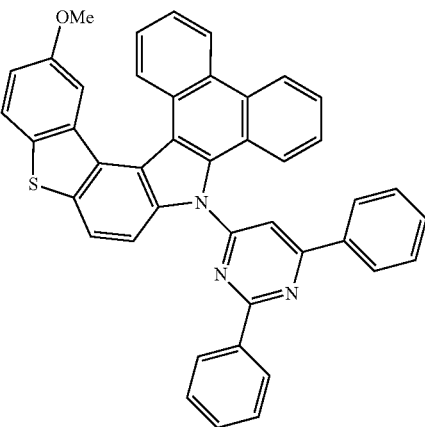
2-67
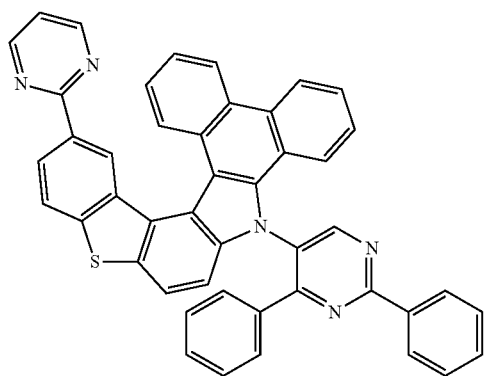
2-68
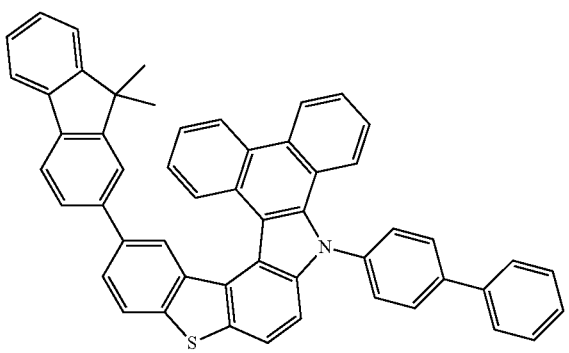
2-69
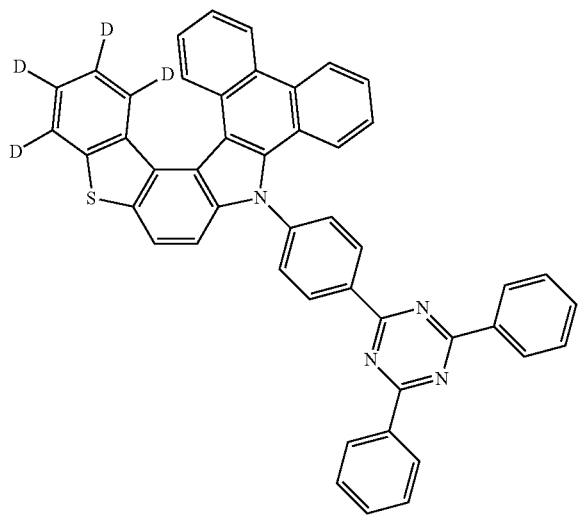
2-70
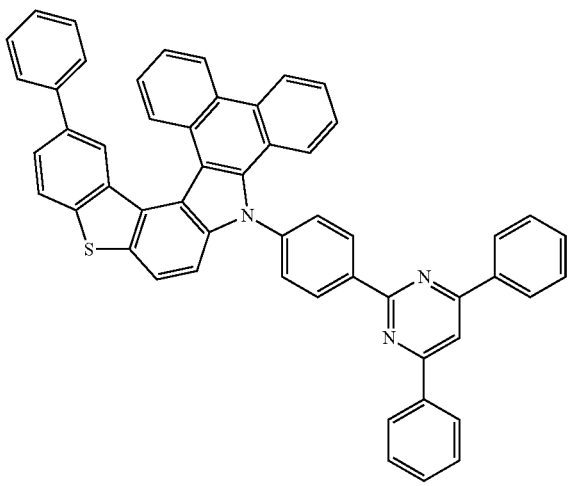

-continued
2-71
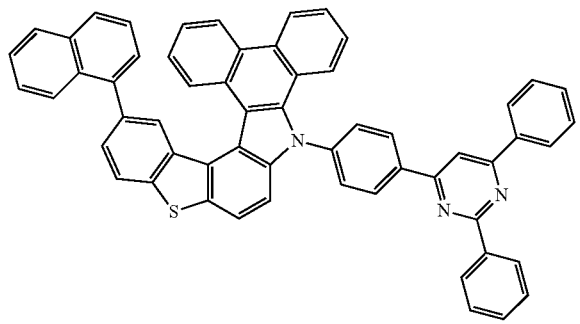
2-72
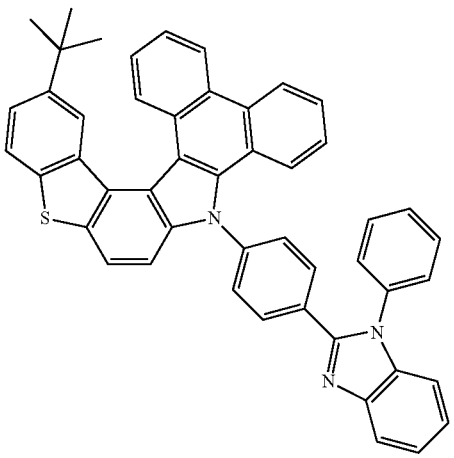
2-73
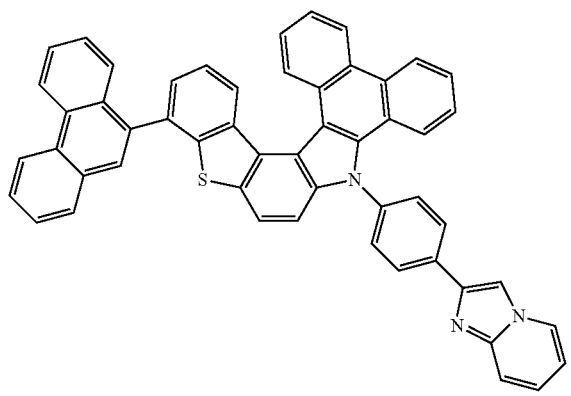
2-74
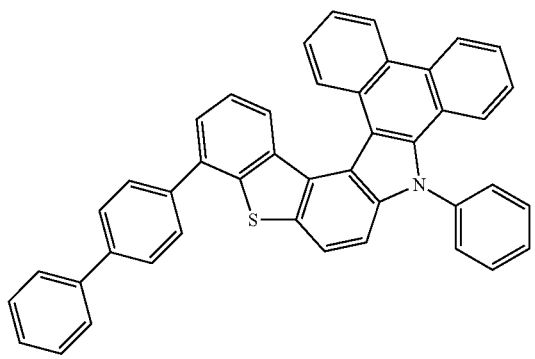
2-75
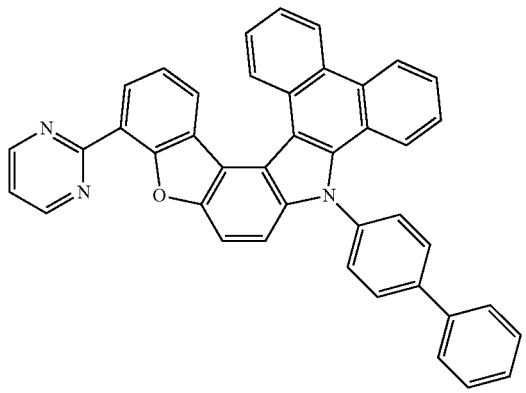
2-76
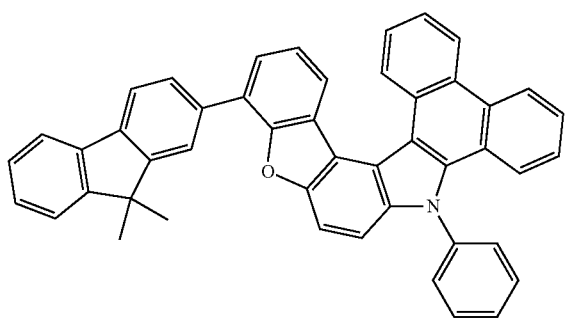

-continued
2-77
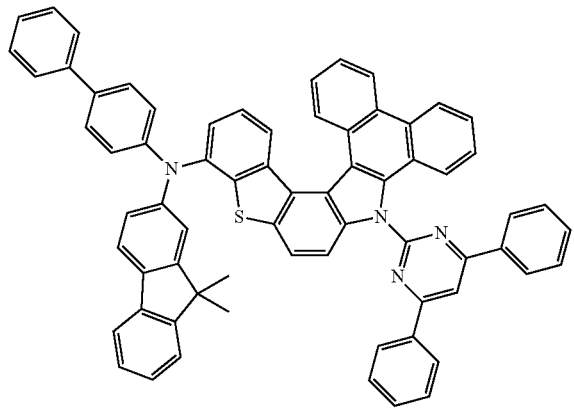
2-78
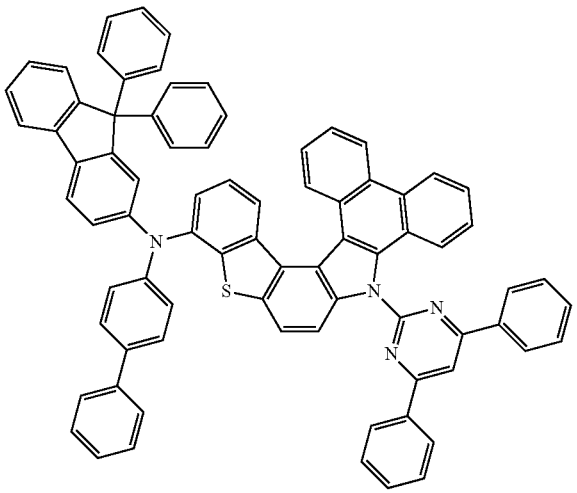
2-79
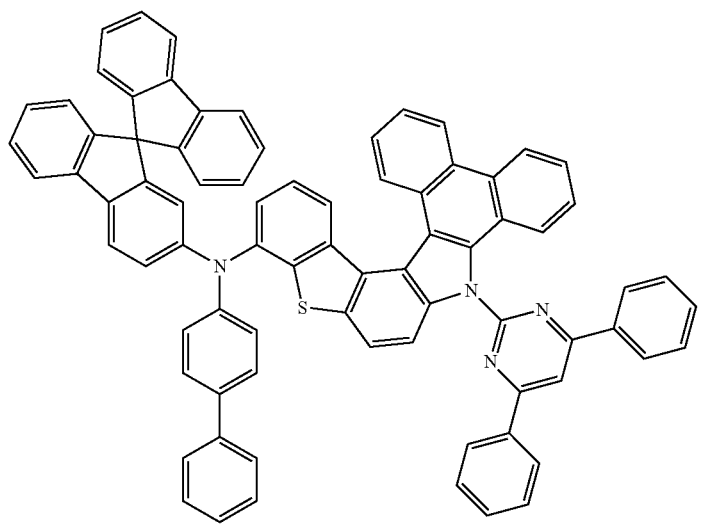
2-80
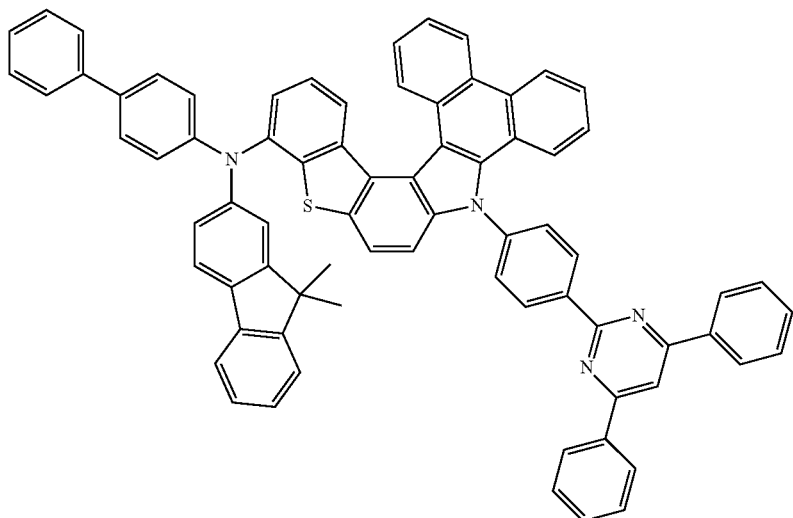

-continued
5-1
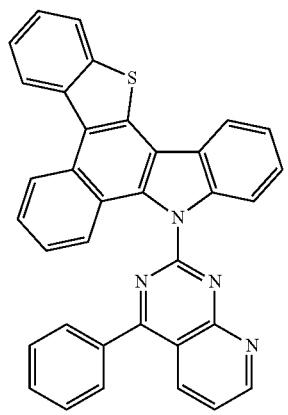
5-2
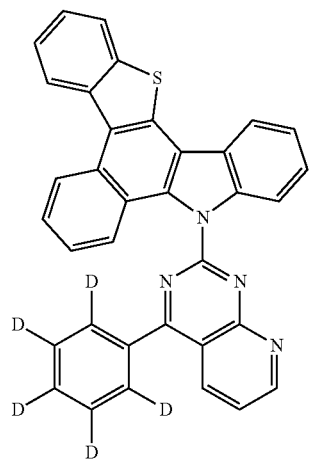
5-3
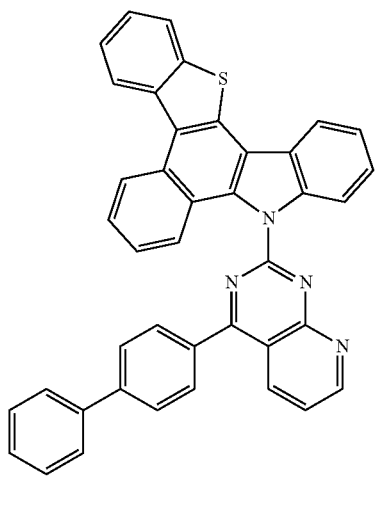
5-4
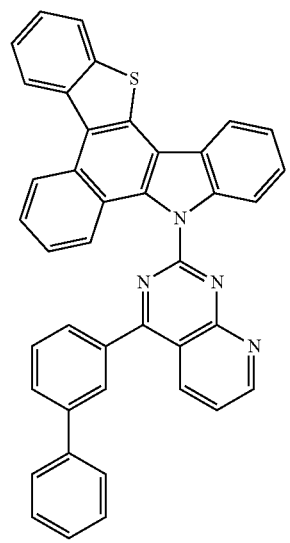
5-5
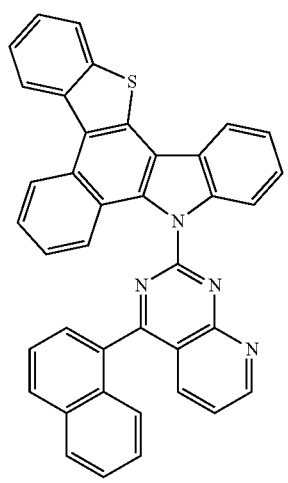
5-6
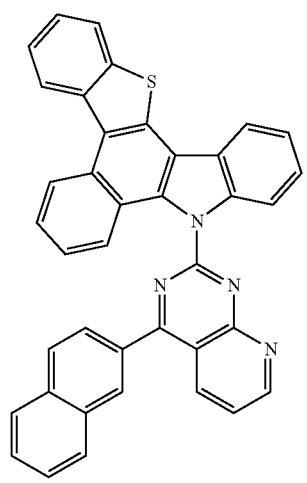

-continued
5-7
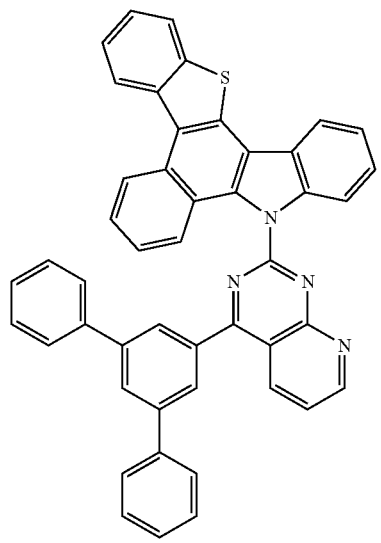
5-8
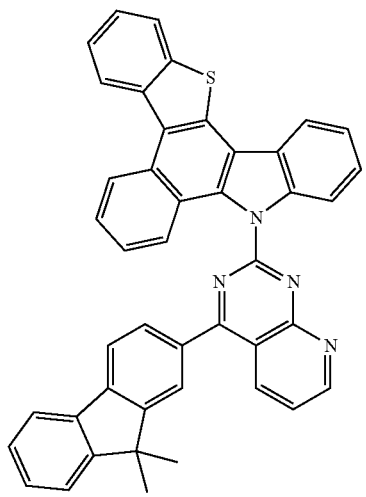
5-9
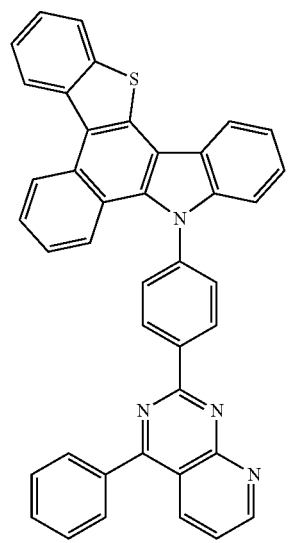
5-10
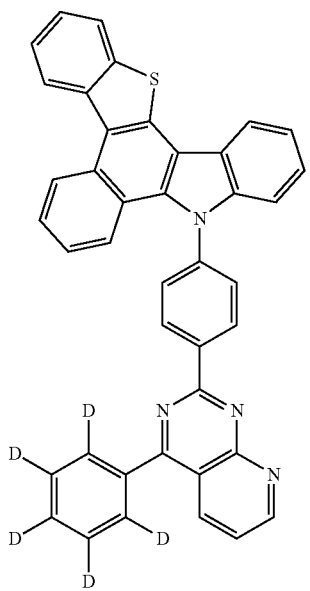

-continued
5-11
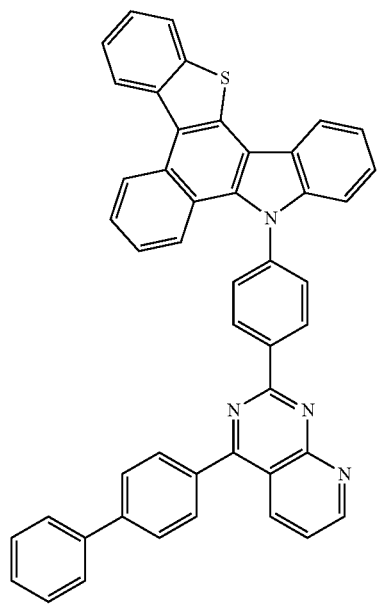
5-12
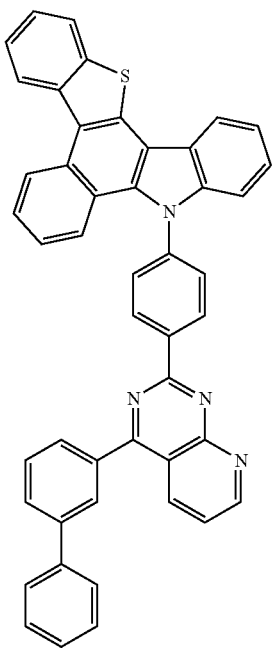
5-13
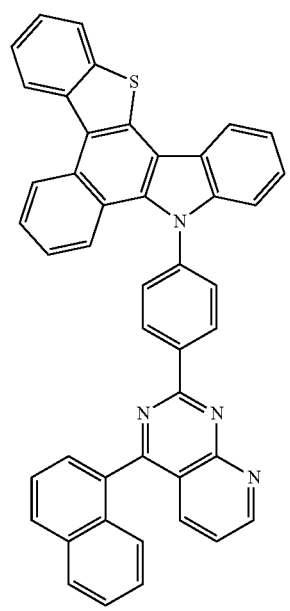
5-14
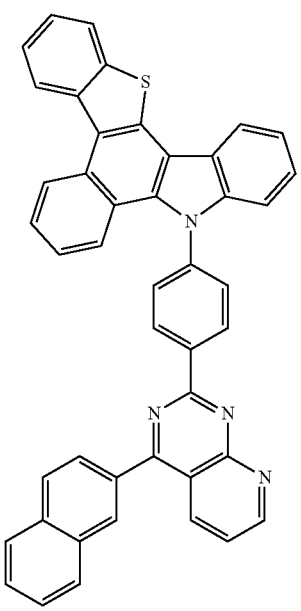

375
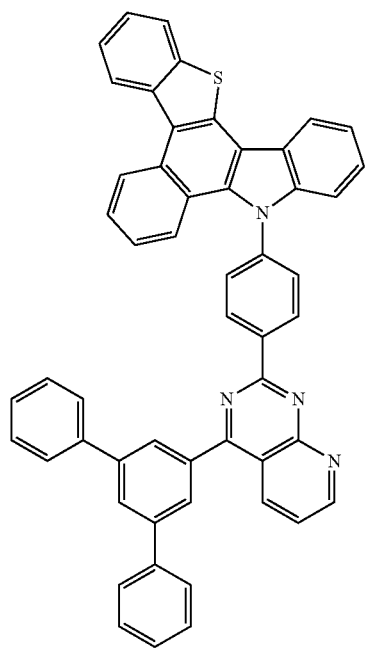
5-15
376
5-16
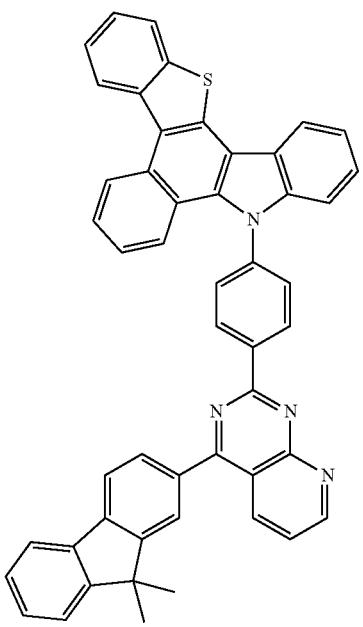
5-17
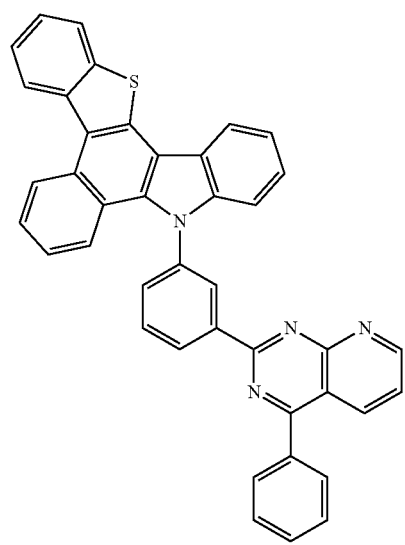
5-18
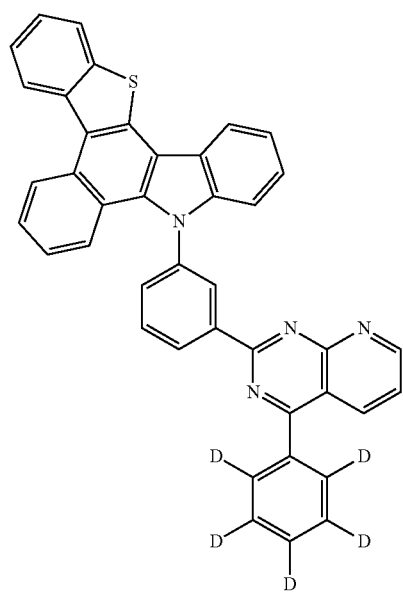

5-19
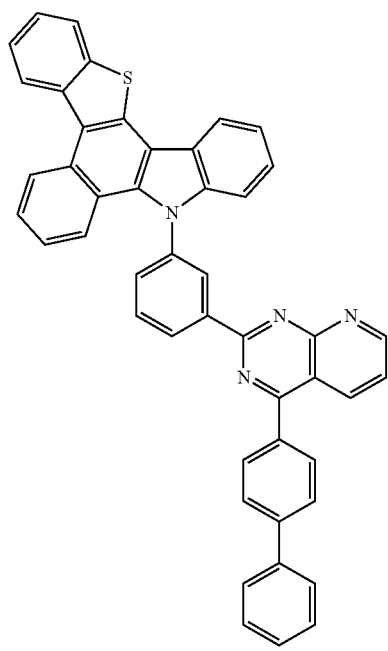
5-20
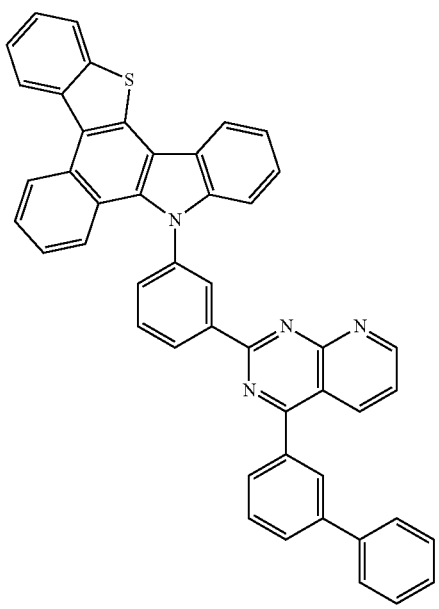
5-21
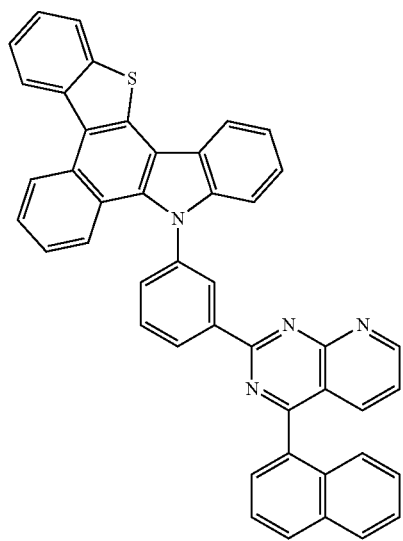
5-22
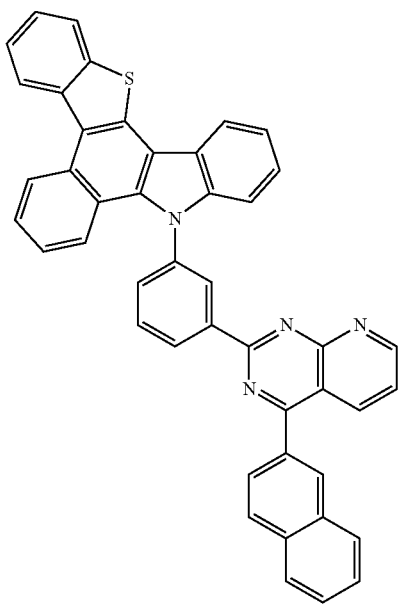

-continued
5-23
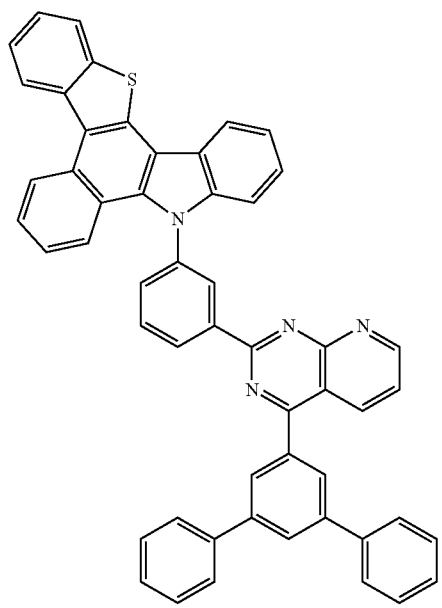
5-24
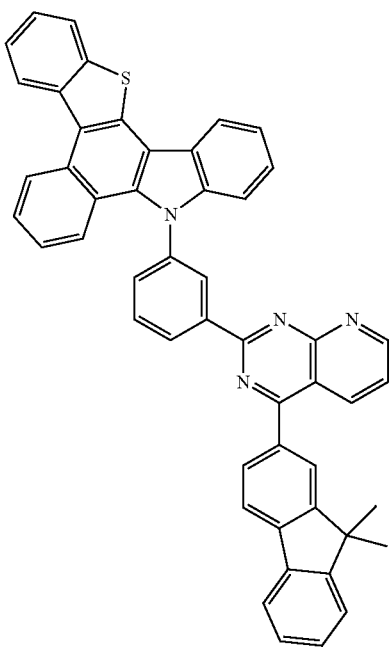
5-25
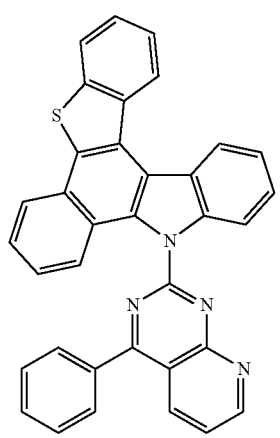
5-26
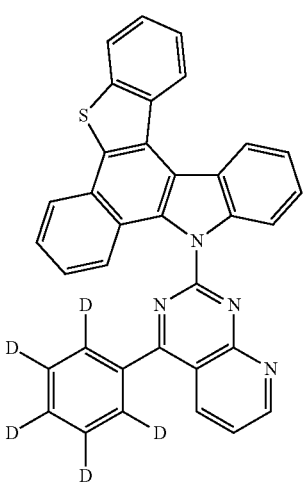

5-27
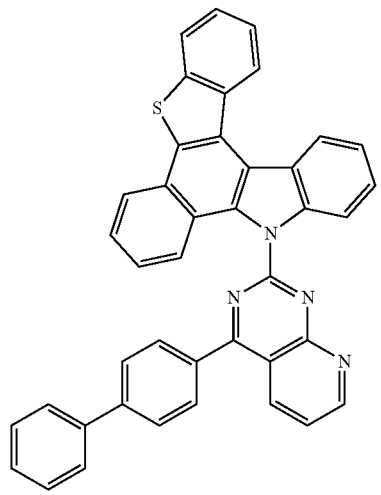
5-28
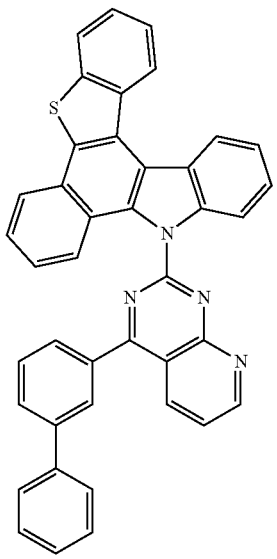
5-29
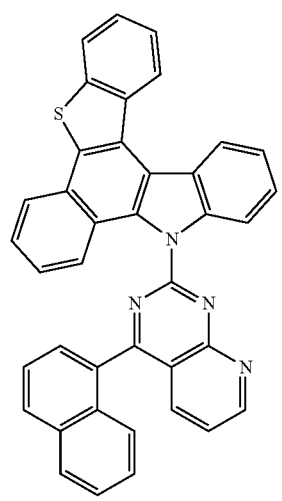
5-30
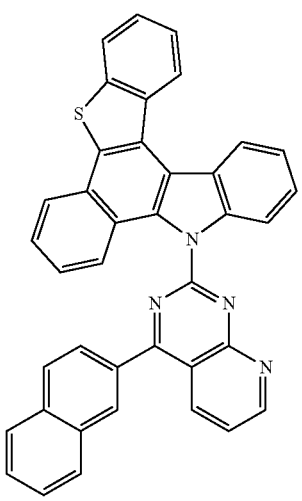
5-31
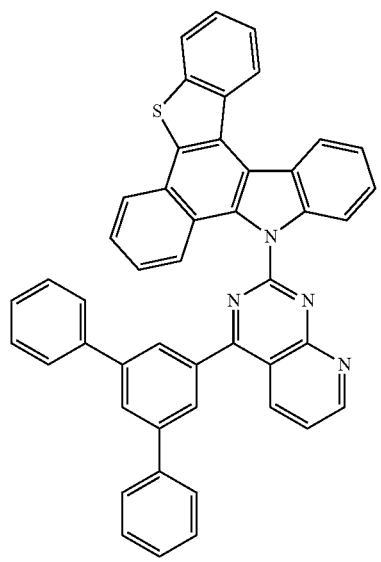
5-32
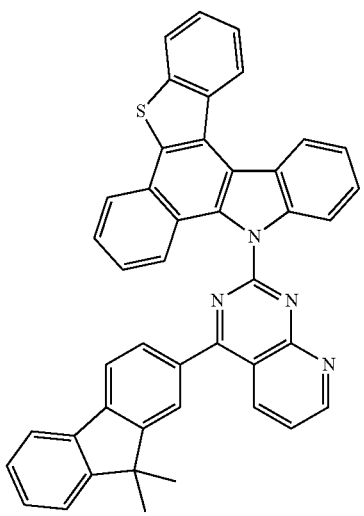

-continued
5-33
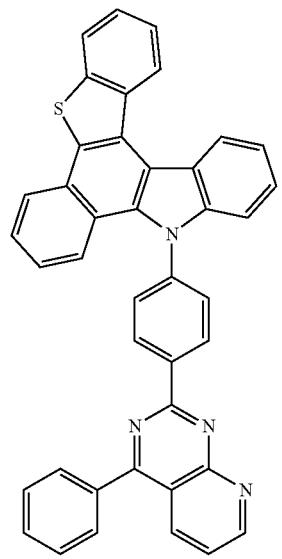
5-34
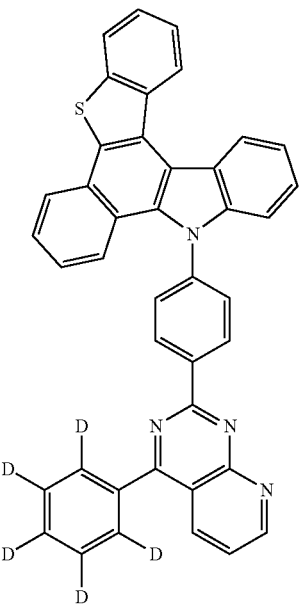
5-35
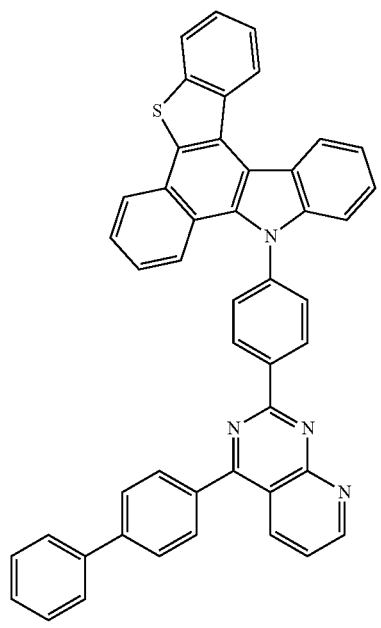
5-36
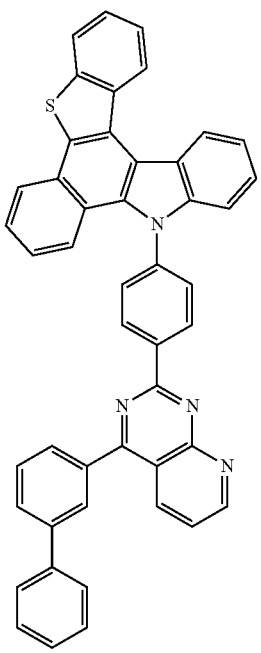

5-37
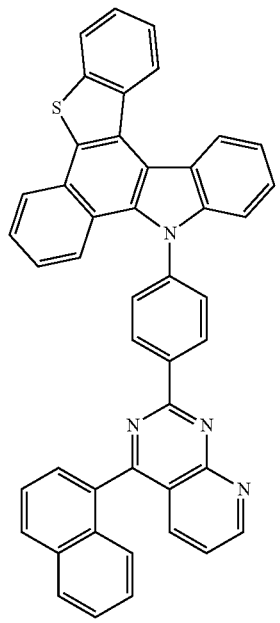
5-38
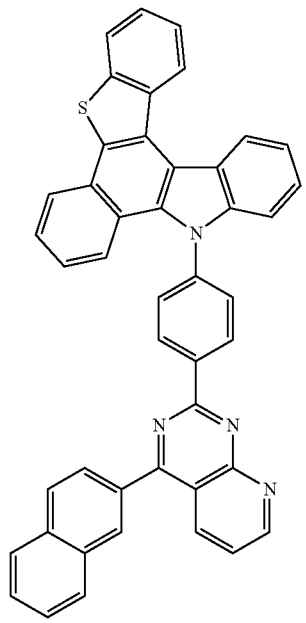
5-39
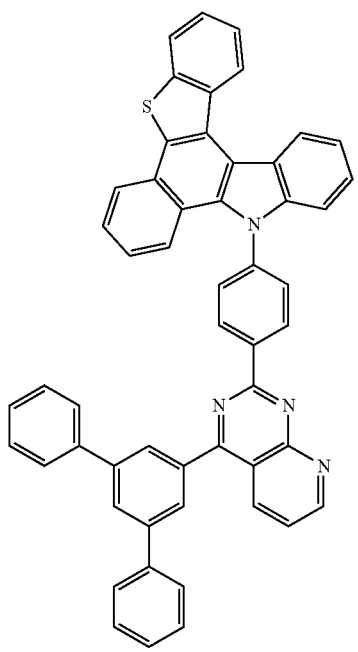
5-40
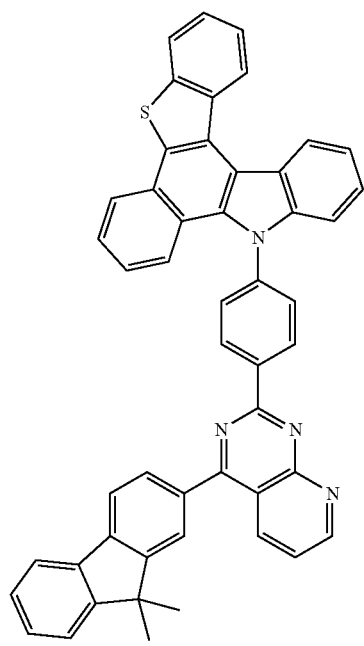

-continued
5-41
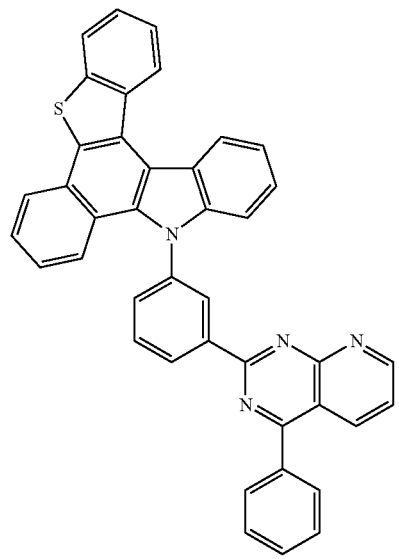
5-42
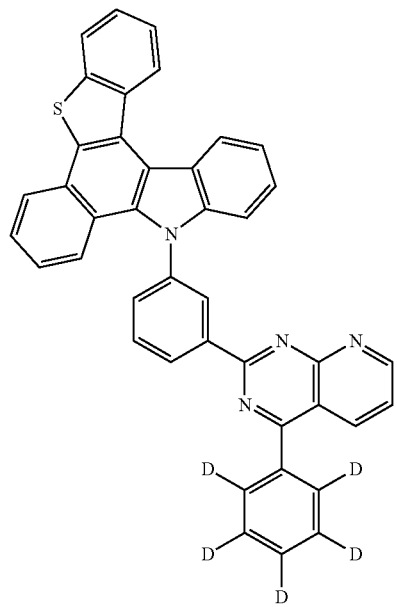
5-43
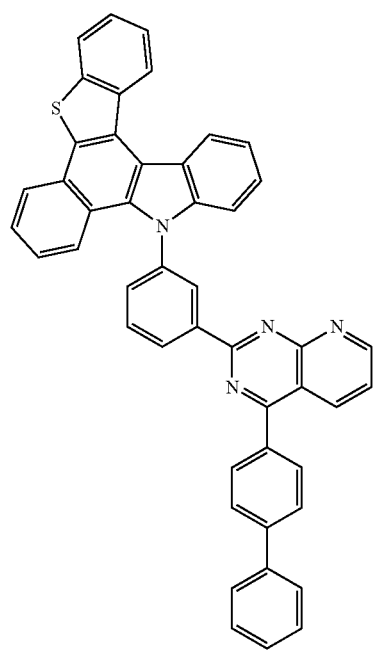
5-44
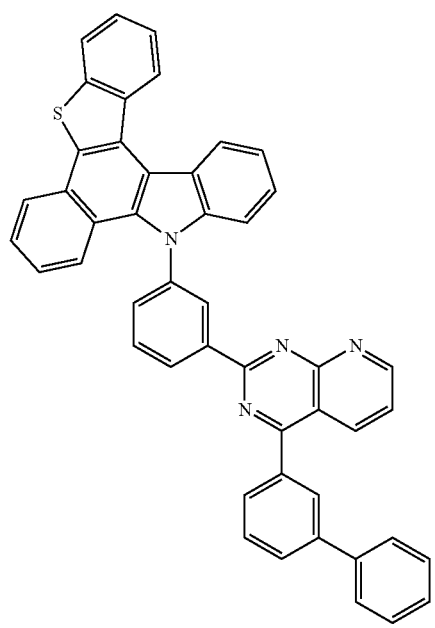

-continued
5-45
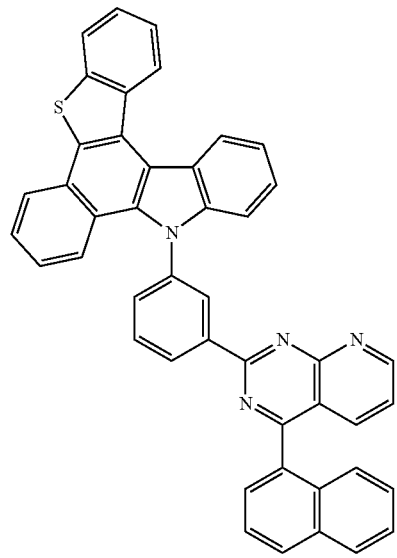
5-46
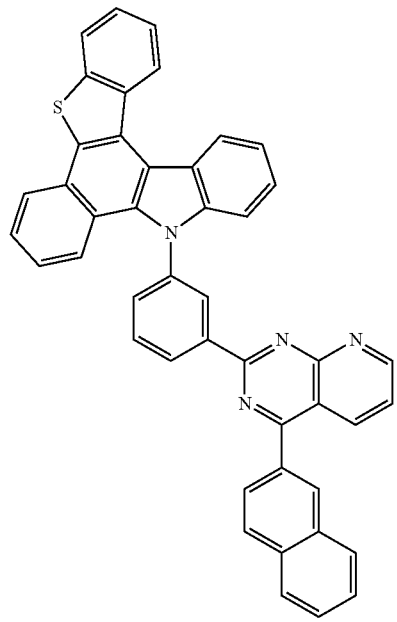
5-47
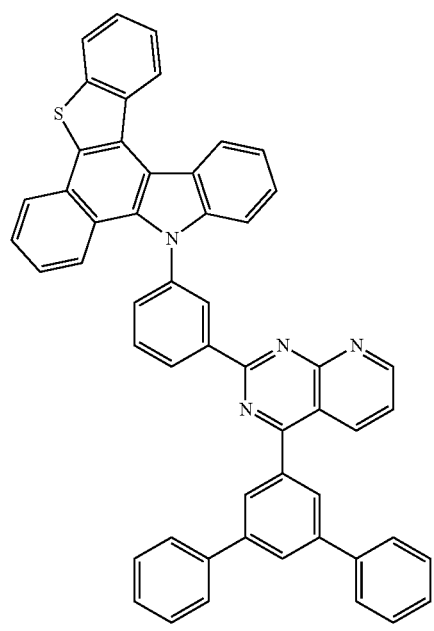
5-48
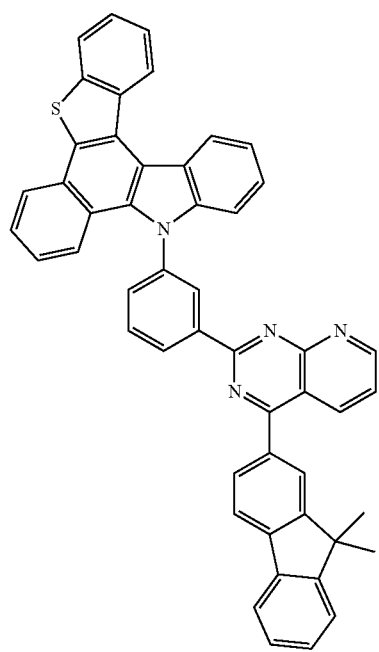

-continued
6-1
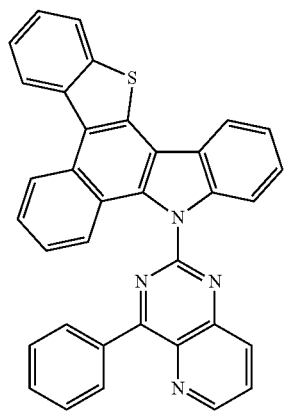
6-2
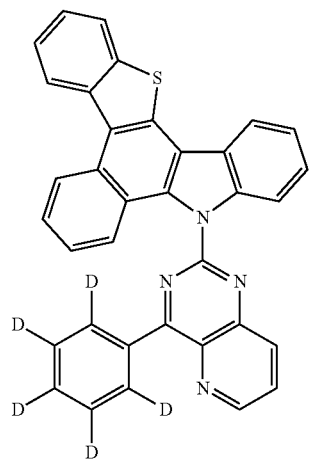
6-3
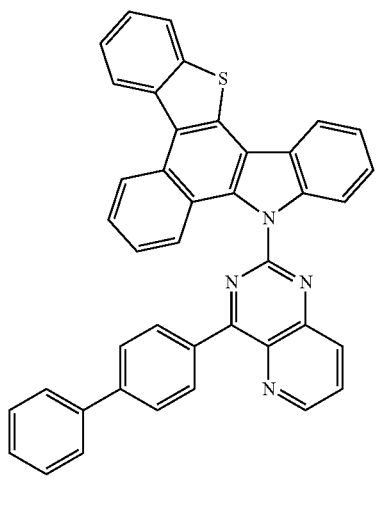
6-4
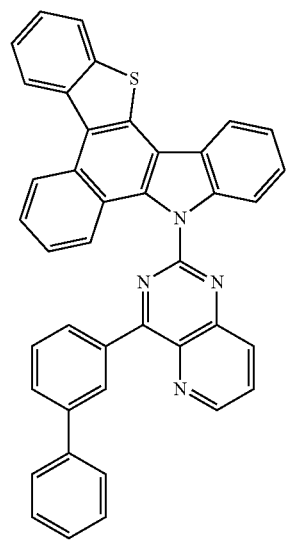
6-5
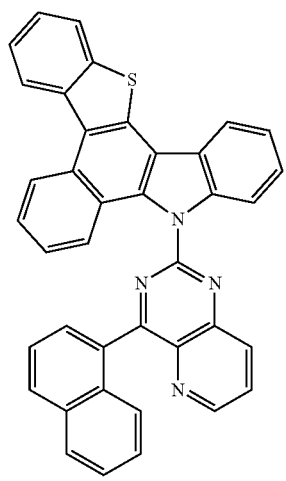
6-6
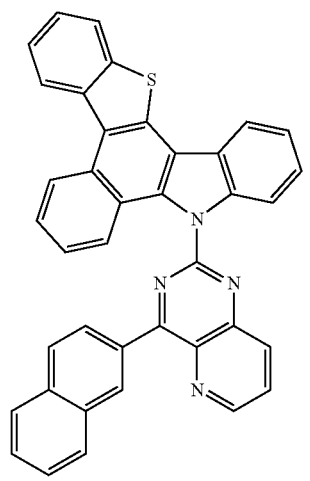

-continued
6-7
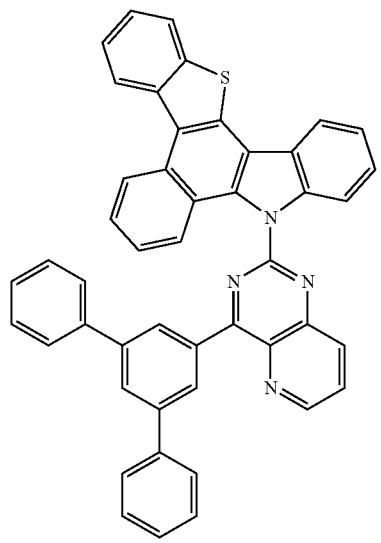
6-8
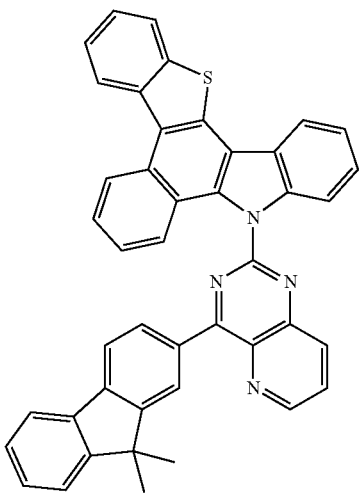
6-9
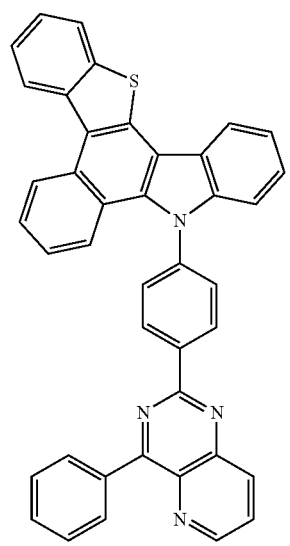
6-10
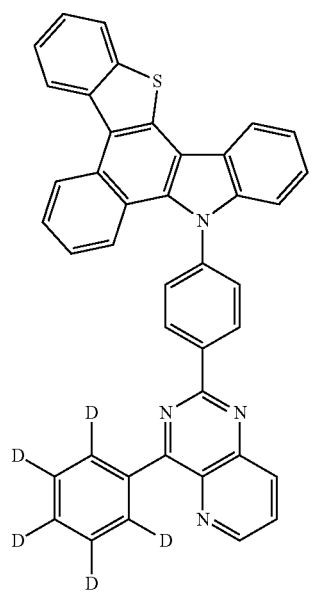

-continued
6-11
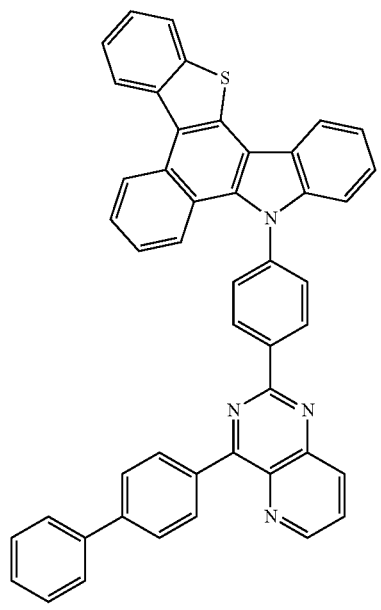
6-12
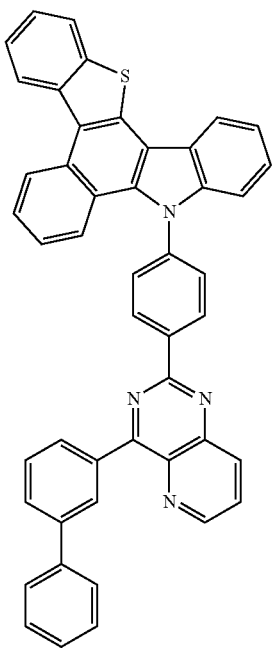
6-13
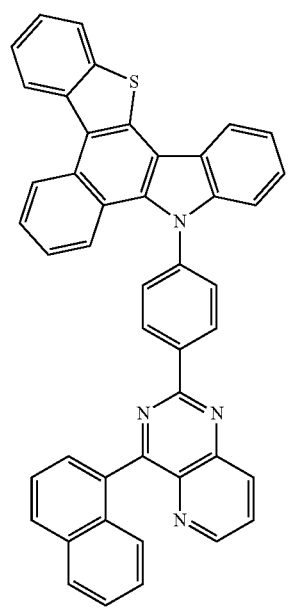
6-14
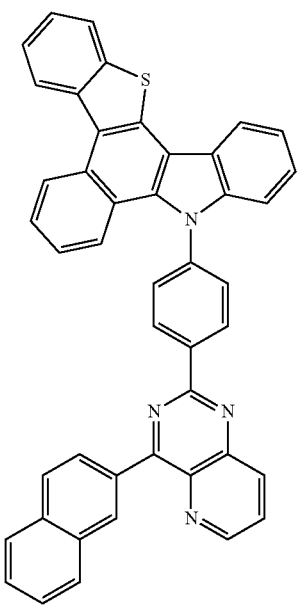

397
-continued
6-15
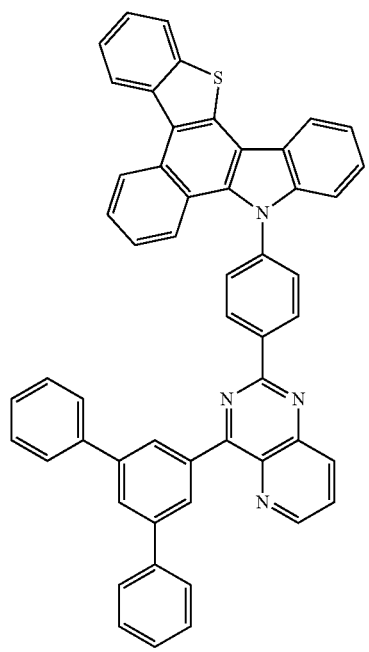
398
6-16
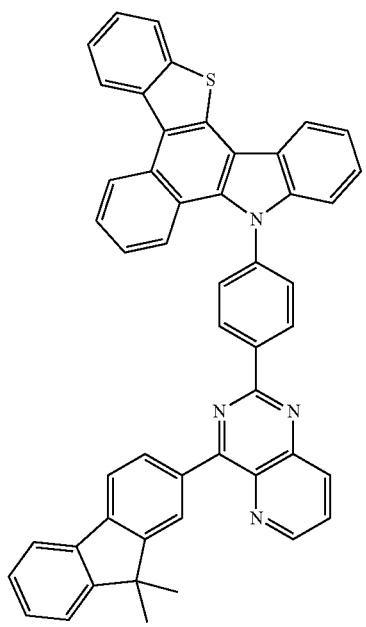
6-17
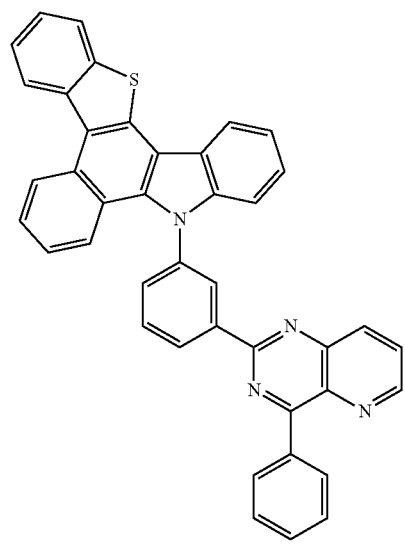
6-18

6-19
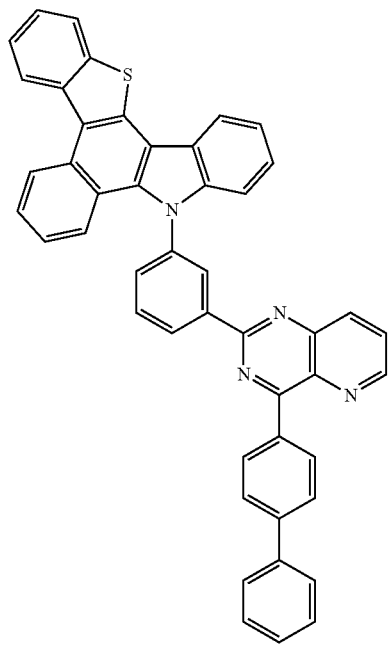
6-20
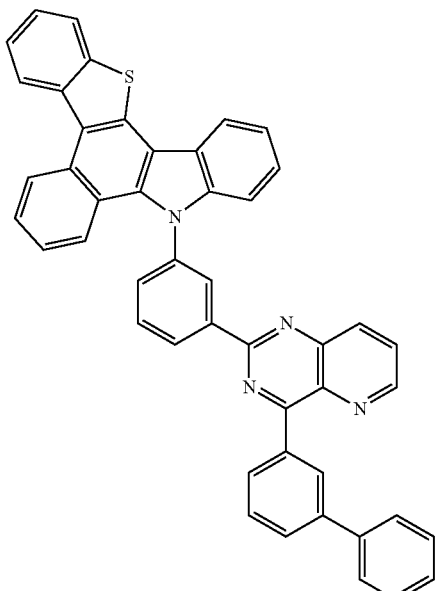
6-21
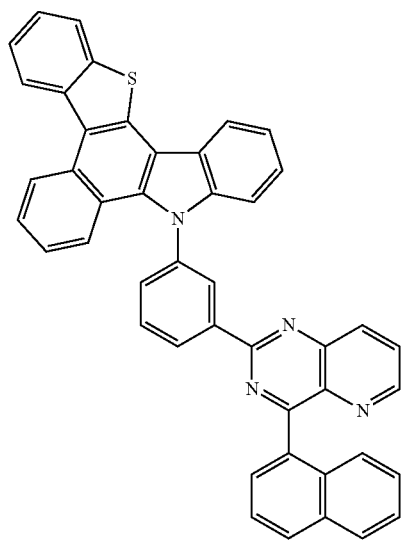
6-22
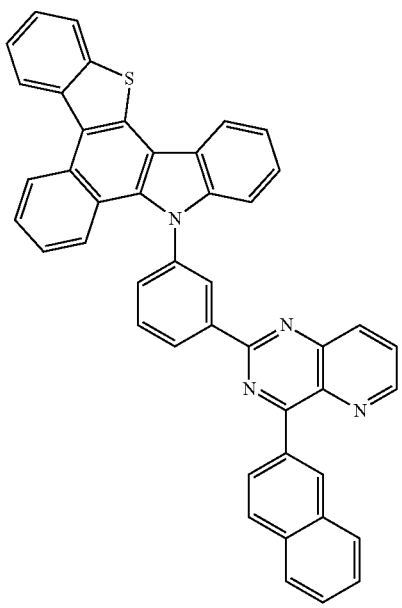

-continued
6-23
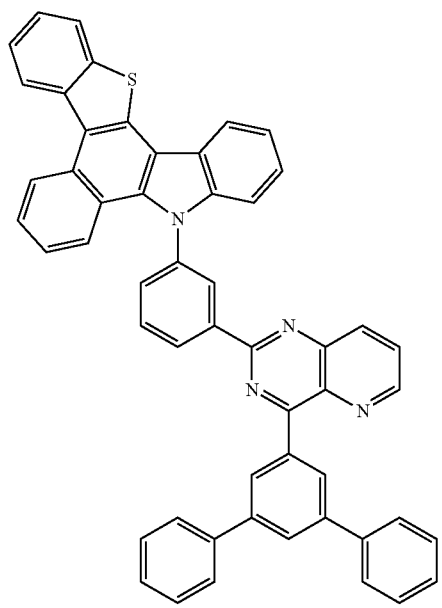
6-24
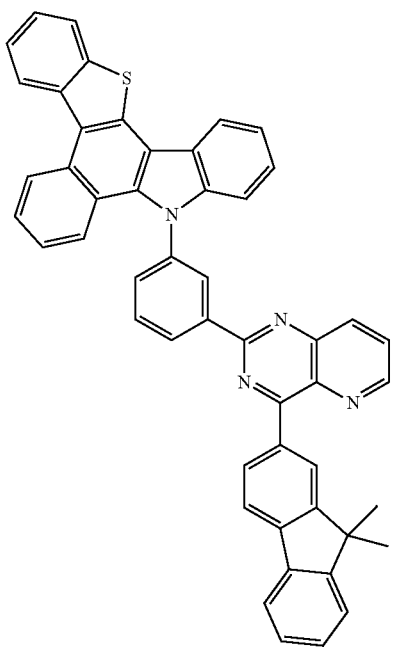
6-25
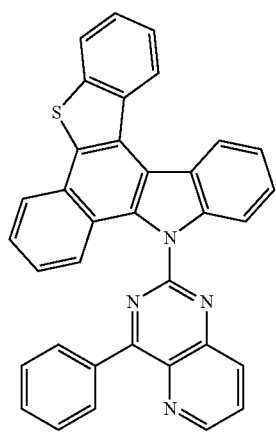
6-26
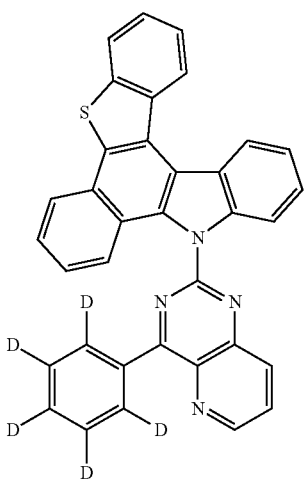

-continued
6-27
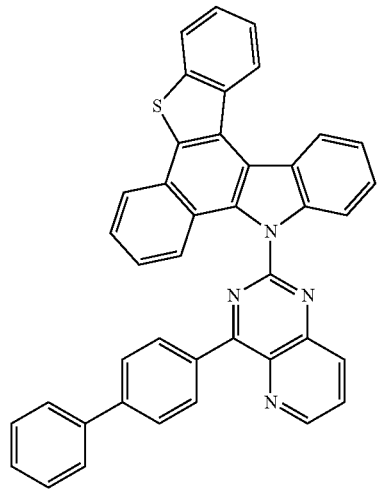
6-28
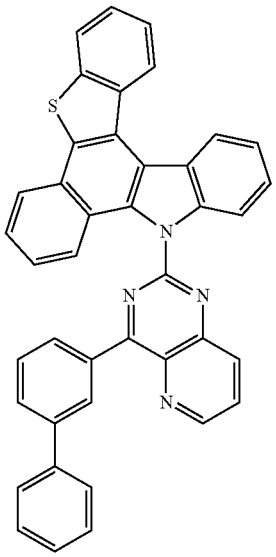
6-29
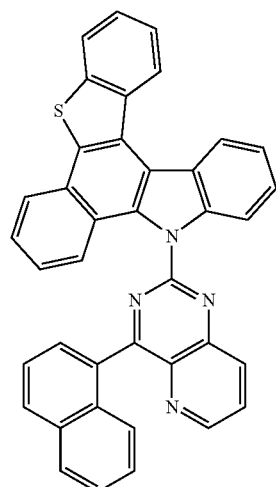
6-30
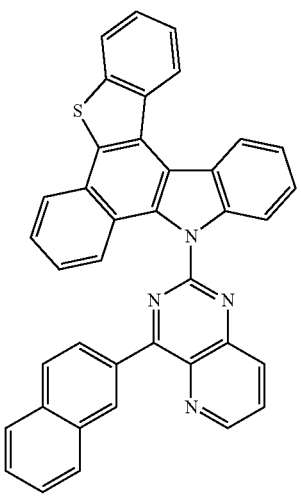
6-31
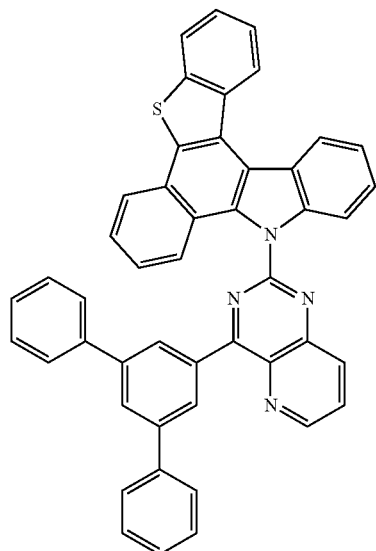
6-32
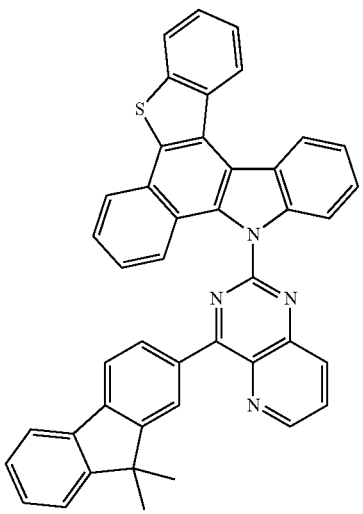

6-33
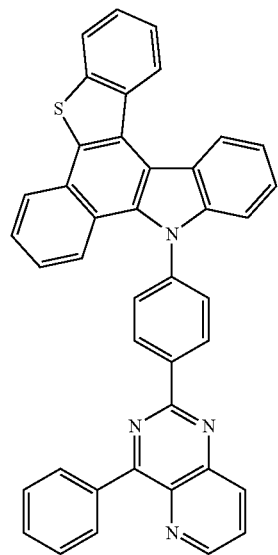
6-34
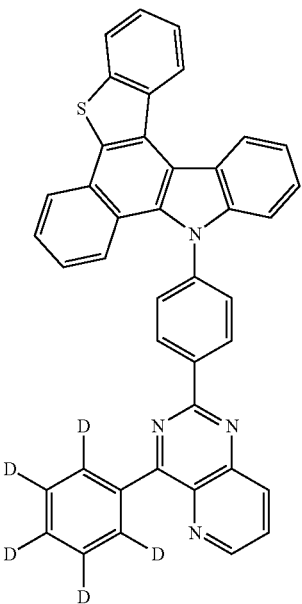
6-35
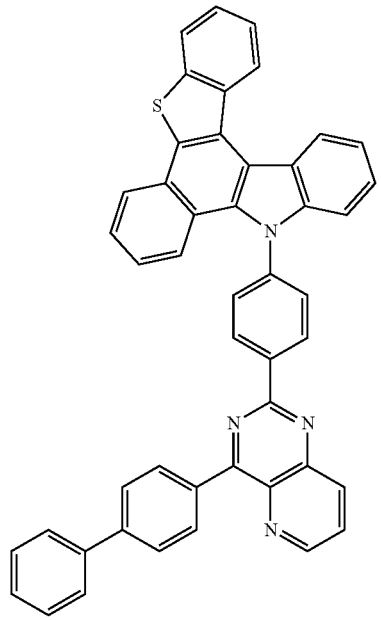
6-36
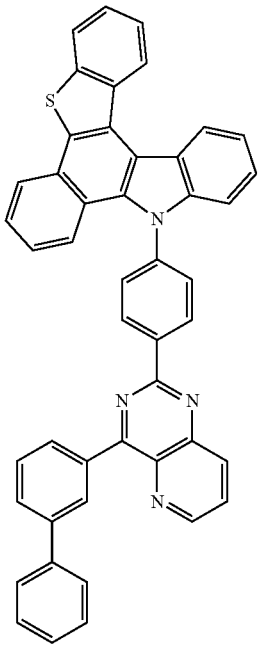

407 408
6-37
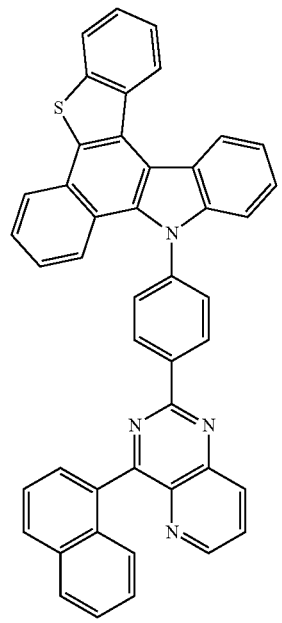
6-38
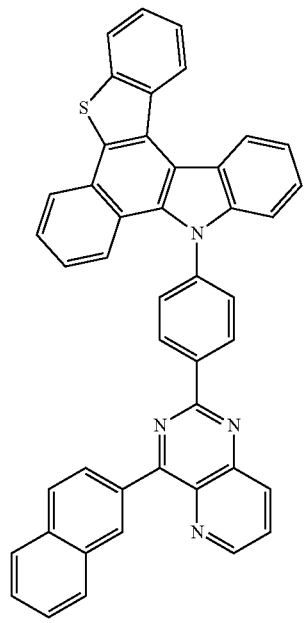
6-39
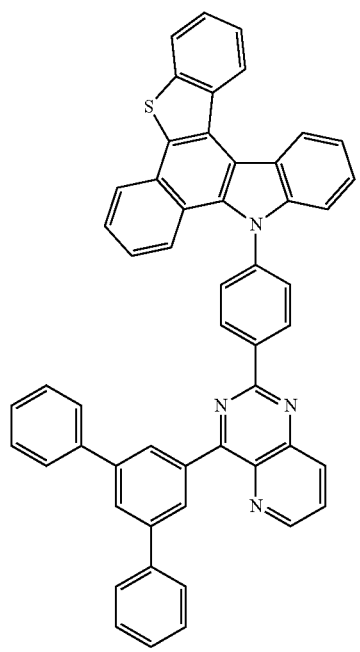
6-40
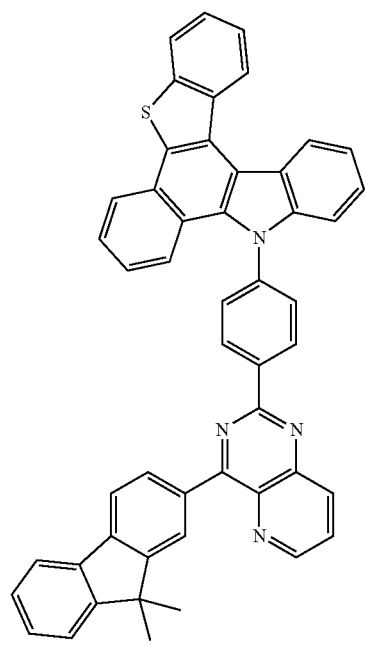

6-41
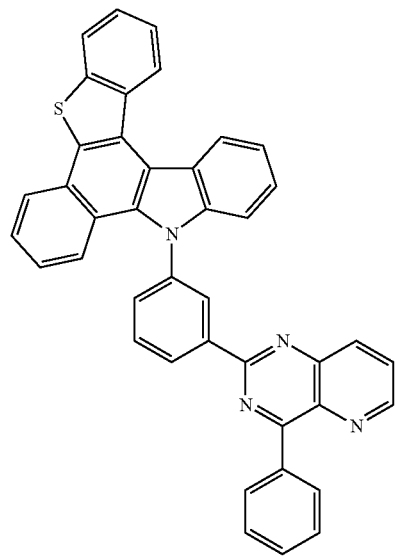
6-42
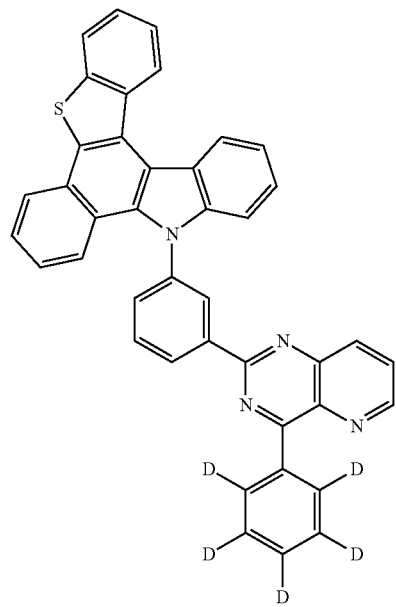
6-43
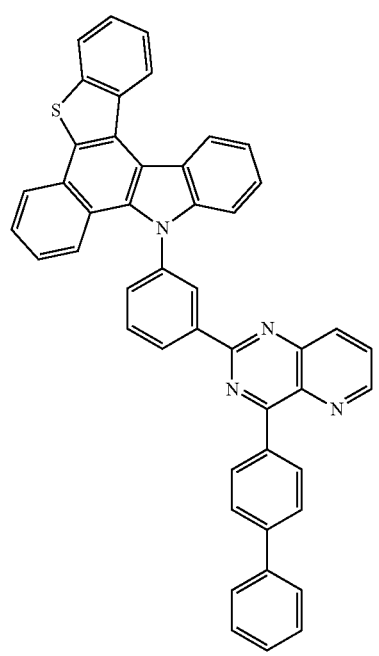
6-44
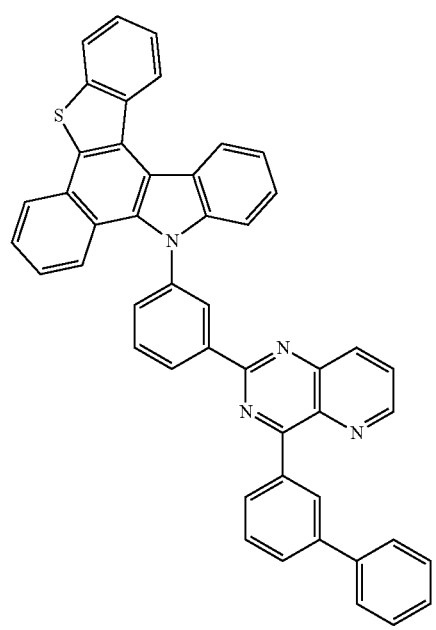

411
412
6-45
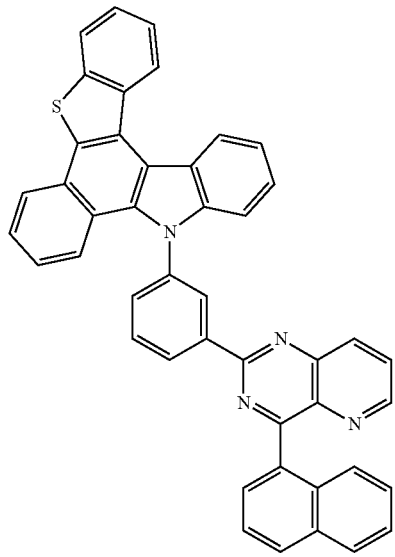
6-46
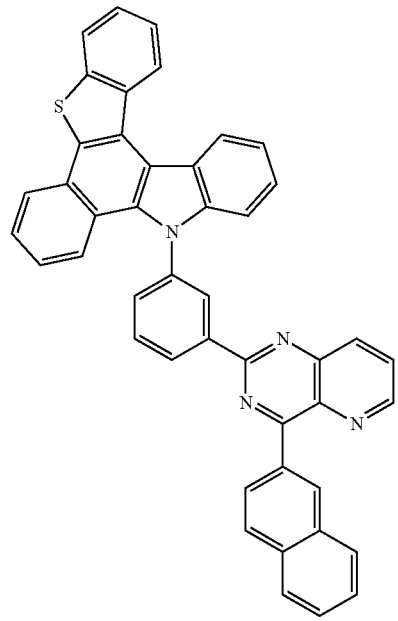
6-47
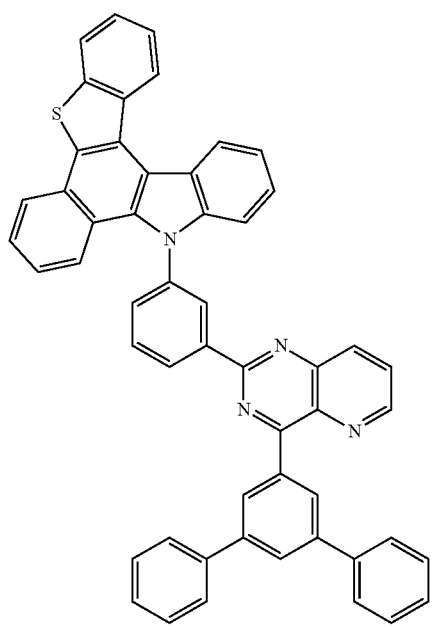
6-48
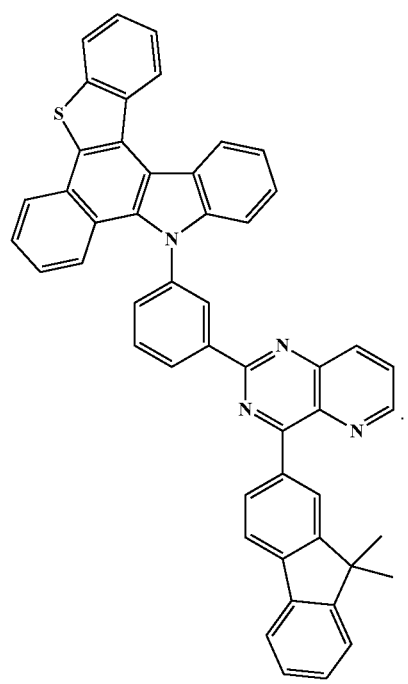

6-45

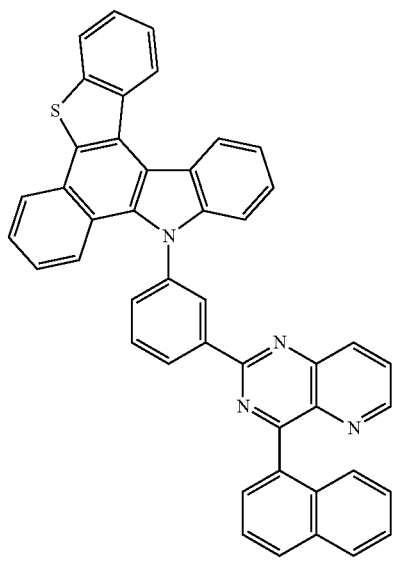

6-46

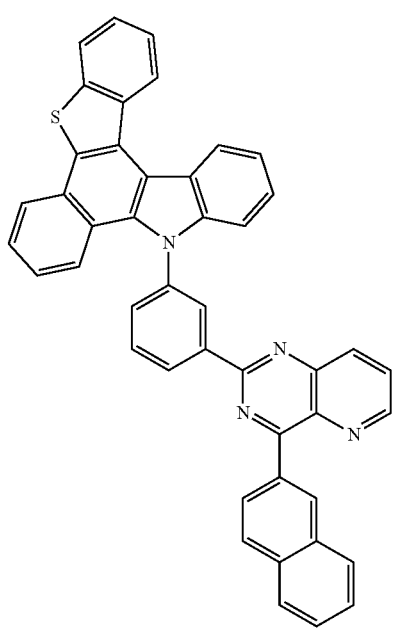

6-47

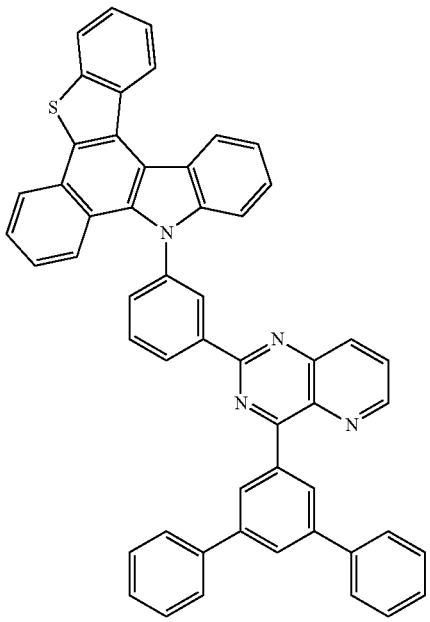

6-48

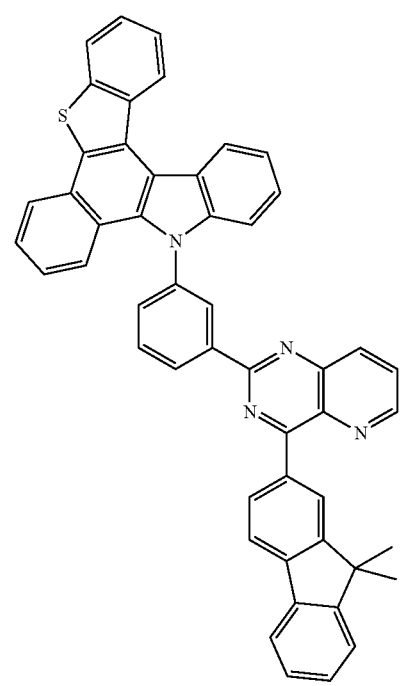

6. An organic electronic element comprising a first electrode, a second electrode, and an organic material layer disposed between the first electrode and the second electrode, wherein the organic material layer comprises the compound of Formula (1) of claim 1.

7. The organic electronic element as claimed in claim 6, wherein the organic material layer comprises the compound formed by a soluble process.

8. The organic electronic element as claimed in claim 6, wherein the organic material layer comprises at least one of a light emitting layer, a hole injection layer, a hole transport layer, an electron injection layer, an electron transport layer, and an emission-auxiliary layer.

9. The organic electronic element as claimed in claim 8, wherein the organic material layer comprises the light emitting layer or the emission-auxiliary layer, and the light emitting layer or the emission-auxiliary layer comprises the compound.

10. An electronic device comprising a display device, which comprises the organic electronic element of claim 6, and a control unit for driving the display device.

11. The electronic device of claim 10, wherein the organic electronic element comprises at least one of an organic light emitting diode (OLED), an organic solar cell, an organic photo conductor (OPC) drum, an organic transistor (organic TFT), and an element for monochromatic or white illumination.

12. The organic electric element of claim 6, wherein the organic material layer comprises a light emitting layer and the light emitting layer comprises the compound of Formula (1).

13. The organic electric element of claim 12, wherein the organic material layer further comprises an emission-auxiliary layer between the first electrode and the light emitting layer, and the emission-auxiliary layer comprises the compound of Formula (1).

14. The organic electric element of claim 12, wherein the organic material layer further comprises a hole injection layer formed on the first electrode, a hole transport layer formed between the hole injection layer and the light emitting layer, an electron transport layer formed on the light emitting layer, an electron injection layer formed between the electron transport layer and the second electrode, and optionally an emission-auxiliary layer between the light emitting layer and the hole transport layer.

15. The organic electric element of claim 14, wherein the light emitting layer or the emission-auxiliary layer comprises the compound of Formula (1).

16. An organic electronic element comprising a first electrode, a second electrode, and an organic material layer disposed between the first electrode and the second electrode, wherein the organic material layer comprises the compound of claim 5.

17. An electronic device comprising a display device, which comprises the organic electronic element of claim 16, and a control unit for driving the display device.

\* \* \* \* \*

UNITED STATES PATENT AND TRADEMARK OFFICE
CERTIFICATE OF CORRECTION

PATENT NO. : 10,991,885 B2
APPLICATION NO. : 15/867334
DATED : April 27, 2021
INVENTOR(S) : Park et al.

Page 1 of 3

It is certified that error appears in the above-identified patent and that said Letters Patent is hereby corrected as shown below:

In the Claims

Column 275, Claim 1, Formula (1):

Please delete " 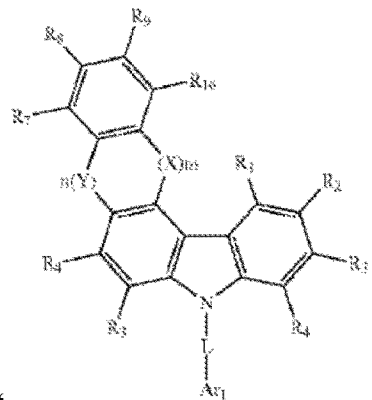 "

And replace with -- 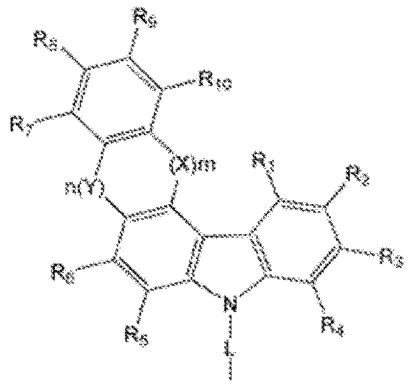 --

Signed and Sealed this
Tenth Day of August, 2021

Drew Hirshfeld
*Performing the Functions and Duties of the
Under Secretary of Commerce for Intellectual Property and
Director of the United States Patent and Trademark Office*

Column 292, Claim 5, Formula 1-32:
Please delete " 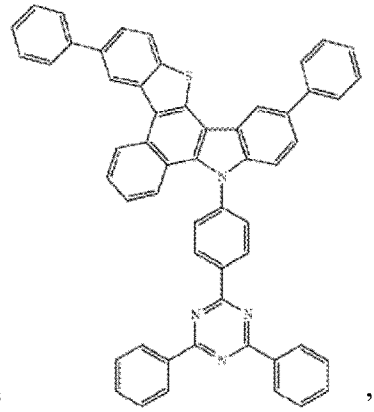 "
And replace with -- 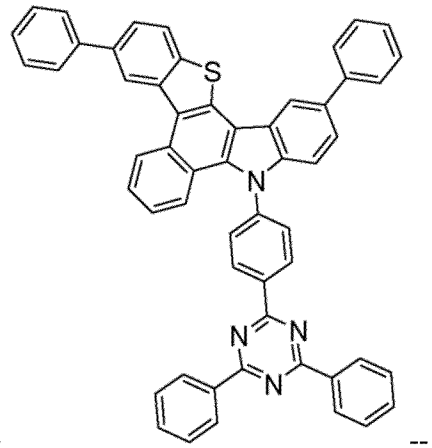 --
Column 338, Claim 5, Formula 1-160:
Please delete " 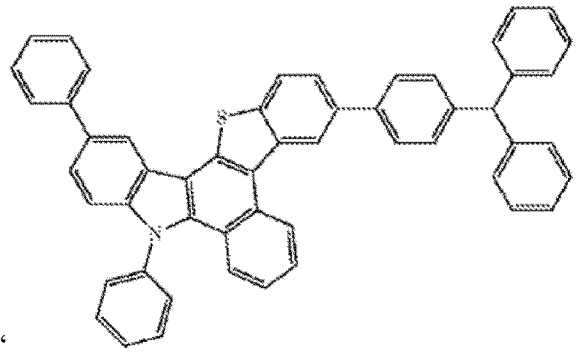 "

CERTIFICATE OF CORRECTION (continued)
U.S. Pat. No. 10,991,885 B2

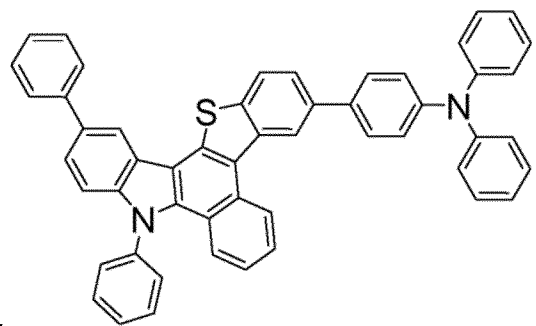

And replace with -- --

Column 340, Claim 5, Formula 2-4:

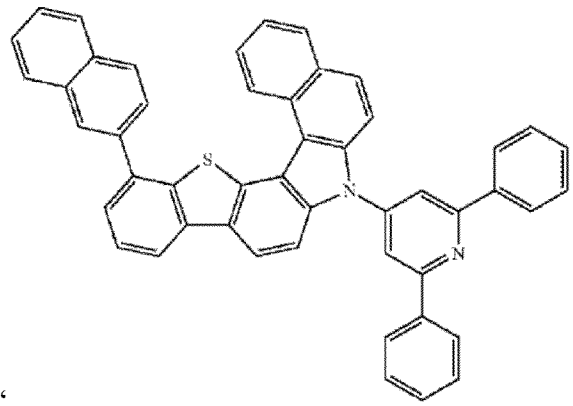

Please delete " "

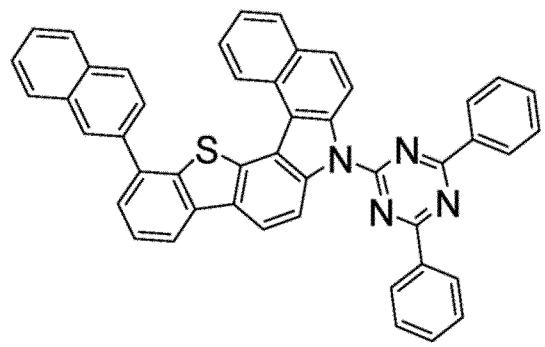

And replace with -- --